United States Patent
Konishi et al.

(10) Patent No.: US 6,555,555 B1
(45) Date of Patent: Apr. 29, 2003

(54) FUSED THIOPHONE DERIVATIVES AND DRUGS CONTAINING THE SAME AS THE ACTIVE INGREDIENT

(75) Inventors: Mikio Konishi, Osaka (JP); Nobuo Katsube, Osaka (JP); Mitoshi Konno, Osaka (JP); Tadamitsu Kishimoto, Osaka (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 10/127,409

(22) Filed: Apr. 23, 2002

Related U.S. Application Data

(62) Division of application No. 09/647,430, filed as application No. PCT/JP99/01648 on Mar. 31, 1999, now Pat. No. 6,420,391.

(30) Foreign Application Priority Data

Apr. 1, 1998 (JP) .................................. 10-104210
Jan. 19, 1999 (JP) .................................. 11-46887

(51) Int. Cl.$^7$ ..................... A61K 31/445; A61K 31/40; A61K 31/38
(52) U.S. Cl. ................. 514/324; 514/422; 514/443
(58) Field of Search ................. 514/324, 422, 514/443

(56) References Cited

U.S. PATENT DOCUMENTS

| | | | |
|---|---|---|---|
| 2,930,800 A | | 3/1960 | Kloetzel et al. |
| 3,629,438 A | | 12/1971 | Schmeling et al. |
| 3,686,216 A | | 8/1972 | Relyea et al. |
| 4,436,748 A | | 3/1984 | Ong et al. |
| 4,737,519 A | | 4/1988 | Yamashita et al. |
| 5,093,351 A | | 3/1992 | Batt |
| 5,496,851 A | | 3/1996 | Grinnell |
| 5,863,936 A | * | 1/1999 | Gaeta et al. ............ 514/443 |
| 5,977,098 A | * | 11/1999 | Palkowitz ............... 514/212 |
| 6,040,309 A | * | 3/2000 | Dack et al. ............. 514/253 |
| 6,271,642 B1 | | 4/2001 | Kunisch et al. |
| 6,251,936 B1 | | 6/2001 | Wrobel et al. |
| 6,294,537 B1 | | 9/2001 | Bichon et al. |
| 6,310,061 B2 | | 10/2001 | Ito et al. |
| 6,329,421 B1 | * | 12/2001 | Prasit et al. ............ 514/443 |
| 6,433,005 B1 | * | 8/2002 | McLaren et al. ......... 514/443 |

FOREIGN PATENT DOCUMENTS

| | | |
|---|---|---|
| DE | 1585930 | 2/1970 |
| EP | 0 659 418 | 6/1995 |
| JP | 57-122080 | 7/1982 |
| JP | 2-288856 | 11/1990 |
| JP | 4-364163 | 12/1992 |
| JP | 9-310078 | 12/1997 |
| JP | 10-298180 | 11/1998 |
| RU | 591474 | 5/1978 |
| WO | 95/27710 | 10/1995 |
| WO | 96/24356 | 8/1996 |
| WO | 98/55454 | 10/1998 |

OTHER PUBLICATIONS

Ong et al, "[(6,7–Dichlorobenzo[b]thein–5–yl)oxy]acetic Acids and 1,1–Dioxides., 1. A Structurally Novel Class of Diuretics with Hyposensitive Activity", *J. Med. Chem.*, 30:2295–2303 (1987).

97. 1,3–Dipolare Addition von 2–Benzonitrilio–2–propanld an 7–Methylthieno[2,3–clpyridin–1, 1–dioxid und Folgereaktionen, *Helvetica Chemica Acta*, vol. 66, Fasc. 3 (1983)–Nr.97.

180. 1,3–Dipolare Addition von 7–Methylthieno[2,3–clpyridin–1, 1–dioxid, *Helvetica Chemica Acta*, vol. 66, Fasc. 6 (1980)–Nr. 180.

Kropp et al, "Bacterial Transformations of Benzothiophene and Methylbenzothiophenes", *Environ. Sci. Technol.*, 28:1348–1356 (1994).

Titus et al, Benzo [b] thiophene Derivatives II, 4– and 6–Substituted Benzo [b] thiophenes, Department of Chemistry, The University of Toledo, Dec. 1967.

\* cited by examiner

*Primary Examiner*—Deborah C. Lambkin
(74) *Attorney, Agent, or Firm*—Sughrue Mion, PLLC

(57) ABSTRACT

The present invention relates to a fused thiophene derivative of the formula (I) (wherein all the symbols are defined as described in the specification) and an inhibitor of producing interleukin-6 and/or interleukin-12 comprising the said derivative as an active ingredient.

A fused thiophene derivative of the formula (I) is useful as an agent for the prevention and/or treatment of various inflammatory diseases, sepsis, multiple myeloma, plasma cell leukemia, osteoporosis, cachexia, psoriasis, nephritis, renal cell carcinoma, Kaposi's sarcoma, rheumatoid arthritis, gammopathy, Castleman's disease, atrial myxoma, diabetes mellitus, autoimmune diseases, hepatitis, multiple sclerosis, colitis, graft versus host immune diseases, infectious diseases.

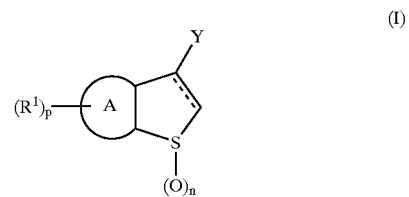

(I)

4 Claims, No Drawings

FUSED THIOPHONE DERIVATIVES AND DRUGS CONTAINING THE SAME AS THE ACTIVE INGREDIENT

This application is a Divisional of U.S. application Ser. No. 09/647,430, filed Oct. 2, 2000, U.S. Pat. No. 6,420,391; which in turn is a 371 of PCT/JP99/01648, filed Mar. 31, 1999. The disclosure of each of which is incorporated herein by reference.

TECHNICAL FIELD

The present invention relates to fused thiophene derivatives and inhibitors of producing Interleukin-6 (abbreviated as IL-6 hereafter) and/or Interleukin-12 (abbreviated as IL-12 hereafter) containing fused thiophene derivatives as an active ingredient.

More particularly, the present invention relates to inhibitors of producing IL-6 and/or IL-12 comprising, as an active ingredient, fused thiophene derivatives of the formula (I)

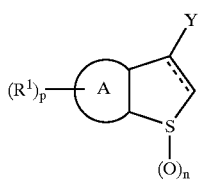

(wherein all the symbols are as defined hereafter.)
and non-toxic salts thereof, novel fused thiophene derivatives of the said formula (IA) or non-toxic salts thereof and methods for preparation thereof.

Moreover, the present invention relates to a method for preparation of a compound of the formula (XI) which is an intermediate for the compounds of the formula (I).

BACKGROUND

Cytokine is a multifunctional factor which plays an important role in the host defence system of living body and it relates to various life phenomena. However, there are many diseases which may be caused by overproduction thereof or by overresponse thereto.

IL-6 is a cytokine produced from various cells, e.g. T cells, B cells, macrophages, kidney mesangial cells, fibroblasts etc., and its various physiological effects are known e.g. induction of B cell differentiation to antibody-producing cells, activation of T cells, increase of platelets, and production of acute phase protein from liver cells etc. But, an abnormal production of IL-6 has been observed in various inflammations, autoimmune diseases and neoplastic diseases and it is suggested that IL-6 plays a certain role in the causes of such pathophysiological situations. In the experiment using an animal model in which IL-6 was forcibly expressed, various types of diseases could be observed and such results strongly suggest the existence of relationship between the abnormal production of IL-6 and the cause of certain diseases (Biochem. J., 265, 621 (1990), Immunol. Today, 11, 443 (1990), J. Autoimmun., 5 Suppl A, 123 (1992), Clin. Immunol. Immunopathol., 62, S60 (1992)).

IL-12 is a cytokine produced from macrophages and dendritic cells etc. and its effects are known; e.g. activation of natural killer (abbreviated as NK hereafter) cells, induction of Interferon-γ (abbreviated as IFN-γ hereafter) production from NK cells and T cells, and regulation of Th1 and Th2 balance etc. Helper T cells are classified into Th1 which stimulates cellular-mediated immunity and Th2 which assists humoral immunity. IL-12 functions to induce Th1 from helper T cell precursors. It is thought that succeedingly, IL-12 induces production of IFN-γ from Th1 cells (which are further differentiated) and accelerates killer activity, so that IL-12 plays a role as a main cytokine causing inflammatory immune reaction which leads to organ disorders (Blood, 84, 4008 (1994)).

Therefore, inhibition of IL-6 and/or IL-12 production(s) is expected to improve various kinds of diseases such as inflammatory diseases as a representative. The present invention is targeted for these cytokines and provides novel medicines through inhibiting the production thereof.

Clinical application of the compounds of the present invention involves those diseases which may be caused and be changed to worse by abnormal production of IL-6 and/or IL-12 or by overresponse to them. Inhibitors of producing IL-6 may be used for the prevention and/or treatment of various inflammatory diseases, sepsis, multiple myeloma, plasma cell leukemia, osteoporosis, cachexia, psoriasis, nephritis, renal cell carcinoma, Kaposi's sarcoma, rheumatoid arthritis, gammopathy, Castleman's disease, atrial myxoma, diabetes mellitus, autoimmune diseases (J. Immunol., 145, 4185 (1990), J. Exp. Med., 172, 1505 (1990), J. Clin. Invest., 87, 739 (1991), J. Clin. Invest., 89, 1681 (1992), EMBO J., 13, 1189 (1994), Hematol. Oncol. Clin. North Am., 11, 159 (1997)). Inhibitors of producing IL-12 may be used for the prevention and/or treatment of various inflammatory diseases, diabetes mellitus, hepatitis, multiple sclerosis, colitis, graft versus host immune diseases, rheumatoid arthritis, infectious diseases, autoimmune diseases (J. Exp. Med., 181, 817 (1995), J. Exp. Med., 181, 381 (1995), J. Exp. Med., 182, 1281 (1995), Ann, NY Acad. Sci., 795, 371 (1996), Int. Immunol., 8, 569 (1996), Proc. Natl. Acad. Sci. USA, 92, 4823 (1996)).

Further, a compound of the formula (XI) is an important intermediate of pharmaceutical agents and an efficient method for preparation thereof has been desired.

For example, (1) In the specifications of U.S. Pat. Nos. 3,629,438 and 3,686,216, it is disclosed that a benzothiophene-1,1-dioxide derivative of the formula (X)

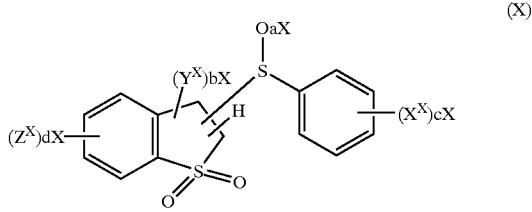

(wherein $X^x$ is halogen, nitro, alkyl alkoxy, haloalkyl, carboxy or sulfonylhalide, $Y^x$ is hydrogen, lower alkyl, lower alkoxy, halogen or hydroxy, $Z^x$ is alkyl, alkoxy, halogen, carboxy, haloalkyl or nitro, aX is 0 or an integer of 2, bX is an integer of 2, cX is 0 or an integer of 1~5 or dX is 0 or an integer of 1~4.)

has an anti-fungal and anti-vital activities.

(2) In the specification of FR1585930, a compound of the formula (Y)

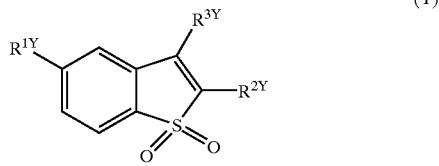

(Y)

(wherein $R^{1Y}$ is hydrogen, halogen or C1~3 alkyl; $R^{2Y}$ and $R^{3Y}$ are hydrogen or C1~3 alkyl) is described as an intermediate of diuretic agent, but there is no description about its biological activity.

(3) In the specification of SU591474, it is described that a compound of the formula (Z)

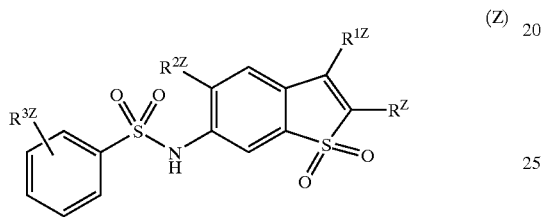

(Z)

(wherein $R^Z$, $R^{1Z}$, $R^{2Z}$ and $R^{3Z}$ are hydrogen or methyl.) has an anti-spasm activity.

(4) In the specification of EP50326, it is described that a compound of the formula (U)

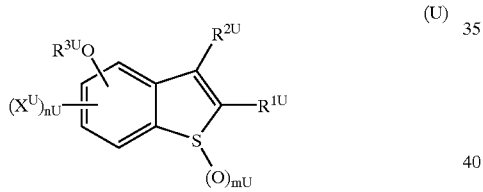

(U)

(wherein $R^{1U}$ and $R^{2U}$ are each hydrogen or C1~6 alkyl, C3~6 cycloalkyl or phenyl which may be substituted with 1~2 of halogen, hydroxy, C1~6 alkyl or alkoxy, $R^{3U}$ is hydrogen or $Z^U$, $Z^U$ is C1~6 alkyl or $CR^{4U}R^{5U}R^{6U}$, $R^{4U}$ and $R^{5U}$ are hydrogen or C1~6 alkyl, $R^{6U}$ is COOH, $CH_2$—OH, C1~6 alkoxycarbonyl or hydroxyaminocarbonyl, $X^U$ is hydrogen, halogen or C1~6 alkyl, nU is 1 or 2, mU is 0~2) has a diuretic activity (In the explanation of groups, essential parts are extracted).

(5) In the specification of WO9527710, it is described that a compound of the formula (V)

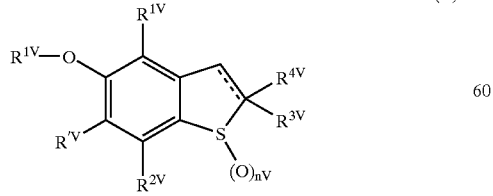

(V)

(wherein $R^{1V}$ is t-butyl, $R^{1V}$ is hydrogen, lower alkyl or acyl, a broken line is arbitrary bond, $R^{2V}$ and $R^{3V}$ are hydrogen, alkyl which may be substituted or alkenyl which may be substituted, $R^{4V}$ does not represent anything when arbitrary bond exists and represents the same meaning as $R^{3V}$ when arbitrary bond does not exist and nV is 0~2.) has an activity as antioxidant of low-density lipoprotein (LDL) (in the explanation of groups, essential parts are extracted).

(6) In the specification of Japanese Patent Application Kokai Hei 10-298180, it is described that a compound of the formula (W)

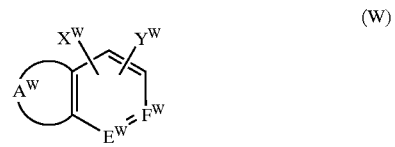

(W)

(wherein $A^Z$ is

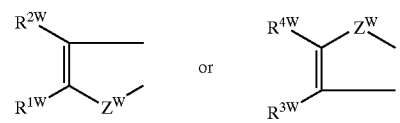

(wherein $Z_W$ is oxygen atom or sulfur atom; $R^{1W}$, $R^{2W}$, $R^{3W}$ and $R^{4W}$ are the same or different, are hydrogen etc.); $E^W$ and $F^W$ are the same or different, are nitrogen atom or CH which may be substituted with $X^W$ or $Y^W$; $X^W$ is straight or branched C1–6 alkyloxy, C3–8 cycloalkyloxy or straight or branched C1–3 alkyloxy substituted with C3–8 cycloalkyl; Y is

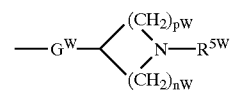

(wherein $G^W$ is —CONH—, —C(O)O—, —NHCO— or —OC(O)—; $R^{5W}$ is (a) straight or branched C1–6 alkyl, (b) C3–8 cycloalkyl, (c) C7–12 spiroalkyl, (d) C7–12 bicycloalky), (e) aryl, (f) aralkyl, (g) heteroarylalkyl, (h) non-aromatic heterocyclic ring which may be substituted with phenyl or (i) C3–8 cycloalkyl-C1–3 alkyl. Each of them may be substituted with one or more of substituent selected from a group consisting of i) straight or branched C1–6 alkyl, ii) straight or branched C1–8 alkyloxy, iii) C1–3 haloalkyl, iv) halogen, v) C3–8 cycloalkyl, vi) carboxy, vii) alkyloxycarbonyl, viii) acyl, ix) formyl and x) nitro; nW is an integer of 1–3, pW is an integer of 1–3, $(CH_2)_{nW}$ and $(CH_2)_{pW}$ may be substituted with a straight or branched C1–6 alkyl or C1–3 haloalkyl) has an antagonistic activity against dopamine receptor.

(7) In the specification of Japanese Patent Application Kokai Hei 10-513470, it is described that a compound of the formula (T)

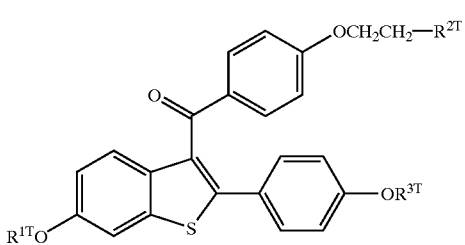

(T)

[wherein $R^{1T}$ and $R^{3T}$ are independently hydrogen, —$CH_3$, —C(O)—(C1~6 alkyl), or —C(O)—$Ar^T$ ($Ar^T$ is phenyl which may optionally be substituted); $R^{2T}$ is selected from a group consisting of pyrrolidino, hexamethyleneimino and piperidino], a pharmaceutically acceptable salt thereof or a solvent additive has an activity of inhibiting the effect of IL-6.

(8) In the specification of Japanese Patent Application Kokai Hei 11-49765, it is described that a compound of the formula (S)

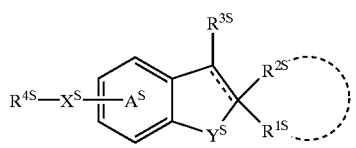

(S)

[wherein each $R^{1S}$ and $R^{2S}$ is hydrogen or hydrocarbon group which may contain substituent(s) or $R^{1S}$ and $R^{2S}$ taken together with the neighboring carbon atom represents 3- to 8-membered homo or heterocyclic ring which may contain substituent(s), $R^{3S}$ is hydrogen or lower alkyl which may contain subtstituent(s) or aromatic group which may contain substituent(s), $R^{4S}$ is (1) aromatic group which may contain substituent(s), (2) aliphatic hydrocarbon which contains aromatic group (this group is unsubstituted or substituted.) and which may contain additional substituent(s) or (3) acyl, $X^S$ and $Y^S$ are each oxygen atom or sulfur atom which may be oxidized, ═══ is single bond or double bond, ring $A^S$ is benzene ring which contains a group of the formula —$X^S$—$R^{4S}$ (wherein each symbols represent the same meaning as defined hereinbefore) and which may contain additional substituent(s), with the proviso that when ═══ is single bond and both $X^S$ and $Y^S$ are oxygen atom, then $R^{4S}$ is not acyl.] or a salt thereof have an excellent inhibitory effect of neurodegeneration.

(9) Further, the following compounds are known.
Compound (1): 3-(Thiophen-2-yl)sulfonyl-2,3-dihydro-1,1-dioxidebenzo[b]thiophene (Maybridge, Catalog No. KM 08156),
Compound (2): 6-Nitro-3-(thiophen-2-yl)thio-2,3-dihydro-1,1-dioxidebenzo[b]thiophene (Maybridge, catalog No. KM 08165),
Compound (3): 3-(Thiophen-2-yl)thio-2,3-dihydro-1,1-dioxidebenzo[b]thiophene (Maybridge, Catalog No. KM 08138),
Compound (4): 3-Phenylsulfonyl-2,3-dihydro-1,1-dioxidebenzo[b]thiophene (Maybridge, Catalog No. KM 08140),
Compound (5): 4,5-Dimethyl-1,1-dioxidebenzo[b]thiophene (CAS Registry No. 102036-04-4),
Compound (6): 4,6-Dimethyl-1,1-dioxidebenzo[b]thiophene (CAS Registry No. 102036-05-5),
Compound (7): 4,7-Dimethyl-1,1-dioxidebenzo[b]thiophene (CAS Registry No. 102036-06-6),
Compound (8): 5,6-Dimethyl-1,1-dioxidebenzo[b]thiophene (CAS Registry No. 102036-07-7),
Compound (9): 5,7-Dimethyl-1,1-dioxidebenzo[b]thiophene (CAS Registry No. 102036-08-8),
Compound (10): 6,7-Dimethyl-1,1-dioxidebenzo[b]thiophene (CAS Registry No. 102036-09-9),
Compound (11): 4-Carboxymethyl-1,1-dioxidebenzo[b]thiophene (CAS Registry No. 102539-83-3),
Compound (12) 6-(2,2-Bis(ethoxycarbonyl)ethenyl)amino-1,1-dioxidebenzo[b]thiophene (CAS Registry No. 118675-43-7),
Compound (13): 4-Methylaminocarbonyloxy-1,1-dioxidebenzo[b]thiophene (CAS Registry No. 13687-26-8),
Compound (14): 5-(2-(N-(5-Methoxy-1,2,3,4-tetrahydronaphthalen-1-ylmethyl)-N-methylamino)ethyl)-1,1-dioxidebenzo[b]thiophene (CAS Registry No.188110-86-3),
Compound (15): 5-(2-Hydroxyethyl)-1,1-dioxidebenzo[b]thiophene (CAS Registry No. 188111-49-1),
Compound (16): 5-Bromo-7-methyl-1,1-dioxidebenzo[b]thiophene (CAS Registry No. 19076-24-5),
Compound (17): 7-Bromo-5-methyl-1,1-dioxidebenzo[b]thiophene (CAS Registry No. 19076-25-6),
Compound (18): 5-Bromo-6-methyl1,1-dioxidebenzo[b]thiophene (CAS Registry No. 19076-26-7),
Compound (19): 5-Bromo-4-methyl-1,1-dioxidebenzo[b]thiophene (CAS Registry No. 19076-27-8),
Compound (20): 6-Bromo-5-methyl-1,1-dioxidebenzo[b]thiophene (CAS Registry No. 19076-28-9),
Compound (21): 4-Bromo-5-methyl-1,1-dioxidebenzo[b]thiophene (CAS Registry No. 19076-29-0),
Compound (22): 6-Amino-1,1-dioxidebenzo[b]thiophene (CAS Registry No. 20503-40-6),
Compound (23): 6-Acetyamino-1,1-dioxidebenzo[b]thiophene (CAS Registry No. 20503-41-7),
Compound (24): 6-(4-Diethylaminophenyl)-1,1-dioxidebenzo[b]thiophene (CAS Registry No. 33431-95-7),
Compound (25): 1,1-Dioxidethieno[2,3-b]pyridine (CAS Registry No. 37049-39-1),
Compound (26): 1,1-Dioxidethieno[3,2-b]pyridine (CAS Registry No. 37049-40-4),
Compound (27): 1,1-Dioxidethieno[2,3-c]pyridine (CAS Registry No. 37049-41-5),
Compound (28): 5-Amino-1,1-dioxidebenzo[b]thiophene (CAS Registry No. 51956-01-5),
Compound (29): 5-(3-Methyl-5-oxo-4,5-dlhydropyrazol-1-yl)-1,1-dioxidebenzo[b]thiophene (CAS Registry No. 51956-06-0),
Compound (30): 4-(2-(1,1-Dioxidebenzo[b]thiophen-3-yl)ethyl)-1,1-dioxidebenzo[b]thiophene (CAS Registry No. 57011-92-4),
Compound (31): 7-Methyl-1,1-dioxidethieno[2,3-c]pyridine (CAS Registry No. 76905-90-3),
Compound (32): 1,1-Dioxidebenzo[b]thiophene (CAS Registry No. 825-44-5),
Compound (33) 4-(4-Methoxyphenyl)-1,1-dioxidethieno[3,2-c]pyridine (CAS Registry No. 97104-25-1).

(10) In addition, as to a method for preparation of a compound of the formula (XI), for example, the method of the following Reaction Scheme 2 is known.

These are described in detail in Nihonkagakuzasshi 1966, 87(2), 186–189, J. Org. Chem., 1953, Vol.18, 1511 and J. Org. Chem. 1973, Vol.38, 146.

Reaction Scheme 2

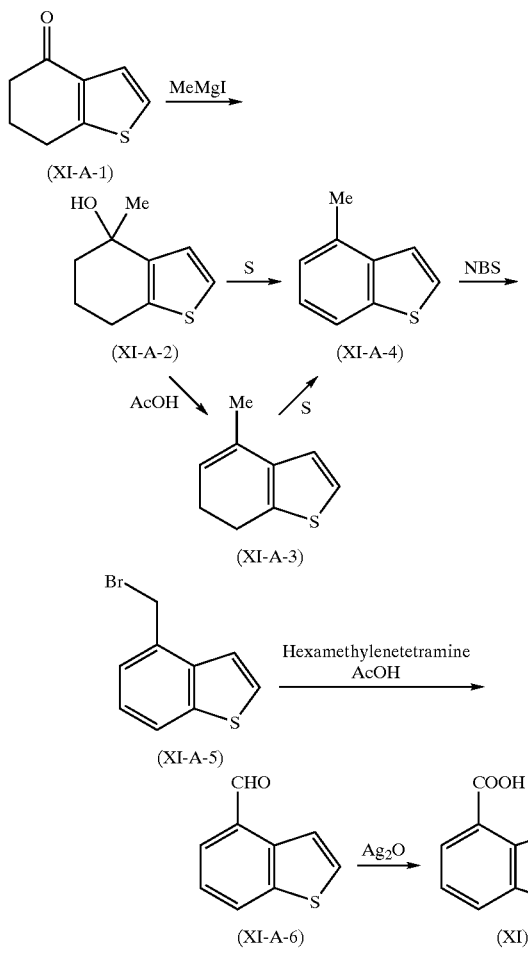

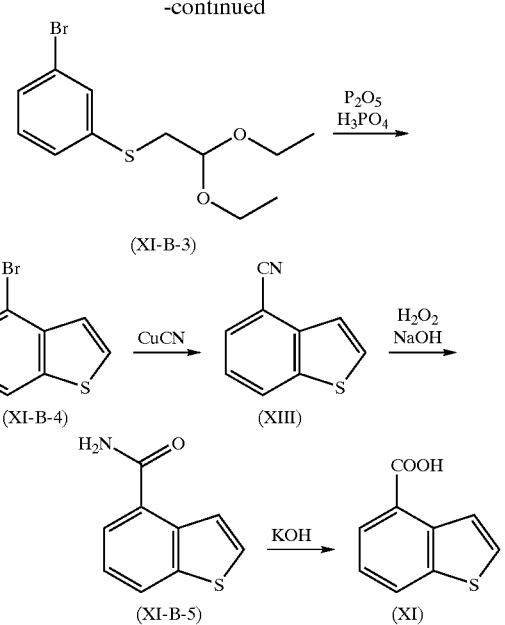

In Reaction Scheme 2, Me is methyl, Ac is acetyl and NBS is N-bromosuccinimide.

The above method of Reaction Scheme 2 requires 5 or 6 steps in total and Ag$_2$O, which is an expensive reagent, in oxidation reaction from the compound of the formula (XI-A-6) to the compound of the formula (XI).

Further, in the specification of Japanese Patent Application Kokai Hei 6-49058, the following Reaction Scheme 3 is disclosed as a method for preparation of the compound of the formula (XI).

Reaction Scheme 3

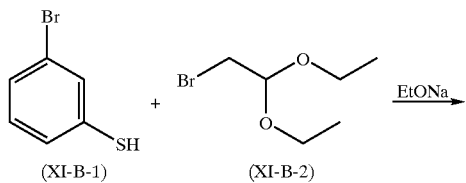

In Reaction Scheme 3, Et is ethyl.

The above method of Reaction Scheme 3 requires 5 steps in total and the total yield is around 2~3%.

In Tetrahedron Letters, 1996, Vol.37, No.19, 3243 and Tetrahedron Letters 1990, Vol.31, No.28, 4011, a reaction wherein ketone is converted into nitrile, followed by dehydrogenation to give aromatic ring is disclosed (Reaction Scheme 4).

Reaction Scheme 4

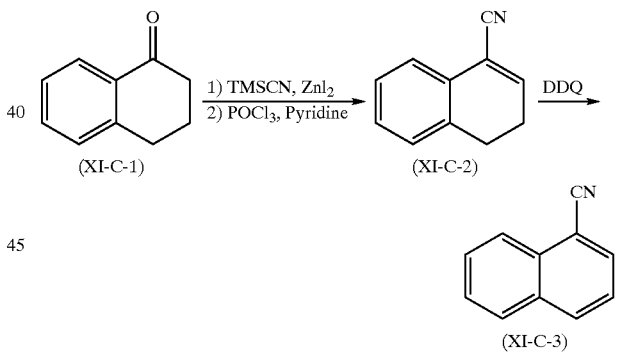

In Reaction Scheme 4, TMS is trimethylsilyl, DDQ is 2,3dichloro-5,6-dicyano-1,4-benzoquinone.

This reaction is a method for preparation of aromatic nitrile of the formula (XI-C-2) which comprises that cyclic ketone of the formula (XI-C-1) is converted into cyanohydrin, followed by dehydration to give nitrile of the formula (XI-C-2), and then followed by dehydrogenation by an oxidizer.

DISCLOSURE OF THE INVENTION

The present inventors have investigated to find new compounds possessing an inhibitory activity of producing IL-6 and/or IL-12, so that the present inventors have found that the purpose has been achieved by fused thiophene derivatives of the formula (I).

Fused heterocyclic compounds of the formula (I) of the present invention has not been known as inhibitors of producing IL-6 and/or IL-12 at all. Further, a fused thiophene derivative of the formula (IA) is a novel compound which is not known at all.

In addition, the present inventors have investigated to find an efficient method for preparation at a low cost, so that the present inventor have found a method of the following Reaction Scheme 5.

Reaction Scheme 5

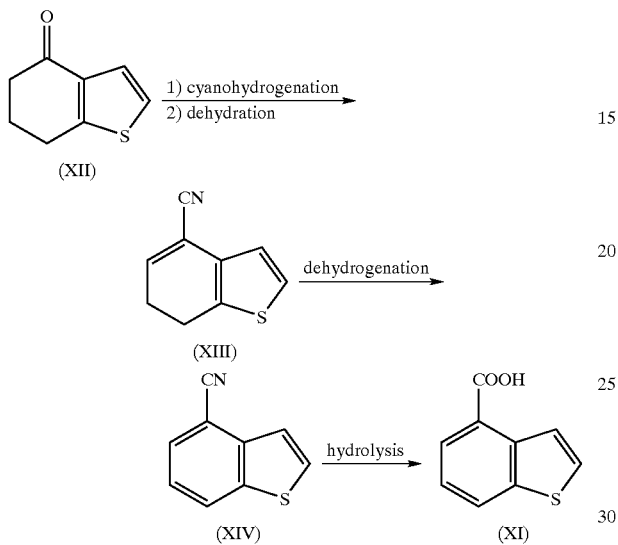

The old methods require 5–6 steps, whereas the method of the present invention diminishes to 3 steps in total, so it become possible to produce efficiently. In addition, it is also confirmed that in mass-production of it, the cost for the production is reduced, so that the present inventors have completed the present invention.

The present invention relates to (1) an inhibitor of producing Interleukin-6 and/or Interleukin-12 comprising, as an active ingredient, a fused thiophene derivative of the formula (I)

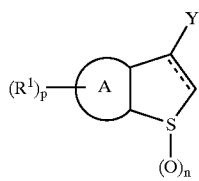

(I)

[wherein === is a single or double bond,
Y is
  (i)

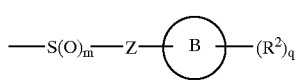

or
  (ii) hydrogen
with a proviso that when === is a double bond, Y is hydrogen, and when === is a single bond, Y is

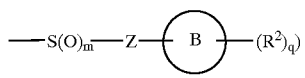

m and n are each independently 0 or an integer of 1–2,
p is 0 or an integer of 1–4,
q is 0 or an integer of 1–5,
Z is single bond, C1–8 alkylene, C2–8 alkenylene or C2–8 alkynylene,

is
(i) benzene ring or
(ii) 6-membered monocyclic hetero aryl containing 1–2 nitrogen atom(s),

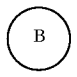

is
(i) C3–15 mono-, bi- or tricyclic carbo ring or
(ii) 4–18 membered mono-, bi- or tricyclic hetero ring containing 1–4 nitrogen atom(s), 1–2 oxygen atom(s) and/or one suifur atom,
each $R^1$ of $(R^1)p$ is independently,
  (i) C1–8 alkyl,
  (ii) C2–8 alkenyl,
  (iii) C2–8 alkynyl,
  (iv) nitro,
  (v) cyano,
  (vi) halogen,
  (vii) $Cyc^1$,
  (viii) C1–8 alkyl, C2–8 alkenyl or C2–8 alkynyl substituted with halogen or $Cyc^1$ or
  (ix) —$A^1$—$A^2$—$A^3$,
$A^1$ is
  (i) single bond,
  (ii) C2–8 alkylene,
  (iii) C2–8 alkenylene or
  (iv) C2–8 alkynylene,
$A^2$ is
  (i) —O—,
  (ii) —$NR^3$—,
  (iii) —C(O)—,
  (iv) —CH(OH)—,
  (v) —C(O)$NR^4$—,
  (vi) —$NR^5$C(O)—,
  (vii) —C(O)O—,
  (viii) —OC(O)—,
  (ix) —$SO_2NR^6$—,
  (x) —$NR^7SO_2$—,
  (xi) —C(O)$NR^9$O—,
  (xii) —OC(O)$NR^{10}$—,
  (xiii) —$NR^{11}$C(O)$NR^{12}$—,
  (xiv) —$NR^{13}$C(O)O— or (xv) —OC(O)O—
(wherein $R^3$, $R^4$, $R^5$, $R^6$, $R^7$, $R^9$, $R^{10}$, $R^{11}$, $R^{12}$ and $R^{13}$ are each independently, hydrogen, C1–8 alkyl, phenyl or C1–8 alkyl substituted with $Cyc^1$, —$OR^{14}$ (wherein $R^{14}$ is hydrogen or C1–8 alkyl.) or cyano, with the proviso that the linkage of the right side of each group represented by $A^2$ binds to $A^3$.

$A^3$ is
- (i) hydrogen,
- (ii) C1–8 alkyl,
- (iii) C2–8 alkenyl,
- (iv) C2–8 alkynyl,
- (v) $Cyc^1$ or
- (vi) C1–8 alkyl, C2–8 alkenyl or C2–8 alkynyl substituted with 1–3 groups selected from the following (a)–(i):
  - (a) halogen,
  - (b) cyano,
  - (c) —$P(O)(R^{15})_2$,
  - (d) —$Si(R_{16})_3$,
  - (e) $Cyc^1$,
  - (f) —$C(O)R^{17}$,
  - (g) —$OR^{18}$,
  - (h) —$NR^{19}R^{20}$,
  - (i) —$SR^{21}$;

plural $R^{15}$s are each independently, hydroxy or C1–8 alkoxy, plural $R^{16}$s are each independently C1–8 alkyl, $R^{17}$ is
  - (i) hydrogen,
  - (ii) C1–8 alkyl,
  - (iii) hydroxy,
  - (iv) C1–8 alkoxy,
  - (v) $Cyc^1$ or
  - (vi) —$NR^{22}R^{23}$ (wherein $R^{22}$ is hydrogen, C1–8 alkyl, phenyl or C1–8 alkyl substituted with phenyl, $R^{23}$ is hydrogen, C1–8 alkyl, $Cyc^1$ or C1–8 alkyl substituted with $Cyc^1$ or $NR^{24}R^{25}$ ($R^{24}$ and $R^{25}$ are each independently hydrogen, C1–8 alkyl, phenyl, C1–8 alkyl substituted with phenyl.).), $R^{18}$ is
  - (i) hydrogen,
  - (ii) C1–8 alkyl,
  - (iii) C2–8 alkenyl,
  - (iv) $Cyc^1$ or
  - (v) C1–8 alkyl substituted with $Cyc^1$, $Si(R^{26})_3$ (wherein plural $R^{26}$s are each independently C1–8 alkyl.) or —$OR^{27}$ (wherein $R^{27}$ is hydrogen, C1–8 alkyl or C2–5 acyl.), $R^{19}$ is
  - (i) hydrogen,
  - (ii) C1–8 alkyl,
  - (iii) phenyl or
  - (iv) C1–8 alkyl substituted with phenyl, $R^{20}$ is
  - (i) hydrogen,
  - (ii) C1–8 alkyl or
  - (iii) —$C(O)R^{28}$ (wherein $R^{28}$ is C1–8 alkyl, C1–8 alkoxy, $Cyc^1$ or $NR^{29}R^{30}$ (wherein $R^{29}$ and $R^{30}$ are each independently, hydrogen or C1–8 alkyl.).),
  - (iv) $Cyc^1$ or
  - (v) C1–8 alkyl substituted with $Cyc^1$ or cyano, $R^{21}$ is
  - (i) hydrogen,
  - (ii) C1–8 alkyl or
  - (iii) $Cyc^1$, $Cyc^1$ is
- (i) C3–15 mono-, bi- or tricyclic carbo ring or
- (ii) 4–18 membered mono-, bi- or tricyclic hetero ring containing 1–4 nitrogen atom(s), 1–2 oxygen atom(s) and/or one sulfur atom, the said carbocyclic ring or heterocyclic ring may be substituted with one or more of (i) C1–8 alkyl, (ii) C2–8 alkenyl, (iii) C2–8 alkynyl, (iv) oxo, (v) cyano, (vi) nitro, (vii) trihalomethyl, (viii) trihalomethoxy, (ix) halogen, (x) diphenylmethyl, (xi) triphenylmethyl, (xii) $Cyc^2$, (xiii) —$OR^{31}$, (xiv) —$SR^{32}$, (xv) —$NR^{33}R^{34}$, (xvi)—$SO_2NR^{35}R^{36}$, (xvii) —$C(O)R^{37}$ or (xviii) C1–8 alkyl, C2–8 alkenyl or C2–8 alkynyl substituted with $Cyc^2$, hydroxy, halogen or —$C(O)$-$Cyc^2$, $R^{31}$ and $R^{32}$ are each independently, hydrogen, C1–8 alkyl or $Cyc^2$, $R^{33}$ is hydrogen or C1–8 alkyl, $R^{34}$ is hydrogen, C1–8 alkyl or —$C(O)$-$Cyc^2$, $R^{35}$ is hydrogen or C1–8 alkyl, $R^{36}$ is hydrogen, C1–8 alkyl or $Cyc^2$, $R^{37}$ is hydrogen, C1–8 alkyl, —$OR^{38}$, —$NR^{39}R^{40}$, $Cyc^2$, or C1–8 alkyl substituted with $Cyc^2$ or —$C(O)$-$Cyc^2$, $R^{38}$, $R^{39}$ and $R^{40}$ are each independently, hydrogen, C1–8 alkyl, or C1–8 alkyl substituted with $Cyc^2$, $Cyc^2$ is
- (i) C3–15 mono-, bi- or tricyclic carbo ring or
- (ii) 4–18 membered mono-, bi- or tricyclic hetero ring containing 1–4 nitrogen atom(s), 1–2 oxygen atom(s) and/or one sulfur atom, the said carbocyclic ring or heterocyclic ring may be substituted with one or more of (i) C1–8 alkyl, (ii) C2–8 alkenyl, (iii) C2–8 alkynyl, (iv) oxo, (v) cyano, (vi) nitro, (vii) trihalomethyl, (viii) trihalomethoxy, (ix) halogen, (x) —$OR^{41}$, (xi) —$SR^{42}$, (xii) —$NR^{43}R^{44}$, (xiii) —$SO_2NR^{45}R^{46}$, (xiv) —$C(O)R^{47}$, (xv) C1–8 alkyl, C2–8 alkenyl or C2–8 alkynyl substituted with hydroxy or halogen or (xvi) phenyl, $R^{41}$, $R^{42}$, $R^{43}$, $R^{44}$, $R^{45}$ and $R^{46}$ are each independently, hydrogen or C1–8 alkyl, $R^{47}$ is hydrogen, C1–8 alkyl or C1–8 alkoxy each $R^2$ of $(R^2)q$ is independently,
- (i) C1–8 alkyl,
- (ii) C2–8 alkenyl,
- (iii) C2–8 alkynyl,
- (iv) —$OR^{48}$,
- (v) —$NR^{49}R^{50}$,
- (vi) —$C(O)R^{51}$,
- (vii) nitro,
- (viii) cyano,
- (ix) halogen or
- (x) C1–8 alkyl, C2–8 alkenyl or C2–8 alkynyl substituted with —$OR^{48}$, —$NR^{49}R^{50}$, —$C(O)R^{51}$, halogen or $Cyc^3$, $R^{48}$ is
  - (i) hydrogen,
  - (ii) C1–8 alkyl,
  - (iii) C2–8 alkenyl,
  - (iv) C2–8 alkynyl,
  - (v) $Cyc^3$ or
  - (vi) C1–8 alkyl, C2–8 alkenyl or C2–8 alkynyl substituted with halogen, —$OR^{52}$, —$NR^{53}R^{54}$, —$C(O)R^{55}$ or $Cyc^3$, $R^{49}$ and $R^{50}$ are each independently, hydrogen, C1–8 alkyl or —$COR^{59}$, $R^{51}$ is hydrogen, C1–8 alkyl, hydroxy, C1–8 alkoxy or —$NR^{60}R^{61}$, R⁵² is hydrogen, C1–8 alkyl, Cyc³, or C1–8 alkyl substituted with Cyc³,
R⁵³ and R⁵⁴ are each independently, hydrogen, C1–8 alkyl, C2–8 alkenyl, C2–8 alkynyl or —C(O)R⁵⁶ (wherein R⁵⁶ is C1–8 alkyl, C1–8 alkoxy, Cyc³, or C1–8 alkyl substituted with Cyc³),
R⁵⁵ is hydroxy, C1–8 alkoxy, or —NR⁵⁷R⁵⁸ (wherein R⁵⁷ and R⁵⁸ are each independently, hydrogen, C1–8 alkyl, or C1–8 alkyl substituted with Cyc³),
R⁵⁹ is C1–8 alkyl or C1–8 alkoxy,
R⁶⁰ and R⁶¹ are each independently, hydrogen or C1–8 alkyl,
Cyc³ is
  (i) C3–15 mono-, bi- or tricyclic carbo ring or
  (ii) 4–18 membered mono-, bi- or tricyclic hetero ring containing 1–4 nitrogen atom(s), 1–2 oxygen atom(s) and/or one sulfur atom,
the said carbocyclic ring or heterocyclic ring may be substituted with one or more of (i) C1–8 alkyl, (ii) C1–8 alkoxy, (iii) nitro, (iv) halogen, (v) cyano, (vi) hydroxy, (vii) benzyloxy, (viii) —NR⁶²R⁶³, (ix) —COOR⁶⁴, (x) trihalomethyl, (xi) trihalomethoxy, (xii) phenyl, (xiii) phenoxy, (xiv) phenylthio, (xv) C1–8 alkyl or C1–8 alkoxy substituted with phenyl, phenoxy, phenylthio, hydroxy, —NR⁶²R⁶³ or —COOR⁶⁴,
R⁶² and R⁶³ are each independently, hydrogen or C1–8 alkyl,
R⁶⁴ is hydrogen or C1–8 alkyl,
with the proviso that when A² is (vi) —NR⁵C(O)—, (x) —NR⁷SO₂—, (xiv) —NR¹³C(O)O— or (xv) —OC(O)O—, then A³ is not hydrogen.],
an N-oxide derivative thereof or a non-toxic salt thereof,
(2) a fused thiophene derivative of the formula (IA)

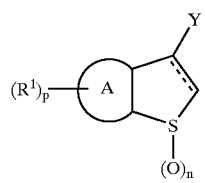
(IA)

[wherein === is a single or double bond,
Y is
  (i)

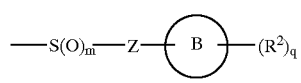

or
  (ii) hydrogen
(with a proviso that when === is a double bond, Y is hydrogen, and when === is a single bond, Y is

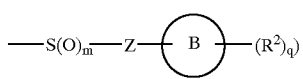

m and n are each independently 0 or an integer of 1–2,
p is 0 or an integer of 1–4,
q is 0 or an integer of 1–5, Z is single bond, C1–8 alkylene, C2–8 alkenylene or C2–8 alkynylene,

is
  (i) enzene ring or
  (ii) 6-membered monocyclic hetero aryl containing 1–2 nitrogen atom(s),

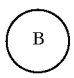

is
  (i) C3–15 mono-, bi- ortricyclic carbo ring or
  (ii) 4–18 membered mono-, bi- or tricyclic hetero ring containing 1–4 nitrogen atom(s), 1–2 oxygen atom(s) and/or one sulfur atom,
each R¹ of (R¹)p is independently,
  (i) C1–8 alkyl,
  (ii) C2–8 alkenyl,
  (iii) C2–8 alkynyl,
  (iv) nitro,
  (v) cyano,
  (vi) halogen,
  (vii) Cyc¹,
  (viii) C1–8 alkyl, C2–8 alkenyl or C2–8 alkynyl substituted with halogen or Cyc¹ or
  (ix) —A¹—A²—A³,
A¹ is
  (i) single bond,
  (ii) C1–8 alkylene,
  (iii) C2–8 alkenylene or
  (iv) C2–8 alkynylene,
A² is
  (i) —O—,
  (ii) —NR³—,
  (iii) —C(O)—,
  (iv) —CH(OH)—,
  (v) —C(O)NR⁴—,
  (vi) —NR⁵C(O)—,
  (vii) —C(O)O—,
  (viii) —OC(O)—,
  (ix) —SO₂NR⁶—,
  (x) —NR⁷SO₂—,
  (xi) —C(O)NR⁹O—,
  (xii) —OC(O)NR¹⁰—,
  (xiii) —NR¹¹C(O)NR¹²—,
  (xiv) —NR¹³C(O)O— or
  (xv) —OC(O)O—
    (wherein R³, R⁴, R⁵, R⁶, R⁷, R⁹, R¹⁰, R¹¹, R¹² and R¹³ are each independently, hydrogen, C1–8 alkyl, phenyl or C1–8 alkyl substituted with Cyc¹, —OR¹⁴ (wherein R¹⁴ is hydrogen or C1–8 alkyl.) or cyano, with the proviso that the linkage of the right side of each group represented by A² binds to A³.

$A^3$ is
- (i) hydrogen,
- (ii) C1–8 alkyl,
- (iii) C2–8 alkenyl,
- (iv) C2–8 alkynyl,
- (v) $Cyc^1$ or
- (vi) C1–8 alkyl, C2–8 alkenyl or C2–8 alkynyl substituted with 1–3 groups selected from the following (a)–(i):
  - (a) halogen,
  - (b) cyano,
  - (c) —$P(O)(R^{15})_2$,
  - (d) —$Si(R^{16})_3$,
  - (e) $Cyc^1$,
  - (f) —$C(O)R^{17}$,
  - (g) —$OR^{18}$,
  - (h) —$NR^{19}R^{20}$,
  - (i) —$SR^{21}$;
    - plural $R^{15}$s are each independently, hydroxy or C1–8 alkoxy,
    - plural $R^{16}$s are each independently C1–8 alkyl,
    - $R^{17}$ is
      - (i) hydrogen,
      - (ii) C1–8 alkyl,
      - (iii) hydroxy,
      - (iv) C1–8 alkoxy,
      - (v) $Cyc^1$ or
      - (vi) –$NR^{22}R^{23}$ (wherein $R^{22}$ is hydrogen, C1–8 alkyl, phenyl or C1–8 alkyl substituted with phenyl, $R^{23}$ is hydrogen, C1–8 alkyl, $Cyc^1$ or C1–8 alkyl substituted with $Cyc^1$ or $NR^{24}R^{25}$ ($R^{24}$ and $R^{25}$ are each independently hydrogen, C1–8 alkyl, phenyl, C1–8 alkyl substituted with phenyl.).),
    - $R^{18}$ is
      - (i) hydrogen,
      - (ii) C1–8 alkyl,
      - (iii) C2–8 alkenyl,
      - (iv) $Cyc^1$ or
      - (v) C1–8 alkyl substituted with $Cyc^1$, $Si(R^{26})_3$ (wherein plural $R^{26}$s are each independently C1–8 alkyl.) or —$OR^{27}$ (wherein $R^{27}$ is hydrogen, C1–8 alkyl or C2–5 acyl.),
    - $R^{19}$ is
      - (i) hydrogen,
      - (ii) C1–8 alkyl,
      - (iii) phenyl or
      - (iv) C1–8 alkyl substituted with phenyl,
    - $R^{20}$ is
      - (i) hydrogen,
      - (ii) C1–8 alkyl or
      - (iii) —$C(O)R^{28}$ (wherein $R^{28}$ is C1–8 alkyl, C1–8 alkoxy, $Cyc^1$ or $NR^{29}R^{30}$ (wherein $R^{29}$ and $R^{30}$ are each independently, hydrogen or C1–8 alkyl.).),
      - (iv) $Cyc^1$ or
      - (v) C1–8 alkyl substituted with $Cyc^1$ or cyano,
    - $R^{21}$ is
      - (i) hydrogen,
      - (ii) C1–8 alkyl or
      - (iii) $Cyc^1$, $Cyc^1$ is
- (i) C3–15 mono-, bi- or tricyclic carbo ring or
- (ii) 4–18 membered mono-, bi- or tricyclic hetero ring containing 1–4 nitrogen atom(s), 1–2 oxygen atom(s) and/or one sulfur atom, the said carbocyclic ring or heterocyclic ring may be substituted with one or more of (i) C1–8 alkyl, (ii) C2–8 alkenyl, (iii) C2–8 alkynyl, (iv) oxo, (v) cyano, (vi) nitro, (vii) trihalomethyl, (viii) trihalomethoxy, (ix) halogen, (x) diphenylmethyl, (xi) triphenylmethyl, (xii) $Cyc^2$, (xiii) —$OR^{31}$, (xiv) —$SR^{32}$, (xv) —$NR^{33}R^{34}$, (xvi)—$SO_2NR^{35}R^{36}$, (xvii) —$C(O)R^{37}$ or (xviii) C1–8 alkyl, C2–8 alkenyl or C2–8 alkynyl substituted with $Cyc^2$, hydroxy, halogen or —$C(O)$-$Cyc^2$, $R^{31}$ and $R^{32}$ are each independently, hydrogen, C1–8 alkyl or $Cyc^2$, $R^{33}$ is hydrogen or C1–8 alkyl, $R^{34}$ is hydrogen, C1–8 alkyl or —$C(O)$-$Cyc^2$, $R^{35}$ is hydrogen or C1–8 alkyl, $R^{36}$ is hydrogen, C1–8 alkyl or $Cyc^2$, $R^{37}$ is hydrogen, C1–8 alkyl, —$OR^{38}$, —$NR^{39}R^{40}$, $Cyc^2$, or C1–8 alkyl substituted with $Cyc^2$ or —$C(O)$-$Cyc^2$, $R^{38}$, $R^{39}$ and $R^{40}$ are each independently, hydrogen, C1–8 alkyl, or C1–8 alkyl substituted with $Cyc^2$, $Cyc^2$ is
- (i) C3–15 mono-, bi- or tricyclic carbo ring or
- (ii) 4–18 membered mono-, bi- or tricyclic hetero ring containing 1–4 nitrogen atom(s), 1–2 oxygen atom(s) and/or one sulfur atom, the said carbocyclic ring or heterocyclic ring may be substituted with one or more of (i) C1–8 alkyl, (ii) C2–8 alkenyl, (iii) C2–8 alkynyl, (iv) oxo, (v) cyano, (vi) nitro, (vii) trihalomethyl, (viii) trihalomethoxy, (ix) halogen, (x) —$OR^{41}$, (xi) —$SR^{42}$, (xii) —$NR^{43}R^{44}$, (xiii) —$SO_2NR^{45}R^{46}$, (xiv) —$C(O)R^{47}$, (xv) C1–8 alkyl, C2–8 alkenyl or C2–8 alkynyl substituted with hydroxy or halogen or (xvi) phenyl, $R^4$, $R^{42}$, $R^{43}$, $R^{44}$, $R^{45}$ and $R^{46}$ are each independently, hydrogen or C1–8 alkyl, $R^{47}$ is hydrogen, C1–8 alkyl or C1–8 alkoxy each $R^2$ of $(R^2)q$ is independently,
- (i) C1–8 alkyl,
- (ii) C2–8 alkenyl,
- (iii) C2–8 alkynyl,
- (iv) —$OR^{48}$,
- (v) —$NR^{49}R^{50}$,
- (vi) —$C(O)R^{51}$,
- (vii) nitro,
- (viii) cyano,
- (ix) halogen or
- (x) C1–8 alkyl, C2–8 alkenyl or C2–8 alkynyl substituted with —$OR^{48}$, —$NR^{49}R^{50}$, —$C(O)R^{51}$, halogen or $Cyc^3$, $R^{48}$ is
- (i) hydrogen,
- (ii) C1–8 alkyl,
- (iii) C2–8 alkenyl,
- (iv) C2–8 alkynyl,
- (v) $Cyc^3$ or
- (vi) C1–8 alkyl, C2–8 alkenyl or C2–8 alkynyl substituted with halogen, —$OR^{52}$, —$NR^{53}R^{54}$, —$C(O)R^{55}$ or $Cyc^3$, $R^{49}$ and $R^{50}$ are each independently, hydrogen, C1–8 alkyl or —$COR^{59}$, $R^{51}$ is hydrogen, C1–8 alkyl, hydroxy, C1–8 alkoxy or —$NR^{60}R^{61}$, $R^{52}$ is hydrogen, C1–8 alkyl, $Cyc^3$, or C1–8 alkyl substituted with $Cyc^3$, $R^{53}$ and $R^{54}$ are each independently, hydrogen, C1–8 alkyl, C2–8 alkenyl, C2–8 alkynyl or —$C(O)R^{56}$ (wherein $R^{56}$ is C1–8 alkyl, C1–8 alkoxy, $Cyc^3$, or C1–8 alkyl substituted with $Cyc^3$), $R^{55}$ is hydroxy, C1–8 alkoxy, or —$NR^{57}R^{58}$ (wherein $R^{57}$ and $R^{58}$ are each independently, hydrogen, C1–8 alkyl, or C1–8 alkyl substituted with $Cyc^3$), $R^{59}$ is C1–8 alkyl or C1–8 alkoxy, $R^{60}$ and $R^{61}$ are each independently, hydrogen or C1–8 alkyl, $Cyc^3$ is
(i) C3–15 mono-, bi- or tricyclic carbo ring or
(ii) 4–18 membered mono-, bi- or tricyclic hetero ring containing 1–4 nitrogen atom(s), 1–2 oxygen atom(s) and/or one sulfur atom, the said carbocyclic ring or heterocyclic ring may be substituted with one or more of (i) C1–8 alkyl, (ii) C1–8 alkoxy, (iii) nitro, (iv) halogen, (v) cyano, (vi) hydroxy, (vii) benzyloxy, (viii) —$NR^{62}R^{63}$, (ix) —$COOR^{64}$, (x) trihalomethyl, (xi) trihalomethoxy, (xii) phenyl, (xiii) phenoxy, (xiv) phenylthio, (xv) C1–8 alkyl or C1–8 alkoxy substituted with phenyl, phenoxy, phenylthio, hydroxy, —$NR^{62}R^{63}$ or —$COOR^{64}$, $R^{62}$ and $R^{63}$ are each independently, hydrogen or C1–8 alkyl, $R^{64}$ is hydrogen or C1–8 alkyl, with the proviso that when (1) when $A^2$ is (vi) —$NR^5C(O)$—, (x) —$NR^7SO_2$—, (xiv) —$NR^{13}C(O)O$— or (xv) —$OC(O)O$—, then $A^3$ is not hydrogen, (2) when === is a double bond and Y is hydrogen, then n is 1 or 2, (3) when === is a single bond, Y is

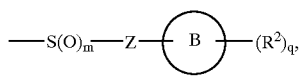

n is 2, m is 0 or 2, p is 0 or an integer of 1–4, ring A and ring B are benzene ring, $R^1$ is C1–8 alkyl, C1–8 alkoxy, halogen, carboxy, nitro or C1–8 alkyl substituted with halogen, then q is not 0, (4) when === is a single bond, Y is

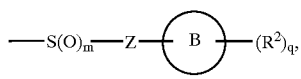

n is 2, m is 0 or 2, p is 0 or an integer of 1–4, ring A and ring B are benzene ring, $R^1$ is C1–8 alkyl, C1–8 alkoxy, halogen, carboxy, nitro or C1–8 alkyl substituted with halogen, and q is an integer of 1–5, then $R^2$ is not C1–8 alkyl, C1–8 alkoxy, halogen, carboxy, nitro or C1–8 alkyl substituted with halogen, (5) when === is a double bond, Y is hydrogen, n is 2, p is 1 and ring A is benzene ring, then $R^1$ is not halogen, C1–8 alkyl, phenylsulfonylamino, 2-methylphenylsulfonylamino, 3-methylphenylsulfonylamino, 4-methylphenylsulfonylamino, hydroxy, C1–8 alkoxy, nitro, or C1–8 alkoxy substituted with carboxy, hydroxy, C1–8 alkoxycarbonyl or hydroxyaminocarbonyl, (6) when === is a double bond, Y is hydrogen, n is 2, p is 2 and ring A is benzene ring and one $R^1$ is phenylsulfonylamino, 2-methylphenylsulfonylamino, 3-methylphenylsulfonylamino or 4-methylphenylsulfonylamino, then the other $R^1$ is not C1–8 alkyl, (7) when === is a double bond, Y is hydrogen, n is 2, p is 2–3, ring A is benzene ring, one $R^1$ is hydroxy, C1–8 alkoxy, or C1–8 alkoxy substituted with carboxy, hydroxy, C1–8 alkoxycarbonyl or hydroxyaminocarbonyl, then the other $R^1$ is neither halogen nor C1–8 alkyl, (8) when === is a double bond, Y is hydrogen, n is 2, p is 3–4 and ring A is benzene ring, then two or three $R^1$ are not t-butyl at the same time, and (9) the following compounds (1)–(32) are excluded:
(1) 3-(thiophen-2-yl)thio-2,3-dihydro-1,1-dioxidebenzo[b]thiophene,
(2) 6-nitro-3-(thiophen-2-yl)thio-2,3-dihydro-1,1-dioxidebenzo[b]thiophene,
(3) 3-(thiophen-2-yl)sulfonyl-2,3-dihydro-1,1-dioxidebenzo[b]thiophene,
(4) 4,5-dimethyl-1,1-dioxidebenzo[b]thiophene,
(5) 4,6-dimethyl-1,1-dioxidebenzo[b]thiophene,
(6) 4,7-dimethyl-1,1-dioxidebenzo[b]thiophene,
(7) 5,6-dimethyl-1,1-dioxidebenzo[b]thiophene,
(8) 5,7-dimethyl-1,1-dioxidebenzo[b]thiophene,
(9) 6,7-dimethyl-1,1-dioxidebenzo[b]thiophene,
(10) 4-carboxymethyl-1,1-dioxidebenzo[b]thiophene,
(11) 6-(2,2-bis(ethoxycarbonyl)ethenyl)amino-1,1-ioxidebenzo[b]thiophene,
(12) 4-methylaminocarbonyloxy-1,1-dioxidebenzo[b]thiophene,
(13) 5-(2-(N-(5-methoxy-1,2,3,4-tetrahydronaphthalen-1-ylmethyl)-N-methylamino)ethyl)-1,1-dioxidebenzo[b]thiophene,
(14) 5-(2-hydroxyethyl)-1,1-dioxidebenzo[b]thiophene,
(15) 5-bromo-7-methyl-1,1-dioxidebenzo[b]thiophene,
(16) 7-bromo-5-methyl-1,1-dioxidebenzo[b]thiophene,
(17) 5-bromo-6-methyl-1,1-dioxidebenzo[b]thiophene,
(18) 5-bromo-4-methyl-1,1-dioxidebenzo[b]thiophene,
(19) 6-bromo-5-methyl-1,1-dioxidebenzo[b]thiophene,
(20) 4-bromo-5-methyl-1,1-dioxidebenzo[b]thiophene,
(21) 6-amino-1,1-dioxidebenzo[b]thiophene,
(22) 6-acetylamino-1,1-dioxidebenzo[b]thiophene,
(23) 6-(4-diethylaminophenyl)-1,1-dioxidebenzo[b]thiophene,
(24) 1,1-dioxidethieno[2,3-b]pyridine,
(25) 1,1-dioxidethieno[3,2-b]pyridine,
(26) 1,1-dioxidethieno[2,3-c]pyridine,
(27) 5-amino-1,1-dioxidebenzo[b]thiophene,
(28) 5-(3-methyl-5-oxo-4,5-dihydropyrazol-1-yl)-1,1-dioxidebenzo[b]thiophene,
(29) 4-(2-(1,1-dioxidebenzo[b]thiophen-3-yl)ethyl)-1,1-dioxidebenzo[b]thiophene,
(30) 7-methyl-1,1-dioxidethieno[2,3-c]pyridine,
(31) 1,1-dioxidebenzo[b]thiophene or
(32) 4-(4-methoxyphenyl)-1,1-dioxidethieno[3,2-c]pyridine.], an N-oxide derivative thereof or a non-toxic salt thereof, (3) a method for preparation of a fused thiophene derivative of the formula (IA), an N-oxide derivative thereof or a non-toxic salt thereof and (4) a method for preparation of a compound of the formula (XI)

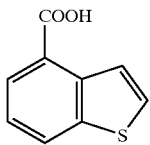
(XI)

which is characterized by cyanization of a compound of the formula (XII)

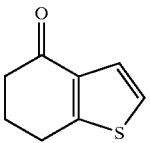
(XII)

to obtain a compound of the formula (XIII)

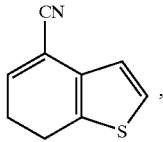
(XIII), then by subjecting to dehydration of the said compound of the formula (XIII) to obtain a compound of the formula (XIV)

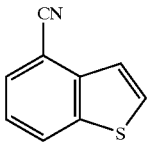
(XIV)

and then by subjecting to hydrolysis of the said compound of the formula (XIV).

DETAILED EXPLANATION OF THE INVENTION

Unless otherwise specified, all isomers are included in the present invention. For example, alkyl, alkenyl, alkynyl, alkoxy, alkylthio, alkylene, alkenylene and alkynylene group include straight or branched ones. In addition, isomers on double bond, ring, fused ring (E-, Z-, cis-, trans-isomer), isomers generated from asymmetric carbon atom(s) (R-, S-, α-, βisomer, enantiomer, diastereomer), optically active isomers (D-, L-, d-, I-isomer), polar compounds generated by chromatographic separation (more polar compound, less polar compound), equilibrium compounds, mixtures thereof at voluntary ratios and racemic mixtures are also included in the present invention.

In the present invention, an N-oxide derivative of a compound of the formula (I) and (IA) means a compound wherein nitrogen atom(s) in a compound containing nitrogen atom(s) of the formula (I) and (IA) is (are) oxidized.

In the present invention, C1–8 alkyl means methyl, ethyl, propyl, butyl, pentyl, hexyl, heptyl, octyl and the isomers thereof.

C2–8 alkenyl means vinyl, propenyl, butenyl, pentenyl, hexenyl, heptenyl, octenyl, butadienyl, pentadienyl, hexadienyl, heptadienyl, octadienyl, hexatrienyl, heptatrienyl, octatrienyl and the isomers thereof.

C2–8 alkynyl means ethynyl, propynyl, butynyl, pentynyl, hexynyl, heptynyl, octynyl and the isomers thereof.

C1–8 alkylene means methylene, ethylene, trimethylene, tetramethylene, pentamethylene, hexamethylene, heptamethylene, octamethylene and the isomers thereof.

C2–8 alkenylene means ethenylene, propenylene, butenylene, pentenylene, hexenylene, heptenylene, octenylene and the isomers thereof.

C2–8 alkynylene means ethynylene, propynylene, butynylene, pentynylene, hexynylene, heptynylene, octynylene and the isomers thereof.

Halogen means chloride, bromide, fluoride and iodide.

C1–8 alkoxy means methoxy, ethoxy, propoxy, butoxy, pentyloxy, hexyloxy, heptyloxy, octyloxy and the isomers thereof.

Trihalomethyl means methyl substituted with three atoms selected from group consisting of chloride, bromide, fluoride and iodide atom.

Trihalomethoxyl means methoxyl substituted with three atoms selected from group consisting of chloride, bromide, fluoride and iodide atom.

C2~5 acyl means acetyl, propionyl, butyryl, valeryl and isomers thereof.

6Membered monocyclic hetero aryl containing 1–2 nitrogen atom(s) includes, for example, pyridine, pyridine-N-oxide, pyrazine, pyrazine-N-monoxide, pyrazine-N-dioxide, pyrimizine, pyrimizine-N-monoxide, pyrimizine-N-dioxide, pyridazine, pyridazine-N-monoxide, pyridazine-N-dioxide ring etc.

C3–15 Mono-, bi- or tricyclic carbo ring includes, for example, cyclopropane, cyclobutane, cyclopentane, cyclohexane, cycloheptane, cyclopenten, cyclohexen, cyclopentadien, cyclohexadien, benzene, penthalene, indene, naphthalene, azulene, florene, phenanthrene, anthracene, acenaphthylene, biphenylene, perhydropentalene, perhydroindene, dihydronaphthalene, tetrahydronaphthalene, perhydronaphthalene, perhydroazulene, perhydrofluorene, perhydrophenanthrene, perhydroanthracene, perhydroacenaphthylene, perhydrobiphenylene ring etc.

4–18 Membered mono-, bi- or tricyclic hetero ring containing 1–4 nitrogen atom(s), 1–2 oxygen atom(s) and/or one sulfur atom includes 4–18 membered mono-, bi- or tricyclic hetero aryl containing 1–4 nitrogen atom(s), 1–2 oxygen atom(s) and/or one sulfur atom or corresponding hetero ring in which ring is saturated partially or fully.

The said 4–18 membered mono-, bi- or tricyclic hetero aryl containing 1–4 nitrogen atom(s), 1–2 oxygen atom(s) and/or one sulfur atom includes, for example, pyrrole, pyrrole-N-oxide, imidazole, triazole, tetrazole, pyrazole, pyridine, pyridine-N-oxide, pyrazine, pyrazine-N-monoxide, pyrazine-N-dioxide, pyrimizine, pyrimizine-N-monoxide, pyrimizine-N-dioxide, pyridazine, pyridazine-N-monoxide, pyridazine-N-dioxide, azepine, diazepine, furan, pyran, oxepine, oxazepine, thiophene, thiain (thiopyran), thiepine, oxazole, isoxazole, thiazole, isothiazole, oxadiazole, oxazine, oxadiazine, oxazepine, oxadiazepine, thiadiazole, thiazine, thiadiazine, thiazepine, thiadiazepine, indole, isoindole, benzofuran, isobenzofuran, benzothiophene, isobenzothiophene, indazole, quinoline, quinoline-N-oxide, isoquinoline, isoquinoline-N-oxide, phthalazine, naphthyridine, naphthyridine-N-monoxide, naphthyridine-N-dioxide, quinoxaline, quinoxaline-N-monoxide, quinoxaline-N-dioxide, quinazoline, quinazoline-N-monoxide, quinazoline-N-dioxide, cinnoline, benzoxazole, benzothiazole, benzoimidazole, carbazole, acridine ring etc.

The said 4–18 membered mono-, bi- or tricyclic hetero ring containing 1–4 nitrogen atom(s), 1–2 oxygen atom(s) and/or one sulfur atom in which ring is saturated partially or fully includes, for example, pyrroline, pyrrolidine, pyrrolidine-N-oxide, imidazoline, imidazolidine, triazoline, triazolidine, tetrazoline, tetrazolidine, dihydropyridine, dihydropyridine-N-oxide, dihydropyrazine, dihydropyrazine-N-monoxide, dihydropyrazine-N-dioxide, dihydropyrimizine, dihydropyrimizine-N-monoxide, dihydropyrimizine-N-dioxide, dihydropyridazine, dihydropyridazine-N-monoxide, dihydropyridazine-N-dioxide, piperidine, piperidine-N-oxide, piperazine, piperazine-N-monoxide, piperazine-N-dioxide, tetrahydropyrimizine, tetrahydropyrimizine-N-monoxide, tetrahydropyrimizine-N-dioxide, tetrahydropyridazine, tetrahydropyridazine-N-monoxide, tetrahydropyridazine-N-dioxide, dihydrofuran, tetrahydrofuran, dihydropyran, tetrahydropyran, dihydrothiophene, tetrahydrothiophene, dihydrothiain (dihydrothiopyran), tetrahydrothiain (tetrahydrothiopyran), dihydroxazole, tetrahydroxazole, dihydroisoxazole, tetrahydroisoxazole, dihydrothiazole, tetrahydrothiazole, dihydroisothiazole, tetrahydroisothiazole, morpholine, morpholine-N-oxide, thiomorpholine, thiomorpholine-N-oxide, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, dihydroquinoline-N-oxide, tetrahydroquinoline, tetrahydroquinoline-N-oxide, perhydroquinoline, perhydroquinoline-N-oxide, dihydroisoquinoline, dihydroisoquinoline-N-oxide, tetrahydroisoquinoline, tetrahydroisoquinoline-N-oxide, perhydroisoquinoline, perhydroisoquinoline-N-oxide, dihydrophthalazine, tetrahydrophthalazine, perhydrophthalazine, dihydronaphthyridine, dihydronaphthyridine-N-monoxide, dihydronaphthyridine-N-dioxide, tetrahydronaphthyridine, tetrahydronaphthyridine-N-monoxide, tetrahydronaphthyridine-N-dioxide, perhydronaphthyridine, perhydronaphthyridine-N-monoxide, perhydronaphthyridine-N-dioxide, dihydroquinoxaline, dihydroquinoxaline-N-monoxide, dihydroquinoxaline-N-dioxide, tetrahydroquinoxaline, tetrahydroquinoxaline-N-monoxide, tetrahydroquinoxaline-N-dioxide, perhydroquinoxaline, perhydroquinoxaline-N-monoxide, perhydroquinoxaline-N-dioxide, dihydroquinazoline, dihydroquinazoline-N-monoxide dihydroquinazoline-N-dioxide, tetrahydroquinazoline, tetrahydroquinazoline-N-monoxide, tetrahydroquinazoline-N-dioxide, perhydroquinazoline, perhydroquinazoline-N-monoxide, perhydroquinazoline-N-dioxide, dihydrocinnoline, tetrahydrocinnoline, perhydrocinnoline, dihydrobenzoxazole, perhydrobenzoxazole, dihydrobenzothiazole, perhydrobenzothiazole, dihydrobenzoimidazole, perhydrobenzoimidazole, benzoxazepine, benzoxadiazepine, benzothiazepine, benzothiadiazepine, benzoazepine, benzodiazepine, indroxoazepine, indrotetrahydroxazepine, indroxadiazepine, indrotetrahydroxadiazepine, indrothiazepine, indrotetrahydrothiazepine, indrothiadiazepine, indrotetrahydrothiadiazepine, indroazepine, indrotetrahydroazepine, indrodiazepine, indrotetrahydrodiazepine, benzofurazane, benzothiadiazole, benzotriazole, camphar, imidazothiazole, dihydrocarbazole, tetrahydrocarbazole, perhydrocarbazole, dihydroacridine, tetrahydroacridine, perhydroacridine, 1,3-dioxaindan, 1,4-dioxoindan ring etc.

In the present invention, m is, preferably, 0 or 2 and most preferably, 2.

n is, preferably, 0 or 2 and most preferably, 2.

p is, preferably, 1 or 2 and most preferably, 2.

q is, preferably, 0 or 1.

Z is, preferably, single bond or C1–8 alkylene, and most preferably, single bond.

is, preferably, pyridine or benzene ring, and most preferably, benzene ring.

is, preferably, C5–10 mono- or bicyclic carbo ring or 5–10 membered mono- or bicyclic hetero ring containing 1–3 nitrogen atom(s), one oxygen atom and/or one sulfur atom, more preferably, benzene, cyclohexane, thiophene, furan, pyridine, pyrimizine, imidazole ring, and most preferably, benzene or thiophene ring.

$R^1$ is, preferably, C1–8 alkyl, nitro, cyano, halogen, $Cyc^1$ or C1–8 alkyl substituted with halogen or $Cyc^1$, or $A^1-A^2-A^3$, and most preferably, C1–8 alkyl substituted with $Cyc^1$ or $A^1-A^2-A^3$.

$A^1$ is, preferably, single bond, C1–8 alkylene, C2–8 alkenylene, and most preferably, single bond or C1–8 alkylene.

$A^2$ is, preferably, —O—, —$NR^3$—, —C(O)—, —C(O)$NR^4$—, —$NR^5$C(O)—, —C(O)O—, —$NR^{13}$C(O)O—, and most preferably, O—, —$NR^3$—, —C(O)—, —C(O)$NR^4$—, —$NR^5$C(O)—.

$A^3$ is, preferably, C1–8 alkyl, $Cyc^1$, or C1–8 alkyl or C2–8 alkenyl substituted with $Cyc^1$, —C(O)$R^{17}$, —$NR^{19}R^{20}$ or —$OR^{18}$, and most preferably, C1–8 alkyl substituted with $Cyc^1$ or $NR^{19}R^{20}$.

$Cyc^1$ is, preferably, C5–10 mono- or bicyclic carbo ring or 5–10 membered mono- or bicyclic hetero ring containing 1–3 nitrogen atom(s), one oxygen atom and/or one sulfur atom, and more preferably, C5–10 monocyclic carbo ring or 5–10 membered monocyclic hetero ring containing 1–2 nitrogen atom(s) and/or one oxygen atom, and most preferably, benzene, piperidine, piperazine, pyrrolidine, pyridine or morpholine ring.

$R^{19}$, $R^{20}$ is, preferably, hydrogen or C1–8 alkyl, and most preferably, methyl, ethyl, propyl or isopropyl.

[Salts]

In the present invention, non-toxic salts include all such salts, for example, ordinal salts, acid-addition salts and hydrate salts.

The compounds of the present invention of the formula (I) may b converted into the corresponding salts by known method. Non toxic and water-soluble salts are preferable. Suitable salts include the salts of alkalimetal (sodium, potassium etc.), alkaline-earth metal (calcium, magnesium etc.), ammonium salts, salts of organic amine which is pharmaceutically permitted (tetramethyl ammonium, triethylamine, methylamine, dimethylamine, cyclopentylamine, benzylamine, phenetylamine, piperidine, monoethanolamine, diethanolamine, tris(hydroxymethyl) amine, lysine, arginine, N-methyl-D-gulcamine etc.).

The compounds of the present invention of the formula (I) may be converted into the corresponding acid-addition salts by known method. Non toxic and water-soluble acid-addition are preferable. Suitable acid-addition salts include the salts with inorganic acids such as hydrochloric acid, hydrobromic acid, sulfonic acid, phosphonic acid, nitric acid and the salts with organic acids such as acetic acid, trifluoroacetic acid, lactic acid, tartaric acid, oxalic acid, fumaric acid, maleic acid, citric acid, benzoic acid, methanesulfonic acid, ethanesulfonic acid, benzenesulfonic acid, toluenesulfonic acid, isethionic acid, glucuronic acid and gluconic acid.

The compounds of the present invention of the formula (I) or salts thereof may be converted into a corresponding hydrate by known methods.

In the compounds of the formula (I), preferred compounds are as follows: the compound of the formula (I-A)

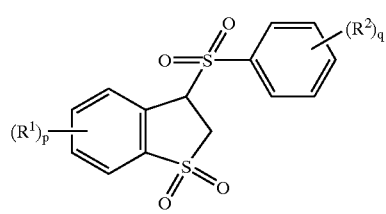
(I-A)

(wherein all the symbols are the same meanings as hereinbefore described.), the compound of the formula (I-B)

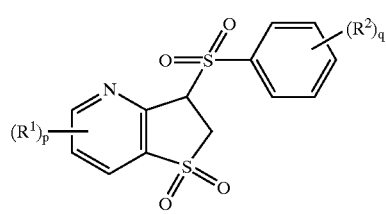
(I-B)

(wherein all the symbols are the same meanings as hereinbefore described.), the compound of the formula (I-C)

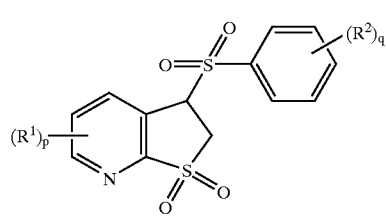
(I-C)

(wherein all the symbols are the same meanings as hereinbefore described.), the compound of the formula (I-D)

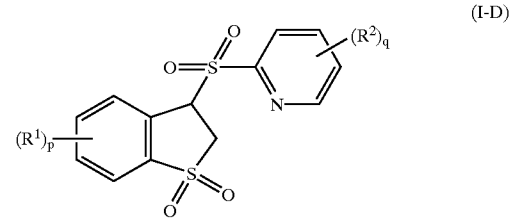
(I-D)

(wherein all the symbols are the same meanings as hereinbefore described.), the compound of the formula (I-E)

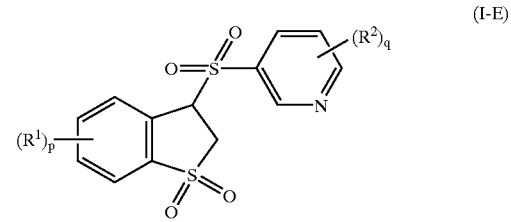
(I-E)

(wherein all the symbols are the same meanings as hereinbefore described.), the compound of the formula (I-F)

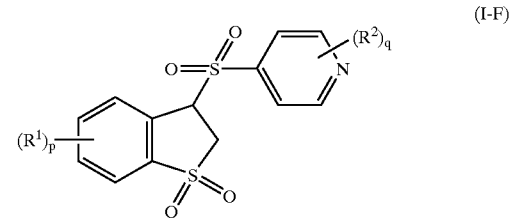
(I-F)

(wherein all the symbols are the same meanings as hereinbefore described.), the compound of the formula (I-G)

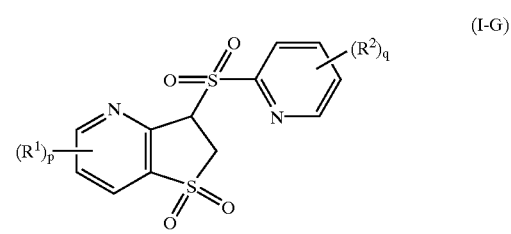
(I-G)

(wherein all the symbols are the same meanings as hereinbefore described.), the compound of the formula (I-H)

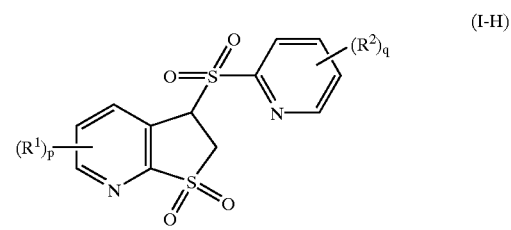
(I-H)

(wherein all the symbols are the same meanings as hereinbefore described.), the compound of the formula (I-J)

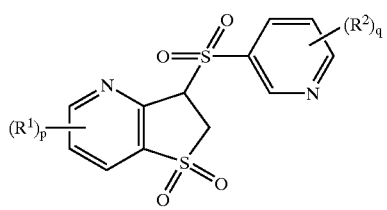
(I-J)

(wherein all the symbols are the same meanings as hereinbefore described.), the compound of the formula (I-K)

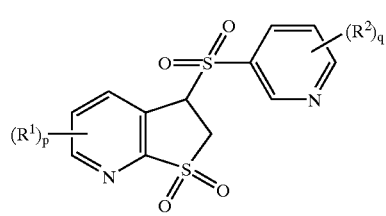
(I-K)

(wherein all the symbols are the same meanings as hereinbefore described.), the compound of the formula (I-L)

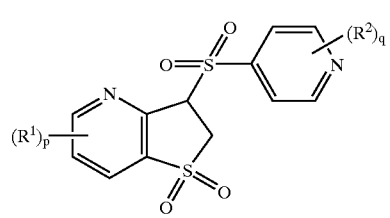
(I-L)

(wherein all the symbols are the same meanings as hereinbefore described.), the compound of the formula (I-M)

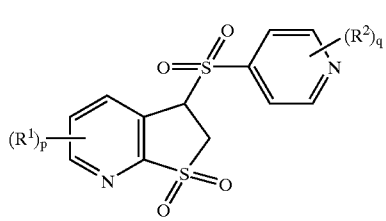
(I-M)

(wherein all the symbols are the same meanings as hereinbefore described.), the compound of the formula (I-N)

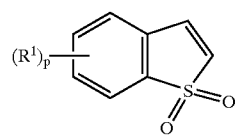
(I-N)

(wherein all the symbols are the same meanings as hereinbefore described.), the compound of the formula (I-O)

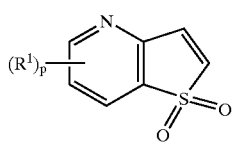
(I-O)

(wherein all the symbols are the same meanings as hereinbefore described.), or the compound of the formula (I-P)

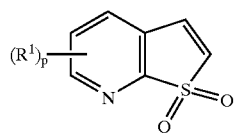
(I-P)

(wherein all the symbols are the same meanings as hereinbefore described.).

In the compounds of the formula (I-A), the compound of the formula (I-A')

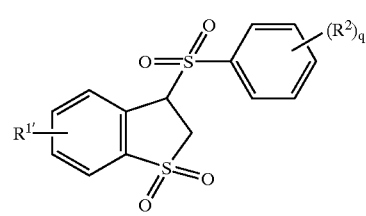
(I-A')

(wherein, $R^{1'}$ is C1–8 alkyl substituted with $Cyc^1$, or $$-A^{1'}-A^{2'}-A^3$$

(wherein, $A^{1'}$ is single bond or C1–8 alkylene, $A^{2'}$ is —O—, —NR$^3$—, —C(O)—, —C(O)NR$^4$— or NR$^5$C(O)— and the other symbols are the same meanings as hereinbefore described.) and the other symbols are the same meanings as hereinbefore described.) is most preferable.

In the compound of the formula (I-N), the compound of the formula (I-N')

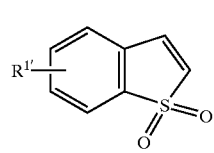
(I-N')

(wherein all the symbols are the same meanings as hereinbefore described.) is most preferable.

The following compounds (1)–(4) are known and marketed ones, but their activities as inhibitor of producing IL-6 and/or IL-12 have not been known at all. The compounds (1)–(4) and non-toxic salts thereof are also preferable ones used in the present invention.

For example,

Compound (1): 3-(thiophene-2-yl)sulfonyl-2,3-dihydro-1,1-dioxidebenzo[b]thiophene (Maybridge, Catalog No. KM 08156):

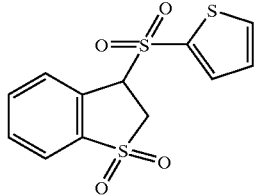

Compound (2): 6-nitro-3-(thiophene-2-yl)thio-2,3-dihydro-1,1-dioxidebenzo[b]thiophene (Maybridge, Catalog No. KM 08165):

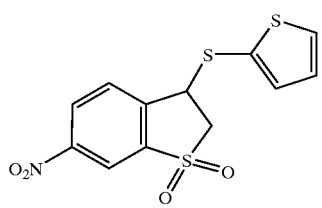

Compound (3): 3-(thiophene-2-yl)thio-2,3-dihydro-1,1-dioxidebenzo[b]thiophene (Maybridge, Catalog No. KM 08138):

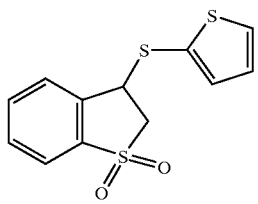

Compound (4): 3-phenylsulfonyl-2,3-dihydro-1,1-dioxidebenzo[b]thiophene (Maybridge, Catalog No. KM 08140):

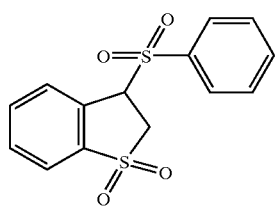

More preferable compounds are the following known compounds and the compounds shown in the Tables 1 to 78 and described in Examples and non-toxic salts thereof.

In the following tables, 3-Py is pyridin-3-yl, Me is methyl, Et is ethyl, n-Pr is normalpropyl, i-Pr is isopropyl, t-Bu is t-butyl and the other symbols are the same meanings as hereinbefore described.

TABLE 1

(I-A)

| No. | p | position | R¹ |
|---|---|---|---|
| 1 | 1 | 4 | —O—(CH$_2$)$_2$-(3-Py) |
| 2 | 1 | 5 | —O—(CH$_2$)$_2$-(3-Py) |
| 3 | 1 | 6 | —O—(CH$_2$)$_2$-(3-Py) |
| 4 | 1 | 7 | —O—(CH$_2$)$_2$-(3-Py) |
| 5 | 1 | 4 | —O—(CH$_2$)$_2$—N(CH$_3$)$_2$ |
| 6 | 1 | 5 | —O—(CH$_2$)$_2$—N(CH$_3$)$_2$ |
| 7 | 1 | 6 | —O—(CH$_2$)$_2$—N(CH$_3$)$_2$ |
| 8 | 1 | 7 | —O—(CH$_2$)$_2$—N(CH$_3$)$_2$ |
| 9 | 0 | — | — |
| 10 | 0 | — | — |
| 11 | 0 | — | — |
| 12 | 0 | — | — |
| 13 | 0 | — | — |
| 14 | 0 | — | — |
| 15 | 0 | — | — |
| 16 | 0 | — | — |
| 17 | 1 | 4 | —O—(CH$_2$)$_2$-(3-Py) |
| 18 | 1 | 5 | —O—(CH$_2$)$_2$-(3-Py) |
| 19 | 1 | 6 | —O—(CH$_2$)$_2$-(3-Py) |
| 20 | 1 | 7 | —O—(CH$_2$)$_2$-(3-Py) |

| No. | q | position | R² |
|---|---|---|---|
| 1 | 0 | — | — |
| 2 | 0 | — | — |
| 3 | 0 | — | — |
| 4 | 0 | — | — |
| 5 | 0 | — | — |
| 6 | 0 | — | — |
| 7 | 0 | — | — |
| 8 | 0 | — | — |
| 9 | 1 | 2' | —O—(CH$_2$)$_2$-(3-Py) |
| 10 | 1 | 3' | —O—(CH$_2$)$_2$-(3-Py) |
| 11 | 1 | 4' | —O—(CH$_2$)$_2$-(3-Py) |
| 12 | 2 | 3', 5' | —O—(CH$_2$)$_2$-(3-Py) |
| 13 | 1 | 2' | —O—(CH$_2$)$_2$—N(CH$_3$)$_2$ |
| 14 | 1 | 3' | —O—(CH$_2$)$_2$—N(CH$_3$)$_2$ |
| 15 | 1 | 4' | —O—(CH$_2$)$_2$—N(CH$_3$)$_2$ |
| 16 | 2 | 3', 5' | —O—(CH$_2$)$_2$—N(CH$_3$)$_2$ |
| 17 | 1 | 2' | —O—(CH$_2$)$_2$-(3-Py) |
| 18 | 1 | 3' | —O—(CH$_2$)$_2$-(3-Py) |
| 19 | 1 | 4' | —O—(CH$_2$)$_2$-(3-Py) |
| 20 | 2 | 3', 5' | —O—(CH$_2$)$_2$-(3-Py) |

TABLE 2

(I-B)

| No. | p | position | R¹ |
|---|---|---|---|
| 1 | 1 | 5 | —O—(CH$_2$)$_2$-(3-Py) |
| 2 | 1 | 6 | —O—(CH$_2$)$_2$-(3-Py) |

TABLE 2-continued

| | | | |
|---|---|---|---|
| 3 | 1 | 7 | —O—(CH$_2$)$_2$-(3-Py) |
| 4 | 2 | 6, 7 | —O—(CH$_2$)$_2$-(3-Py) |
| 5 | 1 | 5 | —O—(CH$_2$)$_2$—N(CH$_3$)$_2$ |
| 6 | 1 | 6 | —O—(CH$_2$)$_2$—N(CH$_3$)$_2$ |
| 7 | 1 | 7 | —O—(CH$_2$)$_2$—N(CH$_3$)$_2$ |
| 8 | 2 | 6, 7 | —O—(CH$_2$)$_2$—N(CH$_3$)$_2$ |
| 9 | 0 | — | — |
| 10 | 0 | — | — |
| 11 | 0 | — | — |
| 12 | 0 | — | — |
| 13 | 0 | — | — |
| 14 | 0 | — | — |
| 15 | 0 | — | — |
| 16 | 0 | — | — |
| 17 | 1 | 5 | —O—(CH$_2$)$_2$-(3-Py) |
| 18 | 1 | 6 | —O—(CH$_2$)$_2$-(3-Py) |
| 19 | 1 | 7 | —O—(CH$_2$)$_2$-(3-Py) |
| 20 | 2 | 6, 7 | —O—(CH$_2$)$_2$-(3-Py) |

TABLE 2-continued

| No. | q | position | R$^2$ |
|---|---|---|---|
| 1 | 0 | — | — |
| 2 | 0 | — | — |
| 3 | 0 | — | — |
| 4 | 0 | — | — |
| 5 | 0 | — | — |
| 6 | 0 | — | — |
| 7 | 0 | — | — |
| 8 | 0 | — | — |
| 9 | 1 | 2' | —O—(CH$_2$)$_2$-(3-Py) |
| 10 | 1 | 3' | —O—(CH$_2$)$_2$-(3-Py) |
| 11 | 1 | 4' | —O—(CH$_2$)$_2$-(3-Py) |
| 12 | 2 | 3', 5' | —O—(CH$_2$)$_2$-(3-Py) |
| 13 | 1 | 2' | —O—(CH$_2$)$_2$—N(CH$_3$)$_2$ |
| 14 | 1 | 3' | —O—(CH$_2$)$_2$—N(CH$_3$)$_2$ |
| 15 | 1 | 4' | —O—(CH$_2$)$_2$—N(CH$_3$)$_2$ |
| 16 | 2 | 3', 5' | —O—(CH$_2$)$_2$—N(CH$_3$)$_2$ |
| 17 | 1 | 2' | —O—(CH$_2$)$_2$-(3-Py) |
| 18 | 1 | 3' | —O—(CH$_2$)$_2$-(3-Py) |
| 19 | 1 | 4' | —O—(CH$_2$)$_2$-(3-Py) |
| 20 | 1 | 3' | —O—(CH$_2$)$_2$-(3-Py) |

TABLE 3

(I-C)

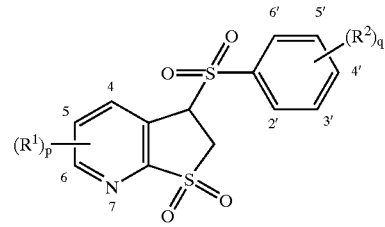

| No. | p | position | R$^1$ | q | position | R$^2$ |
|---|---|---|---|---|---|---|
| 1 | 1 | 4 | —O—(CH$_2$)$_2$—(3-Py) | 0 | — | — |
| 2 | 1 | 5 | —O—(CH$_2$)$_2$—(3-Py) | 0 | — | — |
| 3 | 1 | 6 | —O—(CH$_2$)$_2$—(3-Py) | 0 | — | — |
| 4 | 2 | 4, 5 | —O—(CH$_2$)$_2$—(3-Py) | 0 | — | — |
| 5 | 1 | 4 | —O—(CH$_2$)$_2$—N(CH$_3$)$_2$ | 0 | — | — |
| 6 | 1 | 5 | —O—(CH$_2$)$_2$—N(CH$_3$)$_2$ | 0 | — | — |
| 7 | 1 | 6 | —O—(CH$_2$)$_2$—N(CH$_3$)$_2$ | 0 | — | — |
| 8 | 2 | 4, 5 | —O—(CH$_2$)$_2$—N(CH$_3$)$_2$ | 0 | — | — |
| 9 | 0 | — | — | 1 | 2' | —O—(CH$_2$)$_2$—(3-Py) |
| 10 | 0 | — | — | 1 | 3' | —O—(CH$_2$)$_2$—(3-Py) |
| 11 | 0 | — | — | 1 | 4' | —O—(CH$_2$)$_2$—(3-Py) |
| 12 | 0 | — | — | 2 | 3', 5' | —O—(CH$_2$)$_2$—(3-Py) |
| 13 | 0 | — | — | 1 | 2' | —O—(CH$_2$)$_2$—N(CH$_3$)$_2$ |
| 14 | 0 | — | — | 1 | 3' | —O—(CH$_2$)$_2$—N(CH$_3$)$_2$ |
| 15 | 0 | — | — | 1 | 4' | —O—(CH$_2$)$_2$—N(CH$_3$)$_2$ |
| 16 | 0 | — | — | 2 | 3', 5' | —O—(CH$_2$)$_2$—N(CH$_3$)$_2$ |
| 17 | 1 | 4 | —O—(CH$_2$)$_2$—(3-Py) | 1 | 2' | —O—(CH$_2$)$_2$—(3-Py) |
| 18 | 1 | 5 | —O—(CH$_2$)$_2$—(3-Py) | 1 | 3' | —O—(CH$_2$)$_2$—(3-Py) |
| 19 | 1 | 6 | —O—(CH$_2$)$_2$—(3-Py) | 1 | 4' | —O—(CH$_2$)$_2$—(3-Py) |
| 20 | 2 | 4, 5 | —O—(CH$_2$)$_2$—(3-Py) | 1 | 3' | —O—(CH$_2$)$_2$—(3-Py) |

TABLE 4

(I-D)

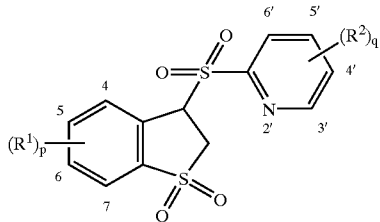

| No. | p | position | R¹ | q | position | R² |
|---|---|---|---|---|---|---|
| 1 | 1 | 4 | —O—(CH$_2$)$_2$—(3-Py) | 0 | — | — |
| 2 | 1 | 5 | —O—(CH$_2$)$_2$—(3-Py) | 0 | — | — |
| 3 | 1 | 6 | —O—(CH$_2$)$_2$—(3-Py) | 0 | — | — |
| 4 | 1 | 7 | —O—(CH$_2$)$_2$—(3-Py) | 0 | — | — |
| 5 | 1 | 4 | —O—(CH$_2$)$_2$—N(CH$_3$)$_2$ | 0 | — | — |
| 6 | 1 | 5 | —O—(CH$_2$)$_2$—N(CH$_3$)$_2$ | 0 | — | — |
| 7 | 1 | 6 | —O—(CH$_2$)$_2$—N(CH$_3$)$_2$ | 0 | — | — |
| 8 | 1 | 7 | —O—(CH$_2$)$_2$—N(CH$_3$)$_2$ | 0 | — | — |
| 9 | 0 | — | — | 1 | 3' | —O—(CH$_2$)$_2$—(3-Py) |
| 10 | 0 | — | — | 1 | 4' | —O—(CH$_2$)$_2$—(3-Py) |
| 11 | 0 | — | — | 1 | 5' | —O—(CH$_2$)$_2$—(3-Py) |
| 12 | 0 | — | — | 1 | 6' | —O—(CH$_2$)$_2$—(3-Py) |
| 13 | 0 | — | — | 1 | 3' | —O—(CH$_2$)$_2$—N(CH$_3$)$_2$ |
| 14 | 0 | — | — | 1 | 4' | —O—(CH$_2$)$_2$—N(CH$_3$)$_2$ |
| 15 | 0 | — | — | 1 | 5' | —O—(CH$_2$)$_2$—N(CH$_3$)$_2$ |
| 16 | 0 | — | — | 1 | 6' | —O—(CH$_2$)$_2$—N(CH$_3$)$_2$ |
| 17 | 1 | 4 | —O—(CH$_2$)$_2$—(3-Py) | 1 | 3' | —O—(CH$_2$)$_2$—(3-Py) |
| 18 | 1 | 5 | —O—(CH$_2$)$_2$—(3-Py) | 1 | 4' | —O—(CH$_2$)$_2$—(3-Py) |
| 19 | 1 | 6 | —O—(CH$_2$)$_2$—(3-Py) | 1 | 5' | —O—(CH$_2$)$_2$—(3-Py) |
| 20 | 1 | 7 | —O—(CH$_2$)$_2$—(3-Py) | 1 | 6' | —O—(CH$_2$)$_2$—(3-Py) |

TABLE 5

(I-E)

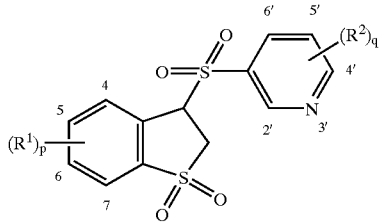

| No. | p | position | R¹ | q | position | R² |
|---|---|---|---|---|---|---|
| 1 | 1 | 4 | —O—(CH$_2$)$_2$—(3-Py) | 0 | — | — |
| 2 | 1 | 5 | —O—(CH$_2$)$_2$—(3-Py) | 0 | — | — |
| 3 | 1 | 6 | —O—(CH$_2$)$_2$—(3-Py) | 0 | — | — |
| 4 | 1 | 7 | —O—(CH$_2$)$_2$—(3-Py) | 0 | — | — |
| 5 | 1 | 4 | —O—(CH$_2$)$_2$—N(CH$_3$)$_2$ | 0 | — | — |
| 6 | 1 | 5 | —O—(CH$_2$)$_2$—N(CH$_3$)$_2$ | 0 | — | — |
| 7 | 1 | 6 | —O—(CH$_2$)$_2$—N(CH$_3$)$_2$ | 0 | — | — |
| 8 | 1 | 7 | —O—(CH$_2$)$_2$—N(CH$_3$)$_2$ | 0 | — | — |
| 9 | 0 | — | — | 1 | 2' | —O—(CH$_2$)$_2$—(3-Py) |
| 10 | 0 | — | — | 1 | 4' | —O—(CH$_2$)$_2$—(3-Py) |
| 11 | 0 | — | — | 1 | 5' | —O—(CH$_2$)$_2$—(3-Py) |
| 12 | 0 | — | — | 1 | 6' | —O—(CH$_2$)$_2$—(3-Py) |
| 13 | 0 | — | — | 1 | 2' | —O—(CH$_2$)$_2$—N(CH$_3$)$_2$ |
| 14 | 0 | — | — | 1 | 4' | —O—(CH$_2$)$_2$—N(CH$_3$)$_2$ |
| 15 | 0 | — | — | 1 | 5' | —O—(CH$_2$)$_2$—N(CH$_3$)$_2$ |
| 16 | 0 | — | — | 1 | 6' | —O—(CH$_2$)$_2$—N(CH$_3$)$_2$ |
| 17 | 1 | 4 | —O—(CH$_2$)$_2$—(3-Py) | 1 | 2' | —O—(CH$_2$)$_2$—(3-Py) |
| 18 | 1 | 5 | —O—(CH$_2$)$_2$—(3-Py) | 1 | 4' | —O—(CH$_2$)$_2$—(3-Py) |
| 19 | 1 | 6 | —O—(CH$_2$)$_2$—(3-Py) | 1 | 5' | —O—(CH$_2$)$_2$—(3-Py) |
| 20 | 1 | 7 | —O—(CH$_2$)$_2$—(3-Py) | 1 | 6' | —O—(CH$_2$)$_2$—(3-Py) |

TABLE 6

(I-F)

[Structure: benzothiophene dioxide with sulfonyl-pyridine substituent, $(R^1)_p$ at positions 4,5,6,7 and $(R^2)_q$ on pyridine ring with positions 2',3',5',6',N4']

| No. | p | position | R¹ |
|---|---|---|---|
| 1 | 1 | 4 | —O—(CH₂)₂-(3-Py) |
| 2 | 1 | 5 | —O—(CH₂)₂-(3-Py) |
| 3 | 1 | 6 | —O—(CH₂)₂-(3-Py) |
| 4 | 1 | 7 | —O—(CH₂)₂-(3-Py) |
| 5 | 1 | 4 | —O—(CH₂)₂—N(CH₃)₂ |
| 6 | 1 | 5 | —O—(CH₂)₂—N(CH₃)₂ |
| 7 | 1 | 6 | —O—(CH₂)₂—N(CH₃)₂ |
| 8 | 1 | 7 | —O—(CH₂)₂—N(CH₃)₂ |
| 9 | 0 | — | — |
| 10 | 0 | — | — |
| 11 | 0 | — | — |
| 12 | 0 | — | — |
| 13 | 0 | — | — |
| 14 | 0 | — | — |
| 15 | 0 | — | — |
| 16 | 0 | — | — |
| 17 | 1 | 4 | —O—(CH₂)₂-(3-Py) |
| 18 | 1 | 5 | —O—(CH₂)₂-(3-Py) |
| 19c | 1 | 6 | —O—(CH₂)₂-(3-Py) |
| 20 | 1 | 7 | —O—(CH₂)₂-(3-Py) |

| No. | q | position | R² |
|---|---|---|---|
| 1 | 0 | — | — |
| 2 | 0 | — | — |
| 3 | 0 | — | — |
| 4 | 0 | — | — |
| 5 | 0 | — | — |
| 6 | 0 | — | — |
| 7 | 0 | — | — |
| 8 | 0 | — | — |
| 9 | 1 | 2' | —O—(CH₂)₂-(3-Py) |
| 10 | 1 | 3' | —O—(CH₂)₂-(3-Py) |
| 11 | 2 | 2', 5' | —O—(CH₂)₂-(3-Py) |
| 12 | 2 | 2', 6' | —O—(CH₂)₂-(3-Py) |
| 13 | 1 | 2' | —O—(CH₂)₂—N(CH₃)₂ |
| 14 | 1 | 3' | —O—(CH₂)₂—N(CH₃)₂ |
| 15 | 2 | 2', 5' | —O—(CH₂)₂—N(CH₃)₂ |
| 16 | 2 | 2', 6' | —O—(CH₂)₂—N(CH₃)₂ |
| 17 | 1 | 2' | —O—(CH₂)₂-(3-Py) |
| 18 | 1 | 3' | —O—(CH₂)₂-(3-Py) |
| 19 | 1 | 2' | —O—(CH₂)₂-(3-Py) |
| 20 | 1 | 3' | —O—(CH₂)₂-(3-Py) |

TABLE 7

(I-G)

[Structure: thienopyridine dioxide with sulfonyl-pyridine substituent]

| No. | p | position | R¹ |
|---|---|---|---|
| 1 | 1 | 5 | —O—(CH₂)₂-(3-Py) |
| 2 | 1 | 6 | —O—(CH₂)₂-(3-Py) |
| 3 | 1 | 7 | —O—(CH₂)₂-(3-Py) |
| 4 | 2 | 6, 7 | —O—(CH₂)₂-(3-Py) |
| 5 | 1 | 5 | —O—(CH₂)₂—N(CH₃)₂ |
| 6 | 1 | 6 | —O—(CH₂)₂—N(CH₃)₂ |
| 7 | 1 | 7 | —O—(CH₂)₂—N(CH₃)₂ |
| 8 | 2 | 6, 7 | —O—(CH₂)₂—N(CH₃)₂ |
| 9 | 0 | — | — |
| 10 | 0 | — | — |
| 11 | 0 | — | — |
| 12 | 0 | — | — |
| 13 | 0 | — | — |
| 14 | 0 | — | — |
| 15 | 0 | — | — |
| 16 | 0 | — | — |
| 17 | 1 | 5 | —O—(CH₂)₂-(3-Py) |
| 18 | 1 | 6 | —O—(CH₂)₂-(3-Py) |
| 19 | 1 | 7 | —O—(CH₂)₂-(3-Py) |
| 20 | 2 | 6, 7 | —O—(CH₂)₂-(3-Py) |

| No. | q | position | R² |
|---|---|---|---|
| 1 | 0 | — | — |
| 2 | 0 | — | — |
| 3 | 0 | — | — |
| 4 | 0 | — | — |
| 5 | 0 | — | — |
| 6 | 0 | — | — |
| 7 | 0 | — | — |
| 8 | 0 | — | — |
| 9 | 1 | 3' | —O—(CH₂)₂-(3-Py) |
| 10 | 1 | 4' | —O—(CH₂)₂-(3-Py) |
| 11 | 1 | 5' | —O—(CH₂)₂-(3-Py) |
| 12 | 1 | 6' | —O—(CH₂)₂-(3-Py) |
| 13 | 1 | 3' | —O—(CH₂)₂—N(CH₃)₂ |
| 14 | 1 | 4' | —O—(CH₂)₂—N(CH₃)₂ |
| 15 | 1 | 5' | —O—(CH₂)₂—N(CH₃)₂ |
| 16 | 1 | 6' | —O—(CH₂)₂—N(CH₃)₂ |
| 17 | 1 | 3' | —O—(CH₂)₂-(3-Py) |
| 18 | 1 | 4' | —O—(CH₂)₂-(3-Py) |
| 19 | 1 | 5' | —O—(CH₂)₂-(3-Py) |
| 20 | 1 | 6' | —O—(CH₂)₂-(3-Py) |

TABLE 8

(I-H)

[Structure: thienopyridine dioxide with sulfonyl-pyridine substituent, N at position 7]

| No. | p | position | R¹ |
|---|---|---|---|
| 1 | 1 | 4 | —O—(CH₂)₂-(3-Py) |
| 2 | 1 | 5 | —O—(CH₂)₂-(3-Py) |
| 3 | 1 | 6 | —O—(CH₂)₂-(3-Py) |
| 4 | 2 | 4, 5 | —O—(CH₂)₂-(3-Py) |
| 5 | 1 | 4 | —O—(CH₂)₂—N(CH₃)₂ |
| 6 | 1 | 5 | —O—(CH₂)₂—N(CH₃)₂ |
| 7 | 1 | 6 | —O—(CH₂)₂—N(CH₃)₂ |
| 8 | 2 | 4, 5 | —O—(CH₂)₂—N(CH₃)₂ |
| 9 | 0 | — | — |
| 10 | 0 | — | — |
| 11 | 0 | — | — |
| 12 | 0 | — | — |
| 13 | 0 | — | — |
| 14 | 0 | — | — |
| 15 | 0 | — | — |
| 16 | 0 | — | — |
| 17 | 1 | 4 | —O—(CH₂)₂-(3-Py) |
| 18 | 1 | 5 | —O—(CH₂)₂-(3-Py) |

TABLE 8-continued

| No. | | position | R² |
|---|---|---|---|
| 19 | 1 | 6 | —O—(CH₂)₂-(3-Py) |
| 20 | 2 | 4, 5 | —O—(CH₂)₂-(3-Py) |

| No. | q | position | R² |
|---|---|---|---|
| 1 | 0 | — | — |
| 2 | 0 | — | — |
| 3 | 0 | — | — |
| 4 | 0 | — | — |
| 5 | 0 | — | — |
| 6 | 0 | — | — |
| 7 | 0 | — | — |
| 8 | 0 | — | — |
| 9 | 1 | 3' | —O—(CH₂)₂-(3-Py) |
| 10 | 1 | 4' | —O—(CH₂)₂-(3-Py) |
| 11 | 1 | 5' | —O—(CH₂)₂-(3-Py) |
| 12 | 1 | 6' | —O—(CH₂)₂-(3-Py) |
| 13 | 1 | 3' | —O—(CH₂)₂—N(CH₃)₂ |
| 14 | 1 | 4' | —O—(CH₂)₂—N(CH₃)₂ |
| 15 | 1 | 5' | —O—(CH₂)₂—N(CH₃)₂ |
| 16 | 1 | 6' | —O—(CH₂)₂—N(CH₃)₂ |
| 17 | 1 | 3' | —O—(CH₂)₂-(3-Py) |
| 18 | 1 | 4' | —O—(CH₂)₂-(3-Py) |
| 19 | 1 | 5' | —O—(CH₂)₂-(3-Py) |
| 20 | 1 | 6' | —O—(CH₂)₂-(3-Py) |

TABLE 9

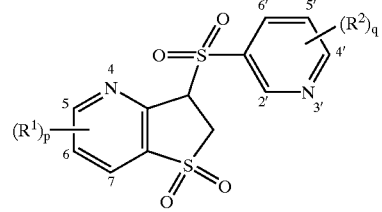

(I-J)

| No. | p | position | R¹ |
|---|---|---|---|
| 1 | 1 | 5 | —O—(CH₂)₂-(3-Py) |
| 2 | 1 | 6 | —O—(CH₂)₂-(3-Py) |
| 3 | 1 | 7 | —O—(CH₂)₂-(3-Py) |
| 4 | 2 | 6, 7 | —O—(CH₂)₂-(3-Py) |
| 5 | 1 | 5 | —O—(CH₂)₂—N(CH₃)₂ |
| 6 | 1 | 6 | —O—(CH₂)₂—N(CH₃)₂ |
| 7 | 1 | 7 | —O—(CH₂)₂—N(CH₃)₂ |
| 8 | 2 | 6, 7 | —O—(CH₂)₂—N(CH₃)₂ |
| 9 | 0 | — | — |
| 10 | 0 | — | — |
| 11 | 0 | — | — |
| 12 | 0 | — | — |
| 13 | 0 | — | — |
| 14 | 0 | — | — |
| 15 | 0 | — | — |
| 16 | 0 | — | — |
| 17 | 1 | 5 | —O—(CH₂)₂-(3-Py) |
| 18 | 1 | 6 | —O—(CH₂)₂-(3-Py) |
| 19 | 1 | 7 | —O—(CH₂)₂-(3-Py) |
| 20 | 2 | 6, 7 | —O—(CH₂)₂-(3-Py) |

| No. | q | position | R² |
|---|---|---|---|
| 1 | 0 | — | — |
| 2 | 0 | — | — |
| 3 | 0 | — | — |
| 4 | 0 | — | — |
| 5 | 0 | — | — |
| 6 | 0 | — | — |
| 7 | 0 | — | — |
| 8 | 0 | — | — |
| 9 | 1 | 2' | —O—(CH₂)₂-(3-Py) |
| 10 | 1 | 4' | —O—(CH₂)₂-(3-Py) |
| 11 | 1 | 5' | —O—(CH₂)₂-(3-Py) |
| 12 | 1 | 6' | —O—(CH₂)₂-(3-Py) |
| 13 | 1 | 2' | —O—(CH₂)₂—N(CH₃)₂ |
| 14 | 1 | 4' | —O—(CH₂)₂—N(CH₃)₂ |
| 15 | 1 | 5' | —O—(CH₂)₂—N(CH₃)₂ |
| 16 | 1 | 6' | —O—(CH₂)₂—N(CH₃)₂ |
| 17 | 1 | 2' | —O—(CH₂)₂-(3-Py) |
| 18 | 1 | 4' | —O—(CH₂)₂-(3-Py) |
| 19 | 1 | 5' | —O—(CH₂)₂-(3-Py) |
| 20 | 1 | 6' | —O—(CH₂)₂-(3-Py) |

TABLE 10

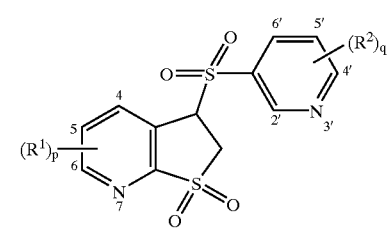

(I-K)

| No. | p | position | R¹ |
|---|---|---|---|
| 1 | 1 | 4 | —O—(CH₂)₂-(3-Py) |
| 2 | 1 | 5 | —O—(CH₂)₂-(3-Py) |
| 3 | 1 | 6 | —O—(CH₂)₂-(3-Py) |
| 4 | 2 | 4, 5 | —O—(CH₂)₂-(3-Py) |
| 5 | 1 | 4 | —O—(CH₂)₂—N(CH₃)₂ |
| 6 | 1 | 5 | —O—(CH₂)₂—N(CH₃)₂ |
| 7 | 1 | 6 | —O—(CH₂)₂—N(CH₃)₂ |
| 8 | 2 | 4, 5 | —O—(CH₂)₂—N(CH₃)₂ |
| 9 | 0 | — | — |
| 10 | 0 | — | — |
| 11 | 0 | — | — |
| 12 | 0 | — | — |
| 13 | 0 | — | — |
| 14 | 0 | — | — |
| 15 | 0 | — | — |
| 16 | 0 | — | — |
| 17 | 1 | 4 | —O—(CH₂)₂-(3-Py) |
| 18 | 1 | 5 | —O—(CH₂)₂-(3-Py) |
| 19 | 1 | 6 | —O—(CH₂)₂-(3-Py) |
| 20 | 2 | 4, 5 | —O—(CH₂)₂-(3-Py) |

| No. | q | position | R² |
|---|---|---|---|
| 1 | 0 | — | — |
| 2 | 0 | — | — |
| 3 | 0 | — | — |
| 4 | 0 | — | — |
| 5 | 0 | — | — |
| 6 | 0 | — | — |
| 7 | 0 | — | — |
| 8 | 0 | — | — |
| 9 | 1 | 2' | —O—(CH₂)₂-(3-Py) |
| 10 | 1 | 4' | —O—(CH₂)₂-(3-Py) |
| 11 | 1 | 5' | —O—(CH₂)₂-(3-Py) |
| 12 | 1 | 6' | —O—(CH₂)₂-(3-Py) |
| 13 | 1 | 2' | —O—(CH₂)₂—N(CH₃)₂ |
| 14 | 1 | 4' | —O—(CH₂)₂—N(CH₃)₂ |
| 15 | 1 | 5' | —O—(CH₂)₂—N(CH₃)₂ |
| 16 | 1 | 6' | —O—(CH₂)₂—N(CH₃)₂ |
| 17 | 1 | 2' | —O—(CH₂)₂-(3-Py) |
| 18 | 1 | 4' | —O—(CH₂)₂-(3-Py) |
| 19 | 1 | 5' | —O—(CH₂)₂-(3-Py) |
| 20 | 1 | 6' | —O—(CH₂)₂-(3-Py) |

TABLE 11

(I-L)

[Structure: thieno-pyridine sulfone dioxide with sulfonyl-pyridine group, showing positions 4, 5, 6, 7 on left ring and 2', 3', 5', 6' on right pyridine ring with N4']

| No. | p | position | R¹ |
|---|---|---|---|
| 1 | 1 | 5 | —O—(CH$_2$)$_2$-(3-Py) |
| 2 | 1 | 6 | —O—(CH$_2$)$_2$-(3-Py) |
| 3 | 1 | 7 | —O—(CH$_2$)$_2$-(3-Py) |
| 4 | 2 | 6, 7 | —O—(CH$_2$)$_2$-(3-Py) |
| 5 | 1 | 5 | —O—(CH$_2$)$_2$—N(CH$_3$)$_2$ |
| 6 | 1 | 6 | —O—(CH$_2$)$_2$—N(CH$_3$)$_2$ |
| 7 | 1 | 7 | —O—(CH$_2$)$_2$—N(CH$_3$)$_2$ |
| 8 | 2 | 6, 7 | —O—(CH$_2$)$_2$—N(CH$_3$)$_2$ |
| 9 | 0 | — | — |
| 10 | 0 | — | — |
| 11 | 0 | — | — |
| 12 | 0 | — | — |
| 13 | 0 | — | — |
| 14 | 0 | — | — |
| 15 | 0 | — | — |
| 16 | 0 | — | — |
| 17 | 1 | 5 | —O—(CH$_2$)$_2$-(3-Py) |
| 18 | 1 | 6 | —O—(CH$_2$)$_2$-(3-Py) |
| 19 | 1 | 7 | —O—(CH$_2$)$_2$-(3-Py) |
| 20 | 2 | 6, 7 | —O—(CH$_2$)$_2$-(3-Py) |

| No. | q | position | R² |
|---|---|---|---|
| 1 | 0 | — | — |
| 2 | 0 | — | — |
| 3 | 0 | — | — |
| 4 | 0 | — | — |
| 5 | 0 | — | — |
| 6 | 0 | — | — |
| 7 | 0 | — | — |
| 8 | 0 | — | — |
| 9 | 1 | 2' | —O—(CH$_2$)$_2$-(3-Py) |
| 10 | 1 | 3' | —O—(CH$_2$)$_2$-(3-Py) |
| 11 | 2 | 2', 3' | —O—(CH$_2$)$_2$-(3-Py) |
| 12 | 2 | 2', 5' | —O—(CH$_2$)$_2$-(3-Py) |
| 13 | 1 | 2' | —O—(CH$_2$)$_2$—N(CH$_3$)$_2$ |
| 14 | 1 | 3' | —O—(CH$_2$)$_2$—N(CH$_3$)$_2$ |
| 15 | 2 | 2', 3' | —O—(CH$_2$)$_2$—N(CH$_3$)$_2$ |
| 16 | 2 | 2', 5' | —O—(CH$_2$)$_2$—N(CH$_3$)$_2$ |
| 17 | 1 | 2' | —O—(CH$_2$)$_2$-(3-Py) |
| 18 | 1 | 3' | —O—(CH$_2$)$_2$-(3-Py) |
| 19 | 2 | 2', 3' | —O—(CH$_2$)$_2$-(3-Py) |
| 20 | 2 | 2', 5' | —O—(CH$_2$)$_2$-(3-Py) |

TABLE 12

(I-M)

[Structure: thieno-pyridine sulfone dioxide with sulfonyl-pyridine group, positions 4, 5, 6 and N7 on left ring and 2', 3', 5', 6' with N4' on right pyridine ring]

| No. | p | position | R¹ |
|---|---|---|---|
| 1 | 1 | 4 | —O—(CH$_2$)$_2$-(3-Py) |
| 2 | 1 | 5 | —O—(CH$_2$)$_2$-(3-Py) |
| 3 | 1 | 6 | —O—(CH$_2$)$_2$-(3-Py) |
| 4 | 2 | 4, 5 | —O—(CH$_2$)$_2$-(3-Py) |
| 5 | 1 | 4 | —O—(CH$_2$)$_2$—N(CH$_3$)$_2$ |
| 6 | 1 | 5 | —O—(CH$_2$)$_2$—N(CH$_3$)$_2$ |
| 7 | 1 | 6 | —O—(CH$_2$)$_2$—N(CH$_3$)$_2$ |
| 8 | 2 | 4, 5 | —O—(CH$_2$)$_2$—N(CH$_3$)$_2$ |
| 9 | 0 | — | — |
| 10 | 0 | — | — |
| 11 | 0 | — | — |
| 12 | 0 | — | — |
| 13 | 0 | — | — |
| 14 | 0 | — | — |
| 15 | 0 | — | — |
| 16 | 0 | — | — |
| 17 | 1 | 4 | —O—(CH$_2$)$_2$-(3-Py) |
| 18 | 1 | 5 | —O—(CH$_2$)$_2$-(3-Py) |
| 19 | 1 | 6 | —O—(CH$_2$)$_2$-(3-Py) |
| 20 | 2 | 4, 5 | —O—(CH$_2$)$_2$-(3-Py) |

| No. | q | position | R² |
|---|---|---|---|
| 1 | 0 | — | — |
| 2 | 0 | — | — |
| 3 | 0 | — | — |
| 4 | 0 | — | — |
| 5 | 0 | — | — |
| 6 | 0 | — | — |
| 7 | 0 | — | — |
| 8 | 0 | — | — |
| 9 | 1 | 2' | —O—(CH$_2$)$_2$-(3-Py) |
| 10 | 1 | 3' | —O—(CH$_2$)$_2$-(3-Py) |
| 11 | 2 | 2', 3' | —O—(CH$_2$)$_2$-(3-Py) |
| 12 | 2 | 2', 5' | —O—(CH$_2$)$_2$-(3-Py) |
| 13 | 1 | 2' | —O—(CH$_2$)$_2$—N(CH$_3$)$_2$ |
| 14 | 1 | 3' | —O—(CH$_2$)$_2$—N(CH$_3$)$_2$ |
| 15 | 2 | 2', 3' | —O—(CH$_2$)$_2$—N(CH$_3$)$_2$ |
| 16 | 2 | 2', 5' | —O—(CH$_2$)$_2$—N(CH$_3$)$_2$ |
| 17 | 1 | 2' | —O—(CH$_2$)$_2$-(3-Py) |
| 18 | 1 | 3' | —O—(CH$_2$)$_2$-(3-Py) |
| 19 | 2 | 2', 3' | —O—(CH$_2$)$_2$-(3-Py) |
| 20 | 2 | 2', 5' | —O—(CH$_2$)$_2$-(3-Py) |

TABLE 13

(I-A-1)

[Structure: benzothiophene dioxide with phenylsulfonyl group and R¹ substituent]

| No. | R¹ |
|---|---|
| 1 | [3-pyridyl methoxymethyl group] |
| 2 | [4-pyridyl ethoxymethyl group / 2-(4-pyridyl)ethoxymethyl] |
| 3 | [CH$_3$C(O)NH—CH$_2$CH$_2$—NEt$_2$] |

TABLE 13-continued (I-A-1)

| No. | R¹ |
|---|---|
| 4 | acetamide-N-CH₂-phenyl |
| 5 | acetamide-N-CH₂-(2,4-dimethoxyphenyl) |
| 6 | acetamide-N-CH₂-(pyridin-3-yl) |
| 7 | acetamide-N-CH₂CH₂-(pyrrolidin-1-yl) |
| 8 | acetamide-N-CH₂CH₂CH₂-(pyrrolidin-1-yl) |
| 9 | acetamide-N-CH₂CH₂-(piperidin-1-yl) |
| 10 | acetamide-N-CH₂CH₂CH₂-(2-oxopyrrolidin-1-yl) |
| 11 | acetamide-N-(1-benzylpyrrolidin-3-yl) |
| 12 | acetamide-N-(1-benzylpiperidin-4-yl) |

TABLE 13-continued (I-A-1)

| No. | R¹ |
|---|---|
| 13 | 1-acetyl-4-benzylpiperazine |
| 14 | acetamide-N-CH₂CH₂-N(Et)-(3-methylphenyl) |
| 15 | ethyl-NH-CH₂-phenyl |
| 16 | ethyl-NH-CH₂-(2,4-dimethoxyphenyl) |
| 17 | ethyl-NH-CH₂-(pyridin-3-yl) |
| 18 | ethyl-NH-CH₂CH₂-(piperidin-1-yl) |
| 19 | ethyl-NH-(1-benzylpiperidin-4-yl) |
| 20 | ethyl-(4-benzylpiperazin-1-yl) |

TABLE 14

(I-A-2)

| No. | R¹ |
|---|---|
| 1 | 3-pyridyl-CH₂-O-CH₂- |
| 2 | 4-pyridyl-CH₂CH₂-O-CH₂- |
| 3 | -C(O)-NH-CH₂CH₂-NEt₂ |
| 4 | -C(O)-NH-CH₂-phenyl |
| 5 | -C(O)-NH-CH₂-(2,4-dimethoxyphenyl) |
| 6 | -C(O)-NH-CH₂-(3-pyridyl) |
| 7 | -C(O)-NH-CH₂CH₂-(1-pyrrolidinyl) |
| 8 | -C(O)-NH-CH₂CH₂CH₂-(1-pyrrolidinyl) |
| 9 | -C(O)-NH-CH₂CH₂-(1-piperidinyl) |
| 10 | -C(O)-NH-CH₂CH₂CH₂-(2-oxo-1-pyrrolidinyl) |
| 11 | -C(O)-NH-(1-benzyl-pyrrolidin-3-yl) |
| 12 | -C(O)-NH-(1-benzyl-piperidin-4-yl) |
| 13 | -C(O)-(4-benzyl-piperazin-1-yl) |
| 14 | -C(O)-NH-CH₂CH₂-N(Et)-(3-methylphenyl) |
| 15 | -NH-CH₂-phenyl |
| 16 | -NH-CH₂-(2,4-dimethoxyphenyl) |
| 17 | -NH-CH₂-(3-pyridyl) |
| 18 | -NH-CH₂CH₂-(1-piperidinyl) |

TABLE 14-continued
(I-A-2)
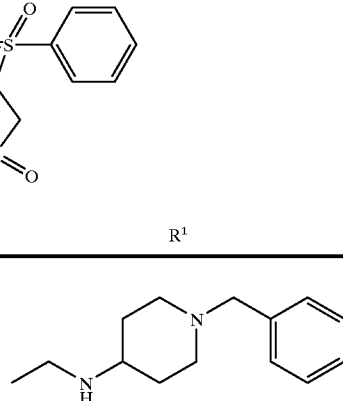
| No. | R¹ |
|---|---|
| 19 | 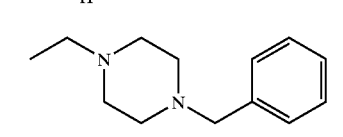 |
| 20 | 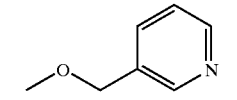 |
TABLE 15
(I-A-3)
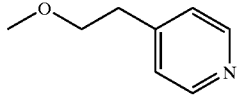
| No. | R¹ |
|---|---|
| 1 | 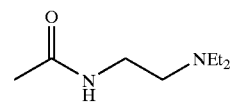 |
| 2 | 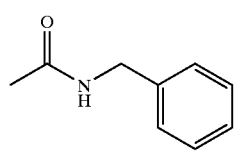 |
| 3 | 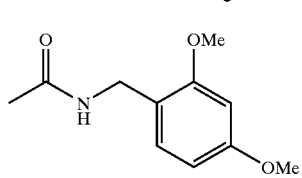 |
| 4 | 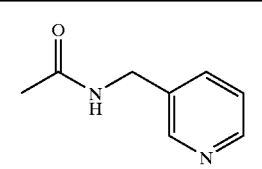 |
| 5 | 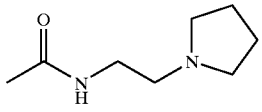 |
TABLE 15-continued
(I-A-3)
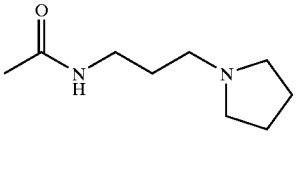
| No. | R¹ |
|---|---|
| 6 | 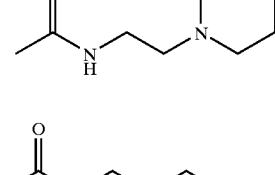 |
| 7 | 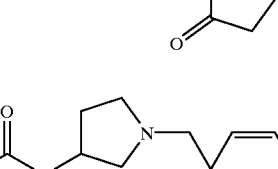 |
| 8 |  |
| 9 | 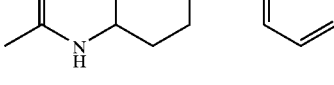 |
| 10 | 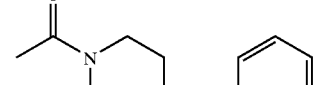 |
| 11 | |
| 12 | |
| 13 | |

TABLE 15-continued (I-A-3)

| No. | R¹ |
|---|---|
| 14 | -CH₂CH₂-NH-C(O)-CH₃ with N(Et)(3-methylphenyl) |
| 15 | -CH₂-NH-CH₂-phenyl |
| 16 | -CH₂-NH-CH₂-(2,4-dimethoxyphenyl) |
| 17 | -CH₂-NH-CH₂-(3-pyridyl) |
| 18 | -CH₂-NH-CH₂CH₂-piperidin-1-yl |
| 19 | -CH₂-NH-(1-benzylpiperidin-4-yl) |
| 20 | -CH₂-(4-benzylpiperazin-1-yl) |

TABLE 16

(I-A-4)

| No. | R¹ |
|---|---|
| 1 | -OCH₂-(3-pyridyl) |
| 2 | -OCH₂CH₂-(4-pyridyl) |
| 3 | -C(O)-NH-CH₂CH₂-NEt₂ |
| 4 | -C(O)-NH-CH₂-phenyl |
| 5 | -C(O)-NH-CH₂-(2,4-dimethoxyphenyl) |
| 6 | -C(O)-NH-CH₂-(3-pyridyl) |
| 7 | -C(O)-NH-CH₂CH₂-pyrrolidin-1-yl |
| 8 | -C(O)-NH-CH₂CH₂CH₂-pyrrolidin-1-yl |
| 9 | -C(O)-NH-CH₂CH₂-piperidin-1-yl |

TABLE 16-continued
(I-A-4)
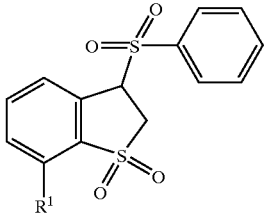
| No. | R¹ |
|---|---|
| 10 | 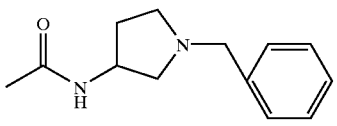 |
| 11 | 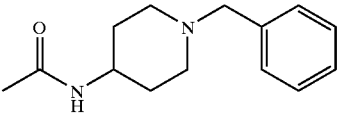 |
| 12 | 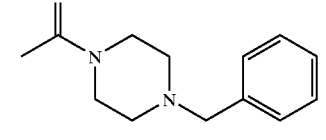 |
| 13 | 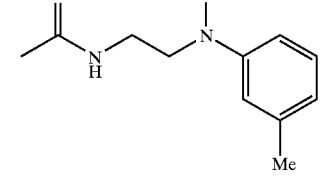 |
| 14 | 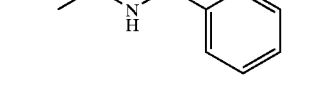 |
| 15 | 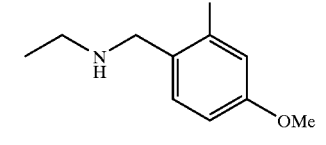 |
| 16 | 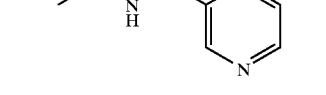 |
| 17 | 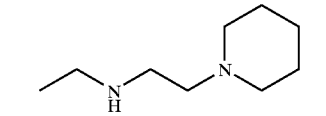 |
| 18 | 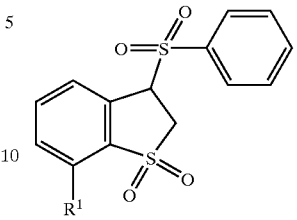 |
TABLE 16-continued
(I-A-4)
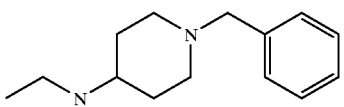
| No. | R¹ |
|---|---|
| 19 | 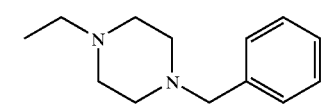 |
| 20 | 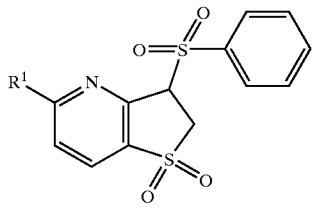 |
TABLE 17
(I-B-1)
| No. | R¹ |
|---|---|
| 1 | 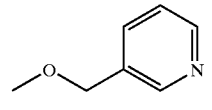 |
| 2 | 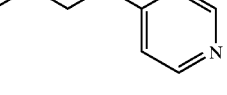 |
| 3 | 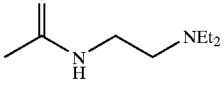 |
| 4 | 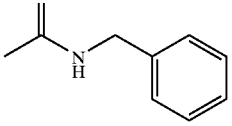 |
| 5 | 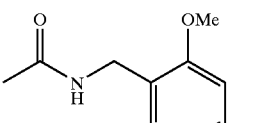 |

TABLE 17-continued (I-B-1)

| No. | R¹ |
|---|---|
| 6 | acetamide-CH₂-(pyridin-3-yl) |
| 7 | acetamide-(CH₂)₂-pyrrolidin-1-yl |
| 8 | acetamide-(CH₂)₃-pyrrolidin-1-yl |
| 9 | acetamide-(CH₂)₂-piperidin-1-yl |
| 10 | acetamide-(CH₂)₃-(2-oxopyrrolidin-1-yl) |
| 11 | acetamide-(1-benzylpyrrolidin-3-yl) |
| 12 | acetamide-(1-benzylpiperidin-4-yl) |
| 13 | 1-acetyl-4-benzylpiperazine |
| 14 | acetamide-(CH₂)₂-N(Et)(3-methylphenyl) |
| 15 | ethylamino-CH₂-phenyl |
| 16 | ethylamino-CH₂-(2,4-dimethoxyphenyl) |
| 17 | ethylamino-CH₂-(pyridin-3-yl) |
| 18 | ethylamino-(CH₂)₂-piperidin-1-yl |
| 19 | ethylamino-(1-benzylpiperidin-4-yl) |
| 20 | 1-ethyl-4-benzylpiperazine |

TABLE 18
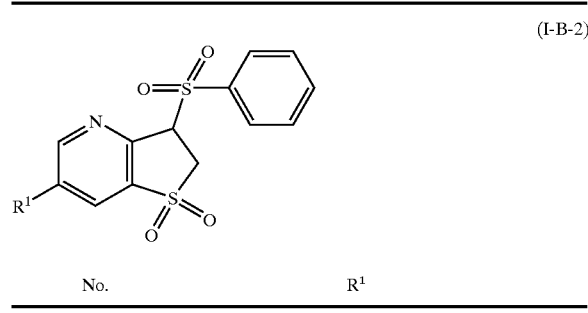
(I-B-2)
| No. | R¹ |
|---|---|
| 1 | 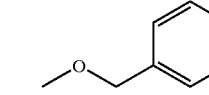 |
| 2 | 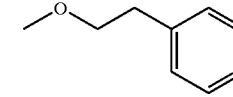 |
| 3 | 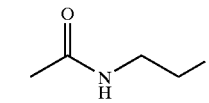 |
| 4 | 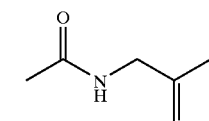 |
| 5 |  |
| 6 | 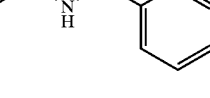 |
| 7 | 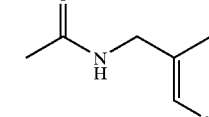 |
| 8 |  |
| 9 | 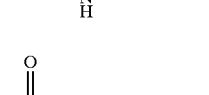 |
TABLE 18-continued
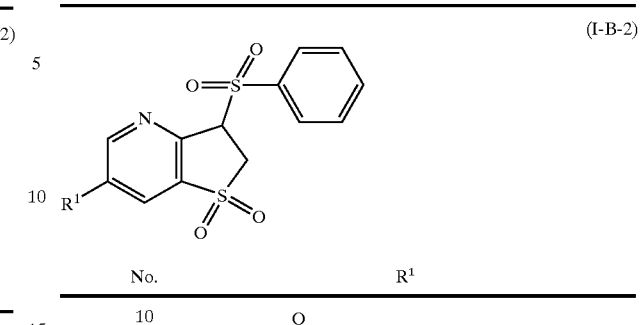
(I-B-2)
| No. | R¹ |
|---|---|
| 10 |  |
| 11 |  |
| 12 |  |
| 13 |  |
| 14 |  |
| 15 |  |
| 16 |  |
| 17 |  |
| 18 |  |

TABLE 18-continued (I-B-2)

[Structure: pyridine-fused thiophene dioxide with phenylsulfonyl group, R¹ substituent]

| No. | R¹ |
|---|---|
| 19 | N-ethyl-(1-benzylpiperidin-4-yl)amine |
| 20 | 1-ethyl-4-benzylpiperazine |

TABLE 19

(I-B-3)

[Structure: pyridine-fused thiophene dioxide with phenylsulfonyl group, R¹ substituent]

| No. | R¹ |
|---|---|
| 1 | (pyridin-2-yl)methyl methyl ether |
| 2 | 2-methoxyethyl-(pyridin-4-yl) |
| 3 | acetamido-ethyl-NEt₂ |
| 4 | N-benzylacetamide |
| 5 | N-(2,4-dimethoxybenzyl)acetamide |

TABLE 19-continued (I-B-3)

[Structure: pyridine-fused thiophene dioxide with phenylsulfonyl group, R¹ substituent]

| No. | R¹ |
|---|---|
| 6 | N-((pyridin-3-yl)methyl)acetamide |
| 7 | N-(2-(pyrrolidin-1-yl)ethyl)acetamide |
| 8 | N-(3-(pyrrolidin-1-yl)propyl)acetamide |
| 9 | N-(2-(piperidin-1-yl)ethyl)acetamide |
| 10 | N-(3-(2-oxopyrrolidin-1-yl)propyl)acetamide |
| 11 | N-(1-benzylpyrrolidin-3-yl)acetamide |
| 12 | N-(1-benzylpiperidin-4-yl)acetamide |
| 13 | 1-acetyl-4-benzylpiperazine |

TABLE 19-continued (I-B-3)

[Structure: pyridine fused with dihydrothiophene-1,1-dioxide bearing phenylsulfonyl group at 3-position and R¹ at 7-position]

| No. | R¹ |
|---|---|
| 14 | CH₃C(O)NH-CH₂CH₂-N(Et)(3-methylphenyl) |
| 15 | EtNH-CH₂-phenyl |
| 16 | EtNH-CH₂-(2,4-dimethoxyphenyl) |
| 17 | EtNH-CH₂-(3-pyridyl) |
| 18 | EtNH-CH₂CH₂-piperidin-1-yl |
| 19 | Et-NH-(1-benzylpiperidin-4-yl) |
| 20 | 4-ethyl-1-benzylpiperazine |

TABLE 20

(I-C-1)

[Structure: pyridine fused with dihydrothiophene-1,1-dioxide bearing phenylsulfonyl group at 3-position and R¹ at 4-position]

| No. | R¹ |
|---|---|
| 1 | MeO-CH₂-(2-pyridyl) |
| 2 | MeO-CH₂CH₂-(4-pyridyl) |
| 3 | CH₃C(O)NH-CH₂CH₂-NEt₂ |
| 4 | CH₃C(O)NH-CH₂-phenyl |
| 5 | CH₃C(O)NH-CH₂-(2,4-dimethoxyphenyl) |
| 6 | CH₃C(O)NH-CH₂-(3-pyridyl) |
| 7 | CH₃C(O)NH-CH₂CH₂-pyrrolidin-1-yl |
| 8 | CH₃C(O)NH-CH₂CH₂CH₂-pyrrolidin-1-yl |
| 9 | CH₃C(O)NH-CH₂CH₂-piperidin-1-yl |

TABLE 20-continued
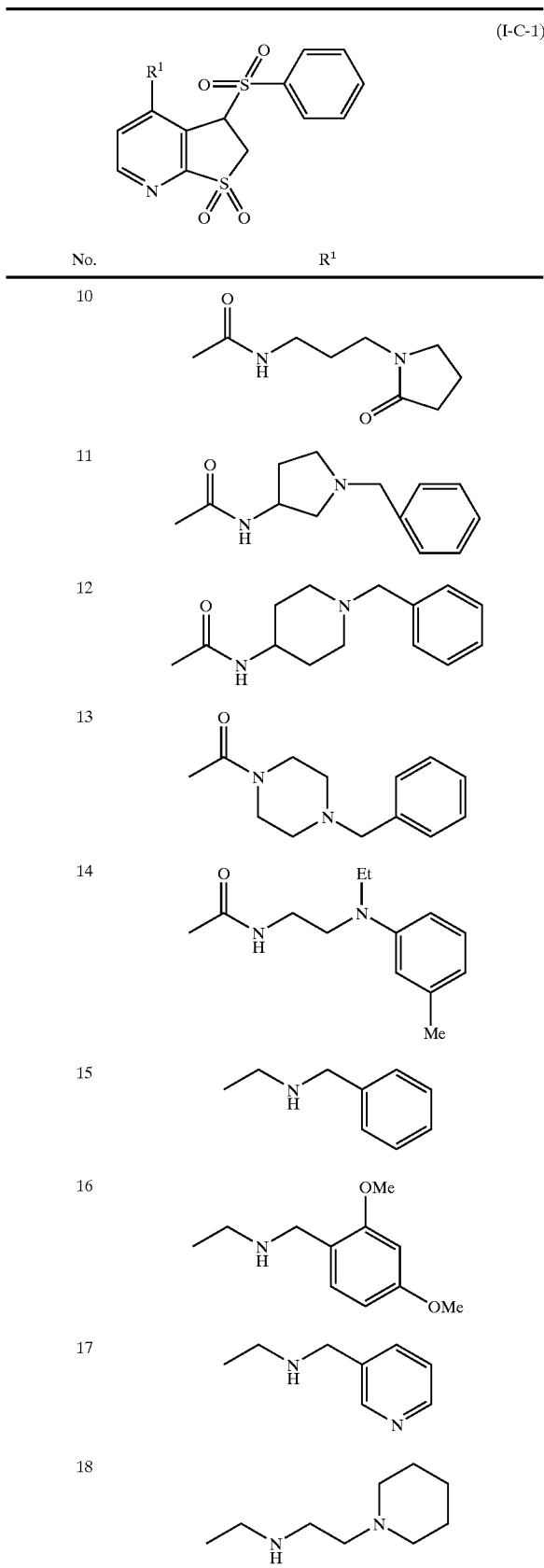
TABLE 20-continued
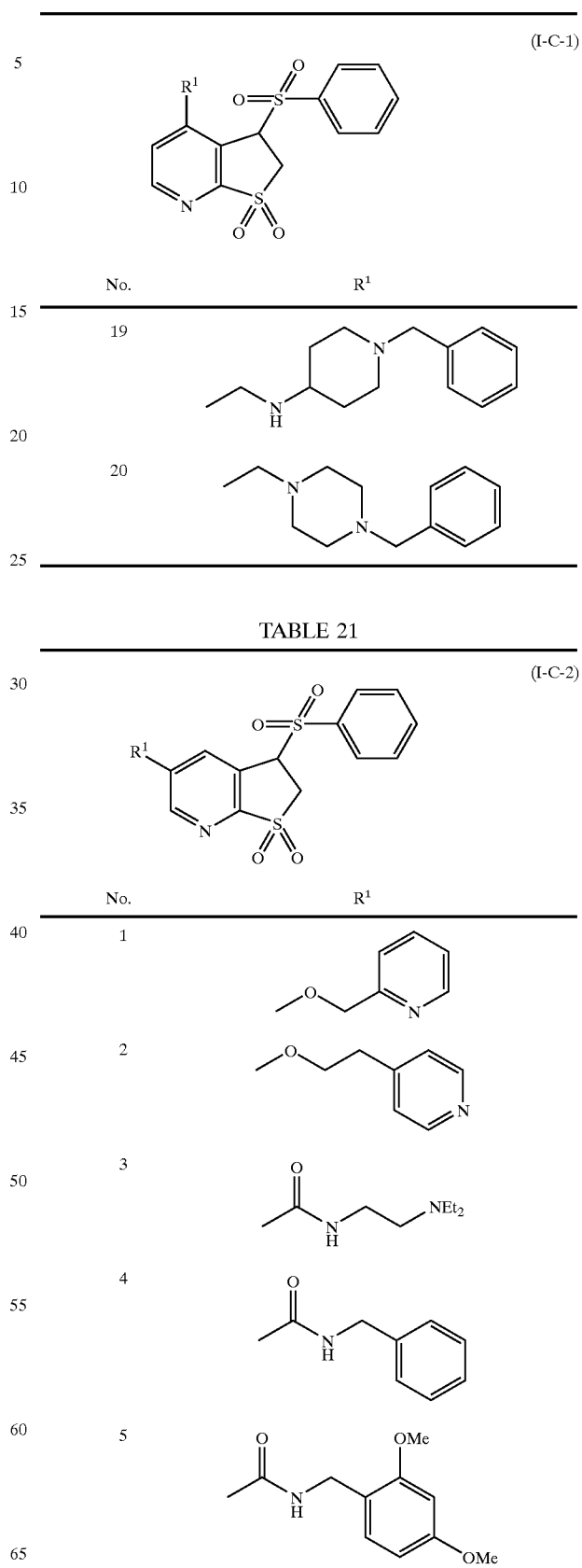

TABLE 21-continued (I-C-2)

| No. | R¹ |
|---|---|
| 6 | acetamidomethyl-3-pyridyl |
| 7 | acetamidoethyl-pyrrolidin-1-yl |
| 8 | acetamidopropyl-pyrrolidin-1-yl |
| 9 | acetamidoethyl-piperidin-1-yl |
| 10 | acetamidopropyl-2-oxopyrrolidin-1-yl |
| 11 | acetamido-(1-benzylpyrrolidin-3-yl) |
| 12 | acetamido-(1-benzylpiperidin-4-yl) |
| 13 | 1-acetyl-4-benzylpiperazine |

TABLE 21-continued (I-C-2)

| No. | R¹ |
|---|---|
| 14 | acetamidoethyl-N-ethyl-N-(3-methylphenyl)amino |
| 15 | ethylaminomethyl-phenyl |
| 16 | ethylaminomethyl-(2,4-dimethoxyphenyl) |
| 17 | ethylaminomethyl-3-pyridyl |
| 18 | ethylaminoethyl-piperidin-1-yl |
| 19 | ethylamino-(1-benzylpiperidin-4-yl) |
| 20 | 1-ethyl-4-benzylpiperazine |

TABLE 22
(I-C-3)
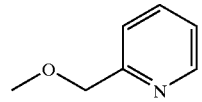
| No. | R¹ |
|---|---|
| 1 | 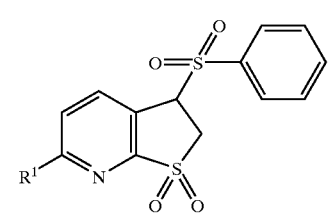 |
| 2 | 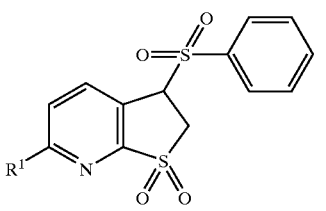 |
| 3 | 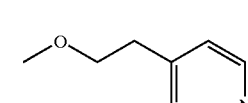 |
| 4 | 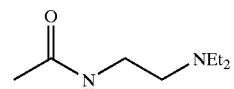 |
| 5 | 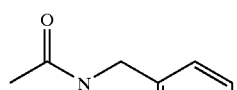 |
| 6 | 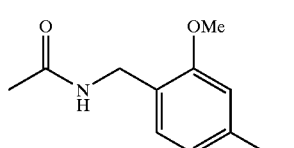 |
| 7 | 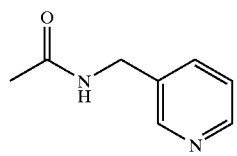 |
| 8 | 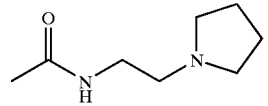 |
| 9 | 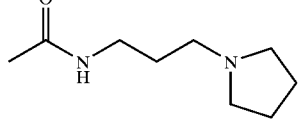 |
TABLE 22-continued
(I-C-3)
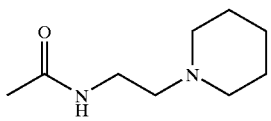
| No. | R¹ |
|---|---|
| 10 | 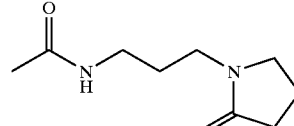 |
| 11 | 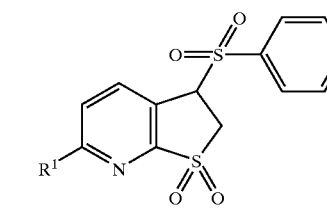 |
| 12 | 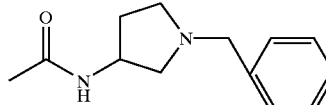 |
| 13 | 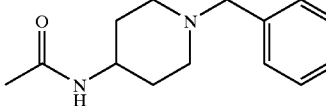 |
| 14 | 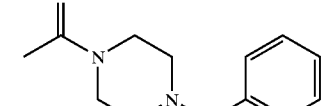 |
| 15 | 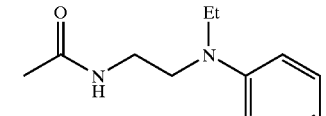 |
| 16 | 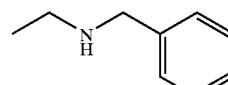 |
| 17 | 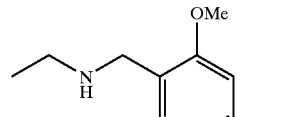 |
| 18 | 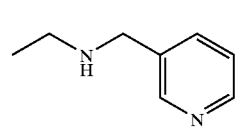 |

TABLE 22-continued (I-C-3)

| No. | R¹ |
|---|---|
| 19 | ethyl-NH-(1-benzylpiperidin-4-yl) |
| 20 | 4-ethyl-1-(benzyl)piperazine |

TABLE 23

(I-D-1)

| No. | R¹ |
|---|---|
| 1 | 2-(methoxymethyl)pyridine |
| 2 | 4-(2-methoxyethyl)pyridine |
| 3 | -C(O)NH-CH₂CH₂-NEt₂ |
| 4 | -C(O)NH-CH₂-phenyl |
| 5 | -C(O)NH-CH₂-(2,4-dimethoxyphenyl) |

TABLE 23-continued (I-D-1)

| No. | R¹ |
|---|---|
| 6 | -C(O)NH-CH₂-(pyridin-3-yl) |
| 7 | -C(O)NH-CH₂CH₂-(pyrrolidin-1-yl) |
| 8 | -C(O)NH-CH₂CH₂CH₂-(pyrrolidin-1-yl) |
| 9 | -C(O)NH-CH₂CH₂-(piperidin-1-yl) |
| 10 | -C(O)NH-CH₂CH₂CH₂-(2-oxopyrrolidin-1-yl) |
| 11 | -C(O)NH-(1-benzylpyrrolidin-3-yl) |
| 12 | -C(O)NH-(1-benzylpiperidin-4-yl) |
| 13 | -C(O)-(4-benzylpiperazin-1-yl) |

TABLE 23-continued (I-D-1)

| No. | R¹ |
|---|---|
| 14 | N-acetyl-N'-ethyl-N'-(3-methylphenyl)ethylenediamine group (acetamido-ethyl-N(Et)(3-methylphenyl)) |
| 15 | benzylamino (ethyl linker: -NH-CH2-Ph) |
| 16 | (2,4-dimethoxybenzyl)amino |
| 17 | (pyridin-3-ylmethyl)amino |
| 18 | 2-(piperidin-1-yl)ethylamino |
| 19 | (1-benzylpiperidin-4-yl)amino |
| 20 | 4-benzylpiperazin-1-yl (ethyl linker) |

TABLE 24

(I-D-2)

| No. | R¹ |
|---|---|
| 1 | (pyridin-2-yl)methoxy |
| 2 | 2-(pyridin-4-yl)ethoxymethyl (methoxyethyl-pyridyl) |
| 3 | N-(2-(diethylamino)ethyl)acetamido |
| 4 | N-benzylacetamido |
| 5 | N-(2,4-dimethoxybenzyl)acetamido |
| 6 | N-(pyridin-3-ylmethyl)acetamido |
| 7 | N-(2-(pyrrolidin-1-yl)ethyl)acetamido |
| 8 | N-(3-(pyrrolidin-1-yl)propyl)acetamido |
| 9 | N-(2-(piperidin-1-yl)ethyl)acetamido |

TABLE 24-continued
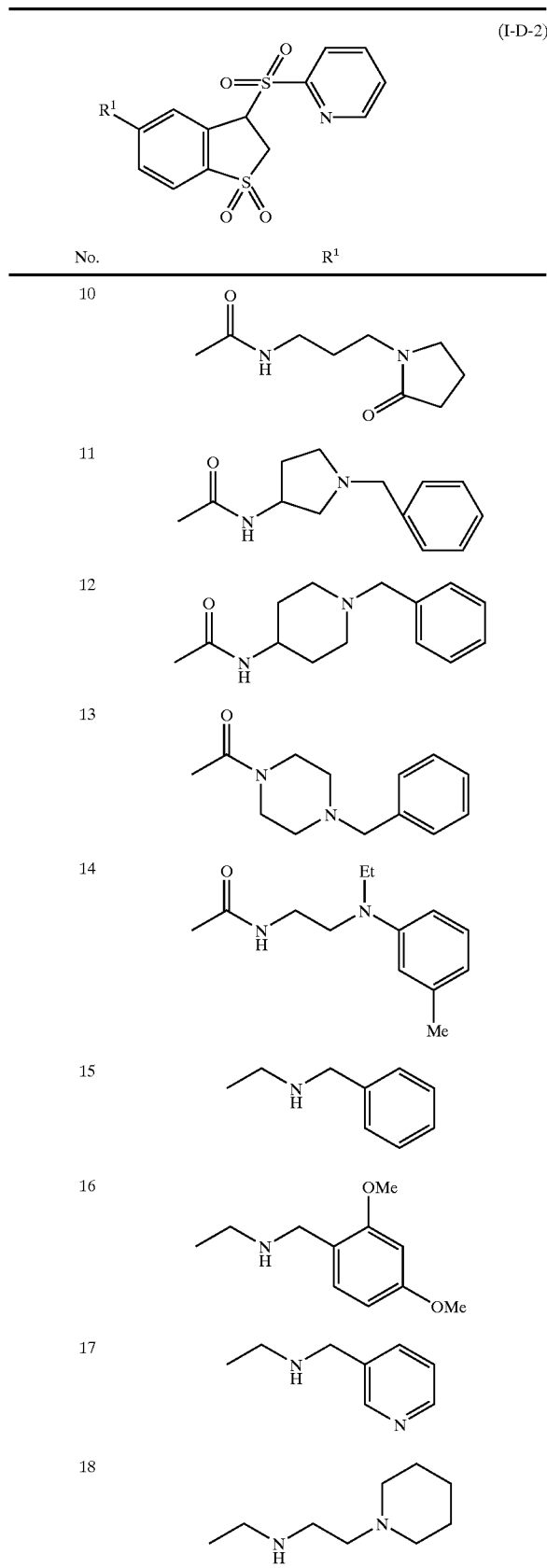
TABLE 24-continued
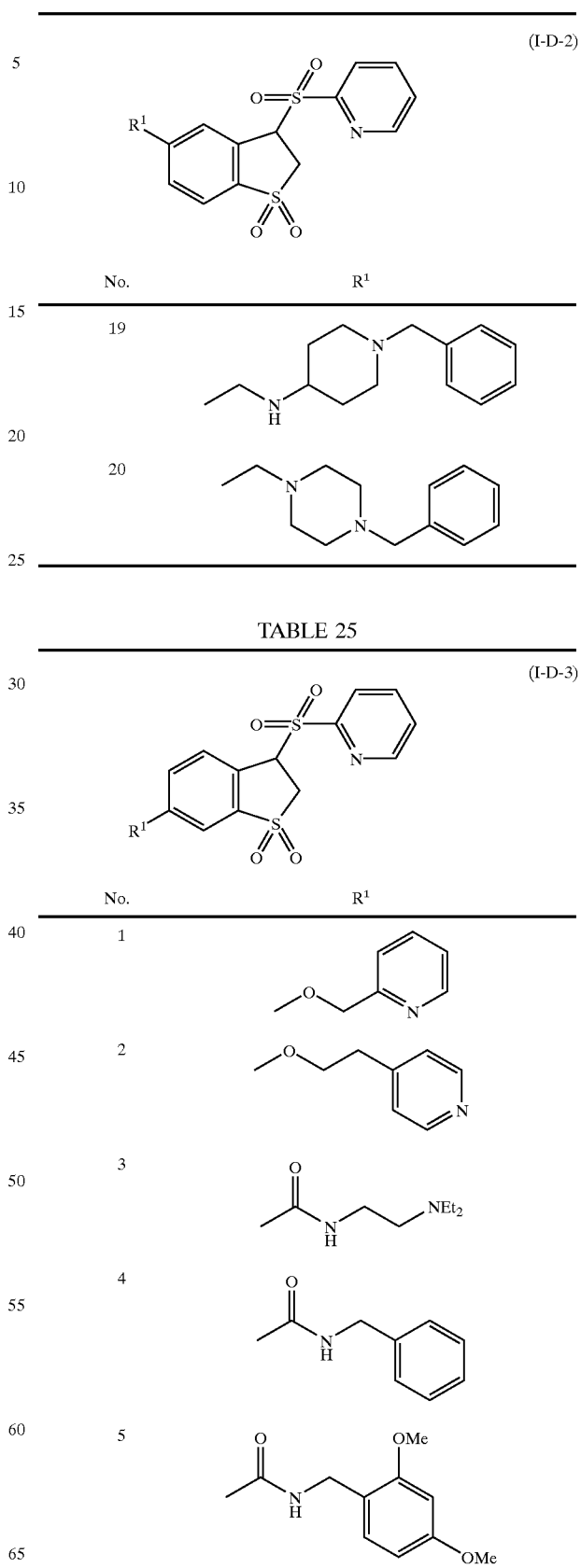

TABLE 25-continued (I-D-3)

[Structure: 2,3-dihydrobenzothiophene-1,1-dioxide with 3-position bearing SO2-(2-pyridyl) group and R1 substituent at 6-position]

| No. | R1 |
|---|---|
| 6 | -C(=O)-NH-CH2-(3-pyridyl) |
| 7 | -C(=O)-NH-CH2CH2-(1-pyrrolidinyl) |
| 8 | -C(=O)-NH-CH2CH2CH2-(1-pyrrolidinyl) |
| 9 | -C(=O)-NH-CH2CH2-(1-piperidinyl) |
| 10 | -C(=O)-NH-CH2CH2CH2-(2-oxo-1-pyrrolidinyl) |
| 11 | -C(=O)-NH-(1-benzyl-3-pyrrolidinyl) |
| 12 | -C(=O)-NH-(1-benzyl-4-piperidinyl) |
| 13 | -C(=O)-(4-benzyl-1-piperazinyl) |
| 14 | -C(=O)-NH-CH2CH2-N(Et)-(3-methylphenyl) |
| 15 | -NH-CH2-phenyl |
| 16 | -NH-CH2-(2,4-dimethoxyphenyl) |
| 17 | -NH-CH2-(3-pyridyl) |
| 18 | -NH-CH2CH2-(1-piperidinyl) |
| 19 | -NH-(1-benzyl-4-piperidinyl) |
| 20 | -(4-benzyl-1-piperazinyl) |

TABLE 26
(I-D-4)
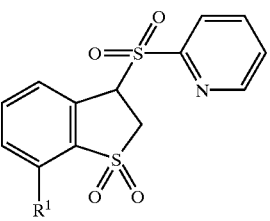
| No. | R¹ |
|---|---|
| 1 | 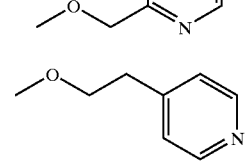 |
| 2 | 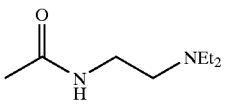 |
| 3 | 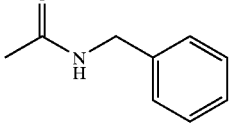 |
| 4 | 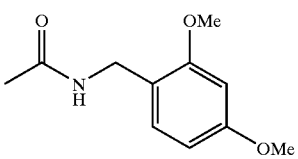 |
| 5 | 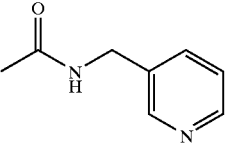 |
| 6 | 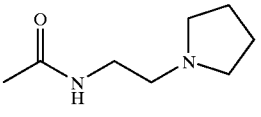 |
| 7 | 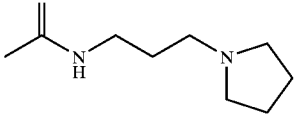 |
| 8 | 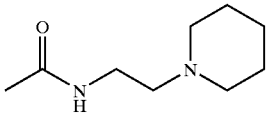 |
| 9 | 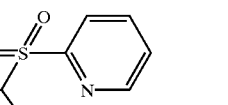 |
TABLE 26-continued
(I-D-4)
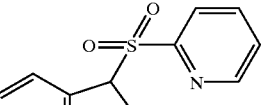
| No. | R¹ |
|---|---|
| 10 | 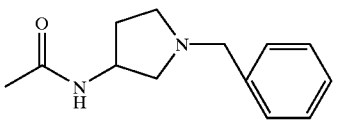 |
| 11 | 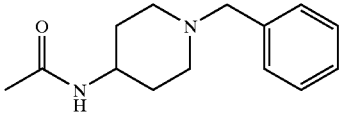 |
| 12 | 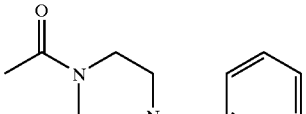 |
| 13 | 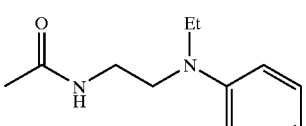 |
| 14 | 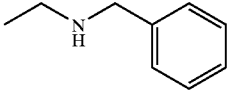 |
| 15 | 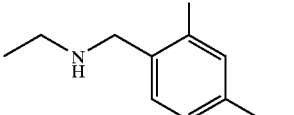 |
| 16 | 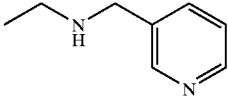 |
| 17 | 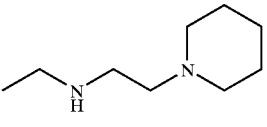 |
| 18 | |

TABLE 26-continued
(I-D-4)
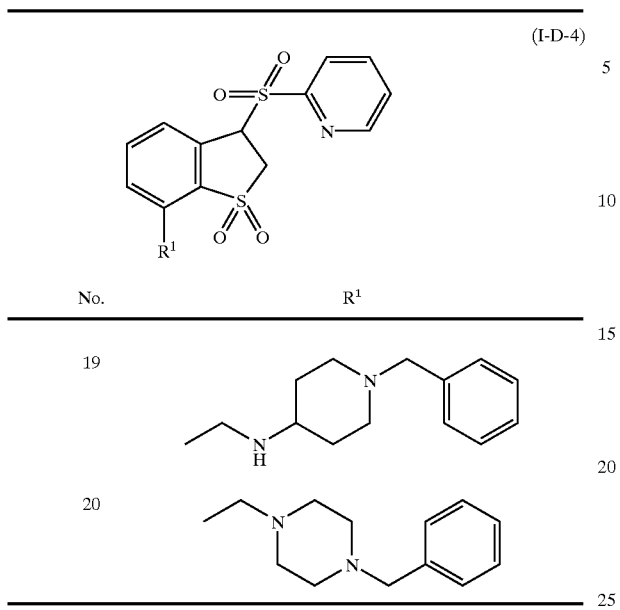
| No. | R¹ |
|---|---|
| 19 | |
| 20 | |
TABLE 27
(I-E-1)
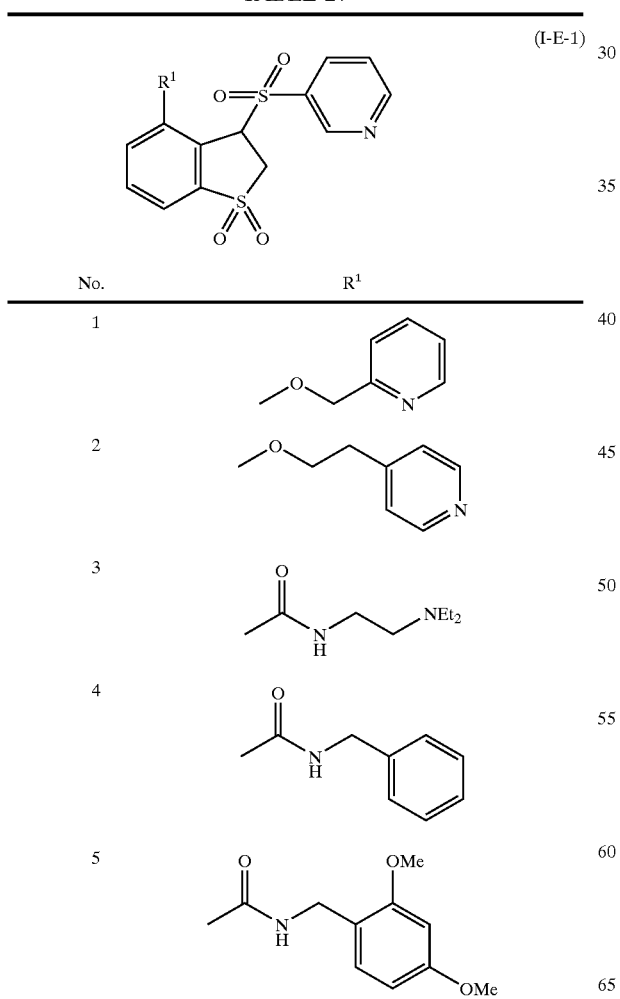
| No. | R¹ |
|---|---|
| 1 | |
| 2 | |
| 3 | |
| 4 | |
| 5 | |
TABLE 27-continued
(I-E-1)
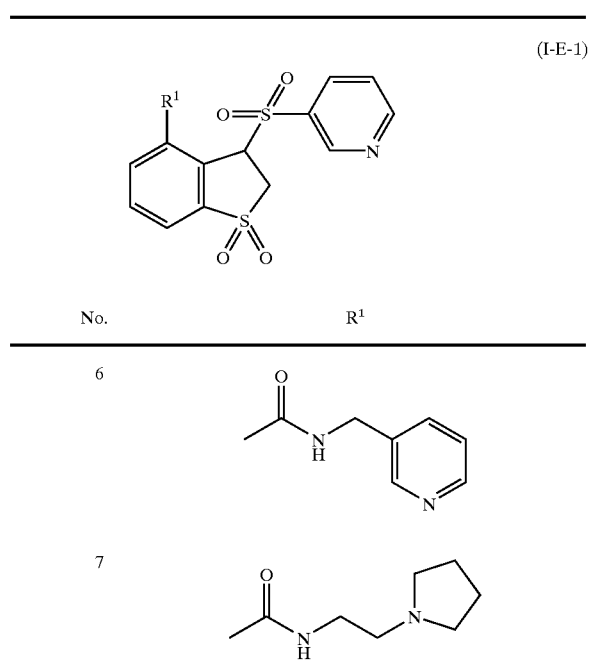
| No. | R¹ |
|---|---|
| 6 | |
| 7 | |
| 8 | |
| 9 | |
| 10 | |
| 11 | |
| 12 | |
| 13 | |

TABLE 27-continued
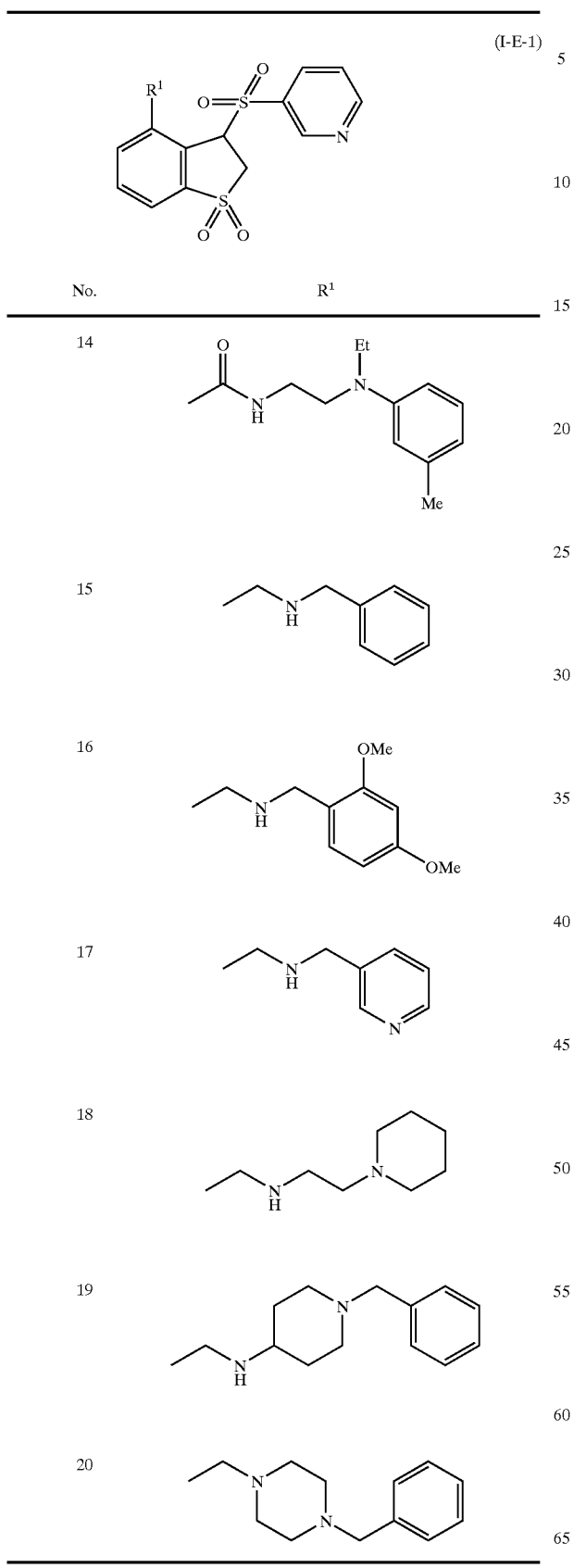
TABLE 28
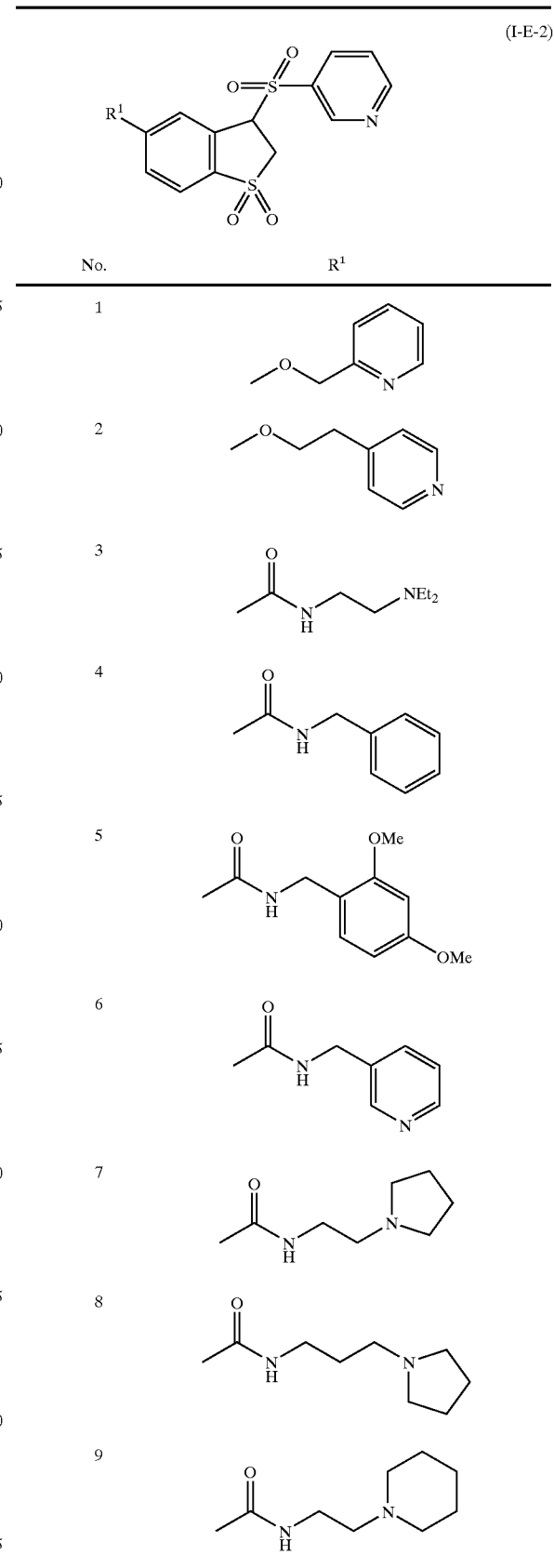

TABLE 28-continued
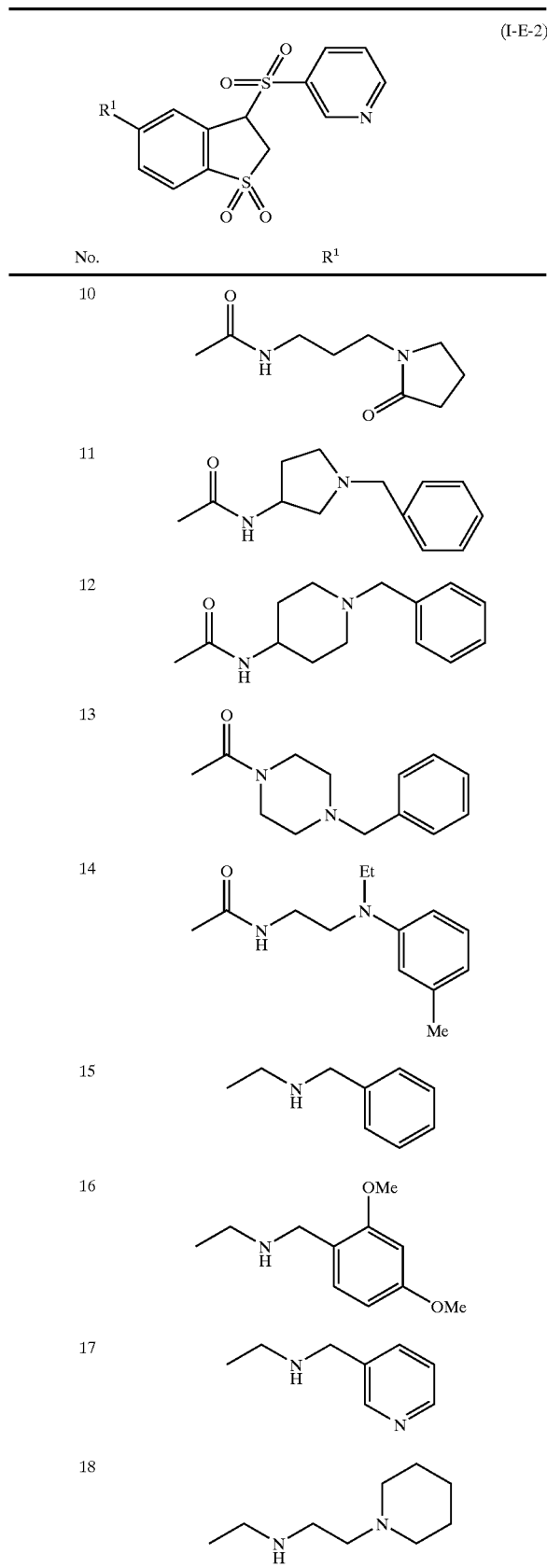
TABLE 29
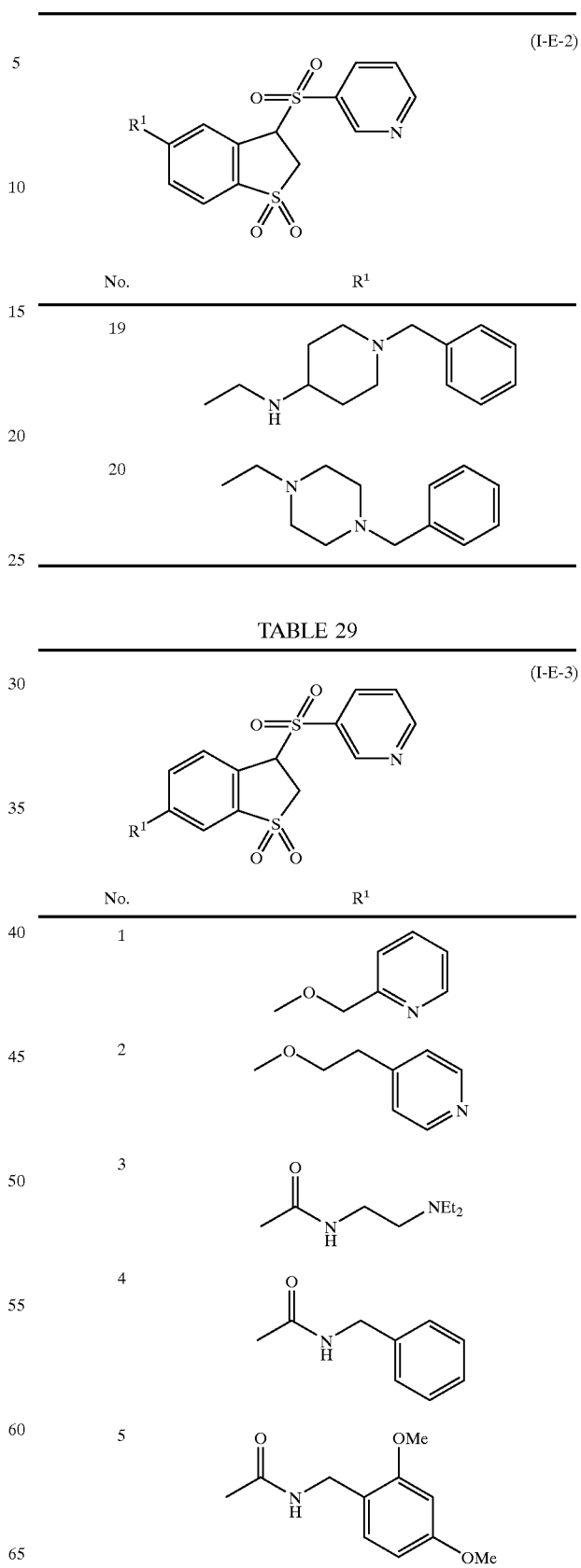

TABLE 29-continued (I-E-3)

| No. | R¹ |
|---|---|
| 6 | acetamidomethyl-pyridin-3-yl |
| 7 | acetamidoethyl-pyrrolidin-1-yl |
| 8 | acetamidopropyl-pyrrolidin-1-yl |
| 9 | acetamidoethyl-piperidin-1-yl |
| 10 | acetamidopropyl-2-oxopyrrolidin-1-yl |
| 11 | acetamido-(1-benzylpyrrolidin-3-yl) |
| 12 | acetamido-(1-benzylpiperidin-4-yl) |
| 13 | 1-acetyl-4-benzylpiperazine |

TABLE 29-continued (I-E-3)

| No. | R¹ |
|---|---|
| 14 | acetamidoethyl-N-ethyl-N-(3-methylphenyl)amino |
| 15 | ethylaminomethyl-phenyl |
| 16 | ethylaminomethyl-(2,4-dimethoxyphenyl) |
| 17 | ethylaminomethyl-pyridin-3-yl |
| 18 | ethylaminoethyl-piperidin-1-yl |
| 19 | ethylamino-(1-benzylpiperidin-4-yl) |
| 20 | 1-ethyl-4-benzylpiperazine |

TABLE 30

(I-E-4)

[Structure: 2,3-dihydrobenzo[b]thiophene 1,1-dioxide with 3-(pyridin-3-ylsulfonyl) substituent and R¹ at the 7-position]

| No. | R¹ |
|---|---|
| 1 | 2-pyridyl-CH₂-O- |
| 2 | 4-pyridyl-CH₂CH₂-O- |
| 3 | -C(O)NH-CH₂CH₂-NEt₂ |
| 4 | -C(O)NH-CH₂-C₆H₅ |
| 5 | -C(O)NH-CH₂-(2,4-dimethoxyphenyl) |
| 6 | -C(O)NH-CH₂-(3-pyridyl) |
| 7 | -C(O)NH-CH₂CH₂-(1-pyrrolidinyl) |
| 8 | -C(O)NH-CH₂CH₂CH₂-(1-pyrrolidinyl) |
| 9 | -C(O)NH-CH₂CH₂-(1-piperidinyl) |

TABLE 30-continued (I-E-4)

[Same core structure as above]

| No. | R¹ |
|---|---|
| 10 | -C(O)NH-CH₂CH₂CH₂-(2-oxo-1-pyrrolidinyl) |
| 11 | -C(O)NH-(1-benzyl-pyrrolidin-3-yl) |
| 12 | -C(O)NH-(1-benzyl-piperidin-4-yl) |
| 13 | -C(O)-(4-benzyl-1-piperazinyl) |
| 14 | -C(O)NH-CH₂CH₂-N(Et)-(3-methylphenyl) |
| 15 | -NH-CH₂-C₆H₅ |
| 16 | -NH-CH₂-(2,4-dimethoxyphenyl) |
| 17 | -NH-CH₂-(3-pyridyl) |
| 18 | -NH-CH₂CH₂-(1-piperidinyl) |

TABLE 30-continued (I-E-4)

| No. | R¹ |
|---|---|
| 19 | ethyl-NH-(1-benzylpiperidin-4-yl) |
| 20 | 4-ethyl-1-(4-benzyl)piperazine |

TABLE 31

(I-F-1)

| No. | R¹ |
|---|---|
| 1 | 2-(methoxymethyl)pyridine |
| 2 | 4-(2-methoxyethyl)pyridine |
| 3 | -C(O)NH-CH₂CH₂-NEt₂ |
| 4 | -C(O)NH-CH₂-phenyl |
| 5 | -C(O)NH-CH₂-(2,4-dimethoxyphenyl) |

TABLE 31-continued (I-F-1)

| No. | R¹ |
|---|---|
| 6 | -C(O)NH-CH₂-(pyridin-3-yl) |
| 7 | -C(O)NH-CH₂CH₂-(pyrrolidin-1-yl) |
| 8 | -C(O)NH-CH₂CH₂CH₂-(pyrrolidin-1-yl) |
| 9 | -C(O)NH-CH₂CH₂-(piperidin-1-yl) |
| 10 | -C(O)NH-CH₂CH₂CH₂-(2-oxopyrrolidin-1-yl) |
| 11 | -C(O)NH-(1-benzylpyrrolidin-3-yl) |
| 12 | -C(O)NH-(1-benzylpiperidin-4-yl) |
| 13 | -C(O)-(4-benzylpiperazin-1-yl) |

TABLE 31-continued
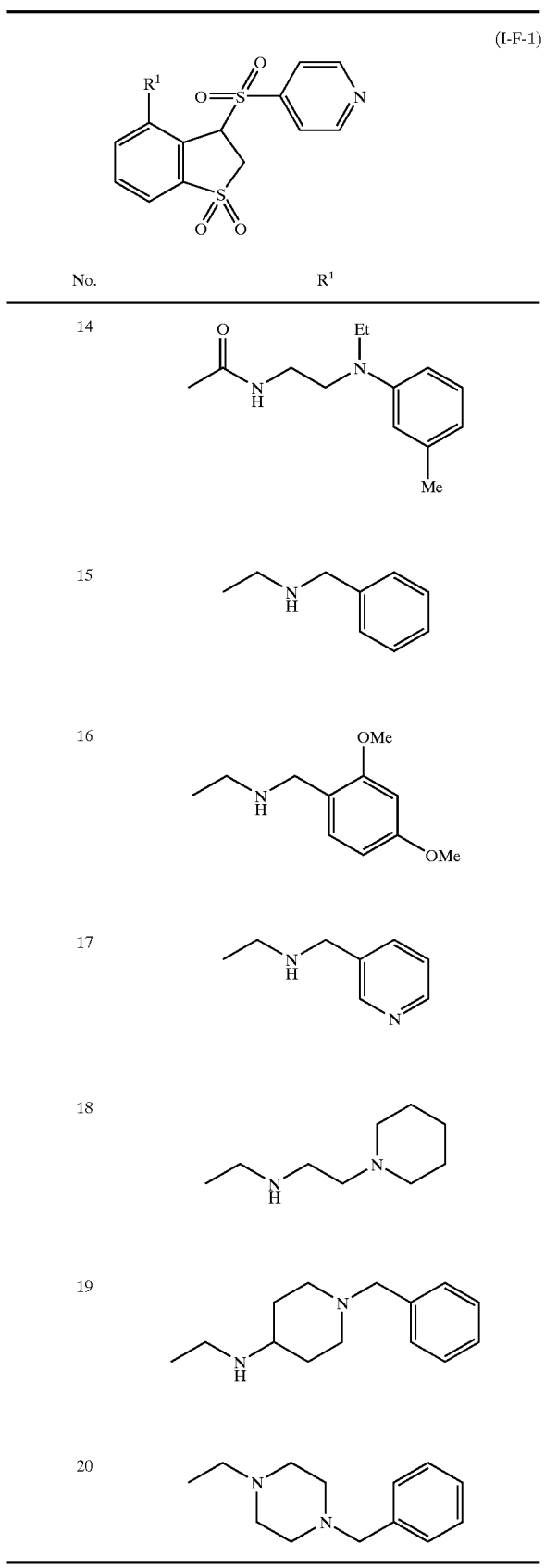
TABLE 32
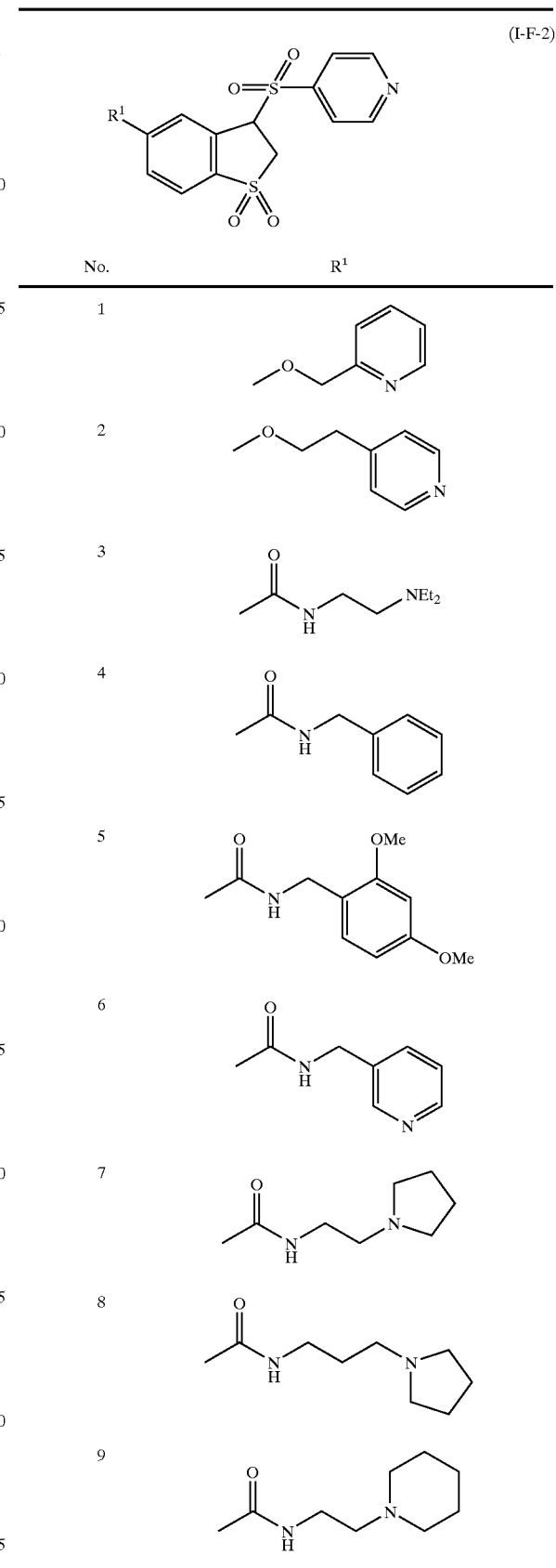

TABLE 32-continued
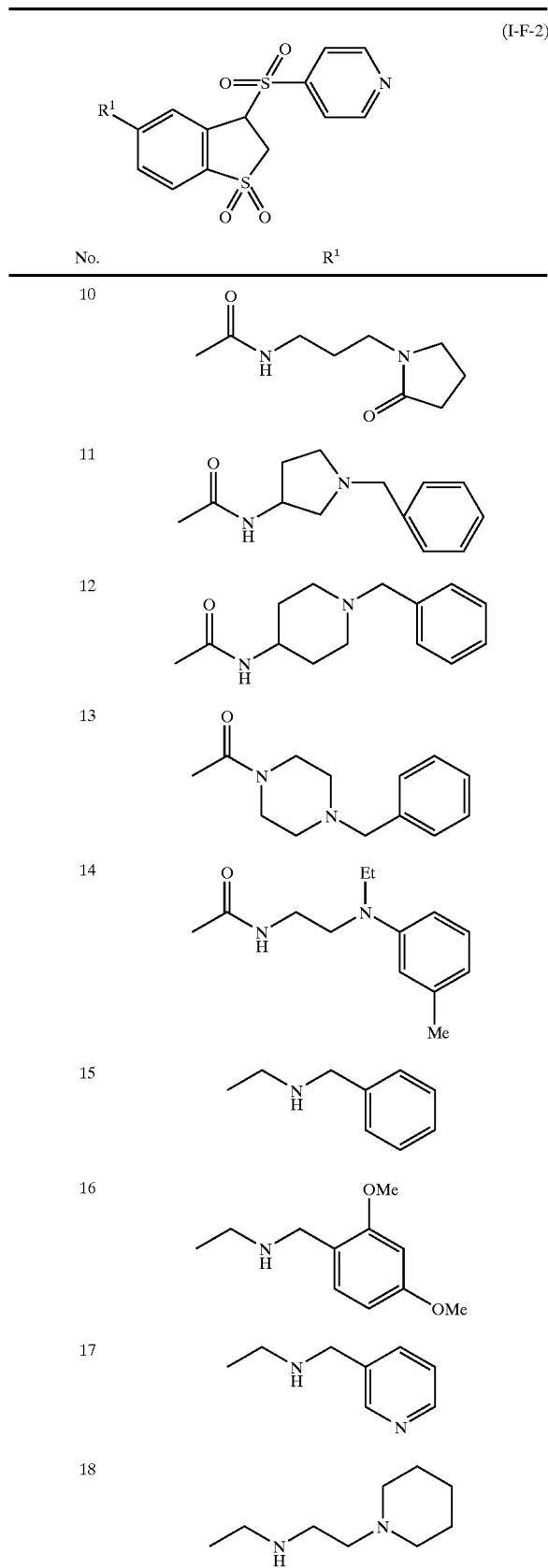
TABLE 32-continued
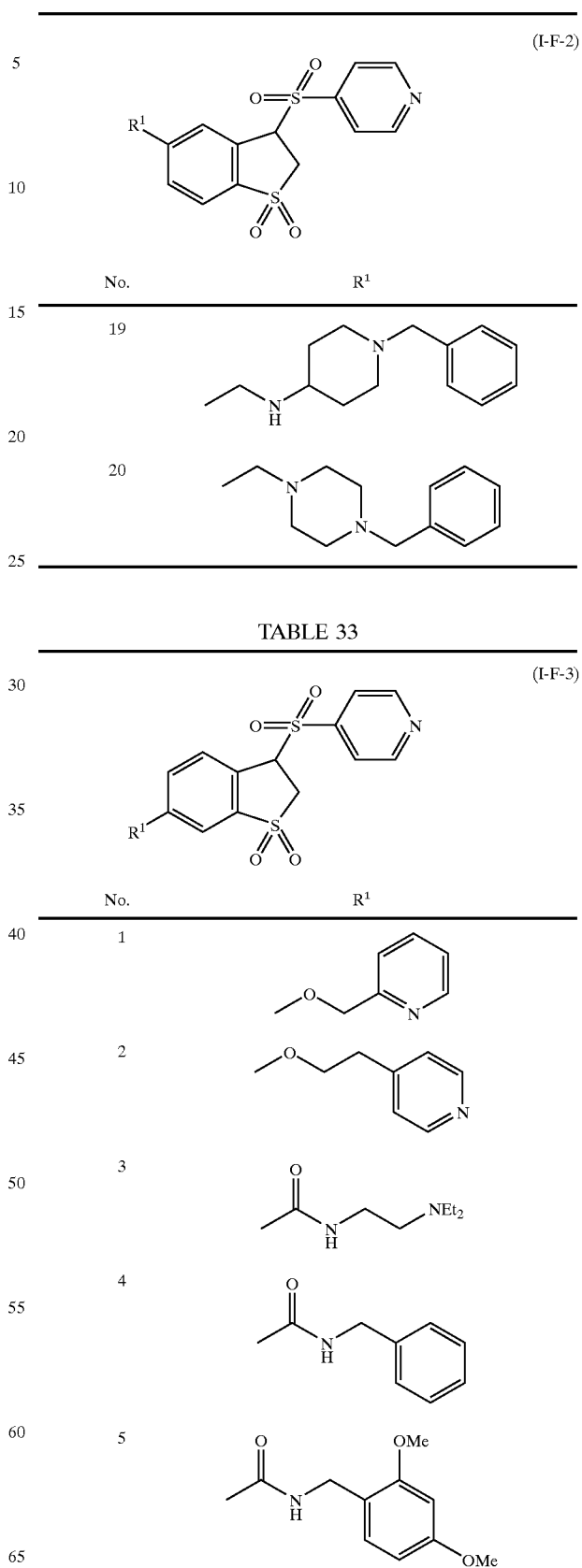

TABLE 33-continued (I-F-3)

| No. | R¹ |
|---|---|
| 6 | CH₂C(O)NH-CH₂-(pyridin-3-yl) |
| 7 | CH₂C(O)NH-CH₂CH₂-(pyrrolidin-1-yl) |
| 8 | CH₂C(O)NH-CH₂CH₂CH₂-(pyrrolidin-1-yl) |
| 9 | CH₂C(O)NH-CH₂CH₂-(piperidin-1-yl) |
| 10 | CH₂C(O)NH-CH₂CH₂CH₂-(2-oxopyrrolidin-1-yl) |
| 11 | CH₂C(O)NH-(1-benzylpyrrolidin-3-yl) |
| 12 | CH₂C(O)NH-(1-benzylpiperidin-4-yl) |
| 13 | CH₂C(O)-(4-benzylpiperazin-1-yl) |
| 14 | CH₂C(O)NH-CH₂CH₂-N(Et)(3-methylphenyl) |
| 15 | CH₂CH₂NH-CH₂-phenyl |
| 16 | CH₂CH₂NH-CH₂-(2,4-dimethoxyphenyl) |
| 17 | CH₂CH₂NH-CH₂-(pyridin-3-yl) |
| 18 | CH₂CH₂NH-CH₂CH₂-(piperidin-1-yl) |
| 19 | CH₂CH₂NH-(1-benzylpiperidin-4-yl) |
| 20 | CH₂CH₂-(4-benzylpiperazin-1-yl) |

TABLE 34

(I-F-4)

| No. | R¹ |
|---|---|
| 1 | (pyridin-2-ylmethoxy) |
| 2 | (2-methoxyethyl-pyridin-4-yl) |
| 3 | -C(O)NH-CH₂CH₂-NEt₂ |
| 4 | -C(O)NH-CH₂-Ph |
| 5 | -C(O)NH-CH₂-(2,4-diOMe-Ph) |
| 6 | -C(O)NH-CH₂-(pyridin-3-yl) |
| 7 | -C(O)NH-CH₂CH₂-(pyrrolidin-1-yl) |
| 8 | -C(O)NH-CH₂CH₂CH₂-(pyrrolidin-1-yl) |
| 9 | -C(O)NH-CH₂CH₂-(piperidin-1-yl) |

TABLE 34-continued (I-F-4)

| No. | R¹ |
|---|---|
| 10 | -C(O)NH-CH₂CH₂CH₂-(2-oxopyrrolidin-1-yl) |
| 11 | -C(O)NH-(1-benzylpyrrolidin-3-yl) |
| 12 | -C(O)NH-(1-benzylpiperidin-4-yl) |
| 13 | -C(O)-(4-benzylpiperazin-1-yl) |
| 14 | -C(O)NH-CH₂CH₂-N(Et)(3-Me-Ph) |
| 15 | -NH-CH₂-Ph |
| 16 | -NH-CH₂-(2,4-diOMe-Ph) |
| 17 | -NH-CH₂-(pyridin-3-yl) |
| 18 | -NH-CH₂CH₂-(piperidin-1-yl) |

TABLE 34-continued (I-F-4)

| No. | R¹ |
|---|---|
| 19 | ethyl-NH-(1-benzylpiperidin-4-yl) |
| 20 | 4-ethyl-1-benzylpiperazine |

TABLE 35

(I-G-1)

| No. | R¹ |
|---|---|
| 1 | 2-(methoxymethyl)pyridine |
| 2 | 4-(2-methoxyethyl)pyridine |
| 3 | CH₃C(O)NH-CH₂CH₂-NEt₂ |
| 4 | CH₃C(O)NH-CH₂-phenyl |
| 5 | CH₃C(O)NH-CH₂-(2,4-dimethoxyphenyl) |

TABLE 35-continued (I-G-1)

| No. | R¹ |
|---|---|
| 6 | CH₃C(O)NH-CH₂-(pyridin-3-yl) |
| 7 | CH₃C(O)NH-CH₂CH₂-(pyrrolidin-1-yl) |
| 8 | CH₃C(O)NH-(CH₂)₃-(pyrrolidin-1-yl) |
| 9 | CH₃C(O)NH-CH₂CH₂-(piperidin-1-yl) |
| 10 | CH₃C(O)NH-(CH₂)₃-(2-oxopyrrolidin-1-yl) |
| 11 | CH₃C(O)NH-(1-benzylpyrrolidin-3-yl) |
| 12 | CH₃C(O)NH-(1-benzylpiperidin-4-yl) |
| 13 | CH₃C(O)-(4-benzylpiperazin-1-yl) |

TABLE 35-continued
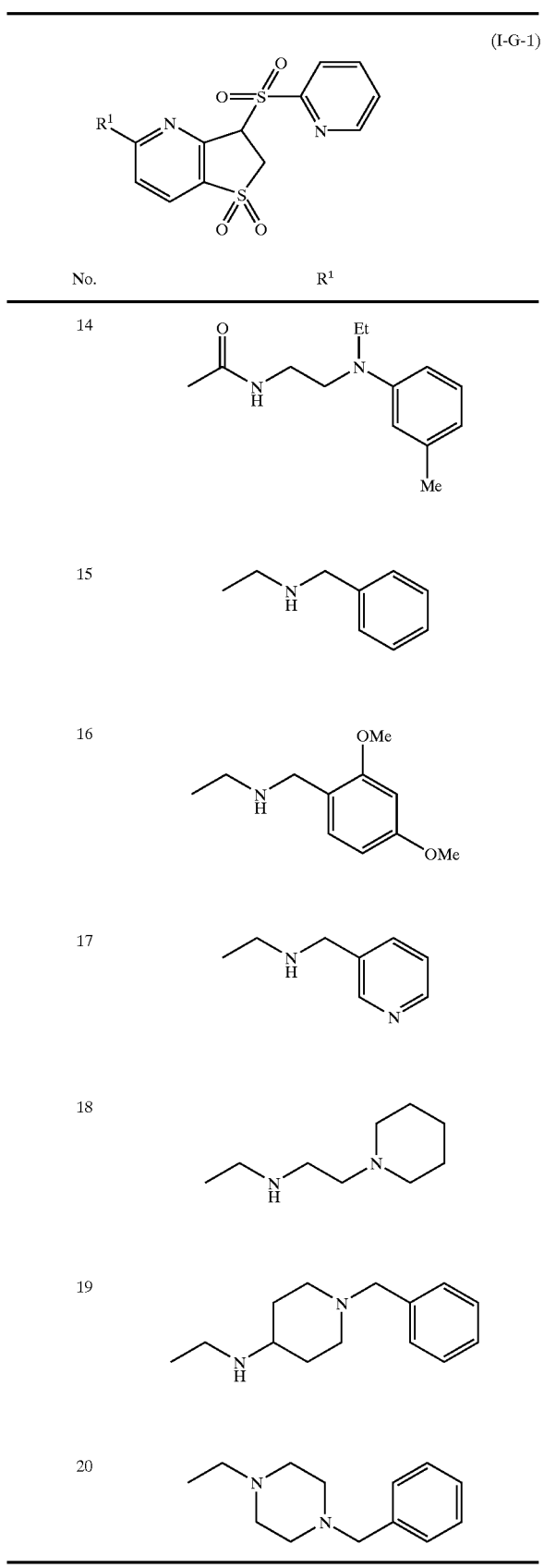
TABLE 36
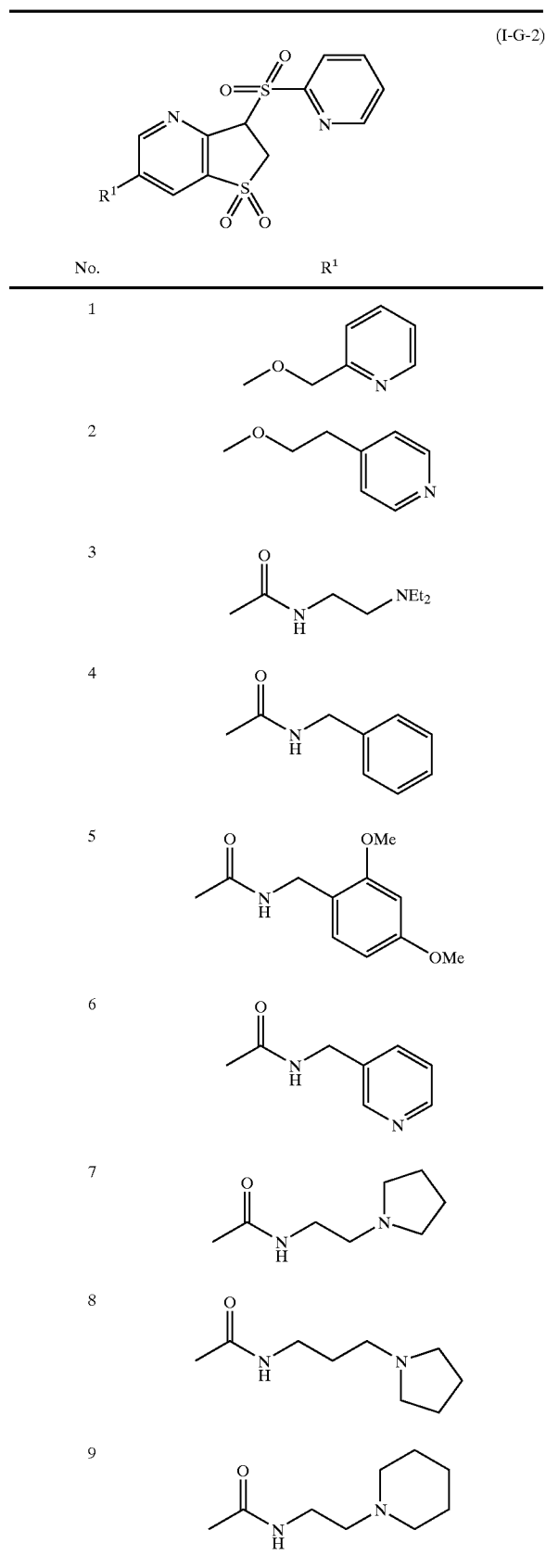

TABLE 36-continued (I-G-2)

| No. | R¹ |
|---|---|
| 10 | acetamido-propyl-(2-oxopyrrolidin-1-yl) |
| 11 | acetamido-(1-benzylpyrrolidin-3-yl) |
| 12 | acetamido-(1-benzylpiperidin-4-yl) |
| 13 | 1-acetyl-4-benzylpiperazine |
| 14 | acetamido-ethyl-N-ethyl-N-(3-methylphenyl)amino |
| 15 | ethylaminomethyl-phenyl (N-benzyl-ethylamine) |
| 16 | ethylaminomethyl-(2,4-dimethoxyphenyl) |
| 17 | ethylaminomethyl-(pyridin-3-yl) |
| 18 | ethylamino-ethyl-piperidin-1-yl |
| 19 | ethylamino-(1-benzylpiperidin-4-yl) |
| 20 | 1-ethyl-4-benzylpiperazine |

TABLE 37

(I-G-3)

| No. | R¹ |
|---|---|
| 1 | methoxymethyl-(pyridin-2-yl) |
| 2 | methoxyethyl-(pyridin-4-yl) |
| 3 | acetamido-ethyl-NEt₂ |
| 4 | acetamido-benzyl |
| 5 | acetamido-methyl-(2,4-dimethoxyphenyl) |

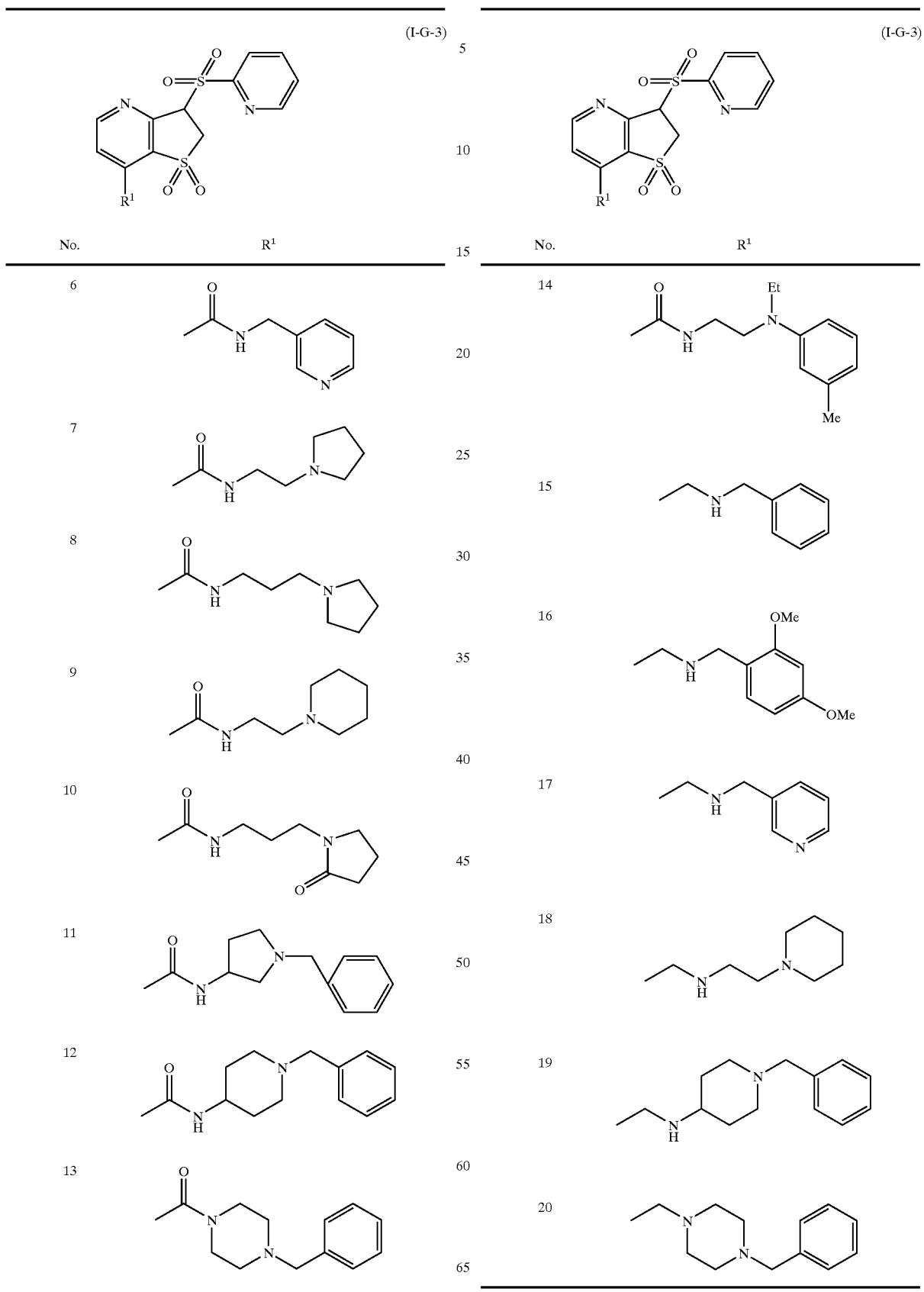

TABLE 38

(I-H-1)

| No. | R¹ |
|---|---|
| 1 | 2-(methoxymethyl)pyridine |
| 2 | 4-(2-methoxyethyl)pyridine |
| 3 | -C(=O)-NH-CH₂CH₂-NEt₂ |
| 4 | -C(=O)-NH-CH₂-Ph |
| 5 | -C(=O)-NH-CH₂-(2,4-dimethoxyphenyl) |
| 6 | -C(=O)-NH-CH₂-(3-pyridyl) |
| 7 | -C(=O)-NH-CH₂CH₂-(1-pyrrolidinyl) |
| 8 | -C(=O)-NH-CH₂CH₂CH₂-(1-pyrrolidinyl) |
| 9 | -C(=O)-NH-CH₂CH₂-(1-piperidinyl) |

TABLE 38-continued (I-H-1)

| No. | R¹ |
|---|---|
| 10 | -C(=O)-NH-CH₂CH₂CH₂-(2-oxo-1-pyrrolidinyl) |
| 11 | -C(=O)-NH-(1-benzyl-pyrrolidin-3-yl) |
| 12 | -C(=O)-NH-(1-benzyl-piperidin-4-yl) |
| 13 | -C(=O)-(4-benzyl-piperazin-1-yl) |
| 14 | -C(=O)-NH-CH₂CH₂-N(Et)-(3-methylphenyl) |
| 15 | -CH₂-NH-CH₂-Ph |
| 16 | -CH₂-NH-CH₂-(2,4-dimethoxyphenyl) |
| 17 | -CH₂-NH-CH₂-(3-pyridyl) |
| 18 | -CH₂-NH-CH₂CH₂-(1-piperidinyl) |

TABLE 38-continued
(I-H-1)
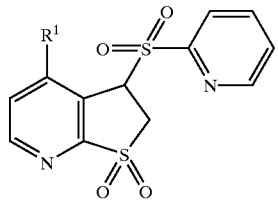
| No. | R¹ |
|---|---|
| 19 | 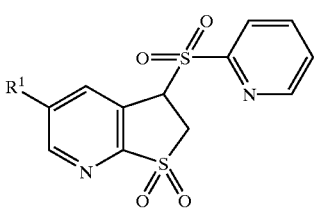 |
| 20 | 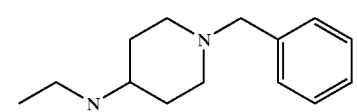 |
TABLE 39
(I-H-2)
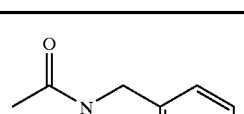
| No. | R¹ |
|---|---|
| 1 | 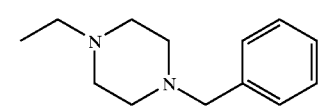 |
| 2 | 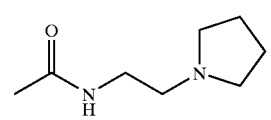 |
| 3 | 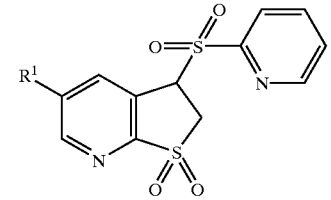 |
| 4 | 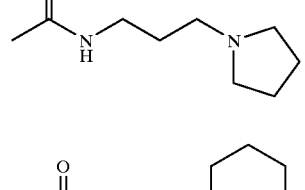 |
| 5 | 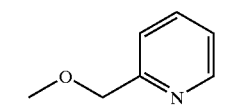 |
TABLE 39-continued
(I-H-2)
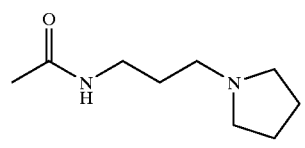
| No. | R¹ |
|---|---|
| 6 | 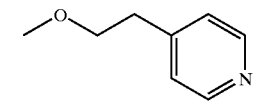 |
| 7 | 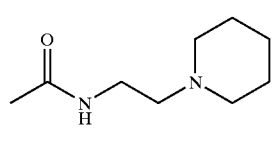 |
| 8 | 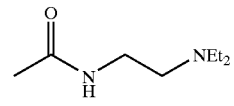 |
| 9 | 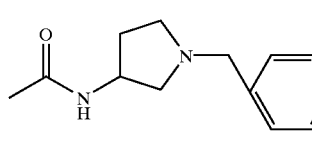 |
| 10 | 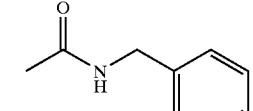 |
| 11 | 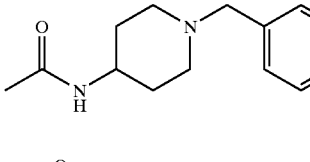 |
| 12 | 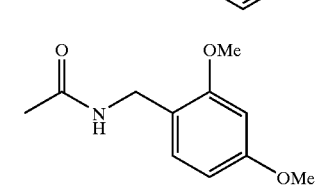 |
| 13 | 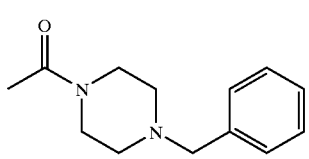 |

TABLE 39-continued
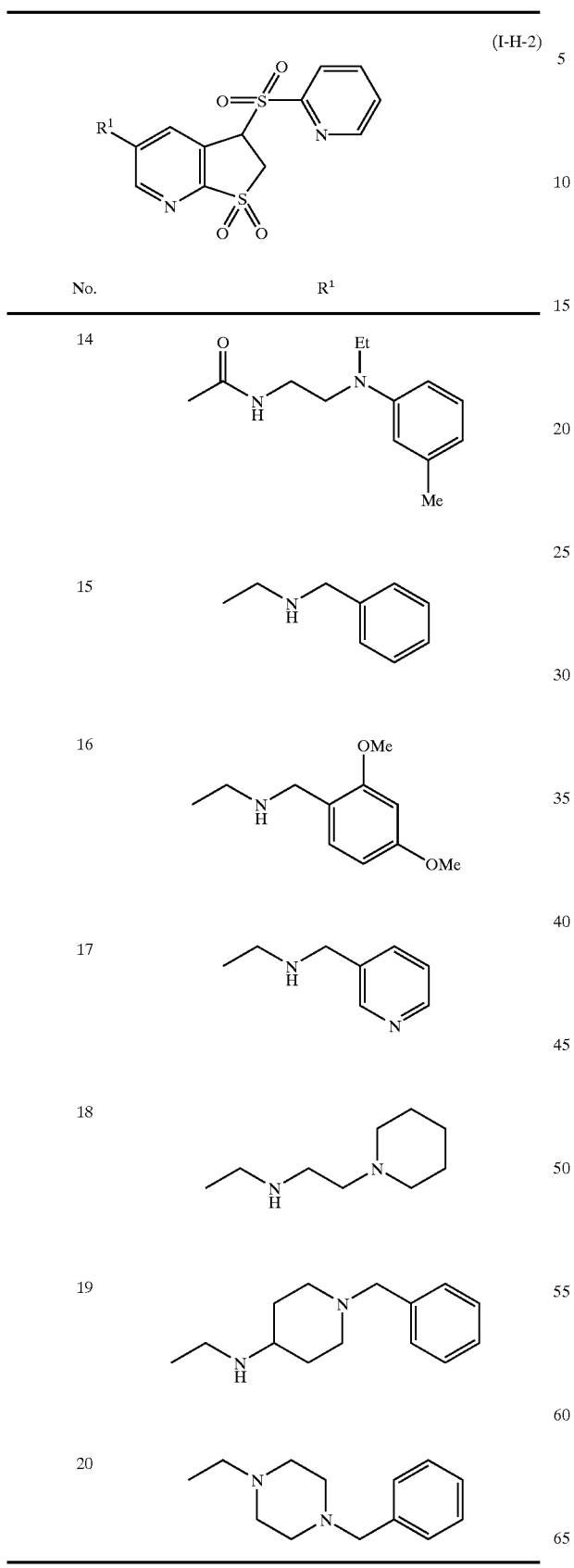
TABLE 40
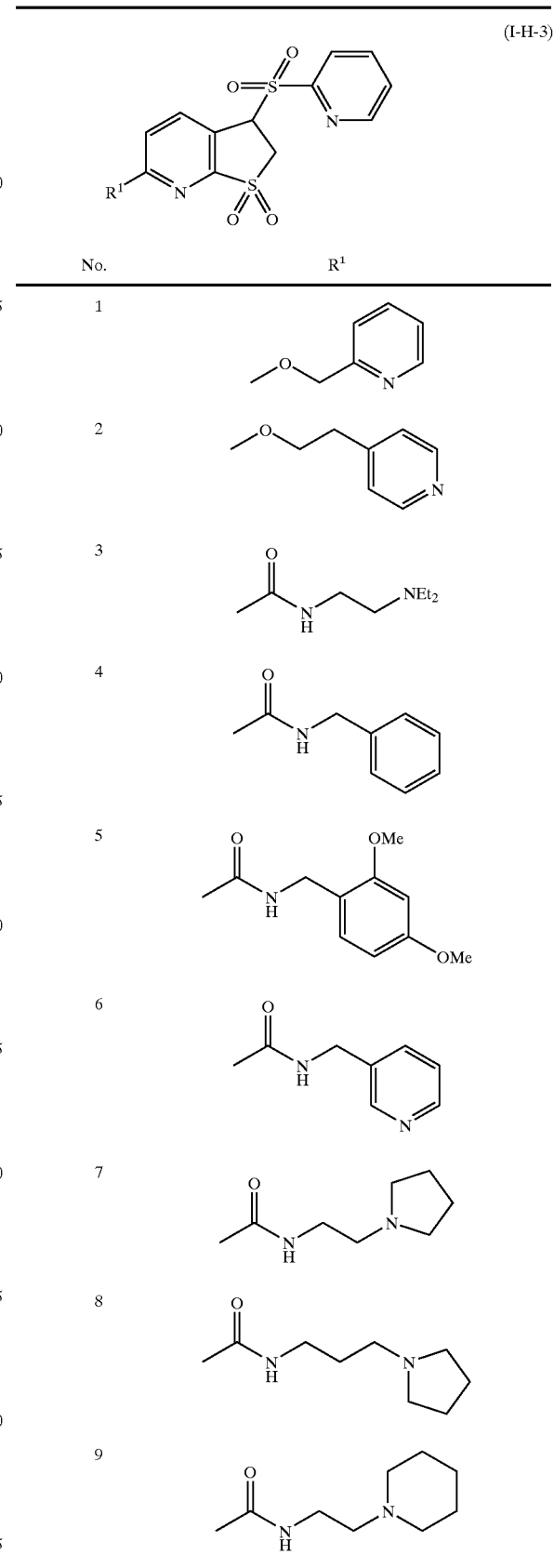

TABLE 40-continued (I-H-3)

| No. | R¹ |
|---|---|
| 10 | acetamido-propyl-(2-oxopyrrolidin-1-yl) |
| 11 | acetamido-(1-benzylpyrrolidin-3-yl) |
| 12 | acetamido-(1-benzylpiperidin-4-yl) |
| 13 | 4-acetyl-1-benzylpiperazine |
| 14 | acetamido-ethyl-N-ethyl-N-(3-methylphenyl)amino |
| 15 | ethylamino-benzyl |
| 16 | ethylamino-methyl-(2,4-dimethoxyphenyl) |
| 17 | ethylamino-methyl-(pyridin-3-yl) |
| 18 | ethylamino-ethyl-piperidin-1-yl |

TABLE 40-continued (I-H-3)

| No. | R¹ |
|---|---|
| 19 | ethylamino-(1-benzylpiperidin-4-yl) |
| 20 | 1-ethyl-4-benzylpiperazine |

TABLE 41

(I-J-1)

| No. | R¹ |
|---|---|
| 1 | methoxymethyl-(pyridin-2-yl) |
| 2 | methoxyethyl-(pyridin-4-yl) |
| 3 | acetamido-ethyl-NEt₂ |
| 4 | acetamido-benzyl |
| 5 | acetamido-methyl-(2,4-dimethoxyphenyl) |

TABLE 41-continued (I-J-1)

| No. | R¹ |
|---|---|
| 6 | acetamidomethyl-pyridin-3-yl |
| 7 | acetamido-ethyl-pyrrolidin-1-yl |
| 8 | acetamido-propyl-pyrrolidin-1-yl |
| 9 | acetamido-ethyl-piperidin-1-yl |
| 10 | acetamido-propyl-2-oxopyrrolidin-1-yl |
| 11 | acetamido-(1-benzylpyrrolidin-3-yl) |
| 12 | acetamido-(1-benzylpiperidin-4-yl) |
| 13 | 1-acetyl-4-benzylpiperazine |
| 14 | acetamido-ethyl-N-ethyl-N-(3-methylphenyl)amino |
| 15 | ethylamino-benzyl |
| 16 | ethylamino-methyl-(2,4-dimethoxyphenyl) |
| 17 | ethylamino-methyl-pyridin-3-yl |
| 18 | ethylamino-ethyl-piperidin-1-yl |
| 19 | ethylamino-(1-benzylpiperidin-4-yl) |
| 20 | 1-ethyl-4-benzylpiperazine |

TABLE 42
(I-J-2)
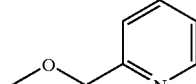
| No. | R¹ |
|---|---|
| 1 | 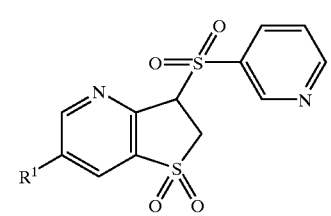 |
| 2 | 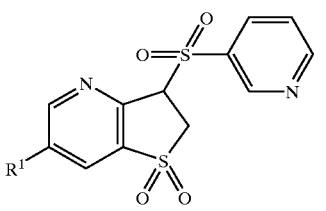 |
| 3 | 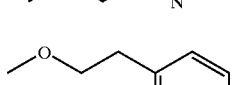 |
| 4 | 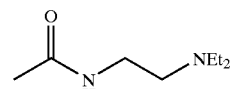 |
| 5 | 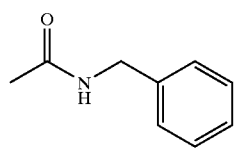 |
| 6 | 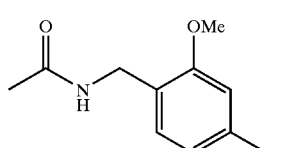 |
| 7 | 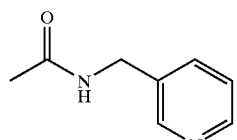 |
| 8 | 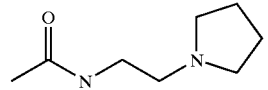 |
| 9 | 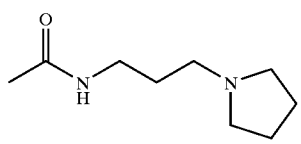 |
TABLE 42-continued
(I-J-2)
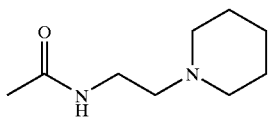
| No. | R¹ |
|---|---|
| 10 | 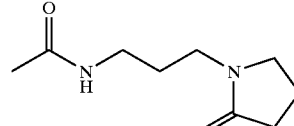 |
| 11 | 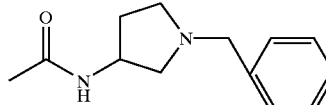 |
| 12 | 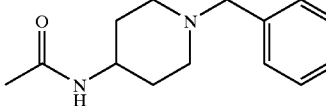 |
| 13 | 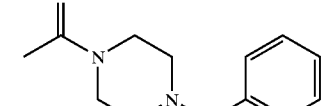 |
| 14 | 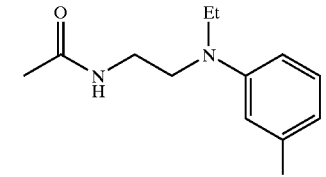 |
| 15 | 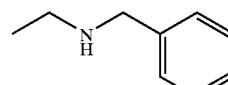 |
| 16 | 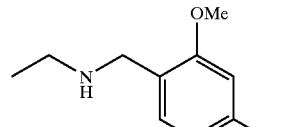 |
| 17 | 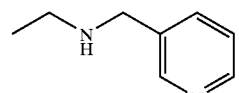 |
| 18 | 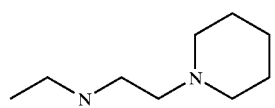 |

TABLE 42-continued
(I-J-2)
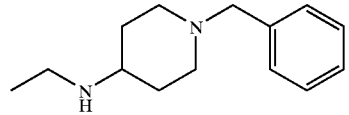
| No. | R¹ |
|---|---|
| 19 | 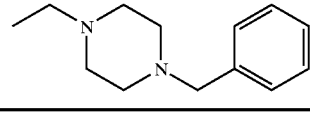 |
| 20 | 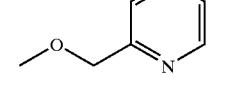 |
TABLE 43
(I-J-3)
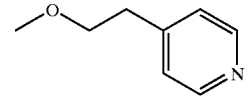
| No. | R¹ |
|---|---|
| 1 | 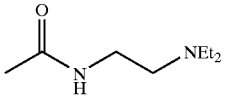 |
| 2 | 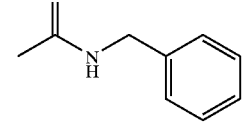 |
| 3 | 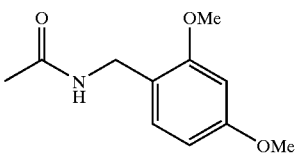 |
| 4 | 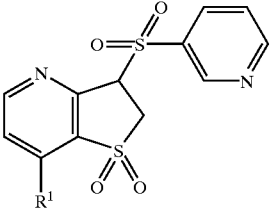 |
| 5 | 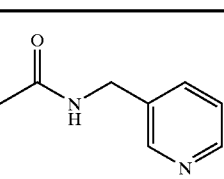 |
TABLE 43-continued
(I-J-3)
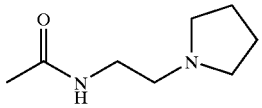
| No. | R¹ |
|---|---|
| 6 | 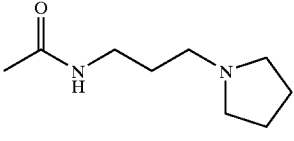 |
| 7 | 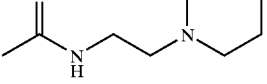 |
| 8 | 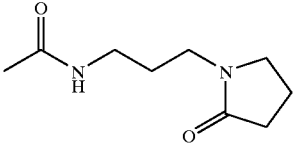 |
| 9 | 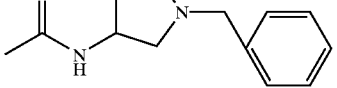 |
| 10 | 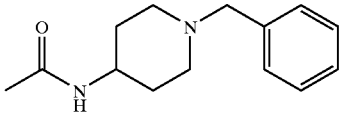 |
| 11 | 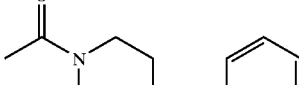 |
| 12 |  |
| 13 |  |

TABLE 43-continued (I-J-3)

| No. | R¹ |
|---|---|
| 14 | acetamide-ethyl-N(Et)-(3-methylphenyl) |
| 15 | N-ethyl-benzyl |
| 16 | N-ethyl-(2,4-dimethoxybenzyl) |
| 17 | N-ethyl-(3-pyridylmethyl) |
| 18 | N-ethyl-2-(piperidin-1-yl)ethyl |
| 19 | N-ethyl-(1-benzylpiperidin-4-yl) |
| 20 | N-ethyl-4-benzylpiperazinyl |

TABLE 44

(I-K-1)

| No. | R¹ |
|---|---|
| 1 | (2-pyridyl)methoxymethyl |
| 2 | 2-methoxyethyl-(4-pyridyl) |
| 3 | N-acetyl-ethyl-NEt₂ |
| 4 | N-acetyl-benzyl |
| 5 | N-acetyl-(2,4-dimethoxybenzyl) |
| 6 | N-acetyl-(3-pyridylmethyl) |
| 7 | N-acetyl-2-(pyrrolidin-1-yl)ethyl |
| 8 | N-acetyl-3-(pyrrolidin-1-yl)propyl |
| 9 | N-acetyl-2-(piperidin-1-yl)ethyl |

TABLE 44-continued
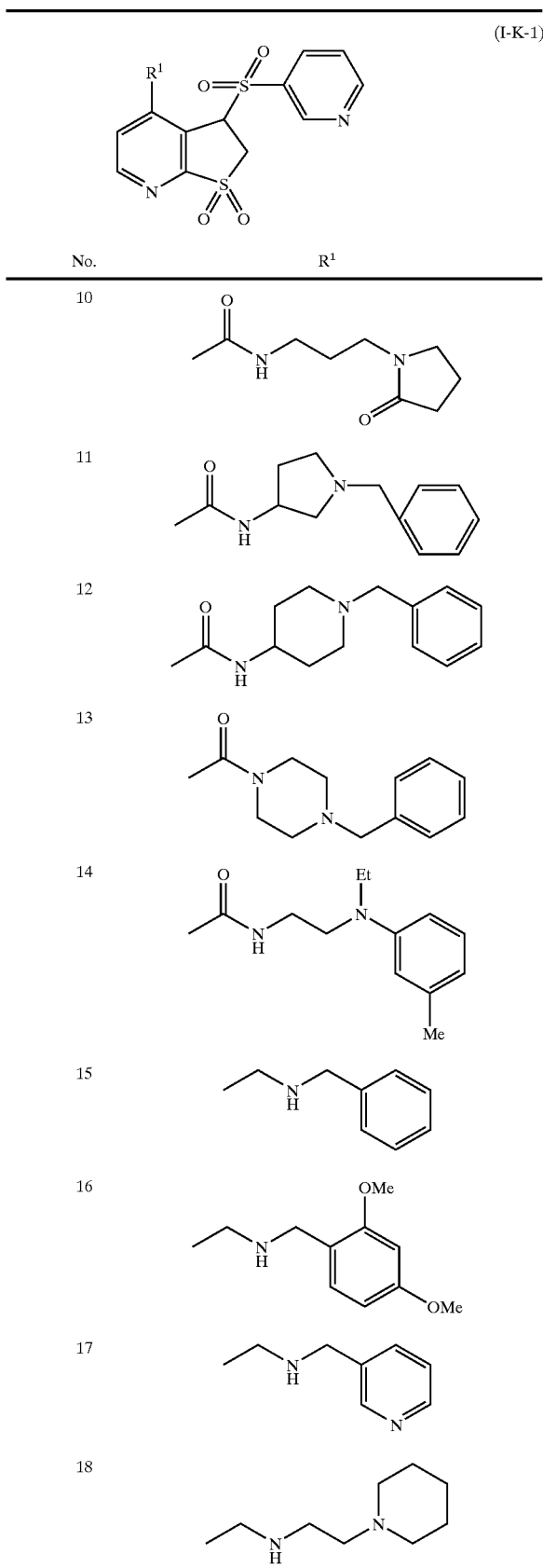
TABLE 45
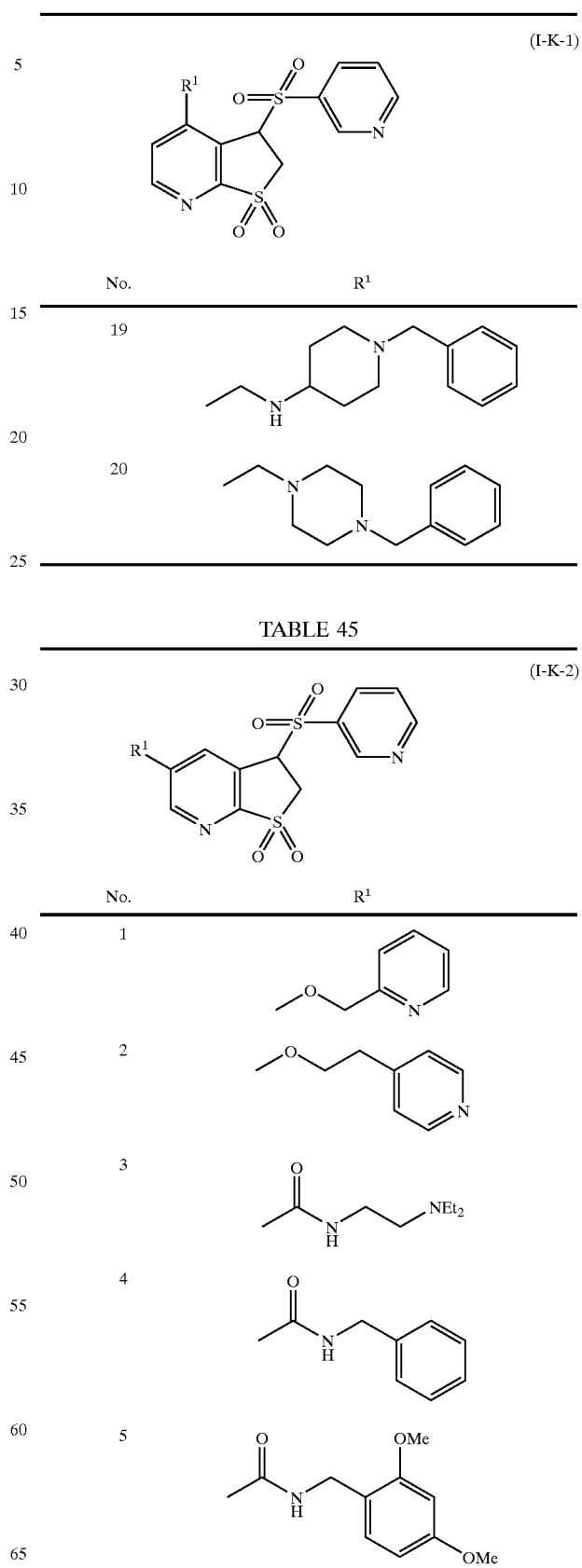

TABLE 45-continued
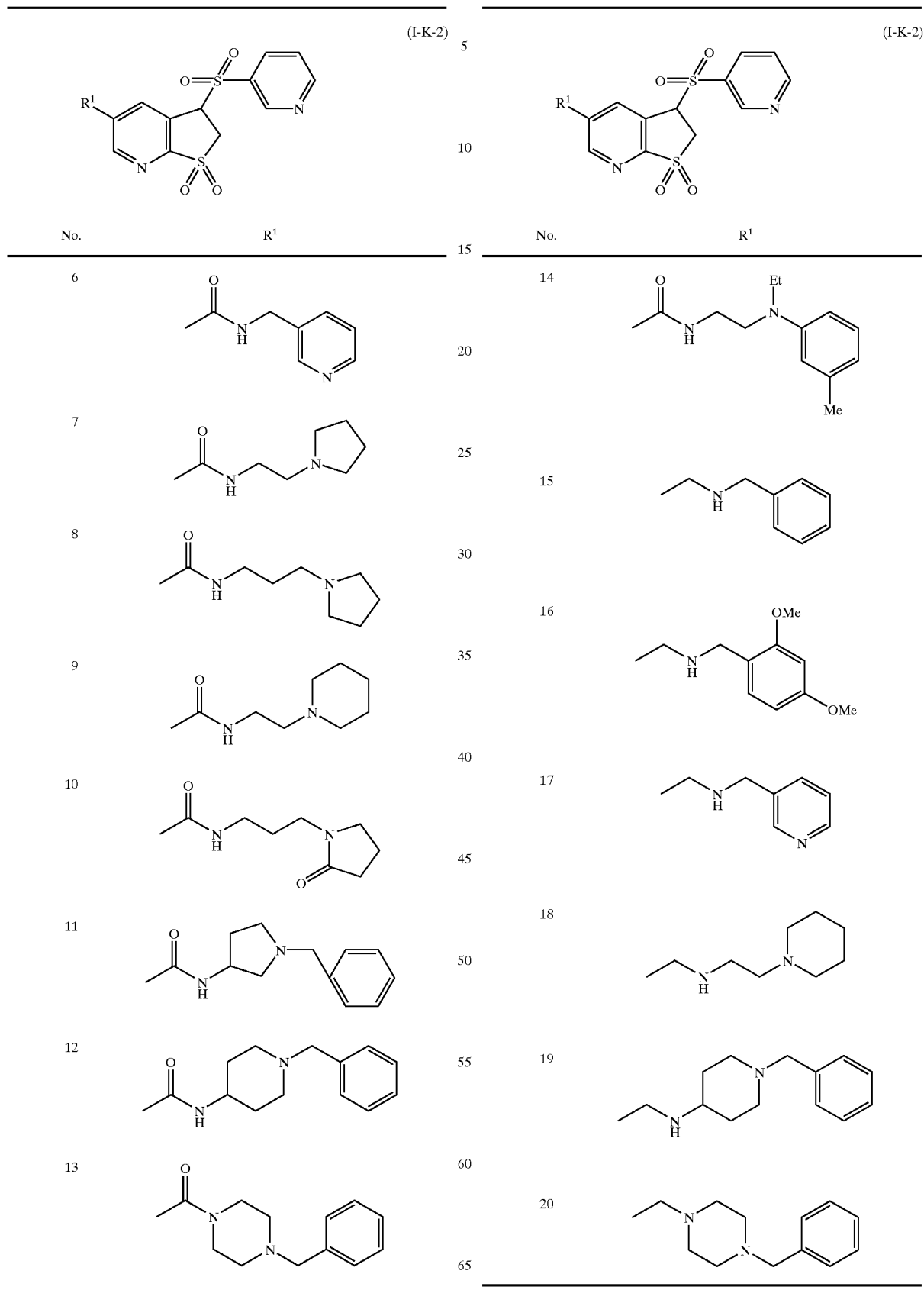

TABLE 46
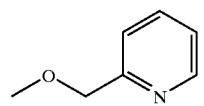
(I-K-3)
| No. | R¹ |
|---|---|
| 1 | 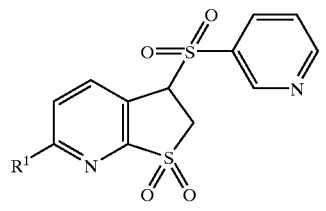 |
| 2 | 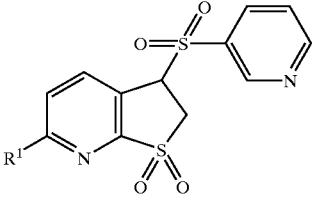 |
| 3 | 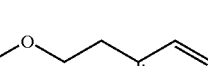 |
| 4 | 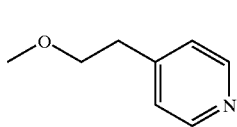 |
| 5 | 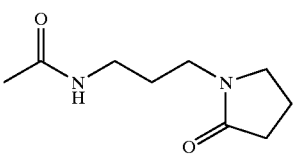 |
| 6 | 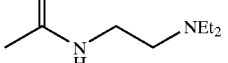 |
| 7 | 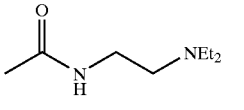 |
| 8 | 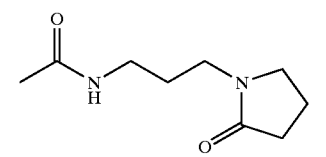 |
| 9 | 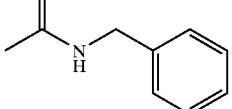 |
TABLE 46-continued
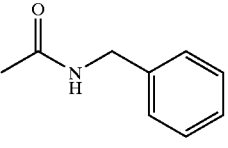
(I-K-3)
| No. | R¹ |
|---|---|
| 10 | 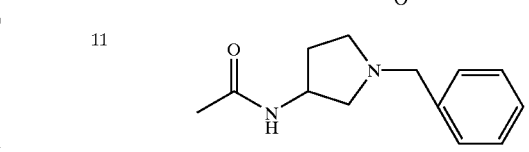 |
| 11 | 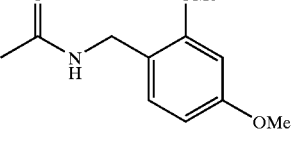 |
| 12 | 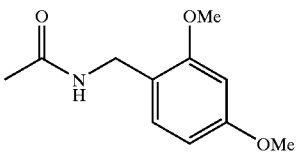 |
| 13 | 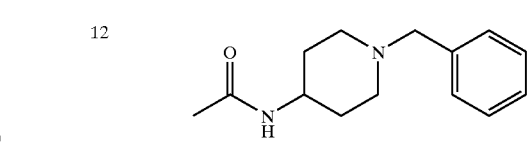 |
| 14 | 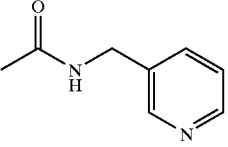 |
| 15 | 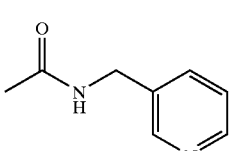 |
| 16 | 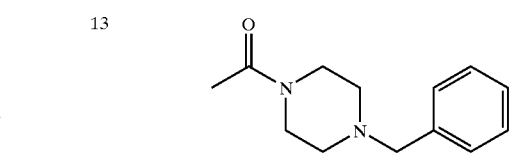 |
| 17 | 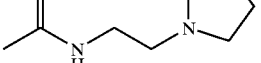 |
| 18 | 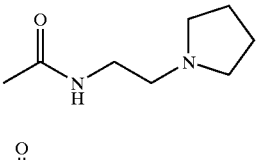 |

TABLE 46-continued (I-K-3)

| No. | R¹ |
|---|---|
| 19 | ethyl-NH-(1-benzylpiperidin-4-yl) |
| 20 | 4-ethyl-1-benzylpiperazine |

TABLE 47

(I-L-1)

| No. | R¹ |
|---|---|
| 1 | pyridin-2-yl-CH₂-O-Me |
| 2 | pyridin-4-yl-CH₂CH₂-O-Me |
| 3 | -C(O)-NH-CH₂CH₂-NEt₂ |
| 4 | -C(O)-NH-CH₂-Ph |
| 5 | -C(O)-NH-CH₂-(2,4-dimethoxyphenyl) |

TABLE 47-continued (I-L-1)

| No. | R¹ |
|---|---|
| 6 | -C(O)-NH-CH₂-(pyridin-3-yl) |
| 7 | -C(O)-NH-CH₂CH₂-(pyrrolidin-1-yl) |
| 8 | -C(O)-NH-CH₂CH₂CH₂-(pyrrolidin-1-yl) |
| 9 | -C(O)-NH-CH₂CH₂-(piperidin-1-yl) |
| 10 | -C(O)-NH-CH₂CH₂CH₂-(2-oxopyrrolidin-1-yl) |
| 11 | -C(O)-NH-(1-benzylpyrrolidin-3-yl) |
| 12 | -C(O)-NH-(1-benzylpiperidin-4-yl) |
| 13 | -C(O)-(4-benzylpiperazin-1-yl) |

TABLE 47-continued (I-L-1)

| No. | R¹ |
|---|---|
| 14 | N-ethyl-N-(3-methylphenyl) with acetamidoethyl chain |
| 15 | N-ethyl benzyl amine |
| 16 | N-ethyl 2,4-dimethoxybenzyl amine |
| 17 | N-ethyl 3-pyridylmethyl amine |
| 18 | N-ethyl 2-piperidinoethyl amine |
| 19 | N-ethyl 1-benzylpiperidin-4-yl amine |
| 20 | 1-ethyl-4-benzylpiperazine |

TABLE 48

(I-L-2)

| No. | R¹ |
|---|---|
| 1 | 2-pyridyl methoxymethyl |
| 2 | 4-pyridyl methoxyethyl |
| 3 | N-(2-diethylaminoethyl)acetamide |
| 4 | N-benzyl acetamide |
| 5 | N-(2,4-dimethoxybenzyl)acetamide |
| 6 | N-(3-pyridylmethyl)acetamide |
| 7 | N-(2-pyrrolidin-1-yl-ethyl)acetamide |
| 8 | N-(3-pyrrolidin-1-yl-propyl)acetamide |
| 9 | N-(2-piperidin-1-yl-ethyl)acetamide |

TABLE 48-continued
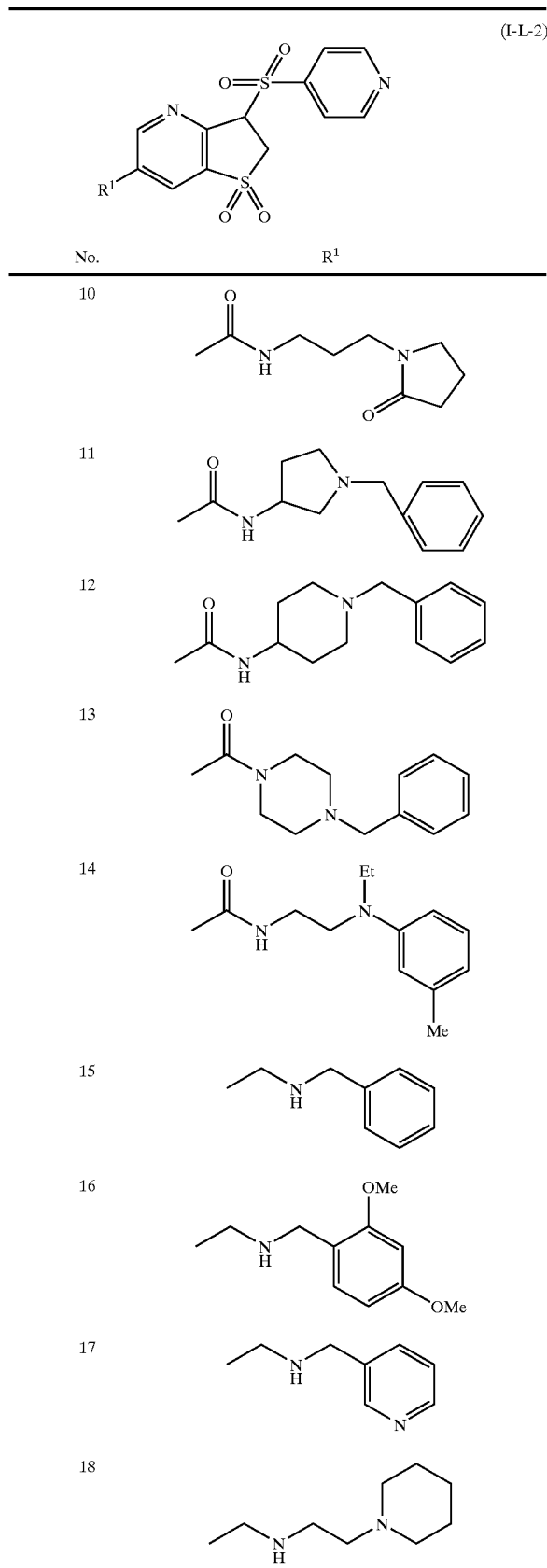
TABLE 48-continued
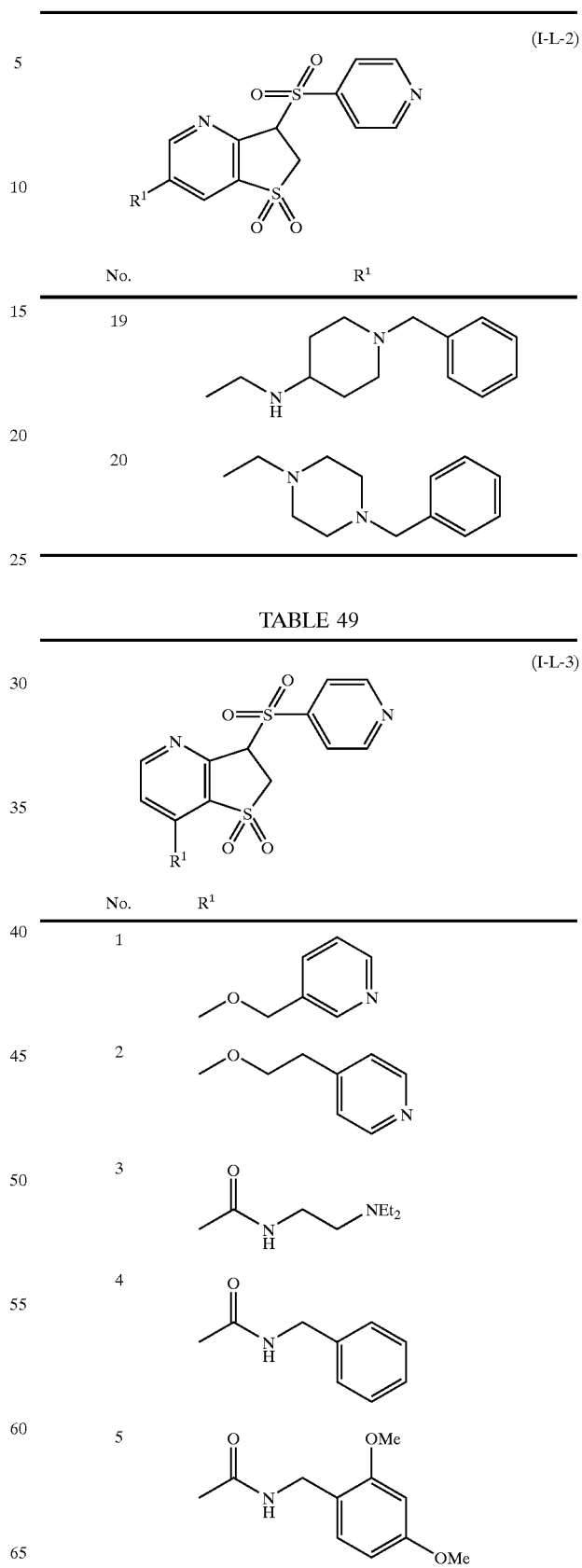

TABLE 49-continued
(I-L-3)
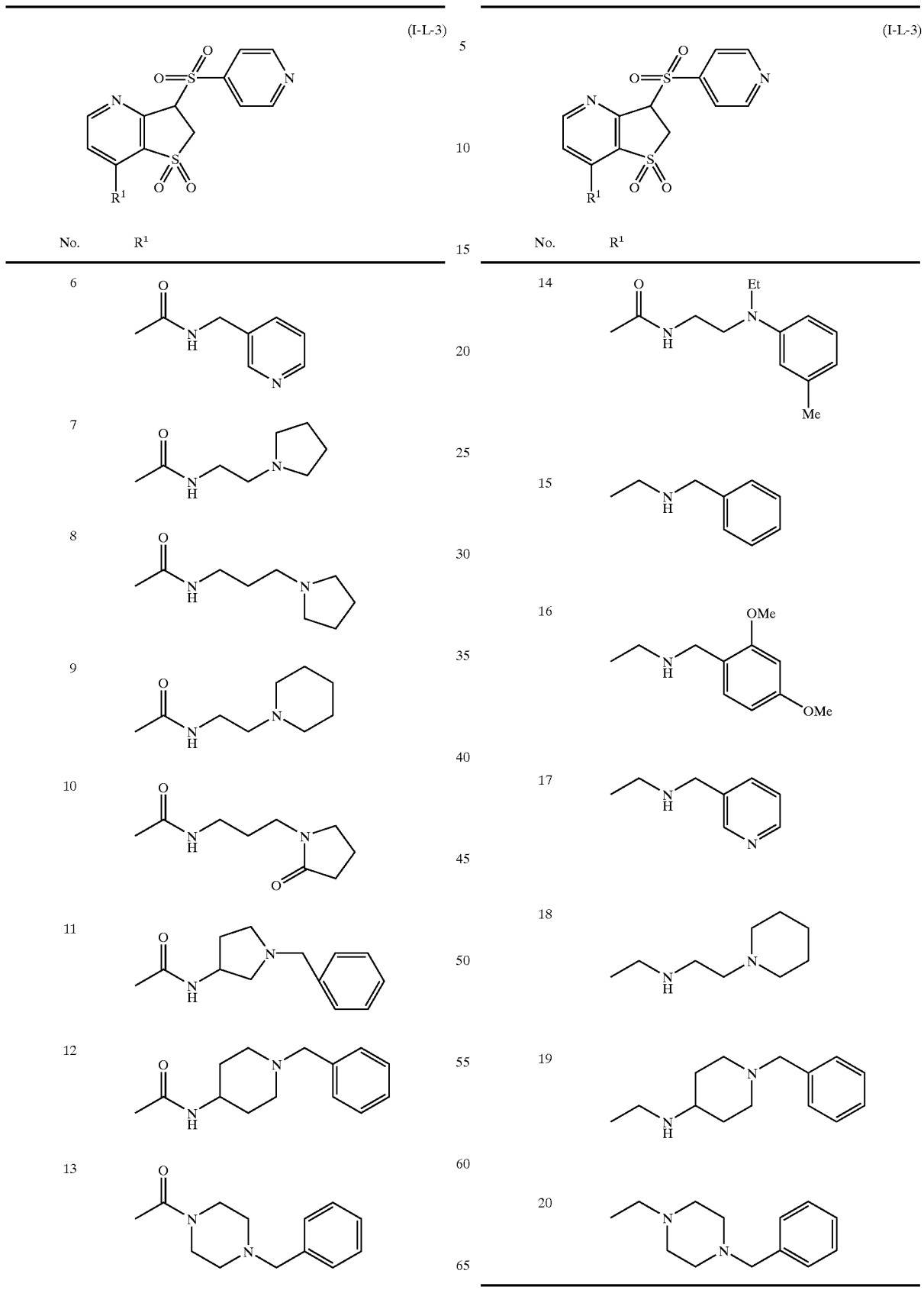

TABLE 50
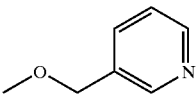
(I-M-1)
| No. | R¹ |
|---|---|
| 1 | 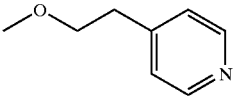 |
| 2 | 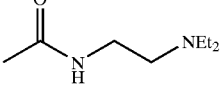 |
| 3 | 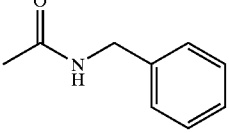 |
| 4 | 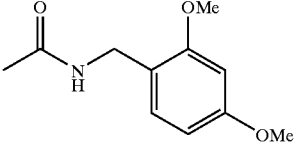 |
| 5 | 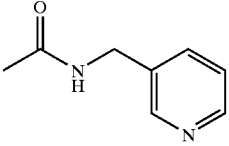 |
| 6 | 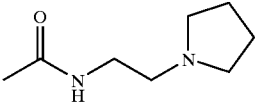 |
| 7 | 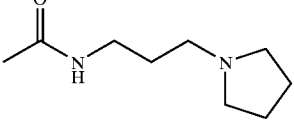 |
| 8 | 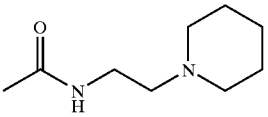 |
| 9 | 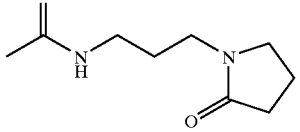 |
TABLE 50-continued
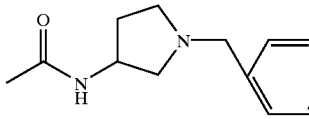
(I-M-1)
| No. | R¹ |
|---|---|
| 10 | 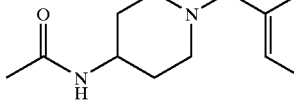 |
| 11 | 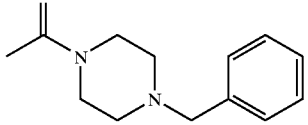 |
| 12 | 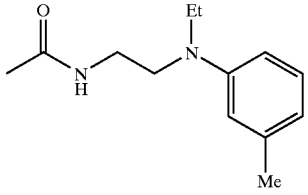 |
| 13 | 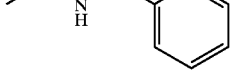 |
| 14 | 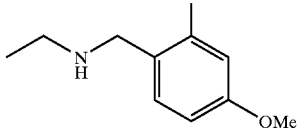 |
| 15 | 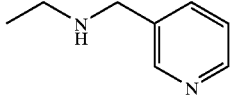 |
| 16 | 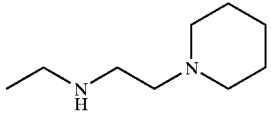 |
| 17 | |
| 18 | |

TABLE 50-continued
(I-M-1)
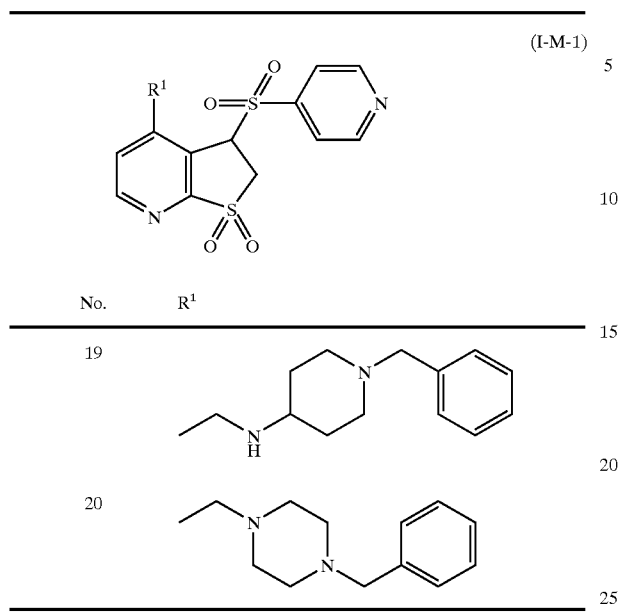
| No. | R¹ |
|---|---|
| 19 | |
| 20 | |
TABLE 51
(I-M-2)
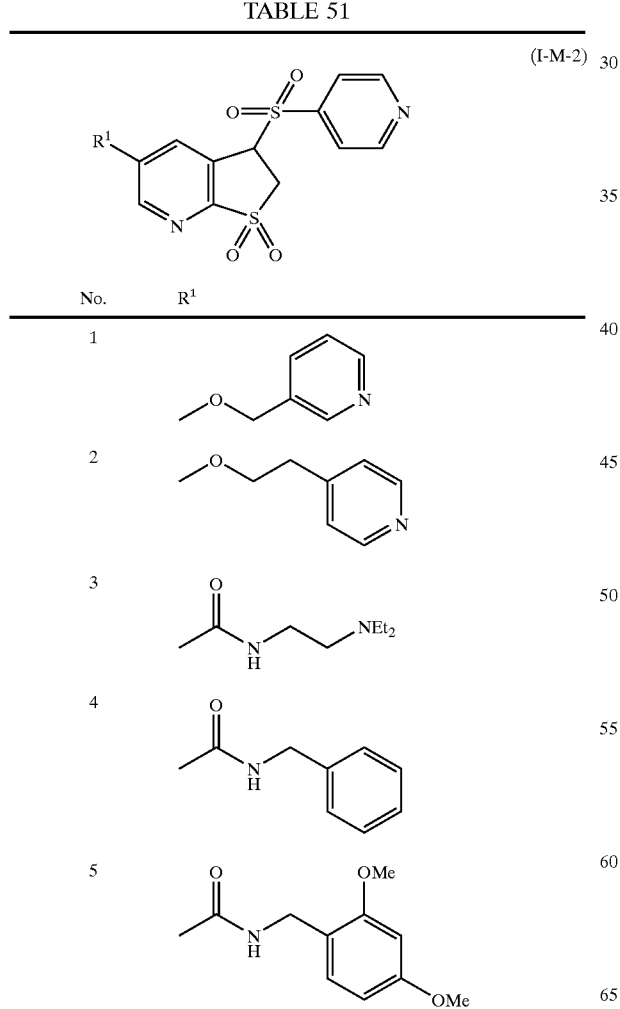
| No. | R¹ |
|---|---|
| 1 | |
| 2 | |
| 3 | |
| 4 | |
| 5 | |
TABLE 51-continued
(I-M-2)
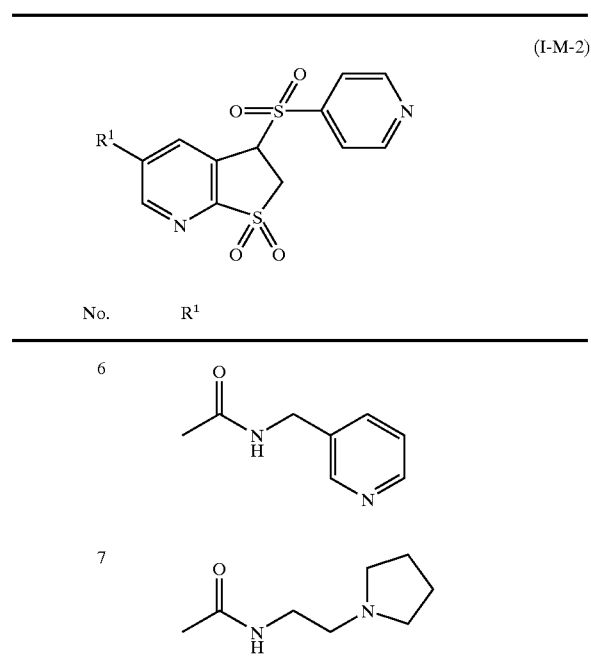
| No. | R¹ |
|---|---|
| 6 | |
| 7 | |
| 8 | |
| 9 | |
| 10 | |
| 11 | |
| 12 | |
| 13 | |

TABLE 51-continued
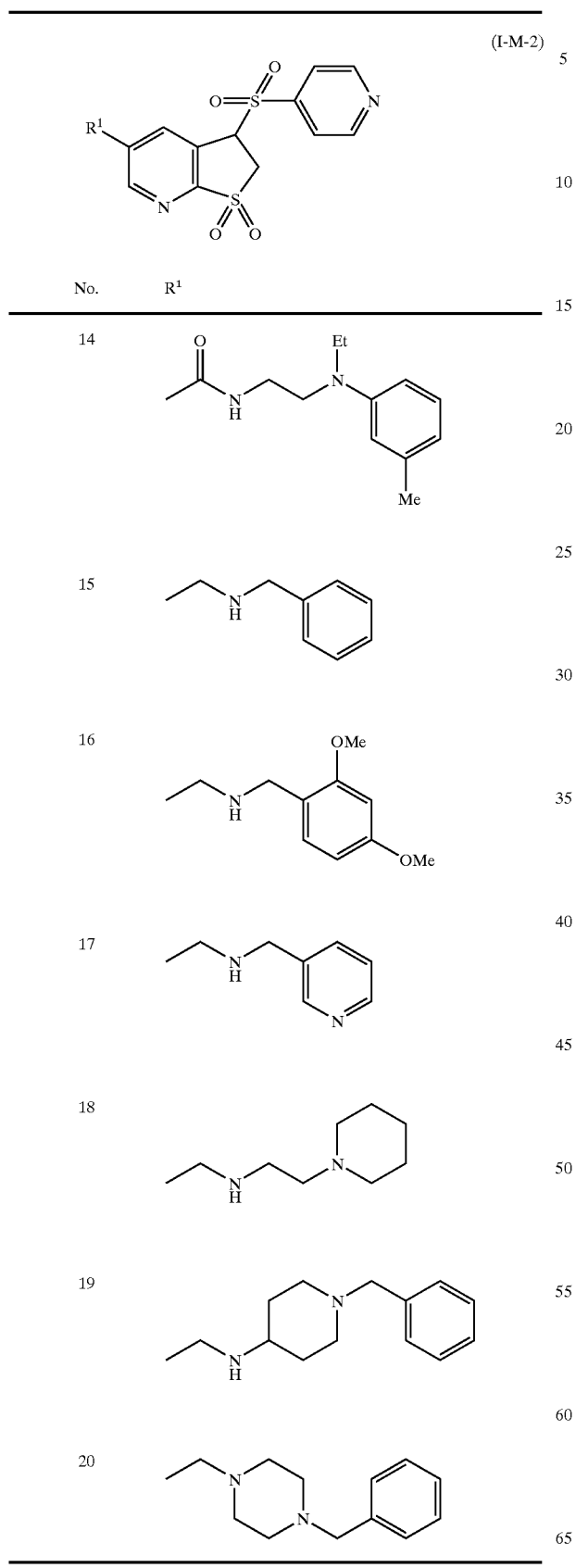
TABLE 52
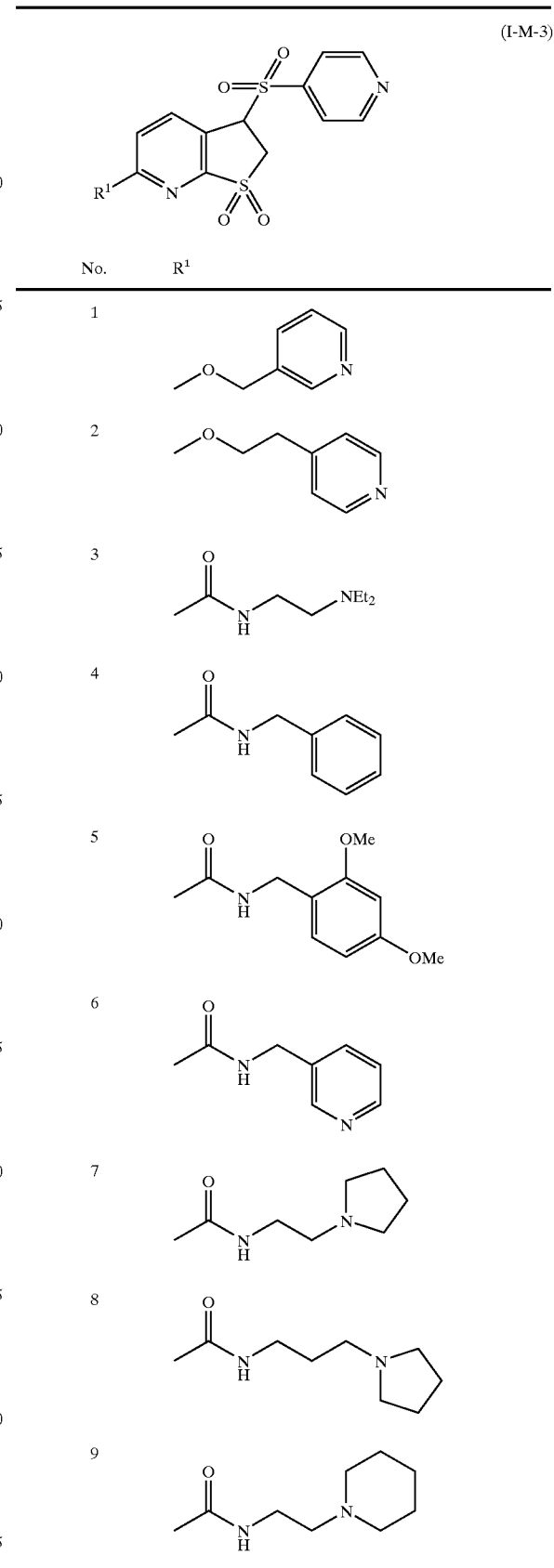

TABLE 52-continued
(I-M-3)
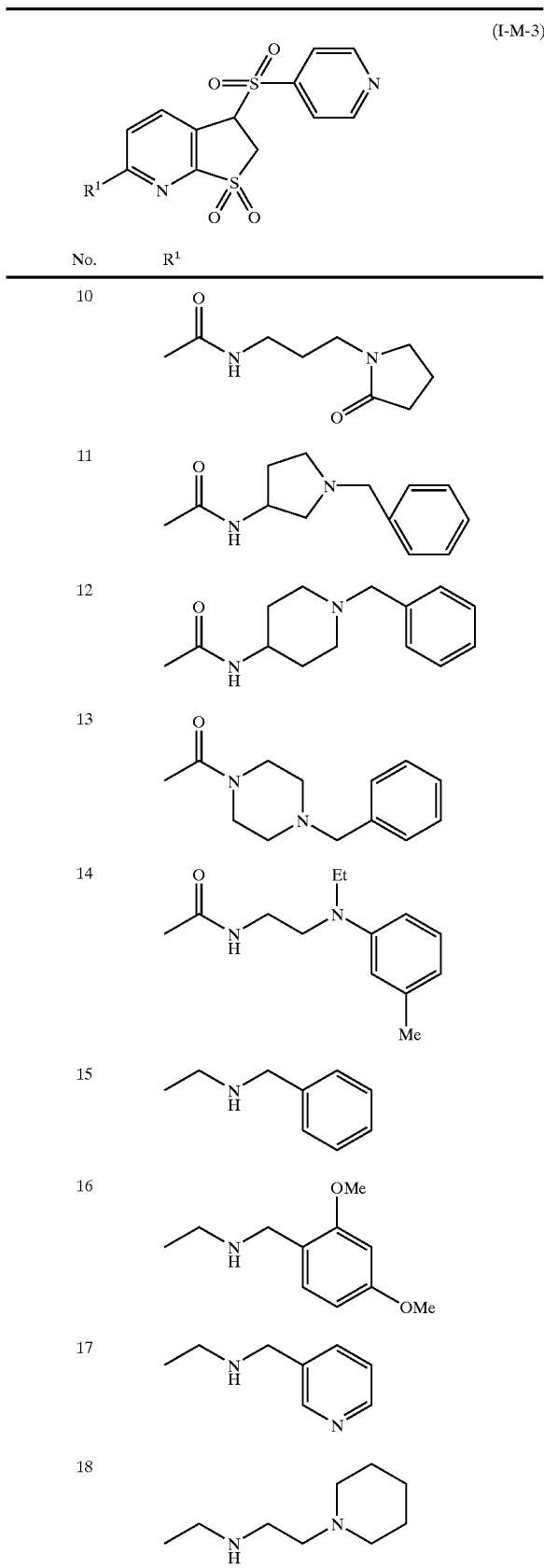
TABLE 52-continued
(I-M-3)
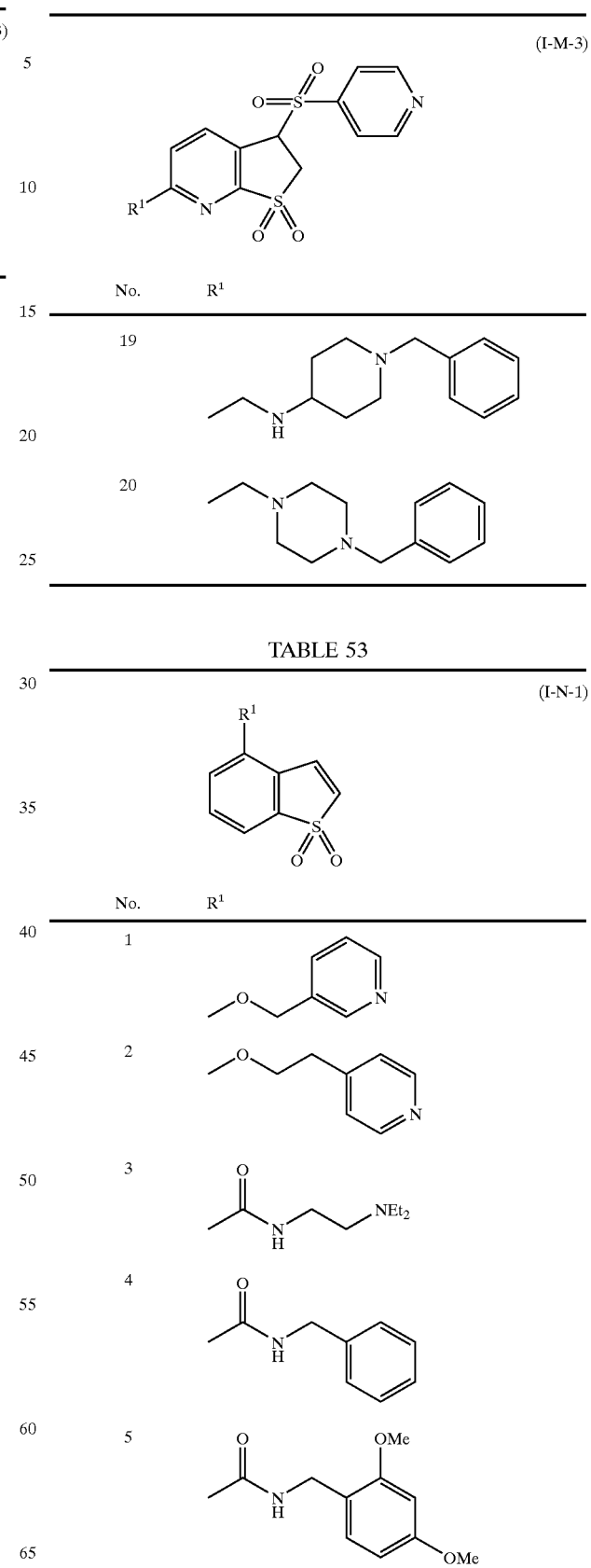
TABLE 53
(I-N-1)

TABLE 53-continued
(I-N-1)
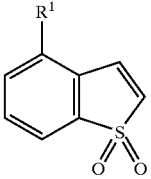
| No. | R¹ |
|---|---|
| 6 | 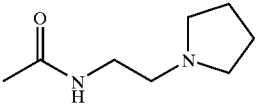 |
| 7 | 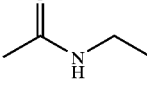 |
| 8 | 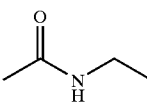 |
| 9 | 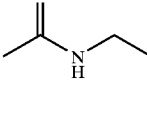 |
| 10 | 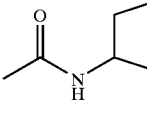 |
| 11 | 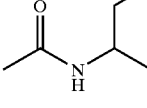 |
| 12 | 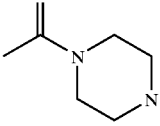 |
| 13 | 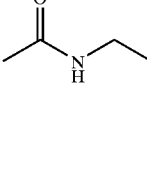 |
| 14 | 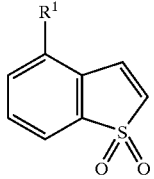 |
TABLE 53-continued
(I-N-1)
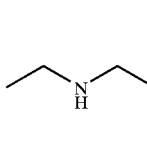
| No. | R¹ |
|---|---|
| 15 | 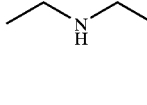 |
| 16 | 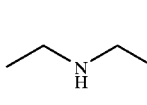 |
| 17 | 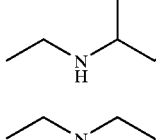 |
| 18 | 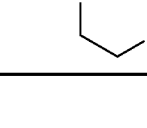 |
| 19 | 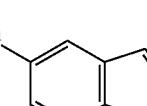 |
| 20 | 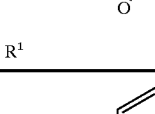 |
TABLE 54
(I-N-2)
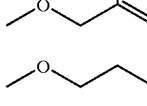
| No. | R¹ |
|---|---|
| 1 | 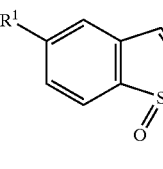 |
| 2 | 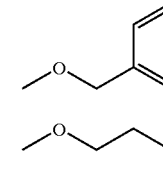 |

TABLE 54-continued (I-N-2)

[Structure: 5-R¹-benzo[b]thiophene 1,1-dioxide]

| No. | R¹ |
|---|---|
| 3 | -C(O)NH-CH₂CH₂-NEt₂ |
| 4 | -C(O)NH-CH₂-phenyl |
| 5 | -C(O)NH-CH₂-(2,4-dimethoxyphenyl) |
| 6 | -C(O)NH-CH₂-(3-pyridyl) |
| 7 | -C(O)NH-CH₂CH₂-(1-pyrrolidinyl) |
| 8 | -C(O)NH-CH₂CH₂CH₂-(1-pyrrolidinyl) |
| 9 | -C(O)NH-CH₂CH₂-(1-piperidinyl) |
| 10 | -C(O)NH-CH₂CH₂CH₂-(2-oxo-1-pyrrolidinyl) |
| 11 | -C(O)NH-(1-benzyl-pyrrolidin-3-yl) |
| 12 | -C(O)NH-(1-benzyl-piperidin-4-yl) |
| 13 | -C(O)-(4-benzyl-piperazin-1-yl) |
| 14 | -C(O)NH-CH₂CH₂-N(Et)-(3-methylphenyl) |
| 15 | -CH₂-NH-CH₂-phenyl |
| 16 | -CH₂-NH-CH₂-(2,4-dimethoxyphenyl) |
| 17 | -CH₂-NH-CH₂-(3-pyridyl) |
| 18 | -CH₂-NH-CH₂CH₂-(1-piperidinyl) |
| 19 | -CH₂-NH-(1-benzyl-piperidin-4-yl) |
| 20 | -CH₂-(4-benzyl-piperazin-1-yl) |

TABLE 55

(I-N-3)

Structure: 6-R¹-benzo[b]thiophene 1,1-dioxide

| No. | R¹ |
|---|---|
| 1 | -OCH₂-(pyridin-3-yl) |
| 2 | -OCH₂CH₂-(pyridin-4-yl) |
| 3 | -NHC(O)CH₂CH₂NEt₂ (acetamide with -CH₂CH₂NEt₂) |
| 4 | -NHC(O)CH₂-benzyl (N-benzyl acetamide) |
| 5 | -NHC(O)CH₂-(2,4-dimethoxybenzyl) |
| 6 | -NHC(O)CH₂-(pyridin-3-ylmethyl) |
| 7 | -NHC(O)CH₂-CH₂CH₂-(pyrrolidin-1-yl) |
| 8 | -NHC(O)CH₂-CH₂CH₂CH₂-(pyrrolidin-1-yl) |
| 9 | -NHC(O)CH₂-CH₂CH₂-(piperidin-1-yl) |
| 10 | -NHC(O)CH₂-CH₂CH₂CH₂-(2-oxopyrrolidin-1-yl) |

TABLE 55-continued (I-N-3)

| No. | R¹ |
|---|---|
| 11 | -NHC(O)CH₃ on 1-benzylpyrrolidin-3-yl |
| 12 | -NHC(O)CH₃ on 1-benzylpiperidin-4-yl |
| 13 | 1-acetyl-4-benzylpiperazine |
| 14 | -NHC(O)CH₂-CH₂CH₂-N(Et)(3-methylphenyl) |
| 15 | -NH-CH₂-phenyl (ethyl linker: -CH₂NH-benzyl) |
| 16 | -NH-CH₂-(2,4-dimethoxyphenyl) |
| 17 | -NH-CH₂-(pyridin-3-yl) |
| 18 | -NH-CH₂CH₂-(piperidin-1-yl) |
| 19 | -NH-(1-benzylpiperidin-4-yl) |

TABLE 55-continued
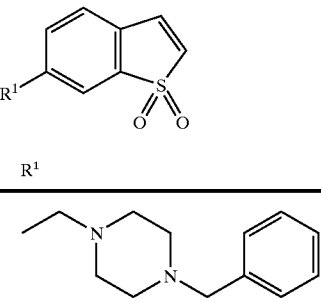
| No. | R¹ |
|---|---|
| 20 | |
TABLE 56
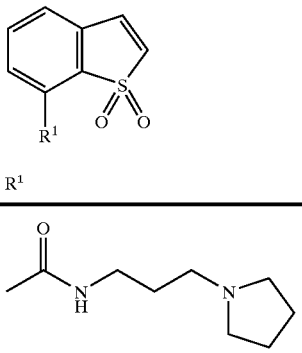
| No. | R¹ |
|---|---|
| 1 | |
| 2 | |
| 3 | |
| 4 | |
| 5 | |
| 6 | |
| 7 | |
TABLE 56-continued
| No. | R¹ |
|---|---|
| 8 | |
| 9 | |
| 10 | |
| 11 | |
| 12 | |
| 13 | |
| 14 | |
| 15 | |
| 16 | |

TABLE 56-continued (I-N-4)

| No. | R¹ |
|---|---|
| 17 | (ethylamino-methyl-pyridin-3-yl) |
| 18 | (ethylamino-ethyl-piperidinyl) |
| 19 | (ethylamino-(1-benzylpiperidin-4-yl)) |
| 20 | (1-ethyl-4-benzylpiperazinyl) |

TABLE 57

(I-O-1)

| No. | R¹ |
|---|---|
| 1 | methoxymethyl-pyridin-3-yl |
| 2 | methoxyethyl-pyridin-4-yl |
| 3 | acetamido-ethyl-NEt₂ |
| 4 | N-benzyl acetamide |

TABLE 57-continued (I-O-1)

| No. | R¹ |
|---|---|
| 5 | N-(2,4-dimethoxybenzyl)acetamide |
| 6 | N-(pyridin-3-ylmethyl)acetamide |
| 7 | N-(2-(pyrrolidin-1-yl)ethyl)acetamide |
| 8 | N-(3-(pyrrolidin-1-yl)propyl)acetamide |
| 9 | N-(2-(piperidin-1-yl)ethyl)acetamide |
| 10 | N-(3-(2-oxopyrrolidin-1-yl)propyl)acetamide |
| 11 | N-(1-benzylpyrrolidin-3-yl)acetamide |
| 12 | N-(1-benzylpiperidin-4-yl)acetamide |
| 13 | 1-acetyl-4-benzylpiperazine |

TABLE 57-continued (I-O-1)

| No. | R¹ |
|---|---|
| 14 | -CH2CH2-N(Ac-H)-... N(Et)(3-Me-C6H4) |
| 15 | -CH2-NH-CH2-C6H5 |
| 16 | -CH2-NH-CH2-(2,4-diOMe-C6H3) |
| 17 | -CH2-NH-CH2-(3-pyridyl) |
| 18 | -CH2-NH-CH2CH2-(piperidin-1-yl) |
| 19 | -CH2-NH-(1-benzylpiperidin-4-yl) |
| 20 | -CH2-(4-benzylpiperazin-1-yl) |

TABLE 58

(I-O-2)

| No. | R¹ |
|---|---|
| 1 | -CH2-O-CH2-(3-pyridyl) |

TABLE 58-continued (I-O-2)

| No. | R¹ |
|---|---|
| 2 | -CH2-O-CH2CH2-(4-pyridyl) |
| 3 | -CH2-C(O)-NH-CH2CH2-NEt2 |
| 4 | -CH2-C(O)-NH-CH2-C6H5 |
| 5 | -CH2-C(O)-NH-CH2-(2,4-diOMe-C6H3) |
| 6 | -CH2-C(O)-NH-CH2-(3-pyridyl) |
| 7 | -CH2-C(O)-NH-CH2CH2-(pyrrolidin-1-yl) |
| 8 | -CH2-C(O)-NH-CH2CH2CH2-(pyrrolidin-1-yl) |
| 9 | -CH2-C(O)-NH-CH2CH2-(piperidin-1-yl) |
| 10 | -CH2-C(O)-NH-CH2CH2CH2-(2-oxopyrrolidin-1-yl) |

TABLE 58-continued (I-O-2)

| No. | R¹ |
|---|---|
| 11 | acetamido-(1-benzylpyrrolidin-3-yl) |
| 12 | acetamido-(1-benzylpiperidin-4-yl) |
| 13 | 1-acetyl-4-benzylpiperazine |
| 14 | N-(2-(N-ethyl-3-methylanilino)ethyl)acetamide |
| 15 | benzylamino-ethyl |
| 16 | (2,4-dimethoxybenzyl)aminoethyl |
| 17 | (pyridin-3-ylmethyl)aminoethyl |
| 18 | (2-piperidin-1-ylethyl)aminoethyl |
| 19 | (1-benzylpiperidin-4-yl)aminoethyl |

TABLE 58-continued (I-O-2)

| No. | R¹ |
|---|---|
| 20 | 1-ethyl-4-benzylpiperazine |

TABLE 59

(I-O-3)

| No. | R¹ |
|---|---|
| 1 | (pyridin-3-yl)methoxymethyl |
| 2 | 2-(pyridin-4-yl)ethoxymethyl |
| 3 | N-(2-(diethylamino)ethyl)acetamide |
| 4 | N-benzylacetamide |
| 5 | N-(2,4-dimethoxybenzyl)acetamide |
| 6 | N-(pyridin-3-ylmethyl)acetamide |
| 7 | N-(2-pyrrolidin-1-ylethyl)acetamide |

TABLE 59-continued
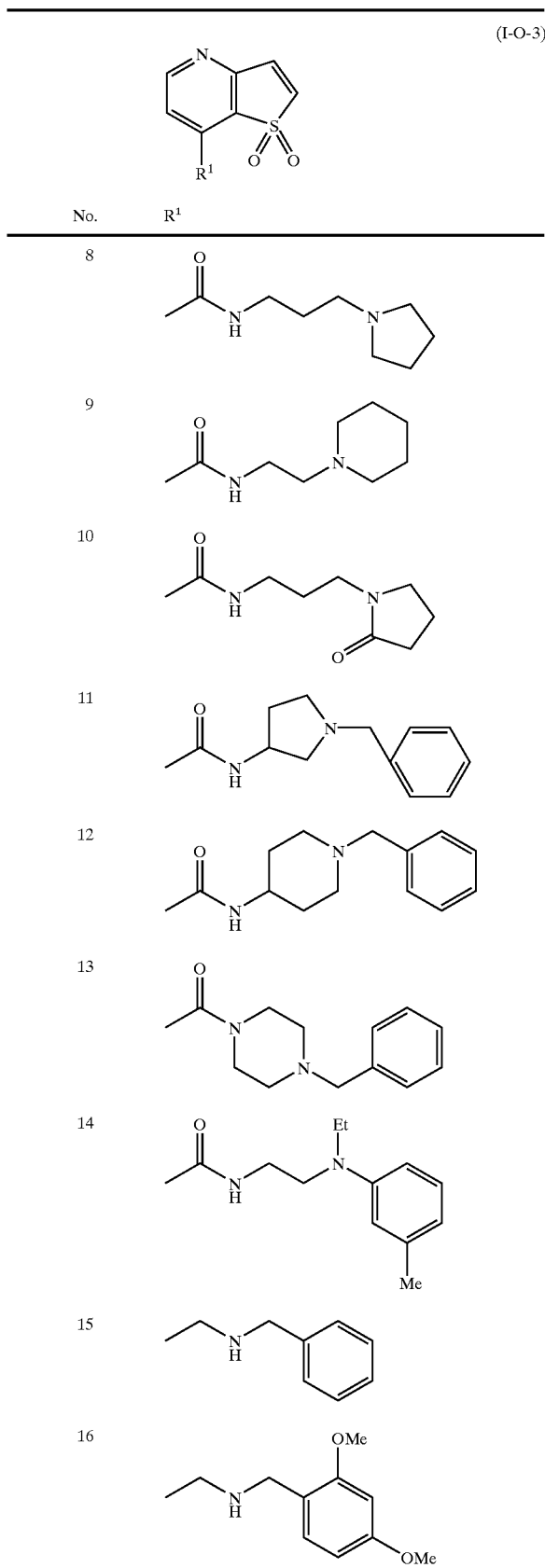
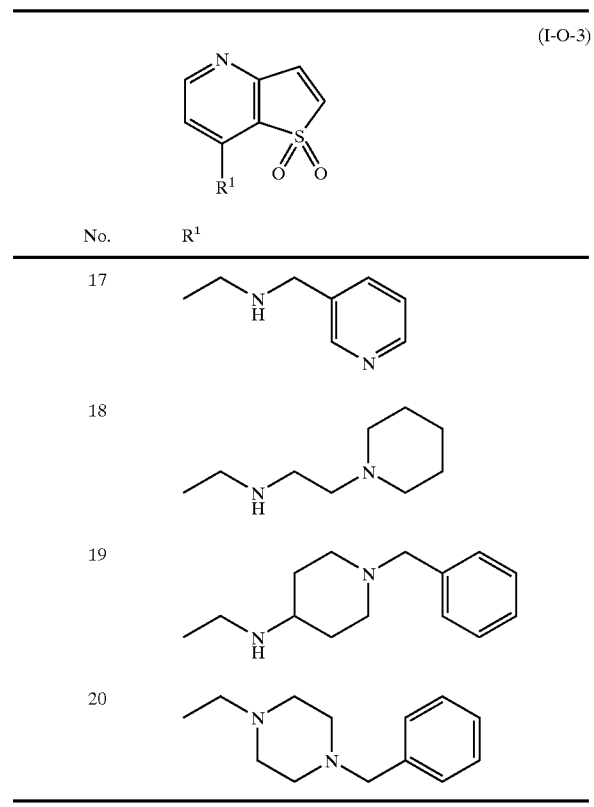
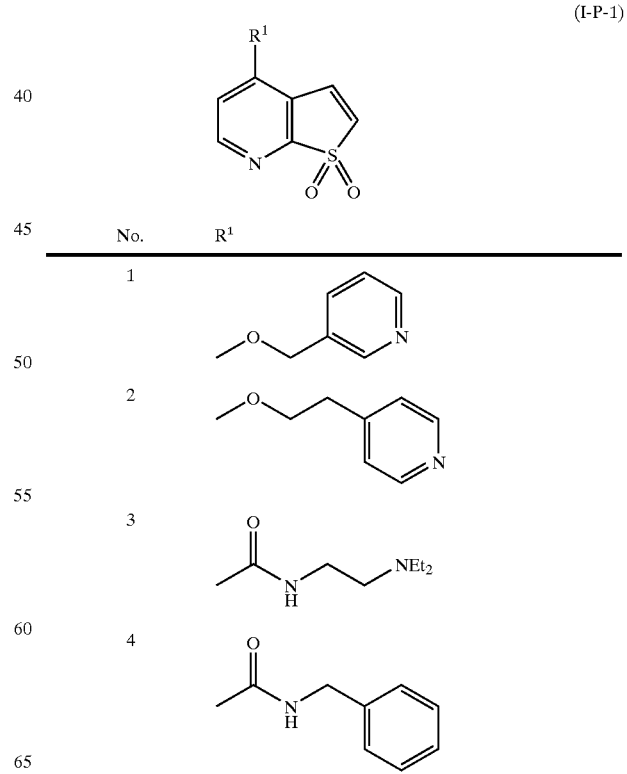

TABLE 60-continued (I-P-1)

| No. | R¹ |
|---|---|
| 5 | acetamido-CH2-(2,4-dimethoxyphenyl) |
| 6 | acetamido-CH2-(pyridin-3-yl) |
| 7 | acetamido-(CH2)2-pyrrolidin-1-yl |
| 8 | acetamido-(CH2)3-pyrrolidin-1-yl |
| 9 | acetamido-(CH2)2-piperidin-1-yl |
| 10 | acetamido-(CH2)3-(2-oxopyrrolidin-1-yl) |
| 11 | acetamido-(1-benzylpyrrolidin-3-yl) |
| 12 | acetamido-(1-benzylpiperidin-4-yl) |
| 13 | acetyl-(4-benzylpiperazin-1-yl) |
| 14 | acetamido-(CH2)2-N(Et)(3-methylphenyl) |
| 15 | NH-CH2-phenyl |
| 16 | NH-CH2-(2,4-dimethoxyphenyl) |
| 17 | NH-CH2-(pyridin-3-yl) |
| 18 | NH-(CH2)2-piperidin-1-yl |
| 19 | NH-(1-benzylpiperidin-4-yl) |
| 20 | 4-benzylpiperazin-1-yl |

TABLE 61

(I-P-2)

| No. | R¹ |
|---|---|
| 1 | -OCH2-(3-pyridyl) |
| 2 | -OCH2CH2-(4-pyridyl) |
| 3 | -C(O)NH-CH2CH2-NEt2 |
| 4 | -C(O)NH-CH2-phenyl |
| 5 | -C(O)NH-CH2-(2,4-dimethoxyphenyl) |
| 6 | -C(O)NH-CH2-(3-pyridyl) |
| 7 | -C(O)NH-CH2CH2-(1-pyrrolidinyl) |
| 8 | -C(O)NH-CH2CH2CH2-(1-pyrrolidinyl) |
| 9 | -C(O)NH-CH2CH2-(1-piperidinyl) |
| 10 | -C(O)NH-CH2CH2CH2-(2-oxo-1-pyrrolidinyl) |
| 11 | -C(O)NH-(1-benzyl-pyrrolidin-3-yl) |
| 12 | -C(O)NH-(1-benzyl-piperidin-4-yl) |
| 13 | -C(O)-(4-benzyl-piperazin-1-yl) |
| 14 | -C(O)NH-CH2CH2-N(Et)-(3-methylphenyl) |
| 15 | -CH2-NH-CH2-phenyl |
| 16 | -CH2-NH-CH2-(2,4-dimethoxyphenyl) |
| 17 | -CH2-NH-CH2-(3-pyridyl) |
| 18 | -CH2-NH-CH2CH2-(1-piperidinyl) |
| 19 | -CH2-NH-(1-benzyl-piperidin-4-yl) |

TABLE 61-continued (I-P-2)

| No. | R¹ |
|---|---|
| 20 | ethyl-piperazine-benzyl |

TABLE 62

(I-P-3)

| No. | R¹ |
|---|---|
| 1 | 3-pyridyl-CH₂-O-CH₂- |
| 2 | 4-pyridyl-CH₂CH₂-O-CH₂- |
| 3 | -C(O)NH-CH₂CH₂-NEt₂ |
| 4 | -C(O)NH-CH₂-phenyl |
| 5 | -C(O)NH-CH₂-(2,4-dimethoxyphenyl) |
| 6 | -C(O)NH-CH₂-(3-pyridyl) |
| 7 | -C(O)NH-CH₂CH₂-pyrrolidinyl |

TABLE 62-continued (I-P-3)

| No. | R¹ |
|---|---|
| 8 | -C(O)NH-CH₂CH₂CH₂-pyrrolidinyl |
| 9 | -C(O)NH-CH₂CH₂-piperidinyl |
| 10 | -C(O)NH-CH₂CH₂CH₂-(2-oxo-pyrrolidinyl) |
| 11 | -C(O)NH-(1-benzyl-pyrrolidin-3-yl) |
| 12 | -C(O)NH-(1-benzyl-piperidin-4-yl) |
| 13 | -C(O)-(4-benzyl-piperazin-1-yl) |
| 14 | -C(O)NH-CH₂CH₂-N(Et)-(3-methylphenyl) |
| 15 | -CH₂-NH-CH₂-phenyl |
| 16 | -CH₂-NH-CH₂-(2,4-dimethoxyphenyl) |

TABLE 62-continued (I-P-3)

[Structure: thieno[2,3-b]pyridine with S,S-dioxide, R¹ substituent]

| No. | R¹ |
|---|---|
| 17 | -NH-CH₂-(3-pyridyl) |
| 18 | -NH-CH₂CH₂-(1-piperidinyl) |
| 19 | -NH-(4-(1-benzylpiperidinyl)) |
| 20 | -N(piperazinyl)-CH₂-phenyl (4-benzylpiperazin-1-yl ethyl) |

TABLE 63

(I-A-1)

[Structure: 2,3-dihydrobenzothiophene-1,1-dioxide with phenylsulfonyl at 3-position and R¹ at 4-position]

| No. | R¹ |
|---|---|
| 21 | -NH-CH₂CH₂-phenyl |
| 22 | -N(Me)-CH₂-phenyl |
| 23 | -NH-CH₂CH₂CH₂-(2-oxopyrrolidin-1-yl) |
| 24 | -NH-CH₂-(4-aminophenyl) |

TABLE 63-continued (I-A-1)

| No. | R¹ |
|---|---|
| 25 | 4-ethylpiperazinyl-CH₂-CH=CH-phenyl |
| 26 | -NH-CH₂-(2-aminophenyl) |
| 27 | -N-(4-benzylpiperidin-1-yl, ethyl) |
| 28 | -NH-CH₂-(4-chlorophenyl) |
| 29 | -NH-CH₂-(3-chlorophenyl) |
| 30 | -NH-CH₂-(3-methoxyphenyl) |
| 31 | -NH-CH₂-(3,4-dichlorophenyl) |
| 32 | -NH-CH₂-(3,4-methylenedioxyphenyl) |
| 33 | -NH-CH₂-(3,4-dimethoxyphenyl) |
| 34 | -NH-CH₂-(3,4,5-trimethoxyphenyl) |

TABLE 63-continued
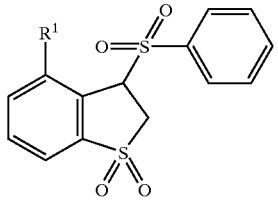
(I-A-1)
| No. | R¹ |
|---|---|
| 35 | 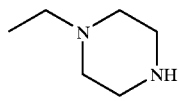 |
| 36 | 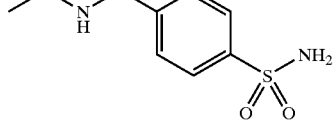 |
| 37 | 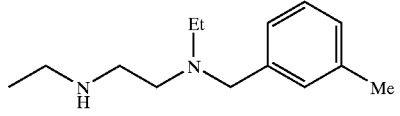 |
| 38 | 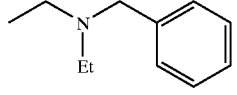 |
| 39 | 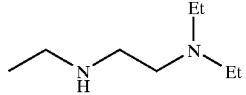 |
| 40 | 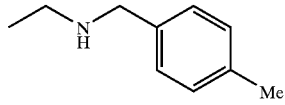 |
| 41 | 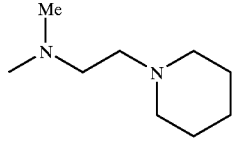 |
| 42 | 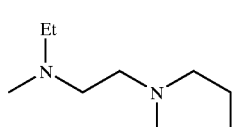 |
| 43 | 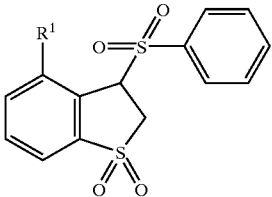 |
TABLE 63-continued
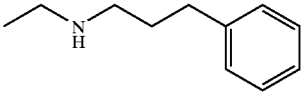
(I-A-1)
| No. | R¹ |
|---|---|
| 44 | 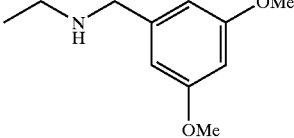 |
TABLE 64
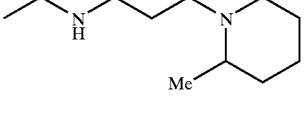
(I-A-1)
| No. | R¹ |
|---|---|
| 45 | 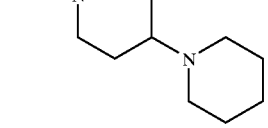 |
| 46 | 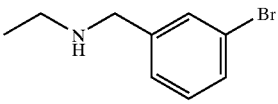 |
| 47 | 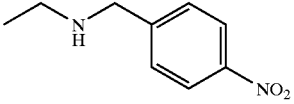 |
| 48 | 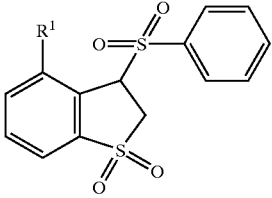 |
| 49 | 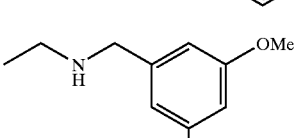 |
| 50 | 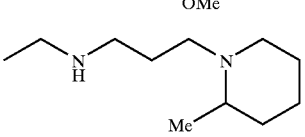 |

TABLE 64-continued (I-A-1)

| No. | R¹ |
|---|---|
| 51 | ethylaminomethyl-(2,4,6-trimethoxyphenyl) |
| 52 | N-ethyl-N-(n-Pr)-2-piperidin-1-yl-ethylamine |
| 53 | N-ethyl-N-(i-Pr)-2-piperidin-1-yl-ethylamine |
| 54 | 3-pyrrolidin-1-yl-propylamine (ethyl) |
| 55 | ethylamino-1-piperidin-1-yl-ethanone |
| 56 | 1-benzo[1,3]dioxol-5-ylmethyl-4-ethyl-piperazine |
| 57 | ethyl-(2-pyrrolidin-1-yl-ethyl)-amine |
| 58 | (1-benzyl-pyrrolidin-3-yl)-ethyl-amine |
| 59 | ethyl-(2-morpholin-4-yl-ethyl)-amine |

TABLE 64-continued (I-A-1)

| No. | R¹ |
|---|---|
| 60 | N-ethyl-N'-(i-Pr)₂-ethylenediamine |
| 61 | ethyl-(3-piperidin-1-yl-propyl)-amine |
| 62 | N-ethyl-N-(2-piperidin-1-yl-ethyl)-acetamide |
| 63 | N-[2-(di-i-Pr-amino)-ethyl]-acetamide |
| 64 | N-(n-Pr)-N-(2-piperidin-1-yl-ethyl)-acetamide |
| 65 | N-(i-Pr)-N-(2-piperidin-1-yl-ethyl)-acetamide |
| 66 | N-(3-piperidin-1-yl-propyl)-acetamide |
| 67 | N-(2-morpholin-4-yl-ethyl)-acetamide |

TABLE 65

(I-A-2)

Structure: R¹ substituted bicyclic with phenylsulfonyl group and SO₂ in ring

| No. | R¹ |
|-----|-----|
| 21 | –NH–CH₂CH₂–C₆H₅ (phenethylamino) |
| 22 | –N(Me)–CH₂–C₆H₅ (N-methylbenzylamino) |
| 23 | –NH–(CH₂)₃–N(pyrrolidin-2-one) |
| 24 | –NH–CH₂–C₆H₄–4-NH₂ |
| 25 | 4-cinnamyl-piperazin-1-yl |
| 26 | –NH–CH₂–C₆H₄–2-NH₂ |
| 27 | 4-benzyl-piperidin-1-yl |
| 28 | –NH–CH₂–C₆H₄–4-Cl |
| 29 | –NH–CH₂–C₆H₄–3-Cl |
| 30 | –NH–CH₂–C₆H₄–3-OMe |
| 31 | –NH–CH₂–C₆H₃–3,4-Cl₂ |

TABLE 65-continued (I-A-2)

| No. | R¹ |
|-----|-----|
| 32 | –NH–CH₂–(3,4-methylenedioxyphenyl) |
| 33 | –NH–CH₂–C₆H₃–3,4-(OMe)₂ |
| 34 | –NH–CH₂–C₆H₂–3,4,5-(OMe)₃ |
| 35 | 4-(t-butoxycarbonyl)piperazin-1-yl |
| 36 | piperazin-1-yl |
| 37 | –NH–CH₂–C₆H₄–4-SO₂NH₂ |
| 38 | –NH–CH₂CH₂–N(Et)–CH₂–C₆H₄–3-Me |
| 39 | –N(Et)–CH₂–C₆H₅ |
| 40 | –NH–CH₂CH₂–N(Et)₂ |
| 41 | –NH–CH₂–C₆H₄–4-Me |

TABLE 65-continued
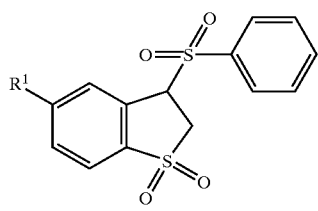
(I-A-2)
| No. | R¹ |
|---|---|
| 42 | 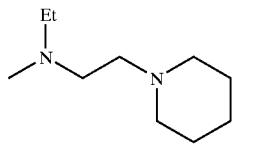 |
| 43 | 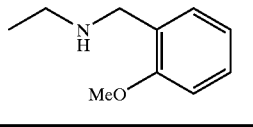 |
| 44 | 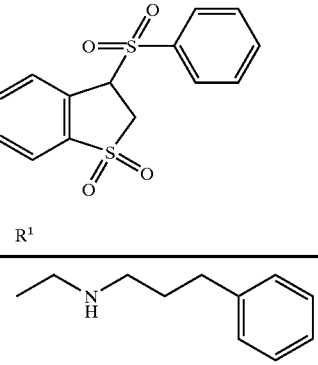 |
TABLE 66
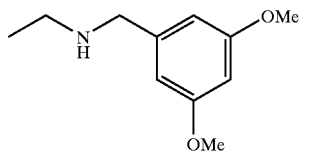
(I-A-2)
| No. | R¹ |
|---|---|
| 45 | 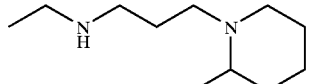 |
| 46 | 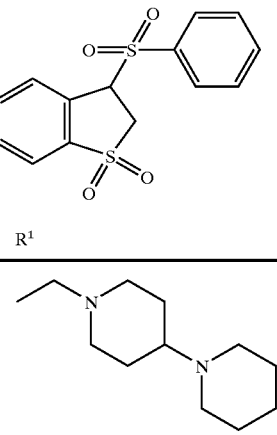 |
| 47 | 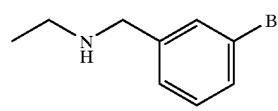 |
TABLE 66-continued
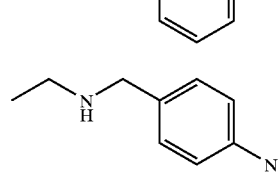
(I-A-2)
| No. | R¹ |
|---|---|
| 48 | 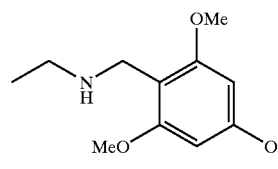 |
| 49 | 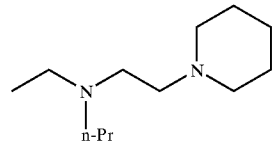 |
| 50 | 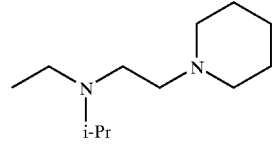 |
| 51 | 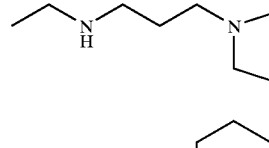 |
| 52 | 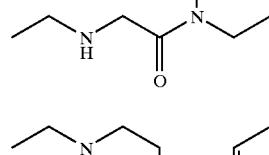 |
| 53 | 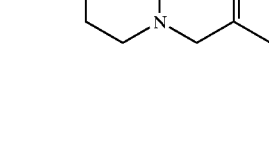 |
| 54 | |
| 55 | |
| 56 | |

TABLE 66-continued
(I-A-2)
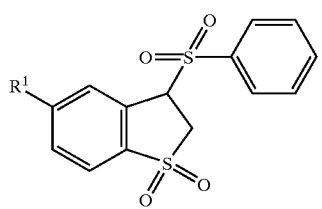
| No. | R¹ |
|---|---|
| 57 | 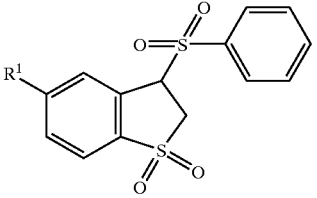 |
| 58 | 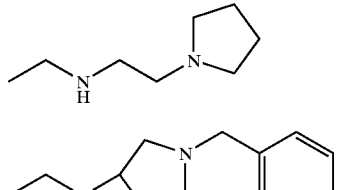 |
| 59 | 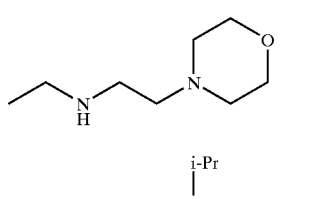 |
| 60 | 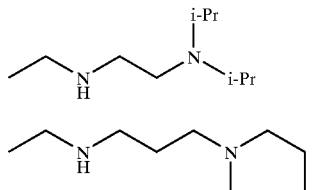 |
| 61 | 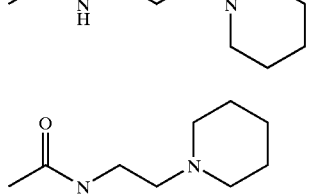 |
| 62 | 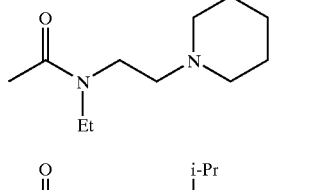 |
| 63 | 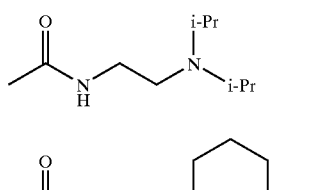 |
| 64 | 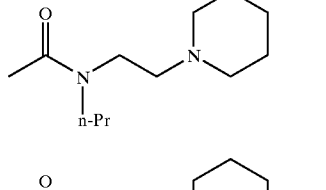 |
| 65 | 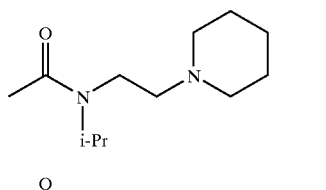 |
| 66 | 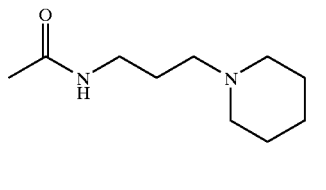 |
TABLE 66-continued
(I-A-2)
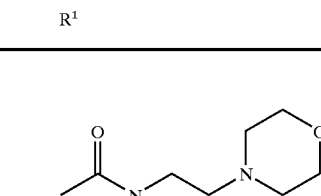
| No. | R¹ |
|---|---|
| 67 | 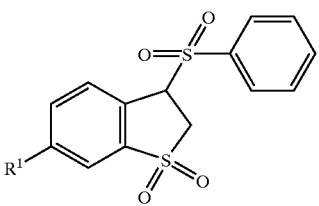 |
TABLE 67
(I-A-3)
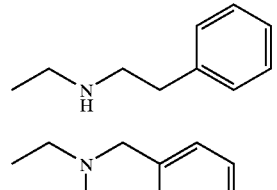
| No. | R¹ |
|---|---|
| 21 | 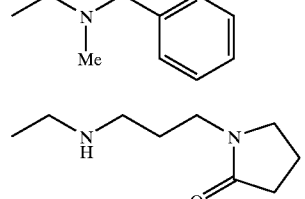 |
| 22 | 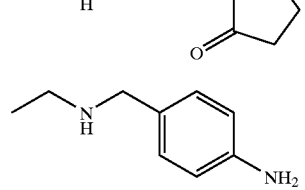 |
| 23 | 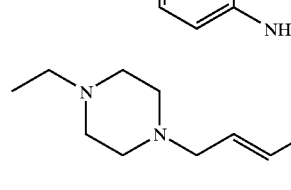 |
| 24 | 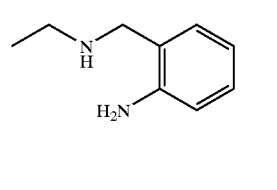 |
| 25 |  |
| 26 | |

TABLE 67-continued (I-A-3)

[Structure: benzothiophene-S,S-dioxide with phenylsulfonyl group and R¹ substituent]

| No. | R¹ |
|---|---|
| 27 | 1-ethyl-4-benzylpiperidine |
| 28 | ethylamino-CH₂-(4-chlorophenyl) |
| 29 | ethylamino-CH₂-(3-chlorophenyl) |
| 30 | ethylamino-CH₂-(3-methoxyphenyl) |
| 31 | ethylamino-CH₂-(3,4-dichlorophenyl) |
| 32 | ethylamino-CH₂-(3,4-methylenedioxyphenyl) |
| 33 | ethylamino-CH₂-(3,4-dimethoxyphenyl) |
| 34 | ethylamino-CH₂-(3,4,5-trimethoxyphenyl) |
| 35 | 1-ethyl-4-(tert-butoxycarbonyl)piperazine |
| 36 | 1-ethylpiperazine |

TABLE 67-continued (I-A-3)

[Structure: benzothiophene-S,S-dioxide with phenylsulfonyl group and R¹ substituent]

| No. | R¹ |
|---|---|
| 37 | ethylamino-CH₂-(4-sulfamoylphenyl) |
| 38 | ethylamino-CH₂CH₂-N(Et)-CH₂-(3-methylphenyl) |
| 39 | N-ethyl-N-ethyl-benzylamine |
| 40 | ethylamino-CH₂CH₂-N(Et)(Et) |
| 41 | ethylamino-CH₂-(4-methylphenyl) |
| 42 | Me₂N-CH₂CH₂-(1-piperidinyl) |
| 43 | N(Et)(Me)-CH₂CH₂-(1-piperidinyl) |
| 44 | ethylamino-CH₂-(2-methoxyphenyl) |

TABLE 68

(I-A-3)

| No. | R¹ |
|---|---|
| 45 | ethyl-NH-propyl-phenyl |
| 46 | ethyl-NH-CH2-(3,5-dimethoxyphenyl) |
| 47 | ethyl-NH-propyl-(2-methylpiperidin-1-yl) |
| 48 | ethyl-(4-piperidinyl)piperidine |
| 49 | ethyl-NH-CH2-(3-bromophenyl) |
| 50 | ethyl-NH-CH2-(4-nitrophenyl) |
| 51 | ethyl-NH-CH2-(2,4,6-trimethoxyphenyl) |
| 52 | ethyl-N(n-Pr)-ethyl-piperidine |
| 53 | ethyl-N(i-Pr)-ethyl-piperidine |

TABLE 68-continued (I-A-3)

| No. | R¹ |
|---|---|
| 54 | ethyl-NH-propyl-pyrrolidine |
| 55 | ethyl-NH-C(=O)-piperidine |
| 56 | ethyl-piperazine-CH2-(benzo[1,3]dioxole) |
| 57 | ethyl-NH-ethyl-pyrrolidine |
| 58 | ethyl-NH-(1-benzylpyrrolidin-3-yl) |
| 59 | ethyl-NH-ethyl-morpholine |
| 60 | ethyl-NH-ethyl-N(i-Pr)2 |
| 61 | ethyl-NH-propyl-piperidine |
| 62 | CH3-C(=O)-N(Et)-ethyl-piperidine |
| 63 | CH3-C(=O)-NH-ethyl-N(i-Pr)2 |

TABLE 68-continued (I-A-3)

| No. | R¹ |
|---|---|
| 64 | acetyl-N(n-Pr)-CH₂CH₂-piperidine |
| 65 | acetyl-N(i-Pr)-CH₂CH₂-piperidine |
| 66 | acetyl-NH-CH₂CH₂CH₂-piperidine |
| 67 | acetyl-NH-CH₂CH₂-morpholine |

TABLE 69

(I-A-4)

| No. | R¹ |
|---|---|
| 21 | -NH-CH₂CH₂-phenyl |
| 22 | -N(Me)-CH₂-phenyl |
| 23 | -NH-CH₂CH₂CH₂-(2-oxopyrrolidin-1-yl) |

TABLE 69-continued (I-A-4)

| No. | R¹ |
|---|---|
| 24 | -NH-CH₂-(4-aminophenyl) |
| 25 | -(4-ethylpiperazin-1-yl)-CH₂-CH=CH-phenyl |
| 26 | -NH-CH₂-(2-aminophenyl) |
| 27 | -(1-ethyl-4-benzylpiperidine) |
| 28 | -NH-CH₂-(4-chlorophenyl) |
| 29 | -NH-CH₂-(3-chlorophenyl) |
| 30 | -NH-CH₂-(3-methoxyphenyl) |
| 31 | -NH-CH₂-(3,4-dichlorophenyl) |
| 32 | -NH-CH₂-(3,4-methylenedioxyphenyl) |
| 33 | -NH-CH₂-(3,4-dimethoxyphenyl) |

TABLE 69-continued
(I-A-4)
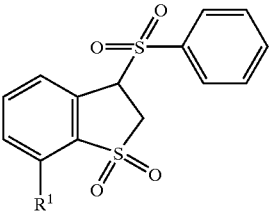
| No. | R¹ |
|---|---|
| 34 | 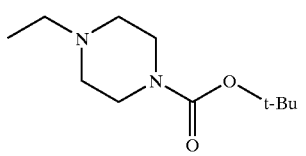 |
| 35 | 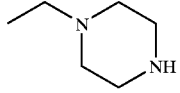 |
| 36 | 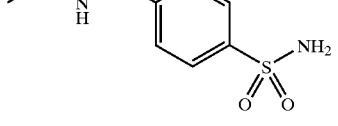 |
| 37 | 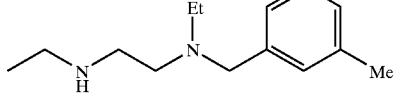 |
| 38 | 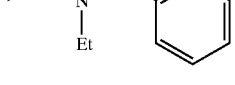 |
| 39 | 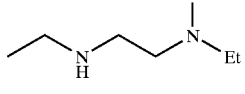 |
| 40 | 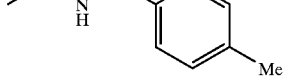 |
| 41 | 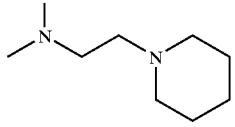 |
| 42 | 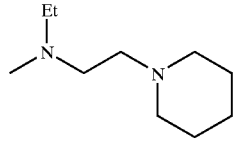 |
TABLE 69-continued
(I-A-4)
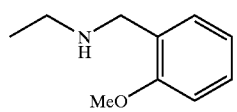
| No. | R¹ |
|---|---|
| 43 | 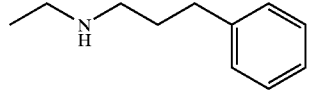 |
| 44 | 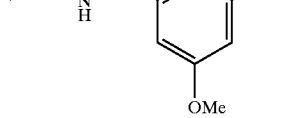 |
TABLE 70
(I-A-4)
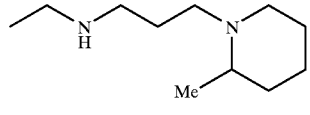
| No. | R¹ |
|---|---|
| 45 | 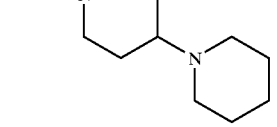 |
| 46 | 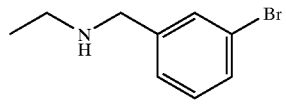 |
| 47 | |
| 48 | |
| 49 | |

TABLE 70-continued (I-A-4)

| No. | R¹ |
|---|---|
| 50 | -CH2-NH-CH2-C6H4-NO2 (4-nitrobenzyl) |
| 51 | -CH2-NH-CH2-(2,4,6-trimethoxyphenyl) |
| 52 | -CH2-N(n-Pr)-CH2CH2-piperidinyl |
| 53 | -CH2-N(i-Pr)-CH2CH2-piperidinyl |
| 54 | -CH2-NH-CH2CH2CH2-pyrrolidinyl |
| 55 | -CH2-NH-CH2-C(=O)-piperidinyl |
| 56 | -CH2-N(piperazinyl)-CH2-(benzo[1,3]dioxol-5-yl) |
| 57 | -CH2-NH-CH2CH2-pyrrolidinyl |
| 58 | -CH2-NH-(1-benzylpyrrolidin-3-yl) |
| 59 | -CH2-NH-CH2CH2-morpholinyl |
| 60 | -CH2-NH-CH2CH2-N(i-Pr)2 |
| 61 | -CH2-NH-CH2CH2CH2-piperidinyl |
| 62 | -C(=O)-N(Et)-CH2CH2-piperidinyl |
| 63 | -C(=O)-NH-CH2CH2-N(i-Pr)2 |
| 64 | -C(=O)-N(-)-CH2CH2-piperidinyl |
| 65 | -C(=O)-N(i-Pr)-CH2CH2-piperidinyl |
| 66 | -C(=O)-NH-CH2CH2CH2-piperidinyl |
| 67 | -C(=O)-NH-CH2CH2-morpholinyl |

TABLE 71

(I-N-1)

| No. | R¹ |
|---|---|
| 21 | -NH-CH₂CH₂-Ph |
| 22 | -N(Me)-CH₂-Ph |
| 23 | -NH-CH₂CH₂CH₂-(2-oxopyrrolidin-1-yl) |
| 24 | -NH-CH₂-(4-aminophenyl) |
| 25 | -(4-cinnamylpiperazin-1-yl) |
| 26 | -NH-CH₂-(2-aminophenyl) |
| 27 | -(4-benzylpiperidin-1-yl) |
| 28 | -NH-CH₂-(4-chlorophenyl) |
| 29 | -NH-CH₂-(3-chlorophenyl) |
| 30 | -NH-CH₂-(3-methoxyphenyl) |
| 31 | -NH-CH₂-(3,4-dichlorophenyl) |

TABLE 71-continued (I-N-1)

| No. | R¹ |
|---|---|
| 32 | -NH-CH₂-(benzo[1,3]dioxol-5-yl) |
| 33 | -NH-CH₂-(3,4-dimethoxyphenyl) |
| 34 | -NH-CH₂-(3,4,5-trimethoxyphenyl) |
| 35 | -(4-(tert-butoxycarbonyl)piperazin-1-yl) |
| 36 | -(piperazin-1-yl) |
| 37 | -NH-CH₂-(4-sulfamoylphenyl) |
| 38 | -NH-CH₂CH₂-N(Et)-CH₂-(3-methylphenyl) |
| 39 | -N(Et)-CH₂-Ph |
| 40 | -NH-CH₂CH₂-N(Et)₂ |
| 41 | -NH-CH₂-(4-methylphenyl) |

TABLE 71-continued (I-N-1)

| No. | R¹ |
|---|---|
| 42 | N(Me)-CH₂CH₂-piperidin-1-yl |
| 43 | N(Et)-CH₂CH₂-N(Me)-(not shown correctly) — Et,Me-N-CH₂CH₂-piperidin-1-yl |
| 44 | -NH-CH₂-(2-MeO-C₆H₄) |

TABLE 72

(I-N-1)

| No. | R¹ |
|---|---|
| 45 | -NH-CH₂CH₂CH₂-Ph |
| 46 | -NH-CH₂-(3,5-(MeO)₂-C₆H₃) |
| 47 | -NH-CH₂CH₂CH₂-(2-Me-piperidin-1-yl) |
| 48 | -N(piperidin-1-yl)-piperidin-4-yl (4-piperidin-1-yl-piperidin-1-yl) |
| 49 | -NH-CH₂-(3-Br-C₆H₄) |
| 50 | -NH-CH₂-(4-NO₂-C₆H₄) |
| 51 | -NH-CH₂-(2,4,6-(MeO)₃-C₆H₂) |
| 52 | N(n-Pr)-CH₂CH₂-piperidin-1-yl |
| 53 | N(i-Pr)-CH₂CH₂-piperidin-1-yl |
| 54 | -NH-CH₂CH₂CH₂-pyrrolidin-1-yl |
| 55 | -NH-CH₂-C(=O)-piperidin-1-yl |
| 56 | -N(piperazin-1-yl)-CH₂-(3,4-methylenedioxyphenyl) |
| 57 | -NH-CH₂CH₂-pyrrolidin-1-yl |
| 58 | -NH-(1-benzyl-pyrrolidin-3-yl) |

TABLE 72-continued
(I-N-1)
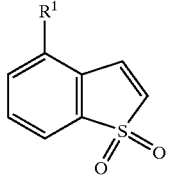
| No. | R¹ |
|---|---|
| 59 | 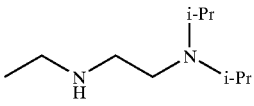 |
| 60 | 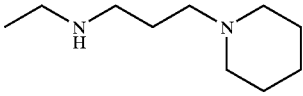 |
| 61 | 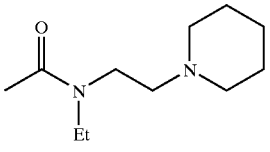 |
| 62 | 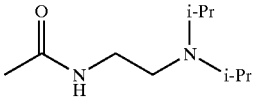 |
| 63 | 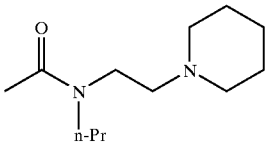 |
| 64 | 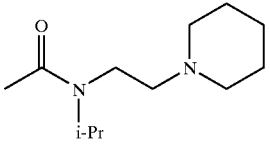 |
| 65 | 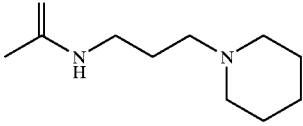 |
| 66 | 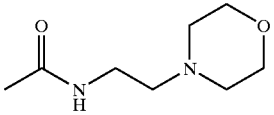 |
| 67 | 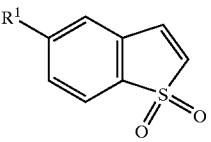 |
TABLE 73
(I-N-2)
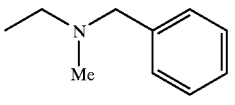
| No. | R¹ |
|---|---|
| 21 | 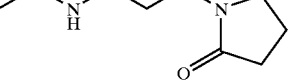 |
| 22 | 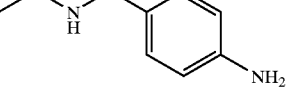 |
| 23 | 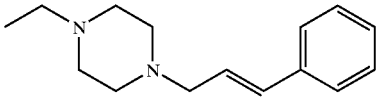 |
| 24 | 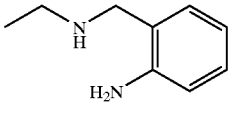 |
| 25 | 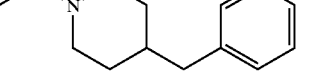 |
| 26 | 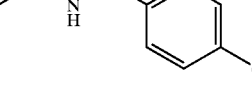 |
| 27 | 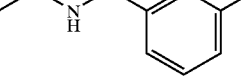 |
| 28 | 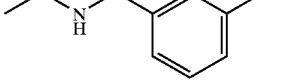 |
| 29 | 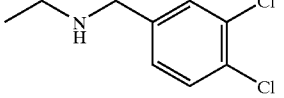 |
| 30 | |
| 31 | |

TABLE 73-continued (I-N-2)

R¹—[benzothiophene-1,1-dioxide]

| No. | R¹ |
|---|---|
| 32 | ethyl-NH-CH₂-(benzo[1,3]dioxole-5-yl) |
| 33 | ethyl-NH-CH₂-(3,4-dimethoxyphenyl) |
| 34 | ethyl-NH-CH₂-(3,4,5-trimethoxyphenyl) |
| 35 | 4-ethyl-piperazine-1-carboxylic acid tert-butyl ester |
| 36 | 1-ethyl-piperazine (NH) |
| 37 | ethyl-NH-CH₂-(4-sulfamoylphenyl) |
| 38 | ethyl-NH-CH₂CH₂-N(Et)-CH₂-(3-methylphenyl) |
| 39 | ethyl-N(Et)-CH₂-phenyl |
| 40 | ethyl-NH-CH₂CH₂-N(Et)₂ |
| 41 | ethyl-NH-CH₂-(4-methylphenyl) |

TABLE 73-continued (I-N-2)

R¹—[benzothiophene-1,1-dioxide]

| No. | R¹ |
|---|---|
| 42 | Me-N(Me)-CH₂CH₂-(piperidin-1-yl) |
| 43 | Et-N(Me)-CH₂CH₂-(piperidin-1-yl) |
| 44 | ethyl-NH-CH₂-(2-methoxyphenyl) |

TABLE 74

(I-N-2)

R¹—[benzothiophene-1,1-dioxide]

| No. | R¹ |
|---|---|
| 45 | ethyl-NH-CH₂CH₂-phenyl |
| 46 | ethyl-NH-CH₂-(3,5-dimethoxyphenyl) |
| 47 | ethyl-NH-CH₂CH₂-(2-methylpiperidin-1-yl) |
| 48 | 1-ethyl-4-(piperidin-1-yl)piperidine |

TABLE 74-continued (I-N-2)

| No. | R¹ |
|---|---|
| 49 | -CH2-NH-CH2-C6H4-Br (3-Br) |
| 50 | -CH2-NH-CH2-C6H4-NO2 (4-NO2) |
| 51 | -CH2-NH-CH2-(2,4,6-triOMe-C6H2) |
| 52 | -CH2-N(n-Pr)-CH2CH2-piperidinyl |
| 53 | -CH2-N(i-Pr)-CH2CH2-piperidinyl |
| 54 | -CH2-NH-CH2CH2CH2-pyrrolidinyl |
| 55 | -CH2-NH-CH2-C(O)-piperidinyl |
| 56 | -CH2-N(piperazinyl-CH2-(3,4-methylenedioxyphenyl)) |
| 57 | -CH2-NH-CH2CH2-pyrrolidinyl |
| 58 | -CH2-NH-(1-benzylpyrrolidin-3-yl) |

TABLE 74-continued (I-N-2)

| No. | R¹ |
|---|---|
| 59 | -CH2-NH-CH2CH2-morpholinyl |
| 60 | -CH2-NH-CH2CH2-N(i-Pr)2 |
| 61 | -CH2-NH-CH2CH2CH2-piperidinyl |
| 62 | -CH2-C(O)-N(Et)-CH2CH2-piperidinyl |
| 63 | -CH2-C(O)-NH-CH2CH2-N(i-Pr)2 |
| 64 | -CH2-C(O)-N(n-Pr)-CH2CH2-piperidinyl |
| 65 | -CH2-C(O)-N(i-Pr)-CH2CH2-piperidinyl |
| 66 | -CH2-C(O)-NH-CH2CH2CH2-piperidinyl |
| 67 | -CH2-C(O)-NH-CH2CH2-morpholinyl |

TABLE 75

(I-N-3)

| No. | R¹ |
|---|---|
| 21 | -NH-CH₂CH₂-C₆H₅ (N-ethyl phenethylamine) |
| 22 | -N(Me)-CH₂-C₆H₅ |
| 23 | -NH-(CH₂)₃-(2-oxopyrrolidin-1-yl) |
| 24 | -NH-CH₂-C₆H₄-4-NH₂ |
| 25 | 4-cinnamylpiperazin-1-yl |
| 26 | -NH-CH₂-C₆H₄-2-NH₂ |
| 27 | 4-benzylpiperidin-1-yl |
| 28 | -NH-CH₂-C₆H₄-4-Cl |
| 29 | -NH-CH₂-C₆H₄-3-Cl |
| 30 | -NH-CH₂-C₆H₄-3-OMe |
| 31 | -NH-CH₂-C₆H₃-3,4-Cl₂ |

TABLE 75-continued (I-N-3)

| No. | R¹ |
|---|---|
| 32 | -NH-CH₂-(benzo[1,3]dioxol-5-yl) |
| 33 | -NH-CH₂-C₆H₃-3,4-(OMe)₂ |
| 34 | -NH-CH₂-C₆H₂-3,4,5-(OMe)₃ |
| 35 | 4-(t-Bu-O-C(O))-piperazin-1-yl |
| 36 | piperazin-1-yl |
| 37 | -NH-CH₂-C₆H₄-4-SO₂NH₂ |
| 38 | -NH-CH₂CH₂-N(Et)-CH₂-C₆H₄-3-Me |
| 39 | -N(Et)-CH₂-C₆H₅ |
| 40 | -NH-CH₂CH₂-N(Et)₂ |
| 41 | -NH-CH₂-C₆H₄-4-Me |

TABLE 75-continued
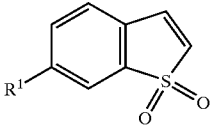
(I-N-3)
| No. | R¹ |
|---|---|
| 42 | 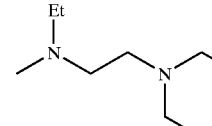 |
| 43 | 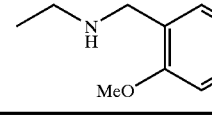 |
| 44 | 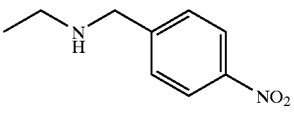 |
TABLE 76
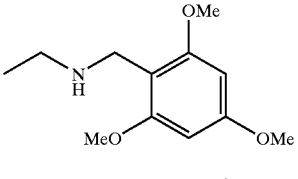
(I-N-3)
| No. | R¹ |
|---|---|
| 45 | 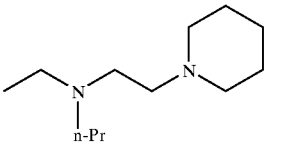 |
| 46 | 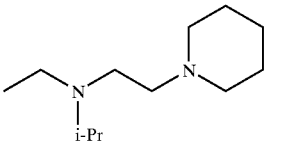 |
| 47 | 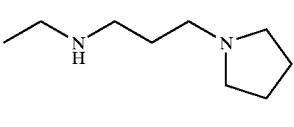 |
| 48 | 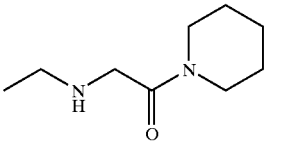 |
| 49 | 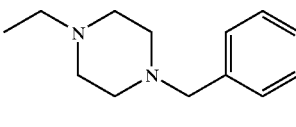 |
TABLE 76-continued
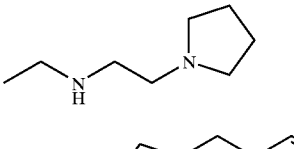
(I-N-3)
| No. | R¹ |
|---|---|
| 50 | 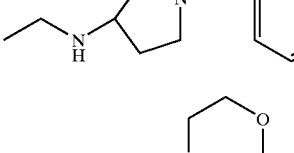 |
| 51 | 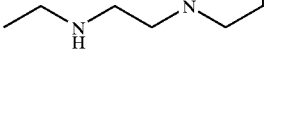 |
| 52 | 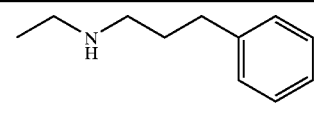 |
| 53 | 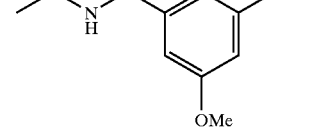 |
| 54 | 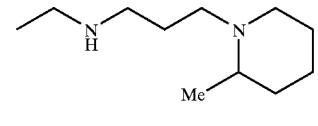 |
| 55 | 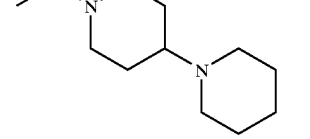 |
| 56 | 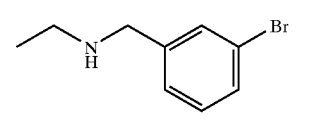 |
| 57 | |
| 58 | |
| 59 | |

TABLE 76-continued
(I-N-3)
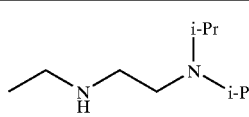
| No. | R¹ |
|---|---|
| 60 | 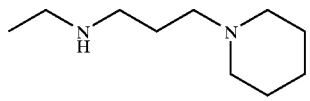 |
| 61 | 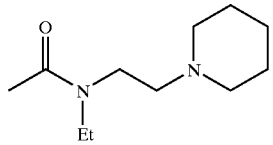 |
| 62 | 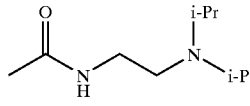 |
| 63 | 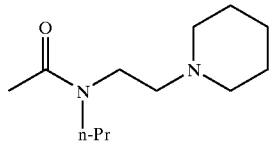 |
| 64 | 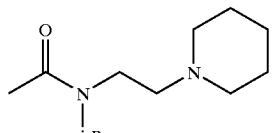 |
| 65 | 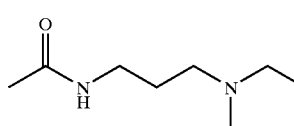 |
| 66 | 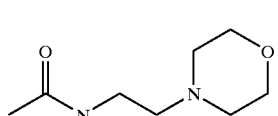 |
| 67 | 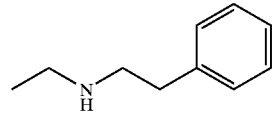 |
TABLE 77
(I-N-4)
| No. | R¹ |
|---|---|
| 21 |  |
| 22 | 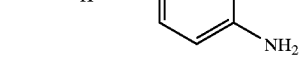 |
| 23 | 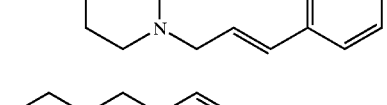 |
| 24 | 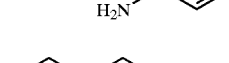 |
| 25 | 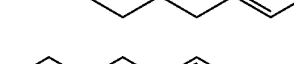 |
| 26 |  |
| 27 | 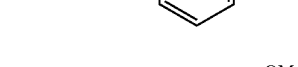 |
| 28 | 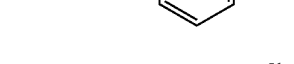 |
| 29 | 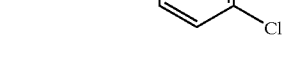 |
| 30 | |
| 31 | |

TABLE 77-continued (I-N-4)

[Structure: benzothiophene 1,1-dioxide with R¹ substituent]

| No. | R¹ |
|---|---|
| 32 | -CH₂-NH-CH₂-(benzo[1,3]dioxole) |
| 33 | -CH₂-NH-CH₂-(3,4-dimethoxyphenyl) |
| 34 | -CH₂-NH-CH₂-(3,4,5-trimethoxyphenyl) |
| 35 | -CH₂-(4-Boc-piperazin-1-yl) |
| 36 | -CH₂-(piperazin-1-yl) |
| 37 | -CH₂-NH-CH₂-(4-sulfamoylphenyl) |
| 38 | -CH₂-NH-CH₂-CH₂-N(Et)-CH₂-(3-methylphenyl) |
| 39 | -CH₂-N(Et)-CH₂-phenyl |
| 40 | -CH₂-NH-CH₂-CH₂-N(Et)₂ |
| 41 | -CH₂-NH-CH₂-(4-methylphenyl) |

TABLE 77-continued (I-N-4)

[Structure: benzothiophene 1,1-dioxide with R¹ substituent]

| No. | R¹ |
|---|---|
| 42 | -CH₂-N(Me)-CH₂-CH₂-(piperidin-1-yl) |
| 43 | -CH₂-N(Et)-CH₂-CH₂-(piperidin-1-yl) |
| 44 | -CH₂-NH-CH₂-(2-methoxyphenyl) |

TABLE 78

(I-N-4)

[Structure: benzothiophene 1,1-dioxide with R¹ substituent]

| No. | R¹ |
|---|---|
| 45 | -CH₂-NH-CH₂-CH₂-CH₂-phenyl |
| 46 | -CH₂-NH-CH₂-(3,5-dimethoxyphenyl) |
| 47 | -CH₂-NH-CH₂-CH₂-CH₂-(2-methylpiperidin-1-yl) |
| 48 | -CH₂-(4-(1-ethylpiperidin-4-yl)piperidin-1-yl) |

TABLE 78-continued (I-N-4)

| No. | R¹ |
|---|---|
| 49 | -CH₂-NH-CH₂-(3-Br-phenyl) |
| 50 | -CH₂-NH-CH₂-(4-NO₂-phenyl) |
| 51 | -CH₂-NH-CH₂-(2,4,6-triOMe-phenyl) |
| 52 | -CH₂-N(n-Pr)-CH₂CH₂-(piperidin-1-yl) |
| 53 | -CH₂-N(i-Pr)-CH₂CH₂-(piperidin-1-yl) |
| 54 | -CH₂-NH-CH₂CH₂CH₂-(pyrrolidin-1-yl) |
| 55 | -CH₂-NH-CH₂-C(=O)-(piperidin-1-yl) |
| 56 | -CH₂-(piperazin-1-yl)-CH₂-(benzo[1,3]dioxol-5-yl) |
| 57 | -CH₂-NH-CH₂CH₂-(pyrrolidin-1-yl) |
| 58 | -CH₂-NH-(1-benzyl-pyrrolidin-3-yl) |
| 59 | -CH₂-NH-CH₂CH₂-(morpholin-4-yl) |
| 60 | -CH₂-NH-CH₂CH₂-N(i-Pr)₂ |
| 61 | -CH₂-NH-CH₂CH₂CH₂-(piperidin-1-yl) |
| 62 | -CH₂-C(=O)-N(Et)-CH₂CH₂-(piperidin-1-yl) |
| 63 | -CH₂-C(=O)-NH-CH₂CH₂-N(i-Pr)₂ |
| 64 | -CH₂-C(=O)-N(n-Pr)-CH₂CH₂-(piperidin-1-yl) |
| 65 | -CH₂-C(=O)-N(i-Pr)-CH₂CH₂-(piperidin-1-yl) |
| 66 | -CH₂-C(=O)-NH-CH₂CH₂CH₂-(piperidin-1-yl) |
| 67 | -CH₂-C(=O)-NH-CH₂CH₂-(morpholin-4-yl) |

[Methods for Preparation of the Compounds of the Present Invention]

The compounds of the present invention of the formula (I) of the present invention may be prepared by the following methods or the methods described in examples.

Among the compounds of the present invention of the formula (I), the compounds of the present invention of the formula (I-1)

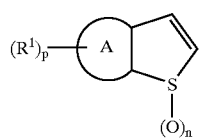

(I-1)

(wherein all the symbols are the same meanings as hereinbefore described.)

may be prepared by the known methods or the following methods [1]~[14].

[1] The compounds of the present invention of the formula (I-1) in which n is 1 or 2 may be also prepared by the following methods (a)~(b).

(a) The compounds of the present invention of the formula (I-1) in which n is 1, i.e., the compounds of the present invention of the formula (I-1-1a)

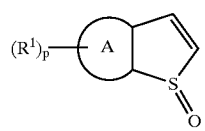

(I-1-1a)

(wherein all the symbols are the same meanings as hereinbefore described.)

may be prepared by oxidation of the compounds of the formula (I-1-1c)

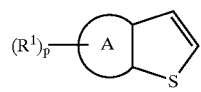

(I-1-1c)

(wherein all the symbols are the same meanings as hereinbefore described.)

The above oxidation is known per se. For example, it may be carried out in an adequate organic solvent (e.g., methylene chloride, chloroform, benzene, hexane, t-butyl alcohol etc.), in the presence of an 1–1.2 equivalent amount of oxidizing agent (e.g., hydrogen peroxide, sodium periodate, acyl nitrite, sodium perborate, peracid (e.g., 3-chloroperbenzoic acid, peracetic acid etc.), potassium peroxymonosulfate, potassium permanganate, chromic acid etc.), at −40° C.~0° C.

(b) The compounds of the present invention of the formula (I-1) in which n is 2, i.e., the compounds of the present invention of the formula (I-1-1b)

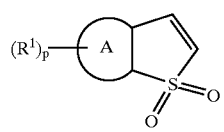

(I-1-1b)

(wherein all the symbols are the same meanings as hereinbefore described.)

may be prepared by oxidation of the said the compounds of the formula (I-1-1c).

The above oxidation is known per se. For example, it may be carried out in an adequate organic solvent (e.g., methylene chloride, chloroform, benzene, hexane, t-butyl alcohol etc.), in the presence of an excess amount of oxidizing agent (e.g., hydrogen peroxide, sodium periodate, acyl nitrite, sodium perborate, peracid (e.g., 3-chloroperbenzoic acid, peracetic acid etc.), potassium peroxymonosulfate, potassium permanganate, chromic acid etc.), at 20° C.~60° C.

[2] The compounds of the present invention of the formula (I-1) in which at least one of $R^1$ (s) is a substituted oxy group or a group containing substituted oxy, i.e., the compounds of the present invention of the formula (I-1-2)

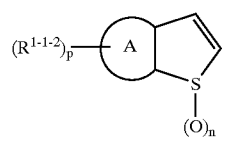

(I-1-2)

(wherein, $R^{1-1-2}$ is the same meanings as hereinbefore described for $R^1$, provided that at least one of $R^{1-1-2}$(s) is a substituted oxy group or a group containing substituted oxy and the other symbols are the same meaning as hereinbefore described.)

may be also prepared by the following methods (a)~(b).

(a) The compounds of the present invention of the formula (I-1-2) may be prepared by etherification of the compounds of the formula (I-1-2) in which at least one of $R^1$(s) is a hydroxy or a group containing hydroxy, i.e., the compounds of the formula (I-1-2a)

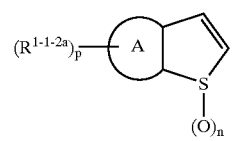

(I-1-2a)

(wherein, $R^{1-1-2a}$ is the same meanings as hereinbefore described for $R^1$, provided that at least one of $R^{1-1-2a}$(s) is a hydroxy or a group containing hydroxy and the other symbols are the same meaning as hereinbefore described.)

with the corresponding compounds containing a group which is removal (chloride, bromide, iodide, mesyl or tosyl etc.).

This etherification is well known. For example, it may be carried out in an organic solvent (dimethylformamide, dimethylsulfoxide, chloroform, methyhlene chloride, diethyl ether, tetrahydrofuran etc.) in the presence of hydroxide of an alkalimetal (sodium hydroxide, potassium hydroxide , lithium hydroxide etc.), hydroxide of an alkaline earth metal (barium hydroxide, calcium hydroxide etc.) or carbonate (sodium carbonate , potassium carbonate etc.) or an aqueous solution thereof or a mixture thereof at 0~100° C.

(b) The compounds of the present invention of the formula (I-1-2) may be prepared by etherification of the compounds of the formula (I-1-2) in which at least one of $R^1$(s) is a hydroxy or a group containing hydroxy, i.e., the compounds of the formula (I-1-2b)

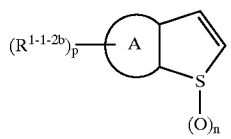

(I-1-2b)

(wherein, $R^{1-1-2b}$ is the same meanings as hereinbefore described for $R^1$, provided that at least one of $R^{1-1-2b}$(s) is a hydroxy or a group containing hydroxy and the other symbols are the same meaning as hereinbefore described.)

with the corresponding compounds containing hydroxy.

This etherification is well known. For example, it may be carried out in an organic solvent (methylene chloride, diethyl ether, tetrahydrofuran, acetonitrile, benzene, toluene etc.) in the presence of azo compounds (diethyl azodicaroxylate, diisopropyl azodicaroxylate, 1,1'-(azodicarbonyl)dipiperidine, 1,1'-azobis(N,N-dimethylformamide) etc.) and phosphine compounds (triphenylphosphine, tributylphosphine, trimethylphosphine etc.), with the corresponding alcohol compounds at 0~60° C.

[3] The compounds of the present invention of the formula (I-1) in which at least one of $R^1$(s) is a substituted amino or a group containing substituted amino, i.e., the compounds of the present invention of the formula (I-1-3)

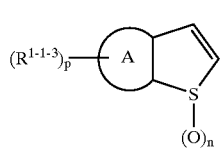

(I-1-3)

(wherein, $R^{1-1-3}$ is the same meanings as hereinbefore described for $R^1$, provided that at least one of $R^{1-1-3}$(s) is a substituted amino or a group containing substituted amino and the other symbols are the same meaning as hereinbefore described.)

may be prepared by the following methods (a)~(d).

(a) The compounds of the present invention of the formula (I-1-3) may be prepared by reacting the compounds of the formula (I-1-3) in which at least one of $R^1$(s) is halogen (chloride, bromide, iodide) or a group containing halogen, i.e., the compounds of the formula (I-1-3a)

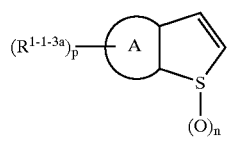

(I-1-3a)

(wherein, $R^{1-1-3a}$ is the same meanings as hereinbefore described for $R^1$, provided that at least one of $R^{1-1-3a}$(s) is a halogen (chloride, bromide, iodide) or a group containing halogen and the other symbols are the same meaning as hereinbefore described.)

and the corresponding compounds containing amino.

This reaction is well known. For example, it may be carried out in an organic solvent (dimethylformamide, dimethylsulfoxide, chloroform, methyhlene chloride, diethyl ether, tetrahydrofuran, acetonitrile etc.) in the presence or absence of base (triethylamine, pyridine etc.) at 0~100° C.

(b) The compounds of the present invention of the formula (I-1-3) may be prepared by reacting the compounds of the formula (I-1-3) in which at least one of $R^1$(s) is an amino or a group containing amino, i.e., the compounds of the formula (I-1-3b)

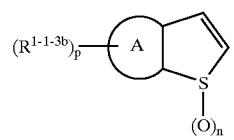

(I-1-3b)

(wherein, $R^{1-1-3b}$ is the same meanings as hereinbefore described for $R^1$, provided that at least one of $R^{1-1-3b}$(s) is an amino or a group containing amino and the other symbols are the same meaning as hereinbefore described.)

and the corresponding compounds containing halogen (chloride, bromide, and iodide).

This reaction may be carried out by the same procedure for the preparation of the said compounds of the formula (I-1-3a).

(c) The compounds of the present invention of the formula (I-1-3) may be prepared by reductive amidation of the compounds of the formula (I-1-3) in which at least one of $R^1$(s) is an amino or a group containing amino, i.e., the compounds of the formula (I-1-3c)

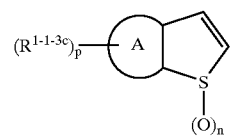

(I-1-3c)

(wherein, $R^{1-1-3c}$ is the same meanings as hereinbefore described for $R^1$, provided that at least one of $R^{1-1-3c}$(s) is an amino or a group containing amino and the other symbols are the same meaning as hereinbefore described.)

with the corresponding compounds containing carbonyl.

This reductive amidation is well known. For example, it may be carried out in an organic solvent (methanol, ethanol, dimethylformamide, dimethylsulfoxide etc.) in the presence of reductant (sodium cyanoborohydride, sodium triacetoxyborohydride, sodium borohydride, Pd—C etc.) and in the presence of acid (acetic acid, hydrochlolride solution etc.), if necessary, at −20~60° C.

(d) The compounds of the present invention of the formula (I-1-3) may be prepared by reductive amidation of the compounds of the formula (I-1-3) in which at least one of $R^1$(s) is a carbonyl or a group containing carbonyl, i.e., the compounds of the formula (I-1-3d)

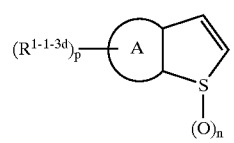

(I-1-3d)

(wherein, $R^{1-1-3d}$ is the same meanings as hereinbefore described for $R^1$, provided that at least one of $R^{1-1-3d}$(s) is a carbonyl or a group containing carbonyl and the other symbols are the same meaning as hereinbefore described.)

with the corresponding compounds containing amino.

This reductive amidation may be carried out by the same procedure for preparation of the said compounds of the formula (I-1-3c).

[4] The compounds of the present invention of the formula (I-1) in which at least one of $R^1(s)$ is an amide or a group containing amide, i.e., the compounds of the present invention of the formula (I-1-4)

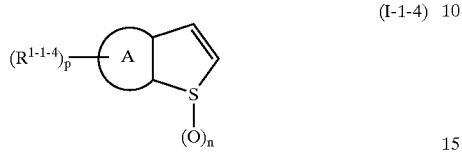

(I-1-4)

(wherein, $R^{1\text{-}1\text{-}4}$ is the same meanings as hereinbefore described for $R^1$, provided that at least one of $R^{1\text{-}1\text{-}4}(s)$ is an amide or a group containing amide and the other symbols are the same meaning as hereinbefore described.)

may be prepared by the following methods (a)~(b).

(a) The compounds of the present invention of the formula (I-1-4) may be prepared by amidation of the compounds of the formula (I-1) in which at least one of $R^1(s)$ is a —COOH or a group containing —COOH, i.e., the compounds of the formula (I-1-4a)

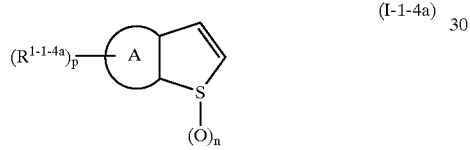

(I-1-4a)

(wherein, $R^{1\text{-}1\text{-}4a}$ is the same meanings as hereinbefore described for $R^1$, provided that at least one of $R^{1\text{-}1\text{-}4a}(s)$ is a —COOH or a group containing —COOH and the other symbols are the same meaning as hereinbefore described.)

with the corresponding compounds containing amino.

The amidation is well known. For example, it may be carried out (1) by the method with using acid halide,
(2) by the method with using mixed acid anhydride,
(3) by the method with using conducing agent etc.

Concrete description of these methods are as follows:

(1) method with using acid halide may be carried out, for example; carboxylic acid is reacted with an acid halide (oxalyl chloride or thionyl chloride etc.) in an organic solvent (chloroform, methylene chloride, diethyl ether or tetrahydrofuran etc.) or without solvents at from −20° C. to a refluxing temperature to give an acid halide. The obtained acid halide and an amine are reacted in an organic solvent (chloroform, methylene chloride, diethyl ether, tetrahydrofuran etc.) in the presence of tertiary amine (pyridine, triethylamine, dimethylaniline or dimethylaminopyridine etc.) at 0–40° C.

(2) method with using mixed acid anhydride may be carried out, for example; carboxylic acid is reacted with an acid halide (pivaloyl chloride, tosyl chloride, mesyl chloride etc.) or an acid derivative (ethyl chloroformate, isobutyl chloroformate etc.) in an organic solvent (chloroform, methylene chloride, diethyl ether, tetrahydrofuran. etc.) or without solvents, in the presence of tertiary amine (pyridine, triethylamine, dimethylaniline or dimethylaminopyridine etc.), at 0–40° C.

(3) method with using condensing agent may be carried out, for example; a carboxylic acid and an amine are reacted in an organic solvent (chloroform, methylene chloride, dimethylformamide, diethyl ether or tetrahydrofuran. etc.) or without solvents in the presence or absence of tertiary amine (pyridine, triethylamine, dimethylaniline or dimethylaminopyridine etc.) using with condensing agent (1,3-dicyclohexylcarbodiimido (DCC), 1-ethyl-3-[3-(dimethylamino)propyl] carbodiimido (EDC), 1,1'-carbonydiimidazole (CDI), 2-chloro-1-methylpyridinium iodide, propane phosphate cyclic anhydride etc.) using or without 1-hydroxybenztriazole (HOBt) at 0–40° C. (etc.)

Preferably, the above reactions (1), (2) and (3) described above are carried out under an atmosphere of an inert gas (argon, nitrogen etc.) on anhydrous condition.

(b) The compounds of the present invention of the formula (I-1-4) may be prepared by amidation of the compounds of the formula (I-1) in which at least one of $R^1(s)$ is an amino or a group containing amino, i.e., the compounds of the formula (I-1-4b)

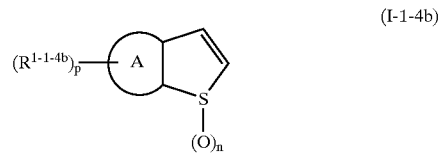

(I-1-4b)

(wherein, $R^{1\text{-}1\text{-}4b}$ is the same meanings as hereinbefore described for $R^1$, provided that at least one of $R^{1\text{-}1\text{-}4b}(s)$ is an amino or a group containing amino and the other symbols are the same meaning as hereinbefore described.) with the corresponding compounds containing carboxy.

The above amidation may be carried out by the same procedure for preparation of the said compounds of the formula (I-1-4a).

[5] The compounds of the present invention of the formula (I-1) in which at least one of $R^1(s)$ is an ester or a group containing ester, i.e., the compounds of the present invention of the formula (I-1-5)

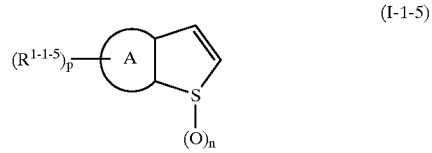

(I-1-5)

(wherein, $R^{1\text{-}1\text{-}5}$ is the same meanings as hereinbefore described for $R^1$, provided that at least one of $R^{1\text{-}1\text{-}5}(s)$ is an ester or a group containing ester and the other symbols are the same meaning as hereinbefore described.)

may be prepared by the following methods (a)~(b).

(a) The compounds of the present invention of the formula (I-1-5) may be prepared by esterification of the compounds of the formula (I-1) in which at least one of $R^1(s)$ is a —COOH or a group containing —COOH, i.e., the compounds of the formula (I-1-5a)

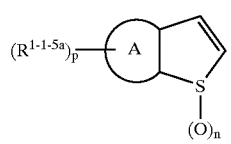

(I-1-5a)

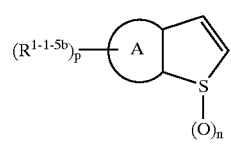

(I-1-5b)

(wherein, $R^{1-1-5a}$ is the same meanings as hereinbefore described for $R^1$, provided that at least one of $R^{1-1-5a}$(s) is a —COOH or a group containing —COOH and the other symbols are the same meaning as hereinbefore described.)

with the corresponding compounds containing hydroxy.

Esterification is well known. For example, it may be carried out (1) by the method with using acid halide,
(2) by the method with using mixed acid anhydride,
(3) by the method with using conducing agent etc.

Concrete description of the above methods are as follows:

(1) method with using acid halide may be carried out, for example; carboxylic acid is reacted with an acid halide (oxalyl chloride or thionyl chloride etc.) in an inert organic solvent (chloroform, methylene chloride, diethyl ether or tetrahydrofuran etc.) or without solvents at from −20° C. to a refluxing temperature to give an acid halide. The obtained acid halide and an alcohol are reacted in an inert organic solvent (chloroform, methylene chloride, diethyl ether, tetrahydrofuran etc.) in the presence of tertiary amine (pyridine, triethylamine, dimethylaniline or dimethylaminopyridine etc.) at 0–40° C.

(2) method with using mixed acid anhydride may be carried out, for example; carboxylic acid is reacted with an acid halide (pivaloyl chloride, tosyl chloride, mesyl chloride etc.) or an acid derivative (ethyl chloroformate, isobutyl chloroformate etc.) in an inert organic solvent (chloroform, methylene chloride, diethyl ether, tetrahydrofuran. etc.) or without solvents, in the presence of tertiary amine (pyridine, triethylamine, dimethylaniline or dimethylaminopyridine etc.), at 0–40° C. to give an acid halide. The obtained acid halide and an alcohol are reacted in an inert organic solvent (chloroform, methylene chloride, diethyl ether, tetrahydrofuran etc.) at 0–40° C.

(3) method with using condensing agent may be carried out, for example; a carboxylic acid and an alcohol are reacted in an organic solvent (chloroform, methylene chloride, dimethylformamide, diethyl ether or tetrahydrofuran. etc.) or without solvents in the presence or absence of tertiary amine (pyridine, triethylamine, dimethylaniline or dimethylaminopyridine etc.) using with condensing agent (1,3-dicyclohexylcarbodiimido (DCC), 1-ethyl-3-[3-(dimethylamino)propyl] carbodiimido (EDC), 1,1'-carbonydiimidazole (CDI), 2-chloro-1-methylpyridinium iodide, propane phosphate cyclic anhydride etc.) using or without 1-hydroxybenztriazole (HOBt) at 0–40° C.

Preferably, the reactions (1), (2) and (3) described above are carried out under an atmosphere of inert gas (argon, nitrogen etc.) on anhydrous condition.

(b) The compounds of the present invention of the formula (I-1-5) may be prepared by esterification of the compounds of the formula (I-1) in which at least one of $R^1$(s) is a hydroxy or a group containing hydroxy, i.e., the compounds of the formula (I-1-5b)

(wherein, $R^{1-1-5b}$ is the same meanings as hereinbefore described for $R^1$, provided that at least one of $R^{1-1-5b}$(s) is a hydroxy or a group containing hydroxy and the other symbols are the same meaning as hereinbefore described.)

with the corresponding compounds containing carboxy.

The esterification may be carried out by the same procedure for preparation of the said compounds of the formula (I-1-5a).

[6] The compounds of the present invention of the formula (I-1) in which at least one of $R^1$(s) is a sulfonamide or a group containing sulfonamide, i.e., the compounds of the present invention of the formula (I-1-6)

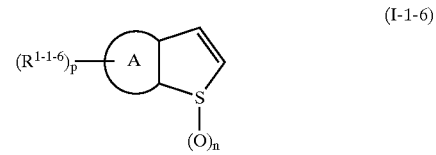

(I-1-6)

(wherein, $R^{1-1-6}$ is the same meanings as hereinbefore described for $R^1$, provided that at least one of $R^{1-1-6}$(s) is a sulfonamide or a group containing sulfonamide and the other symbols are the same meaning as hereinbefore described.) may be prepared by the following methods (a)~(b).

(a) The compounds of the present invention of the formula (I-1-6) may be prepared by sulfonamidation of the compounds of the formula (I-1) in which at least one of $R^1$(s) is a —SO$_3$H or a group containing —SO$_3$H, i.e., the compounds of the formula (II)

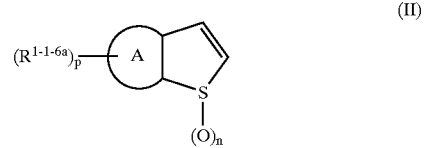

(II)

(wherein, $R^{1-1-6a}$ is the same meanings as hereinbefore described for $R^1$, provided that at least one of $R^{1-1-6a}$(s) is a —SO$_3$H or a group containing —SO$_3$H and the other symbols are the same meaning as hereinbefore described.)

with the corresponding compounds containing amino.

The sulfonamidation is well known. For example, it may be carried out by reacting sulfonic acid with acid halide (oxazolyl chloride, thionyl chloride etc.) in an inert organic solvent (chloroform, methyhlene chloride, diethyl ether, tetrahydrofuran etc.) or without solvent, at −20° C.~refluxing temperature to obtain sulfonylhalide and then by reacting the obtained sulfonylhalide with an amine in an inert organic solvent (chloroform, methyhlene chloride, diethyl ether, tetrahydrofuran etc.) in the presence of tertiary amine (pyridine, triethylamine, dimethylaniline, dimethylaminopyridine etc.) at 0~40° C.

(b) The compounds of the present invention of the formula (I-1-6) may be prepared by sulfonamidation of the compounds of the formula (I-1) in which at least one of $R^1$(s) is an amino or a group containing amino, i.e., the compounds of the formula (I-1-6b)

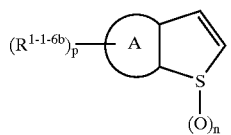
(I-1-6b)

(wherein, $R^{1\text{-}1\text{-}6b}$ is the same meanings as hereinbefore described for $R^1$, provided that at least one of $R^{1\text{-}1\text{-}6b}$(s) is an amino or a group containing amino and the other symbols are the same meaning as hereinbefore described.)

with the corresponding compounds containing sulfo.

The sulfonamidation may be carried out the same procedure for preparation of the said compounds of the formula (I-1-6a).

[7] The compounds of the present invention of the formula (I-1) in which at least one of $R^1$(s) is a substituted aminocarbonyloxy or a group containing a substituted aminocarbonyloxy, i.e., the compounds of the present invention of the formula (I-1-7)

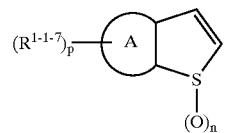
(I-1-7)

(wherein, $R^{1\text{-}1\text{-}7}$ is the same meanings as hereinbefore described for $R^1$, provided that at least one of $R^{1\text{-}1\text{-}7}$(s) is a substituted aminocarbonyloxy or a group containing a substituted aminocarbonyloxy and the other symbols are the same meaning as hereinbefore described.) may be prepared by reacting the compounds of the formula (I-1) in which at least one of $R^1$(s) is a hydroxy or a group containing hydroxy, i.e., the compounds of the formula (I-1-7a)

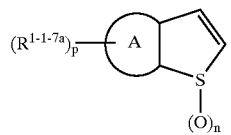
(I-1-7a)

(wherein, $R^{1\text{-}1\text{-}7a}$ is the same meanings as hereinbefore described for $R^1$, provided that at least one of $R^{1\text{-}1\text{-}7a}$(s) is a hydroxy or a group containing hydroxy and the other symbols are the same meaning as hereinbefore described.)

with the corresponding compounds containing isocyanate.

This reaction is well known. For example, it may be carried out in an organic solvent (tetrahydrofuran, methylene chloride, diethyl ether etc.) in the presence of base (1,8-diazabicyclo[5.4.0]undec-7-en (DBU), triethylamine, sodium hydride etc.) at 0~100° C.

[8] The compounds of the present invention of the formula (I-1) in which at least one of $R^1$(s) is a substituted aminocarbonylamino or a group containing a substituted aminocarbonylamino, i.e., the compounds of the present invention of the formula (I-1-8)

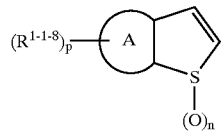
(I-1-8)

(wherein, $R^{1\text{-}1\text{-}8}$ is the same meanings as hereinbefore described for $R^1$, provided that at least one of $R^{1\text{-}1\text{-}8}$(s) is a substituted aminocarbonyl or a group containing a substituted aminocarbonyl and the other symbols are the same meaning as hereinbefore described.) may be prepared by reacting the compounds of the formula (I-1) in which at least one of $R^1$(s) is an amino or a group containing amino, i.e., the compounds of the formula (I-1-8a)

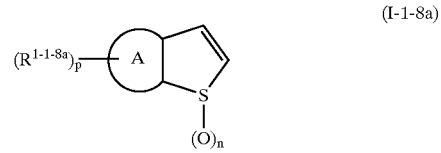
(I-1-8a)

(wherein, $R^{1\text{-}1\text{-}8a}$ is the same meanings as hereinbefore described for $R^1$, provided that at least one of $R^{1\text{-}1\text{-}8a}$(s) is an amino or a group containing amino and the other symbols are the same meaning as hereinbefore described.)

with the corresponding compounds containing isocyanate.

This reaction may be carried out by the same procedure for preparation of the said compounds of the formula (I-1-7).

[9] The compounds of the present invention of the formula (I-1) in which at least one of $R^1$(s) is a substituted oxycarbonylamino or a group containing a substituted oxyocarbonylamino, i.e., the compounds of the present invention of the formula (I-1-9)

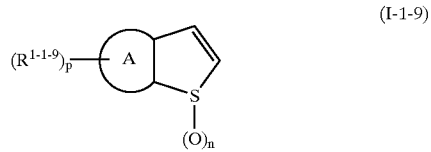
(I-1-9)

(wherein, $R^{1\text{-}1\text{-}9}$ is the same meanings as hereinbefore described for $R^1$, provided that at least one of $R^{1\text{-}1\text{-}9}$(s) is a substituted oxycarbonylamino or a group containing a substituted oxyocarbonylamino and the other symbols are the same meaning as hereinbefore described.) may be prepared by esterification of the compounds of the formula (I-1) in which at least one of $R^1$(s) is an amino or a group containing amino, i.e., the compounds of the formula (I-1-9a)

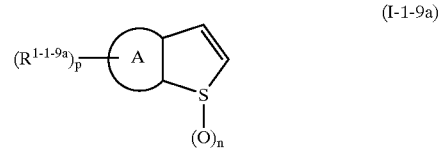
(I-1-9a)

(wherein, $R^{1\text{-}1\text{-}9a}$ is the same meanings as hereinbefore described for $R^1$, provided that at least one of $R^{1\text{-}1\text{-}9a}$(s) is an amino or a group containing amino and the other symbols are the same meaning as hereinbefore described.)

with the corresponding halo formic acid ester.

This reaction is well known. For example, it may be carried out in an organic solvent (tetrahydrofuran, methyhlene chloride, diethyl ether etc.) in the presence of base (triethylamine, pyridine etc.) at −78~40° C.,

[10] The compounds of the present invention of the formula (I-1) in which at least one of $R^1(s)$ is a substituted oxycarbonyloxy or a group containing a substituted oxycarbonyloxy, i.e., the compounds of the present invention of the formula (I-1-10)

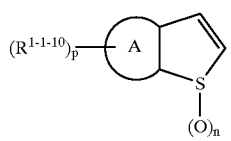

(I-1-10)

(wherein, $R^{1-1-10}$ is the same meanings as hereinbefore described for $R^1$, provided that at least one of $R^{1-1-10}(s)$ is a substituted oxycarbonyloxy or a group containing a substituted oxycarbonyloxy and the other symbols are the same meaning as hereinbefore described.) may be prepared by esterification of the compounds of the formula (I-1) in which at least one of $R^1(s)$ is a hydroxy or a group containing hydroxy, i.e., the compounds of the formula (I-1-10a)

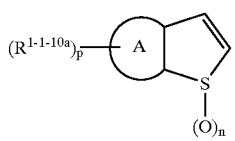

(I-1-10a)

(wherein, $R^{1-1-10a}$ is the same meanings as hereinbefore described for $R^1$, provided that at least one of $R^{1-1-10a}(s)$ is a hydroxy or a group containing hydroxy and the other symbols are the same meaning as hereinbefore described.)

with the corresponding halo formic acid ester.

This reaction may be carried out by the same procedure for preparation of the said compounds of the formula (I-1-9).

[11] The compounds of the present invention of the formula (I-1) in which at least one of $R^1(s)$ is a substituted (hydroxy)methyl or a group containing a substituted (hydroxy)methyl, i.e., the compounds of the present invention of the formula (I-1-11)

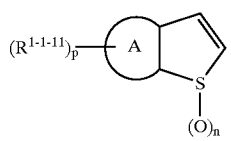

(I-1-11)

(wherein, $R^{1-1-11}$ is the same meanings as hereinbefore described for $R^1$, provided that at least one of $R^{1-1-11}(s)$ is a substituted (hydroxy)methyl or a group containing a substituted (hydroxy)methyl and the other symbols are the same meaning as hereinbefore described.) may be prepared by the following methods (a)~(b).

(a) The compounds of the present invention of the formula (I-1-11) in which n is 0, i.e., the compounds of the present invention of the formula (I-1-11a)

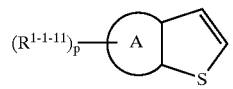

(I-1-11a)

(wherein all the symbols are the same meanings as hereinbefore described.)

may be prepared by reacting the compounds of the formula (I-1) in which at least one of $R^1(s)$ is a formyl i.e., the compounds of the formula (I-1-11aa)

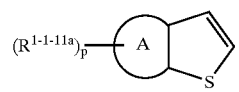

(I-1-11aa)

(wherein, $R^{1-1-11a}$ is the same meanings as hereinbefore described for $R^1$, provided that at least one of $R^{1-1-11a}(s)$ is a formyl and the other symbols are the same meaning as hereinbefore described.)

with the corresponding Grignard's reagents or corresponding derivatives containing lithium.

This reaction is well known. For example, it may be carried out in an organic solvent (tetrahydrofuran, diethyl ether etc.) at −78~0° C.

(b) The compounds of the present invention of the formula (I-1-11) in which n is 1 or 2, i.e., the compounds of the present invention of the formula (I-1-11b)

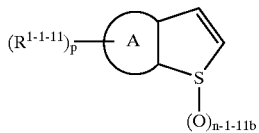

(I-1-11b)

(wherein, n-1-11b is an integer of 1~2 and the other symbols are the same meaning as hereinbefore described.)

may be prepared by oxidizing the said compounds of the formula (I-1-11a) as described in [1].

[12] The compounds of the present invention of the formula (I-1) in which at least one of $R^1(s)$ is a substituted carbonyl or a group containing substituted carbonyformyl, i.e., the compounds of the present invention of the formula (I-1-12)

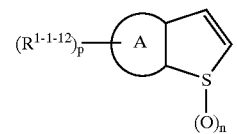

(I-1-12)

(wherein, $R^{1-1-12}$ is the same meanings as hereinbefore described for $R^1$, provided that at least one of $R^{1-1-12}(s)$ is an substituted carbonyl or a group containing substituted carbonyl and the other symbols are the same meaning as hereinbefore described.)

may be prepared by oxidizing the said compounds of the formula (1-1-11).

This oxidation is well known. For example, it may be carried out in an organic solvent (methyhlene chloride, chloroform etc.) using oxidant (manganese dioxide, oxazolyl chloride, pyridinium dichromate etc.) at −78~40° C.

[13] The compounds of the present invention of the formula (I-1) in which at least one of $R^1$(s) is an amino or a group containing amino, i.e., the compounds of the present invention of the formula (I-1-13)

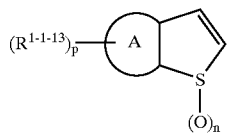

(I-1-13)

(wherein, $R^{1-1-13}$ is the same meanings as hereinbefore described for $R^1$, provided that at least one of $R^{1-1-13}$(s) is an amino or a group containing amino and the other symbols are the same meaning as hereinbefore described.) may be prepared by reducing nitro in the compounds of the formula of (I-1) in which at least one of $R^1$(s) is a nitro or a group containing nitro, i.e., the compounds of the formula (1-1-13a)

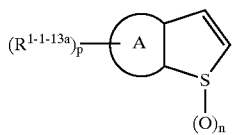

(I-1-13a)

(wherein, $R^{1-1-13a}$ is the same meanings as hereinbefore described for $R^1$, provided that at least one of $R^{1-1-13a}$ (s) is a nitro or a group containing nitro and the other symbols are the same meaning as hereinbefore described.).

The reduction of nitro is well known. For example, it may be carried out by hydrogenolysis and reduction using organic metal.

This hydrogenolysis is well known. For example, it may be carried out in inert solvent [ethers (e.g., tetrahydrofuran, dioxane, dimethoxy ethane, diethyl ether etc.), alcohols (e.g., methanol , ethanol etc.), benzenes (e.g., benzene, toluene etc.), ketones (e.g., acetone, methyl ethyl ketone etc.), nitrites (e.g., acetonitrile etc.), amides (e.g., dimethylformamide etc.), water, ethyl acetate, acetic acid or mixture of the said two or more solvents etc.], in the presence of catalyst to hydrogenate (e.g., Pd—C, palladium black, Pd, palladium hydroxide, platinum oxide, Ni, Raney nickel, ruthenium chloride etc.), in the presence or absence of an inorganic acid (e.g., hydrochloric acid, sulfuric acid, hypochlorous acid, boric acid, tetrafluoroboric acid etc.) or an organic acid (e.g., acetic acid, p-toluenesulfonic acid, bromic acid, trifluoroacetic acid, formic acid etc.), at an ordinary or increased pressure under an atmosphere of hydrogen gas or in the presence of ammonium formate at 0~200° C. When an acid is used, its salt may be used.

The reduction using an organic metal is well known. For example, it may be carried out in a water-admissible solvent (ethanol, methanol etc.) in the presence or absence of an aqueous hydrochloric acid solution, using an organic metal (Zn, Fe, Sn, $SnCl_2$, $FeCl_2$ etc.) at 50~150° C.

[14] The compounds of the present invention of the formula (I-1) in which at least one of $R^1$(s) is a —COOH, hydroxy or amino or a group containing —COOH, hydroxy or amino, i.e., the compounds of the present invention of the formula (I-1-14)

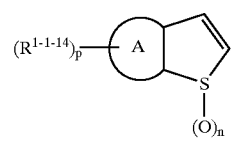

(I-1-14)

(wherein, $R^{1-1-14}$ is the same meanings as hereinbefore described for $R^1$, provided that at least one of $R^{1-1-14}$(s) is a —COOH, hydroxy or amino or a group containing —COOH, hydroxy or amino and the other symbols are the same meaning as hereinbefore described.) may be prepared by removal of protecting group in the compounds of the formula (I-1) containing a protected COOH, hydroxy or amino, i.e., the compounds of the formula (I-1-14a)

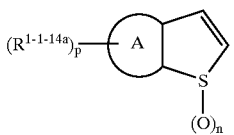

(I-1-14a)

(wherein, $R^{1-1-14a}$ is the same meanings as hereinbefore described for $R^1$, provided that at least one of $R^{1-1-14a}$(s) is a protected COOH (e.g., it is protected by methyl, ethyl, t-butyl and benzyl etc.), protected hydroxy (e.g., it is protected by methoxymethyl, tetrahydropyranyl, t-butyldimethylsilyl, acetyl, benzyl etc.) or protected amino (e.g., it is protected by benzyloxycarbonyl, t-butoxycarbonyloxy, trifluoroacetyl etc.) or a group containing such a group, and the other symbols are the same meaning as hereinbefore described.) according to alkaline hydrolysis, removal of protecting group in an acidic condition, removal of silyl or hydrogenolysis.

The removal of a protecting group according to alkaline hydrolysis is well known. For example, it may be carried out in an organic solvent (methanol, tetrahydrofuran, dioxane etc.), using hydroxide of an alkaline metal (sodium hydroxide, potassium hydroxide , lithium hydroxide etc.), hydroxide of an alkaline earth metal (barium hydroxide, calcium hydroxide etc.) or carbonate (sodium carbonate, potassium carbonate etc.) or an aqueous solution thereof or a mixture thereof at 0~40° C.

The removal of a protecting group in an acidic condition is well known. For example, it may be carried out in an organic solvent (methyhlene chloride, chloroform, dioxane, ethyl acetate, anisole etc.), organic acid (acetic acid, trifluoroacetic acid, methanesulfonic acid, trimethylsilyliodide etc.) or inorganic acid (hydrochloric acid, sulfuric acid etc.) or a mixture thereof (bromohydroacetic acid etc.) at 0~100° C.

The removal of silyl is well known. For example, it may be carried out in a water-admissible organic solvent (tetrahydrofuran, acetonitrile etc.), using tetrabutylammonium fluoride at 0~40° C.

The removal of protecting group according to hydrogenolysis may be carried out by the same procedure of hydrogenolysis described in [13].

Among the compounds of the formula (I), the compounds of the formula (I-2)

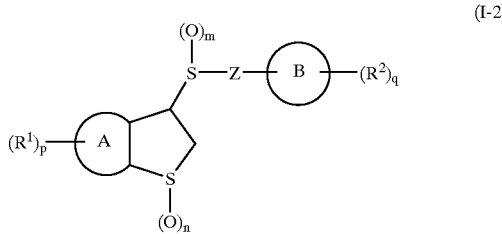
(I-2)

may be prepared by the following methods [15]~[17].

[15] The compounds of the present invention of the formula (I-2) in which m is 0, i.e., the compounds of the present invention of the formula (I-2-15)

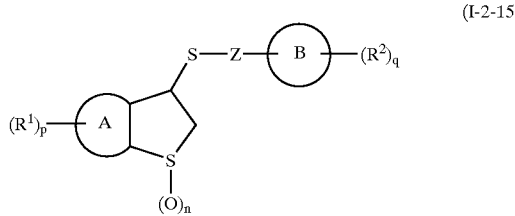
(I-2-15)

(wherein all the symbols are the same meanings as hereinbefore described.) may be prepared by the following methods (a)~(b).

(a) The compounds of the present invention of the formula (I-2-15) in which n is 1 or 2, i.e., the compounds of the present invention of the formula (I-2-15a)

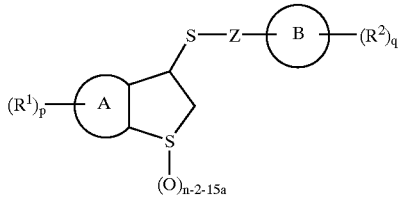
(I-2-15a)

(wherein, n-2-15a is an integer of 1~2 and the other symbols are the same meanings as hereinbefore described.)

may be prepared by reacting the said compounds of the formula (I-1-1a) or the compounds of the formula (I-1-1b) and the compounds of the formula (III)

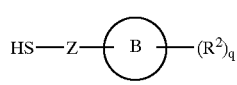
(III)

(wherein all the symbols are the same meanings as hereinbefore described.).

This reaction is known one (to see J. Am. Chem. Soc., 72, 1985 (1950), J. Org. Chem., 54, 4232 (1989). For example, it may be carried out in an inert organic solvent (tetrahydrofuran, diethyl ether, methylene chloride, chloroform, benzene, toluene, dimethylformamide, dimethylsulfoxide, acetonitrile etc.) using hydride of an alkaline metal, hydroxide of an alkaline metal (sodium hydroxide, potassium hydroxide, lithium hydroxide etc.), hydroxide of an alkaline earth metal (barium hydroxide, calcium hydroxide etc.) or tertiary amine (pyridine, triethylamine, dimethylaniline, dimethylaminopyridine etc.) or an aqueous solution thereof, or a mixture thereof at 0~40° C.

(b) The compounds of the present invention of the formula (I-2-15) in which n is 0, i.e., the compounds of the present invention of the formula (I-2-15b)

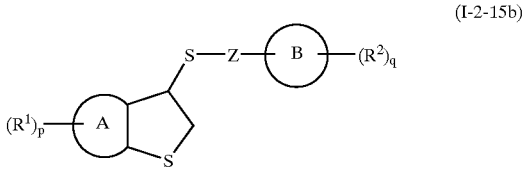
(I-2-15b)

(wherein all the symbols are the same meanings as hereinbefore described.)

may be prepared by reduction of the compounds obtained by the above mentioned method in which m is 0, n is 1, i.e., the compounds of the formula (I-2-15ab)

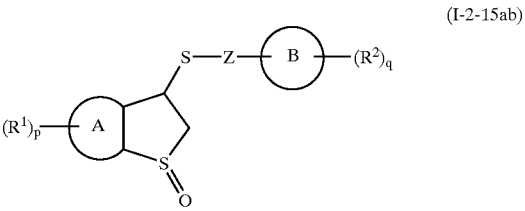
(I-2-15ab)

(wherein all the symbols are the same meanings as hereinbefore described.).

This reduction reaction is well known. For example, this reaction may be carried out in an organic solvent (diethyl ether, tetrahydrofuran etc.) using reductant (lithium aluminum hydride, aluminum diisobutylhydride etc.) at 0~80° C.

[16] The compounds of the present invention of the formula (I-2) in which m is 1, i.e., the compounds of the present invention of the formula (I-2-16)

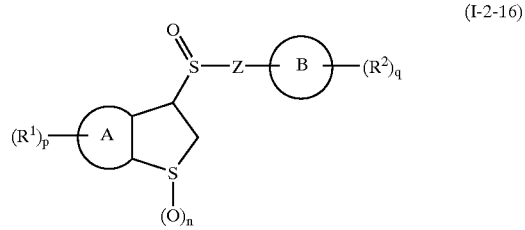
(I-2-16)

(wherein all the symbols are the same meanings as hereinbefore described.)

may be prepared by oxidizing the said compounds of the formula (I-2-15).

This oxidation may be carried out by the same procedure for preparation of the compounds of the formula (I-1-1a) in [1].

[17] The compounds of the present invention of the formula (I-2) in which m is 2, i.e., the compounds of the present invention of the formula (I-2-17)

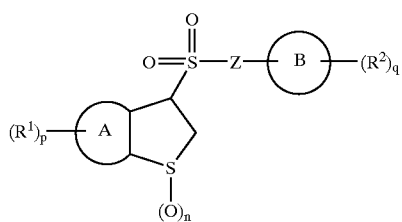

(I-2-17)

(wherein all the symbols are the same meanings as hereinbefore described.)

may be prepared by the following methods (a)~(c).

(a) The compounds of the present invention of the formula (I-2-17) in which n is 1 or 2, i.e., the compounds of the present invention of the formula (I-2-17a)

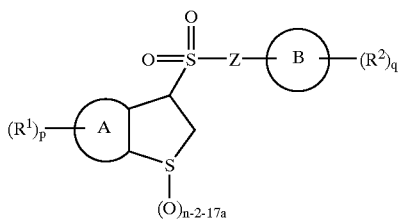

(I-2-17a)

(wherein, n-2-17a is an integer of 1~2 and the other symbols are the same meaning as hereinbefore described.)

may be prepared by reacting the said compounds of the formula (I-1-1a) or the compounds of the formula (I-1-1b) and the compounds of the formula (IV)

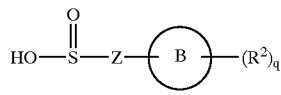

(IV)

(wherein all the symbols are the same meanings as hereinbefore described.).

This reaction may be carried out by the same procedure described in the reaction of the compounds of the formula (I-2-15a) and the compounds of the formula (III) in [15].

(b) The compounds of the present invention of the formula (I-2-17) in which n is 0, i.e., the compounds of the formula (I-2-17b)

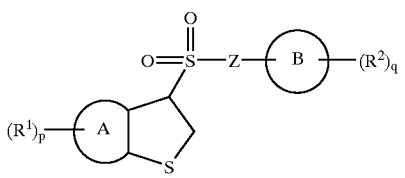

(I-2-17b)

(wherein all the symbols are the same meanings as hereinbefore described.)

may be prepared by reduction of the compounds of the formula (V)

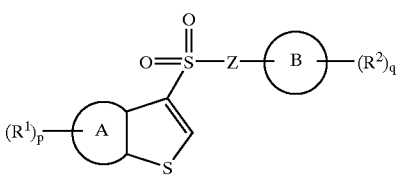

(V)

(wherein all the symbols are the same meanings as hereinbefore described.).

This reduction is known one. For example, it may be carried out by hydrogenation or by the method using triethylsilane.

This hydrogenation is known reaction. For example, it may be carried out in inert solvent [ethers (e.g., tetrahydrofuran, dioxane, dimethoxy ethane, diethyl ether etc.), alcohols (e.g., methanol, ethanol etc.), benzenes (e.g., benzene, toluene etc.), ketones (e.g., acetone, methyl ethyl ketone etc.), nitrites (e.g., acetonitrile etc.), amides (e.g., dimethylformamide etc.), water, ethyl acetate, acetic acid or mixture of the said two or more solvents etc.], in the presence of catalyst to hydrogenate (e.g., Pd—C, palladium black, Pd, palladium hydroxide, platinum oxide, Ni, Raney nickel, ruthenium chloride etc.), in the presence or absence of an inorganic acid (e.g., hydrochloric acid, sulfuric acid, hypochlorous acid, boric acid, tetrafluoroboric acid etc.) or an organic acid (e.g., acetic acid, p-toluenesulfonici acid, bromic acid, trifluoroacetic acid, formic acid etc.), at an ordinary or increased pressure under an atmosphere of hydrogen gas, or in the presence of ammonium formate at 0~200° C. When an acid is used, its salt may be used.

This reduction using triethylsilane is well known. For example, it may be carried out in trifluoroacetic acid, in the presence of triethylsilane at 0~100° C.

(c) The compounds of the present invention of the formula (I-2-17) in which n is 2, i.e., the compounds of the present invention of the formula (I-2-17c)

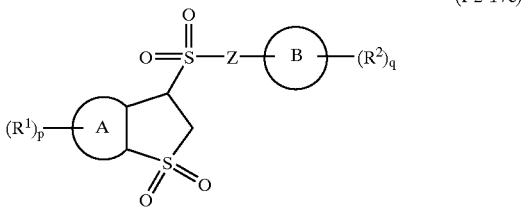

(I-2-17c)

(wherein all the symbols are the same meanings as hereinbefore described.)

may be prepared by oxidizing the compounds obtained by the above mentioned method in which m is 0 and n is 2, i.e., the compounds of the formula (I-2-15ac)

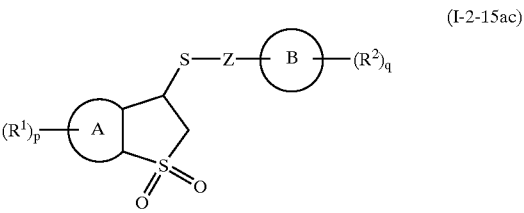

(I-2-15ac)

(wherein all the symbols are the same meanings as hereinbefore described.).

This reaction may be carried out by the same procedure for preparation of the compounds of the formula (I-1-1b) in [1].

The compounds of the present invention of the formula (I-2) may be also prepared by not only the methods described in [15]~[17] but also the following methods [18]~[30].

[18] The compounds of the present invention of the formula (I-2) in which at least one of $R^1$(s) or $R^2$(s) is a substituted oxy or a group containing substituted oxy, i.e., the compounds of the present invention of the formula (I-2-18)

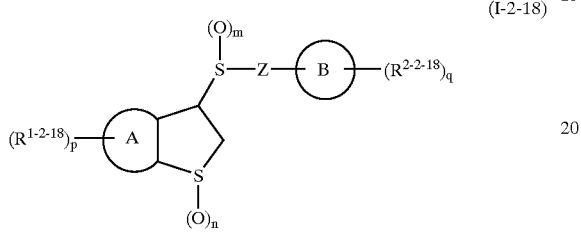

(I-2-18)

(wherein, $R^{1-2-18}$ and $R^{2-2-18}$ are the same meanings as hereinbefore described for $R^1$ and $R^2$, respectively, provided that at least one of $R^{1-2-18}$(s) and $R^{2-2-18}$(s) is a substituted oxy or a group containing substituted oxy and the other symbols are the same meaning as hereinbefore described.) may be prepared by the following methods (a)~(b).

(a) The compounds of the present invention of the formula (I-2-18) may be prepared by eterification of the compounds of the formula (I-2) in which at least one of $R^1$(s) or $R^2$(s) is hydroxy or a group containing hydroxy, i.e., the compounds of the formula (I-2-18a)

(I-2-18a)

(wherein, $R^{1-2-18a}$ and $R^{2-2-18a}$ are the same meanings as hereinbefore described for $R^1$ and $R^2$, respectively, provided that at least one of $R^{1-2-18a}$(s) and $R^{2-2-18a}$(s) is a hydroxy or a group containing hydroxy and the other symbols are the same meaning as hereinbefore described.)
and the corresponding compounds containing a group which is removal (chloride, bromide, iodide, mesyl or tosyl etc.).

This eterification may be carried out by the same procedure for preparation of the compounds of the formula (I-1-2a) in [2].

(b) The compounds of the present invention of the formula (I-2-18) may be prepared by eterification of the compounds of the formula (I-2) in which at least one of $R^1$(s) is a hydroxy or a group containing hydroxy, i.e., the compounds of the formula (I-2-18b)

(I-2-18b)

(wherein, $R^{1-2-18b}$ and $R^{2-2-18b}$ are the same meanings as hereinbefore described for $R^1$ and $R^2$, respectively, provided that at least one of $R^{1-2-18b}$(s) and $R^{2-2-18b}$(s) is a hydroxy or a group containing hydroxy and the other symbols are the same meaning as hereinbefore described.)
with corresponding compounds containing hydroxy.

This eterification may be carried out by the procedure for preparation of the compounds of the formula (I-1-2b) in [2].

[19] The compounds of the present invention of the formula (I-2) in which at least one of $R^1$(s) or $R^2$(S) is a substituted amino or a group containing substituted amino, i.e., the compounds of the present invention of the formula (I-2-19)

(I-2-19)

(wherein, $R^{1-2-19}$ and $R^{2-2-19}$ are the same meanings as hereinbefore described for $R^1$ and $R^2$, respectively, provided that at least one of $R^{1-2-19}$(s) and $R^{2-2-19}$(s) is a substituted amino or a group containing substituted amino and the other symbols are the same meaning as hereinbefore described.) may be prepared by the following methods (a)~(d).

(a) The compounds of the present invention of the formula (I-2-19) may be prepared by reacting the compounds of the formula (I-2) in which at least one of $R^1$(s) or $R^2$(s) is a halogen (chloride, bromide, iodide) or a group containing halogen, i.e., the compounds of the formula (I-2-19a)

(I-2-19a)

(wherein, $R^{1-2-19a}$ and $R^{2-2-19a}$ are the same meanings as hereinbefore described for $R^1$ and $R^2$, respectively, provided that at least one of $R^{1-2-19a}$(s) and $R^{2-2-19a}$(s) is a halogen (chloride, bromide, iodide) or a group containing halogen and the other symbols are the same meaning as hereinbefore described.)
and the compounds containing amino.

This reaction may be carried out by the same procedure for preparation of the compounds of the formula (I-1-3a) in [3].

(b) The compounds of the present invention of the formula (I-2-19) may be prepared by reacting the compounds of the formula (I-2) in which at least one of $R^1$(s) or $R^2$(s) is an amino or a group containing amino, i.e., the compounds of the formula (I-2-19b)

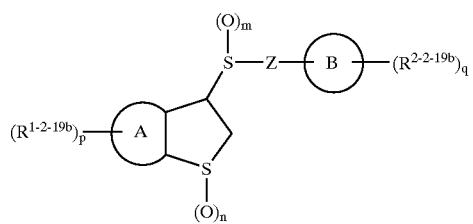

(I-2-19b)

(wherein, $R^{1-2-19b}$ and $R^{2-2-19b}$ are the same meanings as hereinbefore described for $R^1$ and $R^2$, respectively, provided that at least one of $R^{1-2-19b}$(s) and $R^{2-2-19b}$(s) is an amino or a group containing amino and the other symbols are the same meaning as hereinbefore described.) and the corresponding compounds containing halogen (chloride, bromide, and iodide).

This reaction may be carried out by the same procedure for preparation of the compounds of the formula (I-1-3a) in [3].

(c) The compounds of the present invention of the formula (I-2-19) may be prepared by reacting the compounds of the formula (I-2) in which at least one of $R^1$(s) or $R^2$(s) is an amino or a group containing amino, i.e., the compounds of the formula (I-2-19c)

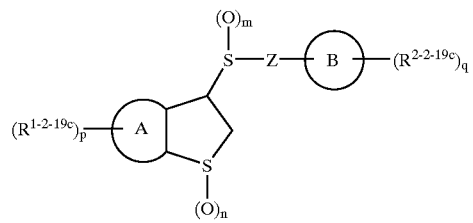

(I-2-19c)

(wherein, $R^{1-2-19c}$ and $R^{2-2-19c}$ are the same meanings as hereinbefore described for $R^1$ and $R^2$, respectively, provided that at least one of $R^{1-2-19c}$(s) and $R^{2-2-19c}$(s) is an amino or a group containing amino and the other symbols are the same meaning as hereinbefore described.) and the corresponding compounds containing carbonyl.

This reaction may be carried out by the same procedure for preparation of the compounds of the formula (I-1-3c) in [3].

(d) The compounds of the present invention of the formula (I-2-19) may be prepared by reductive amidation of the compounds of the formula (I-2) in which at least one of $R^1$(s) or $R^2$(s) is a carbonyl or a group containing carbonyl, i.e., the compounds of the formula (I-2-19d)

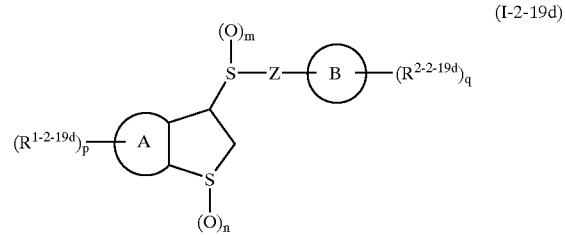

(I-2-19d)

(wherein, $R^{1-2-19d}$ and $R^{2-2-19d}$ are the same meanings as hereinbefore described for $R^1$ and $R^2$, respectively, provided that at least one of $R^{1-2-19d}$(s) and $R^{2-2-19d}$(s) is a carbonyl or a group containing carbonyl and the other symbols are the same meaning as hereinbefore described.) and the corresponding compounds containing amino.

This reductive amidation may be carried out by the same procedure for preparation of the compounds of the formula (I-1-3c) in [3].

[20] The compounds of the present invention of the formula (I-2) in which at least one of $R^1$(s) or $R^2$(s) is an amide or a group containing amide, i.e., the compounds of the present invention of the formula (I-2-20)

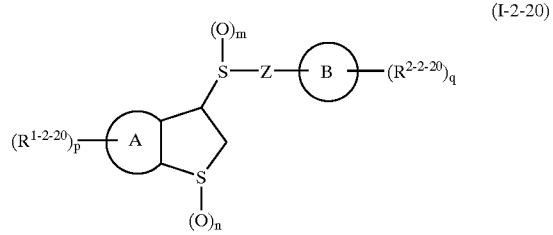

(I-2-20)

(wherein, $R^{1-2-20}$ and $R^{2-2-20}$ are the same meanings as hereinbefore described for $R^1$ and $R^2$, respectively, provided that at least one of $R^{1-2-20}$(s) and $R^{2-2-20}$(s) is an amide or a group containing amide and the other symbols are the same meaning as hereinbefore described.) may be prepared by the following methods (a)–(b).

(a) The compounds of the present invention of the formula (I-2-20) may be prepared by amidation of the compounds of the formula (I-2) in which at least one of at least one of $R^1$(s) or $R^2$(s) is a —COOH or a group containing —COOH, i.e., the compounds of the formula (I-2-20a)

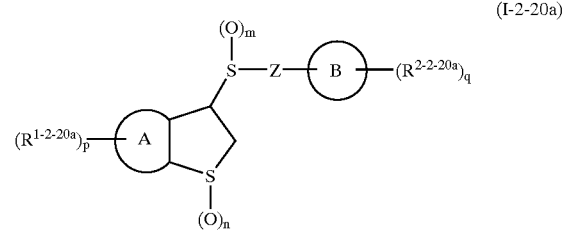

(I-2-20a)

(wherein, $R^{1-2-20a}$ and $R^{2-2-20a}$ are the same meanings as hereinbefore described for $R^1$ and $R^2$, respectively, provided that at least one of $R^{1-2-20a}$(s) and $R^{2-2-20a}$(s) is a —COOH or a group containing —COOH and the other symbols are the same meaning as hereinbefore described.) and the corresponding compounds containing amino.

The amidation may be carried out by the same procedure for preparation of the compounds of the formula (I-1-4) in [4].

(b) The compounds of the present invention of the formula (I-2-20) may be prepared by amidation of the compounds of the formula (I-2) in which at least one of $R^1$(s) or $R^2$(s) is an amino or a group containing amino, i.e., the compounds of the formula (I-2-20b)

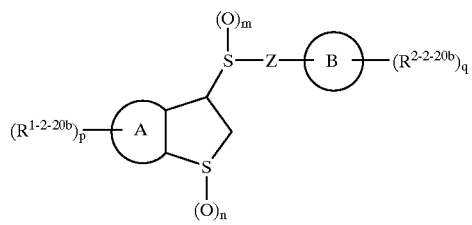

(I-2-20b)

(wherein, $R^{1\text{-}2\text{-}20b}$ and $R^{2\text{-}2\text{-}20b}$ are the same meanings as hereinbefore described for $R^1$ and $R^2$, respectively, provided that at least one of $R^{1\text{-}2\text{-}20b}$(s) and $R^{2\text{-}2\text{-}20b}$(s) is an amino or a group containing amino and the other symbols are the same meaning as hereinbefore described.) and the corresponding compounds containing carboxy.

The amidation may be carried out by the same procedure for preparation of the compounds of the formula (I-1-4) in [4].

[21] The compounds of the present invention of the formula (I-2) in which at least one of $R^1$(s) or $R^2$(s) is an ester or a group containing ester, i.e., the compounds of the present invention of the formula (I-2-21)

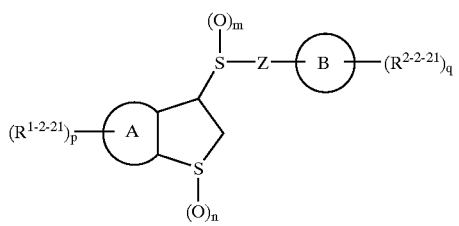

(I-2-21)

(wherein, $R^{1\text{-}2\text{-}21}$ and $R^{2\text{-}2\text{-}21}$ are the same meanings as hereinbefore described for $R^1$ and $R^2$, respectively, provided that at least one of $R^{1\text{-}2\text{-}21}$(s) and $R^{2\text{-}2\text{-}21}$(s) is an ester or a group containing ester and the other symbols are the same meaning as hereinbefore described.) may be prepared by the following methods (a)~(b).

(a) The compounds of the present invention of the formula (I-2-21) may be prepared by esterification of the compounds of the formula (I-2) in which at least one of $R^1$(s) or $R^2$(s) is a —COOH or a group containing —COOH, i.e., the compounds of the formula (I-2-21a)

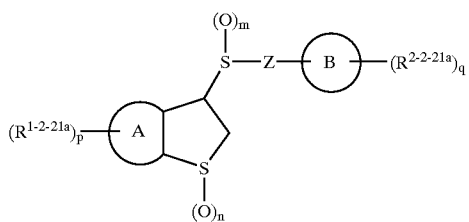

(I-2-21a)

(wherein, $R^{1\text{-}2\text{-}21a}$ and $R^{2\text{-}2\text{-}21a}$ are the same meanings as hereinbefore described for $R^1$ and $R^2$, respectively, provided that at least one of $R^{1\text{-}2\text{-}21a}$(s) and $R^{2\text{-}2\text{-}21a}$(s) is a —COOH or a group containing —COOH and the other symbols are the same meaning as hereinbefore described.) and the corresponding compounds containing hydroxy.

This esterification may be carried out by the same procedure for preparation of the compounds of the formula (I-1-5) in [5].

(b) The compounds of the present invention of the formula (I-2-21) may be prepared by esterification of the compounds of the formula (I-2) in which $R^1$(s) or $R^2$(s) is a hydroxy or a group containing hydroxy, i.e., the compounds of the formula (I-2-21b)

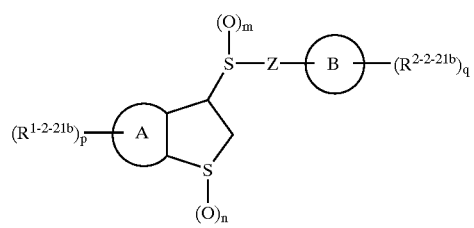

(I-2-21b)

(wherein, $R^{1\text{-}2\text{-}21b}$ and $R^{2\text{-}2\text{-}21b}$ are the same meanings as hereinbefore described for $R^1$ and $R^2$, respectively, provided that at least one of $R^{1\text{-}2\text{-}21b}$(s) and $R^{2\text{-}2\text{-}21b}$(s) is a hydroxy or a group containing hydroxy and the other symbols are the same meaning as hereinbefore described.) and the corresponding compounds containing carboxy.

This esterification may be carried out by the same procedure for preparation of the compounds of the formula (I-1-5) in [5].

[22] The compounds of the present invention of the formula (I-2) in which at least one of $R^1$(s) or $R^2$(s) is a sulfonamide or a group containing sulfonamide, i.e., the compounds of the present invention of the formula (I-2-22)

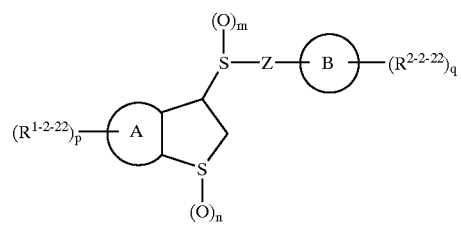

(I-2-22)

(wherein, $R^{1\text{-}2\text{-}22}$ and $R^{2\text{-}2\text{-}22}$ are the same meanings as hereinbefore described for $R^1$ and $R^2$, respectively, provided that at least one of $R^{1\text{-}2\text{-}22}$(s) and $R^{2\text{-}2\text{-}22}$(s) is a sulfonamide or a group containing sulfonamide and the other symbols are the same meaning as hereinbefore described.) may be prepared by the following methods (a)~(b).

(a) The compounds of the present invention of the formula (I-2-22) may be prepared by sulfonamidation of the compounds of the formula (I-2) in which at least one of $R^1$(s) or $R^2$(s) is a —SO$_3$H or a group containing —SO$_3$H, i.e., the compounds of the formula (VI)

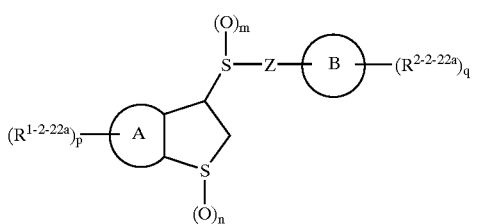

(VI)

(wherein, $R^{1\text{-}2\text{-}22a}$ and $R^{2\text{-}2\text{-}22a}$ are the same meanings as hereinbefore described for $R^1$ and $R^2$, respectively, provided that at least one of $R^{1\text{-}2\text{-}22a}$(s) and $R^{2\text{-}2\text{-}22a}$(s) is a —SO$_3$H or a group containing —SO$_3$H and the other symbols are the same meaning as hereinbefore described.) and the corresponding compounds containing amino.

The sulfonamidation may be carried out by the same procedure for preparation of the compounds of the formula (I-1-6a) in [6].

(b) The compounds of the present invention of the formula (I-2-22) may be prepared by sulfonamidation of the compounds of the formula (I-2) in which at least one of $R^1$(s) or $R^2$(s) is an amino or a group containing amino, i.e., the compounds of the formula (I-2-22b)

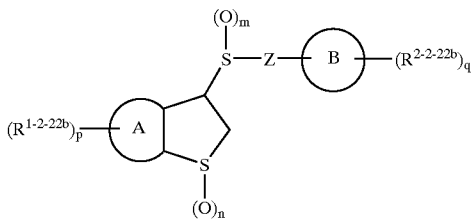

(I-2-22b)

(wherein, $R^{1\text{-}2\text{-}22b}$ and $R^{2\text{-}2\text{-}22b}$ are the same meanings as hereinbefore described for $R^1$ and $R^2$, respectively, provided that at least one of $R^{1\text{-}2\text{-}22b}$(s) and $R^{2\text{-}2\text{-}22b}$(s) is an amino or a group containing amino and the other symbols are the same meaning as hereinbefore described.) and the corresponding compounds containing sulfo.

The sulfonamidation may be carried out by the same procedure for preparation of the compounds of the formula (I-1-6a) in [6].

[23] The compounds of the present invention of the formula (I-2) in which at least one of $R^1$(s) or $R^2$(s) is a substituted aminocarbonyloxy or a group containing a substituted aminocarbonyloxy, i.e., the compounds of the present invention of the formula (I-2-23)

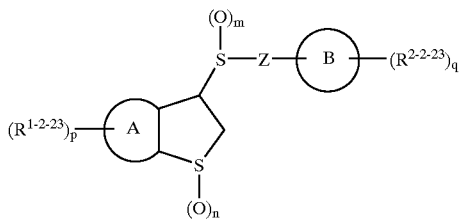

(I-2-23)

(wherein, $R^{1\text{-}2\text{-}23}$ and $R^{2\text{-}2\text{-}23}$ are the same meanings as hereinbefore described for $R^1$ and $R^2$, respectively, provided that at least one of $R^{1\text{-}2\text{-}23}$(s) and $R^{2\text{-}2\text{-}23}$(s) is a substituted aminocarbonyloxy or a group containing a substituted aminocarbonyloxy and the other symbols are the same meaning as hereinbefore described.) may be prepared by reacting the compounds of the formula (I-2) in which at least one of $R^1$(s) or $R^2$(s) is a hydroxy or a group containing hydroxy, i.e., the compounds of the formula (I-2-23a)

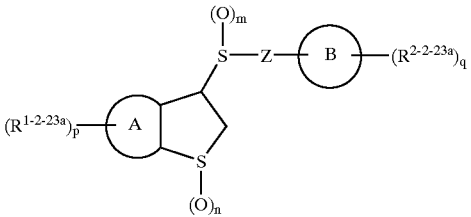

(I-2-23a)

(wherein, $R^{1\text{-}2\text{-}23a}$ and $R^{2\text{-}2\text{-}23a}$ are the same meanings as hereinbefore described for $R^1$ and $R^2$, respectively, provided that at least one of $R^{1\text{-}2\text{-}23a}$(s) and $R^{2\text{-}2\text{-}23a}$(s) is a hydroxy or a group containing hydroxy and the other symbols are the same meaning as hereinbefore described.) and the corresponding compounds containing isocyanate.

This reaction may be carried out by the same procedure for preparation of the compounds of the formula (I-1-7) in [7].

[24] The compounds of the present invention of the formula (I-2) in which at least one of $R^1$(s) or $R^2$(s) is a substituted aminocarbonylamino or a group containing a substituted aminocarbonylamino, i.e., the compounds of the present invention of the formula (I-2-24)

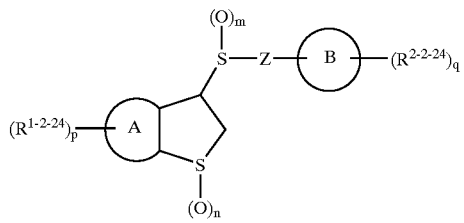

(I-2-24)

(wherein, $R^{1\text{-}2\text{-}24}$ and $R^{2\text{-}2\text{-}24}$ are the same meanings as hereinbefore described for $R^1$ and $R^2$, respectively, provided that at least one of $R^{1\text{-}2\text{-}24}$(s) and $R^{2\text{-}2\text{-}24}$(s) is a substituted aminocarbonylamino or a group containing a substituted aminocarbonylamino and the other symbols are the same meaning as hereinbefore described.) may be prepared by reacting the compounds of the formula (I-2) in which at least one of $R^1$(s) or $R^2$(s) is an amino or a group containing amino, i.e., the compounds of the formula (I-2-24a)

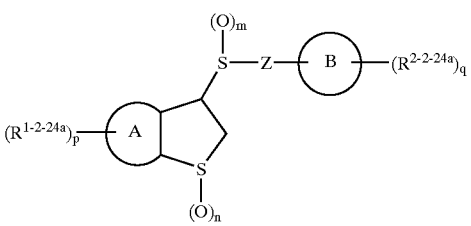

(I-2-24a)

(wherein, $R^{1\text{-}2\text{-}24a}$ and $R^{2\text{-}2\text{-}24a}$ are the same meanings as hereinbefore described for $R^1$ and $R^2$, respectively, provided that at least one of $R^{1\text{-}2\text{-}24a}$(s) and $R^{2\text{-}2\text{-}24a}$(s) is an amino or a group containing amino and the other symbols are the same meaning as hereinbefore described.) and the corresponding compounds containing isocyanate.

This reaction may be carried out by the same procedure for preparation of the compounds of the formula (I-1-7) in [7].

[25] The compounds of the present invention of the formula (I-2) in which at least one of $R^1(s)$ or $R^2(s)$ is a substituted oxycarbonylamino or a group containing a substituted oxyocarbonylamino, i.e., the compounds of the present invention of the formula (I-2-25)

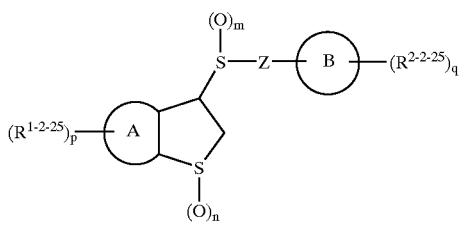

(I-2-25)

(wherein, $R^{1-2-25}$ and $R^{2-2-25}$ are the same meanings as hereinbefore described for $R^1$ and $R^2$, respectively, provided that at least one of $R^{1-2-25}(s)$ and $R^{2-2-25}(s)$ is a substituted oxycarbonylamino or a group containing a substituted oxyocarbonylamino and the other symbols are the same meaning as hereinbefore described.) may be prepared by reacting the compounds of the formula (I-2) in which at least one of $R^1(s)$ or $R^2(s)$ is an amino or a group containing amino, i.e., the compounds of the formula (I-2-25a)

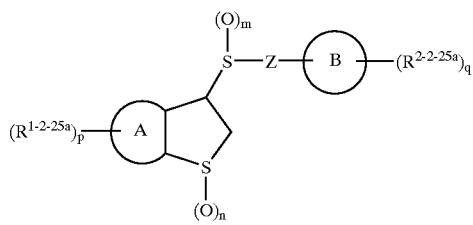

(I-2-25a)

(wherein, $R^{1-2-25a}$ and $R^{2-2-25a}$ are the same meanings as hereinbefore described for $R^1$ and $R^2$, respectively, provided that at least one of $R^{1-2-25a}(s)$ and $R^{2-2-25a}(s)$ is an amino or a group containing amino and the other symbols are the same meaning as hereinbefore described.) and the corresponding compounds containing haloformic acid ester.

This reaction may be carried out by the same procedure for preparation of the compounds of the formula (I-1-9) in [9].

[26] The compounds of the present invention of the formula (I-1) in which at least one of $R^1(s)$ or $R^2(s)$ is a substituted oxycarbonyloxy or a group containing a substituted oxycarbonyloxy, i.e., the compounds of the present invention of the formula (I-2-26)

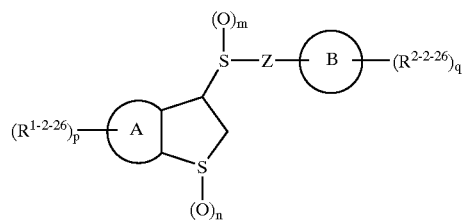

(I-2-26)

(wherein, $R^{1-2-26}$ and $R^{2-2-26}$ are the same meanings as hereinbefore described for $R^1$ and $R^2$, respectively, provided that at least one of $R^{1-2-26}(s)$ and $R^{2-2-26}(s)$ is a substituted oxycarbonyloxy or a group containing a substituted oxycarbonyloxy and the other symbols are the same meaning as hereinbefore described.) may be prepared by reacting the compounds of the formula (I-2) in which at least one of $R^1(s)$ or $R^2(s)$ is a hydroxy or a group containing hydroxy, i.e., the compounds of the formula (I-2-26a)

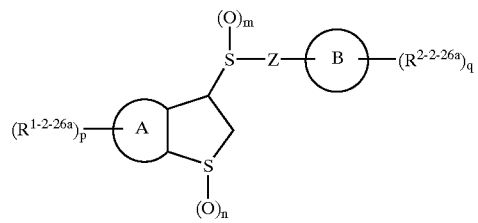

(I-2-26a)

(wherein, $R^{1-2-26a}$ and $R^{2-2-26a}$ are the same meanings as hereinbefore described for $R^1$ and $R^2$, respectively, provided that at least one of $R^{1-2-26a}(s)$ and $R^{2-2-26a}(s)$ is a hydroxy or a group containing hydroxy and the other symbols are the same meaning as hereinbefore described.) and the corresponding compounds containing haloformic acid ester.

This reaction may be carried out by the same procedure for preparation of the compounds of the formula (I-1-9) in [9].

[27] The compounds of the present invention of the formula (I-2) in which at least one of $R^1(s)$ or $R^2(s)$ is a substituted (hydroxy)methyl or a group containing substituted (hydroxy)methyl, i.e., the compounds of the present invention of the formula (I-2-27)

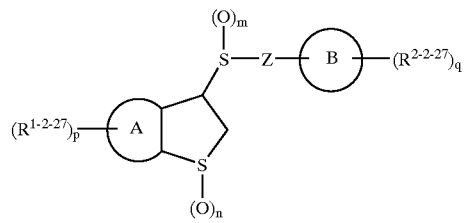

(I-2-27)

(wherein, $R^{1-2-27}$ and $R^{2-2-27}$ are the same meanings as hereinbefore described for $R^1$ and $R^2$, respectively, provided that at least one of $R^{1-2-27}(s)$ and $R^{2-2-27}(s)$ is a substituted (hydroxy)methyl or a group containing a substituted (hydroxy)methyl and the other symbols are the same meaning as hereinbefore described.) may be prepared by reacting the compounds of the formula (I-2) in which at least one of $R^1$(s) or $R^2$(s) is a formyl, i.e., the compounds of the formula (I-2-27a)

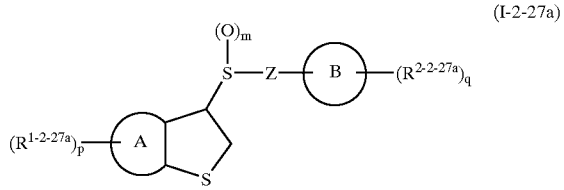

(I-2-27a)

(wherein, $R^{1-2-27a}$ and $R^{2-2-27a}$ are the same meanings as hereinbefore described for $R^1$ and $R^2$, respectively, provided that at least one of $R^{1-2-27a}$(s) and $R^{2-2-27a}$(s) is a formyl and the other symbols are the same meaning as hereinbefore described.) and Grignard's reagents or corresponding derivatives containing lithium.

This reaction may be carried out by the same procedure for preparation of the compounds of the formula (I-1-11a) in [11].

[28] The compounds of the present invention of the formula (I-2) in which at least one of $R^1$(s) or $R^2$(s) is a substituted carbonyl or a group containing a substituted carbonyl, i.e., the compounds of the present invention of the formula (I-2-28)

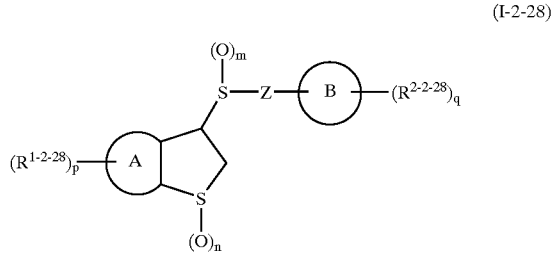

(I-2-28)

(wherein, $R^{1-2-28}$ and $R^{2-2-28}$ are the same meanings as hereinbefore described for $R^1$ and $R^2$, respectively, provided that at least one of $R^{1-2-28}$(s) and $R^{2-2-28}$(s) is a substituted carbonyl or a group containing a substituted carbonyl and the other symbols are the same meaning as hereinbefore described.) may be prepared by oxidizing the said compounds of the formula (I-2-27).

This reaction may be carried out by the same procedure for preparation of the compounds of the formula (I-1-12) in [12].

[29] The compounds of the present invention of the formula (I-2) in which at least one of $R^1$(s) or $R^2$(s) is an amino or a group containing amino, i.e., the compounds of the present invention of the formula (I-2-29)

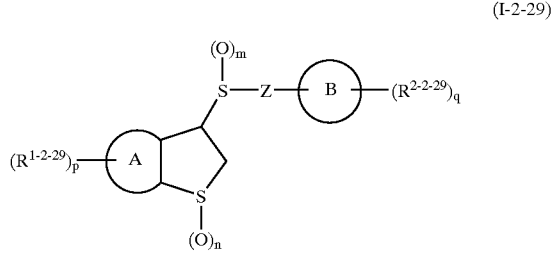

(I-2-29)

(wherein, $R^{1-2-29}$ and $R^{2-2-29}$ are the same meanings as hereinbefore described for $R^1$ and $R^2$, respectively, provided that at least one of $R^{1-2-29}$(s) and $R^{2-2-29}$(s) is an amino or a group containing amino and the other symbols are the same meaning as hereinbefore described.) may be prepared by reduce of nitro in the compounds of the formula (I-2) in which at least one of $R^1$(s) or $R^2$(s) is a nitro or a group containing nitro, i.e., the compounds of the formula (I-2-29a)

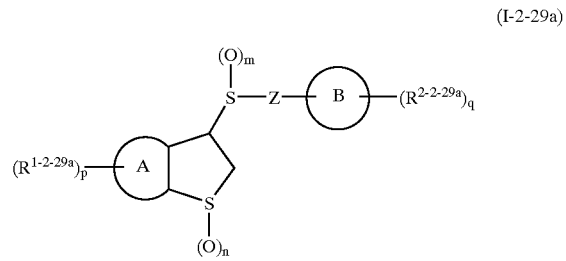

(I-2-29a)

(wherein, $R^{1-2-29a}$ and $R^{2-2-29a}$ are the same meanings as hereinbefore described for $R^1$ and $R^2$, respectively, provided that at least one of $R^{1-2-29a}$(s) and $R^{2-2-29a}$(s) is a nitro or a group containing nitro and the other symbols are the same meaning as hereinbefore described.).

The reduction of nitro may be carried out by the same procedure for preparation of the compounds of the formula (I-1-13) in [13].

[30] The compounds of the present invention of the formula (I-2) in which at least one of $R^1$(s) or $R^2$(s) is a —COOH, hydroxy or amino or a group containing —COOH, hydroxy or amino, i.e., the compounds of the present invention of the formula (I-2-30)

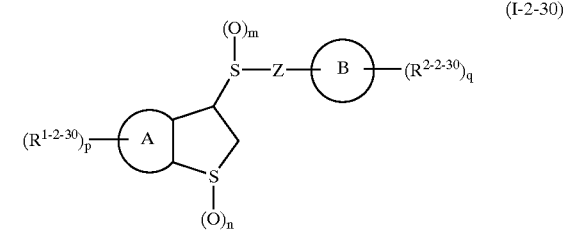

(I-2-30)

(wherein, $R^{1-2-30}$ and $R^{2-2-30}$ are the same meanings as hereinbefore described for $R^1$ and $R^2$, respectively, provided that at least one of $R^{1-2-30}$(s) and $R^{2-2-30}$(s) is a —COOH, hydroxy or amino or a group containing —COOH, hydroxy or amino and the other symbols are the same meaning as hereinbefore described.) may be prepared by removal of protecting group in the compounds of the formula (I-2) in which —COOH, hydroxy or amino which is protected by a protecting group or a group containing —COOH, hydroxy or amino which is protected by a protecting group, i.e., the compounds of the formula (I-2-30a)

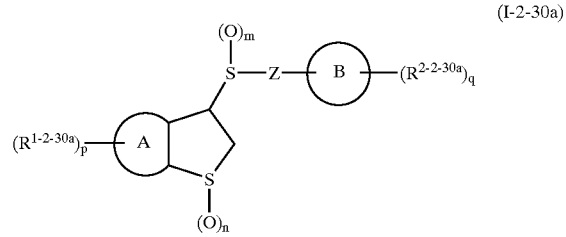

(I-2-30a)

(wherein, $R^{1-2-30a}$ and $R^{2-2-30a}$ are the same meanings as hereinbefore described for $R^1$ and $R^2$, respectively, provided that at least one of $R^{1-2-30a}$(s) and $R^{2-2-30a}$(s) is a protected —COOH (e.g., it is protected by methyl, ethyl, t-butyl and benzyl etc.), protected hydroxy (e.g., it is protected by methoxymethyl, tetrahydropyranyl, t-butyldimethylsilyl, acetyl, benzyl etc.) or protected amino (e.g., it is protected by benzyloxycarbonyl, t-butoxycarbonyloxy, trifluoroacetyl etc.) or a group containing such a group and the other symbols are the same meaning as hereinbefore described.) by an alkaline hydrolysis, by removal of protecting group in an acidic condition, by removal of silyl or by removal of protecting group based on hydrogenelysis. An alkaline hydrolysis, by removal of protecting group in an acidic condition, by removal of silyl or by hydrogenolysis may be carried out by same procedure for preparation of the compounds of the formula (I-1-14) in [14].

Reaction for removal of protecting group in the present invention means an ordinal one which is well known to the person in the art, for example, alkaline hydrolysis, removal of protecting group in an acidic condition and hydrogenolysis. The aimed compounds of the present invention may be prepared easily by choice of these reactions.

As well known to the person in the art, a protecting group of carboxy includes, for example, methyl, ethyl, t-butyl and benzyl. In addition, such a group includes the other protecting group which is removable selectively and easily, for example, one described in T. W. Greene, Protective Groups in Organic Synthesis, Wiley, New York, 1991.

A protecting group of hydroxy includes, for example, methoxymethyl, tetrahydropyranyl, t-butyidimethylsilyl, acetyl, and benzyl. In addition, such a group includes the other protecting group which is removable selectively and easily, for example, one described in T. W. Greene, Protective Groups in Organic Synthesis, Wiley, New York, 1991.

A protecting group of amino includes, for example, benzyloxycarbonyl, t-butoxycarbonyl, trifluoroacetyl. In addition, such a group includes the other protecting group which is removable selectively and easily, for example, one described in T. W. Greene, Protective Groups in Organic Synthesis, Wiley, New York, 1991.

The compounds of the formula (V) are known per se or may be prepared according to the following Reaction Scheme or by known methods easily.

In Reaction Scheme, X is halogen.

Reaction Scheme 1

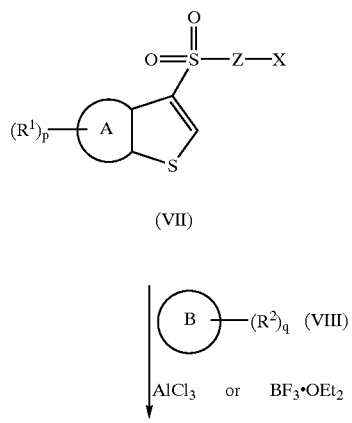

(VII)

AlCl₃ or BF₃·OEt₂

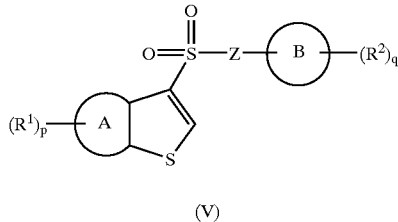

(V)

The compounds of the formulae (III), (IV), (VI), (VII) or (VIII) used as starting materials have been known per se or may be prepared by known methods easily.

Further, the compounds of the formula (I-1-1c) in which A is benzene, R' is carboxy, p is 1 and R' is bonded at 4-position, i.e., the compounds of the formula (XI) are important intermediates of the compounds of the formula (I) of the present invention. The methods for preparation of the compounds of the formula (XI) are shown in the mentioned Reaction Scheme 5. Next, each step is explained in detail.

The reaction to synthesis of the compounds of the formula (XIII) from the compounds of the formula (XII) is well known. For example, it may be carried out in an inert organic solvent (acetonitrile, benzene, toluene, xylene, methyhlene chloride, chloroform, dimethoxy ethane, tetrahydrofuran, tetrahydropyran, dioxane, diethyl ether, acetone etc.) or mixture thereof, in the presence of Lewis acid ($ZnI_2$, $ZnCl_2$, aluminum chloride, $TiCl_2$, lithium hypochloric acid, lithium borotetrafluoride, lithium hexafluoride etc.) and cyanide derivatives (trimethylsilylcyanide, diethyl aluminum cyanide, or diethyl cyanophosphonate etc.) at 0~40° C.

The reaction to synthesis of the compounds of the formula (XIV) from the compounds of the formula (XIII) is well known. For example, it may be carried out in an inert organic solvent (benzene, toluene, ethyl acetate, dioxane, dimethoxy ethane, diethyl ether, tetrahydrofuran, tetrahydropyran, the mixture thereof etc.) in the presence of oxidant (2,3-dichloro-5,6-dicyano-1,4-benzoquinon, chloranil (2,3,5,6-tetrachloro-1,4-benzoquinon) etc.) at room temperature to refluxing temperature. Or it may be carried out, for example, in an organic solvent (ethylene glycol, oleic acid, diethylene glycol, dimethyl ether, toluene, benzene, xylene etc.) in the presence of hydrogen acceptor (nitrobenzene, maleic acid, cyclohexen, oleic acid, 1,5-cycloctadien, phenylacetylene, 2-butylic acid etc.) and in the presence of metal catalyst (Pd—C, palladium hydroxide, palladium black, Pd, platinum oxide, Ni, Raney nickel, ruthenium chloride etc.) at 60° C.~refluxing temperature.

The reaction to synthesis of the compounds of the formula (XI) from the compounds of the formula (XIV) is well known. For example, it may be carried out in alcohol solvent (ethylene glycol, t-butanol, benzyl alcohol, methanol ethanol, propanol, isopropanol etc.) in the presence of alkali (sodium hydroxide, potassium hydroxide, lithium hydroxide etc.) at 60° C.~refluxing temperature.

In each reaction in the present specification, obtained products may be purified by conventional techniques. For example, purification may be carried out by distillation at atmospheric or reduced pressure, by high performance liquid chromatography, by thin layer chromatography or by column chromatography using silica gel or magnesium silicate, by washing or by recrystallization. Purification may be carried out after each reaction, or after a series of reactions.

In addition, the optical isomers of the compounds of the present invention of the formula (I) may be obtained by an ordinal optical separation (e.g., separation by gas chromatography or by high performance liquid chromatography, separation by crystallization to diastermeric salt or clathrate compounds or separation by preferential crystallization etc.) or by ordinal method for preparation of racemic compound.

[Pharmacological Activities]

According to the following experiments, it has been proved that the compounds of the present invention of the formula (I) possess inhibitory activities of producing IL-6 and/or IL-12.

(1) Assaying Inhibitory Activity on IL-6 Production and Cellular Toxicity

[Experimental Method]

$1.5 \times 10^4$ of A549 cells (human lung epithelial cell line) were suspended in dalbeco-modified eagle medium (DMEM) containing 0.5% fetus bovine serum (abbreviated as FBS) (100 μl) and incubated in 96 well-microplate over day and night. The test compound dissolved in various kinds of solvents at various concentrations (20 μl) and Tumor Necrosis Factor-α (TNF-α (Genzyme Co, Cat. No. TNF-H)) dissolved in DMEM at the concentration of 12.5 ng/ml (80 μl) were added thereto. After incubation for 24 hours, the supernatant (200 μl) was recovered to assay the quantity of IL-6 using Enzyme Linked Immuno Solvent Assay (ELISA) Method (R&D Systems Co., Cat. No. D6050), to calculate inhibitory activity of the test compound and determine 50% inhibitory concentration ($IC_{50}$). To the cells from which the supernatant was removed, a solution of brom 3-(4,5-dimethyl-2-thiazolyl)-2,5-diphenyl-2H-tetrazolinium (abbreviated as MTT (Dojin Chemical Laboratory, Cat. No. 345-01821)) dissolved in DMEM containing 10% FBS at the concentration of 0.5 mg/ml (100 μl) was added and incubated for 3 hours. After removing MTT solution, methanol (100 μl) was added thereto. After lyse the cells, the intensity of absorbance on 570 nm as a control of 690 nm was determined to assay cellular toxicity of the test compound. As a result, it has been proved that the compounds of the present invention possess an inhibitory activity on IL-6 production with an $IC^{50}$ value of 20 μM or less. For example, free compound of the compound of Example 20(4) possessed an inhibitory activity on IL-6 production with an $IC_{50}$ value of 4.4 μM and showed no cellular toxicity at 10 μM.

(2) Assaying Inhibitory Activity on IL-12 Production and Cellular Toxicity

[Experimental Method]

$2.0 \times 10^5$ of peripheral monocyte prepared from healthy human blood by Ficole gravity centrifugation method (Pharmacia Biotech Co, Cat. No. 17-1440-02) were suspended in RPMI1640 medium containing 10% FBS (170 μl). The test compound dissolved in various kinds of solvents at the various concentrations (10 μl) and 6000 units/ml of Interferon-γ (IFN-γ (Serotec Co, Cat. No. PHP050)) (10 μl) dissolved in RPMI1640 medium containing 10% FBS. After incubation for 24 hours in 96 well-microplate, lipopolysaccharide (6 μg/ml) dissolved in RPMI1640 medium containing 10% FBS (LPS (Difco Co., Cat. No. 3120-25-0)) (10 μl) was added thereto. After incubation for 20 hours, the supernatant (150 μl) was recovered to assay the quantity of IL-12 using ELISA Method (R&D Systems Co, Cat. No. D1200), calculate for inhibitory activity of the test compound and determine 50% inhibitory concentration ($IC_{50}$) (see J. Exp. Med., 183, 147 (1996)). To the cells from which the supernatant (150 μl) was removed, a solution of MTT dissolved in RPMI1640 medium containing 10% FBS at 1 mg/ml (50 μl) was added and incubated for 3 hours. 2-Propanol containing 0.04N HCl (100 μl) was added thereto. After lyse the cells, the intensity of absorbance on 570 nm as a control of 690 nm was determined to assay cellular toxicity of the test compound. As a results, it has been proved that the compounds of the present invention possess an inhibitory activity on IL-12 production with an $IC_{50}$ value of 10 μM or less. For example, hydrochloride of the compound of Example 20(4) possessed an inhibitory activity on IL-12 production with an $IC_{50}$ of 0.11 μM and showed no cellular toxicity at 1 μM.

[Toxicity]

The toxicity of the compounds of the present invention is very low and therefore, it is confirmed that these compounds are safe for use as medicine.

[Application for Pharmaceuticals]

The compounds of the present invention possess an inhibitory activity of producing IL-6 and/or IL-12 in animal, especially human, so they are useful for prevention and/or treatment of, for example, various inflammatory diseases, sepsis, multiple myeloma, plasma cell leukemia, osteoporosis, cachexia, psoriasis, nephritis, renal cell carcinoma, Kaposi's sarcoma, rheumatoid arthritis, gammopathy, Castleman's disease, atrial myxoma, diabetes mellitus, autoimmune diseases, hepatitis, multiple sclerosis, colitis, graft versus host immune diseases, infectious diseases.

For the purpose above described, the compounds of the general formula (I) of the present invention, non-toxic salts, acid addition salts, or hydrates thereof may be normally administered systematically or locally, usually by oral or parenteral administration.

The doses to be administered are determined depending upon age, body weight, symptom, the desired therapeutic effect, the route of administration, and the duration of the treatment etc. In the human adult, the doses per person per dose are generally between 1 mg and 1000 mg, by oral administration, up to several times per day, and between 0.1 mg and 100 mg, by parenteral administration (preferred into vein) up to several times per day, or continuous administration between 1 and 24 hrs. per day into vein.

As mentioned above, the doses to be used depend upon various conditions. Therefore, there are cases in which doses lower than or greater than the ranges specified above may be used.

The compounds of the present invention may be administered as inner solid composition's or inner liquid compositions for oral administration, or as injections, liniments or suppositories etc. for parenteral administration.

Inner solid compositions for oral administration include compressed tablets, pills, capsules, dispersible powders, and granules. Capsules contain hard capsules and soft capsules.

In such inner solid compositions, one or more of the active compound(s) is or are, admixed with at least one inert diluent (lactose, mannitol, glucose, microcrystalline cellulose, starch etc.), connecting agents (hydroxypropyl cellulose, polyvinylpyrrolidone, magnesium metasilicate aluminate etc.), disintegrating agents (cellulose calcium glycolate etc.), lubricating agents (magnesium stearate), stabilizing agents, assisting agents for dissolving (glutamic acid, asparaginic acid etc.) etc. to prepare pharmaceuticals by known methods. The pharmaceuticals may, if desired, be coated with material such as sugar, gelatin, hydroxypropyl cellulose or hydroxypropyl cellulose phthalate etc., or be coated with two or more films. And further, coating may include containment within capsules of absorbable materials such as gelatin.

Inner liquid compositions for oral administration include pharmaceutically-acceptable water-agents, emulsions, syrups and elixirs etc. In such liquid compositions, one or more of the active compound(s) is or are comprised in inert diluent(s) commonly used in the art (purified water, ethanol or mixture thereof etc.). Besides inert diluents, such compositions may also comprise adjuvants such as wetting agents, suspending agents, sweetening agents, flavouring agents, perfuming agents and preserving agents.

Injections for parenteral administration include solutions, suspensions and emulsions, and solid injections. Aqueous solutions or suspensions include distilled water for injection and physiological salt solution. Non-aqueous solutions or suspensions include propylene glycol, polyethylene glycol, plant oil such as olive oil, alcohol such as ethanol, POLYSOLBATE80 (registered trade mark) etc. Such compositions may comprise additional diluents: e.g. preserving agents, wetting agents, emulsifying agents, dispersing agents, stabilizing agent, assisting agents such as assisting agents for dissolving (for example, glutamic acid, asparaginic acid). They may be sterilized for example, by filtration through a bacteria-retaining filter, by incorporation of sterilizing agents in the compositions or by irradiation. They may also be manufactured in the form of sterile solid compositions and which can be dissolved in sterile water or some other sterile diluent for injection immediately before use.

Other compositions for parenteral administration include liquids for external use, and endermic liniments, ointments, spray, suppositories and pessaries which comprise one or more of the active compound(s) and may be prepared by known methods.

Spray compositions may comprise additional substances other than inert diluents: e.g. stabilizing agents such as sodium hydrogen sulfate, stabilizing agents to give isotonicity, isotonic buffer such as sodium chloride, sodium citrate, citric acid. For preparation of such spray compositions, for example, the method described in the U.S. Pat. Nos. 2,868,691 or 3,095,355 may be used.

BEST MODE FOR CARRYING OUT THE INVENTION

The following reference Examples and Examples are intended to illustrate, but do not limit the present invention.

The solvents in parenthesis show the developing or eluting solvents and the ratios of the solvents used are by volume in chromatographic separations. The solvents in parentheses in NMR show the solvents used for measurement.

EXAMPLE 1

3-Phenylthio-2,3-dihydro-1,1-dioxidebenzo[b]thiophene

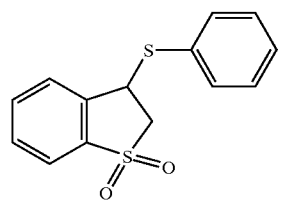

To a solution of benzothiophene-1,1-dioxide (1 g) in tetrahydrofuran (10 ml) were added triethylamine (1.55 ml) and thiophenol (798 mg). The reaction mixture was stirred for 4 hours at room temperature. To the reaction mixture was water added. The mixture was extracted with ethyl acetate. The extract was washed by water, a saturated aqueous solution of sodium chloride successively, dried over anhydrous sodium sulfate, and concentrated. The residue was purified with chromatography on silica gel (hexane:ethyl acetate=1:1). The obtained compound was then recrystallized from ethanol to give the title compound (1.18 g) having the following physical data.

TLC: Rf 0.46 (hexane:ethyl acetate=2:1);

NMR (CDCl$_3$): δ7.85–7.18 (9H, m), 4.98 (1H, t, J=7 Hz), 3.80 (1H, dd, J=14, 7 Hz), 3.51 (1H, dd, J=14, 7 Hz).

EXAMPLES 1(1)~1(18)

By the same procedure as described in Example 1 using a corresponding thiol instead of thiophenol, the following compounds of the present invention were obtained.

EXAMPLE 1 (1)

3-(Thiophen-2-yl)thio-2,3-dihydro-1,1-di oxidebenzo[b]thiophene

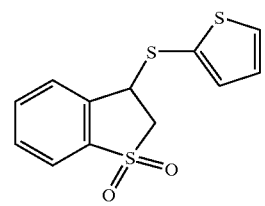

TLC: Rf 0.53 (hexane:ethyl acetate=1:1);

NMR (CDCl$_3$): δ7.81–7.66 (m, 3H), 7.58–7.51 (m, 1H), 7.42 (dd, J=5.4, 1.4 Hz, 1H), 7.14 (dd, J=3.6, 1.4 Hz, 1H), 7.00 (dd, J=5.4, 3.6 Hz, 1H), 4.78 (t-like, J=6.9 Hz, 1H), 3.80 (dd, J=14.0, 7.2 Hz, 1H), 3.51 (dd, J=14.0, 6.6 Hz, 1H).

EXAMPLE 1 (2)

3-(4-Methylphenyl)thio-2,3-dihydro-1,1-dioxidebenzo[b]thiophene

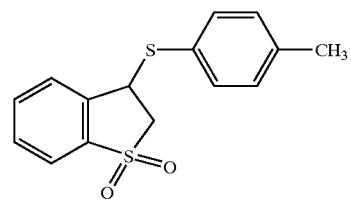

TLC: Rf 0.40 (hexane:ethyl acetate=2:1);

NMR (CDCl$_3$): δ7.85–7.57 (m, 4H), 7.42 (d, J=8.0 Hz, 2H), 7.21 (d, J=8.0 Hz, 2H), 4.80 (t-like, J=6.5 Hz, 1H), 3.85 (dd, J=14.0, 7.5 Hz, 1H), 3.38 (dd, J=14.0, 6.0 Hz, 1H).

EXAMPLE 1 (3)

3-(4-Methoxyphenyl)thio-2,3-dihydro-1,1-dioxidebenzo[b]thiophene

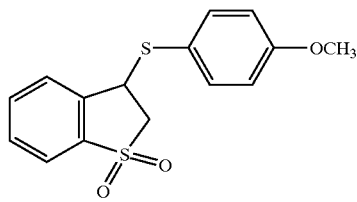

TLC: Rf 0.38 (hexane:ethyl acetate=2:1);

NMR (CDCl$_3$): δ7.82–7.45 (4H, m), 7.36 (2H, d, J=7 Hz), 6.85 (2H, d, J=7 Hz), 4.83 (1H, t, J=7 Hz), 3.83 (3H, s), 3.74 (1H, dd, J=13, 7 Hz), 3.46 (1H, dd, J=13, 7 Hz).

EXAMPLE 1 (4)

3-(4-Chlorophenyl)thio-2,3-dihydro-1,1-dioxidebenzo[b]thiophene

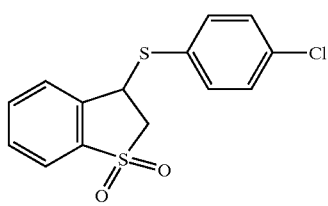

TLC: Rf 0.37 (hexane:ethyl acetate=2:1);

NMR (CDCl$_3$): δ7.88–7.67 (m, 4H), 7.32 (d, J=8.0 Hz, 2H), 7.25 (d, J=8.0 Hz, 2H), 4.83 (t-like, J=7.0 Hz, 1H), 3.83 (dd, J=14.5, 6.5 Hz, 1H), 3.52 (dd, J=14.5, 7.8 Hz, 1H).

EXAMPLE 1 (5)

3-(4-Fluorophenyl)thio-2,3-dihydro-1,1-dioxidebenzo[b]thiophene

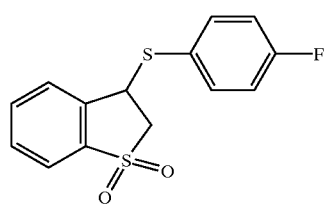

TLC: Rf 0.36 (hexane:ethyl acetate=2:1);

NMR (CDCl$_3$): δ7.80–7.32 (m, 6H), 7.04 (t-like, J=8.8 Hz, 2H), 4.90 (t-like, J=6.6 Hz, 1H), 3.78 (dd, J=13.6, 7.6 Hz, 1H), 3.50 (dd, J=13.6, 6.4 Hz, 1H).

EXAMPLE 1 (6)

3-(4-Hydroxyphenyl)thio-2,3-dihydro-1,1-dioxidebenzo[b]thiophene

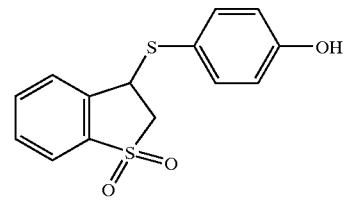

TLC: Rf 0.33 (hexane:ethyl acetate=1:1);

NMR (CDCl$_3$): δ3.45 (dd, J=15, 7.5 Hz, 1H), 3.75 (dd, J=15, 7.5 Hz, 1H), 4.80 (t, J=7.5 Hz, 1H), 5.60 (s, 1H), 6.75 (d, J=7.5 Hz, 2H), 7.30 (d, J=7.5 Hz, 2H), 7.45–7.80 (m, 4H).

EXAMPLE 1 (7)

3-(3-Hydroxyphenyl)thio-2,3-dihydro-1,1-dioxidebenzo[b]thiophene

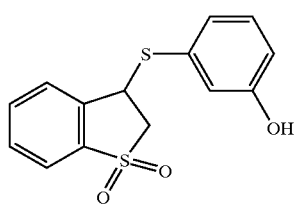

TLC: Rf 0.36 (hexane:ethyl acetate=1:1);

NMR (CDCl$_3$): δ3.50 (dd, J=15, 7.5 Hz, 1H), 3.85 (dd, J=15, 7.5 Hz, 1H), 5.00 (t, J=7.5 Hz, 1H), 5.65 (s, 1H), 6.75–7.00 (m, 3H), 7.10–7.30 (m, 1H), 7.50–7.80 (m, 4H).

EXAMPLE 1 (8)

3-(2-Hydroxyphenyl)thio-2,3-dihydro-1,1-dioxidebenzo[b]thiophene

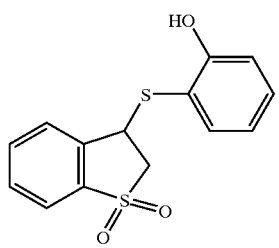

TLC: Rf 0.33 (hexane:ethyl acetate=1:1);

NMR (CDCl$_3$): δ3.45 (dd, J=12.5, 5.0 Hz, 1H), 3.70 (dd, J=12.5, 7.5 Hz, 1H), 4.80 (dd, J=7.5, 5.0 Hz, 1H), 6.65 (s, 1H), 6.90 (t, J=7.5 Hz, 1H), 7.00 (d, J=7.5 Hz, 1H), 7.30–7.80 (m, 6H).

EXAMPLE 1 (9)

3-(Pyridin-4-yl)thio-2,3-dihydro-1,1-dioxidebenzo[b]thiophene

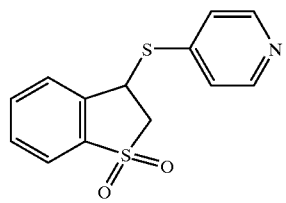

TLC: Rf 0.45 (ethyl acetate)

NMR (CDCl$_3$): δ3.58 (dd, J=13, 6 Hz, 1H), 4.00 (dd, J=13, 6 Hz, 1H), 5.22 (t, J=6 Hz, 1H), 7.20 (m, 2H), 7.69 (m, 4H), 8.51 (m, 2H).

EXAMPLE 1 (10)

3-(Pyrimidin-2-yl)thio-2,3-dihydro-1,1-dioxidebenzo[b]thiophene

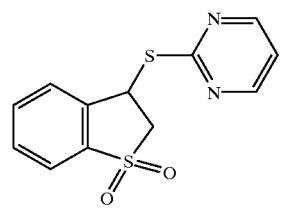

TLC: Rf 0.55 (hexane:ethyl acetate=1:2);

NMR (CDCl$_3$): δ3.71 (dd, J=14, 7 Hz, 1H), 4.24 (dd, J=14, 7 Hz, 1H), 5.70 (t, J=7 Hz, 1H), 7.10 (t, J=5 Hz, 1H), 7.52–7.85 (m, 4H), 8.58 (d, J=5 Hz, 2H).

EXAMPLE 1 (11)

3-(Thiazol-2-yl)thio-2,3-dihydro-1,1-dioxidebenzo[b]thiophene

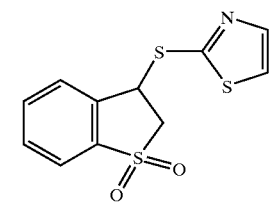

TLC: Rf 0.52 (hexane:ethyl acetate=1:1);

NMR (CDCl$_3$): δ3.55 (dd, J=13, 4 Hz, 1H), 3.81 (dd, J=13, 7 Hz, 1H), 5.60 (dd, J=7, 4 Hz, 1H), 7.57–7.80 (m, 6H).

EXAMPLE 1 (12)

3-(3-Methylfuran-2-yl)thio-2,3-dihydro-1,1-dioxidebenzo[b]thiophene

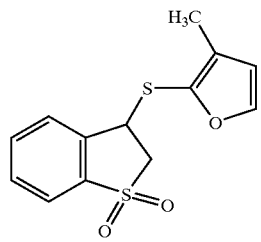

TLC: Rf 0.45 (hexane:ethyl acetate=4:1);

NMR (CDCl$_3$): δ2.27 (s, 3H), 3.39 (dd, J=14.0 Hz, 6.0 Hz, 1H), 3.75 (dd, J=14.0 Hz, 6.0 Hz, 1H), 4.69 (t, J=6.0 Hz, 1H), 6.07 (d, J=2.0 Hz, 1H), 7.25 (d, J=2.0 Hz, 1H), 7.48–7.77 (m, 4H).

EXAMPLE 1 (13)

3-(3-Methoxyphenyl)thio-2,3-dihydro-1,1-dioxidebenzo[b]thiophene

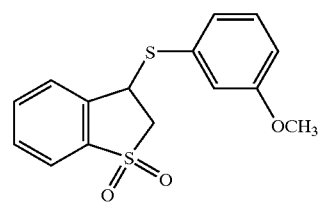

TLC: Rf 0.44 (hexane:ethyl acetate=1:1)

NMR (CDCl$_3$): δ3.50 (dd, J=12.5, 7.5 Hz, 1H), 3.75 (s, 3H), 3.80 (dd, J=12.5, 7.5 Hz, 1H), 5.00 (t, J=7.5 Hz, 1H), 6.85–7.05 (m, 3H), 7.20–7.30 (m, 1H), 7.50–7.80 (m, 4H).

EXAMPLE 1 (14)

3-(2-Methoxycarbonylphenyl)thio-2,3-dihydro-1,1-dioxidebenzo[b]thiophene

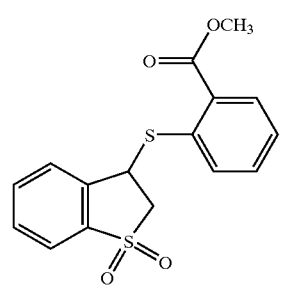

TLC: Rf 0.40 (hexane:ethyl acetate=1:1);

NMR (CDCl$_3$): δ3.60 (dd, J=15, 7.5 Hz, 1H), 3.90 (s, 3H), 3.95 (dd, J=15, 7.5 Hz, 1H), 5.25 (t, J=7.5 Hz, 1H), 7.30–7.80 (m, 7H), 7.95–8.05 (m, 1H).

EXAMPLE 1 (15)

3-Cyclohexylthio-2,3-dihydro-1,1-dioxidebenzo[b]thiophene

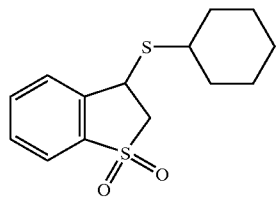

TLC: Rf 0.32 (hexane:ethyl acetate=3:1);

NMR (CDCl$_3$): δ1.26–2.10 (m, 10H), 2.80–2.93 (m, 1H), 3.52 (dd, J=13.4, 7.4 Hz, 1H), 3.92 (dd, J=13.4, 7.4 Hz, 1H), 4.68 (t, J=7.4 Hz, 1H), 7.47–7.54 (m, 1H), 7.59–7.67 (m, 1H), 7.70–7.75 (m, 2H).

EXAMPLE 1 (16)

3-(Naphthalen-1-yl)thio-2,3-dihydro-1,1-dioxidebenzo[b]thiophene

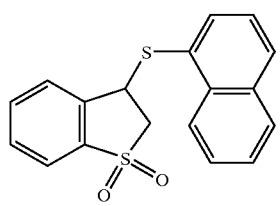

TLC: Rf 0.36 (hexane:ethyl acetate=2:1);

NMR (CDCl$_3$): δ3.51 (dd, J=13.6, 5.8 Hz, 1H), 3.64 (dd, J=13.6 Hz, 7.3 Hz, 1H), 5.01 (t-like, J=6.4 Hz, 1H), 7.40–7.79 (m, 8H), 7.90–7.94 (m, 2H), 8.52–8.56 (m, 1H).

EXAMPLE 1 (17)

3-(2-Methoxyphenyl)thio-2,3-dihydro-1,1-dioxidebenzo[b]thiophene

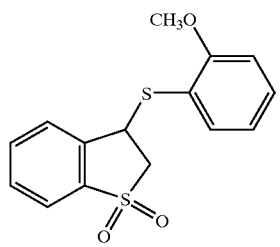

TLC: Rf 0.49 (hexane:ethyl acetate=1:1);

NMR (CDCl$_3$): δ3.55 (dd, J=12.5, 7.5 Hz, 1H), 3.75 (dd, J=12.5, 7.5 Hz, 1H), 3.90 (s, 3H), 5.10 (t, J=7.5 Hz, 1H), 6.90–7.00 (m, 2H), 7.30–7.80 (m, 6H).

EXAMPLE 1 (18)

3-(1-Methylimidazol-2-yl)thio-2,3-dihydro-1,1-dioxidebenzo[b]thiophene

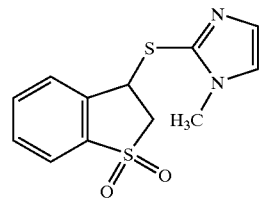

TLC: Rf 0.50 (hexane:ethyl acetate=1:2);

NMR (CDCl$_3$): δ3.54 (dd, J=14, 3 Hz, 1H), 3.65 (s, 3H), 4.04 (dd, J=14, 9 Hz, 1H), 6.58 (d, J=2.7 Hz, 1H), 6.65 (d, J=2.7 Hz, 1H), 6.95 (dd, J=9, 3 Hz, 1H), 7.56 (m, 1H), 7.67 (m, 2H), 7.85 (m, 1H).

EXAMPLE 2

3-Phenylsulfinyl-2,3-dihydro-1,1-dioxidebenzo[b]thiophene

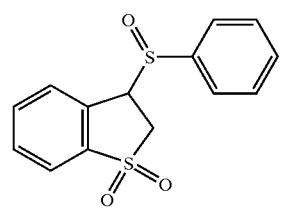

To potassium peroxymonosulfate ("OXONE" (trade name) marketed from Aldrich Co., abbreviated as OXONE©; 2.14 g), water (10 ml) was added. To a solution of a compound prepared in Example 1 (0.961 g) in methanol (50 ml), thus obtained aqueous solution of OXONE© (5.5 ml) was added at 0° C. The reaction mixture was stirred at 0° C. for 30 minutes. To the reaction mixture, water was added. The mixture was extracted by ethyl acetate. The extract was washed by water (twice) and a saturated aqueous solution of sodium chloride, and dried over anhydrous sodium sulfate and concentrated. The residue was recrystallized from ethanol to give the title compound (361 mg) having the following physical data.

TLC: Rf 0.13 (hexane:ethyl acetate=1:1);

NMR (CDCl$_3$): δ7.85–7.45 (9H, m), 4.57 (1H, t, J=7 Hz), 3.98 (1H, dd, J=14, 7 Hz), 3.19 (1H, dd, J=14, 7 Hz).

EXAMPLES 2 (1)~2 (2)

By the same procedure as described in Example 2 using the compounds prepared in Example 1 (1) and Example 1 (14) instead of the compound prepared in Example 1, the following compounds of the present invention were obtained.

EXAMPLE 2 (1)

3-(Thiophen-2-yl)sulfinyl-2,3-dihydro-1,1-dioxidebenzo[b]thiophene

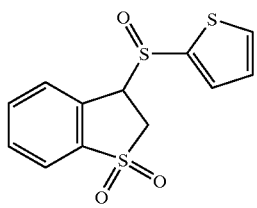

TLC: Rf 0.01 (hexane:ethyl acetate=1:1);

NMR (CDCl$_3$): δ7.95–7.50 (4.5H m), 7.50–7.25 (1.5H, m), 7.25–7.10 (1H, m), 4.99 (0.5H, dd, J=8.4, 4 Hz), 4.81(0.5H, dd, J=8.4, 4 Hz), 4.02 (0.5H, dd, J=14.2, 4.4 Hz), 3.72–3.40 (1.5H, m).

EXAMPLE 2 (2)

3-(2-Methoxycarbonylphenyl)sulfinyl-2,3-dihydro-1,1-dioxidebenzo[b]thiophene

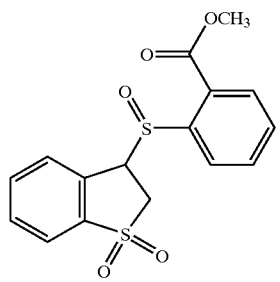

TLC: Rf 0.33 (hexane:ethyl acetate=1:1);

NMR (CDCl$_3$): δ2.90 (dd, J=12.5, 7.5 Hz, 1H), 4.00 (s, 3H), 4.00(dd, J=12.5, 7.5 Hz, 1H), 5.05 (t, J=7.5 Hz, 1H), 7.55–7.90 (m, 5H), 8.10–8.25 (m, 3H).

EXAMPLE 3

3-Phenylsulfonyl-2,3-dihydro-1,1-dioxidebenzo[b]thiophene

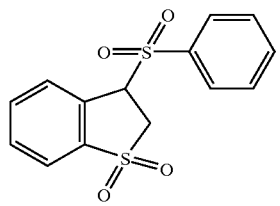

To OXONE© (2.14 g), water (10 ml) was added. To a solution of the compound prepared in Example 1 (0.961 g) in methanol (50 ml), was added thus obtained aqueous solution of OXONE© at room temperature. The reaction mixture was stirred for 2 hours at room temperature. To the reaction mixture, water was added. The mixture was extracted by ethyl acetate. The extract was washed by water (twice) and a saturated aqueous solution of sodium chloride successively, dried over anhydrous sodium sulfate, and concentrated. The residue was recrystallized from ethanol to give the compound of the present invention (1.54 g) having the following physical data.

TLC: Rf 0.45 (hexane:ethyl acetate=1:1);

NMR (CDCl$_3$): δ3.65–3.85 (m, 2H), 5.10 (dd, J=10, 5.0 Hz, 1H), 7.40–7.80 (m, 8H), 8.05 (d, J=10 Hz, 1H).

EXAMPLES 3 (1)~3 (17)

By the same procedure as described in Example 3 using the compounds prepared in Examples 1 (1)~1 (17) instead of the compound prepared in Example 1, or using 3-chloroperbenzoic acid instead of OXONE© as an oxidant, the following compounds of the present invention were obtained.

EXAMPLE 3 (1)

3-(Thiophen-2-yl)sulfonyl-2,3-dihydro-1,1-dioxidebenzo[b]thiophene

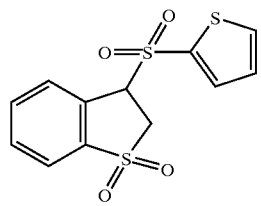

TLC: Rf 0.18 (hexane:ethyl acetate=2:1);

NMR (CDCl$_3$): δ8.08 (d, J=5.0 Hz, 1H), 7.82–7.66 (m, 5H), 7.20 (dd, J=5.0, 3.8 Hz, 1H), 5.82 (dd, J=9.4, 3.1 Hz, 1H), 4.07 (dd, J=15.4, 9.4 Hz, 1H), 3.83 (dd, J=15.4, 3.1 Hz, 1H).

EXAMPLE 3 (2)

3-(4-Methylphenyl)sulfonyl-2,3-dihidro-1,1-dioxidebenzo[b]thiophene

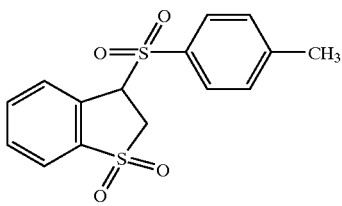

TLC: Rf 0.11 (hexane:ethyl acetate=2:1);

NMR (CDCl$_3$): δ8.04 (1H, d, J=8 Hz), 7.82–7.58 (3H, m), 7.53 (2H, d, J=9 Hz), 7.28 (2H, d, J=9 Hz), 5.08 (1H, dd, J=11, 8 Hz), 3.86–3.55 (2H, m), 2.42 (3H, s).

EXAMPLE 3 (3)

3-(4-Methoxyphenyl)sulfonyl-2,3-dihydro-1,1-dioxidebenzo[b]thiophene

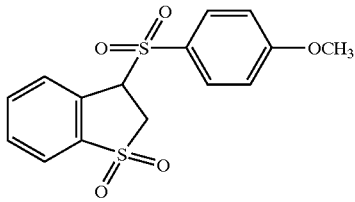

TLC: Rf 0.23 (hexane:ethyl acetate=1:1);

NMR (CDCl$_3$): δ8.04 (1H, d, J=8 Hz), 7.88–7.60 (3H, m), 7.54 (2H, d, J=7 Hz), 6.91 (2H, d, J=7 Hz), 5.06 (1H, t, J=7 Hz), 3.85 (3H, s), 3.80–3.60 (2H, m).

EXAMPLE 3 (4)

3-(4-Chlorophenyl)sulfonyl-2,3-dihydro-1,1-dioxidebenzo[b]thiophene

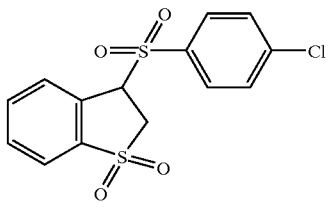

TLC: Rf 0.26 (hexane:ethyl acetate=2:1);

NMR (CDCl$_3$): δ8.02 (1H, d, J=8 Hz), 7.85–7.58 (3H, m), 7.58–7.32 (4H, m), 5.09 (1H, t, J=7 Hz), 3.90–3.65 (2H, m).

EXAMPLE 3 (5)

3-(4-Fluorophenyl)sulfonyl-2,3-dihydro-1,1-dioxidebenzo[b]thiophene

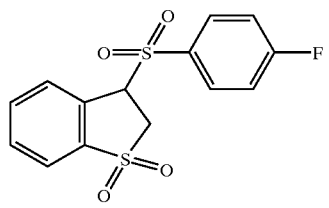

TLC: Rf 0.41 (hexane:ethyl acetate=1:1);

NMR (CDCl$_3$): δ8.03 (1H, d, J=8 Hz), 7.90–7.45 (5H, m), 7.20–7.00 (2H, m), 5.08 (1H, t, J=7 Hz), 3.80–3.75 (2H, m).

EXAMPLE 3 (6)

3-(4-Hydroxyphenyl)sulfonyl-2,3-dihydro-1,1-dioxidebenzo[b]thiophene

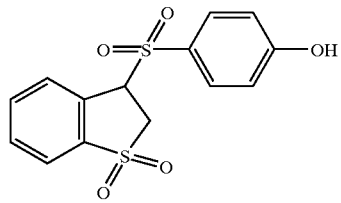

TLC: Rf 0.27 (hexane:ethyl acetate=1:1);

NMR (CD$_3$OD+CDCl$_3$): δ7.97 (1H, d, J=7 Hz), 7.85–7.55 (3H, m), 7.46 (2H, d, J=9 Hz), 6.84 (2H, d, J=9 Hz), 5.09 (1H, t, J=7 Hz), 3.90–3.60 (2H, m).

EXAMPLE 3(7)

3-(3-Hydroxyphenyl)sulfonyl-2,3-dihydro-1,1-dioxidebenzo[b]thiophene

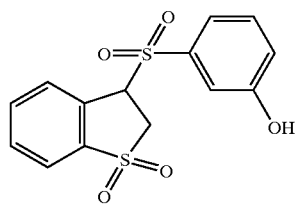

TLC: Rf 0.22 (hexane:ethyl acetate 1:1);

NMR (CDCl$_3$+DMSO-d$_6$): δ9.83 (1H, brs), 7.90–7.78 (1H, m), 7.78–7.50 (3H, m), 7.42–7.08 (4H, m), 5.28–5.10 (1H, m), 3.90–3.58 (2H, m).

EXAMPLE 3 (8)

3-(2-Hydroxyphenyl)sulfonyl-2,3-dihydro-1,1-dioxidebenzo[b]thiophene

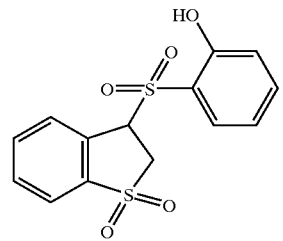

TLC: Rf 0.15 (hexane:ethyl acetate=1:1);

NMR (CDCl$_3$+DMSO-d$_6$): δ7.90–7.42 (6H, m), 7.13 (1H, d, J=8 Hz), 6.98 (1H, t, J=7 Hz), 5.71 (1H, dd, J=9, 5 Hz), 3.86 (1H, dd, J=14, 5 Hz), 3.65 (1H, dd, J=14, 9 Hz).

EXAMPLE 3 (9)

3-(Pyridin-4-yl)sulfonyl-2,3-dihydro-1,1-dioxidebenzo[b]thiophene

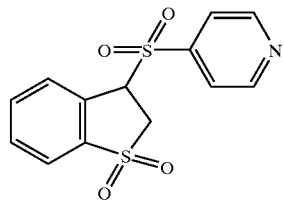

TLC: Rf 0.25 (hexane:ethyl acetate=1:2);

NMR (DMSO-$d_6$): δ3.87 (dd, J=15, 3 Hz, 1H), 4.03 (dd, J=15, 9 Hz, 1H), 5.94 (dd, J=9, 3 Hz, 1H), 7.70 (dd, J=4, 2 Hz, 2H), 7.81 (m, 4H), 8.88 (dd, J=4, 2 Hz, 2H).

EXAMPLE 3 (10)

3-(Pyrimidin-2-yl)sulfonyl-2,3-dihydro-1,1-dioxidebenzo[b]thiophene

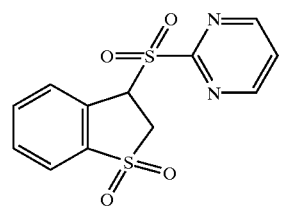

TLC: Rf 0.15 (methylene chloride);

NMR (DMSO-$d_6$): δ4.00 (dd, J=16, 4 Hz, 1H), 4.12 (dd, J=16, 9 Hz, 1H), 6.17 (dd, J=9, 4 Hz, 1H), 7.78 (m, 3H), 7.90 (m, 2H), 9.09 (dd, J=5, 1 Hz, 2H).

EXAMPLE 3 (11)

3-(Thiazol-2-yl)sulfonyl-2,3-dihydro-1,1-dioxidebenzo[b]thiophene

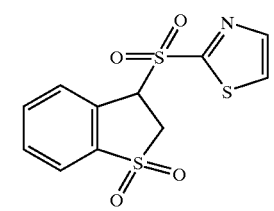

TLC: Rf 0.40 (hexane:ethyl acetate=1:1);

NMR (CDCl$_3$): δ3.87 (dd, J=15, 9 Hz, 1H), 4.20 (dd, J=15, 5 Hz, 1H), 5.39 (dd, J=9, 5 Hz, 1H), 7.61–7.81 (m, 4H), 7.99–8.08 (m, 2H).

EXAMPLE 3 (12)

3-(3-Methylfuran-2-yl)sulfonyl-2,3-dihydro-1,1-dioxidebenzo[b]furan

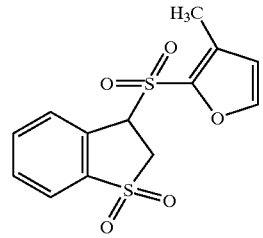

TLC: Rf 0.50 (hexane:ethyl acetate=3:2);

NMR (CDCl$_3$): δ2.39 (s, 3H), 3.78 (dd, J=15, 4 Hz, 1H), 3.88 (dd, J=15, 8 Hz, 1H), 5.00 (dd, J=8, 4 Hz, 1H), 5.98 (d, J=2 Hz, 1H), 7.18 (d, J=2 Hz, 1H), 7.60–7.80 (m, 3H), 8.02 (m, 1H).

EXAMPLE 3 (13)

3-(3-Methyoxyphenyl)sulfonyl-2,3-dihydro-1,1-dioxidebenzo[b]thiophene

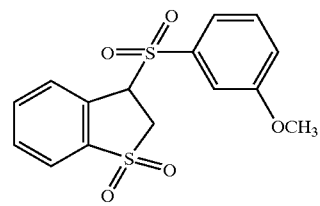

TLC: Rf 0.33 (hexane:ethyl acetate=1:1);

NMR (CDCl$_3$): δ3.65–3.90 (m, 2H), 3.75 (s, 3H), 5.10 (dd, J=10, 5.0 Hz, 1H), 7.10–7.50 (m, 4H), 7.60–7.80 (m, 3H), 8.00 (d, J=7.5 Hz, 1H).

EXAMPLE 3 (14)

3-(2-Methoxycarbonylphenyl)sulfonyl-2,3-dihydro-1,1-dioxidebenzo[b]thiophene

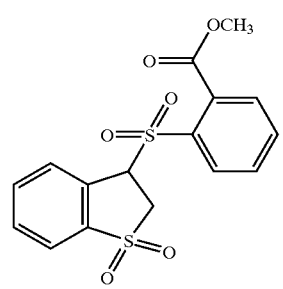

TLC: Rf 0.59 (methylene chloride:ethyl acetate=9:1);

NMR (CDCl3): δ8.01–7.97 (m, 1H), 7.84–7.63 (m, 7H), 6.06 (dd, J=9.0, 4.5 Hz, 1H), 4.04 (s, 3H), 3.92 (dd, J=14.0, 4.5 Hz, 1H), 3.63 (dd, J=14.0, 9.0 Hz, 1H).

EXAMPLE 3 (15)

3-Cyclohexylsulfonyl-2,3-dihydro-1,1-dioxidebenzo[b]thiophene

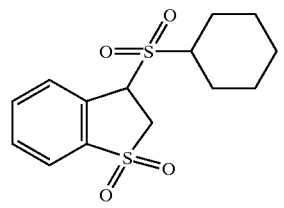

TLC: Rf 0.37 (hexane:ethyl acetate=1:1);

NMR (CDCl$_3$): δ1.13–1.68 (m, 8H), 1.90–1.96 (m, 1H), 2.15–2.19 (m, 1H), 3.07–3.23 (m, 1H), 3.87 (dd, J=14.5, 8.2 Hz, 1H), 3.95 (dd, J=14.5, 5.2 Hz, 1H), 4.96 (dd, J=8.2, 5.2 Hz, 1H), 7.63–7.83 (m, 3H), 7.96–8.00 (m, 1H).

EXAMPLE 3 (16)

3-(Naphthalen-1-yl)sulfonyl-2,3-dihydro-1,1-dioxidebenzo[b]thiophene

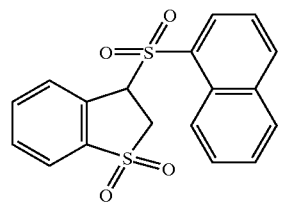

TLC: Rf 0.40 (hexane:ethyl acetate=1:1);

NMR (CDCl$_3$): δ3.38 (dd, J=14.4, 8.8 Hz, 1H), 3.77 (dd, J=14.4, 5.0 Hz, 1H), 5.31 (dd, J=8.8, 5.0 Hz, 1H), 7.60–7.81 (m, 7H), 8.00–8.05 (m, 1H), 8.22–8.28 (m, 2H), 8.72–8.77 (m, 1H).

EXAMPLE 3 (17)

3-(2-Methoxyphenyl)sulfonyl-2,3-dihydro-1,1-dioxidebenzo[b]thiophene

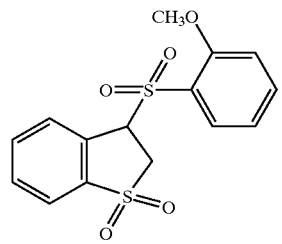

TLC: Rf 0.20 (hexane:ethyl acetate=1:1);

NMR (CDCl$_3$+DMSO-d$_6$): δ3.65 (dd, J=15, 10 Hz, 1H), 3.80 (dd, J=15, 5.0 Hz, 1H), 4.00 (s, 3H), 5.55 (dd, J=10, 5.0 Hz, 1H), 7.05–7.20 (m, 2H), 7.60–7.95 (m, 6H).

EXAMPLE 4

3-(4-(2-(Piperidin-1-yl)ethoxy)phenyl)sulfonyl-2,3-dihydro-1,1-dioxidebenzo[b]thiophene

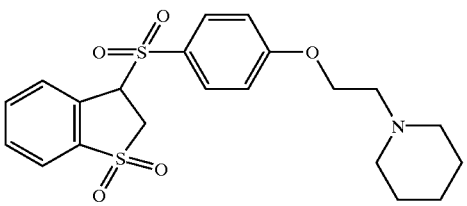

To a solution of the compound prepared in Example 3 (6) (283 mg) in dimetyhylformamide (5 ml) were added N-chloroethylpiperidine (193 mg) and cesium carbonate (1.0 g). The reaction mixture was stirred at room temperature overnight. To the reaction mixture water was added. The mixture was extracted by ethyl acetate. The extract was washed by water (three times), a saturated aqueous solution of sodium chloride, dried over anhydrous sodium sulfate, and concentrated. The residue was purified with column chromatography on silica gel (hexane:ethyl acetate=1:1) to give the compound of the present invention (186 mg) having the following physical data.

TLC: Rf 0.54 (ethyl acetate:methanol:28% ammonia water=100:10:1);

NMR (CDCl$_3$): δ8.03 (1H, d, J=7 Hz), 7.85–7.55 (3H, m), 7.53 (2H, d, J=9 Hz), 6.92 (2H, d, J=9 Hz), 5.05 (1H, t, J=7 Hz), 4.13 (2H, t, J=6 Hz), 3.85–3.60 (2H, m), 2.76 (2H, t, J=6 Hz), 2.49 (4H, brt, J=6 Hz), 1.68–1.45 (6H, m).

EXAMPLES 4 (1)~4 (4)

By the same procedure as described in Example 4 by using the compounds prepared in Examples 3 (6)~3 (8) and corresponding halogenated compounds, the following compounds of the present invention were obtained.

EXAMPLE 4 (1)

3-(4-(2-(pyrrolidin-1-yl)ethoxy)phenyl)sulfonyl)-2,3-dihydro-1,1-dioxidebenzo[b]thiophene

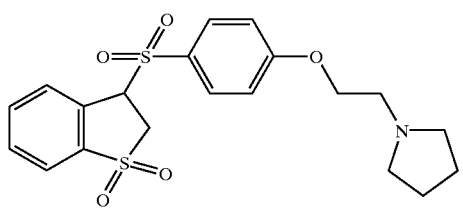

TLC: Rf 0.35 (ethyl acetate:methanol:28% ammonia water=100:10:1);

NMR (CDCl$_3$): δ8.03 (1H, d, J=7 Hz), 7.90–7.40 (5H, m), 6.93 (2H, d, J=7 Hz), 5.18–4.95 (1H, m), 4.14 (2H, t, J=6 Hz), 3.90–3.60 (2H, m), 2.91 (2H, t, J=6 Hz), 2.75–2.40 (4H, m), 1.84–1.74 (4H, m).

EXAMPLE 4 (2)

3-(4-(2-(Morpholine-1-yl)ethoxy)phenyl)sulfonyl-2,3-dihydro-1,1-dioxidebenzo[b]thiophene

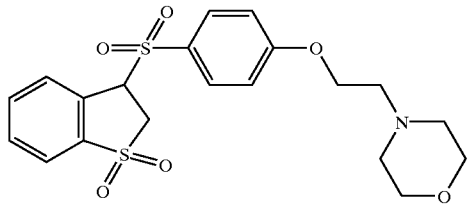

TLC: Rf 0.44 (ethyl acetate:methanol:28% ammonia water=100:10:1);

NMR (CDCl$_3$): δ8.05 (1H, d, J=7 Hz), 7.85–7.40 (5H, m), 6.91 (2H, d, J=7 Hz), 5.06 (1H, t, J=7 Hz), 4.13 (2H, t, J=6 Hz), 3.95–3.50 (6H, m), 2.80 (2H, t, J=6 Hz), 2.70–2.40 (4H, m).

EXAMPLE 4 (3)

3-(3-Benzyloxyphenyl)sulfonyl-2,3-dihydro-1,1-dioxidebenzo[b]thiophene

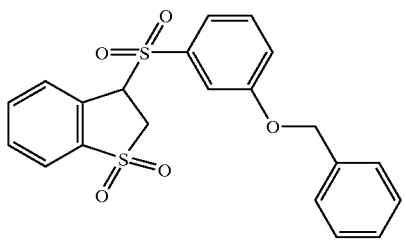

TLC: Rf 0.55 (hexane:ethyl acetate=1:1);

NMR (CDCl$_3$): δ8.02 (1H, d, J=7 Hz), 7.85–7.52 (3H, m), 7.52–7.10 (9H, m), 5.15–4.85 (3H, m), 3.80–3.45 (2H, m).

EXAMPLE 4 (4)

3-(2-Benzyloxyohenyl)sulfonyl-2,3-dihydro-1,1-dioxidebenzo[b]thiophene

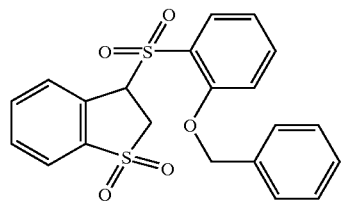

TLC: Rf 0.37 (hexane:ethyl acetate=1:1);

NMR (CDCl$_3$): δ7.93 (1H, dd, J=8, 2 Hz), 7.85–7.30 (10H, m), 7.25–7.08 (2H, m), 5.52 (1H, dd, J=9, 5 Hz), 5.28 (2H, s), 3.79 (1H, dd, J=14, 5 Hz), 3.48 (1H, dd, J=14, 9 Hz).

EXAMPLE 5

3-(4-(Pyridin-2-ylmethyloxy)phenyl)thio-2,3-dihydro-1,1-dioxidebenzo[b]thiophene

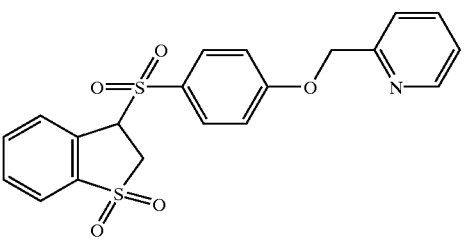

By the same procedure as described in Example 4 using the compound prepared in Example 1 (6) instead of the compound prepared in Example 3 (6), and using a corresponding halogenated compound instead of N-chloroethylpiperidine, the compound of the present invention having the following physical data was obtained.

TLC: Rf 0.58 (ethyl acetate);

NMR (CDCl$_3$): δ8.65–8.55 (1H, m), 7.80–7.20 (9H, m), 7.00–6.90 (2H, m), 5.20 (2H, s), 4.85 (1H, t, J=7.5 Hz), 3.75 (1H, dd, J=12.5, 7.5 Hz), 3.45 (1H, dd, J=12.5, 7.5 Hz).

EXAMPLES 5 (1)~5 (9)

By the same procedure as described in Example 5 using the compounds prepared in Examples 1 (6)~1 (8), the following compounds of the present invention were obtained.

EXAMPLE 5 (1)

3-(4-Pyridin-3-ylmethyloxy)phenyl)thio-2,3-dihydro-1,1-dioxidebenza[b]thiophene

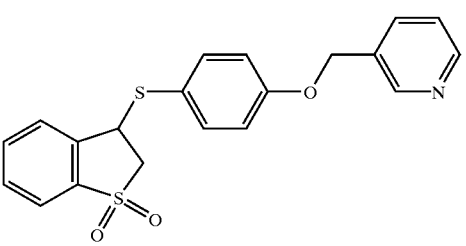

TLC: Rf 0.42 (ethyl acetate);

NMR (CDCl$_3$): δ8.70–8.60 (2H, m), 7.80–7.30 (8H, m), 7.00–6.90 (2H, m), 5.05 (2H, s), 4.85 (1H, t, J=5 Hz), 3.75 (1H, dd, J=15, 5 Hz), 3.45 (1H, dd, J=15, 5 Hz).

EXAMPLE 5 (2)

3-(4-(Pyridin-4-ylmethyloxy)phenyl)thio-2,3-dihydro-1,1-dioxidebenzo[b]thiophene

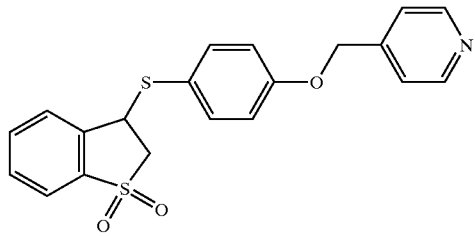

TLC: Rf 0.33 (ethyl acetate);

NMR (CDCl₃): δ8.65–8.60 (2H, m), 7.80–7.30 (8H, m), 7.00–6.90 (2H, m), 5.10 (2H, s), 4.85 (1H, t, J=5 Hz), 3.75 (1H, dd, J=15, 5 Hz), 3.45 (1H, dd, J=15, 5 Hz).

EXAMPLE 5 (3)

3-(4-(3-Hydroxypropyloxy)phenyl)thio-2,3-dihydro-1,1-dioxidebenzo[b]thiophene

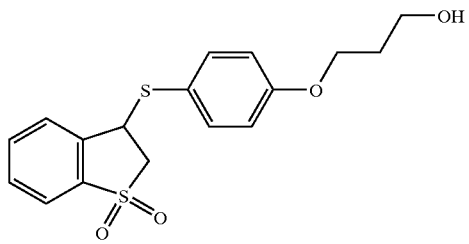

TLC: Rf 0.14 (hexane:ethyl acetate=1:1);

NMR (CD₃OD): δ1.90–2.10 (m, 2H), 3.30–3.50 (m, 1H), 3.50–4.00 (m, 3H), 4.00–4.20 (m, 2H), 4.90–5.10 (m, 1H), 6.80–7.00 (m, 2H), 7.30–7.50 (m, 2H), 7.50–7.80 (m, 4H).

EXAMPLE 5(4)

3-(3-(Pyridin-3-ylmethyloxy)phenyl)thio-2,3-dihydro-1,1-dioxidebenzo[b]thiophene

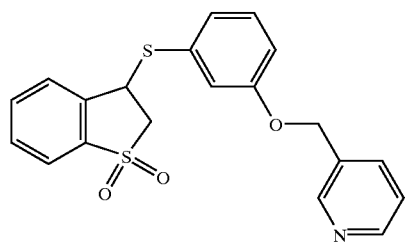

TLC: Rf 0.44 (ethyl acetate);

NMR (CDCl₃): δ3.50 (dd, J=12.5, 7.5 Hz, 1H), 3.80 (dd, J=12.5, 7.5 Hz, 1H), 4.95–5.10 (m, 1H), 5.00 (s, 2H), 6.90–7.10 (m, 3H), 7.20–7.40 (m, 2H), 7.50–7.80 (m, 5H), 8.50–8.70 (m, 2H).

EXAMPLE 5(5)

3-(3-(3-Hydroxypropyloxy)phenyl)thio-2,3-dihydro-1,1-dioxidebenzo[b]thiophene

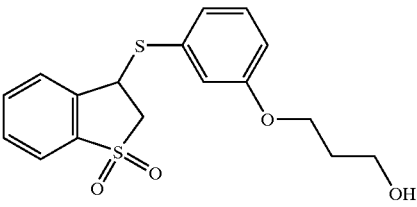

TLC: Rf 0.17 (hexane:ethyl acetate=1:1);

NMR (CDCl₃): δ1.95–2.05 (m, 2H), 3.50 (dd, J=12.5, 7.5 Hz, 1H), 3.80 (dd, J=12.5, 7.5 Hz, 1H), 3.85 (t, J=7.5 Hz, 2H), 4.05 (t, J=7.5 Hz, 2H), 5.00 (t, J=7.5 Hz, 1H), 6.80–7.05 (m, 3H), 7.20–7.30 (rr, 1H), 7.50–7.80 (m, 4H).

EXAMPLE 5 (6)

3-(2-(Pyridin-3-ylmethyloxy)phenyl)thio-2,3-dihydro-1,1-dioxidebenzo[b]thiophene

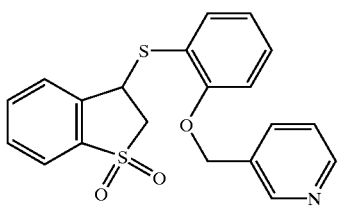

TLC: Rf 0.16 (hexane:ethyl acetate=1:1);

NMR (CD₃OD): δ3.50 (dd, J=15, 5.0 Hz, 1H), 3.85 (dd, J=15, 7.5 Hz, 1H), 5.20 J=7.5, 5.0 Hz, 1H), 5.25 (s, 2H), 7.00 (t, J=7.5 Hz, 1H), 7.20 (d, J=7.5 Hz, 1H), 7.35–7.70 (m, 7H), 8.00 (d, J=7.5 Hz, 1 H), 8.50 (dd, J=5.0, 2.5 Hz, 1H), 8.70 (d, J=2.5 Hz, 1H).

EXAMPLE 5 (7)

3-(2-(3-Hydroxypropyloxy)phenyl)thio-2,3-dihydro-1,1-dioxidebenzo[b]thiophene

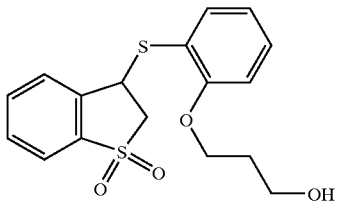

TLC: Rf 0.30 (hexane:ethyl acetate=1:2);

NMR (CDCl₃): δ2.05–2.10 (m, 2H), 2.30–2.60 (m, 1H), 3.50 (dd, J=15, 5.0 Hz, 1H), 3.70 (dd, J=15, 7.5 Hz, 1H), 3.90 (t, J=5.0 Hz, 2H), 4.20–4.40 (m, 2H), 5.10 (dd, J=7.5, 5.0 Hz, 1H), 6.90–7.00 (m, 2H), 7.30–7.80 (m, 6H).

EXAMPLE 5 (8)

3-(4-(2-(t-Butoxycarbonylamino)ethyloxy)phenyl)thio-2,3-dihydro-1,1-dioxidebenzo[b]thiophene

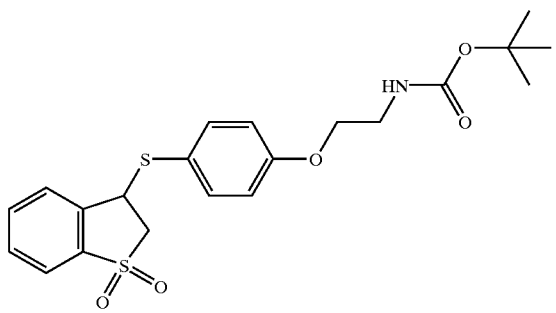

TLC: Rf 0.30 (toluene:ethyl acetate=4:1);

NMR (CDCl$_3$): δ7.80–7.10 (6H, m), 6.80 (2H, d, J=10 Hz), 5.10–4.70 (2H, m), 4.00 (2H, t, J=5 Hz), 3.75 (1H, dd, J=15, 7.5 Hz), 3.60–3.40 (3H, m), 1.45 (9H, s).

EXAMPLE 5 (9)

3-(3-(2-(t-Butoxycarbonylamino)ethyloxy)phenyl)thio-2,3-dihydro-1,1-dioxidebenzo[b]thiophene

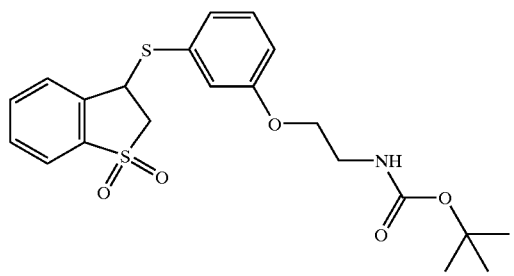

TLC: Rf 0.40 (hexane:ethyl acetate=1:1);

NMR (CDCl$_3$): δ7.80–7.50 (4H, m), 7.40–7.20 (1H, m), 7.05–6.70 (3H, m), 5.05–4.90 (2H, m), 3.95 (2H, t, J=5 Hz), 3.80 (1H, dd, J=15, 5 Hz), 3.60–3.40 (3H, m), 1.45 (9H, s).

EXAMPLE 6

3-(4-(Pyridin-2-ylmethyloxy)phenyl)sulfonyl-2,3-dihydro-1,1-dioxidebenzo[b]thiophene

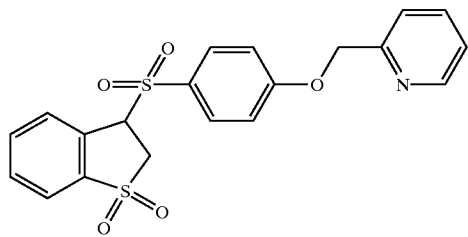

By the same procedure as described in Example 3 using the compound prepared in Example 5 instead of the compound prepared in Example 1, and then by converting into the corresponding hydrochloride by a known method, the compound of the present invention having the following physical data was obtained.

Free Compound

TLC: Rf 0.44 (ethyl acetate);

NMR (DMSO-d$_6$): δ8.60–8.55 (1H, m), 7.90–7.60 (7H, m), 7.50 (1H, d, J=7.5 Hz), 7.40–7.30 (1H, m), 7.20 (2H, d, J=7.5 Hz), 5.70 (1H, dd, J=10, 2.5 Hz), 5.30 (2H, s), 4.00 (1H, dd, J=15, 10 Hz), 3.75 (1H, dd, J=15, 2.5 Hz).

Hydrochloride

TLC: Rf 0.49 (ethyl acetate:triethylamine=19:1);

NMR (CD$_3$OD): δ3.80 (dd, J=15, 2.5 Hz, 1H), 3.95 (dd, J=15, 10 Hz, 1H), 5.50 (dd, J=10, 2.5 Hz, 1H), 5.60 (s, 2H), 7.20 (d, J=7.5 Hz, 2H), 7.55–8.00 (m, 4H), 7.70 (d, J=7.5 Hz, 2H), 8.05–8.25 (m, 2H), 8.60–8.95 (m, 2H).

EXAMPLES 6 (1)~6 (9)

Using the compounds prepared in Examples 5 (1)~5 (9) instead of the compound prepared in Example 5, by the same procedure as described in Example 5, or by the same reaction using 3-chloroperbenzoic acid instead of OXONE© as an oxidant, and if necessary, by converting into corresponding salts, the following compounds of the present invention were obtained.

EXAMPLE 6 (1)

3-(4-(Pyridin-3-ylmethyloxy)phenyl)sulfonyl-2,3-dihydro-1,1-dioxidebenzo[b]thiophene

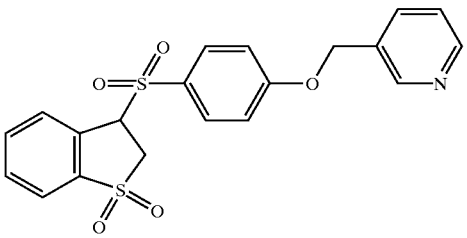

Free Compound

TLC: Rf 0.27 (ethyl acetate);

NMR (CDCl$_3$): δ8.70–8.55 (2H, m), 8.10–8.00 (1H, m), 7.80–7.50 (6H, m), 7.40–7.30 (1H, m), 7.10–6.90 (2H, m), 5.15 (2H, s), 5.20–5.00 (1H, m), 3.90–3.70 (2H, m).

Hydrochloride

TLC: Rf 0.38 (ethyl acetate:triethylamine=19:1);

NMR (CD$_3$OD): δ3.80 (dd, J=15, 2.5 Hz, 1H), 3.95 (dd, J=15, 10 Hz, 1H), 5.45 (s, 2H), 5.45–5.55 (m, 1H), 7.20 (d, J=10 Hz, 2H), 7.60–8.00 (m, 4H), 7.60 (d, J=10 Hz, 2H), 8.10–8.20 (m, 1H), 8.70–9.00 (m, 3H).

EXAMPLE 6 (2)

3-(4-(Pyridin-4-ylmethyloxy)phenyl)sulfonyl-2,3-dihydro-1,1-dioxidebenzo[b]thiophene

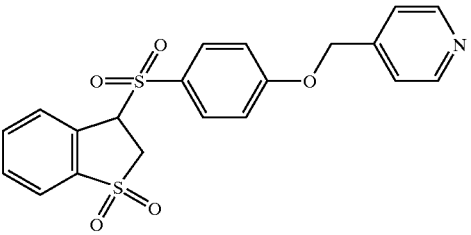

Free Compound

TLC: Rf 0.22 (ethyl acetate);

NMR (DMSO-d$_6$): δ8.60 (2H, d, J=5 Hz), 7.90–7.65 (6H, m), 7.45 (2H, d, J=5 Hz), 7.20 (2H, d, J=7.5 Hz), 5.75 (1H, dd, J=7.5, 2.5 Hz), 5.30 (2H, s), 4.00 (1H, dd, J=15, 7.5 Hz), 3.80 (1H, dd, J=15, 2.5 Hz).

Hydrochloride

TLC: Rf 0.35 (ethyl acetate:triethylamine=19:1);

NMR (DMSO-$d_6$): $\delta$3.80 (dd, J=15, 2.5 Hz, 1H), 4.00 (dd, J=15, 10 Hz, 1H), 5.55 (s, 2H), 5.75 (dd, J=10, 2.5 Hz, 1H), 7.25 (d, J=10 Hz, 2H), 7.65–7.90 (m, 4H), 7.70 (d, J=10 Hz, 2H), 7.95 (d, J=7.5 Hz, 2H), 8.90 (d, J=7.5 Hz, 2H).

EXAMPLE 6 (3)

3-(4-(3-Hydroxypropylpxy)phenyl)sulfonyl-2,3-dihydro-1,1-dioxidebenzo[b]thiophene

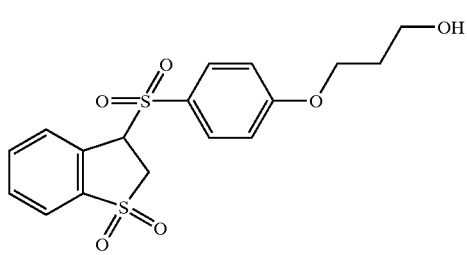

TLC: Rf 0.33 (ethyl acetate );

NMR (CDCl$_3$): $\delta$2.05 (quint., J=5.0 Hz, 2H), 3.70–3.90 (m, 2H), 3.85 (t, J=5.0 Hz, 2H), 4.15 (t, J=5.0 Hz, 2H), 5.05 (t, J=7.5 Hz, 1H), 6.90 (d, J=10 Hz, 2H), 7.50 (d, J=10 Hz, 2H), 7.60–7.80 (m, 3H), 8.05 (d, J=7.5 Hz, 1H).

EXAMPLE 6 (4)

3-(3-(Pyridin-3-ylmethyloxy)phenyl)sulfonyl-2,3-dihydro-1,1-dioxidebenzo[b]thiophene.hydrochloride

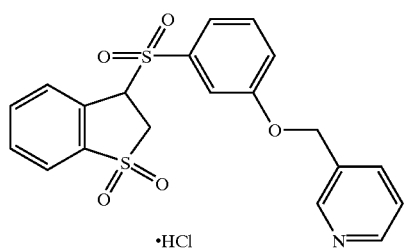

TLC: Rf 0.60 (ethyl acetate:methanol:triethylamine= 16:2:1);

NMR (CD$_3$OD): $\delta$3.85 (dd, J=15, 5.0 Hz, 1H), 3.95 (dd, J=15, 10 Hz, 1H), 5.35 (d, J=12.5 Hz, 1H), 5.45 (d, J=12.5 Hz, 1H), 5.55 (dd, J=10, 5.0 Hz, 1H), 7.20–7.85 (m, 7H), 7.95 (d, J=7.5 Hz, 1H), 8.15 (dd, J=10, 7.5 Hz, 1H), 8.75 (d, J=7.5 Hz, 1H), 8.85 (d, J=5.0 Hz, 1H), 9.00 (s, 1H).

EXAMPLE 6 (5)

3-(3-(3-Hydroxypropyloxy)phenyl)sulfonyl-2,3-dihydro-1,1-dioxidebenzo[b]thiophene

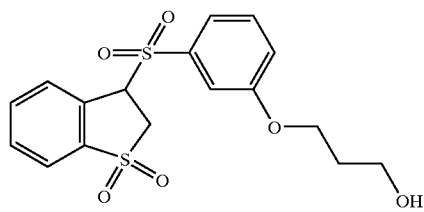

TLC: Rf 0.33 (ethyl acetate );

NMR (CDCl$_3$): $\delta$1.90–2.20 (m, 2H), 3.65–3.90 (m, 4H), 3.95–4.20 (m, 2H), 5.10 (dd, J=10, 5.0 Hz, 1H), 7.10–7.30 (m, 3H), 7.30–7.45 (m, 1H), 7.60–7.80 (m, 3H), 8.00 (d, J=5.0 Hz, 1H).

EXAMPLE 6 (6)

3-(2-(Pyridin-3-ylmethyloxy)phenyl)sulfonyl-2,3-dihydro-1,1-dioxidebenzo[b]thiophene.hydrochloride

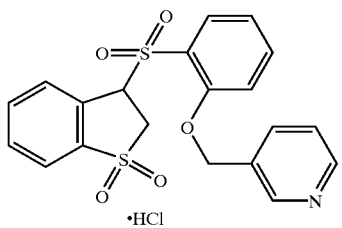

TLC: Rf 0.51 (ethyl acetate:methanol:triethylamine= 16:2:1);

NMR (DMSO-$d_6$): $\delta$3.70 (dd, J=15, 2.5 Hz, 1H), 3.95 (dd, J=15, 10 Hz, 1H), 5.60 (s, 2H) 5.75 (dd, J=10, 2.5 Hz, 1H), 7.20–7.35 (m,1H), 7.40–7.60 (m, 2H), 7.60–7.90 (m, 5H), 7.95–8.10 (m, 1H), 8.60 (d, J=7.5 Hz, 1H), 8.90 (d, J=5.0 Hz, 1H), 9.05 (s, 1H).

EXAMPLE 6 (7)

3-(2-(3-Hydropropylpxy)phenyl)sulfonyl-2,3-dyhydro-1,1-dioxidebenzo[b]thiophene

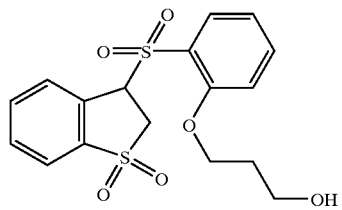

TLC: Rf 0.37 (ethyl acetate);

NMR (CDCl$_3$): $\delta$2.00–2.30 (m, 2H), 2.50–2.80 (m, 1H), 3.55 (dd, J=15, 10 Hz, 1H), 3.80 (dd, J=15, 5.0 Hz, 1H), 3.95 (t, J=5.0 Hz, 2H), 4.25–4.50 (m, 2H), 5.65 (dd, J=10, 5.0 Hz, 1H), 7.10–7.20 (m, 2H), 7.60–7.80 (m, 4H), 7.80–7.95 (m, 2H).

EXAMPLE 6 (8)

3-(4-(2-(t-Butoxycarbonylamino)ethyloxy)phenyl)sulfonyl-2,3-dihydro-1,1-dioxidebenzo[b]thiophene

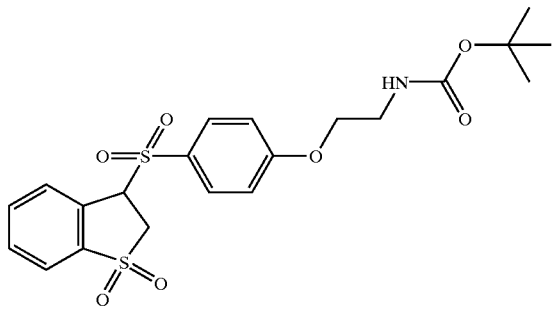

TLC: Rf 0.40 (hexane:ethyl acetate=1:2);
NMR (DMSO-$d_6$): δ1.40 (s, 9H), 3.80 (dd, J=15, 2.5 Hz, 1H), 3.90–4.15 (m, 5H), 5.75 (dd, J=10, 2.5 Hz, 1H), 6.90–7.10 (m, 1H), 7.10 (d, J=7.5 Hz, 2H), 7.60–7.85 (m, 4H), 7.65 (d, J=7.5 Hz, 2H).

EXAMPLE 6 (9)

3-(3-(2-(t-Butoxycarbonylamino)ethyloxy)phenyl)sulfonyl-2,3-dihydro-1,1-dioxidebenzo[b]thiophene

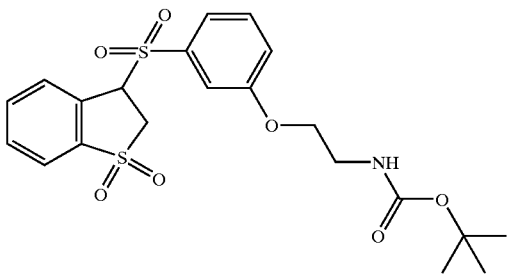

TLC: Rf 0.13 (hexane:ethyl acetate=1:1);
NMR (CDCl$_3$): δ1.45 (s, 9H), 3.45–3.55 (m, 2H), 3.70–4.00 (m, 4H), 4.85–5.00 (m, 1H), 5.10 (dd, J=10, 5.0 Hz, 1H), 7.00–7.50 (m, 4H), 7.60–7.80 (m, 3H), 8.05 (d, J=7.5 Hz, 1H).

EXAMPLE 7

3-(4-($_2$-Aminoethyloxy)phenyl)sulfonyl-2,3-dihydro-1,1-dioxidebenzo[b]thiophene.hydrochloride

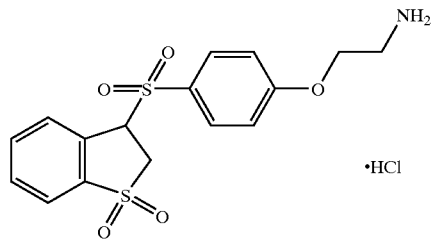

To a solution of the compound prepared in Example 6 (8) (200 mg) in dioxane (25 ml) and methanol (5 ml), was added a solution of 4N hydrochloric acid in dioxane (10 ml) at room temperature. The reaction mixture was stirred at room temperature for 30 minutes. The reaction mixture was concentrated to give the compound of the present invention (160 mg) having the following physical data.

TLC: Rf 0.16 (ethyl acetate:methanol:triethylamine=16:3:1);
NMR (CD$_3$OD): δ3.35 (t, J=5.0 Hz, 2H), 3.80 (dd, J=15, 5.0 Hz, 1H), 3.95 (dd, J=15, 10 Hz, 1H), 4.30 (t, J=5.0 Hz, 2H), 5.45 (dd, J=10, 5.0 Hz, 1H), 7.10 (d, J=7.5 Hz, 2H), 7.60 (d, J=7.5 Hz, 2H), 7.60–8.00 (m, 4H).

EXAMPLE 7 (1)

3-(3-(2-Aminoethyloxy)phenyl)sulfonyl-2,3-dihydro-1,1-dioxidebenzo[b]thiophene.hydrochloride

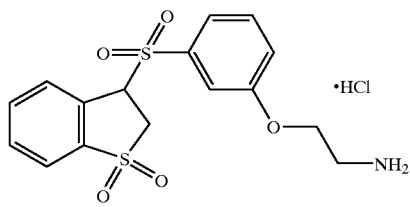

By the same procedure as described in Example 7 using the compound prepared in Example 6 (9) instead of the compound prepared in Example 6 (8), the compound of the present invention having the following physical data was obtained.

TLC: Rf 0.60 (ethyl acetate:methanol:triethylamine=14:3:1);
NMR (CD$_3$OD): δ3.25–3.45 (m, 2H), 3.80–4.00 (m, 2H), 4.15–4.35 (m, 2H), 5.55 (dd, J=7.5, 2.5 Hz, 1H), 7.20–7.50 (m, 4H), 7.60–8.00 (m, 4H).

EXAMPLE 8

3-(4-(2-(N,N-Dimethylamino)ethyloxy)phenyl)sulfonyl-2,3-dihydro-1,1-dioxidebenzo[b]thiophene.hydrochloride

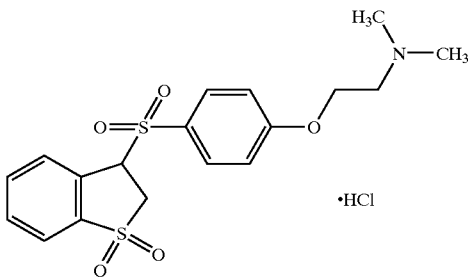

To a solution of the compound prepared in Example 7 (105 mg) and 90% paraformaldehyde (87 mg) in a mixture of acetic acid (3 ml) and methanol (3 ml), was added sodium cyanoborohydride (86 mg) at 0° C. The reaction mixture was stirred at room temperature overnight. To the reaction mixture, a saturated aqueous solution of sodium bicarbonate was added. The mixture was extracted by ethyl acetate. The extract was washed by water, dried over anhydrous magnesium sulfate, and concentrated. The residue was purified with column chromatography on silica gel (ethyl acetate:methanol:triethylamine=16:3:1). Then to a solution of the obtained compound in dioxane (25 ml) and methanol (5 ml), was added a solution of 4N hydrochloric acid-dioxane (10 ml) at room temperature. The reaction mixture was stirred for 30 minutes and concentrated to give the compound of the present invention (35 mg) having the following physical data.

TLC: Rf 0.40 (ethyl acetate:methanol:triethylamine= 16:3:1);

NMR (CD$_3$OD): δ3.10 (s, 6H), 3.60 (t, J=5.0 Hz, 2H), 3.80 (dd, J=15, 2.5 Hz, 1H), 3.95 (dd, J=15, 10 Hz, 1H), 4.45 (t, J=5.0 Hz, 2H), 5.50 (dd, J=10, 2.5 Hz, 1H), 7.10 (d, J=7.5 Hz, 2H), 7.60 (d, J=7.5 Hz, 2H), 7.60–8.00 (m, 4H).

EXAMPLE 8 (1)

3-(3-(2-(N,N-Dimethylamino)ethyloxy)phenyl) sulfonyl-2,3-dihydro-1,1-dioxidebenzo[b] thiophene.hydrochloride

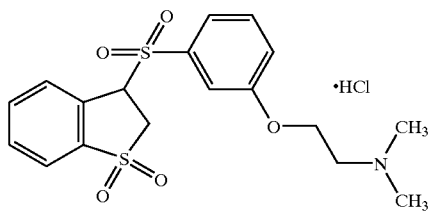

By the same procedure as described in Example 8 using the compound prepared in Example 7 (1) instead of the compound prepared in Example 7, the compound of the present invention having the following physical data was obtained.

TLC: Rf 0.44 (ethyl acetate:methanol:triethylamine= 16:2:1);

NMR (DMSO-d$_6$): δ2.80 (s, 6H), 3.50 (t, J=5.0 Hz, 2H), 3.85 (dd, J=15, 2.5 Hz, 1H), 4.00 (dd, J=15, 10 Hz, 1H), 4.30–4.55 (m, 2H), 5.90 (dd, J=10, 2.5 Hz, 1H), 7.30–7.60 (m, 4H), 7.70–7.90 (m, 4H).

EXAMPLE 9

5-Nitro-3-phenylthio-2,3-dihydro-1,1-dioxidebenzo [b]thiophene

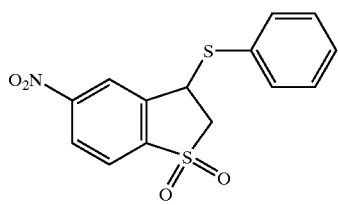

By the same procedure as described in Example 1 using 5-nitrobenzothiophene-1,1-dioxide instead of benzothiophene-1,1-dioxide, the compound of the present invention having the following physical data was obtained.

TLC: Rf 0.35 (hexane:ethyl acetate=2:1);

NMR (CDCl$_3$): δ8.52 (1H, d, J=2 Hz), 8.38 (1H, dd, J=8.4, 2.0 Hz), 7.89 (1H, d, J=8.4 Hz), 7.48–7.36 (5H, m), 4.97 (1H, dd, J=7.2, 6.8 Hz), 3.92 (1H, dd, J=13.6, 7.2 Hz), 3.60 (1H, dd, J=13.6, 6.8 Hz).

EXAMPLES 9 (1)~9 (17)

By the same procedure as described in Example 9 using a corresponding benzothiophene-1,1-dioxide instead of 5-nitrobenzothiophene-1,1-dioxide, the following compounds were obtained.

EXAMPLE 9 (1)

6-Methoxy-3-phenylthio-2,3-dihydro-1,1-dioxidebenzo[b]thiophene

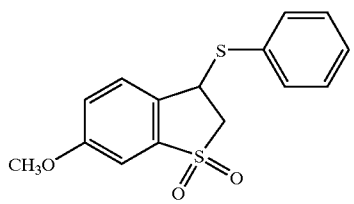

TLC: Rf 0.60 (hexane:ethyl acetate=1:1);

NMR (CDCl$_3$): δ3.52 (dd, J=13.6 Hz, 6.8 Hz, 1H), 3.81 (dd, J=13.6 Hz, 6.8 Hz, 1H), 3.86 (s, 3H), 4.92 (t, J=6.8 Hz, 1H), 7.14–7.21 (m, 2H), 7.32–7.40 (m, 3H), 7.40–7.43 (m, 2H), 7.57–7.61 (m, 1H).

EXAMPLE 9 (2)

4-Methoxy-3-phenylthio-2,3-dihydro-1,1-dioxidebenzo[b]thiophene

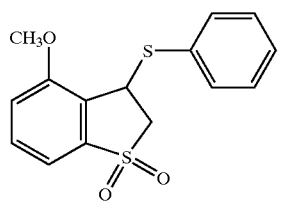

TLC: Rf 0.21 (hexane:methylene chloride=1:4);

NMR (CDCl$_3$): δ3.60 (dd, J=14.0 Hz, 1.8 Hz, 1H), 3.71 (dd, J=14.0 Hz, 6.9 Hz, 1H), 3.91 (s, 3H), 5.05 (dd, J=6.9 Hz, 1.8 Hz, 1H), 7.07 (dd, J=8.1 Hz, 0.7 Hz, 1H), 7.29–7.37 (m, 4H), 7.48–7.56 (m, 3H).

EXAMPLE 9 (3)

5-Methoxy-3-phenylthio-2,3-dihydro-1,1-dioxidebenzo[b]thiophene

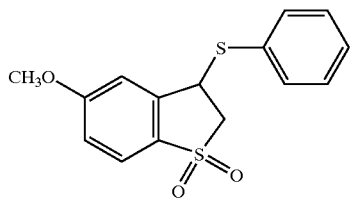

TLC: Rf 0.62 (hexane:ethyl acetate 1:1);

NMR (CDCl$_3$): δ3.51 (dd, 1H, J=14, 5 Hz), 3.79 (dd, 1H, J=14, 5 Hz), 3.88 (s, 3H), 4.92 (t, 1H, J=5 Hz), 7.04 (dd, 1H, J=5 Hz, 2 Hz), 7.13 (d, 1H, J=2 Hz), 7.35 (m, 3H), 7.44 (m, 2H), 7.63 (d, 1 H, J=5 Hz).

EXAMPLE 9 (4)

7-Methoxy-3-phenylthio-2,3-dihydro-1,1-dioxidebenzo[b]thiophene

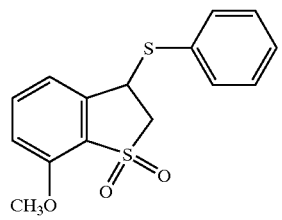

TLC: Rf 0.42 (hexane:ethyl acetate=1:1);

NMR (CDCl$_3$): δ7.62–7.38 (1 H, m), 7.58–7.28 (6H, m), 6.79 (1 H, d, J=8.4 Hz), 4.89 (1H, t, J=7.6 Hz), 3.97 (3H, s), 3.78 (1H, dd, J=13.5, 7.6 Hz), 3.52 (1H, dd, J=13.5, 7.6 Hz).

EXAMPLE 9 (5)

4-Chloro-3-phenylthio-2,3-dihydro-1,1-dioxidebenzo[b]thiophene

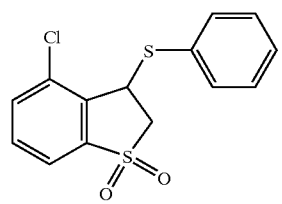

TLC: Rf 0.31 (hexane:ethyl acetate=2:1);

NMR (CDCl$_3$): δ3.68 (dd, J=14.2, 3.0 Hz, 1H), 3.75 (dd, J=14.2, 5.6 Hz, 1H), 5.00 (dd, J=5.6, 3.0 Hz, 1H), 7.35–7.40 (m, 3H), 7.49–7.59 (m, 3H), 7.64–7.69 (m, 2H).

EXAMPLE 9 (6)

5-(t-Butoxycarbonylamino)methyl-3-phenylthio-2,3-dihydro-1,1-dioxidebenzo[b]thiophene

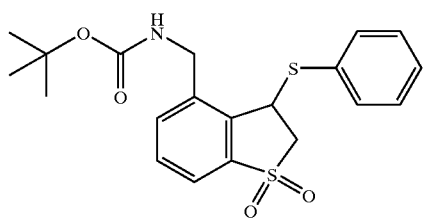

TLC: Rf 0.44 (hexane:ethyl acetate=1:1);

NMR (CDCl$_3$): δ1.45 (s, 9H), 3.60 (dd, J=12.5, 2.5 Hz, 1H), 3.75 (dd, J=12.5 Hz, 7.5 Hz, 1H), 4.50 (dd, J=15, 5.0 Hz, 1H), 4.85 (dd, J=15, 7.5 Hz, 1H), 5.00–5.20 (m, 2H) 7.30–7.45 (m, 3H), 7.50–7.75 (m, 5 H).

EXAMPLE 9 (7)

4,7-Dimethyl-3-phenylthio-2,3-dihydro-1,1-dioxidebenzo[b]thiophene

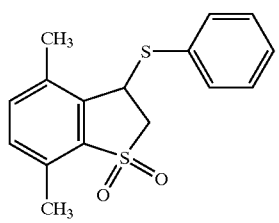

TLC: Rf 0.45 (hexane:ethyl acetate=2:1);

NMR (CDCl$_3$): δ7.50–7.30 (5H, m), 7.20 (1H, d, J=7.8 Hz), 4.89 (1H, dd, J=5.8, 2.2 Hz), 3.75–3.55 (2H, m), 2.60 (3H, s), 2.54 (3H, s).

EXAMPLE 9 (8)

4,6-Dimethyl-3-phenylthio-2,3-dihydro-1,1-dioxidebenzo[b]thiophene

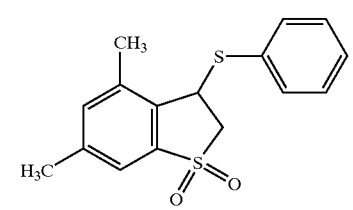

TLC: Rf 0.50 (hexane:ethyl acetate=2:1);

NMR (CDCl$_3$): δ7.56–7.24 (7H, m), 4.90 (1H, dd, J=6.0, 1.8 Hz), 3.80–3.66 (2H, m), 2.56 (3H, s), 2.42 (3H, s).

EXAMPLE 9 (9)

4-Ethyl-3-phenylthio-2,3-dihydro-1,1-dioxidebenzo[b]thiophene

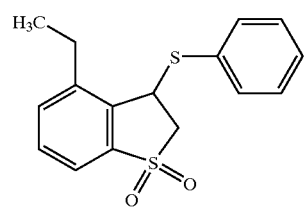

TLC: Rf 0.44 (hexane:ethyl acetate=2:1);

NMR (CDCl$_3$): δ7.65–7.30 (8H, m), 4.99 (1H, dd, J=5.9, 2.4 Hz), 3.75–3.57 (2H, m), 2.98 (2H, q, J=7.6 Hz), 1.37 (3H, t, J=7.6 Hz).

EXAMPLE 9 (10)

4-Methoxy-5-ethoxycarbonyl-3-phenylthio-2,3-dihydro-1,1-dioxidebenzo[b]thiophene

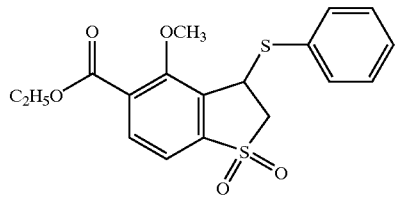

TLC: Rf 0.44 (hexane:ethyl acetate=2:1);

NMR (CDCl$_3$): δ7.99 (1H, d, J=8.0 Hz), 7.60–7.50 (3H, m), 7.45–7.35 (3H, m), 5.11 (1H, dd, J=5.9, 2.8 Hz), 4.45 (2H, q, J=7.0 Hz), 4.09 (3H, s), 3.75–3.60 (2H, m), 1.44 (3H, t, J=7.0 Hz).

EXAMPLE 9 (11)

4-Bromo-3-phenylthio-2,3-dihydro-1,1-dioxidebenzo[b]thiophene

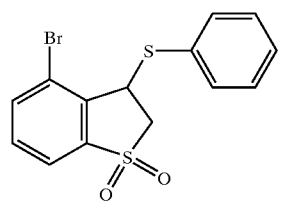

TLC: Rf 0.20 (hexane:ethyl acetate=3:1);

NMR (CDCl$_3$): δ3.69 (dd, J=13.9, 2.8 Hz, 1H), 3.74 (dd, J=13.9, 5.3 Hz, 1H), 4.94 (dd, J=5.3, 2.8 Hz, 1H), 7.37–7.39 (m, 3H), 7.45 (t, J=7.8 Hz, 1H), 7.57–7.60 (m, 2H), 7.71 (d, J=7.8 Hz, 1H), 7.84 (dd, J=7.8, 0.9 Hz, 1H).

EXAMPLE 9 (12)

4-Hydroxy-3-phenylthio-2,3-dihydro-1,1-dioxidebenzo[b]thiophene

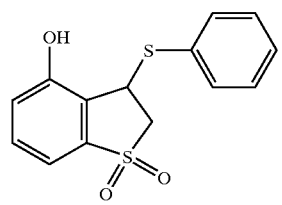

TLC: Rf 0.21 (hexane:ethyl acetate=1:1);

NMR (CDCl$_3$): δ3.49 (dd, J=13.9, 5.9 Hz, 1H), 3.81 (dd, J=13.9, 7.5 Hz, 1H), 4.93 (dd, J=7.5, 5.9 Hz, 1H), 7.17 (dd, J=8.0, 0.5 Hz, 1H), 7.25–7.51 (m, 7H).

EXAMPLE 9 (13)

5-Hydroxy-3-phenylthio-2,3-dihydro-1,1-dioxidebenzo[b]thiophene

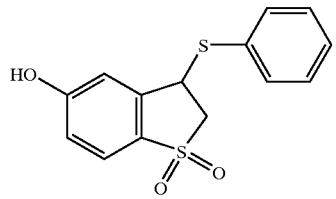

TLC: Rf 0.50 (hexane:ethyl acetate=1:1);

NMR (CDCl$_3$): δ3.51 (dd, J=14.0, 7.0 Hz, 1H), 3.78 (dd, J=14.0, 7.0 Hz, 1H), 4.89 (t, J=7.0 Hz, 1H), 6.32 (s, 1H), 6.94 (dd, J=5.0 Hz, 2.0 Hz, 1H), 7.12 (d, J=2.0 Hz, 1H), 7.35 (m, 3H), 7.43 (m, 2H), 7.58 (d, J=5.0 Hz, 1H).

EXAMPLE 9 (14)

6-Hydroxy-3-phenylthio-2,3-dihydro-1,1-dioxidebenzo[b]thiophene

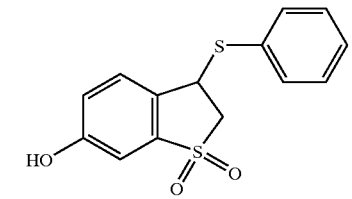

TLC: Rf 0.28 (hexane:ethyl acetate=1:1);

NMR (CDCl$_3$): δ3.54 (dd, J=13.8, 5.9 Hz, 1H), 3.83 (dd, J=13.8, 7.4 Hz, 1H), 4.91 (t-like, J=6.6 Hz, 1H), 7.10–7.15 (m, 2H), 7.31–7.42 (m, 5H), 7.51–7.56 (m, 1H).

EXAMPLE 9 (15)

7-Hydroxy-3-phenylthio-2,3-dihydro-1,1-dioxidebenzo[b]thiophene

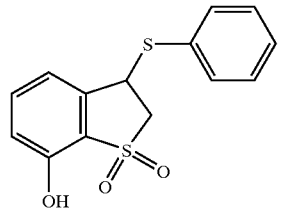

TLC: Rf 0.52 (hexane:ethyl acetate=2:1);

NMR (CDCl$_3$): δ7.50–7.20 (5H, m), 7.11 (1H, d, J=8.0 Hz), 6.85 (1H, d, J=8.0 Hz), 6.68 (1H, dd, J=32.6, 6.6 Hz), 4.91 (1H, t, J=7.5 Hz), 3.79 (1H, dd, 14, 7.5 Hz), 3.50 (1H, dd, J=14, 7.5 Hz).

EXAMPLE 9 (16)

3-Phenylthio-2,3-dihydro-1,1-dioxidethieno[2,3-b]pyridine

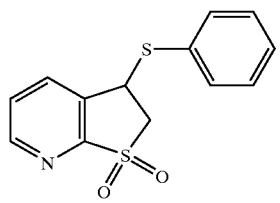

TLC: Rf 0.50 (hexane:ethyl acetate=1:1);

NMR (CDCl$_3$): δ3.49 (dd, J=14.0, 7.0 Hz, 1H), 3.85 (dd, J=14.0, 8.0 Hz, 1H), 4.91 (dd, J=8.0, 7.0 Hz, 1H), 7.40 (m, 5H), 7.58 (dd, J=8.0, 5.0 Hz, 1H), 8.08 (m, 1H), 8.76 (m, 1H).

EXAMPLE 9 (17)

4,7-dihydroxy-3-phenylthio-2,3-dihydro-1,1-dioxidebenzo[b]thiophene

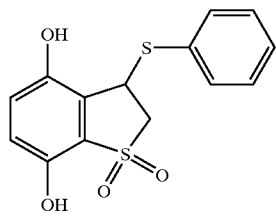

TLC: Rf 0.33 (methylene chloride:ethyl acetate=1:1);

NMR (CDCl$_3$): δ9.25 (2H, brs), 7.55–7.45 (2H, m), 7.40–7.30 (3H, m), 6.96 (1H, d, J=8.8 Hz), 6.85 (1H, d, J=8.8 Hz), 5.09 (1H, dd, J=7.4, 1.6 Hz), 3.71 (1H, dd, 13.9, 7.4 Hz), 3.50 (1H, dd, J=13.9, 1.6 Hz).

EXAMPLE 10

5-Nitro-3-phenylsulfonyl-2,3-dihydro-1,1-dioxidebenzo[b]thiophene

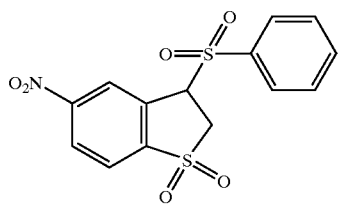

To a solution of the compound prepared in Example 9 (790 mg) in chloroform (45 ml) was added 3-chloroperbenzoic acid (70% purity, 1.21 g). The reaction mixture was stirred at room temperature for 2 hours. To the reaction mixture, water was added. The mixture was extracted by ethyl acetate. The extract was washed by 2N aqueous solution of sodium hydroxide, water, a saturated aqueous solution of sodium chloride successively, dried over anhydrous magnesium sulfate and concentrated. The residue was purified with column chromatography on silica gel (hexane:ethyl acetate=3:2) to give the compound of the present invention (497 mg) having the following physical data.

TLC: Rf 0.39 (hexane:ethyl acetate=1:1);

NMR (CDCl$_3$): δ3.98 (dd, J=15.5, 3.0 Hz, 1H), 4.19 (dd, J=15.5, 9.3 Hz, 1H), 5.95 (dd, J=9.3, 3.0 Hz, 1H), 7.59–7.67 (m 2H), 7.78–7.84 (m, 3H), 8.11 (d, J=8.6 Hz, 1H), 8.41 (d, J=2.0 Hz, 1H), 8.51 (dd, J=8.6, 2.0 Hz, 1H).

EXAMPLES 10 (1)–10 (16)

Using the compounds prepared in Examples 9 (1)–9 (16) instead of the compound prepared in Example 9, by the same procedure as described in Example 10, or by the same reaction using 3-chloroperbenzoic acid instead of OXONE©, the following compounds of the present invention were obtained.

EXAMPLE 10 (1)

6-Methoxy-3-phenylsulfonyl-2,3-dihydro-1,1-dioxidebenzo[b]thiophene

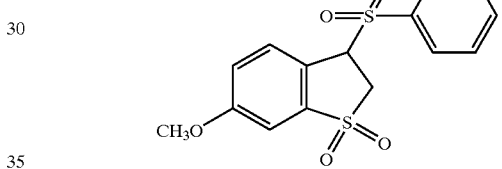

TLC: Rf 0.34 (hexane:ethyl acetate=1:1);

NMR (CDCl$_3$): δ3.66–3.82 (m, 2H), 3.87 (s, 3H), 5.00 (dd, J=7.5, 5.5 Hz, 1H), 7.06 (d, J=2.4 Hz, 1H), 7.24 (dd, J=8.8, 2.4 Hz, 1H), 7.46–7.54 (m, 2H), 7.63–7.71 (m, 3H), 7.86 (d, J=8.8 Hz, 1H).

EXAMPLE 10 (2)

4-Methoxy-3-phenylsulfonyl-2,3-dihydro-1,1-dioxidebenzo[b]thiophene

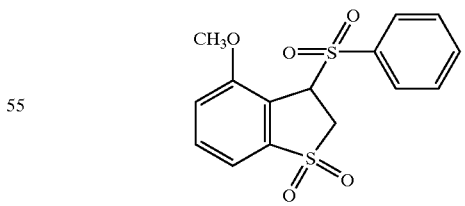

TLC: Rf 0.17 (hexane:ethyl acetate=1:1);

NMR (CDCl$_3$): δ3.49 (s, 3H), 3.76 (dd, J=14.9, 9.2 Hz, 1H), 4.31 (dd, J=14.9, 1.3 Hz, 1H), 5.23 (dd, J=9.2, 1.3 Hz, 1H), 6.90 (d, J=8.0 Hz, 1H), 7.31 (d, J=7.8 Hz, 1H), 7.45–7.54 (m, 3H), 7.58–7.68 (m, 1H), 7.72–7.77 (m, 2H).

EXAMPLE 10 (3)

5-Methoxy-3-phenylsulfonyl-2,3-dihydro-1,1-dioxidebenzo[b]thiophene

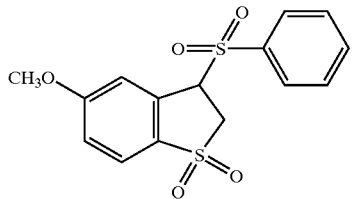

TLC: Rf 0.50 (hexane:ethyl acetate=1:1);

NMR (CDCl$_3$): δ3.70(dd, J=12, 8 Hz, 1H), 3.77(dd, J=12, 4 Hz, 1H), 3.94(s, 3H), 5.01(dd, J=8, 4 Hz, 1H), 7.12(d, J=8 Hz, 1H), 7.44(s, 1H), 7.53(m, 3H), 7.68(m, 3H).

EXAMPLE 10 (4)

7-Methoxy-3-phenylsulfonyl-2,3-dihydro-1,1-dioxidebenzo[b]thiophene

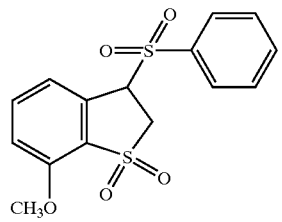

TLC: Rf 0.40 (hexane:ethyl acetate=1:2);

NMR (DMSO-d$_6$): δ7.80–7.55 (6H, m), 7.27 (1H, d, J=8.2 Hz), 7.15 (1H, d, J=8.2 Hz),5.73(1H, dd, J=9.5, 3.4 Hz), 3.91 (1H, dd, J=15, 9.5 Hz), 3.87 (3H, s), 3.69 (1H, dd, J=15, 3.4 Hz).

EXAMPLE 10 (5)

4-Chloro-3-phenylsulfonyl-2,3-dihydro-1,1-dioxidebenzo[b]thiophene

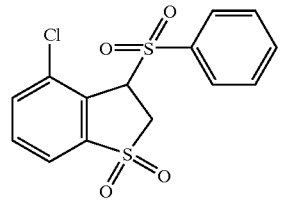

TLC: Rf 0.43 (methylene chloride:ethyl acetate=15:1);

NMR (CDCl$_3$): δ3.79 (dd, J=15.0, 9.2 Hz, 1H), 4.24 (dd, J=15.0, 1.0 Hz, 1H), 5.26 (dd, J=9.2, 1.0 Hz, 1H), 7.46–7.66 (m, 6H), 7.77–7.81 (m, 2H).

EXAMPLE 10 (6)

4-(t-Butoxycarbonylamino)methyl-3-phenylsulfonyl-2,3-dihydro-1,1-dioxidebenzo[b]thiophene

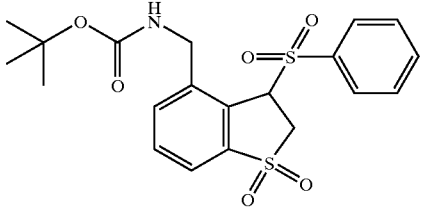

TLC: Rf 0.26 (hexane:ethyl acetate=1:1);

NMR (CDCl$_3$): δ1.45 (s, 9H), 3.75 (dd, J=15, 10 Hz, 1H), 3.85 (dd, J=15, 2.5 Hz, 1H), 4.40 (dd, J=15, 5.0 Hz, 1H), 4.95 (dd, J=15, 7.5 Hz, 1H), 5.35 (m, 2H), 7.45–7.90 (m, 8H).

EXAMPLE 10 (7)

4,7-Dimethyl-3-phenylsulfonyl-2,3-dihydro-1,1-dioxidebenzo[b]thiophene

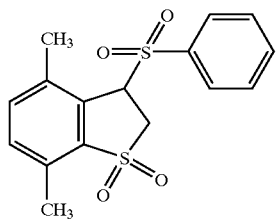

TLC: Rf 0.18 (hexane:ethyl acetate=2:1);

NMR (DMSO-d$_6$): δ7.81–7.70 (3H, m), 7.70–7.55 (2H, m), 7.48 (1H, d, J=7.8 Hz), 7.38 (1H, d, J=7.8 Hz), 5.73 (1H, t, J=5.2 Hz), 3.84 (2H, d-like, J=5.2 Hz), 240 (3H, s), 2.36 (3H, s).

EXAMPLE 10 (8)

4,6-Dimethyl-3-phenylsulfonyl-2,3-dihydro-1,1-dioxidebenzo[b]thiophene

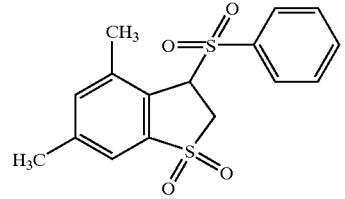

TLC: Rf 0.18 (hexane:ethyl acetate=2:1);

NMR (DMSO-d$_6$): δ7.82–7.70 (3H, m), 7.70–7.55 (2H, m), 7.42 (2H, d, J=5.4 Hz), 5.73 (1H, t, J=4.8 Hz), 3.86–3.80 (2H, m), 2.38 (6H, s).

EXAMPLE 10 (9)

4-Ethyl-3-phenylsulfonyl-2,3-dihydro-1,1-dioxidebenzo[b]thiophene

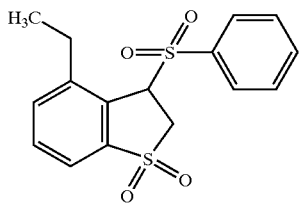

TLC: Rf 0.22 (hexane:ethyl acetate=2:1);

NMR (CDCl$_3$): δ7.68–7.40 (8H, m), 5.22 (1H, d, J=9.2 Hz), 3.99 (1H, d, J=15.2 Hz), 3.76 (1H, dd, J=15.2, 9.2 Hz), 3.07 (2H, dq, J=7.6, 2.2 Hz), 1.33 (3H, t, J=7.6 Hz).

EXAMPLE 10 (10)

4-Methoxy-5-ethoxycarbonyl-3-phenylsulfonyl-2,3-dihydro-1,1-dioxidebenzo[b]thiophene

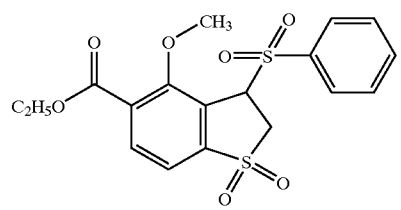

TLC: Rf 0.38 (hexane:ethyl acetate=1:1);

NMR (CDCl$_3$): δ7.91 (1H, d, J=8.0 Hz), 7.83–7.45 (5H, m), 7.41 (1H, d, J=8.0 Hz), (1H, d-like, J=8.0 Hz), 4.42 (2H, q, J=7.0 Hz), 4.17 (1H, dd, J=15, 1.6 Hz), 3.86 (3H, 3.75 (1H, dd, J=15, 8.0 Hz), 1.43 (3H, t, J=7.0 Hz).

EXAMPLE 10 (11)

4-Bromo-3-phenylsulfonyl-2,3-dihydro-1,1-dioxidebenzo[b]thiophene

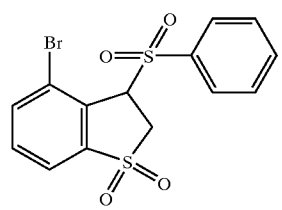

TLC: Rf 0.35 (hexane:ethyl acetate=1:1);

NMR (CDCl$_3$) δ3.79 (dd, J=15.0, 9.2 Hz, 1H), 4.23 (dd, J=15.0, 1.1 Hz, 1H), 5.23 (d-like, J=8.8 Hz, 1H), 7.44–7.54 (m, 3H), 7.62–7.70 (m, 2H), 7.78–7.83 (m, 3H).

EXAMPLE 10 (12)

4-Hydroxy-3-phenylsulfonyl-2,3-dihydro-1,1-dioxidebenzo[b]thiophene

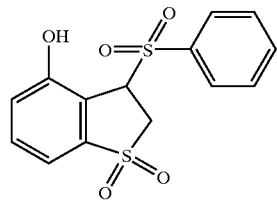

TLC: Rf 0.22 (hexane:ethyl acetate=1:2);

NMR (DMSO-d$_6$): δ3.96 (dd, J=15.0, 8.4 Hz, 1H), 4.08 (dd, J=15.0, 1.8 Hz, 1H), 5.51 (dd, J=8.4, 1.8 Hz, 1H), 7.00 (d-like, J=8.0 Hz, 1H), 7.16 (d, J=7.0 Hz, 1H), 7.47 (t, J=8.0 Hz, 1H), 7.56–7.63 (m, 2H), 7.71–7.81 (m, 3H).

EXAMPLE 10 (13)

5-Hydroxy-3-phenylsulfonyl-2,3-dihydro-1,1-dioxidebenzo[b]thiophene

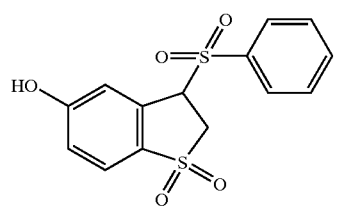

TLC: Rf 0.30 (hexane:ethyl acetate=1:1);

NMR (DMSO-d$_6$): δ3.66 (dd, J=14, 4 Hz, 1H), 3.90 (dd, J=14, 9 Hz, 1H), 5.71 (dd, J=9, 4 Hz, 1H), 7.07 (m, 2H), 7.55–7.82 (m, 6H), 10.80 (brs, 1H).

EXAMPLE 10 (14)

6-Hydroxy-3-phenylsulfonyl-2,3-dyhydro-1,1-dioxidebenzo[b]thiophene

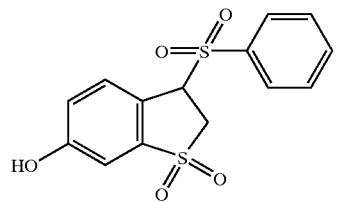

TLC: Rf 0.37 (hexane:ethyl acetate=1:2);

NMR (DMSO-d$_6$): δ3.73 (dd, J=15.2, 3.2 Hz, 1H), 3.96 (dd, J=15.2, 9.2 Hz, 1H), 5.60 (dd, J=9.2, 3.2 Hz, 1H), 6.94 (s-like, 1H), 7.16 (d-like, J=8.4 Hz, 1H), 7.50 (d, J=8.4 Hz, 1H), 7.57–7.64 (m, 2H), 7.71–7.76 (m, 3H).

EXAMPLE 10 (15)

7-Hydroxy-3-phenylsulfonyl-2,3-dihydro-1,1-dioxidebenzo[b]thiophene

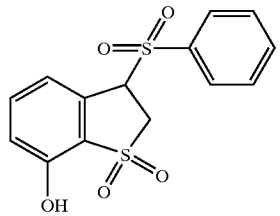

TLC: Rf 0.31 (hexane:ethyl acetate=1:2);

NMR (DMSO-$d_6$): δ7.80–7.45 (6H, m), 6.98 (2H, d, J=8.4 Hz), 5.66 (1 H, dd, J=9.6, 3.2 Hz), 3.85 (1H, dd, J=15, 9.6 Hz), 3.68–3.58 (1H, m).

EXAMPLE 10 (16)

3-Phenylsulfonyl-2,3-dihydro-1,1-dioxidethieno[2,3-b]pyridine

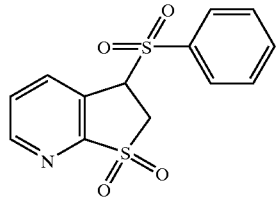

TLC: Rf 0.20 (hexane:ethyl acetate=1:1);

NMR (CDCl$_3$): δ3.65 (dd, J=15, 8 Hz, 1H), 3.74 (dd, J=15, 6 Hz, 1H), 5.04 (dd, J=8, 6 Hz, 1H), 7.58 (m, 2H), 7.69 (m, 4H), 8.48 (m, 1H), 8.86 (m, 1H).

EXAMPLE 11

5-Amino-3-phenylsulfonyl-2,3-dihydro-1,1-dioxidebenzo[b]thiophene

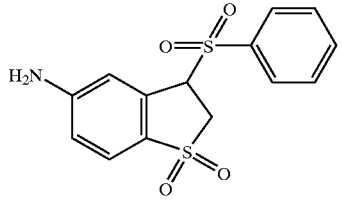

Under an atmosphere of argon, to a solution of the compound prepared in Example 10 (110 mg) in ethanol (7.5 ml) and ethyl acetate (7.5 ml), was added 5% palladium-carbon (20 mg). The reaction mixture was stirred at room temperature for 2 hours under an atmosphere of hydrogen. The reaction mixture was filtrated through celite (trade name). The filtrate was concentrated. The residue was purified with column chromatography on silica gel (methylene chloride:ethyl acetate=2:1) to give the compound of the present invention (94 mg) having the following physical data. Then, it was converted into a corresponding salt by a known method to give the compound of the present invention having the following physical data.

Free Compound

TLC: Rf 0.29 (hexane:ethyl acetate=1:2);

NMR (CDCl$_3$): δ3.61 (dd, J=14.6, 8.3 Hz, 1H), 3.70 (dd, J=14.6, 5.6 Hz, 1H), 4.34 (brs, 2H), 4.94 (dd, J=8.3, 5.6 Hz, 1H), 6.79 (dd, J=8.0, 2.0 Hz, 1H), 7.21 (d, J=2.0 Hz, 1H), 7.40 (d, J=8.0 Hz, 1H), 7.49–7.55 (m, 2H), 7.63–7.74 (m, 3H).

Hydrochloride

TLC: Rf 0.47 (methylene chloride:methanol=18:1);

NMR (DMSO-$d_6$): δ3.53 (dd, J=14.9, 3.8 Hz, 1H), 3.75 (dd, J=14.9, 9.4 Hz, 1H), 5.58 (dd, J=9.4, 3.8 Hz, 1H), 6.76 (dd, J=8.6, 2.1 Hz, 1H), 6.90 (d, J=2.1 Hz, 1H), 7.31 (d, J=8.6 Hz, 1H), 7.57–7.65 (m, 2H), 7.72–7.79 (m, 3H).

EXAMPLE 12

5-Acetylamino-3-phenylsulfonyl-2,3-dihydro-1,1-dioxidebenzo[b]thiophene

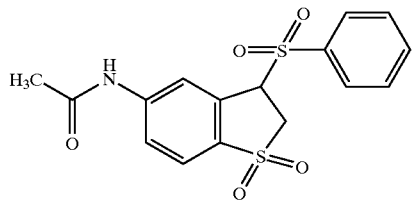

To a solution of the compound prepared in Example 11 (91 mg) in pyridine (2 ml), was added acetic anhydride (1 ml). The reaction mixture was stirred at room temperature for 2 hours. The reaction mixture was concentrated. The residue was purified with column chromatography on silica gel (hexane:ethyl acetate=1:1) to give the compound of the present invention (86 mg) having the following physical data.

TLC: Rf 0.20 (hexane:ethyl acetate=1:2);

NMR (CDCl$_3$): δ2.24 (s, 3H), 3.66 (dd, J=14.8, 8.3 Hz, 1H), 3.75 (dd, J=14.8, 5.2 Hz, 1H), 5.04 (dd, J=8.3, 5.2 Hz, 1H), 7.49–7.59 (m, 3H), 7.66–7.75 (m, 3H), 7.87–7.94 (m, 2H), 8.04 (s-like, 1H).

EXAMPLE 13

5-Aminomethyl-3-phenylsulfonyl-2,3-dihydro-1,1-dioxidebenzo[b]thiophene.hydrochloride

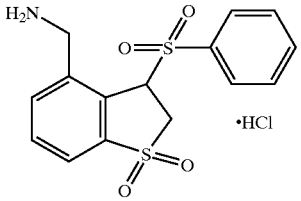

By the same procedure as described in Example 7 using the compound prepared in Example 10 (6) instead of the compound prepared in Example 6 (8), the compound of the present invention having the following physical data was obtained.

TLC: Rf 0.16 (ethyl acetate:methanol:triethylamine=16:2:1);

NMR (DMSO-$d_6$): δ3.80–4.00 (m, 2H), 4.35 (d, J=15 Hz, 1H), 4.55 (d, J=15 Hz, 1H), 6.30–6.40 (m, 1H), 7.60–7.70 (m, 2H), 7.75–7.95 (m, 5H), 8.00–8.15 (m, 1H), 8.30–8.65 (m, 2H).

EXAMPLE 14

4-(N,N-dimethylamino)methyl-3-phenylsulfonyl-2,3-dihydro-1,1-dioxidebenzo[b]thiophene.hydrochloride

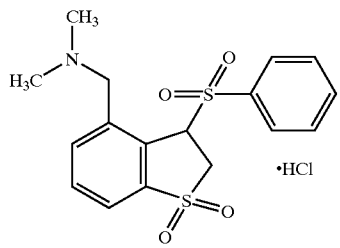

By the same procedure as described in Example 8 using the compound prepared in Example 13 instead of the compound prepared in Example 7, the compound of the present invention having the following physical data was obtained.

TLC: Rf 0.50 (ethyl acetate:methanol:triethylamine=16:2:1);

NMR (DMSO-$d_6$): δ2.65 and 2.70 (both s, total 3H), 2.85 and 2.90 (both s, total 3H), 3.80 (d, J=12.5 Hz, 1H), 4.05 (dd, J=12.5, 7.5 Hz, 1H), 4.50–4.70 (m, 1H), 4.70–4.90 (m, 1H), 6.35 (d, J=7.5 Hz, 1H), 7.60–8.00 (m, 7H), 8.20–8.35 (m, 1H), 10.85 (brs, 1H).

EXAMPLE 15

4-Methoxy-5-formyl-3-phenylsulfonyl-2,3-dihydro-1,1-dioxidebenzo[b]thiophene

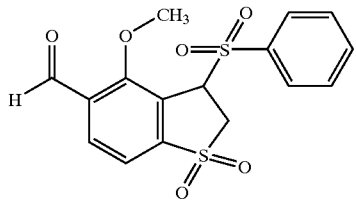

To a suspension of lithium aluminum hydride (54 mg) in tetrahydrofuran (10 ml), was added a solution of the compound prepared in Example 10 (10) (300 mg) in tetrahydrofuran (10 ml) at −78° C. dropwise. The reaction mixture was stirred at −78° C. for 1 hour. The reaction mixture was poured into ice-water. The mixture was extracted by ethyl acetate. The extract was washed by water, a saturated aqueous solution of sodium chloride, successively, dried over anhydrous sodium sulfate, and concentrated. The residue was purified with column chromatography on silica gel (hexane:ethyl acetate=1:1) to give the compound of the present invention (51 mg) having the following physical data.

TLC: Rf 0.27 (hexane:ethyl acetate=1:2);

NMR (CDCl$_3$): δ3.80 (dd, J=15.2, 9.3 Hz, 1H), 4.05 (s, 3H), 4.14 (dd, J=15.2, 1.4 Hz, 1H), 5.28 (dd, J=9.3, 1.4 Hz, 1H), 7.46–7.54 (m, 3H), 7.63–7.78 (m, 3H), 8.05 (d, J=8.0 Hz, 1H), 10.33 (d, J=0.6 Hz, 1H).

EXAMPLE 16

4-Methoxy-3-(thiophen-2-yl)thio-2,3-dihydro-1,1-dioxidebenzo[b]thiophene

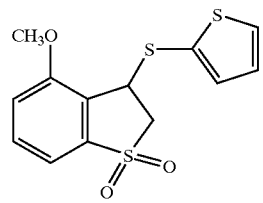

By the same procedure as described in Example 1 using 2-thiophenthiol and 4-methoxybenzothiophen-1,1-diol, the compound of the present invention having the following physical data was obtained.

TLC: Rf 0.27 (methylene chloride:hexane=4:1);

NMR (CDCl$_3$): δ3.66 (d, J=15.5, 5.4 Hz, 1H), 3.73 (dd, J=15.5, 4.2 Hz, 1H), 3.95 (s, 3H), 4.88 (dd, J=5.4, 4.2 Hz, 1H), 7.01 (dd, J=5.4, 3.6 Hz, 1H), 7.09 (d, J=8.0 Hz, 1H), 7.19 (dd, J=3.6, 1.2 Hz, 1H), 7.27 (d, J=8.0 Hz, 1H), 7.44 (dd, J=5.4, 1.2 Hz, 1H), 7.53 (t, J=8.0 Hz, 1H).

EXAMPLE 17

4-Methoxy-3-(thioiphen-2-yl)sulfonyl-2,3-dihydro-1,1-dioxidebenzo[b]thiophene

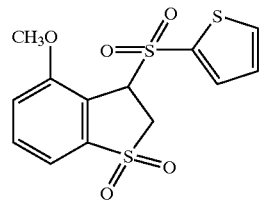

By the same procedure using the compound prepared in Example 16 instead of the compound prepared in Example 9, the compound of the present invention having the following physical data was obtained.

TLC: Rf 0.46 (methylene chloride:ethyl acetate=10:1);

NMR (CDCl$_3$): δ3.73 (s, 3H), 3.79 (dd, J=15.0, 9.2 Hz, 1H), 4.23 (dd, J=15.0, 1.2 Hz, 1H), 5.32 (dd, J=9.2, 1.2 Hz, 1H), 7.04 (d, J=8.0 Hz, 1H), 7.11 (dd, J=4.9, 3.8 Hz, 1H), 7.30 (d, J=8.0 Hz, 1H), 7.53 (dd, J=3.8, 1.4 Hz, 1H), 7.59 (t, J=8.0 Hz, 1H), 7.73 (dd, J=4.9, 1.4 Hz, 1H).

EXAMPLE 18

4-(4-Nitrophenylmethyl)oxy-3-phenylthio-2,3-dihydro-1,1-dioxidebenzo[b]thiophene

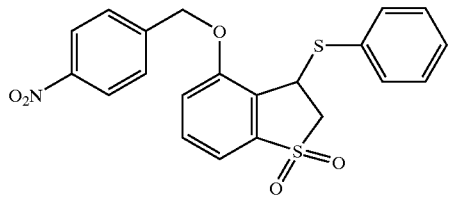

To a solution of a compound prepared in Example 9 (12) (1.0 g) in dimethylformamide (30 ml), were added 4-nitrobenzylbromide (947 mg) and potassium carbonate (1.0 g). The reaction mixture was stirred at room temperature overnight. To the reaction mixture, water was added. The mixture was extracted by ethyl acetate. The extract was washed by water (three times), a saturated aqueous solution of sodium chloride, dried over anhydrous sodium sulfate, and concentrated. The residue was purified with column chromatography on silica gel (hexane:ethyl acetate=1:1) to give the compound of the present invention (1.1 g) having the following physical data.

TLC: Rf 0.29 (hexane:ethyl acetate=1:1);

NMR (CDCl$_3$): δ8.25 (2H, d, J=8.5 Hz), 7.71 (2H, d, J=8.5 Hz), 7.60–7.20 (7H, m), 7.10 (1H, d, J=8 Hz), 5.32 (2H, s), 5.11 (1H, dd, J=7, 2 Hz), 3.85–3.55 (2H, m).

EXAMPLE 18 (1)~18 (40)

By the sane procedure as described in Example 18 using compounds prepared in Examples 9 (12)~9 (15) or Example 9 (17) and a corresponding halogenated compound, the following compounds of the present invention were obtained.

EXAMPLE 18 (1)

4-(3-Phenyloxypropyl)oxy-3-phenylthio-2,3-dihydro-1,1-dioxidebenzo[b]thiophene

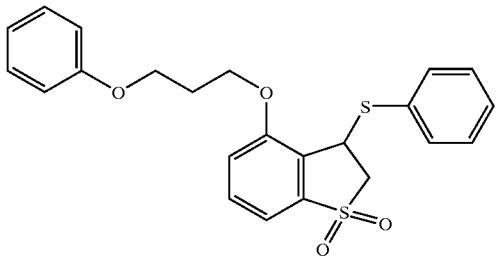

TLC: Rf 0.27 (hexane:ethyl acetate=2 1);

NMR (CDCl$_3$): δ7.54–7.42 (3H, m), 7.32–7.19 (6H, m), 7.10 (1H, d, J=8.0 Hz), 6.95–6.84 (3H, m), 5.01 (1H, dd, J=6.6, 2.2 Hz), 4.31 (2H, t, J=6.0 Hz), 4.20 (2H, t, J=6.0 Hz), 3.69 (1H, dd, J=13.9, 6.6 Hz), 3.59 (1H, dd, J=13.9, 2.2 Hz), 2.31 (2H, quint, J=6.0 Hz).

EXAMPLE 18 (2)

4-Benzyloxy-3-phenylthio-2,3-dihydro-1,1-dioxidebenzo[b]thiophene

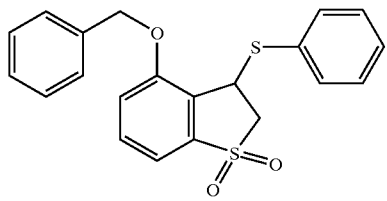

TLC: Rf 0.45 (hexane:ethyl acetate=2:1);

NMR (CDCl$_3$): δ7.54–7.26 (12H, m), 7.13 (1H, d, J=9.0 Hz), 5.22 (2H, s), 5.03 (1H, dd, J=6.0, 2.6 Hz), 3.71 (1H, dd, J=13.8, 6.0 Hz), 3.63 (1H, dd, J=13.8, 2.6 Hz).

EXAMPLE 18 (3)

4-(3-Benzyloxypropyl)oxy-3-phenylthio-2,3-dihydro-1,1-dioxidebenzo[b]thiophene

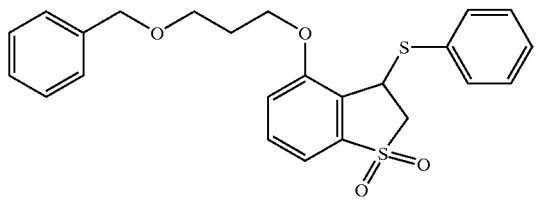

TLC: Rf 0.47 (hexane:ethyl acetate=1:1);

NMR (CDCl$_3$): δ2.13 (quint, J=6.0 Hz, 2H), 3.58 (dd, J=14.0, 2.4 Hz, 1H), 3.67 (dd, J=14.0, 6.6 Hz, 1H), 3.69 (t, J=6.0 Hz, 2H), 4.22 (t, J=6.0 Hz, 2H), 4.44 (d, J=12.0 Hz, 1H), 4.52 (d, J=12.0 Hz, 1H), 4.92 (dd, J=6.6, 2.4 Hz, 1H), 7.08 (d-like, J=7.4 Hz, 1H), 7.26 (s, 5H), 7.30–7.35 (m, 4H), 7.43–7.54 (m, 3H).

EXAMPLE 18 (4)

4-(Pyridin-3-ylmethyl)oxy-3-phenylthio-2,3-dihydro-1,1-dioxidebenzo[b]thiophene

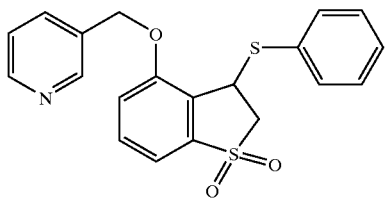

TLC: Rf 0.46 (ethyl acetate);

NMR (CDCl$_3$): δ3.62 (dd, J=14.0, 2.2 Hz, 1H), 3.72 (dd, J=14.0, 6.2 Hz, 1H), 5.04 (dd, J=6.2, 2.2 Hz, 1H), 5.23 (s, 2H), 7.15 (dd, J=8.0, 1.0 Hz, 1H), 7.26–7.45 (m, 7H), 7.54 (t, J=8.0 Hz, 1H), 7.85–7.92 (m, 1H), 8.63 (dd, J=4.7, 2.0 Hz, 1H), 8.76 (dd, J=2.0, 0.6 Hz, 1H).

EXAMPLE 18 (5)

4-(Quinolin-2-ylmethyl)oxy-3-phenylthio-2,3-dihydro-1,1-dioxidebenzo[b]thiophene

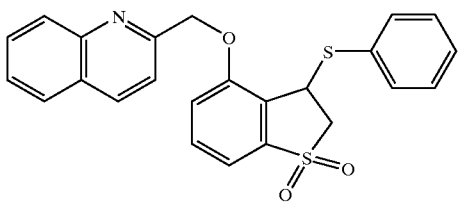

TLC: Rf 0.25 (hexane:ethyl acetate=1:1);

NMR (CDCl$_3$): δ8.18 (1H, d, J=8 Hz), 8.10 (1H, d, J=8 Hz), 7.92–7.68 (3H, m), 7.68–7.40 (4H, m), 7.40–7.22 (4H, m), 7.16 (1H, d, J=8 Hz), 5.53 (2H, s), 5.18 (1H, dd, J=7, 2 Hz), 3.76 (1H, dd, J=14, 7 Hz), 3.66 (1H, dd, J=14, 2 Hz).

EXAMPLE 18 (6)

4-(Pyridin-2-ylmethyl)oxy-3-phenylthio-2,3-dihydro-1,1-dioxidebenzo[b]thiophene

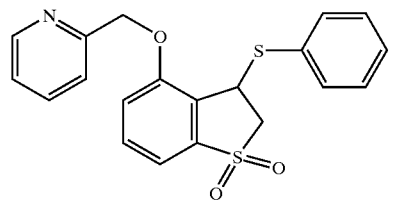

TLC: Rf 0.33 (ethyl acetate);

NMR (CDCl$_3$): δ8.62 (1H, d, J=5 Hz), 7.80–7.58 (2H, m), 7.58–7.38 (3H, m), 7.38–7.18 (5H, m), 7.11 (1H, d, J=8 Hz), 5.35 (2H, s), 5.15 (1H, dd, J=7, 2 Hz), 3.85–3.58 (2H, m).

EXAMPLE 18 (7)

4-(Pyridin-4-ylmethyl)oxy-3-phenylthio-2,3-dihydro-1,1-dioxidebenzo[b]thiophene

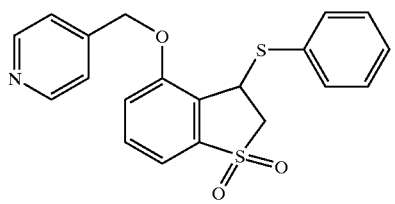

TLC: Rf 0.15 (ethyl acetate);

NMR (CDCl$_3$): δ8.78–8.55 (2H, m), 7.65–7.18 (9H, m), 7.07 (1H, d, J=8 Hz), 5.23 (2H, s), 5.11 (1H, dd, J=7, 2 Hz), 3.82–3.53 (2H, m).

EXAMPLE 18 (8)

4-(3-(Pyridin-3-yl)propyl)oxy-3-phenylthio-2,3-dihydro-1,1-dioxidebenzo[b]thiophene

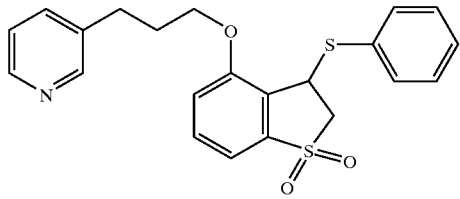

TLC: Rf 0.18 (ethyl acetate);

NMR (CDCl$_3$): δ8.48–8.35 (m, 2H), 7.67–7.33 (m, 9H), 6.95 (d, J=8.0 Hz, 1H), 5.01 (d-like, J=8.5 Hz, 1H), 4.15–3.86 (m, 4H), 2.81 (t, J=7.0 Hz, 2H), 2.21–2.01 (m, 2H).

EXAMPLE 18 (9)

4-(3-Hydroxypropyl)oxy-3-phenylthio-2,3-dihydro-1,1-dioxidebenzo[b]thiophene

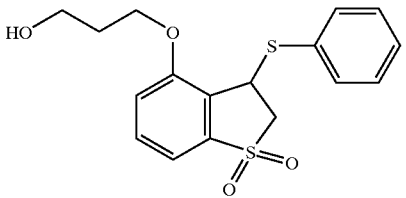

TLC: Rf 0.24 (hexane:ethyl acetate=1:2);

NMR (CDCl$_3$): δ2.06–2.17 (m, 2H), 3.57 (dd, J=14.0, 2.2 Hz, 1H), 3.67 (dd, J=14.0, 6.6 Hz, $_1$H), 3.91 (br, 2H), 4.27 (t, J=5.8 Hz, 2H), 5.05 (dd, J=6.6, 2.2 Hz, 1H), 7.11 (d, J=8.0 Hz, 1H), 7.30–7.38 (m, 4H), 7.49–7.56 (m, 3H).

EXAMPLE 18 (10)

5-Pentoxy-3-phenylthio-2,3-dihydro-1,1-dioxidebenzo[b]thiophene

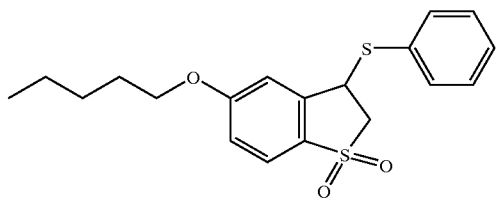

TLC: Rf 0.70 (hexane:ethyl acetate=2:1);

NMR (CDCl$_3$): δ0.95 (t, J=7.0 Hz, 3H), 1.38–1.47 (m, 4H), 1.82 (quint, J=6.8 Hz, 2H), 3.51 (dd, J=15, 7 Hz, 1H), 3.79 (dd, J=15, 7 Hz, 1H), 4.00 (t, J=6.8 Hz, 2H), 4.89 (t, J=7.0 Hz, 1H), 7.01 (dd, J=8, 2 Hz, 1H), 7.12 (d, J=2 Hz, 1H), 7.36–7.38 (m, 3H), 7.41–7.43 (m, 2H), 7.61 (d, J=8 Hz, 1H).

EXAMPLE 18 (11)

5-(2-Phenyloxyethyl)oxy-3-phenylthio-2,3-dihydro-1,1-dioxidebenzo[b]thiophene

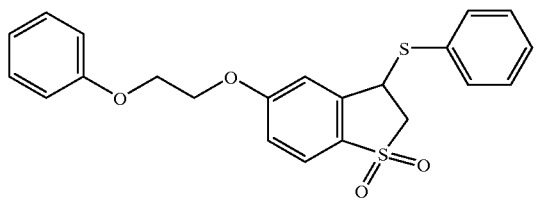

TLC: Rf 0.75 (hexane:ethyl acetate=1:1);

NMR (CDCl$_3$): δ7.65 (1H, d, J=8.5 Hz), 7.45–7.42 (2H, m), 7.34–7.29 (5H, m), 7.21 (1H, d, J=2.2 Hz), 7.09 (1H, dd, J=8.5, 2.2 Hz), 7.00 (1H, t, J=7.0 Hz), 6.95 (1H, d, J=8.5 Hz), 4.93 (1H, t, J=7.0 Hz), 4.38 (4H, m), 3.78 (1H, dd, J=14.0, 7.0 Hz), 3.52 (1H, dd, J=14.0, 7.0 Hz).

EXAMPLE 18 (12)

5-(3-Hydroxypropyl)oxy-3-phenylthio-2,3-dihydro-1,1-dioxidebenzo[b]thiophene

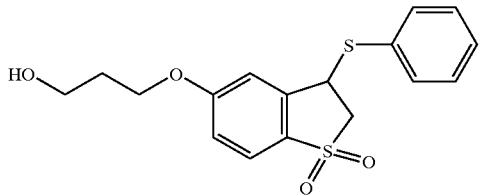

TLC: Rf 0.25 (hexane:ethyl acetate=1:1);

NMR (CDCl$_3$): δ2.10 (quint, J=6.5 Hz, 2H), 3.60 (dd, J=14, 6.7 Hz, 1H), 3.82 (dd, J=14, 6.7 Hz, 1H), 3.89 (t, J=6.5 Hz, 2H), 4.20 (t, J=6.5 Hz, 2H), 4.98 (t, J=6.7 Hz, 1H), 7.20 (dd, J=8.5, 2.2 Hz, 1H), 7.35–7.47 (m, 6H), 7.61 (d, J=8.5 Hz, 1H).

EXAMPLE 18 (13)

5-(pyridin-3-ylmethyl)oxy-3-phenylthio-2,3-dioxidebenzo[b]thiophene

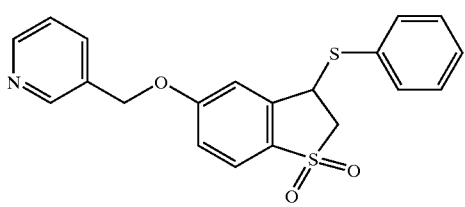

TLC: Rf 0.40 (ethyl acetate);

NMR (CDCl$_3$): δ3.51 (dd, J=9.0, 4.5 Hz, 1H), 3.79 (dd, J=9.0, 5.0 Hz, 1H), 4.91 (t-like, J=4.7 Hz, 1H), 5.14 (s, 2H), 7.11 (dd, J=5.6, 1.6 Hz, 1H), 7.21 (d, J=1.6 Hz, 1H), 7.33–7.42 (m, 6H), 7.65 (d, J=5.6 Hz, 1H), 7.77 (dt, J=5.4, 1.3 Hz, 1H), 8.63 (dd, J=3.2, 1.3 Hz, 1H), 8.70 (d, J=1.3 Hz, 1H).

EXAMPLE 18 (14)

5-(3-(Pyridin-3-yl)propyl)oxy-3-phenylthio-2,3-dihydro-1,1-dioxidebenzo[b]thiophene

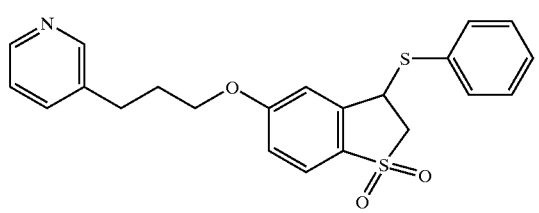

TLC: Rf 0.16 (ethyl acetate);

NMR (CDCl$_3$): δ8.36–8.28 (m, 2H), 7.78–7.55 (m, 4H), 7.42–7.36 (m, 5H), 7.01 (d, J=8.0 Hz, 1H), 5.11 (d-like, J=9.0 Hz, 1H), 4.12 (t, J=7.0 Hz, 2H), 3.88–3.64 (m, 2H), 3.05 (t, J=7.0 Hz, 2H), 2.35–2.26 (m, 2H).

EXAMPLE 18 (15)

6-(3-Phenyloxypropyl)oxy-3-phenylthio-2,3-dihydro-1,1-dioxidebenzo[b]thiophene

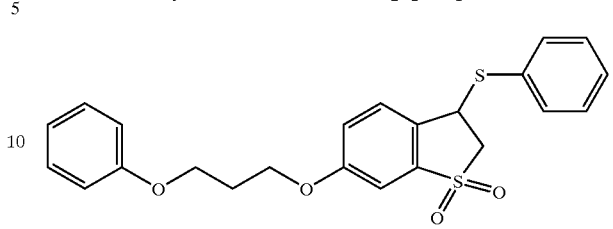

TLC: Rf 0.42 (hexane:ethyl acetate=2:1);

NMR (CDCl$_3$): δ7.61–7.56 (1H, m), 7.43–7.25 (7H, m), 7.19–7.15 (2H, m), 6.95–6.89 (3H, m), 4.91 (1H, t-like, J=6.6 Hz), 4.22 (2H, t, J=6.0 Hz), 4.15 (2H, t, J=6.0 Hz), 3.80 (1H, dd, J=13.8, 7.3 Hz), 3.51 (1H, dd, J=13.8, 7.3 Hz), 2.28 (2H, quint, J=6.0 Hz).

EXAMPLE 18 (16)

6-Benzyloxy-3-phenylthio-2,3-dihydro-1,1-dioxidebenzo[b]thiophene

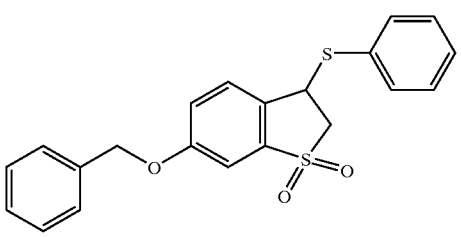

TLC: Rf 0.58 (hexane:ethyl acetate=2:1);

NMR (CDCl$_3$): δ7.63–7.58 (1H, m), 7.45–7.31 (10H, m), 7.27–7.23 (2H, m), 5.10 (2H, s), 4.92 (1H, t-like, J=6.7 Hz), 3.81 (1H, dd, J=13.7, 7.5 Hz), 3.52 (1H, dd, J=13.7, 6.1 Hz).

EXAMPLE 18 (17)

6-Pentoxy-3-phenylthio-2,3-dihydro-1,1-dioxidebenzo[b]thiophene

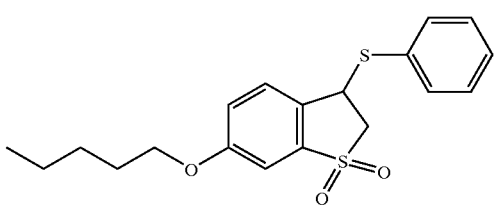

TLC: Rf 0.51 (hexane:ethyl acetate=2:1);

NMR (CDCl$_3$): δ7.60–7.55 (1H, m), 7.43–7.31 (5H, m), 7.19–7.12 (2H, m), 4.91 (1H, t, J=6.8 Hz), 3.99 (2H, t, J=6.6 Hz), 3.80 (1H, dd, J=13.8, 7.3 Hz), 3.51 (1H, dd, J=13.8, 6.2 Hz), 1.80 (2H, quint, J=7.0 Hz), 1.50–1.30 (4H, m), 0.92 (3H, t, J=7.0 Hz).

EXAMPLE 18 (18)

6-(2-(Morpholin-4-yl)ethyl)oxy-3-phenylthio-2,3-dihydro-1,1-dioxidebenzo[b]thiophene

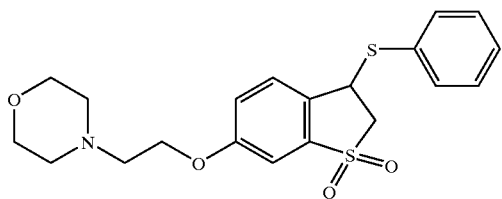

TLC: Rf 0.41 (hexane:ethyl acetate:triethylamine=2:4:1);

NMR (CDCl$_3$): δ7.60 (1H, d, J=8.4 Hz), 7.42–7.32 (5H, m), 7.22–7.16 (2H, m), 4.92 (1H, t-like, J=6.8 Hz), 4.15 (2H, t, J=5.8 Hz), 3.81 (1H, dd, J=13.8, 7.2 Hz), 3.73 (4H, t-like, J=4.6 Hz), 3.52 (1H, dd, J=13.8, 6.1 Hz), 2.82 (2H, t, J=5.8 Hz), 2.57 (4H, t-like, J=4.6 Hz).

EXAMPLE 18 (19)

6-(3-Hydroxypropyl)oxy-3-phenylthio-2,3-dihydro-1,1-dioxidebenzo[b]thiophene

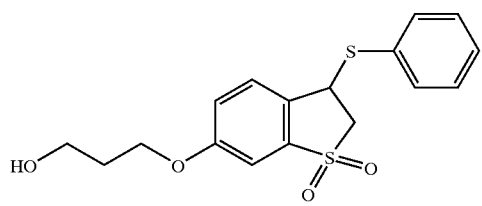

TLC: Rf 0.33 (hexane:ethyl acetate=1:2);

NMR (CDCl$_3$): δ2.06 (quint, J=6.1 Hz, 2H), 3.51 (dd, J=13.6, 6.2 Hz, 1H), 3.80 (dd, J=13.6, 7.4 Hz, 1H), 3.85 (t, J=6.1 Hz, 2H), 4.17 (t, J=6.1 Hz, 2H), 4.92 (t-like, J=6.8 Hz, 1H), 7.16–7.21 (m, 2H), 7.32–7.45 (m, 5H), 7.57–7.61 (m, 1H).

EXAMPLE 18 (20)

6-(Pyridin-3-ylmethyl)oxy-3-phenylthio-2,3-dihydro-1,1-dioxidebenzo[b]thiophene

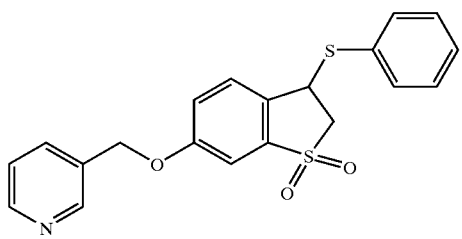

TLC: Rf 0.31 (methylene chloride:ethyl acetate=2:1);

NMR (CDCl$_3$): δ3.53 (dd, J=13.6, 6.2 Hz, 1H), 3.82 (dd, J=13.6, 7.2 Hz, 1H), 4.93 (t-like, J=6.6 Hz, 1H), 5.12 (s, 2H), 7.23–7.28 (m, 2H), 7.33–7.46 (m, 6H), 7.61–7.65 (m, 1H), 7.75–7.79 (m, 1H), 8.63 (dd, J=5.0, 1.6 Hz, 1H), 8.70 (d, J=1.6 Hz, 1H).

EXAMPLE 18 (21)

6-(3-Nitrophenylmethyl)oxy-3-phenylthio-2,3-dihydro-1,1-dioxidebenzo[b]thiophene

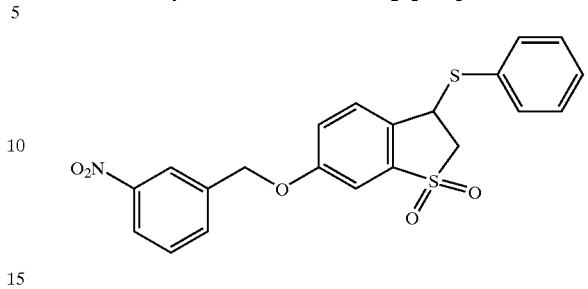

TLC: Rf 0.49 (hexane:ethyl acetate=1:1);

NMR (CDCl$_3$): δ8.33 (1H, brs), 8.22 (1H, dd, J=8, 2 Hz), 7.76 (1H, d, J=7.8 Hz), 7.70–7.48 (2H, m), 7.48–7.16 (7H, m), 5.21 (2H, s), 4.93 (1H, t-like, J=6.8 Hz), 383 (1H, dd, J=13.6, 7.6 Hz), 3.54 (1H, dd, J=13.6, 6.2 Hz).

EXAMPLE 18 (22)

6-(3-Bromopropyl)oxy-3-phenylthio-2,3-dihydro-1,1-dioxidebenzo[b]thiophene

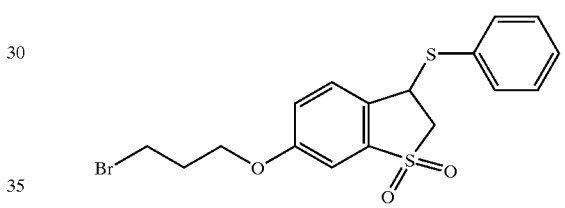

TLC: Rf 0.48 (hexane:ethyl acetate=3:1);

NMR (CDCl$_3$): δ2.35 (quint, J=7.5 Hz, 2H), 3.55 (t, J=7.5 Hz, 2H), 3.59 (dd, J=15, 7 Hz, 1H), 3.80 (dd, J=15, 7 Hz, 1H), 4.18 (t, J=7.5 Hz, 2H), 4.92 (t, J=7 Hz, 1H), 7.20 (dd, J=9, 2 Hz, 1H), 7.34–7.43 (m, 6H), 7.60 (d, J=9 Hz, 1H).

EXAMPLE 18 (23)

7-Pentoxy-3-phenylthio-2,3-dihydro-1,1-dioxidebenzo[b]thiophene

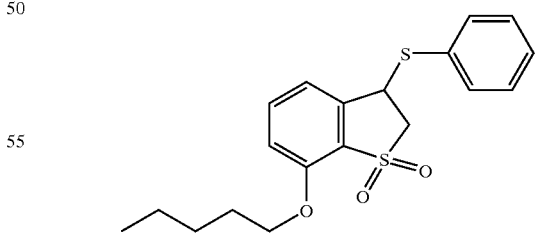

TLC: Rf 0.80 (hexane:ethyl acetate=1:1);

NMR (CDCl$_3$) δ7.54 (1H, t, J=7.8 Hz), 7.45–7.21 (6H, m), 6.91 (1H, d, J=8.6 Hz), 4.88 (1H, t, J=7.6 Hz), 4.11 (2H, t, J=7.0 Hz), 3.77 (1H, dd, J=13.6, 7.6 Hz), 3.50 (1H, dd, J=13.6, 7.6 Hz), 1.87 (2H, quint, J=7.0 Hz), 1.50–1.30 (4H, m), 0.92 (3H, t, J=7.2 Hz).

EXAMPLE 18 (24)

7-(2-Phenyloxyethyl)oxy-3-phenylthio-2,3-dihydro-1,1-dioxidebenzo[b]thiophene

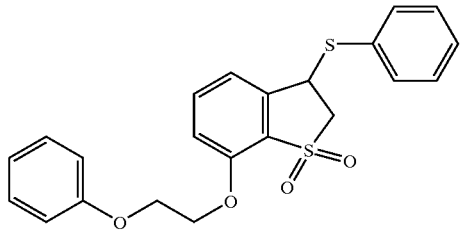

TLC: Rf 0.55 (hexane:ethyl acetate=1:1);

NMR (CDCl$_3$): δ7.58 (1H, t, J=7.8 Hz), 7.45–7.25 (8H, m), 7.06 (1H, d, J=8.4 Hz), 7.05–6.90 (3H, m), 4.89 (1H, t, J=7.6 Hz), 4.58–4.45 (2H, m), 4.45–4.35 (2H, m), 3.78 (1H, dd, J=13.6, 7.6 Hz), 3.52 (1H, dd, J=13.6, 7.6 Hz).

EXAMPLE 18 (25)

7-(3-Hydroxypropyl)oxy-3-phenylthio-2,3-dihydro-1,1-dioxidebenzo[b]thiophene

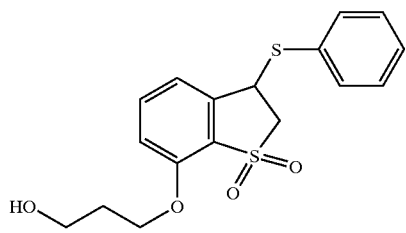

TLC: Rf 0.25 (hexane:ethyl acetate=1:2);

NMR (CDCl$_3$): δ7.60–6.60 (8H, m), 4.90 (1H, t, J=6.8 Hz), 4.36–4.26 (2H, m), 3.90 (2H, br) 3.79 (1H, d, J=13.8, 6.8 Hz), 3.52 (1H, dd, J=13.8, 6.8 Hz), 2.50–2.05 (2H, m).

EXAMPLE 18 (26)

7-(Pyridin-3-ylmethyl)oxy-3-phenylthio-2,3-dihydro-1,1-dioxidebenzo[b]thiophene

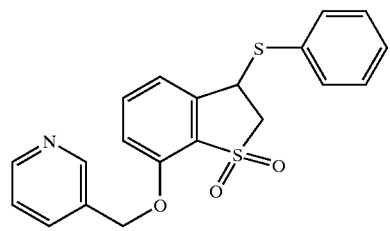

TLC: Rf 0.12 (hexane:ethyl acetate=1:2);

NMR (CDCl$_3$): δ8.66 (1H, d, J=2.2 Hz), 8.57 (1H, dd, J=4.8, 1.8 Hz), 7.93 (1H, d, J=8.2 Hz), 7.56 (1H, t, J=8.2 Hz), 7.45–7.30 (4H, m), 6.97 (1H, d, J=8.2 Hz), 5.30 (2H, s), 4.92 (1H, t, J=7.0 Hz), 3.82 (1H, dd, J=13.8, 7.8 Hz), 3.54 (1H, dd, J=13.8, 7.8 Hz).

EXAMPLE 18 (27)

4-(t-Butoxycarbonylmethyl)oxy-3-phenylthio-2,3-dihydro-1,1-dioxidebenzo[b]thiophene

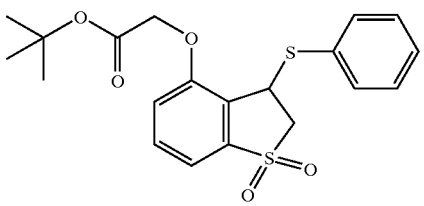

TLC: Rf 0.33 (hexane:ethyl acetate=2:1);

NMR (CDCl$_3$): δ7.57–7.46 (3H, m), 7.37–7.32 (4H, m), 6.93 (1H, d-like, J=8.0 Hz), 5.16 (1H, dd, J=6.6, 2.0 Hz), 4.61 (2H, s), 3.72 (1H, dd, J=13.9, 6.6 Hz), 3.61 (1H, dd, J=13.9, 2.0 Hz), 1.49 (9H, s).

EXAMPLE 18 (28)

5-(t-Butoxycarbonylmethyl)oxy-3-phenylthio-2,3-dihydro-1,1-dioxidebenzo[b]thiophene

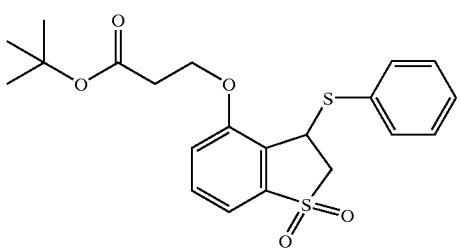

TLC: Rf 0.52 (hexane:ethyl acetate=2:1);

NMR (CDCl$_3$): δ1.50 (s, 9H), 3.48 (dd, J=14, 6.7 Hz, 1H), 3.82 (dd, J=14, 6.7 Hz, 1H), 4.66 (s, 2H), 4.95 (t, J=6.7 Hz, 1H), 7.18 (dd, J=9, 2.3 Hz, 1H) 7.40–7.53 (m, 6H), 7.62 (d, J=9 Hz, 1H).

EXAMPLE 18 (29)

6-(t-Butoxycarbonylmethyl)oxy-3-phenylthio-2,3-dihydro-1,1-dioxidebenzo[b]thiophene

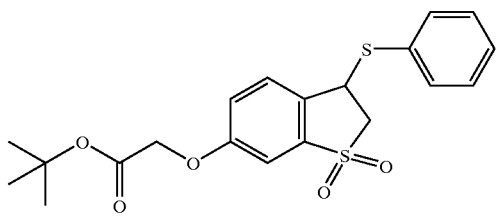

TLC: Rf 0.44 (hexane:ethyl acetate=2:1);

NMR (CDCl$_3$): δ7.61 (1H, d, J=8.7 Hz), 7.44–7.32 (5H, m), 7.24 (1H, dd, J=8.7, 2.6 Hz), 7.08 (1H, d, J=2.6 Hz), 4.91 (1H, t-like, J=6.7 Hz), 4.56 (2H, s), 3.80 (1H, dd, J=13.7, 7.3 Hz), 3.51 (1H, dd, J=13.7, 6.1 Hz), 1.49 (9H, s).

EXAMPLE 18 (30)

7-(t-Butoxycarbonylmethyl)oxy-3-phenylthio-2,3-dihydro-1,1-dioxidebenzo[b]thiophene

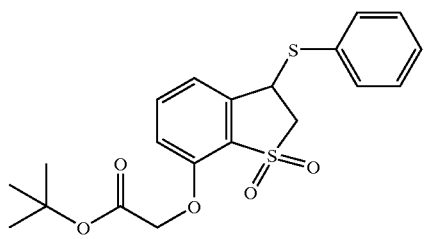

TLC: Rf 0.55 (hexane:ethyl acetate=1:1);

NMR (CDCl): δ7.54 (1H, t, J=7.6 Hz), 7.45–7.27 (6H, m), 6.80 (1H, d, J=8.0 Hz), 4.90 (1H, t, J=7.6 Hz), 4.69 (2H, s), 3.79 (1H, dd, J=13.6, 7.6 Hz), 3.52 (1H, dd, J=13.6, 7.6 Hz), 1.46 (9H, s).

EXAMPLE 18 (31)

4-(2-(t-Butoxycarbonylamino)ethyl)oxy-3-phenylthio-2,3-dihydro-1,1-dioxidebenzo[b]thiophene

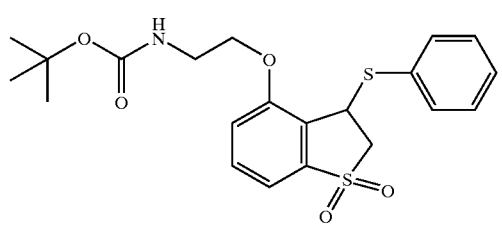

TLC: Rf 0.35 (hexane:ethyl acetate=1:2);

NMR (CDCl$_3$): δ1.35 (s, 9H), 3.46–3.66 (m, 2H), 3.62 (dd, J=14.2, 2.2 Hz, 1H), 3.73 (dd, J=14.2, 6.8 Hz, 1H), 4.11–4.25 (m, 2H), 5.06 (dd, J=6.8, 2.2 Hz, 1H), 5.39 (br, 1H), 7.08 (d, J=7.6 Hz, 1H), 7.31–7.39 (m, 4H), 7.44–7.57 (m, 3H).

EXAMPLE 18 (32)

4-(3-(t-Butoxycarbonylamino)propyl)oxy-3-phenylthio-2,3-dihydro-1,1-dioxidebenzo[b]thiophene

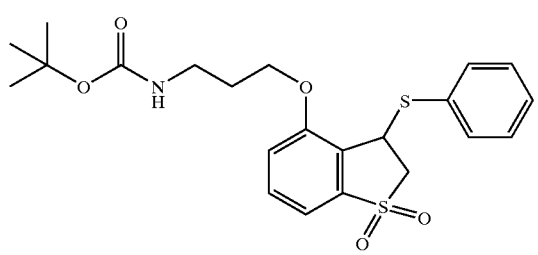

TLC: Rf 0.28 (hexane:ethyl acetate=1:1);

NMR (CDCl$_3$): δ1.38 (s, 9H), 2.00–2.11 (m, 2H), 3.33–3.44 (m, 2H), 3.59 (dd, J=14.0, 2.2 Hz, 1H), 3.69 (dd, J=14.0, 6.6 Hz, 1H), 4.17 (t, J=5.9 Hz, 2H), 4.90 (br, 1H), 5.08 (dd, J=6.6, 2.2 Hz, 1H), 7.08 (dd, J=8.1, 0.7 Hz, 1H), 7.29–7.38 (m, 4H), 7.48–7.56 (m, 3H).

EXAMPLE 18 (33)

5-(2-(t-Butoxycarbonylamino)ethyl)oxy-3-phenylthio-2,3-dihydro-1,1-dioxidebenzo[b]thiophene

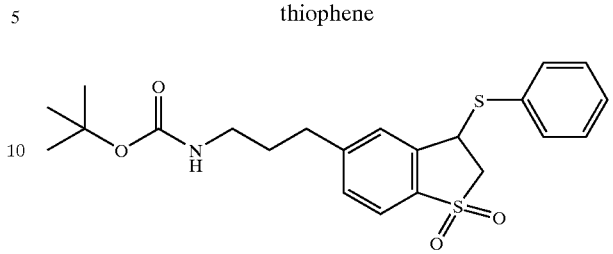

TLC: Rf 0.40 (hexane:ethyl acetate=2:1);

NMR (CDCl$_3$): δ1.46 (s, 9H), 3.52 (dd, J=15, 6 Hz, 1H), 3.56 (t, J=7.5 Hz, 2H), 3.80 (dd, J=15, 6 Hz, 1H), 4.10 (t, J=7.5 Hz, 2H), 4.88 (t, J=6 Hz, 1H), 4.99 (br, 1H), 7.03 (dd, J=9, 2 Hz, 1H), 7.12 (d, J=2 Hz, 1H), 7.35–7.47 (m, 5H), 7.64 (d, J=9 Hz, 1H).

EXAMPLE 18 (34)

6-(3-(t-Butoxycarbonylamino)propyl)oxy-3-phenylthio-2,3-dihydro-1,1-dioxidebenzo[b]thiophene

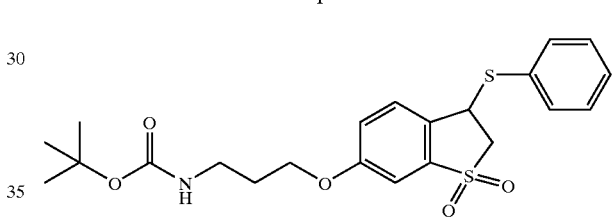

TLC: Rf 0.43 (hexane:ethyl acetate=1:1);

NMR (CDCl$_3$): δ1.44 (s, 9H), 2.01 (quint, J=6.2 Hz, 2H), 3.32 (q, J=6.2 Hz, 2H), 3.51 (dd, J=13.6, 6.0 Hz, 1H), 3.80 (dd, J=13.6, 7.4 Hz, 1H), 4.06 (t, J=6.2 Hz, 2H), 4.69 (br, 1H), 4.91 (t-like, J=6.8 Hz, 1H), 7.14–7.21 (m, 2H), 7.32–7.45 (m, 5H), 7.59 (d, J=8.4 Hz, 1H).

EXAMPLE 18 (35)

6-(2-(t-Butoxycarbonylamino)ethyl)oxy-3-phenylthio-2,3-dihydro-1,1-dioxidebenzo[b]thiophene

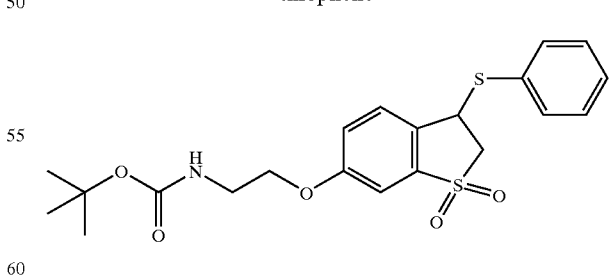

TLC: Rf 0.47 (hexane:ethyl acetate=1:1):

NMR (CDCl$_3$): δ1.46 (s, 9H), 3.51 (dd, J=13.8, 6.2 Hz, 1H), 3.55 (q, J=5.2 Hz, 2H), 3.81 (dd, J=13.8, 7.4 Hz, 1H), 4.06 (t, J=5.2 Hz, 2H), 4.92 (t-like, J=6.4 Hz, 1H), 4.96 (br, 1H), 7.13 (d, J=2.4 Hz, 1H), 7.18 (dd, J=8.5, 2.4 Hz, 1H), 7.32–7.45 (m, 5H), 7.60 (d, J=8.5 Hz, 1H).

EXAMPLE 18 (36)

7-(2-(t-Butoxycarbonylamino)ethyl)oxy-3-phenylthio-2,3-dihydro-1,1-dioxidebenzo[b]thiophene

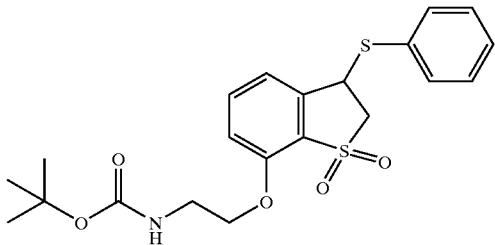

TLC: Rf 0.60 (hexane:ethyl acetate=1:2);
NMR (CDCl$_3$): δ7.60–7.24 (7H, m), 6.94 (1H, d, J=8.4 Hz), 5.38 (1H, bs), 4.90 (1H, t, J=7.4 Hz), 4.30–4.05 (2H, m), 3.79 (1H, dd, J=13.7, 7.4 Hz), 3.60–3.40 (3H, m), 1.42 (9H, s).

EXAMPLE 18 (37)

4-(N-(t-Butoxycarbonyl)piperidin-4-yl)oxy-3-phenylthio-2,3-dihydro-1,1-dioxidebenzo[b]thiophene

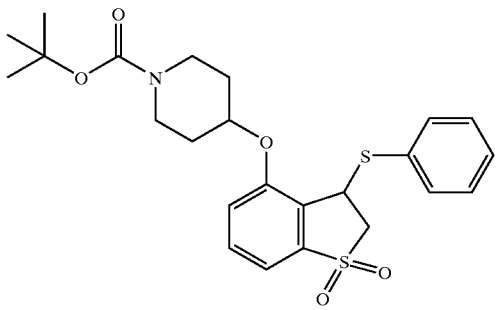

TLC: Rf 0.41 (hexane:ethyl acetate=1:1);
NMR (CDCl$_3$): δ7.60–7.42 (3H, m), 7.42–7.25 (4H, m), 7.04 (1H, d, J=8.2 Hz), 5.05 (1H, dd, J=6.6, 2.2 Hz), 4.80–4.60 (1H, m), 3.85–3.32 (6H, m), 2.15–1.65 (4H, m), 1.48 (9H, s).

EXAMPLE 18 (38)

4,7-Bis[(2-(t-butoxycarbonylamino)ethyl)oxy]-3-phenylthio-2,3-dihydro-1,1-dioxidebenzo[b]thiophene

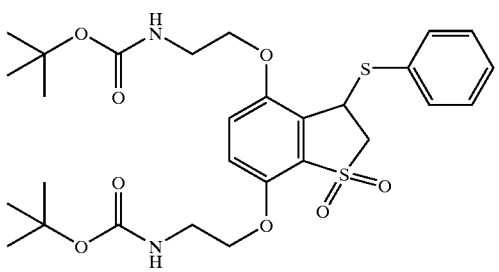

TLC: Rf 0.35 (hexane:ethyl acetate=1:2);
NMR (CDCl$_3$): δ7.53–7.30 (5H, m), 7.20–6.85 (2H, m), 5.40 (2H, brs), 5.03–4.85 (1H, m), 4.25–4.00 (4H, m), 3.90–3.40 (6H, m), 1.43 (18H, s).

EXAMPLE 18 (39)

4-(3-Nitrophenylmethyl)oxy-3-phenylthio-2,3-dihydro-1,1-dioxidebenzo[b]thiophene

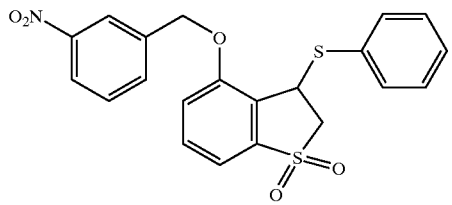

TLC: Rf 0.29 (hexane:ethyl acetate=1:1);
NMR (CDCl$_3$): δ8.44 (1H, s), 8.24 (1H, d, J=8.4 Hz), 7.86 (1H, d, J=8.0 Hz), 7.65–7.20 (8H, m), 7.14 (1H, d, J=7.2 Hz), 5.31 (2H, s), 5.13 (1H, dd, J=2.6, 6.6 Hz), 3.80–3.56 (2H, m).

EXAMPLE 18 (40)

4,7-Bis(pyridin-3-ylmethyloxy)-3-phenylthio-2,3-dihydro-1,1-dioxidebenzo[b]thiophene

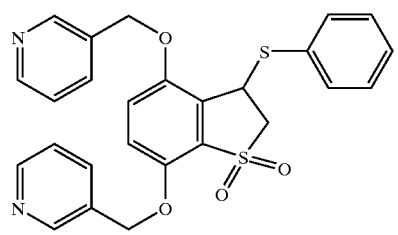

TLC: Rf 0.20 (ethyl acetate:methanol=10:1);
NMR (CDCl$_3$): δ8.75–8.72 (1H, m), 8.70–8.50 (4H, m), 7.96–7.82 (2H, m), 7.46–7.24 (6H, m), 7.05 (1H, d, J=9.0 Hz), 6.93 (1H, d, J=9.0 Hz), 5.25 (2H, s), 5.15 (2H, s), 5.01–4.95 (1H, m), 3.81–3.59 (2H, m).

EXAMPLE 19

4-(3-Hydroxypropyl)oxy-3-phenylsulfynyl-2,3-dihydro-1,1-dioxidebenzo[b]thiophene

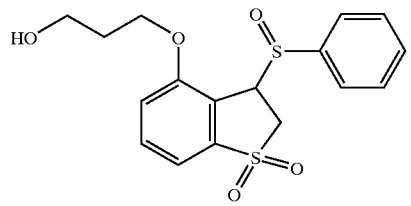

By the same procedure as described in Example 2 using the compound prepared in Example 18 (9) instead of the compound prepared in Example 1, the compound of the present invention having the following physical data was obtained.

TLC: Rf 0.18 (hexane:ethyl acetate=1:1);
NMR (CDCl$_3$): δ2.17 (quint, J=6.0 Hz, 2H), 3.08 (dd, J=14.0, 8.6 Hz, 1H), 3.94 (t, J=6.0 Hz, 2H), 3.98 (dd, J=14.0, 4.8 Hz, 1H), 4.32 (t, J=6.0 Hz, 2H), 4.15 (dd, J=8.6, 4.8 Hz, 1H), 7.18 (d, J=7.9 Hz, 1H), 7.35 (d, J=7.9 Hz, 1H), 7.55–7.66 (m, 6H).

EXAMPLE 20

4-(4-Nitrophenylmethyl)oxy-3-phenylsulfonyl-2,3-dihydro-1,1-dioxidebenzo[b]thiophene

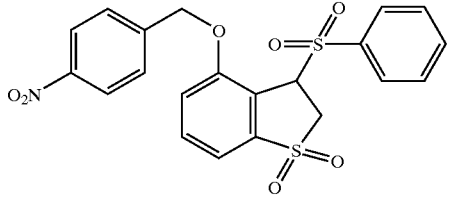

By the same procedure as described in Example 10 using the compound prepared in Example 18 instead of the compound prepared in Example 9, the compound of the present invention having the following physical data was obtained.

TLC: Rf 0.67 (ethyl acetate:methanol:28% ammonia water=100:10:1);

NMR (DMSO-$d_3$): $\delta$8.25 (2H, d, J=9 Hz), 7.78–7.52 (6H, m), 7.52–7.20 (4H, m), 5.74 (1H, d, J=9 Hz), 5.26 (1H, d, J=14 Hz), 4.99 (1H, d, J=14 Hz), 4.19 (1H, d, J=15 Hz), 4.00 (1H, dd, J=15, 9 Hz).

EXAMPLES 20 (1)~20 (39)

Using the compounds prepared in Examples 18 (1)~18 (39) instead of the compound prepared in Example 18 by the same procedure as described in Example 20, or by the same reaction using 3-chloroperbenzoic acid instead of OXONE® as an oxidizer, and, if necessary, by converting into the corresponding salts by known methods, the following compounds of the present invention were obtained.

EXAMPLE 20 (1)

4-(3-Phenyloxypropyl)oxy-3-phenylsulfonyl-2,3-dihydro-1,1-dioxidebenzo[b]thiophene

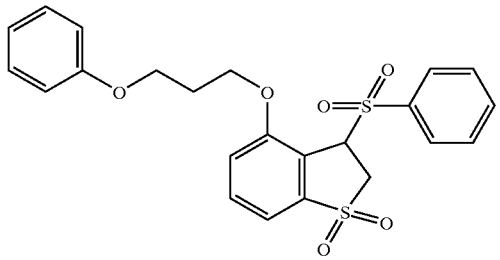

TLC: Rf 0.33 (hexane:ethyl acetate=1:1);

NMR (CDCl$_3$): $\delta$2.20 (quint, J=6.0 Hz, 2H), 3.70 (dd, J=14.8, 9.3 Hz, 1H), 3.99–4.28 (m, 4H), 4.20 (dd, J=14.8, 1.2 Hz, 1H), 5.19 (dd, J=9.3, 1.2 Hz, 1H), 6.89–7.01 (m, 4H), 7.21–7.50 (m, 6H), 7.52–7.60 (m, 1H), 7.65–7.70 (m, 2H).

EXAMPLE 20 (2)

4-Benzyloxy-3-phenylsulfonyl-2,3-dihydro-1,1-dioxidebenzo[b]thiophene

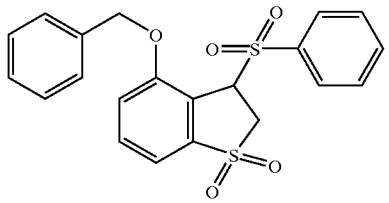

TLC: Rf 0.39 (hexane:ethyl acetate=1:1);

NMR (CDCl$_3$): $\delta$3.73 (dd, J=15.0, 9.0 Hz, 1H), 4.22 (d, J=15.0 Hz, 1H), 4.88 (d, J=11.7 Hz, 1H), 4.99 (d, J=11.7 Hz, 1H), 5.28 (d, J=9.0 Hz, 1H), 7.04 (d, J=7.8 Hz, 1H), 7.26–7.40 (m, 8H), 7.49–7.58 (m, 2H), 7.64–7.69 (m, 2H).

EXAMPLE 20 (3)

4-(3-Benzyloxypropyl)oxy-3-phenylsulfonyl-2,3-dihydro-1,1-dioxidebenzo[b]thiophene

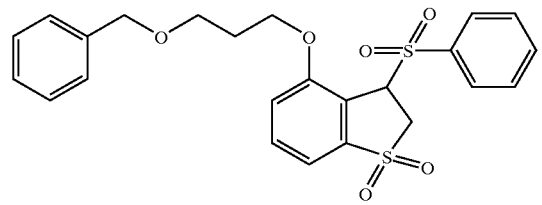

TLC: Rf 0.26 (hexane:ethyl acetate=1:1);

NMR (CDCl$_3$): $\delta$1.96 (quint, J=6.1 Hz, 2H), 3.57–3.67 (m, 2H), 3.67 (dd, J=14.9, 9.2 Hz, 1H), 3.82–3.92 (m, 1H), 3.98–4.09 (m, 1H), 4.21 (dd, J=14.9, 0.5 Hz, 1H), 4.46 (d, J=12.1 Hz, 1H), 4.56 (d, J=12.1 Hz, 1H). 5.05 (dd, J=9.2, 0.5 Hz, 1H), 6.94 (d, J=8.4 Hz, 1H), 7.22–7.27 (m, 6H), 7.35–7.60 (m, 4H), 7.65–7.69 (m, 2H).

EXAMPLE 20 (4)

4-(Pyridin-3-ylmethyl)oxy-3-phenylsulfonyl-2,3-dihydro-1,1-dioxidebenzo[b]thiophene

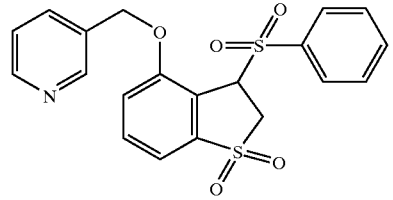

Free Compound
TLC: Rf 0.17 (ethyl acetate);
NMR (DMSO-$d_6$): $\delta$3.95 (dd, J=15.0, 8.8 Hz, 1H), 4.16 (dd, J=15.0, 1.2 Hz, 1H), 4.93 (d, J=12.5 Hz, 1H), 5.15 (d, J=12.5 Hz, 1H), 5.66 (d-like, J=8.0 Hz, 1H), 7.35–7.45 (m, 5H), 7.55–7.72 (m, 4H), 7.80 (dt, J=8.0, 1.4 Hz, 1H), 8.56 (dd, J=5.0, 1.4 Hz, 1H), 8.61 (d, J=1.4 Hz, 1H).
Hydrochloride
TLC: Rf 0.17 (ethyl acetate);
NMR (DMSO-$d_6$): $\delta$3.98 (dd, J=15.2, 8.6 Hz, 1H), 4.16 (d, J=15.2 Hz, 1H), 5.10 (d, J=12.8 Hz, 1H), 5.29 (d, J=12.8

Hz, 1H), 5.85 (d, J=8.6 Hz, 1H), 7.38–7.59 (m, 5H), 7.66–7.75 (m, 3H), 7.94 (dd, J=8.0, 5.4 Hz, 1H), 8.38 (d, J=8.0 Hz, 1H), 8.84 (d, J=5.4 Hz, 1H), 8.88 (s, 1H).

Methanesulfonic Acid Salt

TLC: Rf 0.31 (ethyl acetate:methanol=9:1);

NMR (DMSO-$d_6$): δ2.37 (3H, s), 4.00 (dd, J=15.0, 8.8 Hz, 1H), 4.17 (d-like, J=15.4 Hz, 1H), 5.13 (d, J=13.0 Hz, 1H), 5.32 (d, J=13.0 Hz, 1H), 5.85 (d-like, J=8.0 Hz, 1H), 7.39–7.45 (m, 4H), 7.52–7.59 (m, 1H), 7.66–7.77 (m, 3H), 8.05 (dd, J=8.2, 5.8 Hz, 8.49 (d, J=8.2 Hz, 1H), 8.89–8.92 (m, 2H).

EXAMPLE 20 (5)

4-(N-Oxidequinolin-2-ylmethyl)oxy-3-phenylsulfonyl-2,3-dihydro-1,1-dioxidebenzo[b]thiophene

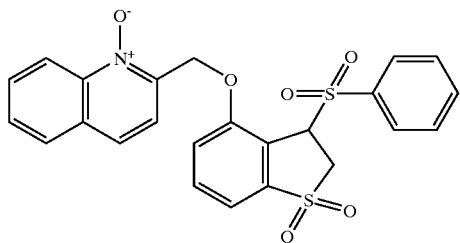

TLC: Rf 0.38 (ethyl acetate:methanol:28% ammonia water=100:10:1);

NMR (CDCl$_3$): δ8.77 (1H, d, J=8 Hz), 8.00–7.75 (4H, m), 7.75–7.63 (3H, m), 7.63–7.45 (2H, m), 7.45–7.22 (3H, m), 7.17 (1H, d, J=8 Hz), 5.72–5.25 (3H, m), 4.28 (1H, d, 15 Hz), 3.84 (1H, dd, J=15, 9 Hz).

EXAMPLE 20 (6a)

4-(Pyridin-2-ylmethyl)oxy-3-phenylsulfonyl-2,3-dihydro-1,1-dioxidebenzo[b]thiophene

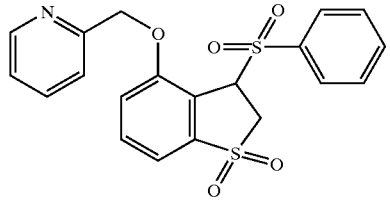

TLC: Rf 0.43 (ethyl acetate:methanol:28% ammonia water=100:10:1);

NMR (CDCl$_3$): δ8.61 (1H, d, J=4 Hz), 7.88–7.18 (10H, m), 7.04 (1H, d, J=8 Hz), 5.37 (1H, d, J=9 Hz), 5.11 (1H, d, J=14 Hz), 4.98 (1H, d, J=14 Hz), 4.24 (1H, d, J=15 Hz), 3.78 (1H, dd, J=15, 9 Hz).

EXAMPLE 20 (6b)

4-(N-Oxidepyridin-2-ylmethyl)oxy-3-phenylsulfonyl-2,3-dihydro-1,1-dioxidebenzo[b]thiophene

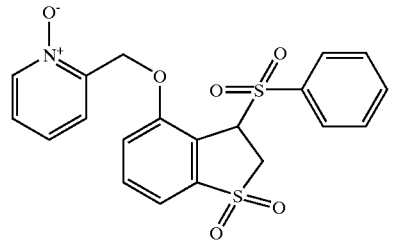

TLC: Rf 0.09 (ethyl acetate:methanol:28% ammonia water=100:10:1);

NMR (CDCl$_3$+DMSO-$d_6$): δ8.42–8.22 (1H, m), 7.90–7.20 (11H, m), 5.83 (1H, d, J=8.5 Hz), 5.18 (1H, d, J=15 Hz), 4.93 (1H, d, J=15 Hz), 4.21 (1H, d, J=15 Hz), 4.03 (1H, dd, J=15, 8.5 Hz).

EXAMPLE 20 (7)

4-(Pyridin-4-ylmethyl)oxy-3-phenylsulfonyl-2,3-dihydro-1,1-dioxidebenzo[b]thiophene

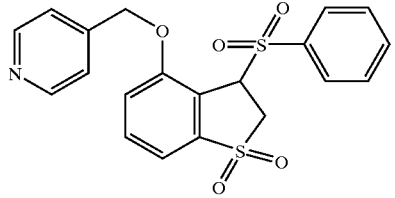

Free Compound

TLC: Rf 0.26 (ethyl acetate:methanol:28% ammonia water=100:10:1);

NMR (CDCl$_3$+DMSO-$d_6$): δ8.57 (2H, d, J=6 Hz), 7.80–7.15 (10H, m), 5.75 (1H, d, J=9 Hz), 5.15 (1H, d, J=14 Hz), 4.90 (1H, d, J=14 Hz), 4.19 (1H, d, J=15 Hz), 4.00 (1H, dd, J=15, 9 Hz).

Hydrochloride

TLC: Rf 0.31 (ethyl acetate:methanol=9:1);

NMR (DMSO-d6): δ8.93 (d, J=6.5 Hz, 2H), 8.00 (d, J=6.5 Hz, 2H), 7.74–7.68 (m, 3H), 7.60–7.54 (m, 1H), 7.47–7.42 (m, 3H), 7.33 (d, J=8.0 Hz, 1H), 5.93 (d, J=9.0 Hz, 1H), 5.46 (d, J=16.0 Hz, 1H), 5.18 (d, J=16.0 Hz, 1H), 4.19 (d, J=15.0 Hz, 1H), 4.03 (dd, J=15.0, 9.0 Hz, 1H).

Methanesulfonic Acid Salt

TLC: Rf 0.31 (ethyl acetate:methanol=9:1);

NMR (DMSO-$d_6$): δ8.94 (d, J=6.3 Hz, 2H), 8.03 (d, J=6.3 Hz, 2H), 7.74–7.68 (m, 3H), 7.60–7.55 (m, 1H), 7.47–7.42 (m, 3H), 7.34 (d, J=8.0 Hz, 1H), 5.92 (d, J=9.0 Hz, 1H), 5.46 (d, J=16.0 Hz, 1H), 5.19 (d, J=16.0 Hz, 1H), 4.19 (d, J=15.0 Hz, 1H), 4.03 (dd, J=15.0, 9.0 Hz, 1H), 2.38 (s, 3H).

EXAMPLE 20 (8)

4-(3-(Pyridin-3-yl)propyl)oxy-3-phenylsulfonyl-2,3-dihydro-1,1-dioxidebenzo[b]thiophene

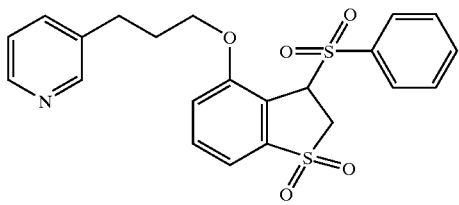

TLC: Rf 0.41 (ethyl acetate:methanol:28% ammonia water=100:10:1);

NMR (CDCl$_3$+CD$_3$OD): δ8.50–8.36 (2H, m), 7.80–7.23 (9H, m), 7.00 (1H, d, J=8 Hz), 5.27 (1H, d, J=9 Hz), 4.26–3.68 (4H, m), 2.88 (2H, t, J=7 Hz), 2.20–1.90 (2H, m).

EXAMPLE 20 (9)

4-(3-Hydroxypropyl)oxy-3-phenylsulfonyl-2,3-dihydro-1,1-dioxidebenzo[b]thiophene

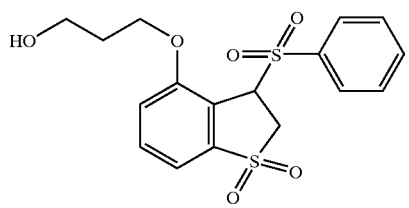

TLC: Rf 0.26 (hexane:ethyl acetate=1:1);

NMR (CDCl$_3$): δ2.02 (quint, J=5.6 Hz, 2H), 2.28 (t, J=5.6 Hz, 1H), 3.71 (dd, J=14.8, 9.2 Hz, 1H), 3.91 (m, J=5.6 Hz, 2H), 4.05 (dd, J=14.8, 1.0 Hz, 1H), 4.10–4.17 (m, 2H), 5.28 (d-like, J=8.8 Hz, 1H), 7.08 (d, J=8.4 Hz, 1H), 7.23 (d, J=7.8 Hz, 1H), 7.42–7.62 (m, 4H), 7.66–7.73 (m, 2H).

EXAMPLE 20 (10)

5-Pentoxy-3-phenylsulfonyl-2,3-dihydro-1,1-dioxidebenzo[b]thiophene

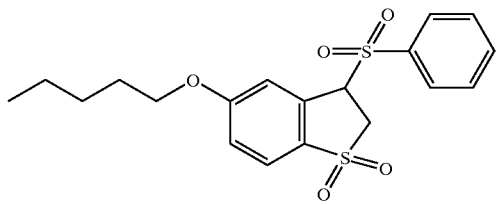

TLC: Rf 0.40 (hexane:ethyl acetate=2:1);

NMR (CDCl$_3$): δ0.96 (t, J=8 Hz, 3H), 1.42 (m, 4H), 1.86 (m, 2H), 3.70 (dd, J=14, 8 Hz, 1H), 3.80 (dd, J=14,6 Hz, 1H), 4.07 (m, 2H), 5.00 (dd, J=8, 6 Hz, 1H), 7.10 (dd, J=8, 2 Hz, 1H), 7.44 (d, J=2 Hz,1H), 7.46–7.77 (m, 6H).

EXAMPLE 20 (11)

5-(2-Phenyloxyethyl)oxy-3-phenylsulfonyl-2,3-dihydro-1,1-dioxidebenzo[b]thiophene

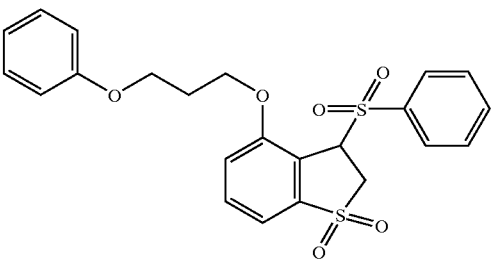

TLC: Rf 0.25 (hexane:ethyl acetate=1:1);

NMR (CDCl$_3$): δ3.70 (dd, J=14, 8 Hz, 1H), 3.77 (dd, J=14, 6 Hz, 1H), 4.41 (m, 4H), 5.02 (dd, J=8, 6 Hz, 1H), 7.00 (m, 3H), 7.19 (dd, J=8, 2 Hz, 1H), 7.30–7.77 (m, 9H).

EXAMPLE 20 (12)

5-(3-Hydroxypropyl)oxy-3-phenylsulfonyl-2,3-dihydro-1,1-dioxidebenzo[b]thiophene

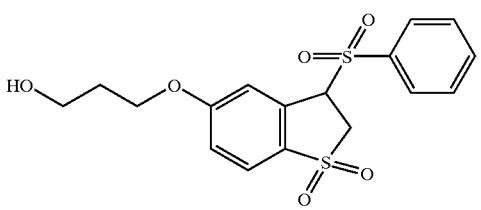

TLC: Rf 0.15 (hexane:ethyl acetate=1:1);

NMR (CDCl$_3$): δ2.11 (m, 2H), 3.65 (dd, J=14, 8 Hz, 1H), 3.78 (dd, J=14, 5 Hz, 1H), 3.89 (m, 2H), 4.25 (m, 2H), 5.01 (dd, J=8, 5 Hz, 1H), 7.12 (dd, J=9, 2 Hz, 1H), 7.45–7.77 (m, 7H).

EXAMPLE 20 (13)

5-(Pyridin-3-ylmethyl)oxy-3-phenylsulfonyl-2,3-dihydro-1,1-dioxidebenzo[b]thiophene

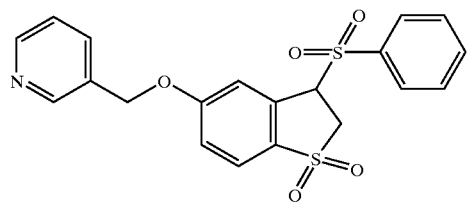

Free Compound

TLC: Rf 0.30 (ethyl acetate);

NMR (DMSO-d$_6$): δ3.79 (dd, J=15.1, 3.2 Hz, 1H), 4.00 (dd, J=15.1, 9.4 Hz, 1H), 5.27 (s, 2H), 5.74 (dd, J=9.4, 3.2 Hz, 1H), 7.20 (d, J=2.2 Hz, 1H), 7.36 (dd, J=8.7, 2.2 Hz, 1H), 7.47 (dd, J=7.8, 4.9 Hz, 1H), 7.57–7.65 (m, 2H), 7.71–7.82 (m, 4H), 7.91 (dt, J=7.8, 2.0 Hz, 1H), 8.58 (dd, J=4.9, 2.0 Hz, 1H), 8.71 (d, J=2.0 Hz, 1H).

Hydrochloride

TLC: Rf 0.65 (ethyl acetate:triethylamine=10:1);

NMR (DMSO-d$_5$): δ3.77 (dd, J=15.0, 3.4 Hz, 1H), 3.99 (dd, J=15.0, 9.6 Hz, 1H), 5.43 (s, 2H), 5.77 (dd, J=9.6, 3.4

Hz, 1H), 7.30 (d, J=2.0 Hz, 1H), 7.41 (dd, J=8.8, 2.2 Hz, 1H), 7.59–7.66 (m, 2H), 7.74–7.82 (m, 4H), 8.02 (dd, J=8.4, 5.6 Hz, 1H), 8.57 (d-like, J=8.4 Hz, 1H), 8.88 (d-like, J=5.6 Hz, 1H), 9.04 (s-like, 1H).

Methanesulfonic Acid Salt

TLC: Rf 0.30 (ethyl acetate);

NMR (DMSO-$d_6$): δ2.37 (3H, s), 3.77 (dd, J=15.0, 3.3 Hz, 1H), 4.00 (dd, J=15.0, 9.3 Hz, 1H), 5.77 (dd, J=9.3, 3.3 Hz, 1H), 7.31 (d, J=2.2 Hz, 1H), 7.41 (dd, J=8.7, 2.2 Hz, 1H), 7.59–7.66 (m, 2H), 7.74–7.83 (m, 4H), 8.06 (dd, J=8.0, 5.6 Hz, 1H), 8.61 (d-like, J=8.0 Hz, 1H), 8.91 (dd, J=5.6, 1.0 Hz, 1H), 9.07 (d, J=1.6 Hz, 1H).

EXAMPLE 20 (14)

5-(3-(Pyridin-3-yl)propyl)oxy-3-phenylsulfonyl-2,3-dihydro-1,1-dioxidebenzo[b]thiophene.hydrochloride

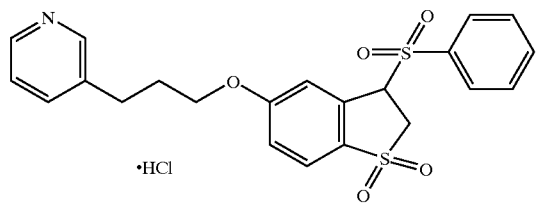

TLC: Rf 0.32 (ethyl acetate:methanol=10:1);

NMR (CD$_3$QD): δ8.80 (1H, s), 8.71 (1H, d, J=6 Hz), 8.56 (1H, d, J=8 Hz), 8.02 (1H, t, J=7 Hz), 7.85–7.42 (6H, m), 7.27 (1H, d, J=10 Hz), 7.14 (1H, s), 5.50–5.32 (1H, m), 4.16 (2H, t, J=6 Hz), 3.98–3.65 (2H, m), 3.10 (2H, t, J=7 Hz), 2.40–2.10 (2H, m).

EXAMPLE 20 (15)

6-(3-Phenyloxypropyl)oxy-3-phenylsulfonyl-2,3-dihydro-1,1-dioxidebenzo[b]thiophene

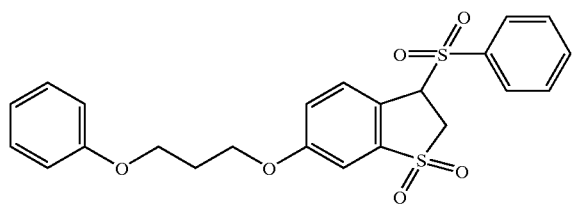

TLC: Rf 0.43 (hexane:ethyl acetate=1:1);

NMR (CDCl$_3$): δ2.29 (quint, J=6.0 Hz, 2H), 3.65–3.81 (m, 2H), 4.15 (t, J=6.0 Hz, 2H), 4.21 (t, J=6.0 Hz, 2H), 4.99 (dd, J=7.3, 5.9 Hz, 1H), 6.89–6.99 (m, 3H), 7.08 (d, J=2.2 Hz, 1H), 7.23 (dd, J=8.8, 2.2 Hz, 1H), 7.25–7.33 (m, 2H), 7.45–7.52 (m, 2H), 7.62–7.70 (m, 3H), 7.85 (d, J=8.8 Hz, 1H).

EXAMPLE 20 (16)

6-Benzyloxy-3-phenylsulfonyl-2,3-dihydro-1,1-dioxidebenzo[b]thiophene

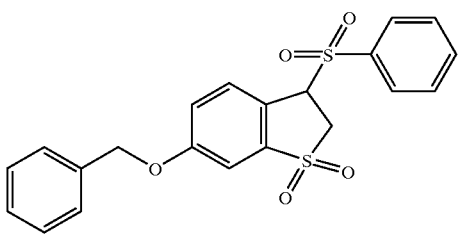

TLC: Rf 0.50 (hexane:ethyl acetate=1:1);

NMR (CDCl$_3$): δ3.71 (dd, J=14.7, 7.7 Hz, 1H), 3.80 (dd, J=14.7, 5.5 Hz, 1H), 5.00 (dd, J=7.7, 5.5 Hz, 1H), 5.10 (s, 2H), 7.15 (d, J=2.5 Hz, 1H), 7.30 (dd, J=8.5, 2.5 Hz, 1H), 7.40–7.53 (m, 7H), 7.63–7.71 (m, 3H), 7.87 (d, J=8.5 Hz, 1H).

EXAMPLE 20 (17)

6-Pentoxy-3-phenylsulfonyl-2,3-dihydro-1,1-dioxidebenzo[b]thiophene

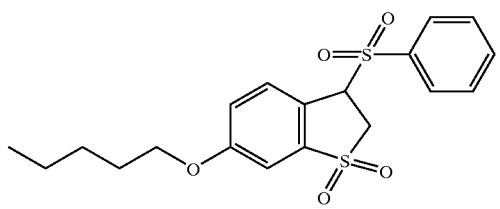

TLC: Rf 0.26 (hexane:ethyl acetate=2 1);

NMR (CDCl$_3$): δ0.94 (t, J=6.4 Hz, 3H), 1.42 (m, 4H), 1.81 (m, 2H), 3.70 (dd, J=14.9, 7.6 Hz, 1H), 3.79 (dd, J=14.9, 5.7 Hz, 1H), 3.99 (t, J=6.4 Hz, 2H), 5.00 (dd, J=7.6, 5.7 Hz, 1H), 7.04 (d, J=2.4 Hz, 1H), 7.23 (dd, J=8.8, 2.4 Hz, 1H), 7.46–7.54 (m, 2H), 7.64–7.72 (m, 3H), 7.84 (d, J=8.8 Hz, 1H).

EXAMPLE 20 (18)

6-(2-(Morpholin-4-yl)ethyl)oxy-3-phenylsulfonyl-2,3-dihydro-1,1-dioxidebenzo[b]thiophene

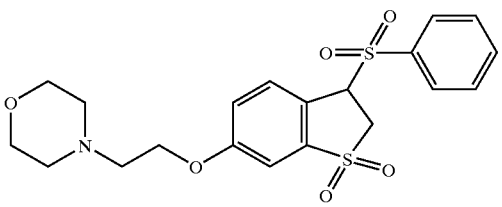

Free Compound

TLC: Rf 0.27 (hexane:ethyl acetate:triethylamine=2:4:1);

NMR (CDCl$_3$): δ2.56 (t, J=4.5 Hz, 4H), 2.81 (t, J=5.6 Hz, 2H), 3.70–3.77 (m, 6H), 4.14 (t, J=5.6 Hz, 2H), 5.01 (dd, J=7.5, 5.7 Hz, 1H), 7.08 (d, J=2.3 Hz, 1H), 7.25 (dd, J=8.7, 2.3 Hz, 1H), 7.47–7.54 (m, 2H), 7.64–7.72 (m, 3H), 7.83 (d, J=8.7 Hz, 1H).

Hydrochloride

TLC: Rf 0.27 (hexane:ethyl acetate:triethylamine=4:8:1);

NMR (CD$_3$OD): δ3.43–3.53 (m, 4H), 3.68 (t, J=4.8 Hz, 2H), 3.80 (dd, J=15.4, 8.4 Hz, 1H), 3.95 (dd, J=15.4, 4.0 Hz, 1H), 3.92–4.02 (m, 4H), 4.51 (t, J=4.8 Hz, 2H), 5.45 (dd, J=8.4, 4.0 Hz, 1H), 7.33 (d, J=2.6 Hz, 1H), 7.42 (dd, J=8.8, 2.6 Hz, 1H), 7.55–7.63 (m, 2H), 7.71–7.81 (m, 4H).

EXAMPLE 20 (19)

6-(3-Hydroxypropyl)oxy-3-phenylsulfonyl-2,3-dihydro-1,1-dioxidebenzo[b]thiophene

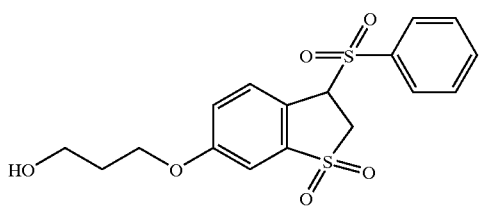

TLC: Rf 0.22 (hexane:ethyl acetate=1:2);

NMR (CDCl$_3$): δ2.06 (quint, J=6.0 Hz, 2H), 3.71 (dd, J=14.6, 7.5 Hz, 1H), 3.79 (dd, J=14.6, 5.6 Hz, 1H), 3.85 (t, J=6.0 Hz, 2H), 4.16 (t, J=6.0 Hz, 2H), 5.00 (dd, J=7.5, 5.6 Hz, 1H), 7.08 (d, J=2.4 Hz, 1H), 7.24 (dd, J=8.8, 2.4 Hz, 1H), 7.47–7.55 (m, 2H), 7.64–7.71 (m, 3H), 7.84 (d, J=8.8 Hz, 1H).

EXAMPLE 20 (20)

6-(Pyridin-3-ylmethyl)oxy-3-phenylsulfonyl-2,3-dihydro-1,1-dioxidebenzo[b]thiophene

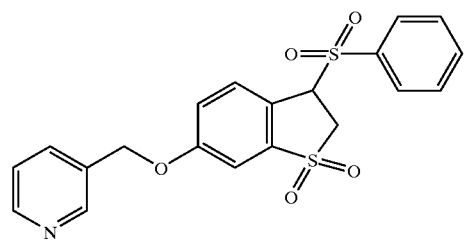

Free Compound

TLC: Rf 0.39 (ethyl acetate);

NMR (DMSO-d$_6$): δ3.78 (dd, J=15.2, 3.1 Hz, 1H), 4.01 (dd, J=15.2, 9.2 Hz, 1H), 5.29 (s, 2H), 5.69 (dd, J=9.2, 3.1 Hz, 1H), 7.42–7.47 (m, 3H), 7.58–7.66 (m, 3H), 7.74–7.82 (m, 3H), 7.89 (dt, J=8.0, 1.0 Hz, 1H), 8.57 (dd, J=4.8, 1.6 Hz, 1H), 8.69 (d, J=1.6 Hz, 1H).

Hydrochloride

TLC: Rf 0.39 (ethyl acetate);

NMR (DMSO-d$_6$): δ3.78 (dd, J=15.2, 3.0 Hz, 1H), 4.01 (dd, J=15.2, 9.4 Hz, 1H), 5.72 (dd, J=9.4, 3.0 Hz, 1H), 7.46–7.51 (m, 2H), 7.59–7.66 (m, 3H), 7.75–7.83 (m, 3H), 7.99 (dd, J=8.0, 5.4 Hz, 1H), 8.52 (d, J=8.0 Hz, 1H), 8.87 (dd, J=5.4, 1.2 Hz, 1H), 8.99 (d, J=1.2 Hz, 1H).

EXAMPLE 20 (21)

6-(3-Nitrophenylmethyl)oxy-3-phenylsulfonyl-2,3-dihydro-1,1-dioxidebenzo[b]thiophene

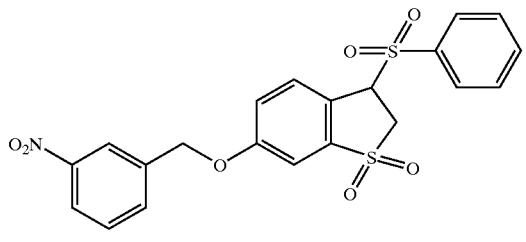

TLC: Rf 0.55 (hexane:ethyl acetate=1:2);

NMR (DMSO-d$_6$): δ8.36–8.34 (m, 1H), 8.25–8.20 (m, 1H), 7.93 (d-like, J=7.6 Hz, 1H), 7.82–7.72 (m, 4H), 7.68–7.58 (m, 3H), 7.50–7.43 (m, 2H), 5.70 (dd, J=9.4, 3.0 Hz, 1H), 5.40 (s, 2H), 4.02 (dd, J=15.2, 9.4 Hz, 1H), 3.79 (dd, J=15.2, 3.0 Hz, 1H).

EXAMPLE 20 (22)

6-(3-Bromopropyl)oxy-3-phenylsulfonyl-2,3-dihydro-1,1-dioxidebenzo[b]thiophene

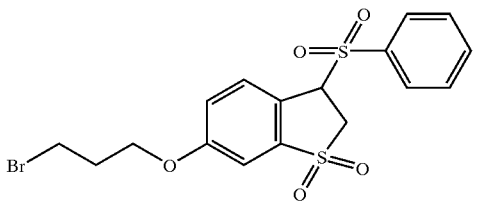

TLC: Rf 0.60 (hexane:ethyl acetate=1:1);

NMR (CDCl$_3$): δ2.35 (m, 2H), 3.60 (t, J=6.0 Hz, 2H), 3.70–3.91 (m, 2H), 4.17 (t, J=6.0 Hz, 2H), 5.01 (dd, J=14, 7 Hz, 1H), 7.09 (d, J=3.0 Hz, 1H), 7.25 (m, 1H), 7.53 (m, 2H), 7.67 (m, 3H), 7.89 (m, 1H).

EXAMPLE 20 (23)

7-Pentoxy-3-phenylsulfonyl-2,3-dihydro-1,1-dioxidebenzo[b]thiophene

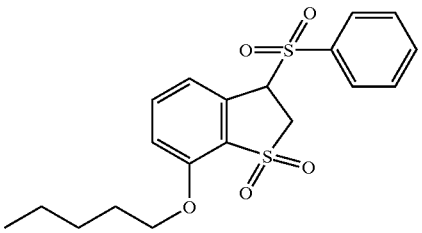

TLC: Rf 0.48 (hexane:ethyl acetate=1:1);

NMR (CDCl): δ7.70–7.43 (7H, m), 6.99 (1H, d, J=8.2 Hz), 5.01 (1H, dd, J=8.6, 5.4 Hz), 4.07 (2H, t, J=6.8 Hz), 3.73–3.68 (2H, m), 1.80 (2H, quint., J=6.8 Hz), 1.50–1.20 (4H, m), 0.89 (3H, t, J=6.8 Hz).

EXAMPLE 20 (24)

7-(2-Phenyloxyethyl)oxy-3-phenylsulfonyl-2,3-dihydro-1,1-dioxidebenzo[b]thiophene

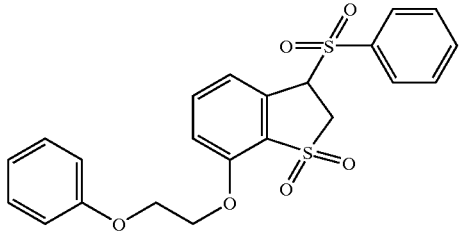

TLC: Rf 0.27 (hexane:ethyl acetate=1:1);

NMR (CDCl$_3$): δ7.70–6.88 (13H, m), 5.01 (1H, dd, J=8.1, 5.4 Hz), 4.50–4.40 (2H, m), 4.40–4.31 (2H, m), 3.76–3.70 (2H, m).

EXAMPLE 20 (25)

7-(3-Hydroxypropyl)oxy-3-phenylsulfonyl-2,3-dihydro-1,1-dioxidebenzo[b]thiophene

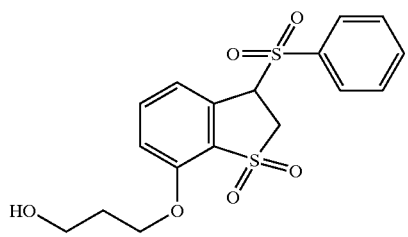

TLC: Rf 0.46 (ethyl acetate);

NMR (CDCl$_3$): δ7.75–7.40 (7H, m), 7.07 (1H, d, J=8.0 Hz), 5.05 (1H, dd, J=8.4, 5.4 Hz), 4.26 (2H, t, J=5.8 Hz), 3.85–3.65 (4H, m), 2.03 (2H, quint, J=5.8 Hz).

EXAMPLE 20 (26a)

7-(Pyridin-3-ylmethyl)oxy-3-phenylsulfonyl-2,3-dihydro-1,1-dioxidebenzo[b]thiophene.hydrochloride

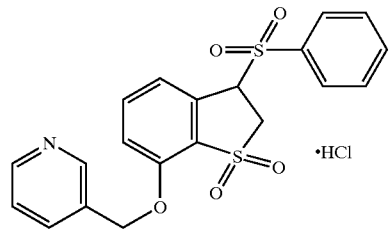

TLC: Rf 0.30 (ethyl acetate:triethylamine=20:1);

NMR (DMSO-d$_6$): δ8.85–8.75 (2H, m), 8.27 (1H, d, J=7.6 Hz), 7.92–7.55 (7H, m), 7.43 (1H, d, J=8.2 Hz), 7.26 (1H, d, J=7.6 Hz), 5.80 (1H, dd, J=9.4, 3.2 Hz), 5.51 (2H, s), 3.99 (1H, dd, J=15.3, 9.4 Hz), 3.77 (1H, dd, J=15.3, 3.2 Hz).

EXAMPLE 20 (26b)

7-(N-Oxidepyridin-3-ylmethyl)oxy-3-phenylsulfonyl-2,3-dihydro-1,1-dioxidebenzo[b]thiophene

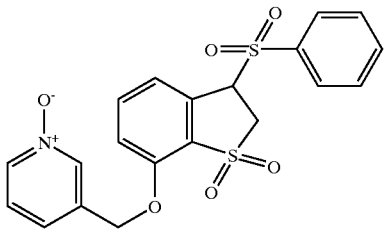

TLC: Rf 0.26 (ethyl acetate:methanol triethylamine=16:3:1);

NMR (DMSO-d$_6$): δ8.38 (1H, s), 8.30 (1H, d, J=5.4 Hz), 7.90–7.42 (8H, m), 7.39 (1H, d, J=7.8 Hz), 7.23 (1H, d, J=7.8 Hz), 5.78 (1H, dd, J=9.7, 3.4 Hz), 5.39 (2H, s), 3.99 (1H, dd, J=15, 9.7 Hz), 3.78 (1H, dd, J=15, 3.4 Hz).

EXAMPLE 20 (27)

4-(t-Butoxycarbonylmethyl)oxy-3-phenylsulfonyl-2,3-dihydro-1,1-dioxidebenzo[b]thiophene

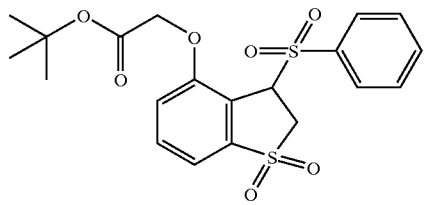

TLC: Rf 0.28 (hexane:ethyl acetate=1:1);

NMR (CDCl$_3$): δ1.48 (s, 9H), 3.76 (dd, J=14.9, 9.2 Hz, 1H), 4.16 (d, J=16.0 Hz, 1H), 4.25 (dd, J=1.9, 1.2 Hz, 1H), 4.31 (d, J=16.0 Hz, 1H), 5.36 (dd, J=9.2, 1.2 Hz, 1H), 6.82 (dd, J=8.1, 0.7 Hz, 1H), 7.35 (d, J=7.4 Hz, 1H), 7.44–7.57 (m, 3H), 7.59–7.67 (m, 1H), 7.78–7.83 (m, 2H).

EXAMPLE 20 (28)

5-(t-Butoxycarbonylmethyl)oxy-3-phenylsulfonyl-2,3-dihydro-1,1-dioxidebenzo[b]thiophene

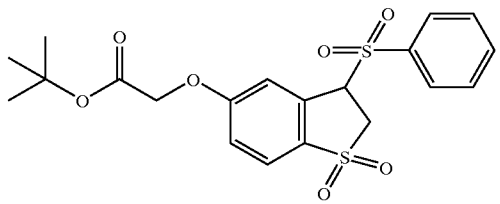

TLC: Rf 0.50 (hexane:ethyl acetate=1:1);

NMR (CDCl$_3$): δ1.53 (s, 9H), 3.74 (d-like, J=6 Hz, 2H), 4.67 (m, 2H), 5.00 (t, J=6 Hz, 1H), 7.17 (dd, J=8, 2 Hz, 1H), 7.45 (d, J=2 Hz, 1H), 7.50 (m, 2H), 7.55 (d, J=8 Hz, 1H), 7.66 (m, 3H).

EXAMPLE 20 (29)

6-(t-Butoxycarbonylmethyl)oxy-3-phenylsulfonyl-2,3-dihydro-1,1-dioxidebenzo[b]thiophene

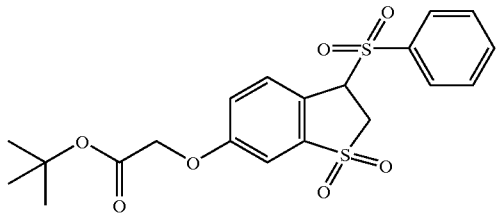

TLC: Rf 0.42 (hexane:ethyl acetate=1:1);

NMR (CDCl$_3$): δ1.48 (s, 3H), 3.67–3.83 (m, 2H), 4.56 (s, 2H), 5.00 (dd, J=7.4, 5.6 Hz, 1H), 6.99 (d, J=2.6 Hz, 1H), 7.29 (dd, J=8.8, 2.6 Hz, 1H), 7.46–7.53 (m, 2H), 7.61–7.70 (m, 3H), 7.89 (d, J=8.8 Hz, 1H).

EXAMPLE 20 (30)

7-(t-Butoxycarbonylmethyl)oxy-3-phenylsulfonyl-2,3-dihydro-1,1-dioxidebenzo[b]thiophene

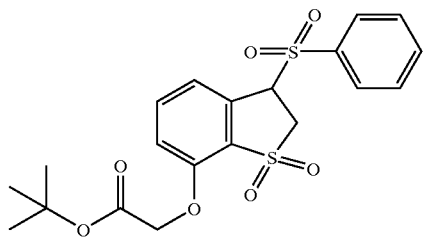

TLC: Rf 0.28 (hexane:ethyl acetate=1:1);

NMR (CDCl$_3$): δ7.70–7.47 (7H, m), 6.91–6.86 (1H, m), 5.02 (1H, dd, J=8.3, 5.6 Hz), 4.64 (2H, s), 3.76–3.72 (2H, m), 1.44 (9H, s).

EXAMPLE 20 (31)

4-(2-(t-Butoxycarbonylamino)ethyl)oxy-3-phenylsulfonyl-2,3-dihydro-1,1-dioxidebenzo[b]thiophene

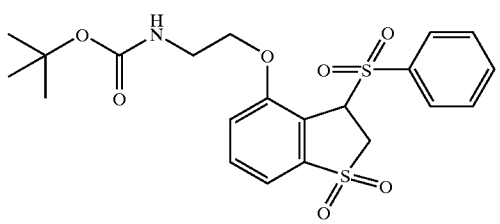

TLC: Rf 0.35 (hexane:ethyl acetate=1:2);

NMR (CDCl$_3$): δ3.42–3.56 (m, 1H), 3.63–3.76 (m, 1H), 3.73 (dd, J=15.2, 9.6 Hz, 1H), 4.02–4.34 (m, 2H), 4.10 (dd, J=15.2, 1.2 Hz, 1H), 5.29 (dd, J=9.6, 1.2 Hz, 1H), 5.78 (br, 1H), 7.02 (d-like, J=7.5 Hz, 1H), 7.22 (d, J=7.5 Hz, 1H), 7.40–7.64 (m, 4H), 7.21–7.76 (m, 2H).

EXAMPLE 20 (32)

4-(3-(t-Butoxycarbonylamino)propyl)oxy-3-phenylsulfonyl-2,3-dihydro-1,1-dioxidebenzo[b]thiophene

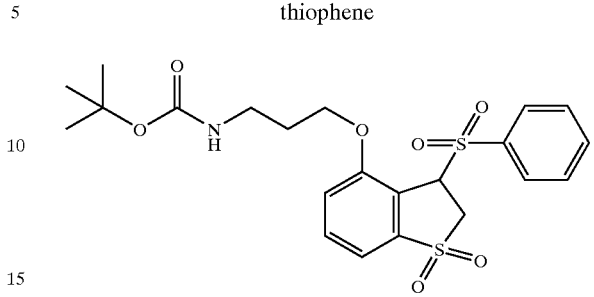

TLC: Rf 0.30 (hexane:ethyl acetate=1:2);

NMR (CDCl$_3$): δ1.41 (s, 9H), 1.93 (m, 2H), 3.35 (m, 2H), 3.72 (dd, J=15.0, 9.0 Hz, 1H), 3.99 (t, J=6.1 Hz, 2H), 4.09 (d, J=15.0 Hz, 2H), 4.95 (br, 1H), 5.35 (d, J=9.0 Hz, 1H), 7.02 (d, J=7.5 Hz, 1H), 7.25 (d, J=7.5 Hz, 1H), 7.43–7.67 (m, 4H), 7.70–7.75 (m, 2H).

EXAMPLE 20 (33)

5-(2-(t-Butoxycarbonylamino)ethyl)oxy-3-phenylsulfonyl-2,3-dihydro-1,1-dioxidebenzo[b]thiophene

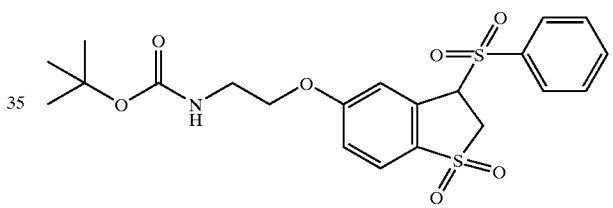

TLC: Rf 0.40 (hexane:ethyl acetate=1:1);

NMR (CDCl$_3$): δ1.47 (s, 9H), 3.54 (m, 2H), 3.66 (dd, J=15, 8Hz, 1H), 3.80 (dd, J=15, 5 Hz, 1H), 4.13 (t, J=5 Hz, 2H), 5.00 (dd, J=8, 5 Hz, 1H), 5.00 (br, 1H), 7.12 (dd, J=8, 2 Hz, 1H), 7.44 (d, J=2 Hz, 1H), 7.55 (m, 3H), 7.72 (m, 3H).

EXAMPLE 20 (34)

6-(3-(t-Butoxycarbonylamino)propyl)oxy-3-phenylsulfonyl-2,3-dihydro-1,1-dioxidebenzo[b]thiophene

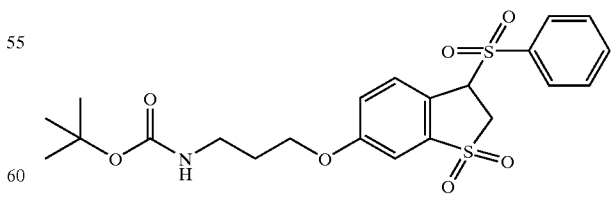

TLC: Rf 0.41 (hexane:ethyl acetate=1:2);

NMR (CDCl$_3$): δ1.44 (s, 9H), 2.01 (quint, J=6.2 Hz, 2H), 3.32 (q, J=6.2 Hz, 2H), 3.71 (dd, J=14.6, 7.7 Hz, 1H), 3.79 (dd, J=14.6, 5.5 Hz, 1H), 4.06 (t, J=6.2 Hz, 2H), 4.68 (br, 1H), 5.00 (dd, J=7.7, 5.5 Hz, 1H), 7.05 (d, J=2.4 Hz, 1H), 7.23 (dd, J=8.8, 2.4 Hz, 1H), 7.47–7.54 (m, 2H), 7.64–7.72 (m, 3H), 7.85 (d, J=8.8 Hz, 1H).

EXAMPLE 20 (35)

6-(2-(t-Butoxycarbonylamino)ethyl)oxy-3-phenysulfonyl-2,3-dihydro-1,1-dioxidebenzo[b]thiophene

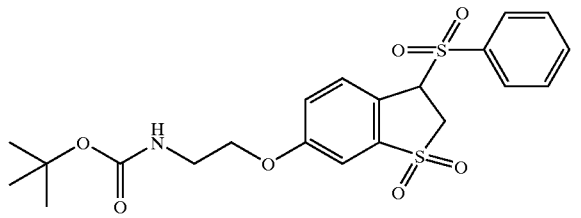

TLC: Rf 0.24 (hexane:ethyl acetate=1:1);

NMR (CDCl₃): δ1.46 (s, 9H), 3.56 (q, J=5.4 Hz, 2H), 3.71 (dd, J=14.8, 7.7 Hz, 1H), 3.79 (dd, J=14.8, 5.6 Hz, 1H), 4.06 (t, J=5.4 Hz, 2H), 4.97 (br, 1H), 5.00 (dd, J=7.7, 5.6 Hz, 1H), 7.05 (d, J=2.6 Hz, 1H), 7.24 (dd, J=8.8, 2.6 Hz, 1H), 7.47–7.55 (m, 2H), 7.65–7.72 (m, 3H), 7.88 (d, J=8.8 Hz, 1H).

EXAMPLE 20 (36)

7-(2-(t-Butoxycarbonylamino)ethyl)oxy-3-phenylsulfonyl-2,3-dihydro-1,1-dioxidebenzo[b]thiophene

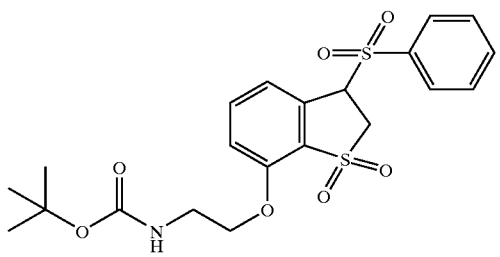

TLC: Rf 0.36 (hexane:ethyl acetate=2:1);

NMR (CDCl₃): δ7.72–7.40 (7H, m), 7.04 (1H, d, J=8.2 Hz), 5.22 (1H, bs), 5.02 (1H, dd, J=8.7, 5.0 Hz), 4.25–4.10 (2H, m), 3.85–3.65 (2H, m), 3.60–3.46 (2H, m), 1.42 (9H, s).

EXAMPLE 20 (37)

4-(N-(t-Butoxycarbonyl)piperidin-4-yl)oxy-3-phenylsulfonyl-2,3-dihydro-1,1-dioxidebenzo[b]thiophene

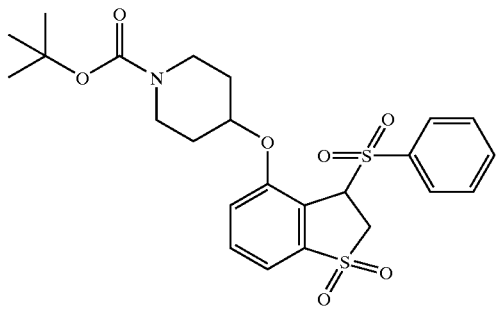

TLC: Rf 0.19 (hexane:ethyl acetate=1:1);

NMR (CDCl₃): δ7.80–7.38 (6H, m), 7.23 (1H, d, J=8 Hz), 7.05 (1H, d, J=8 Hz), 5.23 (1H, d, J=9 Hz), 4.70–4.45 (1H, m), 4.08 (1H, d, J=15 Hz), 3.95–3.60 (2m), 3.72 (1H, dd, J=15, 9 Hz), 3.50–3.22 (2H, m), 2.15–1.58 (4H, m), 1.48 (9H, s).

EXAMPLE 20 (38)

4,7-Bis[(2-(t-butoxycarbonylamino)ethyl)oxy]-3-phenylsulfonyl-2,3-dihydro-1,1-dioxidebenzo[b]thiophene

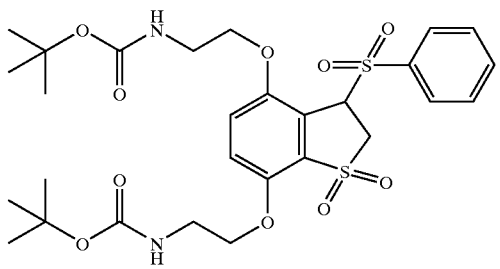

TLC: Rf 0.25 (hexane:ethyl acetate=1:3);

NMR (CDCl₃): δ7.77 (2H, d, J=8.2 Hz), 7.70–7.55 (1H, m), 7.55–7.40 (2H, m), 6.95 (2H, s), 5.71 (1H, brs), 5.40–5.15 (2H, mn), 4.20–3.30 (10H, m), 1.43 (18H, s).

EXAMPLE 20 (39)

4-(3-Nitrophenylmethyl)oxy-3-phenylsulfonyl-2,3-dihydro-1,1-dioxidebenzo[b]thiophene

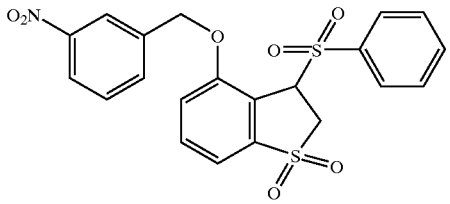

TLC: Rf 0.13 (hexane:ethyl acetate=1:1);

NMR (CDCl₃+CD₃OD): δ8.35 (1H, s), 8.27 (1H, d, J=8 Hz), 7.87 (1H, d, J=8 Hz), 7.80–7.50 (5H, m), 7.50–7.25

(3H, m), 7.13 (1H, d, J=8 Hz), 5.36 (1H, d-like, J=9 Hz), 5.25–4.98 (2H, m), 4.11 (1H, dd, J=15, 1 Hz), 3.76 (1H, dd, J=15, 9 Hz).

EXAMPLE 21

4-Carboxymethoxy-3-phenylsulfonyl-2,3-dihydro-1, 1-dioxidebenzo[b]thiophene

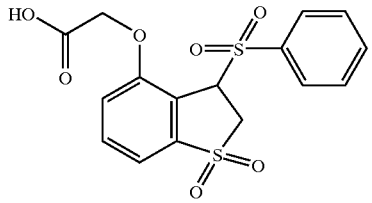

To a solution of the compound prepared in Example 20 (27) (105 mg) in methylene chloride (5 ml), was added trifluoroacetic acid (5 ml) at 0° C. The reaction mixture was stirred at room temperature for 1 hour. The reaction mixture was concentrated. The residue was recrystallized from diethyl ether to give the compound of the present invention (63 mg) having the following physical data.

TLC: Rf 0.20 (chloroform:methanol=4:1);

NMR (CDCl$_3$+CD$_3$OD): δ3.79 (dd, J=14.9, 9.0 Hz, 1H), 4.23 (dd, J=14.9, 1.0 Hz, 1H), 4.26 (d, J=16.1 Hz, 1H), 4.43 (d, J=16.1 Hz, 1H), 5.45 (dd, J=9.0, 1.0 Hz, 1H), 6.91 (d, J=8.0 Hz, 1H), 7.36 (d, J=7.6 Hz, 1H), 7.45–7.59 (m, 3H), 7.62–7.70 (m, 1H), 7.77–7.81 (m, 2H).

EXAMPLES 21 (1)~21 (3)

By the same procedure as described in Example 21 using the compounds prepared in Examples 20 (28)~20 (30) instead of the compound prepared in Example 20 (27), the following compounds of the present invention were obtained.

EXAMPLE 21 (1)

5-Carboxymethoxy-3-phenylsulfonyl-2,3-dihydro-1, 1-dioxidebenzo[b]thiophene

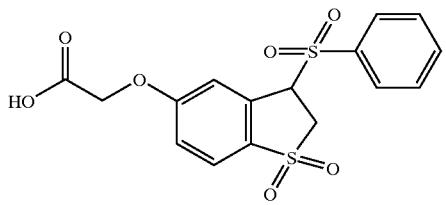

TLC: Rf 0.30 (chloroform:methanol=4:1);

NMR (CDCl$_3$+CD$_3$OD): δ3.79 (d-like, J=6 Hz, 2H), 4.76 (s, 2H), 5.10 (t, J=6 Hz, 1H), 7.20 (dd, J=8,2 Hz, 1H), 7.39 (d, J=2 Hz, 1H), 7.51 (d, J=8 Hz, 1H), 7.55 (m, 2H), 7.69 (m, 3H).

EXAMPLE 21 (2)

6-Carboxymethoxy-3-phenylsulfonyl-2,3-dihydro-1, 1-dioxidebenzo[b]thiophene

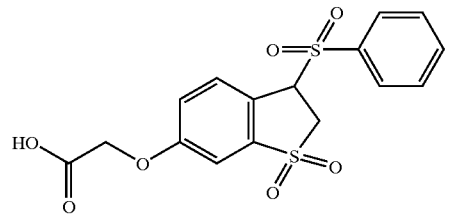

TLC: Rf 0.25 (chloroform:methanol=4:1);

NMR (CDCl$_3$+CD$_3$OD): δ3.70–3.85 (m, 2H), 4.68 (s, 2H), 5.07 (t-like, J=6.6 Hz, 1H), 7.07 (d, J=2.5 Hz, 1H), 7.32 (dd, J=8.8, 2.5 Hz, 1H), 7.47–7.55 (m, 2H), 7.63–7.73 (m, 3H), 7.83 (d, J=8.8 Hz, 1H).

EXAMPLE 21 (3)

7-Carboxymethoxy-3-phenylsulfonyl-2,3-dihydro-1, 1-dioxidebenzo[b]thiophene

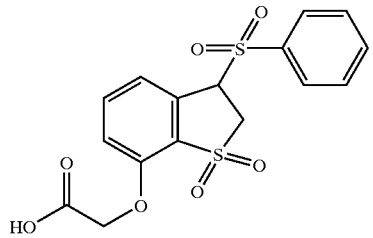

TLC: Rf 0.29 (ethyl acetate:acetic acid=10:1);

NMR (CDCl$_3$+DMSO-d$_6$): δ7.52–7.26 (6H, m), 7.20 (1H, d, J=7.8 Hz), 6.77 (1H, d, J=8.2 Hz), 4.98 (1H, dd, J=7.8, 5.6 Hz), 4.52 (2H, s), 3.58–3.54 (2H, m).

EXAMPLE 22

4-(N-(Pyridin-3-ylmethyl)carbamoylmethyl)oxy-3-phenylsulfonyl-2,3-dihydro-1,1-dioxidebenzo[b]thiophene

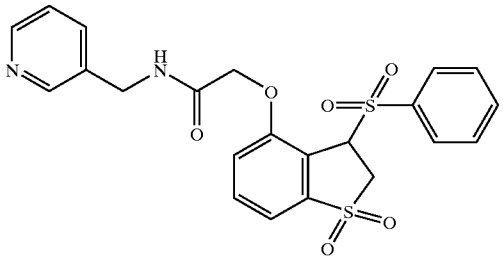

A suspension of the compound prepared in Example 21 (480 mg) in thionyl chloride (10 ml) was refluxed for 15 minutes. After removing thionylchloride, the residue was dissolved in methylene chloride (5 ml). Thereto was added dropwise a solution of 3-(aminomethyl)pyridine (0.15 ml) and triethylamine (1 ml) in methylene chloride (10 ml) under cooling with ice. The reaction mixture was stirred at room temperature for 2 hours. To the reaction mixture was added water. The mixture was extracted by ethyl acetate. The extract was washed by water, a saturated aqueous solution of sodium chloride successively, dried over anhydrous sodium sulfate and concentrated. The residue was purified with column chromatography on silica gel (ethyl acetate:triethylamine=100:1) to give the compound of the present invention (421 mg) having the following physical data.

Free Compound

TLC: Rf 0.49 (ethyl acetate:methanol:triethylamine= 8:1:1);

NMR (DMSO-$d_6$): δ4.03 (dd, J=14.9, 8.4 Hz, 1H), 4.11 (d, J=14.5 Hz, 1H), 4.12 (dd, J=14.9, 1.6 Hz, 1H), 4.33 (dd, J=15.3, 6.0 Hz, 1H), 4.44 (dd, J=15.3, 6.0 Hz, 1H), 4.57 (d, J=14.5 Hz, 1H), 6.00 (dd, J=8.4, 1.6 Hz, 1H), 7.24 (d, J=8.0 Hz, 1H), 7.34 (dd, J=8.0, 4.7 Hz, 1H), 7.40 (d, J=8.0 Hz, 1H), 7.49–7.54 (m, 2H), 7.63–7.73 (m, 5H), 8.39 (t, J=6.0 Hz, 1H), 8.46 (dd, J=4.7, 1.7 Hz, 1H), 8.51 (d, J=1.7 Hz, 1H).

Hydrochloride

TLC: Rf 0.49 (ethyl acetate:methanol:triethylamine= 8:1:1);

NMR (DMSO-$d_6$): δ4.04 (dd, J=15.0, 8.7 Hz, 1H), 4.12 (d, J=14.7 Hz, 1H), 4.13 (dd, J=15.0, 1.5 Hz, 1H), 4.49 (dd, J=15.8, 6.2 Hz, 1H), 4.57 (dd, J=15.8, 6.2 Hz, 1H), 4.60 (d, J=14.7 Hz, 1H), 6.15 (dd, J=8.7, 1.5 Hz, 1H), 7.25 (d, J=8.2 Hz, 1H), 7.40 (d, J=7.6 Hz, 1H), 7.52–7.57 (m, 2H), 7.64 (d, J=8.2 Hz, 1H), 7.68–7.74 (m, 3H), 7.93 (dd, J=8.0, 5.5 Hz, 1H), 8.37 (d, J=8.0 Hz, 1H), 8.68 (t, J=6.2 Hz, 1H), 8.78 (d, J=5.4 Hz, 1H), 8.81 (s 1H).

EXAMPLES 22 (1) AND 22 (2)

By the same procedure as described in Example 22 using a corresponding amine compound instead of 3-(aminomethyl)pyridine, and if necessary, by converting into the corresponding salt by a known method, the following compounds of the present invention were obtained.

EXAMPLE 22 (1)

4-((2-(N,N-Dimethylamino)ethylamino) carbonylmethyl)oxy-3-phenylsulfonyl-2,3-dihydro-1,1-dioxidebenzo[b]thiophene

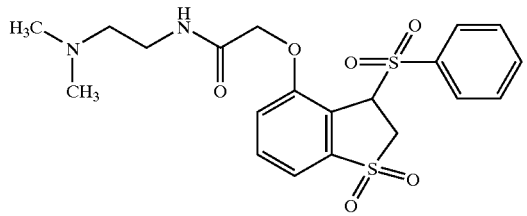

Free Compound

TLC: Rf 0.29 (ethyl acetate:methanol:triethylamine= 8:1:1);

NMR (CDCl$_3$): δ2.24 (s, 6H), 2.51 (t-like, J=6.0 Hz, 2H), 3.49 (m, J=6.0 Hz, 2H), 3.77 (dd, J=15.3, 9.6 Hz, 1H), 4.05 (dd, J=15.3, 1.3 Hz, 1H), 4.53 (d, J=14.2 Hz, 1H), 4.64 (d, J=14.2 Hz, 1H), 5.39 (d-like, J=9.0 Hz, 1H), 7.04 (d, J=8.0 Hz, 1H), 7.27 (d, J=8.0 Hz, 1H), 7.42–7.48 (m, 2H), 7.57 (t, J=8.0 Hz, 1H), 7.59–7.65 (m, 1H), 7.70–7.74 (m, 2H), 7.94 (br, 1H).

Hydrochloride

TLC: Rf 0.29 (ethyl acetate:methanol:triethylamine= 8:1:1);

NMR (DMSO-$d_6$): δ2.76 (s, 6H), 3.14–3.18 (m, 2H), 3.44–3.56 (m, 2H), 4.00 (dd, J=15.0, 9.3 Hz, 1H), 4.03 (d, J=14.4 Hz, 1H), 4.17 (d, J=15.0 Hz, 1H), 4.50 (d, J=14.4 Hz, 1H), 6.24 (d-like, J=8.7 Hz, 1H), 7.25 (d, J=8.0 Hz, 1H), 7.39 (d, J=8.0 Hz, 1H), 7.56–7.62 (m, 2H), 7.64 (t, J=8.0 Hz, 1H), 7.70–7.77 (m, 3H), 8.23 (t, J=5.5 Hz, 1H).

EXAMPLE 22 (2)

4-((N-Benzyl-2-(N',N'-dimethylamino)ethylamino) carbonylmethyl)oxy-3-phenylsulfonyl-2,3-dihydro-1,1-dioxidebenzo[b]thiophene

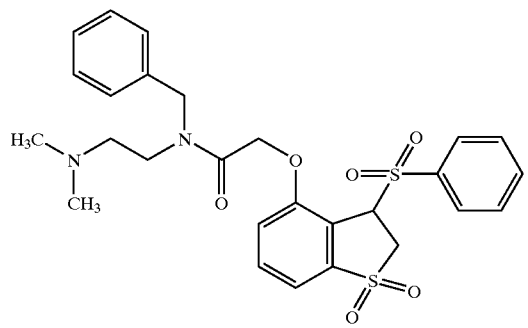

TLC: Rf 0.52 (ethyl acetate:methanol:triethylamine= 9:1:1);

NMR (CDCl$_3$): δ2.22 (s, 3H), 2.29 (s, 3H), 2.44–2.55 (m, 2H), 3.29–3.35 (m, 1H), 3.56–3.60 (m, 1H), 3.73–3.75 (m, 2H), 4.60 (d, J=15.0 Hz, 0.5H), 4.67 (s-like, 1H), 4.76 (d, J=15.0 Hz, 0.5H), 4.88 (s, 1H), 4.94–5.00 (m, 1H), 5.05 (d, J=15.0 Hz, 0.5H), 5.18 (d, J=15.0 Hz, 0.5H), 7.10–7.36 (m, 6H), 7.41–7.53 (m, 4H), 7.61–7.68 (m, 3H).

EXAMPLE 23

4-(2-Aminoethyl)oxy-3-phenylsulfonyl-2,3-dihydro-1,1-dioxidebenzo[b]thiophene.hydrochloride

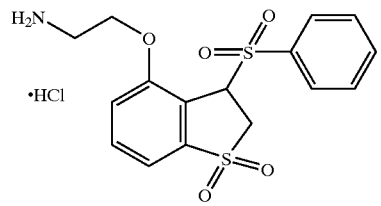

By the same procedure as described in Example 7 using the compound prepared in Example 20 (31) instead of the compound prepared in Example 6 (8), the compound of the present invention having the following physical data was obtained.

TLC: Rf 0.21 (ethyl acetate:methanol:triethylamine= 8:2:1);

NMR (DMSO-$d_6$): δ2.66–2.78 (m, 1H), 3.02–3.12 (m, 1H), 3.83–4.18 (m, 4H), 6.23 (d-like, J=6.6 Hz, 1H), 7.27 (d, J=8.0 Hz, 1H), 7.39 (d, J=7.6 Hz, 1H), 7.58–7.68 (m, 3H), 7.72–7.79 (m, 3H), 8.02 (br, 2H).

EXAMPLES 23 (1)–23 (7)

By the same procedure as described in Example 23 using the compounds prepared in Examples 20 (32)–20 (38) instead of the compound prepared in Example 20 (31), the following compounds of the present invention were obtained.

EXAMPLE 23 (1)

4-(3-Aminopropyl)oxy-3-phenylsulfonyl-2,3-dihydro-1,1-dioxidebenzo[b]thiophene.hydrochloride

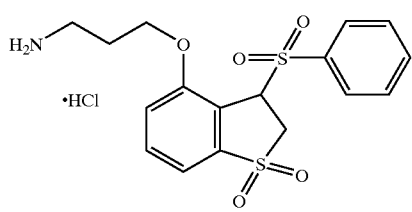

TLC: Rf 0.12 (ethyl acetate:methanol:triethylamine= 8:4:1);

NMR (DMSO-d$_6$): δ1.85–1.93 (m, 2H), 2.93 (q, J=6.4 Hz, 2H), 3.87–4.08 (m, 2H), 3.97 (dd, J=15.0, 8.4 Hz, 1H), 4.11 (dd, J=15.0, 1.4 Hz, 1H), 5.65 (dd, J=8.4, 1.4 Hz, 1H), 7.26 (d, J=7.8 Hz, 1H), 7.33 (d, J=7.8 Hz, 1H), 7.59–7.78 (m, 6H), 8.15 (br, 3H).

EXAMPLE 23 (2)

5-(2-Aminoethyl)oxy-3-phenylsulfonyl-2,3-dihydro-1,1-dioxidebenzo[b]thiophene.hydrochloride

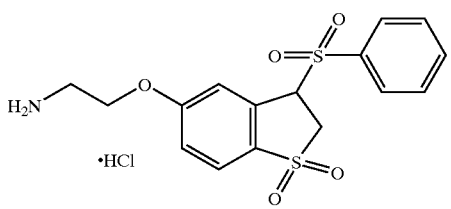

TLC: Rf 0.25 (ethyl acetate:methanol:triethylamine= 8:2:1);

NMR (DMSO-d$_6$): δ7.81–7.72 (m, 4H), 7.66–7.59 (m, 2H), 7.32–7.27 (m, 2H), 5.77 (dd, J=9, 3.5 Hz, 1H), 4.27 (m, 2H), 3.94 (dd, J=15, 9 Hz, 1H), 3.71 (dd, J=15, 3.5 Hz, 1H), 3.38–3.32 (m, 2H).

EXAMPLE 23 (3)

6-(3-Aminopropyl)oxy-3-phenylsulfonyl-2,3-dihydro-1,1-dioxidebenzo[b]thiophene.hydrochloride

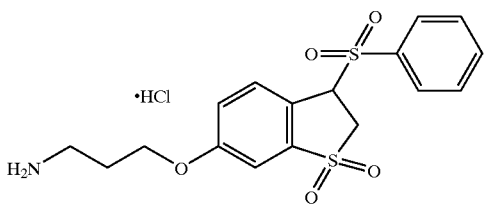

TLC: Rf 0.40 (ethyl acetate:methanol:triethylamine= 8:2:1);

NMR (DMSO-d$_6$): δ2.05 (quint, J=6.8 Hz, 2H), 2.95 (t, J=6.8 Hz, 2H), 3.76 (dd, J=15.2, 3.0 Hz, 1H), 4.00 (dd, J=15.2, 9.4 Hz, 1H), 4.18 (t, J=6.8 Hz, 2H), 5.70 (dd, J=9.4, 3.0 Hz, 1H), 7.29–7.38 (m, 2H), 7.56–7.67 (m, 3H), 7.76–7.79 (m, 3H), 8.08 (br, 2H).

EXAMPLE 23 (4)

6-(2-Aminoethyl)oxy-3-phenylsulfonyl-1,3-dihydro-1,1-dioxidebenzo[b]thiophene.hydrochloride

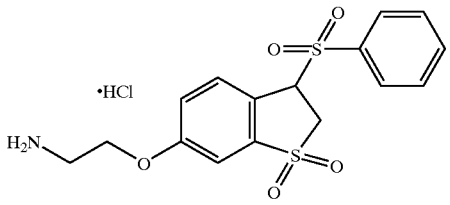

TLC: Rf 0.16 (ethyl acetate:methanol:triethylamine= 9:1:1);

NMR (DMSO-d$_6$): δ3.22 (t, J=4.9 Hz, 2H), 3.79 (dd, J=15.1, 3.0 Hz, 1H), 4.01 (dd, J=15.1, 9.4 Hz, 1H), 4.32 (t, J=4.9 Hz, 2H), 5.73 (dd, J=9.4, 3.0 Hz, 1H), 7.35 (d, J=2.4 Hz, 1H), 7.40 (dd, J=8.8, 2.4 Hz, 1H), 7.62 (d, J=8.8 Hz, 1H), 7.64–7.66 (m, 2H), 7.76–7.81 (m, 3H), 8.35 (br, 3H).

EXAMPLE 23 (5)

7-(2-Aminoethyl)oxy-3-phenylsulfonyl-2,3-dihydro-1,1-dioxidebenzo[b]thiophene.hydrochloride

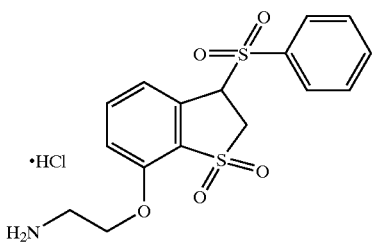

TLC: Rf 0.38 (ethyl acetate:acetic acid:water=3:1:1);

NMR (DMSO-d$_6$): δ8.18 (3H, brs), 7.83–7.60 (6H, m), 7.40 (1H, d, J=8 Hz), 7.22 (1H, d, J=8 Hz), 5.81 (1H, dd, J=9.6, 3.2 Hz), 4.44–3.30 (2H, m), 3.96 (1H, dd, J=15, 9.6 Hz), 3.76 (1H, dd, J=15, 3.2 Hz), 3.18 (2H, t, J=6 Hz).

EXAMPLE 23 (6)

4-(Piperidin-4-yl)oxy-3-phenylsulfonyl-2,3-dihydro-1,1-dioxidebenzo[b]thiophene.hydrochloride

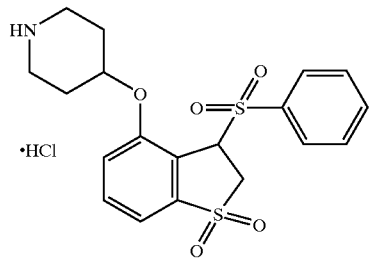

TLC: Rf 0.47 (ethyl acetate:acetic acid:water=3:1:1);

NMR (DMSO-d$_6$): δ8.91 (2H, brs), 7.90–7.52 (6H, m), 7.41 (1H, d, J=8 Hz), 7.33 (1H, d, J=8 Hz), 5.71 (1H, d, J=7 Hz), 4.95–4.70 (1H, m), 4.20–3.80 (2H, m), 3.50–2.95 (4H, m), 2.30–1.60 (4H, m).

EXAMPLE 23 (7)

4,7-Bis[(2-aminoethyl)oxy]-3-phenylsulfonyl-2,3-dihydro-1,1-dioxidebenzo[b]thiophene.2hydrochloride

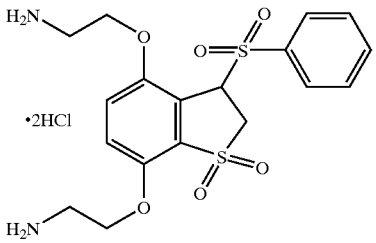

TLC: Rf 0.22 (ethyl acetate:methanol:triethylamine= 4:1:1);

NMR (DMSO-$d_6$): δ8.10 (6H, brs), 7.85–7.70 (3H, m), 7.70–7.50 (2H, m), 7.37 (1H, d, J=8.6 Hz), 7.23 (1H, d, J=8.6 Hz), 6.14 (1H, d, J=6.0 Hz), 4.50–4.15 (2H, m), 4.15–3.90 (4H, m), 3.85–3.65 (1H, m), 3.25–3.15 (2H, m), 3.15–2.90 (1H, m).

EXAMPLE 24

4-(2-(N,N-Dimethylamino)ethyl)oxy-3-phenylsulfonyl-2,3-dihydro-1,1-dioxidebenzo[b]thiophene

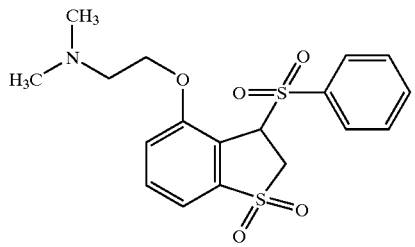

By the same procedure as described in Example 8 using the compound prepared in Example 23 instead of the compound prepared in Example 7, the compounds of the present invention having the following physical data were obtained.
Free Compound
TLC: Rf 0.47 (ethyl acetate:methanol:triethylamine= 8:2:1);
NMR (CDCl$_3$): δ2.33 (s, 6H), 2.52–2.77 (m, 2H), 3.72 (dd, J=15.0, 9.4 Hz, 1H), 3.79–3.89 (m, 1H), 4.00–4.12 (m, 1H), 4.18 (dd, J=15.0, 1.1 Hz, 1H), 5.35 (d-like, J=8.8 Hz, 1H), 6.99 (d, J=8.2 Hz, 1H), 7.28 (d, J=7.2 Hz, 1H), 7.43–7.66 (m, 4H), 7.72–7.77 (m, 2H).
Hydrochloride
TLC: Rf 0.47 (ethyl acetate:methanol:triethylamine= 8:2:1);
NMR (CD$_3$OD): δ3.05 (s, 6H), 3.52–3.76 (m, 2H), 3.83–3.99 (m, 2H), 4.38–4.63 (m, 2H), 5.89 (t, J=5.4 Hz, 1H), 7.30 (d, J=7.7 Hz, 1H), 7.39 (d, J=7.7 Hz, 1H), 7.51–7.59 (m, 2H), 7.66–7.78 (m, 4H).

EXAMPLES 24 (1)~24 (5)

By the same procedure as described in Example 14 using the compounds prepared in Examples 23 (1)~23 (5) instead of the compound prepared in Example 23, and if necessary, by converting into the corresponding salts by known methods, the following compounds of the present invention were obtained, with the proviso that when compounds of Example 23 (1) and Example 23 (3) were used, compounds of Example 24 (1b) and Example 24 (3b) were also generated respectively.

EXAMPLE 24 (1a)

4-(3-(N,N-Dimethylamino)propyl)oxy-3-phenylsulfonyl-2,3-dihydro-1,1-dioxidebenzo[b]thiophene

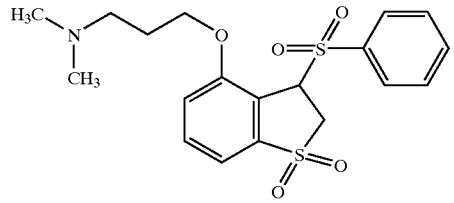

Free Compound
TLC: Rf 0.35 (ethyl acetate:methanol:triethylamine= 8:2:1);
NMR (CDCl$_3$): δ1.86 (quint, J=7.0 Hz, 2H), 2.26 (s, 6H), 2.47 (t, J=7.0 Hz, 2H), 3.74 (dd, J=15.0, 9.2 Hz, 1H), 3.83–4.03 (m, 2H), 4.21 (dd, J=15.0, 1.2 Hz, 1H), 5.25 (d-like, J=8.8 Hz, 1H), 6.99 (d, J=7.8 Hz, 1H), 7.24 (d, J=7.8 Hz, 1H), 7.48–7.74 (m, 6H).
Hydrochloride
TLC: Rf 0.35 (ethyl acetate:methanol:triethylamine= 8:2:1);
NMR (DMSO-$d_6$): δ2.15 (m, 2H), 2.80 (s, 6H), 3.31 (t, J=7.5 Hz, 2H), 3.75 (dd, J=15.2, 9.2 Hz, 1H), 4.15 (t, J=6.2 Hz, 2H), 4.31 (dd, J=15.2, 1.1 Hz, 1H), 5.69 (dd, J=9.2, 1.1 Hz, 1H), 7.32–7.39 (m, 2H), 7.55–7.72 (m, 3H), 7.80–7.85 (m, 3H).

EXAMPLE 24 (1b)

4-(3-(N-Cyanomethyl-N-methylamino)propyl)oxy-3-phenylsulfonyl-2,3-dihydro-1,1-dioxidebenzo[b]thiophene

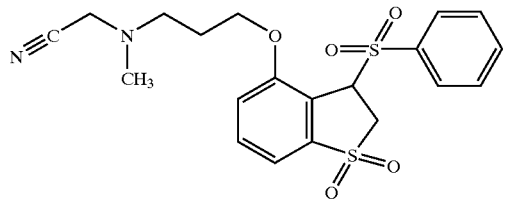

TLC: Rf 0.36 (ethyl acetate:triethylamine=9:1);

NMR (CDCl$_3$): δ1.88 (quint, J=6.6 Hz, 2H), 2.38 (s, 3H), 2.69 (m, 2H), 3.51 (d, J=17.0 Hz, 1H), 3.61 (d, J=17.0 Hz, 1H), 3.73 (dd, J=15.0, 9.4 Hz, 1H), 3.96 (m, 2H), 4.13 (dd, J=15.0, 1.0 Hz, 1H), 5.28 (d-iike, J=8.4 Hz, 1H), 7.00 (d, J=7.8 Hz, 1H), 7.24 (d, J=7.8 Hz, 1H), 7.42–7.74 (m, 6H).

EXAMPLE 24 (2)

5-(2-(N,N-Dimethylamino)ethyl)oxy-3-phenylsulfonyl-2,3-dihydeo-1,1-dioxidebenzo[b]thiophene

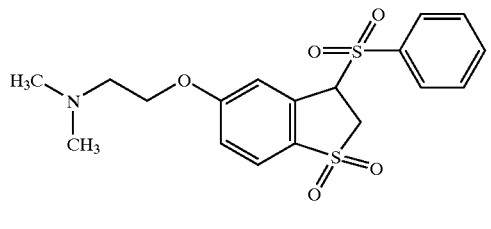

Free Compound

TLC: Rf 0.55 (ethyl acetate:methanol:triethylamine=8:2:1);

NMR (DMSO-$d_6$): δ2.23 (s, 6H) 2.66 (t, J=6 Hz, 2H), 3.77 (dd, J=15, 3 Hz, 1H), 3.98 (dd, J=15, 10 Hz, 1H), 4.10 (m, 2H), 5.71 (dd, J=10, 3 Hz, 1H), 7.05 (d, J=2 Hz, 1H), 7.25 (dd, J=9, 2 Hz, 1H), 7.58–7.84 (m, 6H).

Hydrochloride

TLC: Rf 0.55 (ethyl acetate:methanol:triethylamine=8:2:1);

NMR (DMSO-$d_6$): δ2.84 (s, 6H), 3.56 (m, 2H), 3.75 (dd, J=15, 4 Hz, 1H), 3.97 (dd, J=15, 9 Hz, 1H), 4.45 (m, 2H), 5.76 (dd, J=9, 4 Hz, 1H), 7.22 (d, J=2 Hz, 1H), 7.33 (dd, J=9, 2 Hz, 1H), 7.64 (m, 2H), 7.79 (m, 4H).

EXAMPLE 24 (3a)

6-(3-(N,N-Dimethylamino)propyl)oxy-3-phenylsulfonyl-2,3-dihydro-1,1-dioxidebenzo[b]thiophene

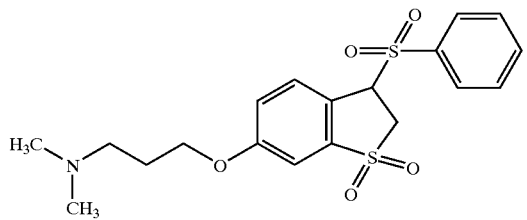

Free Compound

TLC: Rf 0.53 (ethyl acetate:methanol:triethylamine=8:2:1);

NMR (CDCl$_3$): δ1.97 (quint, J=6.6 Hz, 2H), 2.25 (s, 6H), 2.44 (t, J=6.6 Hz, 2H), 3.71 (dd, J=14.6, 7.6 Hz, 1H), 3.79 (dd, J=14.6, 5.6 Hz, 1H), 4.07 (t, J=6.6 Hz, 2H), 5.00 (dd, J=7.6, 5.6 Hz, 1H), 7.08 (d, J=2.6 Hz, 1H), 7.23 (dd, J=8.8, 2.6 Hz, 1H), 7.46–7.54 (m, 2H), 7.63–7.72 (m, 3H), 7.85 (d, J=8.8 Hz, 1H).

Hydrochloride

TLC: Rf 0.53 (ethyl acetate:methanol:triethylamine=8:2:1);

NMR (DMSO-$d_6$): δ2.17 (m, 2H), 2.78 (s, 6H), 3.20 (t, J=7.9 Hz, 2H), 3.77 (dd, J=15.4, 3.2 Hz, 1H), 4.00 (dd, J=5.4, 9.4 Hz, 1H), 4.18 (t, J=6.0 Hz, 2H), 5.71 (dd, J=9.4, 3.2 Hz, 1H), 7.30–7.38 (m, 2H), 7.58–7.67 (m, 3H), 7.75–7.79 (m, 3H).

EXAMPLE 24 (3b)

6-(3-(N-Cyanomethyl-N-methylamino)propyl)oxy-3-phenylsulfonyl-2,3-dihydro-1,1-dioxidebenzo[b]thiophene

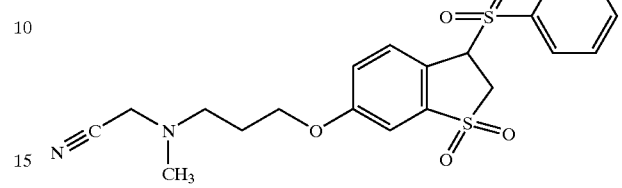

TLC: Rf 0.33 (ethyl acetate:hexane:triethylamine=6:3:1);

NMR (CDCl$_3$): δ1.97 (quint, J=6.5 Hz, 2H), 2.38 (s, 3H), 2.65 (t, J=6.5 Hz, 2H), 3.54 (s, 2H), 3.71 (dd, J=14.8, 7.8 Hz, 1H), 3.79 (dd, J=14.8, 5.2 Hz, 1H), 4.06 (t, J=6.5 Hz, 2H), 5.00 (dd, J=7.8, 5.2 Hz, 1H), 7.07 (d, J=2.6 Hz, 1H), 7.23 (dd, J=9.0, 2.6 Hz, 1H), 7.47–7.55 (m, 2H), 7.65–7.72 (m, 3H), 7.84 (d, J=9.0 Hz, 1H).

EXAMPLE 24 (4)

6-(2-(N,N-Dimethylamino)ethyl)oxy-3-phenylsulfonyl-2,3-dihydro-1,1-dioxidebenzo[b]thiophene

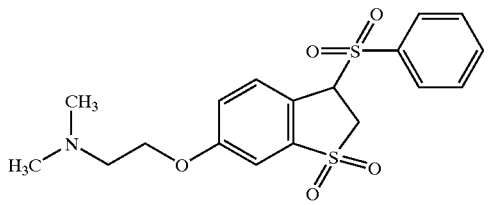

Free Compound

TLC: Rf 0.47 (ethyl acetate:methanol:triethylamine=9:1:1);

NMR (CDCl$_3$): δ2.34 (s, 6H), 2.75 (t, J=5.4 Hz, 2H), 3.74 (dd, J=14.8, 7.8 Hz, 1H), 3.79 (dd, J=14.8, 5.4 Hz, 1H), 4.09 (t, J=5.4 Hz, 2H), 5.00 (dd, J=7.8, 5.4 Hz, 1H), 7.06 (d, J=2.4 Hz, 1H), 7.28 (dd, J=8.8, 2.4 Hz, 1H), 7.47–7.52 (m, 2H), 7.62–7.69 (m, 3H), 7.84 (d, J=8.8 Hz, 1H).

Hydrochloride

TLC: Rf 0.47 (ethyl acetate:methanol:triethylamine=9:1:1);

NMR (DMSO-$d_6$): δ2.83 (d, J=4.5 Hz, 6H), 3.50–3.54 (m, 2H), 3.78 (dd, J=15.0, 3.0 Hz, 1H), 4.01 (dd, J=15.0, 9.4 Hz, 1H), 4.49 (t, J=5.1 Hz, 2H), 5.73 (dd, J=9.4, 3.0 Hz, 1H), 7.41–7.44 (m, 2H), 7.60–7.67 (m, 3H), 7.77–7.80 (m, 3H), 10.83 (br, 1H).

EXAMPLE 24 (5)

7-(2-(N,N-Dimethylamino)ethyl)oxy-3-phenylsulfonyl-2,3-dihydro-1,1-dioxidebenzo[b]thiophene.hydrochloride

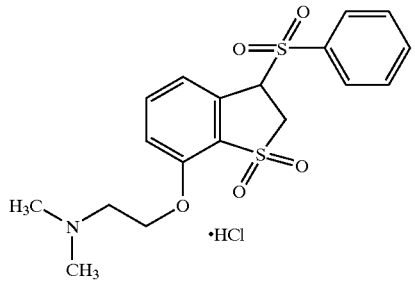

TLC: Rf 0.32 (ethyl acetate:methanol:triethylamine= 16:3:1);

NMR (DMSO-$d_6$): δ7.85–7.60 (6H, m), 7.37 (1H, d, J=8.2 Hz), 7.22 (1H, d, J=8.2 Hz), 5.81 (1H, dd, J=9.4, 3.2 Hz), 4.65–4.56 (2H, m), 3.97 (1H, dd, J=15, 9.4 Hz), 3.75 (1H, dd, J=15, 3.2 Hz), 3.56–3.45 (2H, m), 2.82 (6H, s).

EXAMPLE 25

4-(3-Aminophenylmethyl)oxy-3-phenylsulfonyl-2,3-dihydro-1,1-dioxidebenzo[b]thiophene

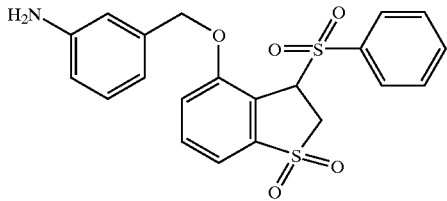

By the same procedure as described in Example 11 using the compound prepared in Example 20 (39) instead of the compound prepared in Example 10, the compound of the present invention having the following physical data was obtained.

TLC: Rf 0.34 (chloroform:tetrahydrofuran:28% ammonia water=100:50:1);

NMR (DMSO-$d_6$): δ7.80–7.55 (4H, m), 7.49 (2H, t, J=8 Hz), 7.31 (2H, dd, J=12, 8 Hz), 7.02 (1H, t, J=8 Hz), 6.60–6.45 (2H, m), 5.54 (1H, d, J=9 Hz), 5.10 (2H, bs), 4.91 (1H, d, J=12 Hz), 4.69 (1H, d, J=12 Hz), 4.20 (1H, d, J=15 Hz), 3.98 (1H, dd, J=15, 9 Hz).

EXAMPLE 26

4-(3-(Pyridin-3-ylcarbonylamino)phenylmethyl)oxy-3-phenylsulfonyl-2,3-dihydro-1,1-dioxidebenzo[b]thiophene

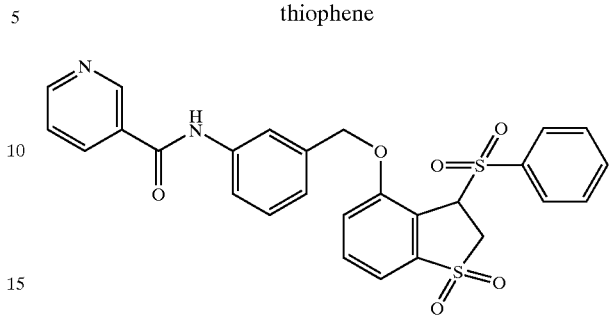

To a solution of the compound prepared in Example 25 (143 mg) in pyridine (6 ml) was added nicotinyl chloride-hydrochloride (77 mg). The mixture was stirred at room temperature for 1.5 hours. To the reaction mixture, water was added. The mixture was extracted by ethyl acetate. The extract was washed by water, a saturated aqueous solution of sodium chloride successively, dried over anhydrous sodium sulfate and concentrated. The residue was recrystallized from ethanol to give the compound of the present invention (127 mg) having the following physical data.

TLC: Rf 0.34 (ethyl acetate:methanol:28% ammonia water=100:10:1);

NMR (DMSO-$d_6$): δ9.12 (1H, d, J=2 Hz), 8.77 (1H, dd, J=5, 2 Hz), 8.31 (1H, d, J=8 Hz), 7.82 (1H, s), 7.78–7.52 (7H, m), 7.52–7.25 (5H, m), 7.19 (1H, d, J=7 Hz), 5.59 (1H, d, J=8.5 Hz), 5.11 (1H, d, J=12 Hz), 4.86 (1H, d, J=12 Hz), 4.20 (1H, d, J=15 Hz), 4.01 (1H, dd, J=15, 8.5 Hz).

EXAMPLE 26 (1)

4-(2-(Pyridin-3-ylcarbonylamino)ethyl)oxy-3-phenylsulfonyl-2,3-dihydro-1,1-dioxidebenzo[b]thiophene

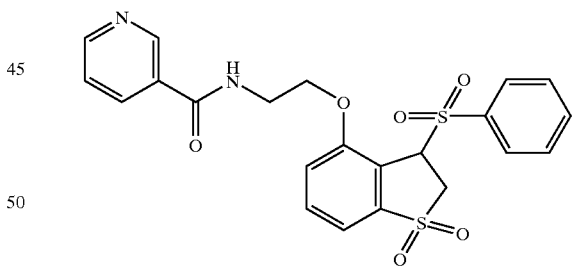

By the same procedure as described in Example 26 using the compound prepared in Example 23 instead of the compound prepared in Example 25, and if necessary, by converting into the corresponding salt by known methods, the compounds of the present invention having the following physical data were obtained.

Free Compound

TLC: Rf 0.43 (ethyl acetate:methanol:triethylamine= 8:1:1);

NMR (DMSO-$d_6$): δ3.36–3.55 (m, 2H), 3.81–3.88 (m, 1H), 4.02 (dd, J=15.0, 8.7 Hz, 1H), 4.04–4.10 (m, 1H), 4.13 (dd, J=15.0, 1.3 Hz, 1H), 5.61 (d-like, J=7.5 Hz, 1H), 7.31 (d, J=8.1 Hz, 1H), 7.35 (d, J=7.2 Hz, 1H), 7.48 (dd, J=8.1, 4.8 Hz, 1H), 7.56–7.68 (m, 3H), 7.71–7.77 (m, 3H), 8.15 (dt, J=8.1, 1.8 Hz, 1H), 8.65–8.68 (m, 1H), 8.68 (dd, J=4.8, 1.8 Hz, 1H), 8.98 (d, J=1.8 Hz, 1H).

Hydrochloride

TLC: Rf 0.43 (ethyl acetate:methanol:triethylamine= 8:1:1);

NMR (DMSO-$d_6$): δ3.41–3.56 (m, 2H), 3.83–3.89 (m, 1H), 4.01 (dd, J=15.0, 8.7 Hz, 1H), 4.07–4.12 (m, 1H), 4.12 (dd, J=15.0, 1.2 Hz, 1H), 5.67 (d-like, J=7.5 Hz, 1H), 7.31 (d, J=8.0 Hz, 1H), 7.34 (d, J=8.0 Hz, 1H), 7.56–7.61 (m, 2H), 7.65 (t, J=8.0 Hz, 1H), 7.71–7.76 (m, 3H), 7.83 (dd, J=8.1, 5.4 Hz, 1H), 8.59 (dt, J=8.1, 1.6 Hz, 1H), 8.87 (dd, J=5.4, 1.6 Hz, 1H), 9.10 (t, J=5.4 Hz, 1H), 9.19 (d, J=1.6 Hz, 1H).

EXAMPLE 27

5-Methyl-3-phenylsulfonyl-2,3-dihydro-1,1-dioxidebenzo[b]thiophene

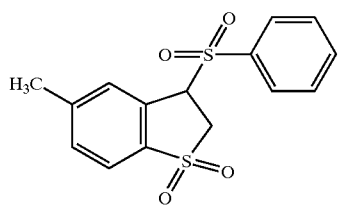

To a solution of 5-methyl-1,1-dioxidebenzo[b]thiophene (353 mg) in ethanol (19.5 ml), were added water (0.5 ml), acetic acid (0.4 ml) and benzenesulfonic acid sodium salt (940 mg) successively. The reaction mixture was refluxed for 7 hours. The reaction mixture was cooled to room temperature. The crystals that appeared were separated by filtration. The crystals were washed by water, ethanol and hexane, successively, to give the compound of the present invention (381 mg) having the following physical data.

TLC: Rf 0.32 (hexane:ethyl acetate=1:1);

NMR (CDCl$_3$): δ2.52 (s, 3H), 3.66 (dd, J=14.6, 8.7 Hz, 1H), 3.77 (dd, J=14.6, 4.9 Hz, 1H), 5.02 (dd, J=8.7, 4.9 Hz, 1H), 7.41–7.57 (m, 4H), 7.64–7.69 (m, 3H), 7.80 (s-like, 1H).

EXAMPLES 27 (1)–27 (5)

By the same procedure as described in Example 27 using corresponding benzo[b]thiophene compounds instead of 5-methyl-1,1-dioxidebenzo[b]thiophene, the following compounds of the present invention were obtained.

EXAMPLE 27 (1)

5-(4-Chlorophenylcarbonyl)amino-3-phenylsulfonyl-2,3-dihydro-1,1-dioxidebenzo[b]thiophene

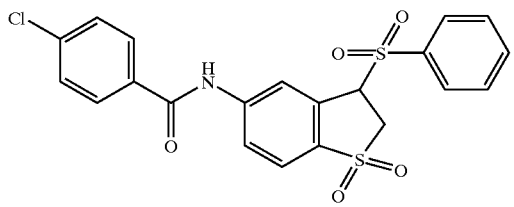

TLC: Rf 0.27 (methylene chloride:ethyl acetate=8:1);

NMR (DMSO-$d_6$): δ3.74 (dd, J=15.1, 3.7 Hz, 1H), 3.95 (dd, J=15.1, 9.3 Hz, 1H), 5.83 (dd, J=9.3, 3.7 Hz, 1H), 7.58–7.65 (m, 2H), 7.66 (d, J=8.7 Hz, 2H), 7.73–7.83 (m, 4H), 8.04 (d, J=8.7 Hz, 2H), 8.10 (dd, J=8.8, 2.0 Hz, 1H), 8.40 (d, J=2.0 Hz, 1H), 10.86 (s, 1H).

EXAMPLE 27 (2)

4-Cyano-3-phenylsulfonyl-2,3-dihydro-1,1-dioxidebenzo[b][thiophene

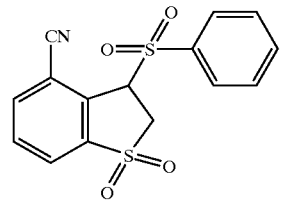

TLC: Rf 0.60 (methylene chloride:ethyl acetate=8:1);

NMR (DMSO-$d_6$): δ3.95 (dd, J=15, 10 Hz, 1H), 4.15 (d, J=15 Hz, 1H), 5.80 (d, J=10 Hz, 1H), 7.60–7.80 (m, 2H), 7.80–7.90 (m, 3H), 7.95 (t, J=7.5 Hz, 1H), 8.20 (d, J=7.5 Hz, 1H), 8.35 (d, J=7.5 Hz, 1H).

EXAMPLE 27 (3)

6-Nitro-3-phenylsulfonyl-2,3-dihydro-1,1-dioxidebenzo[b]thiophene

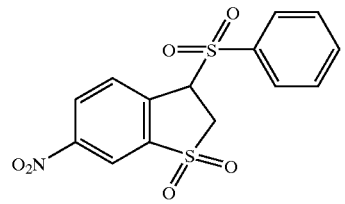

TLC: Rf 0.44 (hexane:ethyl acetate=1:1);

NMR (DMSO-$d_6$): δ3.97 (dd, J=15.3, 3.0 Hz, 1H), 4.16 (dd, J=15.3, 9.3 Hz, 1H), 6.00 (dd, J=9.3, 3.0 Hz, 1H), 7.62–7.67 (m, 2H), 7.79–7.83 (m, 3H), 8.02 (d, J=8.4 Hz, 1H), 8.61 (s-like, 1H), 8.62 (dd, J=8.4, 2.1 Hz, 1H).

EXAMPLE 27 (4)

4,7-Dimethoxy-3-phenylsulfonyl-2,3-dihydro-1,1-dioxidebenzo[b]thiophene

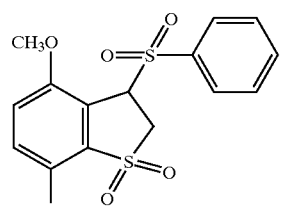

TLC: Rf 0.48 (ethyl acetate );

NMR (DMSO-$d_6$): δ3.27 (s, 3H), 3.85 (s, 3H), 3.96 (dd, J=15.2, 8.8 Hz, 1H), 4.12 (dd, J=15.2, 1.5 Hz, 1H), 5.49 (dd, J=8.8, 1.5 Hz, 1H), 7.12 (d, J=9.0 Hz, 1H), 7.21 (d, J=9.0 Hz, 1H), 7.60–7.78 (m, 5H).

EXAMPLE 27 (5)

4,7-Bis(3-hydroxypropyl)oxy-3-phenylsulfonyl-2,3-dihydro-1,1-dioxidebenzo[b]thiophene

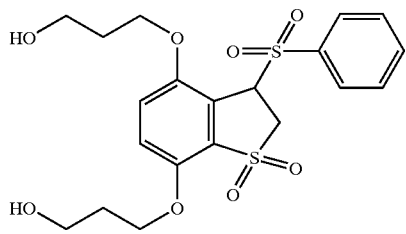

TLC: Rf 0.34 (ethyl acetate:methanol=9:1);

NMR (DMSO-$d_6$): δ1.52–1.57 (m, 2H), 1.83 (quint, J=6.3 Hz, 2H), 3.43 (q, J=6.3 Hz, 2H), 3.55 (q, J=5.8 Hz, 2H), 3.60–3.67 (m, 1H), 3.80–3.87 (m, 1H), 3.96 (dd, J=14.8, 9.0 Hz, 1H), 4.09 (d-like, J=14.8 Hz, 1H), 4.08–4.21 (m, 2H), 4.46 (t, J=5.1 Hz, 1H), 4.52 (t, J=5.1 Hz, 1H), 5.45 (d-like, J=7.8 Hz, 1H), 7.14 (d, J=9.0 Hz, 1H), 7.20 (d, J=9.0 Hz, 1H), 7.58–7.63 (m, 2H), 7.72–7.77 (m, 3H).

EXAMPLE 28

4-(Pyridin-3-ylmethyl)carbamoyl-1,1-dioxidebenzo[b]thiophene

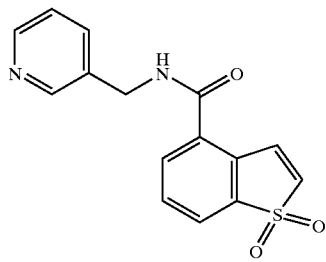

To 4-carboxy-1,1-dioxidebenzo[b]thiophene (prepared by the method described in Example 107 hereafter) (270 mg), was added thionyl chloride (2.0 ml). The mixture was refluxed for 2 hours, and concentrated. To a solution of (pyridin-3-ylmethyl)amine (154 mg) dissolved in methylene chloride (6.0 ml) and triethylamine (260 mg), a solution of the said chloride in methylene chloride (4.0 ml) were added dropwise. The mixture was stirred for 2 hours at room temperature. To the reaction mixture, ice-water and a 1N aqueous solution of sodium hydroxide (1.5 ml) were added dropwise. The mixture was extracted by ethyl acetate (40 ml). The extract was washed by a saturated sodium chloride, dried over anhydrous magnesium sulfate, and concentrated. The residue was recrystallized from a mixed solvent of ethyl acetate and hexane to give the compound of the present invention (330 mg) having the following physical data.

TLC: Rf 0.48 (methylene chloride:methanol=10:1);

NMR (CDCl$_3$): δ8.56 (d, J=2.1 Hz, 1H), 8.53 (dd, J=4.5, 2.1 Hz, 1H), 7.93 (dd, J=7.2, 0.6 Hz, 1H), 7.79–7.72 (m, 2H), 7.70 (dd, J=7.5, 0.6 Hz, 1H), 7.55 (t, J=7.8 Hz, 1H), 7.31 (dd, J=7.8, 4.5 Hz, 1H), 6.86 (t, J=6.3 Hz, 1H), 6.77 (d, J=7.2 Hz, 1H), 4.65 (d, J=6.3 Hz, 2H).

EXAMPLES 28 (1)~28 (33)

By the same procedure as described in Example 28 using carboxylic acid corresponding to 4-carboxy-1,1-dioxidebenzo[b]thiophene and amine derivative corresponding to (pyridin-3-ylmethyl)amine, and if necessary, by converting into the corresponding salt by a known method, the compounds of the present invention were obtained.

In the preparation of a compound of Example 28 (33), 4-aminomethyl-1,1-dioxidebenzo[b]thiophene and pyridin-3-ylcarboxylic acid were subjected to reaction.

EXAMPLE 28 (1)

4-(4-Benzylpiperazin-1-yl)carbonyl-1,1-dioxidebenzo[b]thiophene

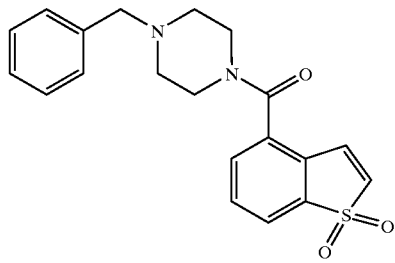

TLC: Rf 0.30 (ethyl acetate:methanol=50:1);

NMR (CDCl$_3$): δ7.75 (d, J=7.4 Hz, 1H), 7.56 (t, J=7.4 Hz, 1H), 7.47 (d, J=7.4 Hz, 1H), 7.40–7.20 (m, 6H), 6.78 (d, J=7.0 Hz, 1H), 3.83 (m, 2H), 3.55 (s, 2H), 3.34 (m, 2H), 2.55 (m, 2H), 2.37 (m, 2H).

EXAMPLE 28 (2)

4-(N-(2-(Pyridin-3-yl)ethyl)-N-methylcarbamoyl)-1,1-dioxidebenzo[b]thiophene

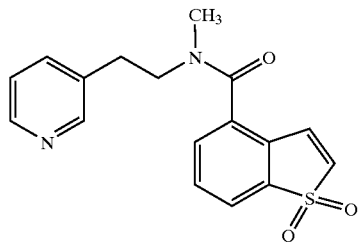

MS (APCI, Pos.): m/z 361 (M+MeOH+H)$^+$, 329 (M+H)$^+$.

EXAMPLE 28 (3)

4-(2-(2-Hydroxyethoxy)ethyl)carbamoyl-1,1-dioxidebenzo[b]thiophene

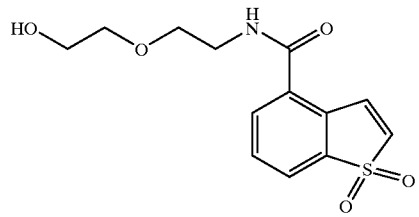

MS (APCI, Pos.): m/z 330 (M+MeOH+H)$^+$, 298 (M+H)$^+$.

EXAMPLE 28 (4)

4-(2,4-Dimethoxyphenylmethyl)carbamoyl-1,1-dioxidebenzo[b]thiophene

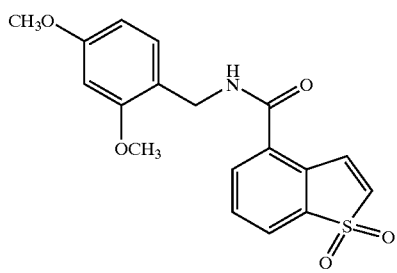

TLC: Rf 0.68 (ethyl acetate);

NMR (CDCl$_3$): δ7.90 (d, J=7.5 Hz, 1H), 7.75 (d, J=7.5 Hz, 1H), 7.60 (d, J=7.5 Hz, 1H), 7.55 (t, J=7.5 Hz, 1H), 7.25 (d, J=10 Hz, 1H), 6.75 (d, J=7.5 Hz, 1H), 6.60–6.40 (m, 3H), 4.55 (d, J=7.5 Hz, 2H), 3.85 (s, 3H), 3.80 (s, 3H).

EXAMPLE 28 (5)

4-(1-Benzylpiperidin-4-yl)carbamoyl-1,1-dioxidebenzo[b]thiophene

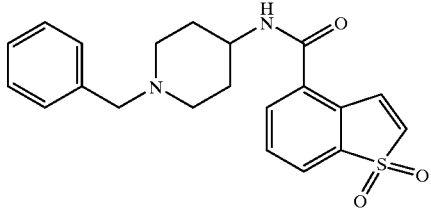

Free Aicd

TLC: Rf 0.50 (ethyl acetate:methanol=8:1.5);

NMR (CDCl$_3$): δ7.90 (d, J=7.5 Hz, 1H), 7.80 (d, J=7.5 Hz, 1H), 7.60 (d, J=7.5 Hz, 1H), 7.55 (t, J=7.5 Hz, 1H), 7.50–7.20 (m, 5H), 6.75 (d, J=7.5 Hz, 1H), 6.05–5.95 (m, 1H) 4.10–3.90 (m, 1 H), 3.55 (s, 2H), 3.00–2.90 (m, 2H), 2.30–2.10 (m, 2H), 2.10–1.90 (m, 2H), 1.70–1.50 (m, 2H).

Hydrochloride

TLC: Rf 0.44 (methanol:ethyl acetate=1:10);

NMR (CD$_3$OD): δ7.90–7.75 (m, 3H), 7.75–7.45 (m, 6H), 7.08 (d, J=7.0 Hz, 1H), 4.34 (s, 2H), 4.27–4.05 (m, 1H), 3.61–3.42 (m, 2H), 3.33–3.10 (m, 2H), 2.34–2.15 (m,2H), 2.12–1.81 (m, 2H).

Methanesulfonic Acid Salt

TLC: Rf 0.44 (methanol:ethyl acetate=1:10);

NMR (CD$_3$OD). δ7.89–7.74 (m, 3H), 7.73–7.60 (m, 1H), 7.60–7.45 (m, 5H), 7.08 (d, J=7.0 Hz, 1H), 4.34 (s, 2H), 4.27–4.03 (m, 1H), 3.68–3.38 (m, 2H), 3.38–3.06 (m, 2H), 2.67 (s, 3H), 2.38–1.72 (m, 4H).

EXAMPLE 28 (6)

4-(Pyridin-4-ylmethyl)carbamoyl-1,1-dioxidebenzo[b]thiophene

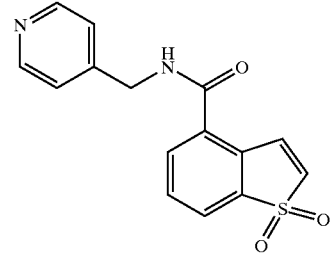

TLC: Rf 0.29 (ethyl acetate:methanol=19:1);

NMR (CDCl$_3$+CD$_3$OD): δ8.50 (d, J=7 Hz, 2H), 8.25 (broad-t, J=7 Hz, 1H), 7.95 (d, J=7 Hz, 1H), 7.80 (d, J=8 Hz, 2H), 7.60 (t, J=8 Hz, 1H), 7.30 (d, J=7 Hz, 2H), 6.80 (d, J=7 Hz, 1H), 4.60 (d, J=7 Hz, 2H).

EXAMPLE 28 (7)

4-(2-t-Butoxycarbonylethyl)carbamoyl-1,1-dioxidebenzo[b]thiophene

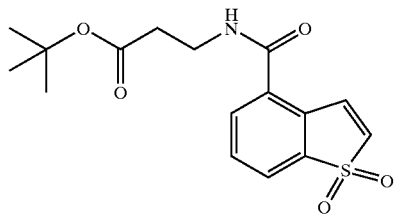

TLC: Rf 0.40 (ethyl acetate:hexane=3:2);

NMR (CDCl$_3$): δ8.00 (d, J=7 Hz, 1H), 7.80 (d, J=8 Hz, 1H), 7.70 (d, J=8 Hz, 1H), 7.60 (t, J=8 Hz, 1H), 6.95 (broad-s, 1H), 6.80 (d, J=7 Hz, 1H), 3.70 (q, J=7 Hz, 2H), 2.60 (t, J=7 Hz, 2H), 1.45 (s, 9H).

EXAMPLE 28 (8)

4-(Thiophen-2-ylmethyl)carbamoyl-1,1-dioxidebenzo[b]thiophene

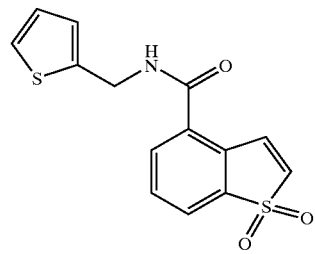

TLC: Rf 0.48 (chloroform:methanol=9:1);

NMR (CDCl$_3$+DMSO-d$_6$): δ8.50 (t, J=7 Hz, 1H), 7.95 (d, J=6 Hz, 1H), 7.85 (d, J=8 Hz, 1H), 7.75 (d, J=8 Hz, 1H), 7.55 (t, J=8 Hz, 1H), 7.25 (d, J=6 Hz, 1H), 7.05 (d, J=3 Hz, 1H), 6.95 (dd, J=3 Hz and 6 Hz, 1H), 6.80 (d, J=6 Hz, 1H), 4.75 (d, J=7 Hz, 2H).

EXAMPLE 28 (9)

4-Benzylcarbamoyl-1,1-dioxidebenzo[b]thiophene

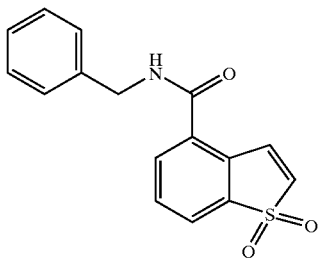

TLC: Rf 040 (ethyl acetate:hexane=1:1);

NMR (CDCl$_3$+DMSO-d$_6$): δ7.99 (d, J=7.2 Hz, 1H), 7.81–7.75 (m, 2H), 7.56 (t, J=7.5 Hz, 1H), 7.43 (t, J=5.7 Hz, 1H), 7.40–7.27 (m, 5H), 6.78 (d, J=7.2 Hz, 1H), 4.63 (d, J=5.7 Hz, 2H).

EXAMPLE 28 (10)

4-(Pyridin-2-ylmethyl)carbamoyl-1,1-dioxidebenzo[b]thiophene

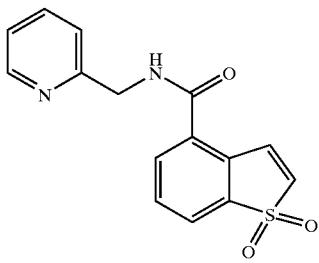

TLC: Rf 0.30 (ethyl acetate:hexane=1:1);

NMR (CDCl$_3$): δ8.56 (d, J=5.1 Hz, 1H), 8.05 (dd, J=7.2, 0.9 Hz, 1H), 7.84 (t, J=7.2 Hz, 1H), 7.73 (dt, J=0.9, 7.8 Hz, 1H), 7.68 (t, J=5.1 Hz, 1H), 7.61 (t, J=7.8 Hz, 1H), 7.33 (d, J=7.8 Hz, 1H), 7.59–7.23 (m, 2H), 6.78 (d, J=6.9 Hz, 1H), 4.76 (d, J=5.1 Hz, 2H).

EXAMPLE 28 (11)

4-(2-(Piperidin-1-yl)ethyl)carbamoyl-1,1-dioxidebenzo[b]thiophene

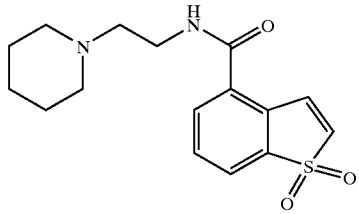

Free Aicd

TLC: Rf 0.35 (methylene chloride:methanol=10:1);

NMR (CDCl$_3$): δ8.04 (dd, J=7.2, 0.9 Hz, 1H), 7.80 (dt, J=7.8, 0.9 Hz, 1H), 7.72 (dd, J=7.8, 0.9 Hz, 1H), 7.59 (t, J=7.8 Hz, 1H), 7.02 (bs, 1H), 6.77 (d, J=7.2 Hz, 1H), 3.54 (q, J=5.7 Hz, 2H), 2.58 (t, J=5.7 Hz, 2H), 2.50–2.40 (m, 4H), 1.76–1.43 (m, 6H).

Hydrochloride

TLC: Rf 0.60 (methylene chloride:methanol:triethylamine=8:1.5:0.5);

NMR (DMSO-d$_6$): δ10.20 (br. s, 1H), 9.25–9.10 (m, 1H), 8.01 (d, J=7.0 Hz, 1H), 7.99 (d, J=7.0 Hz, 1H), 7.93 (d, J=6.9 Hz, 1H), 7.73 (t, J=7.0 Hz, 1H), 7.47 (d, J=6.9 Hz, 1H), 3.80–3.60 (m, 2H), 3.60–3.50 (m, 2H), 3.45–3.15 (m, 2H), 3.10–2.80 (m, 2H), 2.00–1.70 (m, 5H), 1.55–1.30 (m, 1H).

EXAMPLE 28 (12)

4-((1S)-1-t-Butoxycarbonyl-2-methylpropyl)carbamoyl-1,1-dioxidebenzo[b]thiophene

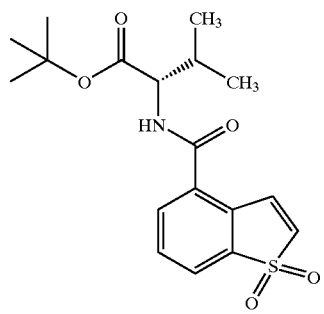

TLC: Rf 0.48 (hexane:ethyl acetate=1:1);

NMR (CDCl$_3$): δ7.95 (d, J=7.2 Hz, 1H), 7.81 (d, J=7.8 Hz, 1H), 7.77 (d, J=7.8 Hz, 1H), 7.59 (t, J=7.8 Hz, 1H), 6.78 (d, J=7.2 Hz, 1H), 6.56 (d, J=8.4 Hz, 1H), 4.64 (dd, J=8.4, 4.2 Hz, 1H), 2.36–2.27 (m, 1H), 1.51 (s, 9H), 1.02 (d, J=6.9 Hz, 3H), 0.98 (d, J=6.9 Hz, 3H).

EXAMPLE 28 (13)

4-(2-Fluorophenylmethyl)carbamoyl-1,1-dioxidebenzo[b]thiophene

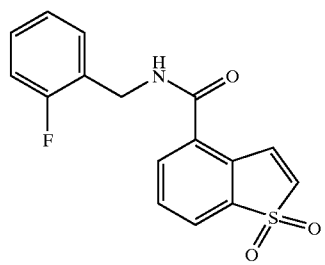

TLC: Rf 0.60 (chloroform:methanol=9:1);

NMR (CDCl$_3$+DMSO-d$_6$): δ7.95 (broad peak, 1H), 7.95 (d, J=7 Hz, 1H), 7.80 (d, J=8 Hz, 1H), 7.78 (d, J=8 Hz, 1H), 7.55 (t, J=8 Hz, 1H), 7.50–7.20 (m, 2H), 7.50–7.00 (m, 2H), 6,77 (d, J=7 Hz, 1H), 4.62 (d, J=7 Hz, 2H).

EXAMPLE 28 (14)

4-(3-Fluorophenylmethyl)carbamoyl-1,1-dioxidebenzo[b]thiophene

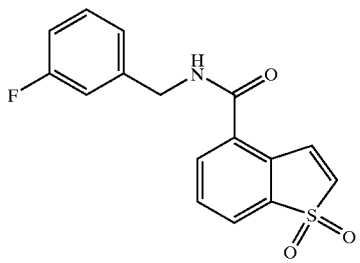

TLC: Rf 0.50 (chloroform:methanol=9:1);

NMR (CDCl$_3$+DMSO-d$_6$): δ8.40 (broad peak, 1H), 7.98 (d, J=7 Hz, 1H), 7.85 (d, J=8 Hz, 1H), 7.80 (d, J=8 Hz, 1H), 7.55 (t, J=8 Hz, 1H), 7.40–7.25 (m, 1H), 7.20–6.90 (m, 3H), 6.80 (d, J=7 Hz, 1H), 4.60 (d, J=7 Hz, 2H).

EXAMPLE 28 (15)

4-(3-Methylphenylmethyl)carbamoyl-1,1-dioxidebenzo[b]thiophene

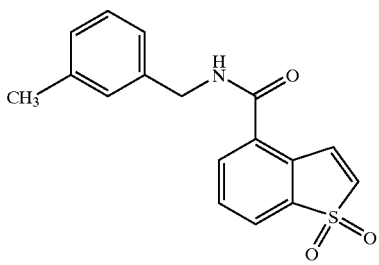

TLC: Rf 0.60 (chloroform:methanol=9:1);

NMR (CDCl$_3$): δ7.95 (d, J=7 Hz, 1H), 7.75 (d, J=8 Hz, 1H), 7.65 (d, J=8 Hz, 1H), 7.52 (t, J=8 Hz, 1H), 7.30–7.20 (m, 1H), 7.20–7.10 (m, 3H), 6.75 (d, J=7 Hz, 1H), 6.40 (broad peak, 1H), 4.60 (d, J=7 Hz, 2H), 2.40 (s, 3H).

EXAMPLE 28 (16)

4-(2-Methoxyphenylmethyl)carbamoyl-1,1-dioxidebenzo[b]thiophene

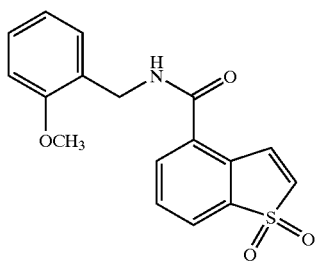

TLC: Rf 0.64 (chloroform:methanol=9:1);

NMR (CDCl$_3$+DMSO-d$_6$): δ7.93 (d, J=7 Hz, 1H), 7.85–7.70 (m, 3H), 7.55 (t, J=8 Hz, 1H), 7.30 (m, 2H), 6.92 (m, 2H), 6.78 (d, J=7 Hz, 1H), 4.60 (d, J=7 Hz, 2H), 3.90 (s, 3H).

EXAMPLE 28 (1)

4-(2,3-dimethoxyphenylmethyl)carbamoyl-1,1-dioxidebenzo[b]thiophene

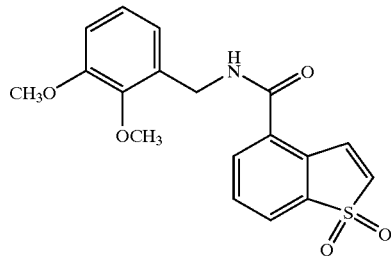

TLC: Rf 0.63 (chloroform:methanol=9:1);

NMR (CDCl$_3$+DMSO-d$_6$): δ7.97 (d, J=7.2 Hz, 1H), 7.77 (d, J=7.6 Hz, 1H), 7.76 (d, J=7.6 Hz, 1H), 7.73 (broad peak, 1H), 7.54 (t, J=7.6 Hz, 1H), 7.06 (t, J=7.8 Hz, 1H), 7.00–6.85 (m, 2H), 6.77 (d, J=7.2 Hz, 1H), 4.63 (d, J=5.6 Hz, 2H), 3.90 (s, 3H), 3.88 (s, 3H).

EXAMPLE 28 (18)

4-(3,4-Dimethoxyphenylmethyl)carbamoyl-1,1-dioxidebenzo[b]thiophene

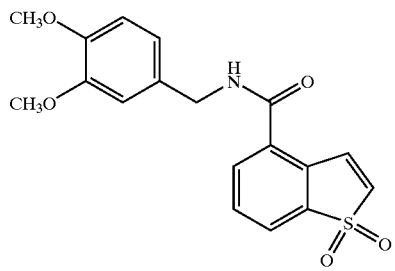

TLC: Rf 0.53 (chloroform:methanol=9:1);

NMR (CDCl$_3$+DMSO-d$_6$): δ8.57 (t-like, J=5.8 Hz, 1H), 7.97 (d, J=7.2 Hz, 1H), 7.86 (d, J=7.8 Hz, 1H), 7.77 (d, J=7.8 Hz, 1H), 7.57 (t, J=7.8 Hz, 1H), 7.00–6.80 (m, 4H), 4.53 (d, J=5.8 Hz, 2H), 3.88 (s, 3H), 3.87 (s, 3H).

EXAMPLE 28 (19)

4-(2,5-Difluorophenylmethyl)carbamoyl-1,1-dioxidebenzo[b]thiophene

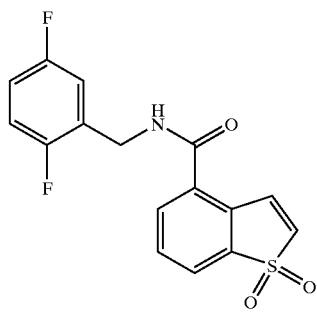

TLC: Rf 0.45 (chloroform:methanol=9:1);

NMR (CDCl$_3$+DMSO-d$_6$): δ8.78 (t, J=6.0 Hz, 1H), 7.97 (dd, J=7.0 Hz and 1.0 Hz, 1H), 7.89 (dd, J=7.6 Hz and 1.0

Hz, 1H), 7.79 (d, J=7.6 Hz, 1H), 7.59 (t, J=7.6 Hz, 1H), 7.20–6.90 (m, 3H), 6.82 (d, J=7.0 Hz, 1H), 4.60 (d, J=6.0 Hz, 1H).

EXAMPLE 28 (20)

4-(3,4,5-Trimethoxyphenylmethyl)carbamoyl-1,1-dioxidebenzo[b]thiophene

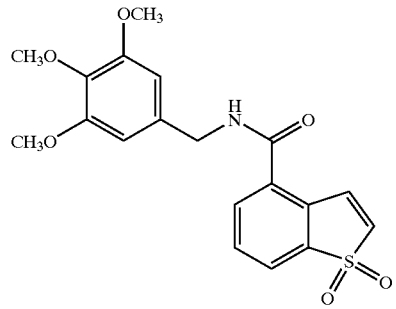

TLC: Rf 0.33 (chloroform:methanol=9:1);

NMR (CDCl$_3$+DMSO-d$_6$): δ8.00 (broad peak, 1H), 7.98 (dd, J=7.2 Hz and 1.0 Hz, 1H), 7.82 (dd, 7.6 Hz and 1.0 Hz, 1H), 7.78 (d, J=7.6 Hz, 1H), 7.56 (t, J=7.6 Hz, 1H), 6.79 (d, J=7.2 Hz, 1H), 6.61 (s, 2H), 4.54 (d, J=5.8 Hz, 2H), 3.86 (s, 6H), 3.83 (s, 3H).

EXAMPLE 28 (21)

4-(Benzimidazol-2-ylmethyl)carbamoyl-1,1-dioxidebenzo[b]thiophene

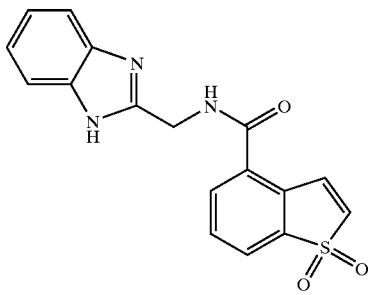

TLC: Rf 0.28 (chloroform:methanol=9:1);

NMR (CDCl$_3$+DMSO-d$_6$): δ8.97 (t, J=56Hz, 1H), 8.08 (d, J=7.2 Hz, 1H), 7.94 (dd, J=7.8 Hz and 1.0 Hz, 1H), 7.79 (dd, J=7.8 Hz and 1.0 Hz, 1H), 7.62–7.50 (m, 3H), 730–7.15 (m, 2H), 6.81 (d, J=7.2 Hz, 1H), 4.85 (d, J=5.6 Hz, 2H).

EXAMPLE 28 (22)

4-(3,5-Difluorophenylmethyl)carbamoyl-1,1-dioxidebenzo[b]thiophene

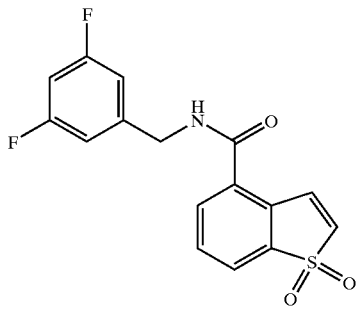

TLC: Rf 0.57 (chloroform:methanol=9:1);

NMR (CDCl$_3$+DMSO-d$_6$): δ9.11 (t, J=5.8 Hz, 1H), 7.98 (dd, J=7.2 Hz and 1.0 Hz, 1H), 7.93 (dd, J=7.6 Hz and 1.0 Hz, 1H), 7.81 (d, J=7.6 Hz, 1H), 7.62 (t, J=7.6 Hz, 1H), 7.00–6.90 (m, 2H), 6.90 (d, J=7.2 Hz, 1H), 6.80–6.68 (m, 1H), 4.55 (d, J=5.8 Hz, 2H).

EXAMPLE 28 (23)

4-(N-Benzyl-N-methylcarbamoyl)-1,1-dioxidebenzo[b]thiophene

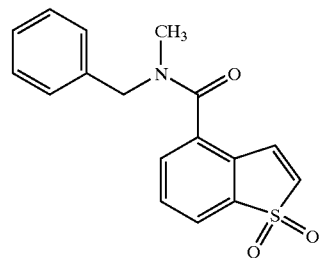

TLC: Rf 0.69 (chloroform:methanol=9:1);

NMR (CDCl$_3$): δ7.80–7.70 (m, 1H), 7.65–7.47 (m, 2H), 7.47–7.25 (m, 5H), 7.15–7.00 (m, 1H), 6.80–6.72 (m, 1H), 4.78 and 4.44 (each s, total 2H), 3.12 and 2.84 (each s, total 3H).

EXAMPLE 28 (24)

4-(4-Nitrophenylmethyl)carbamoyl-1,1-dioxidebenzo[b]thiophene

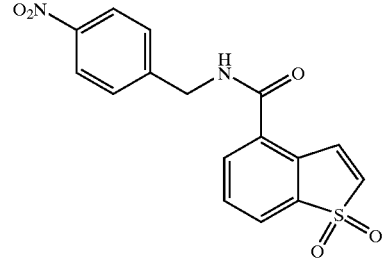

TLC: Rf 0.44 (chloroform:methanol=9:1);

NMR (CDCl$_3$+DMSO-d$_6$): δ9.20 (t, J=5.8 Hz, 1H), 8.20 (d, J=8 Hz, 2H), 7.98 (d, J=7 Hz, 1H), 7.93 (d, J=7.5 Hz,

1H), 7.81 (d, J=7.5 Hz, 1H), 7.62 (t, J=7.5 Hz, 1H), 7.57 (d, J=8 Hz, 2H), 6.89 (d, J=7 Hz, 1H), 4.67 (d, J=5.8 Hz, 2H).

EXAMPLE 28 (25)

5-(2-Hydroxyethyl)carbamoyl-1,1-dioxidebenzo[b]thiophene

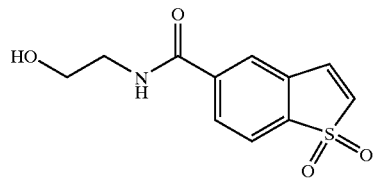

TLC: Rf 0.38 (ethyl acetate);

NMR (CDCl$_3$+CD$_3$OD): δ7.98 (dd, J=8.0 Hz, 1.2 Hz, 1H), 7.88 (d, J=1.2 Hz, 1H), 7.77 (d, J=8.0 Hz, 1H), 7.31 (d, J=6.8 Hz, 1H), 6.81 (d, J=6.8 Hz, 1H), 3.78 (t, J=4.8 Hz, 2H), 3.57 (t, J=4.8 Hz, 2H).

EXAMPLE 28 (26)

5-(Pyridin-3-ylmethyl)carbamoyl-4-methoxy-1,1-dioxidebenzo[b]thiophene

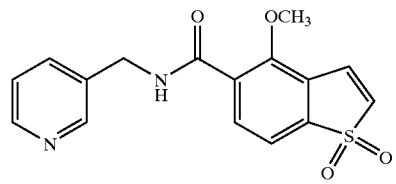

MS (APCI,J Pos.): m/z 363 (M+MeOH+H)$^+$, 331 (M+H)$^-$.

EXAMPLE 28 (27)

5-(2-Dimethylaminoethyl)carbamoyl-4-methoxy-1,1-dioxidebenzo[b]thiophene

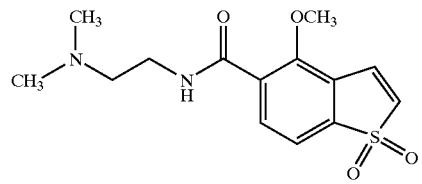

TLC: Rf 0.27 (methylene chloride:methanol=10:1);

NMR (CDCl$_3$): δ8.23 (d, J=8.1 Hz, 1H), 8.03 (t, J=5.7 Hz, 1H), 7.55 (d, J=8.1 Hz, 1H), 7.41 (d, J=6.9 Hz, 1H), 6.76 (d, J=6.9 Hz, 1H), 3.94 (s, 3H) 3.57 (q, J=5.7 Hz, 2H), 2.53 (t, J=5.7 Hz, 2H), 2.30 (s, 6H).

EXAMPLE 28 (28)

5-Dimethylcarbamoyl-4-methoxy-1,1-dioxidebenzo[b]thiophene

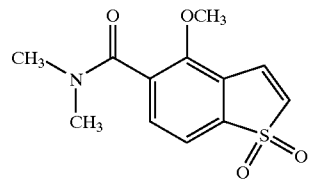

TLC: Rf 0.35 (methanol:ethyl acetate=5:95);

NMR (CDCl$_3$): δ7.52–7.38 (m, 3H), 6.75 (d, J=7.4 Hz, 1H), 3.93 (s, 3H), 3.15 (s, 3H), 2.88 (s, 3H).

EXAMPLE 28 (29)

5-(2,3,4,5,6,7-Hexahydro-1H-azepin-1-yl)carbonyl-4-methoxy-1,1-dioxidebenzo[b]thiophene

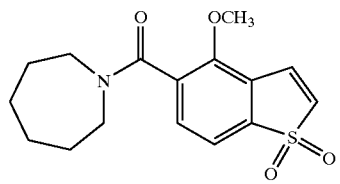

TLC: Rf 0.60 (methylene chloride:methanol=10:1);

NMR (CDCl$_3$): δ7.48 (dd, J=7.5, 0.9 Hz, 1H), 7.42 (dd, J=6.9, 0.9 Hz, 1H), 7.38 (d, J=7.5 Hz, 1H), 6.74 (d, J=6.9 Hz, 1H), 3.95 (s, 3H), 3.80–3.56 (m, 2H), 3.30–3.20 (m, 2H), 1.90–1.75 (m, 2 H), 1.75–1.40 (m, 6H).

EXAMPLE 28 (30)

5-(2,3-Dihydroindol-1-yl)carbonyl-4-methoxy-1,1-dioxidebenzo[b]thiophene

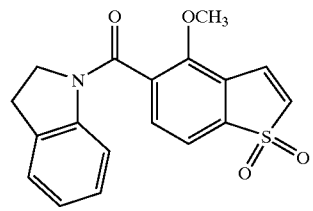

TLC: Rf 0.82 (methylene chloride:methanol=10:1);

NMR (CDCl$_3$): δ8.31 (d, J=7.8 Hz, 1H), 7.54 (s, 2H), 7.45 (d, J=6.9 Hz, 1H), 7.33–7.20 (m, 2H), 7.20–7.07 (m, 1H), 6.77 (d, J=6.9 Hz, 1H), 3.97 (s, 3H), 3.90–3.66 (m, 2H), 3.25–3.10 (m, 2H).

EXAMPLE 28 (31)

5-(4-(2-Chlorophenyl)piperazin-1-yl)carbonyl-4-methoxy-1,1-dioxidebenzo[b]thiophene

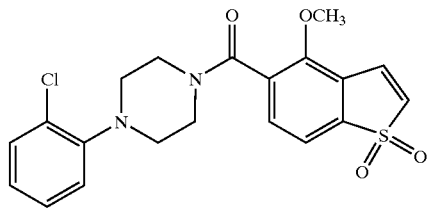

TLC: Rf 0.30 (ethyl acetate:hexane=1:1);

NMR (CDCl$_3$): δ7.51 (d, J=7.8 Hz, 1H), 7.46 (d, J=7.8 Hz, 1H), 7.43–7.35 (m, 2H), 7.30–7.20 (m, 1H), 7.06–6.99 (m, 2H), 6.76 (d, J=6.9 Hz, 1H), 4.10–3.90 (m, 2H), 3.98 (s, 3H), 3.54–3.37 (m, 2 H),3.20–2.90 (m, 4H).

EXAMPLE 28 (32)

5-(4-(2-(2-Trifluoromentylphenyl)ethyl)piperazin-1-yl)carbonyl-4-methoxy-1,1-dioxidebenzo[b]thiophene

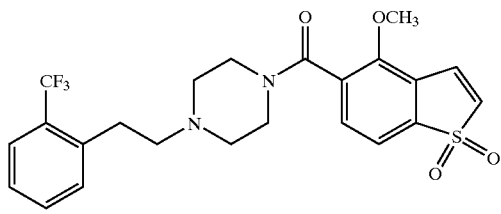

TLC: Rf 0.33 (ethyl acetate);

NMR (CDCl$_3$): δ7.63 (d, J=7.8 Hz, 1H), 7.49 (d, J=7.5 Hz, 2H), 7.46–7.40 (m, 2H), 7.40–7.27 (m, 2H), 6.75 (d, J=7.5 Hz, 1H), 3.94 (s, 3H), 3.90–3.80 (m, 2H), 3.35–3.20 (m, 2H), 3.04–2.94 (m, 2H), 2.68–2.60 (m, 4H), 2.58–2.40 (m, 2H).

EXAMPLE 28 (33)

4-(Pyridin-3-ylcarbonyl)aminomethyl-1,1-dioxidebenzo[b]thiophene

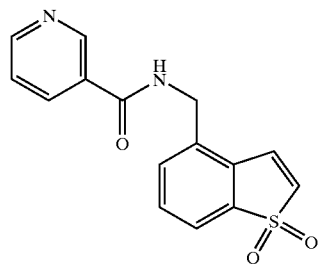

MS (APCI, Pos.): m/z 333 (M+MeOH+H)$^+$, 301 (M+H)$^+$.

EXAMPLE 29

4-(3-(Pyrrol-1-yl)-propyl)oxy-1,1-dioxidebenzo[b]thiophene

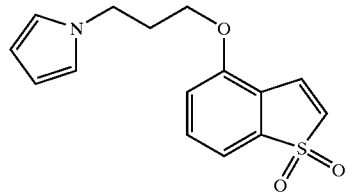

4-Hydroxy-1,1-dioxidebenzo[b]thiophene (370 mg), triphenylphosphine (630 mg) and 1-(3-hydroxypropyl)pyrrole (300 mg) were dissolved in anhydrous tetrahydrofuran (15 ml). Under an atmosphere of argon to the mixture, was added a solution of diethylazodicarboxylate (323 mg) in anhydrous tetrahydrofuran (4 ml) dropwise. The mixture was stirred at room temperature for 2 hours. To the reaction mixture methanol was added. The mixture was stirred for 10 minutes. The reaction mixture was concentrated. The residue was purified with column chromatography on silica gel (hexane:ethyl acetate=2:1) to give the compound of the present invention (473 mg) having the following physical data.

TLC: Rf 0.47 (hexane:ethyl acetate=1:1);

NMR (CDCl$_3$): δ7.55–7.35 (m, 2H), 7.30 (d, J=8 Hz, 1H), 6.97 (d, J=8 Hz, 1H), 6.75–6.54 (m, 3H), 6.16 (t, J=2 Hz, 2H), 4.12 (t, J=6 Hz, 2H), 4.00 (t, J=6 Hz, 2H), 2.27 (q, J=6 Hz, 2H).

EXAMPLES 30~30 (13)

By the same procedure as described in Example 18 using alcohol derivative corresponding to the compound prepared in Example 9 (12) and halogenated compound corresponding to 4-nitrobenzylbromide, or by the same procedure as described in Example 29 using alcohol derivative corresponding to 4-hydroxy-1,1-dioxidebenzo[b]thiophene and alcohol derivative corresponding to 1-(3-hydroxypropyl)pyrrole, the following compounds of the present invention were obtained.

EXAMPLE 30

4-(Quinolin-2-ylmethyl)oxy-1,1-dioxidebenzo[b]thiophene

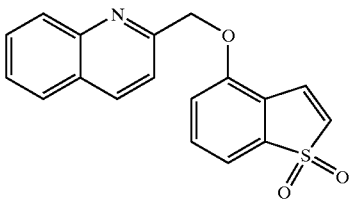

TLC: Rf 0.27 (hexane:ethyl acetate=1:1);

NMR (CDCl$_3$): δ8.23 (d, J=8 Hz,1H), 8.09 (d, J=8 Hz, 1H), 7.95–7.68 (m, 2H), 7.68–7.50 (m, 3H), 7.50–7.22 (m, 2H), 7.14 (d, J=8 Hz, 1H), 6.66 (d, J=7 Hz, 1H), 5.49 (s, 2H).

EXAMPLE 30 (1)

4-(2-(Pyrrol-1-yl)ethyl)oxy-1,1-dioxidebenzo[b]thiophene

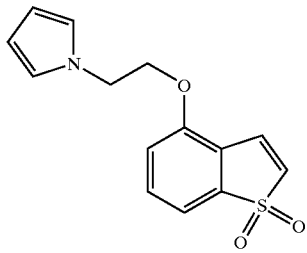

TLC: Rf 0.50 (ethyl acetate:hexane=2:1);

NMR (CDCl$_3$): δ7.55–7.22 (m, 3H), 6.94 (d, J=8 Hz, 1H), 6.73 (t, J=2 Hz, 2H), 6.62 (d, J=7 Hz, 1H), 6.19 (t, J=2 Hz, 2H), 4.32 (s, 4H).

EXAMPLE 30 (2)

4-(2-(4-Methylazol-5-yl)ethyl)oxy-1,1-dioxidebenzo[b]thiophene

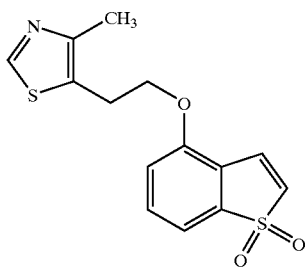

TLC: Rf 0.1 5 (ethyl acetate:hexane=2:1);

NMR (CDCl$_3$): δ8.63 (s, 1H), 7.58–7.37 (m, 2H), 7.31 (d, J=8 Hz, 1H), 7.03 (d, J=8 Hz, 1H), 6.64 (d, J=8 Hz, 1H), 4.26 (t, J=6 Hz, 2H), 3.31 (t, J=6 Hz, 2H), 2.46 (s, 3H).

EXAMPLE 30 (3)

4-(3-(Pyridin-4-yl)propyl)oxy-1,1-dioxidebenzo[b]thiophene

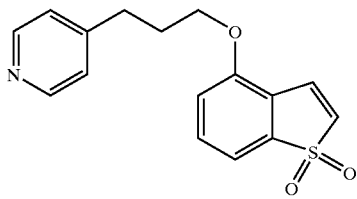

TLC: Rf 0.36 (ethyl acetate:methanol=10:1);

NMR (CDCl$_3$): δ8.53 (dd, J=1.6, 4.5 Hz, 2H), 7.60–7.22 (m, 3H), 7.14 (d, J=5.8 Hz, 2H), 7.00 (d, J=8.0 Hz, 1H), 6.62 (d, J=7.4 Hz, 1H), 4.09 (t, J=6.2 Hz, 2H), 2.84 (t, J=7.4 Hz, 2H), 2.19 (quint, J=6,2 Hz, 2H).

EXAMPLE 30 (4)

4-(1-t-Butoxycarbonylpiperidin-3-ylmethy)oxy-1,1-dioxidebenzo[b]thiophene

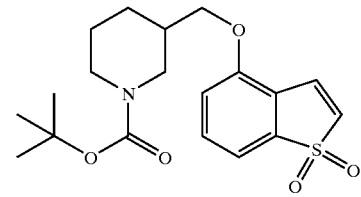

TLC: Rf 0.46 (hexane:ethyl acetate=1:1);

NMR (CDCl$_3$): δ7.58–7.38 (m, 2H), 7.30 (d, J=7.6 Hz, 1H), 7.04 (d, J=8.2 Hz, 1H), 6.61 (d, J=7.0 Hz, 3.15–2.50 (m, 4H), 1.45 (s, 9H).

EXAMPLE 30 (5)

4-(2-(Pyrrolidin-1-yl)ethyl)oxy-1,1-dioxidebenzo[b]thiophene

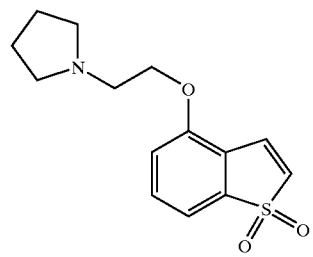

TLC: Rf 0.36 (ethyl acetate:acetic acid:water=3:1:1);

NMR (CDCl$_3$): δ7.55–7.35 (m, 2H), 7.29 (d, J=7 Hz, 1H), 7.06 (d, J=8 Hz, 1H), 6.61 (d, J=7 Hz, 1H), 4.22 (t, J=6 Hz, 2H), 2.94 (t, J=6 Hz, 2H), 2.64 (t, J=6 Hz, 4H), 2.20–1.65 (m, 4H).

EXAMPLE 30 (6)

4-(2-(Piperidin-1-yl)ethyl)oxy-1,1-dioxidebenzo[b]thiophene

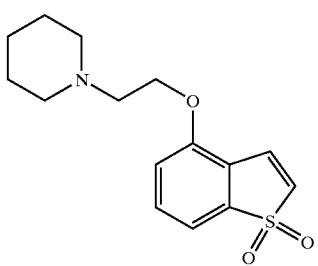

TLC: Rf 0.44 (ethyl acetate:acetic acid:water=3:1:1);

NMR (CDCl$_3$): δ7.60–7.58 (m, 2H), 7.29 (d, J=8 Hz, 1H), 7.07 (d, J=8 Hz, 1H), 6.61 (d, J=7 Hz, 1H), 4.21 (t, J=6 Hz, 2H), 2.80 (t, J=6 Hz, 2H), 2.51 (t, J=6 Hz, 4H), 1.90–1.35 (m 6H).

EXAMPLE 30 (7)

4-(2-(2-Acetyloxyethoxy)ethyl)oxy-1,1-dioxidebenzo[b]thiophene

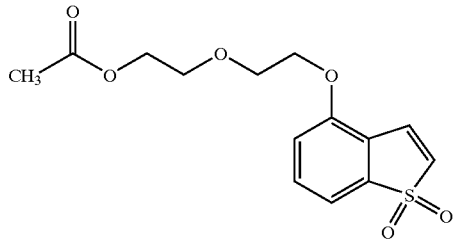

TLC: Rf 0.46 (ethyl acetate:hexane=2:1);

NMR (CDCl$_3$): δ7.58–7.38 (m, 2H), 7.31 (d, J=7 Hz, 1H), 7.08 (d, J=9 Hz, 1H), 6.62 (d, J=7 Hz, 1H), 4.25 (t, J=5 Hz, 4H), 3.88 (t, J=5 Hz, 2H), 3.76 (t, J=5 Hz, 2H), 2.07 (s, 3H).

EXAMPLE 30 (8)

4-(2-(4-Benzylpiperazin-1-yl)ethyl)oxy-1,1-dioxidebenzo[b]thiophene

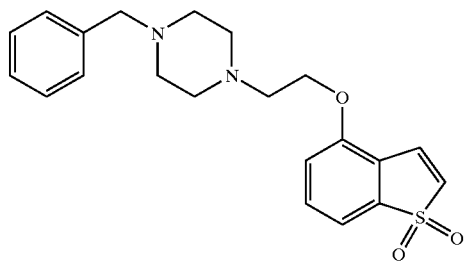

TLC: Rf 0.57 (chloroform:methanol 5:1);

NMR (CDCl$_3$): δ7.58–7.38 (m, 2H), 7.38–7.18 (m, 6H), 7.05 (d, J=8 Hz, 1H), 6.60 (d, J=7 Hz, 1H), 4.35–4.05 (m, 2H), 3.52 (s, 2H), 2.85 (t, J=6 Hz, 2H), 2.78–2.35 (m, 8H).

EXAMPLE 30 (9)

4-Diethylcarbamoylmethyloxy-1,1-dioxidebenzo[b]thiophene

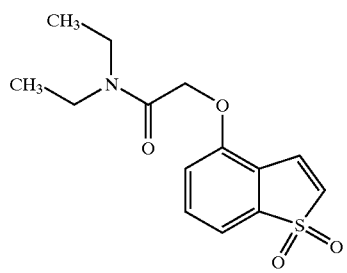

TLC: Rf 0.25 (hexane:ethyl acetate=1:2);

NMR (CDCl$_3$): δ7.52 (d, J=7.0 Hz, 1H), 7.46 (t, J=8.0 Hz, 1H), 7.32 (d, J=8.0 Hz, 1H), 7.05 (d, J=8.0 Hz, 1H), 6.63 (d, J=7.0 Hz, 1H), 4.80 (s, 2H), 3.41 (q, J=7.2 Hz, 2H), 3.36 (q, J=7.2 Hz, 2H), 1.23 (t, J=6 Hz, 3H), 1.15 (t, J=7.2 Hz, 3H).

EXAMPLE 30 (10)

4-Cyanomethyloxy-1,1-dioxidebenzo[b]thiophene

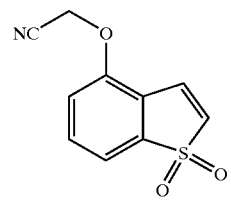

TLC: Rf 0.30 (hexane:ethyl acetate=1:1);

NMR (CDCl$_3$): δ7.65–7.35 (m, 3H), 71.5 (d, J=7.5 Hz, 1H), 6.70 (d, J=7.5 Hz, 1H), 4.90 (s, 2H).

EXAMPLE 30 (11)

5-(Pyridin-3-yloxy)methyl-4-methoxy-1,1-dioxidebenzo[b]thiophene

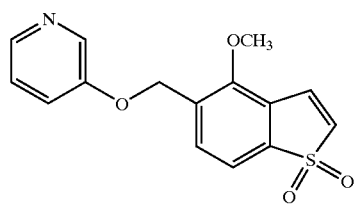

MS (APCI, Pos.): m/z 336 (M+MEOH+H)$^+$, 304 (M+H)$^+$.

EXAMPLE 30 (12)

5-(2t-Butoxycarbonylaminoethyl)oxy-4-nitro-1,1-dioxidebenzo[b]thiophene

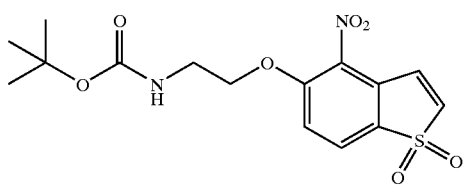

TLC: Rf 0.32 (hexane:ethyl acetate=1:1);

NMR (CDCl$_3$): δ7.80 (d, J=8.6 Hz, 1H), 7.33 (d, J=7.0 Hz, 1H), 7.18 (d, J=8.6 Hz, 1H), 6.93 (d, J=7.0 Hz, 1H), 5.00 (br, 1H), 4.24 (t, J=5.2 Hz, 2H), 3.57 (q, J=5.2 Hz, 2H), 1.45 (s, 9H).

EXAMPLE 30 (13)

5-((2E)-3-Ethoxycarbonyl-2-propenyl)oxy-1,1-dioxidebenzo[b]thiophene

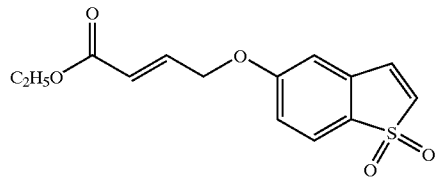

TLC: Rf 0.51 (hexane:ethyl acetate=1:1);

NMR (CDCl$_3$): δ7.65 (d) J=8.8 Hz, 1H), 7.14 (d, J=6.8 Hz, 1H), 7.12–6.85 (m, 4H), 6.74 (d, J=6.8 Hz, 1H), 6.23–6.10 (m, 1H), 4.82–4.73 (m, 2H), 4.23 (q, J=7.0 Hz, 2H), 1.31 (t, J=7.0 Hz, 3H).

EXAMPLE 31

4-(2,4-Dimethoxyphenylmethyl)aminomethyl-1,1-dioxidebenzo[b]thiophene

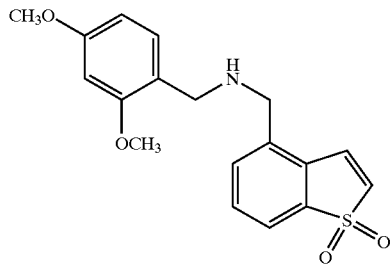

4-Bromomethyl-1,1-dioxidebenzo[b]thiophene (198 mg) was dissolved in acetonitrile (10 ml). Thereto was added a solution of 2,4-dimethoxybenzylamine hydrochloride (188 mg) and triethylamine (0.26 ml) in acetonitrile (6 ml). The mixture was stirred at room temperature for 1 hour. To the reaction mixture a saturated aqueous solution of sodium bicarbonate was added. The mixture was extracted by ethyl acetate. The extract was washed by a saturated solution of sodium chloride, dried over anhydrous sodium sulfate and concentrated. The residue was purified with column chromatography on silica gel (ethyl acetate:hexane=1:1→2:1) to give the compound of the present invention (113 mg) having the following physical data.

TLC: Rf 0.29 (ethyl acetate);

NMR (CDCl$_3$): δ7.63–7.39 (m, 4H), 7.07 (d, J=8.0 Hz, 1H), 6.66 (d, J=7.0 Hz, 1H), 6.49–6.39 (m, 2H), 3.83 (s, 2H), 3.81 (s, 3H), 3.79 (s, 3H), 3.72 (s, 2H), 1.98 (s, 1H).

EXAMPLES 31 (1)~31 (12)

By the same procedure as described in Example 31 using 4-bromomethyl-1,1-dioxidebenzo[b]thiophene and an amine derivative corresponding to 2,4-dimethoxybenzylamine.hydrochloride, and if necessary, by converting into the corresponding salt by a known method, the following compounds of the present invention were obtained.

EXAMPLE 31 (1)

4-(Pyridin-3-ylmethyl)aminomethyl-1,1-dioxidebenzo[b]thiophene.2hydrochloride

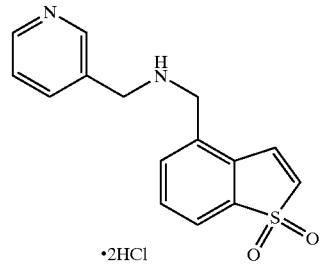

·2HCl

TLC: Rf 0.37 (ethyl acetate:methanol=5:1);

NMR (CD$_3$OD): δ9.11 (d, J=1.7 Hz, 1H), 8.92 (dd, J=5.5, 1.7 Hz, 1H), 8.73 (dt, J=8.2, 1.7 Hz, 1H), 8.10 (dd, J=8.2, 5.5 Hz, 1H), 7.94–7.90 (m, 2H), 7.84 (d, J=7.4 Hz, 1H), 7.20 (t, J=7.4 Hz, 1H), 7.18 (d, J=7.4 Hz, 1H), 4.68 (s, 2H), 4.63 (s, 2H).

EXAMPLE 31 (2)

4-(2-(Dimethylamino)ethyl)aminomethyl-1,1-dioxidebenzo[b]thiophene

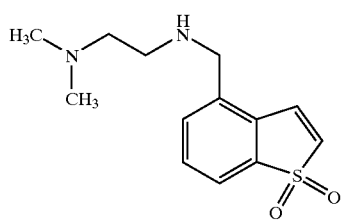

MS (APCI, Pos.): m/z 299 (M+MeOH+H)$^+$, 267 (M+H)$^+$.

EXAMPLE 31 (3)

4-(N,N-Bis(2-hydroxyethyl)amino)methyl-1,1-dioxidebenzo[b]thiophene

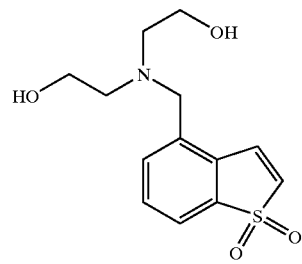

MS (APCI, Pos.): m/z 316 (M+MeOH+H)$^+$, 284 (M+H)$^+$.

EXAMPLE 31 (4)

4-(2-(2-Hydroxyethoxy)ethyl)aminoethyl)aminomethyl-1,1-dioxidebenzo[b]thiophene

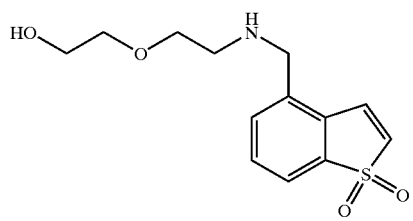

MS (APCI, Pos.): m/z 599 (2M+MeOH+H)$^+$, 567 (2M+H)$^+$, 316 (M+MeOH+H)$^+$, 284 (M+H)$^+$.

EXAMPLE 31 (5)

4-(4-Benzylpiperazin-1-yl)methyl-1,1-dioxidebenzo[b]thiophene

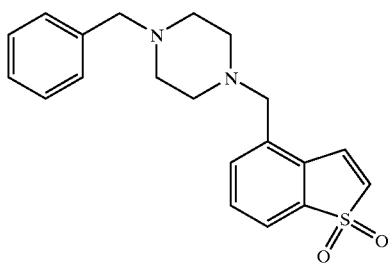

Free Compound
TLC: Rf 0.27 (ethyl acetate:hexane=1:1);
NMR (CDCl$_3$): δ7.71 (d, J=7.0 Hz, 1H), 7.62 (t, J=4.6 Hz, 1H), 7.44 (d, J=4.6 Hz, 2H), 7.35–7.25 (m, 5H), 6.68 (d, J=7.0 Hz, 1H), 3.60 (s, 2H), 3.51 (s, 2H), 2.46 (brs, 8H).
2hydrochloride
TLC: Rf 0.32 (ethyl acetate);
NMR (CD$_3$OD): δ7.86 (d, J=7.2 Hz, 1H), 7.76–7.70 (m, 2H), 7.63 (d, J=7.8 Hz, 1H), 7.58–7.47 (m, 5H), 7.07 (d, J=7.2 Hz, 1H), 4.38 (s, 2H), 4.13 (s, 2H), 3.41 (br, 4H), 3.13 (br, 4H).

EXAMPLE 31 (6)

4-(4-(Pyridin-2-yl)piperazin-1-yl)methyl-1,1-dioxidebenzo[b]thiophene

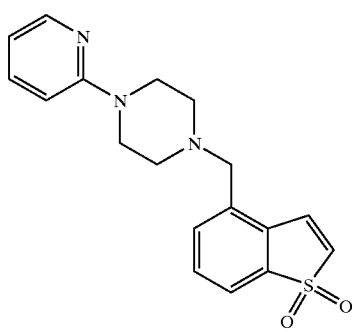

MS (APCI, Pos.): m/z 374 (M+MeOH+H)$^+$, 342 (M+H)$^+$.

EXAMPLE 31 (7)

4-(4-Ethoxycarbonylpiperazin-1-yl)methyl-1,1-dioxidebenzo[b]thiophene

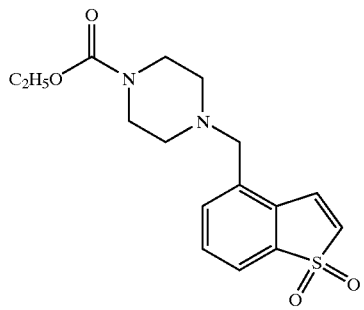

MS (APCI, Pos.): m/z 369 (M+MeOH+H)$^+$, 337 (M+H)$^+$.

EXAMPLE 31 (8)

4-(4-(2-Hydroxyethyl)piperazin-1-yl)methyl-1,1-dioxidebenzo[b]thiophene

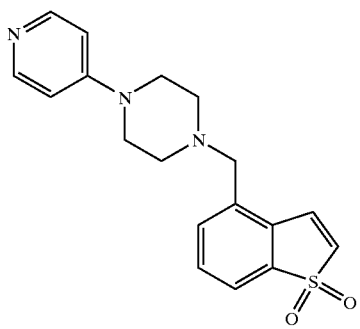

MS (APCI, Pos.): m/z 649 (2M+MEOH+H)$^+$, 617 (2M+H)$^+$, 341 (M+MeOH+H)$^-$, 309 (M+H)$^+$.

EXAMPLE 31 (9)

4-(4-(Pyridin-4-yl)piperazin-1-yl)methyl-1,1l-dioxidebenzo[b]thiophene

MS (APCI, Pos.): m/z 374 (M+MeOH+H)$^+$, 342 (M+H)$^+$.

EXAMPLE 31 (10)

4-Benzylaminomethyl-1,1-dioxidebenzo[b]thiophene

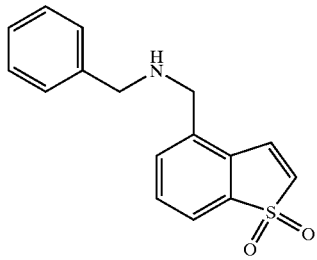

Free Compound

TLC: Rf 0.66 (ethyl acetate);

NMR (CDCl$_3$): δ7.62 (d, J=7.2 Hz, 1H), 7.56 (d, J=7.5 Hz, 1H), 7.52 (d, J=7.5 Hz, 1H), 7.46 (t, J=7.5 Hz, 1H), 7.39–7.24 (m, 5H), 6.69 (d, J=7.2 Hz, 1H), 3.89 (s, 2H), 3.81 (s, 2H), 1.59 (s, 1H).

Hydrochloride

TLC: Rf 0.47 (ethyl acetate:hexane=2:1);

NMR (CD$_3$OD): δ7.95–7.18 (m, 8H), 7.15 (d, J=7 Hz, 1H), 6.98 (d, J=7 Hz, 1H), 4.48 (s, 2H), 4.36 (s, 2H).

EXAMPLE 31 (11)

4-(1-Benzylpiperidin-4-yl)aminomethyl-1,1-dioxidebenzo[b]thiophene

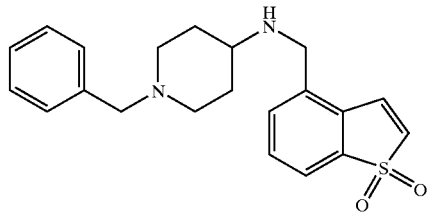

Free Compound

TLC: Rf 0.27 (ethyl acetate:methanol=4:1);

NMR (CDCl$_3$): δ7.65 (d, J=7.0 Hz, 1H), 7.61 (d, J=6.8 Hz, 1H), 7.56–7.40 (m, 2H), 7.34–7.22 (m, 5H), 6.68 (d, J=7.0 Hz, 1H), 3.91 (s, 2H), 3.50 (s, 2H), 2.91–2.77 (m, 2H), 2.60–2.43 (m, 1H), 2.12–1.95 (m, 2H), 1.95–1.80 (m, 2H), 1.60–1.32 (m, 3H).

2hydrochloride

TLC: Rf 0.30 (ethyl acetate:methanol:triethylamine= 8:1.5:0.5);

NMR (DMSO-d$_6$+CD$_3$OD): δ7.97 (d, J=7.2 Hz, 1H), 7.95 (d, J=7.8 Hz, 1H), 7.88 (d, J=7.5 Hz, 1H),7.65–7.55 (m, 3H), 7.50–7.40 (m, 4H), 4.42 (s, 2H), 4.33 (s, 2H), 3.80–3.40 (m, 3H), 3.10–2.95 (m, 2H), 2.50–2.35 (m, 2H), 2.35–2.05 (m, 2H).

EXAMPLE 31 (12)

4-(Morpholin-4-yl)methyl-1,1-dioxidebenzo[b]thiophene

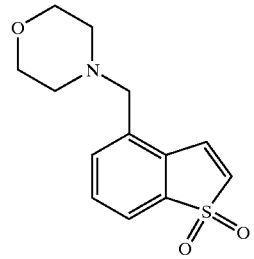

TLC: Rf 0.31 (ethyl acetate:methylene chloride=1:1);

NMR (CDCl$_3$): δ7.69 (d, J=7.2 Hz, 1H), 7.64 (t, J=4.8 Hz, 1H), 7.46 (d, J=4.8 Hz, 2H), 6.71 (d, J=7.2 Hz, 1H), 3.68 (t, J=4.5 Hz, 4H), 3.60 (s, 2H), 2.44 (t, J=4.5 Hz, 4H).

EXAMPLE 32

4-Ethoxycarbonyl-1,1-dioxidebenzo[b]thiophene

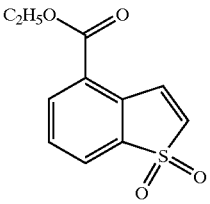

To a solution of 4-Carboxy-1,1-dioxidebenzo[b]thiophene (2.42 g) in dimethylformamide (50 ml), were added potassium carbonate (3.10 g) and bromoethane (44.3 g). The mixture was stirred at room temperature overnight. To a reaction mixture, water was added. The mixture was extracted by ethyl acetate. The extract was washed by water and a saturated aqueous solution of sodium chloride sucessively, dried over anhydrous sodium sulfate and concentrated to give the compound of the present invention (2.08 g) having the following physical data.

TLC: Rf 0.24 (ethyl acetate:hexane=1:4);

NMR (CDCl$_3$): δ8.25 (d, J=7.4 Hz, 1H), 8.20 (d, J=7.8 Hz, 1H), 7.88 (d, J=7.8 Hz, 1H), 7.61 (t, J=7.8 Hz, 1H), 6.84 (d, J=7.4 Hz, 1H), 4.44 (q, J=7.2 Hz, 2H), 1.44 (t, J=7.2 Hz, 3H).

EXAMPLE 32 (1)

4-Benzyloxycarbonyl-1,1-dioxidebenzo[b]thiophene

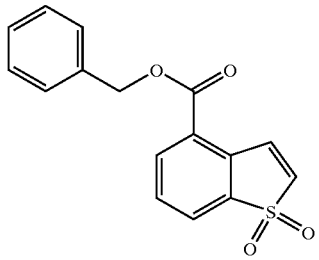

By the same procedure as described in Example 32 using 4-carboxy-1,1-dioxidebenzo[b]thiophene and benzylbromnide instead of bromoethane, the compound of the present invention having the following physical data was obtained.

MS (APCI, Pos.): m/z 301 (M+H)$^+$.

EXAMPLE 33

4-(Pyridin-3-yl)-1,1-dioxidebenzo[b]thiophene

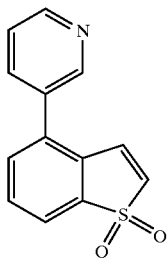

To a solution of 4-bromo-1,1-dioxidebenzo[b]thiophene (492 mg) in dimethylformamide (5.0 ml), were added diethyl(3-pyridyl)boran (440 mg) and trispotassium phosphate (637 mg) and tetrakis(triphenylphosphine)palladium (0) (116 mg). The mixture was stirred at 80° C. for 2 hours. The reaction mixture was poured into water. The mixture was extracted by ethyl acetate. The extract was washed by a saturated aqueous solution of sodium chloride, dried over anhydrous magnesium sulfate and concentrated. The residue was purified with column chromatography on silica gel (chloroform:methanol=50:1) to give the compound of the present invention (490 mg) having the following physical data.

TLC: Rf 0.59 (chloroform:methanol=9:1);
MS (APCI, Pos.): m/z 276 (M+MeOH+H)$^+$, 244 (M+H)$^+$.

EXAMPLE 33 (1)

6-(Pyridin-3-yl)-1,1-dioxidebenzo[b]thiophene

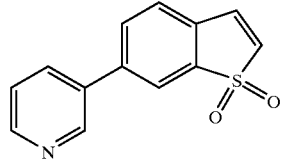

By the same procedure as described in Example 33, using 6-bromo-1,1-dioxidebenzo[b]thiophene instead of 4-bromo-1,1-dioxidebenzo[b]thiophene, and diethyl(3-pyridyl)borane, the compound of the present invention having the following physical data was obtained.

MS (APCI, Pos.): m/z 276 (M+MeOH+H)$^+$, 244 (M+H)$^+$.

EXAMPLE 34

4-(4,4-Dimethyl-4,5-dihydroxazol-2-yl)-1,1-dioxidebenzo[b]thiophene

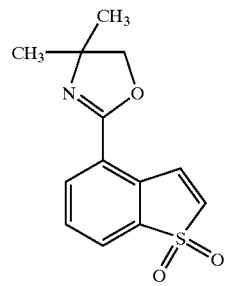

To the compound prepared in the following Example 72 (519 mg), was added thionyl chloride (2.1 ml). The mixture was stirred at room temperature for 1 hour. To the reaction mixture was added ethyl acetate. The extract was washed by a saturated aqueous solution of sodium chloride, dried over anhydrous sodium sulfate, concentrated to give the compound of the present invention (392 mg) having the following physical data.

TLC: Rf 0.42 (ethyl acetate:hexane=1:1);
NMR (CDCl$_3$): δ8.43 (d, J=7.0 Hz, 1H), 8.08 (d, J=7.8 Hz, 1H), 7.78 (d, J=7.8 Hz, 1H), 7.56 (t, J=7.8 Hz, 1H), 6.76 (d, J=7.0 Hz, 1H), 4.13 (s, 2H), 1.40 (s, 6H).

EXAMPLES 35~35 (68)

By the same procedure as described in Example 27, using the compounds prepared in Examples 28~28 (33), 29, 30~30 (13), 31~31 (12), 32~32 (1), 33~33 (1), 34 or corresponding compounds instead of 5-methyl-1,1-dioxidebenzo[b] thiophene, and if necessary, by converting into the corresponding salt by a known method, the compounds of the present invention having the following physical data were obtained.

EXAMPLE 35

4-(Pyridin-3-ylmethyl)carbamoyl-3-phenylsulfonyl-2,3-dihydro-1,1-dioxidebenzo[b]thiophene

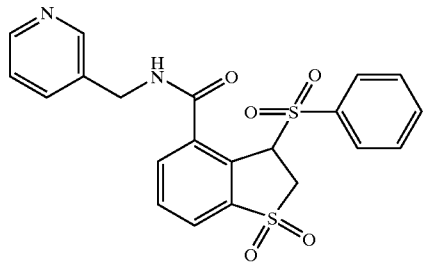

Free Aicd
TLC: Rf 0.44 (methylene chloride:methanol=10:1);
NMR (DMSO-d$_6$): δ9.41 (t, J=5.7 Hz, 1H), 8.67 (d, J=1.8 Hz, 1H), 8.46 (dd, J=4.8, 1.8 Hz, 1H), 8.06 (d, J=6.3 Hz, 1H), 7.96 (d, J=6.9 Hz, 1H), 7.90–7.67 (m, 5H), 7.66–7.58

(m, 2H), 7.36 (dd, J=8.1, 5.1 Hz, 1H), 6.27 (d, J=6.9 Hz, 1H), 4.54 (d, J=5.7 Hz, 2H), 4.10 (dd, J=15.6, 9.3 Hz, 1H), 3.98 (dd, J=15.6, 1.5 Hz, 1H).

Hydrochloride

TLC: Rf 0.45 (chloroform:methanol=9:1);

NMR (DMSO-d$_6$): δ9.70–9.62 (br, 1H), 8.95 (s, 1H), 8.75 (d, J=5.4 Hz, 1H), 8.55 (d, J=7.5 Hz, 1H), 8.13 (d, J=7.5 Hz, 1H), 7.98 (d, J=6.9 Hz, 1H), 7.94 (d, J=7.5 Hz, 1H), 7.91–7.85 (m, 1H), 7.81–7.72 (m, 1H), 7.67–7.58 (m, 4H), 6.21 (d, J=9.0 Hz, 1H), 4.76 (dd, J=15.6, 6.0 Hz, 1H), 4.62 (dd, J=15.6, 5.1 Hz, 1H), 4.07 (dd, J=15.0, 9.0 Hz, 1H), 3.93 (d, J=15.0 Hz, 1H).

EXAMPLE 35 (1)

4-(4-Benzylpiperazin-1-yl)carbonyl-3-phenylsulfonyl-2,3-dihydro-1,1-dioxidebenzo[b]thiophene.hydrochloride

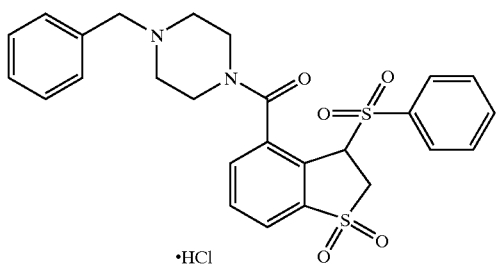

TLC: Rf 0.46 (chloroform:methanol=19:1);

NMR (DMSO-d$_6$): δ11.60–11.40 and 11.40–11.20 (each br, total 1H), 8.05–7.52 (m, 10H), 7.51–7.23 (m, 3H), 5.88 and 5.81 (each d, J=9.3 Hz, total 1H), 4.80–3.85 (m, 6H), 3.70–2.78 (m, 6H).

EXAMPLE 35 (2)

4-(N-(2-(Pyridin-3-yl)ethyl)-N-methylcarbamoyl)-3-phenylsulfonyl-2,3-dihydro-2,2-dioxidebenzo[b]thiophene.hydrochloride

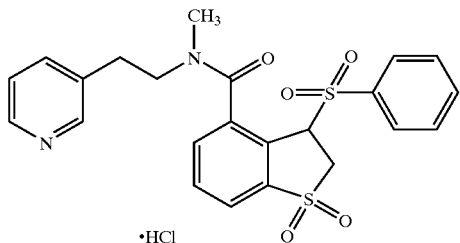

TLC: Rf 0.2 7 (chloroform:methanol=19:1);

NMR (DMSO-d$_6$): δ8.96 and 8.81 (each s, total 1H), 8.75 and 8.73 (each d, J=5.4 Hz, total 1H), 8.55 and 8.32 (each d, J=7.5 Hz, total 1H), 7.95–7.62 (m, 9H), 5.81 and 5.79 (each d, J=8.4 Hz, total 1H), 4.15–3.84 and 3.73–3.62 (each m, total 4H), 3.50–3.05 (m, 2H), 3.16 and 3.13 (each s, total 3H).

EXAMPLE 35 (3)

4-(2-(2-Hydroxyethoxy)ethyl)carbamnoyl-3-phenylsulfonyl-2,3-dihydro-1,1-dioxidebenzo[b]thiophene

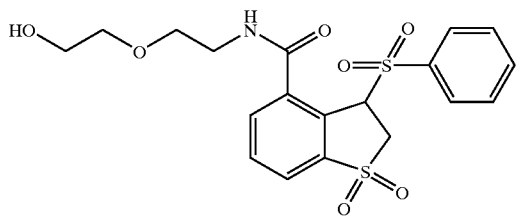

TLC: Rf 0.55 (methylene chloride:methanol=9:1);

NMR (DMSO-d$_6$): δ8.84 (t, J=5.4 Hz, 1H), 7.98–7.90 (m, 2H), 7.84 (d, J=7.5 Hz, 1H), 7.81–7.73 (m, 3H), 7.69–7.60 (m, 2H), 6.36 (d, J=8.9 Hz, 1H), 4.58 (t, J=5.1 Hz, 1H), 4.09 (dd, J=15.3, 8.9 Hz, 1H), 3.96 (d, J=15.3 Hz, 1H), 3.67–3.53 (m, 2H), 3.53–3.35 (m, 6H).

EXAMPLE 35 (4)

4-(2,4-Dimethoxyphenylmethyl)carbamoyl-3-phenylsulfonyl-2,3-dihydro-1,1-dioxidebenzo[b]thiophene

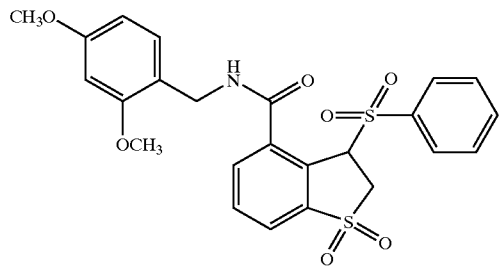

TLC: Rf 0.48 (methylene chloride:methanol=95:5);

NMR (DMSO-d$_6$): δ9.04 (t, J=5 Hz, 1H), 8.03 (d, J=7.2 Hz, 1H), 7.92 (d, J=7.2 Hz, 1H), 7.90–7.70 (m, 5H), 7.62 (t, J=7.2 Hz, 1H), 7.32 (d, J=8.4 Hz, 1H, 6.57 (d, J=2.4 Hz, 1H), 6.47 (dd , J=8.4, 2.4 Hz, 1H), 6.27 (d, J=8.5 Hz, 1H), 4.47 (dd, J=15, 5 Hz, 1H), 4.29 (dd, J=15, 5 Hz, 1H), 4.08 (dd, J=15, 8.5 Hz, 1H), 3.97 (d, J=15 Hz, 1H), 3.83 (s, 3H), 3.74 (s, 3H).

EXAMPLE 35 (5)

4-(1-Benzylpiperidin-4-yl)carbamoyl-3-phenylsulfonyl-2,3-dihydro-1,1-dioxidebenzo[b]thiophene

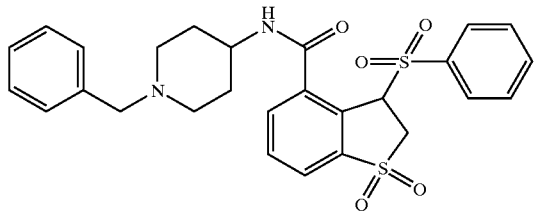

Free Compound

TLC: Rf 0.30 (methylene chloride:methanol=9:1);

NMR (CDCl$_3$+CD$_3$OD): δ8.00–7.50 (m, 8H), 7.45–7.20 (m, 5H), 6.25 (dd, J=7.5, 2.5 Hz, 1H), 4.10–3.90 (m, 1H), 3.80 (dd, J=15, 2.5 Hz, 1H), 3.70–3.60 (m, 1H), 3.55 (s, 2H), 3.10–2.90 (m, 2H), 2.30–1.95 (m, 4H), 1.90–1.70 (m, 2H).

Hydrochloride

TLC: Rf 0.40 (methanol:ethyl acetate=1:10);

NMR (CD$_3$OD): δ8.04–7.43 (m, 13H), 6.15 (dd, J=8.2 Hz, 2.6Hz, 1H), 4.35 (s, 2H), 4.34–4.06 (m, 1H), 3.94 (dd, J=15.2 Hz, 8.2 Hz, 1H), 3.83 (dd, J=15.2 Hz, 2.6 Hz, 1H), 3.74–3.08 (m, 4H), 2.56–1.56 (m, 4H).

Methanesulfonic Acid Salt

TLC: Rf 0.40 (methanol:ethyl acetate=1:10);

NMR (CD$_3$OD): δ8.06–7.44 (m, 13H), 6.14 (dd, J=8.2 Hz, 2.6 Hz, 1H), 4.34 (s, 2H), 4.32–4.12 (m, 1H), 4.01–3.77 (m, 2H), 3.68–3.08 (m, 4H), 2.69 (s, 3H), 2.54–1.74 (m, 4H).

EXAMPLE 35 (6)

4-(Pyridin-4-ylmethyl)carbamoyl-3-phenylsulfonyl-2,3-dihydro-1,1-dioxidebenzo[b]thiophene

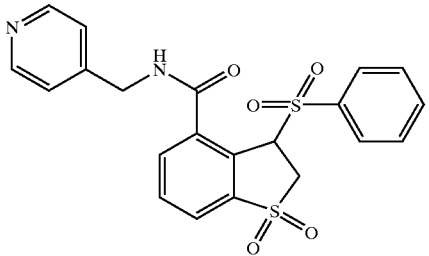

TLC: Rf 0.35 (chloroform:methanol=9:1);

NMR (DMSO-d$_6$): δ9.45 (t. J=7 Hz, 1H), 8.50 (d, J=8 Hz, 2H), 8.10 (d, J=8 Hz, 1H), 8.00 (d, J=8 Hz, 4H), 7.90 (t, J=8 Hz, 1H), 7.80–7.55 (m, 5H), 7.45 (d, J=8 Hz, 2H), 6.30 (dd, J=1 Hz and 7 Hz, 1H), 4.55 (m, 2H), 4.10 (dd, J=7 Hz and 15 Hz, 1H), 4.00 (dd, J=1 Hz and 15 Hz, 1H).

EXAMPLE 35 (7)

4-(2-t-Butoxycarbonylethyl)carbamoyl-3-phenylsulfonyl-2,3-dihydro-1,1-dioxidebenzo[b]thiophene

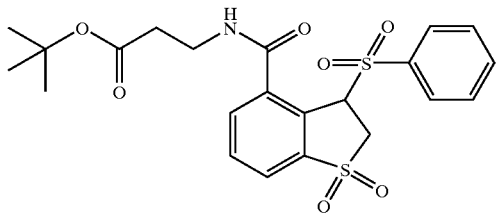

TLC: Rf 0.37 (ethyl acetate:hexane=3:2);

NMR (DMSO-d$_6$): δ8.90 (t, J=7 Hz, 1H), 8.00–7.55 (m, 8H), 6.25 (dd, J=1 Hz and 7 Hz, 1H), 4.10 (dd, J=7 Hz and 15 Hz, 1H), 3.95 (dd, J=1 Hz and 15 Hz, 1H), 3.45 (m, 2H), 2.60 (t, J=7 Hz, 2H).

EXAMPLE 35 (8)

4-(Thiophen-2-ylmethyl)carbamoyl-3-phenylsulfonyl-2,3-dihydro-1,1-dioxidebenzo[b]thiophene

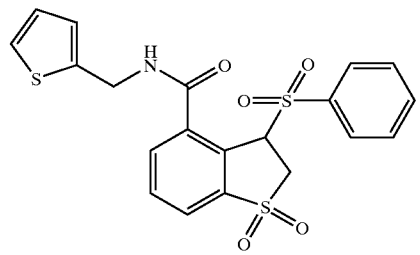

TLC: Rf 0.67 (chloroform:methanol=4:1);

NMR (DMSO-d$_6$): δ9.40 (t, J=7 Hz, 1H), 8.00–7.60 (m, 8H), 7.40 (d, J=6 Hz, 1H), 7.10 (d, J=4 Hz, 1H), 7.00 (dd, J=4 Hz and 6 Hz, 1H), 6.30 (dd, J=1 Hz and 7 Hz, 1H), 4.75 (dd, J=7 Hz and 16 Hz, 1H), 4.55 (dd, J=7 Hz and 16 Hz, 1H), 4.10 (dd, J=7 Hz and 12 Hz, 1H), 4.00 (dd, J=1 Hz and 12 Hz, 1H).

EXAMPLE 35 (9)

4-Benzylcarbamoyl-3-phenyisulfonyl-2,3-dihydro-1,1-dioxidebenzo[b]thiophene

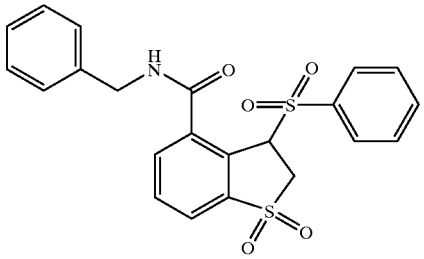

TLC: Rf 0.58 (methylene chloride:methanol=10:1);

NMR (CDCl$_3$+DMSO-d$_6$): δ8.74 (t, J=5.7 Hz, 1H), 8.03 (dd, J=7.8, 0.9 Hz, 1H), 7.93–7.80 (m, 3H), 7.78–7.68 (m, 2H), 7.59 (t, J=7.8 Hz, 2H), 7.50 (d, J=6.9 Hz, 2H), 7.39–7.20 (m, 3H), 6.36 (d, J=7.8 Hz, 1H), 4.71 (dd, J=14.9, 5.7 Hz, 1H), 4.62 (dd, J=14.9, 5.7 Hz, 1H), 3.86 (d, J=15.0 Hz, 1H), 3.69 (dd, J=15.0, 7.8 Hz, 1H).

EXAMPLE 35 (10)

4-(Pyridin-2-ylmethyl)carbamoyl-3-phenylsulfonyl-2,3-dihydro-1,1-dioxidebenzo[b]thiophene

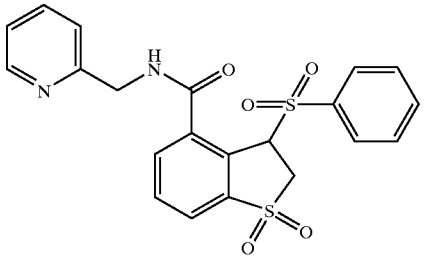

TLC: Rf 0.56 (methylene chloride:methanol=10:1);

NMR (DMSO-d$_6$): δ9.42 (t, J=6.3 Hz, 1H), 8.54 (d, J=5.1 Hz, 1H), 8.11 (d, J=7.5 Hz, 1H), 7.97 (d, J=8.1 Hz, 1H), 7.95–7.82 (m, 1H), 7.80–7.70 (m, 4H), 7.62 (t, J=8.1 Hz, 2H), 7.55 (d, J=8.1 Hz, 1H), 7.30–7.24 (m, 1H), 6.30 (d, J=8.7 Hz, 1H), 4.65 (dd, J=16.0, 4.8 Hz, 1H), 4.54 (dd, J=16.0, 4.8 Hz, 1H), 4.10 (dd, J=15.6, 4.8 Hz, 1H), 4.00 (d, J=15.6, 9.3 Hz, 1H).

EXAMPLE 35 (11)

4-(2-(Piperidin-1-yl)ethyl)carbamoyl-3-phenylsulfonyl-2,3-dihydro-1,1-dioxidebenzo[b]thiophene

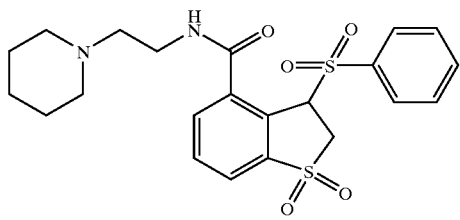

Free Compound

TLC: Rf 0.10 (methylene chloride:methanol=10:1);

NMR (CDCl₃): δ7.90–7.78 (m, 4H), 7.75–7.64 (m, 2H), 7.62–7.51 (m, 2H), 7.42 (bs, 1H), 6.29 (d, J=8.1 Hz, 1H), 3.84 (dd, J=15.0, 1.5 Hz, 1H), 3.75–3.60 (m, 2H), 3.58–3.45 (m, 1H), 2.77–2.60 (m, 2H), 2.55–2.40 (m, 4H), 1.80–1.40 (m, 6H).

Hydrochloride

TLC: Rf 0.30 (ethyl acetate:methanol:triethylamine= 8:1.5:0.5);

NMR (DMSO-d₆): δ10.25 (br. s, 1H), 9.32 (t, J=5.4 Hz, 1H), 8.10 (dd, J=7, 1.4 Hz, 1H), 8.00–7.80 (m, 2H), 7.80–7.70 (m, 3H), 7.70–7.55 (m, 2H), 6.30 (d, J=8 Hz, 1H), 4.14 (dd, J=15, 8 Hz, 1H ), 3.97 (d, J=15 Hz, 1H), 3.90–3.70 (m, 2H), 3.70–3.50 (m, 2H), 3.50–3.10 (m, 3H), 3.10–2.80 (m, 2H), 2.00–1.60 (m, 4H), 1.60–1.20 (m, 1H).

Methanesulfonic Acid Salt

TLC: Rf 0.30 (ethyl acetate:methanol:triethylamine= 8:1.5:0.5);

NMR (DMSO-d₆): δ9.13 (t, J=5 Hz, 1H), 9.00 (br. s, 1H), 8.05 (dd, J=7, 1.4 Hz, 1H), 8.00–7.80 (m, 2H), 7.80–7.70 (m, 3H), 7.70–7.55 (m, 2H), 6.28 (d, J=8.2 Hz, 1H), 4.12 (dd, J=16, 8.2 Hz, 1H), 3.94 (d, J=16 Hz, 1H), 3.90–3.50 (m, 5H), 3.50–3.20 (m, 2H), 3.15–2.90 (m, 2H), 2.00–1.60 (m, 4H), 1.60–1.30 (m, 1H).

EXAMPLE 35 (12a)

4-((1S)-1-t-Butoxycarbonyl-2-methylpropyl)carbamoyl-3-phenylsulfonyl-2,3-dihydro-1,1-dioxidebenzo[b]thiophene

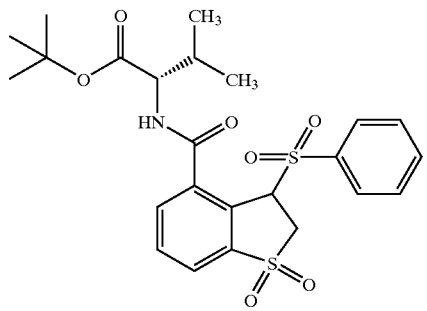

TLC: Rf 0.34 (hexane:ethyl acetate=1:1);

NMR (CDCl₃): δ7.99 (dd, J=7.5, 0.9 Hz, 1H), 7.87–7.84 (m, 3H), 7.75 (t, J=7.5 Hz, 1H), 7.72–7.67 (m, 1H), 7.60–7.55 (m, 2H), 6.80 (d, J=8.8 Hz, 1H), 6.25 (d, J=8.7 Hz, 1H), 4.67 (dd, J=8.8, 3.9 Hz, 1H), 3.80 (d-like, J=15.0 Hz, 1H), 3.65 (dd, J=15.0, 8.7 Hz, 1H), 2.47–2.41 (m, 1H), 1.54 (s, 9H), 1.12 (d, J=7.0 Hz, 3H), 1.06 (d, J=7.0 Hz, 3H).

(The determination of the absolute configuration of the carbon atom to which phenylsulfonyl is bonded is not performed, but this compound is a single isolated one.)

EXAMPLE 35 (12b)

4-((1S)-1-t-Butoxycarbonyl-2-methypropyl)carbamoyl-3-phenylsulfonyl-2,3-dihydro-1,1-dioxidebenzo[b]thiophene

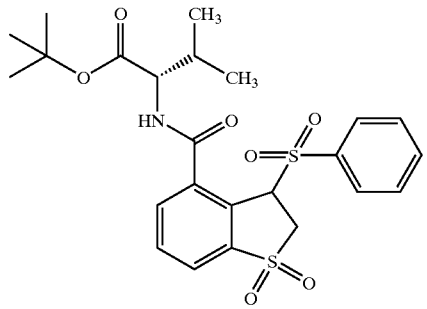

TLC: Rf 0.34 (hexane:ethyl acetate=1:1);

NMR (CDCl₃): δ7.98 (d, J=7.8 Hz, 0.5H), 7.91–7.80 (m, 3.5H), 7.76–7.67 (m, 2H), 7.60–7.55 (m, 2H), 6.92 (d, J=8.1 Hz, 0.5H), 6.84 (d, J=8.7 Hz, 0.5H), 6.25 (dd, J=9.3, 1.5 Hz, 0.5H), 6.18 (dd, J=9.3, 1.5 Hz, 0.5H), 4.66 (dd, J=8.7, 3.9 Hz, 0.5H), 4.62 (dd, J=8.1, 5.3 Hz, 0.5H), 3.87 (dd, J=15.0, 1.5 Hz, 0.5H), 3.80 (dd, J=15.0, 1.5 Hz, 0.5H), 3.67 (dd, J=15.0, 9.3 Hz, 0.5H), 2.41–2.36 (m, 0.5H), 2.33–2.24 (m, 0.5H), 1.54 (s, 4.5H), 1.46 (s, 4.5H), 1.11 (d, J=6.9 Hz, 1.5H), 1.07 (d, J=6.9 Hz, 1.5H), 1.06 (d, J=6.9 Hz, 1.5H), 1.05 (d, J=6.9 Hz, 1.5H).

EXAMPLE 35 (13)

4-(2-Fluorophenylmethyl)carbamoyl-3-phenylsufonyl-2,3-dihydro-1,1-dioxidebenzo[b]thiophene

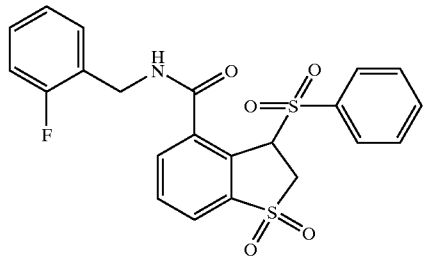

TLC: Rf 0.60 (chloroform:methanol=9:1);

NMR (DMSO-$d_6$): δ9.35 (t, J=7 Hz, 1H), 8.05 (d, J=8 Hz, 1H), 7.95 (d, J=8 Hz, 1H), 7.85 (t, J=8 Hz, 1H), 7.80–7.50 (m, 6H), 7.40–7.10 (m, 3H), 6.25 (d, J=10 Hz, 1H), 4.60 (dd, J=16 Hz and 7 Hz, 1H), 4.45 (dd, J=16 Hz and 7 Hz, 1H), 4.10 (dd, J=16 Hz and 10 Hz, 1H), 4.00 (d, J=16 Hz, 1H).

EXAMPLE 35 (14)

4-(3-Fluorophenylmethyl)carbamoyl-3-phenylsulfonyl-2,3-dihydro-1,1-dioxidebenzo[b]thiophene

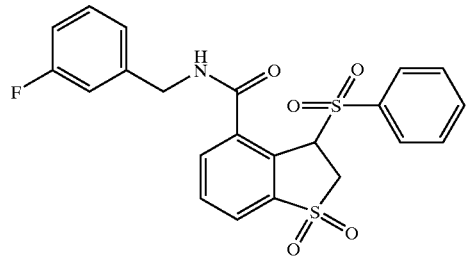

TLC: Rf 0.60 (chloroform:methanol=9:1);

NMR (DMSO-$d_6$): δ9.40 (t, J=7 Hz, 1H), 8.05 (d, J=8 Hz, 1H), 7.95 (d, J=8 Hz, 1H), 7.85 (t, J=8 Hz, 1H), 7.80–7.70 (m, 3H), 7.70–7.55 (m, 2H), 7.45–7.20 (m, 3H), 7.05 (m, 1H), 6.25 (d, J=10 Hz, 1H), 4.55 (d, J=7 Hz, 2H), 4.10 (dd, J=16 Hz and 10 Hz, 1H), 3.97 (dd, J=16 Hz, 1H).

EXAMPLE 35 (15)

4-(3-Methylphenylmethyl)carbamoyl-3-phenylsulfonyl-2,3-dihydro-1,1-dioxidebenzo[b]thiophene

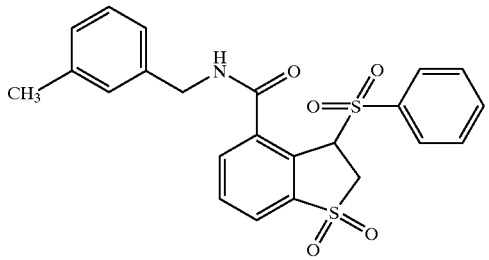

TLC: Rf 0.69 (chloroform:methanol=9:1);

NMR (DMSO-$d_6$): δ9.31 (t, J=6.0 Hz, 1H), 8.06 (d, J=7.6 Hz, 1H), 7.96 (d, J=7.6 Hz, 1H), 7.85 (t, J=7.6 Hz, 1H), 7.80–7.70 (m, 3H), 7.70–7.55 (m, 2H), 7.30–7.15 (m, 3H), 7.15–7.00 (m, 1H), 6.31 (dd, J=8.6 Hz and 2.0 Hz, 1H), 4.48 (m, 2H), 4.10 (dd, J=15 Hz and 8.6 Hz, 1H), 3.98 (dd, J=15 Hz and 2.0 Hz, 1H), 2.27 (s, 3H).

EXAMPLE 35 (16)

4-(2-Methoxyphenylmethyl)carbamoyl-3-phenylsulfonyl-2,3-dihydro-1,1-dioxidebenzo[b]thiophene

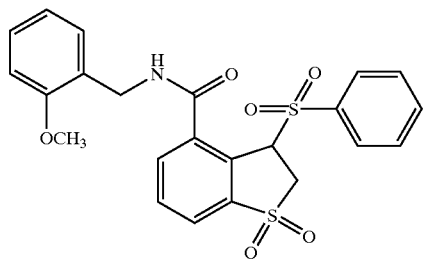

TLC: Rf 0.70 (chloroform:methanol=9:1);

NMR (DMSO-$d_6$): δ9.15 (t-like, J=6 Hz, 1H), 8.08 (d, J=7.5 Hz, 1H), 7.95 (d, J=7.5 Hz, 1H), 7.85 (t, J=7.5 Hz, 1H), 7.80–7.70 (m, 3H), 7.70–7.55 (m, 2H), 7.50–7.35 (m, 1H), 7.35–7.20 (m, 1H), 7.10–6.80 (m, 2H), 6.28 (d, J=8 Hz, 1H), 4.57 (dd, J=16 Hz and 6 Hz, 1H), 4.35 (dd, J=16 Hz and 6 Hz, 1H), 4.10 (dd, J=15.5 Hz and 8 Hz, 1H), 4.00 (d, J=15.5 Hz, 1H), 3.85 (s, 3H).

EXAMPLE 35 (17)

4-(2,3-Dimethoxyphenylmethyl)carbamoyl-3-phenylsulfonyl-2,3-dihydro-1,1-dioxidebenzo[b]thiophene

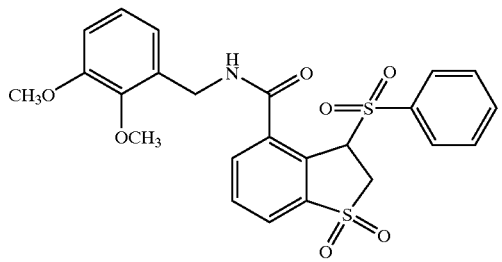

TLC: Rf 0.52 (chloroform:methanol=9:1);

NMR (DMSO-$d_6$): δ9.22 (t, J=5.5 Hz, 1H), 8.05 (d, J=7.0 Hz, 1H), 7.95 (d, J=7.0 Hz, 1H), 7.85 (t, J=7.0 Hz, 1H), 7.80–7.70 (m, 3H), 7.70–7.57 (m, 2H), 7.15–6.90 (m, 3H), 6.29 (dd, J=8.5 Hz and 2.0 Hz, 1H), 4.62 (dd, J=15.0 Hz and 5.5 Hz, 1H), 4.38 (dd, J=15.0 Hz and 5.5 Hz, 1H), 4.11 (dd, J=15.5 Hz and 8.5 Hz, 1H), 3.99 (dd, J=15.5 Hz and 2.0 Hz, 1H), 3.82 (s, 6H).

EXAMPLE 35 (18)

4-(3,4-Dimethoxyphenylmethyl)carbamoyl-3-phenylsulfonyl-2,3-dihydro-1,1-dioxidebenzo[b]thiophene

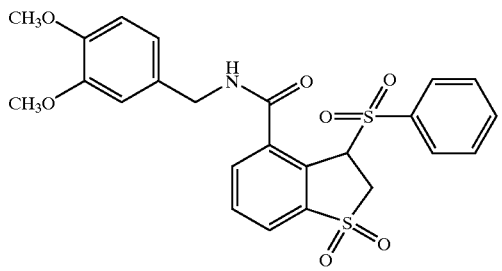

TLC: Rf 0.48 (chloroform:methanol=9:1);

NMR (DMSO-$d_6$): δ9.27 (t, J=6.0 Hz, 1H), 8.04 (d, J=7.5 Hz, 1H), 7.95 (d, J=7.5 Hz, 1H), 7.85 (t, J=7.5 Hz, 1H), 7.80–7.70 (m, 3H), 7.70–7.57 (m, 2H), 7.44 (s, 1H), 7.00–6.85 (m, 2H), 6.31 (dd, J=8.6 Hz and 1.4 Hz, 1H), 4.45 (m, 2H), 4.11 (dd, J=15.0 Hz and 8.6 Hz, 1H), 3.99 (dd, J=15.0 Hz and 1.4 Hz, 1H), 3.73 (s, 3H), 3.72 (s, 3H).

EXAMPLE 35(19)

4-(2,5-Difluorophenylmethyl)carbamoyl-3-phenylsulfonyl-2,3-dihydro-1,1-dioxidebenzo[b]thiophene

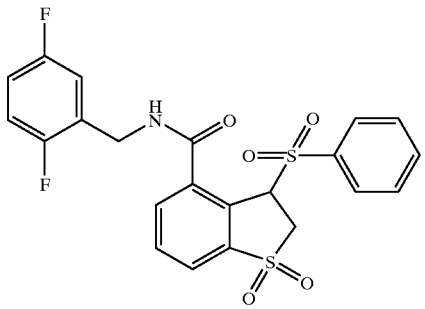

TLC: Rf 0.59 (chloroform:methanol=9:1);

NMR (DMSO-$d_6$): δ9.41 (t, J=5.8 Hz, 1H), 8.09 (dd, J=7.6 Hz and 1.5 Hz, 1H), 7.98 (dd, J=7.6 Hz and 1.5 Hz, 1H), 7.87 (t, J=7.6 Hz, 1H), 7.80–7.70 (m, 3H), 7.70–7.57 (m, 2H), 7.50–7.35 (m, 1H), 7.35–7.07 (m, 2H), 6.26 (dd, J=15 Hz and 8.4 Hz,1H), 4.54 (d, J=5.8 Hz, 2H), 4.10 (dd, J=15 Hz and 8.4 Hz, 1H), 3.97 (dd, J=15 Hz and 2.0 Hz, 1H).

EXAMPLE 35 (20)

4-(3,4,5-Trimethoxyphenylmethyl)carbamoyl-3-phenylsulfonyl-2,3-dihydro-1,1-dioxidebenzo[b]thiophene

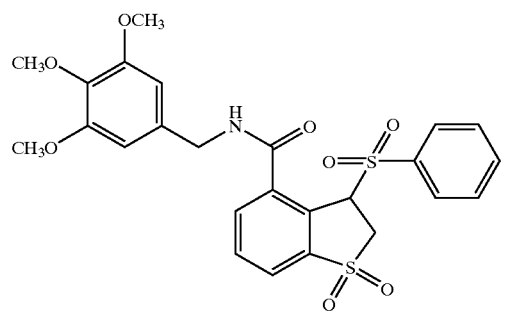

TLC: Rf 0.58 (chloroform:methanol=9:1);

NMR (DMSO-$d_6$): δ9.31 (m, 1H), 8.06 (d, J=7.6 Hz, 1H), 7.95 (d, J=7.6 Hz, 1H), 7.85 (t, J=7.6 Hz, 1H),7.80–7.70 (m, 3H), 7.70–7.55 (m, 2H), 6.79 (s, 2H), 6.32 (d, J=8.4 Hz, 1H), 4.61 (dd, J=15.2 Hz and 6.6 Hz, 1H), 4.37 (dd, J=15.2 Hz and 4.6 Hz, 1H), 4.12 (dd, J=15 Hz and 8.4 Hz, 1H), 3.99(d, J=15 Hz, 1H), 3.73 (s, 6H), 3.61 (s, 3H).

EXAMPLE 35 (21)

4-(Benzimidazol-2-ylmethyl)carbamoyl-3-phenylsulfonyl-2,3-dihydro-1,1-dioxidebenzo[b]thiophene

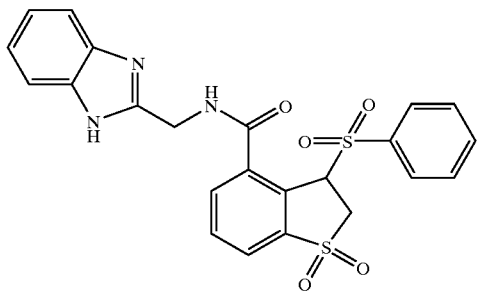

TLC: Rf 0.27 (chloroform:methanol=9:1);

NMR (DMSO-$d_6$): δ12.23 (broad-s, 1H), 9.48 (m, 1H), 8.17 (d, J=7 Hz, 1H), 8.00–7.80 (m, 2H), 7.80–7.70 (m, 3H), 7.70–7.45 (m, 4H), 7.20–7.10 (m, 2H), 6.29 (d, J=8 Hz, 1H), 4.89 (dd, J=16 Hz and 6 Hz, 1H), 4.51 (dd, J=16 Hz and 5 Hz, 1H), 4.13 (dd, J=15 Hz and 8 Hz, 1H), 3.99 (d, J=15 Hz, 1H).

EXAMPLE 35 (22)

4(3,5-Difluorophenylmethyl)carbamoyl-3-phenylsulfonyl-2,3-dihydro-1,1-dioxidebenzo[b]thiophene

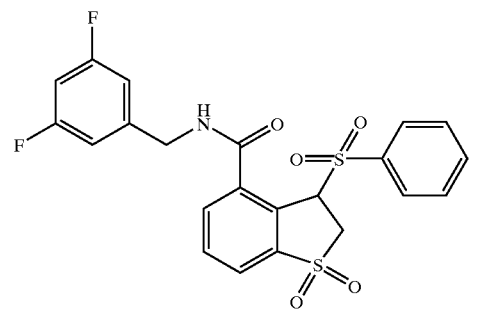

TLC: Rf 0.63 (chloroform:methanol=9:1);

NMR (DMSO-$d_6$): δ9.44 (t, J=5.6 Hz, 1H), 8.11 (d, J=7.4 Hz, 1H), 7.98 (d, J=7.4 Hz, 1H), 7.88 (t, J=7.4 Hz, 1H), 7.80–7.70 (m, 3H), 7.70–7.55 (m, 2H), 7.30–7.00 (m, 3H), 6.29 (dd, J=8.5 Hz and 2 Hz, 1H), 4.55 (m, 2H), 4.11 (dd, J=15 Hz and 8.5 Hz, 1H), 3.98 (dd, J=15 Hz and 2Hz, 1H).

EXAMPLE 35 (23)

4-(N-Benzyl-N-methylcarbamoyl)-3-phenylsulfonyl-2,3-dihydro-1,1-dioxidebenzo[b]thiophene

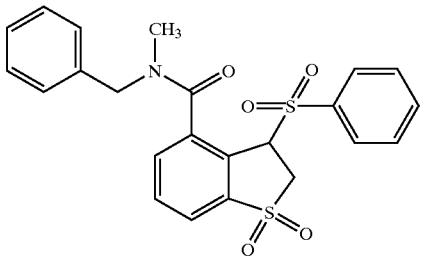

NMR (CDCl$_3$): δ8.00–7.25 (m, 13H), 6.00–5.90 (m, 1H), 5.19 (d, J=15 Hz) and 5.03 (d, J=18 Hz, total 1H), 4.49 (d, J=15 Hz) and 4.40 (d, J=18 Hz, total 1H), 3.75 (dd, J=2 Hz and 15 Hz, 1H), 3.63 (dd, J=8.5 Hz and 15 Hz, 1H), 3.18 and 3.12 (each s, total 3H).

EXAMPLE 35 (24)

4-(4-Nitrophenylmethyl)carbamoyl-3-phenylsulfonyl-2,3-dihydro-1,1-dioxidebenzo[b]thiophene

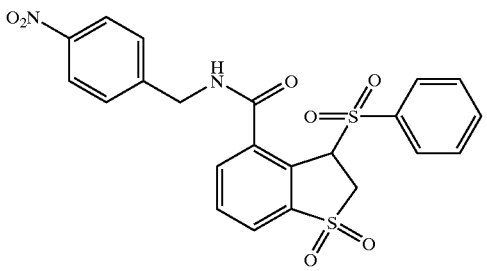

TLC: Rf 0.50 (chloroform:methanol=9:1);

NMR (DMSO-$d_6$): δ9.52 (m, 1H), 8.30–7.55 (m, 13H), 6.27 (d, J=6.4 Hz, 1H), 4.65 (m, 2H), 4.10 (dd, J=15.5 Hz and 6.4 Hz, 1H), 3.97 (d, J=15.5 Hz, 1H).

EXAMPLE 35 (25)

5-(2-Hydroxyethyl)carbamoyl-3-phenylsulfonyl-2,3-dihydro-1,1-dioxidebenzo[b]thiophene

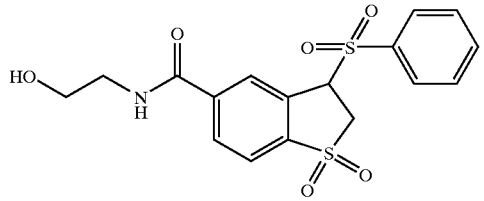

TLC: Rf 0.39 (ethyl acetate:methanol=95:5);

NMR (DMSO-$d_6$): δ8.79 (t, J=5.7 Hz, 1H), 8.18 (brs, 1H), 8.14 (d, J=8.1 Hz, 1H), 7.91 (d, J=8.1 Hz, 1H), 7.82–7.75 (m, 3H), 7.68–7.58 (m, 2H), 5.83 (dd, J=9.4 Hz, 3.0 Hz, 1H), 4.77 (t, J=5.7 Hz, 1H), 4.03 (dd, J=15.0 Hz, 9.6 Hz, 1H), 3.84 (dd, J=15.0 Hz, 3.0 Hz, 1H), 3.54 (q, J=5.7 Hz, 2H), 3.36 (q, J=5.7 Hz, 2H).

EXAMPLE 35 (26)

5-(Pyridin-3-ylmethyl)carbamoyl-4-methoxy-3-phenylsulfonyl-2,3-dihydro-1,1-dioxidebenzo[b]thiophene

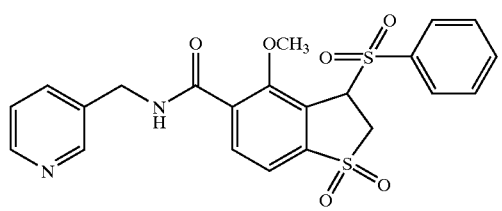

Free Compound

TLC: Rf 0.32 (ethyl acetate:methanol=9:1);

NMR (CDCl$_3$): δ8.59–8.56 (m, 2H), 8.04 (d, J=8.5 Hz, 1H), 7.74–7.68 (m, 3H), 7.58–7.53 (m, 1H), 7.47–7.31 (m, 5H), 5.16 (d, J=8.5 Hz, 1H), 4.68 (dd, J=15.0, 6.0 Hz, 1H), 4.59 (dd, J=15.0, 6.0 Hz, 1H), 4.11 (d, J=15.0 Hz, 1H), 3.77 (dd, J=15.0, 8.5 Hz, 1H), 3.67 (s,3 H).

Hydrochloride

TLC: Rf 0.32 (ethyl acetate:methanol=9:1);

NMR (DMSO-d$_6$): δ9.37 (t, J=5.5 Hz, 1H), 8.90 (s, 1H), 8.84 (d, J=5.5 Hz, 1H), 8.49 (d, J=8.0 Hz, 1H), 8.02 (dd, J=8.0, 5.5 Hz, 1H), 7.85–7.75 (m, 4H), 7.67–7.56 (m, 3H), 5.70 (d, J=9.0 Hz, 1H), 4.72–4.60 (m, 2H), 4.15 (d, J=15.0 Hz, 1H), 4.02 (dd, J=15.0, 9.0 Hz, 1H), 3.56 (s, 3H).

EXAMPLE 35 (27)

5-(2-Dimethylaminoethyl)carbamoyl-4-methoxy-3-phenylsulfonyl-2,3-dihydro-1,1-dioxidebenzo[b]thiophene

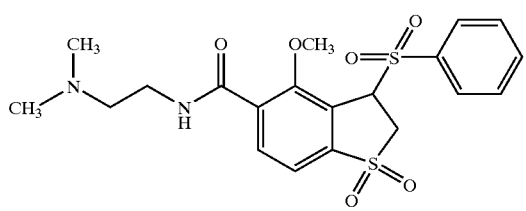

Free Compound

TLC: Rf 0.24 (ethyl acetate:methanol:triethylamine=8:1:1);

NMR (CDCl$_3$): δ8.00 (d, J=8.0 Hz, 1H), 7.76–7.73 (m, 2H), 7.67–7.61 (m, 1H), 7.51–7.41 (m, 3H), 7.32 (bt, J=5.0 Hz, 1H), 5.23 (t, J=9.0 Hz, 1H), 4.19 (d, J=15.0 Hz, 1H), 3.81 (dd, J=15.0, 9.0 Hz, 1H), 3.77 (s, 3H), 3.64–3.42 (m, 2H), 2.51 (t, J=6.0 Hz, 1H), 2.28 (s, 6H).

Hydrochloride

TLC: Rf 0.24 (ethyl acetate:methanol:triethylamine=8:1:1);

NMR (DMSO-d$_6$): δ10.47 (br, 1H), 8.90 (t, J=5.5 Hz, 1H), 7.86–7.76 (m, 4H), 7.69–7.64 (m, 2H), 7.56 (d, J=8.0 Hz, 1H), 5.69 (d, J=8.5 Hz, 1H), 4.13 (d, J=15.0 Hz, 1H), 4.00 (d, J=15.0, 8.5 Hz, 1H), 3.65–3.60 (m, 2H), 3.63 (s, 3H), 3.25 (t, J=6.0 Hz, 2H), 2.82 (s, 6H).

EXAMPLE 35 (28)

5-Dimethylcarbamoyl-4-methoxy-3-phenylsulfonyl-2,3-dihydro-1,1-dioxidebenzo[b]thiophene

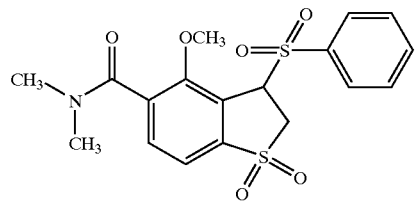

TLC: Rf 0.35 (ethyl acetate);

NMR (DMSO-d$_6$): δ7.83 (d, J=8.0 Hz, 2H), 7.44 (t, J=7.5 Hz, 1H), 7.63 (dd, J=8.0 Hz, 7.5 Hz, 2H), 7.49 (d, J=8.0 Hz, 1H), 7.46 (d, J=7.5 Hz, 1H), 5.63 (d, J=8.5 Hz, 1H), 4.13 (d, J=14.5 Hz, 1H), 4.02 (dd, J=14.5 Hz, 8.5 Hz, 1H), 3.59 (s, 3H), 3.01 (s, 3H), 2.78 (s, 3H).

EXAMPLE 35 (29)

5-(2,3,4,5,6,7-Hexahydro-1H-azepin-1-yl)carbonyl-4-methoxy-3-phenylsulfonyl-2,3-dihydro-1,1-dioxidebenzo[b]thiophene

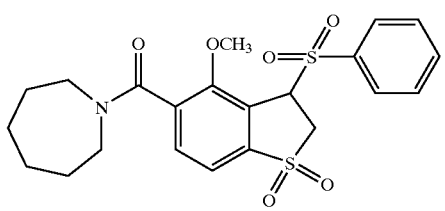

TLC: Rf 0.21 (ethyl acetate:hexane=2:1);

NMR (DMSO-d$_6$): δ7.87–7.70 (m, 3H), 7.70–7.60 (m, 2H), 7.60–7.53 (m, 2H), 5.67 (d, J=8.7 Hz, 1H), 4.26 (d, J=15.0 Hz, 1H), 4.05 (dd, J=15.0, 8.7 Hz, 1H), 3.70–3.54 (m, 2H), 3.48 (s, 3H), 3.20–3.15 (m, 2H),1.85–1.40 (m, 8H).

EXAMPLE 35 (30)

5-(2,3-Dihydroindol-1-yl)carbonyl-4-methoxy-3-phenylsulfonyl-2,3-dihydro-1,1-dioxidebenzo[b]thiophene

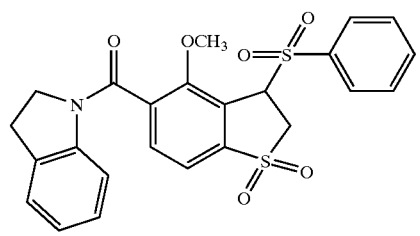

TLC: Rf 0.54 (ethyl acetate:hexane=2:1);

NMR (DMSO-d$_6$): δ8.13 (d, J=7.8 Hz, 1H), 7.87 (d, J=7.5 Hz, 1H), 7.83–7.70 (m, 2H), 7.70–7.56 (m, 2H), 7.66 (t, J=7.8 Hz, 2H), 7.31 (d, J=7.5 Hz, 1H), 7.25 (t, J=7.5 Hz, 1H), 7.12 (t, J=7.5 Hz, 1H), 5.72 (d, J=8.7 Hz, 1H), 4.39–3.97 (m, 2H), 3.76 (dd, J=18.6, 8.7 Hz, 1H), 3.70–3.50 (m, 1H), 3.57 (s, 3H), 3.21–3.08 (m, 2H).

EXAMPLE 35 (31)

5-(4-(2-Chlorophenyl)piperazin-1-yl)carbonyl-4-methoxy-3-phenylsulfonyl-2,3-dihydro-1,1-dioxidebenzo[b]thiophene

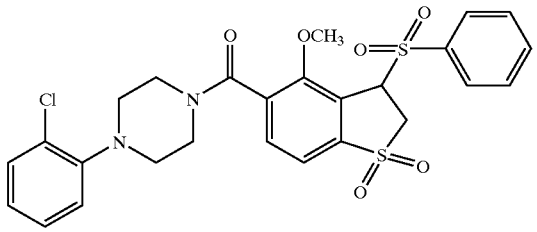

TLC: Rf 0.78 (methylene chloride:methanol=10:1);

NMR (CDCl$_3$+DMSO-d$_6$): δ7.94–7.86 (m, 1H), 7.77–7.66 (m, 2H), 7.64–7.50 (m, 4H), 7.44–7.16 (m, 2H), 7.10–6.99 (m, 2H), 5.38–5.27 (m, 1H), 4.26–4.00 (m, 2H), 3.95 and 3.78 (each s, total 3H), 3.90 –3.65 (m, 2H) 3.50–2.80 (m, 6H).

EXAMPLE 35 (32)

5-(4-(2-(2-Trifluoromethylphenyl)ethyl)piperazin-1-yl)carbonyl-4-methoxy-3-phenylsulfonyl-2,3-dihydro-1,1-dioxidebenzo[b]thiophene

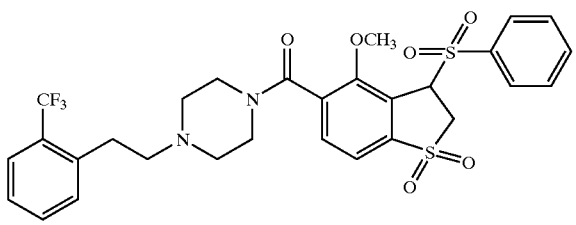

TLC: Rf 0.51 (methylene chloride:methanol=10:1);

NMR (CDCl$_3$): δ7.93–7.86 (m, 1H), 7.74–7.43 (m, 7H), 7.40–7.30 (m, 3H), 5.31–5.20 (m, 1H), 4.24–3.64 (m, 7H), 3.34–3.10 (m, 2H), 3.06–2.90 (m, 2H), 2.70–2.30 (m, 6H).

EXAMPLE 35 (33)

4-(Pyridin-3-ylcarbonyl)aminomethyl-3-phenylsulfonyl-2,3-dihydro-1,1-dioxidebenzo[b]thiophene

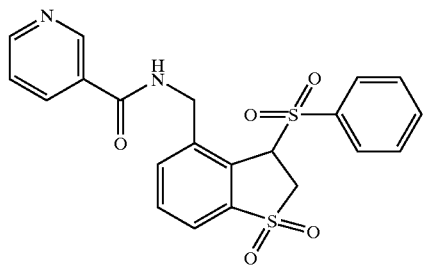

Free Compound

TLC: Rf 0.38 (ethyl acetate:methanol=9:1);

NMR (DMSO-d$_6$): δ9.31 (t, J=6.0 Hz, 1H), 9.05 (d, J=1.5 Hz, 1H), 8.72 (dd, J=5.0, 1.5 Hz, 1H), 8.23 (dt, J=8.0, 1.5 Hz, 1H), 7.87–7.63 (m, 8H), 7.52 (dd, J=8.0, 5.0 Hz, 1H), 6.05 (d, J=8.5 Hz, 1H), 5.01 (dd, J=16.0, 6.0 Hz, 1H), 4.78 (dd, J=16.0, 6.0 Hz, 1H), 4.02 (dd, J=15.3, 8.5 Hz, 1H), 3.86 (d, J=15.3 Hz, 1H).

Hydrochloride

TLC: Rf 0.38 (ethyl acetate:methanol=9:1);

NMR (DMSO-d$_6$): δ9.63–9.59 (m, 1H), 9.20 (s, 1H), 8.86 (d, J=5.0 Hz, 1H), 8.57–8.54 (m, 1H), 7.87–7.63 (m, 9H), 6.11 (d, J=8.5 Hz, 1H), 5.02 (dd, J=15.8, 5.7 Hz, 1H), 4.80 (dd, J=15.8, 5.7 Hz, 1H), 4.00 (dd, J=15.5, 8.5 Hz, 1H), 3.86 (d, J=15.5 Hz, 1H).

EXAMPLE 35 (34)

4-(3-Pyrrol-1-yl)propyl)oxy-3-phenylsulfonyl-2,3-dihydro-1,1-dioxidebenzo[b]thiophene

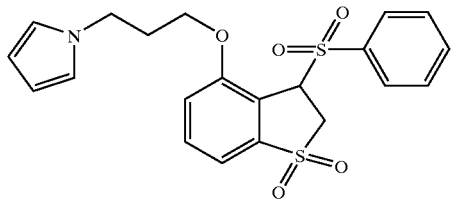

TLC: Rf 0.20 (ethyl acetate:hexane=1:1);

NMR (CDCl$_3$): δ7.75–7.35 (m, 6H), 7.24 (d, J=8 Hz, 1H), 6.93 (d, J=8 Hz, 1H), 6.68 (t, J=2 Hz, 2H), 6.15 (t, J=2 Hz, 2H), 5.21 (d, J=9Hz, 1H), 4.53–4.00 (m, 2H), 4.10 (d, J=15 Hz, 1H), 4.00–3.65 (m, 2H), 3.73 (dd, J=9, 15 Hz, 1H), 2.19 (quint, J=5 Hz, 2H).

EXAMPLE 35 (35)

4-(Quinolin-2-ylmethyl)oxy-3-phenylsulfonyl-2,3-dihydro-1,1-dioxidebenzo[b]thiophene

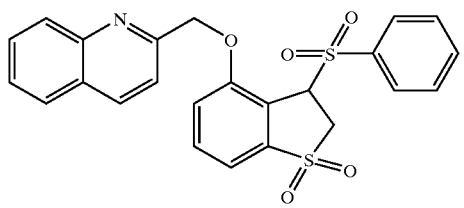

Free Compound

TLC: Rf 0.21 (benzene:ethyl acetate=2:1);

NMR (CDCl$_3$): δ8.42 (d, J=9 Hz, 1H), 8.03 (d, J=8 Hz, 2H), 7.90–7.20 (m, 11H), 5.80 (d, J=8 Hz, 1H), 5.31 (d, J=13 Hz, 1H), 5.09 (d, J=13 Hz, 1H), 4.24 (d, J=15 Hz, 1H), 4.02 (dd, J=8, 15 Hz, 1H).

Hydrochloride

TLC: Rf 0.30 (hexane:ethyl acetate=1:2);

NMR (DMSO-d$_6$): δ8.64 (d, J=8.5 Hz, 1H), 8.20 (d, J=8.5 Hz, 1H), 8.13 (d, J=8.5 Hz, 1H), 7.92 (t-like, J=8.5 Hz, 1H), 7.81–7.65 (m, 5H), 7.48–7.31 (m, 5H), 5.91 (d, J=9.0 Hz, 1H), 5.42 (d, J=13.5 Hz, 1H), 5.21 (d, J=13.5 Hz, 1H), 4.22 (d, J=15.0 Hz, 1H), 4.02 (dd, J=9.0 Hz, 1H).

EXAMPLE 35 (36)

4-(2-(Pyrrol-1-yl)ethyl)oxy-3-phenylsulfonyl-2,3-dihydro-1,1-dioxidebenzo[b]thiophene

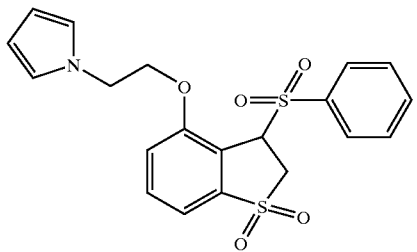

TLC: Rf 0.36 (hexane:ethyl acetate=1:2);

NMR (CDCl$_3$+CD$_3$OD): δ7.85–7.58 (m, 3H), 7.58–7.42 (m, 3H), 7.28 (d, J=8 Hz, 1H), 6.92 (d, J=8 Hz, 1H), 6.74 (t, J=2 Hz, 2H), 6.18 (t, J=2 Hz, 2H), 5.16 (d, J=9 Hz, 1H), 4.30–4.05 (m, 5H), 3.73 (dd, J=9, 15 Hz, 1H).

EXAMPLE 35 (37)

4-(2-(4-Methylthiazol-5-yl)ethyl)oxy-3-phenylsulfonyl-2,3-dihydro-1,1-dioxidebenzo[b]thiophene.hydrochloride

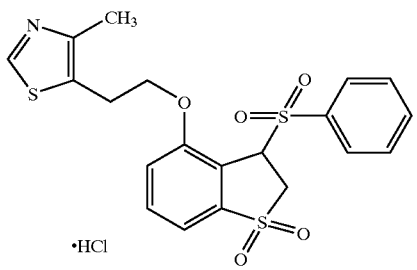

TLC: Rf 0.25 (ethyl acetate);

NMR (CD$_3$OD): δ9.88 (s, 1H), 7.80–7.40 (m, 6H), 7.26 (d, J=8 Hz, 1H), 7.25 (d, J=8 Hz, 1H), 5.48 (d, J=9 Hz, 1H), 4.42–4.18 (m, 2H), 4.08 (d, J=15 Hz, 1H), 3.92 (dd, J=9, 15 Hz, 1H), 3.55–3.15 (m, 2H), 2.60 (s, 3H).

EXAMPLE 35 (38)

4-(3-(Pyridin-4-yl)propyl)oxy-3-phenylsulfonyl-2,3-dihydro-1,1-dioxidebenzo[b]thiophene

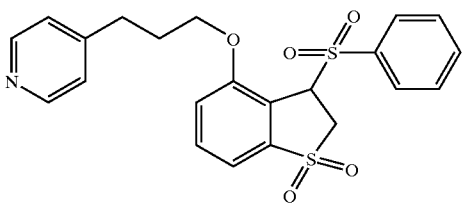

Free Compound

TLC: Rf 0.26 (ethyl acetate:methanol=10:1);

NMR (CDCl$_3$): δ8.53 (dd, J=1, 5 Hz, 2H), 7.78–7.35 (m, 6H), 7.25 (d, J=7 Hz, 1H), 7.17 (d, J=6 Hz, 2H), 6.95 (d, J=8 Hz, 1H), 5.17 (d, J=9 Hz, 1H), 4.14 (d, J=15 Hz, 1H), 4.05–3.82 (m, 2H), 3.74 (dd, J=9, 15 Hz, 1H), 2.87 (t, J=6 Hz, 2H), 2.10 (quint, J=6 Hz, 2H).

Hydrochloride

TLC: Rf 0.39 (ethyl acetate:methanol:ammonia water=100:10:1);

NMR (DMSO-d$_6$): δ8.83 (d, J=6 Hz, 2H), 7.90 (d, J=5 Hz, 2H), 7.85–7.52 (m, 6H), 7.34 (d, J=8 Hz, 1H), 7.24 (d, J=8 Hz, 1H), 5.64 (d, J=9 Hz, 1H), 4.18 (d, J=15 Hz, 1H), 4.00 (dd, J=9, 15 Hz, 1H), 3.10–2.80 (m, 2H), 2.10–1.60 (m, 2H).

EXAMPLE 35 (39)

4-(1-t-Butoxycarbonylpiperidin-3-ylmethyl)oxy-3-phenylsulfonyl-2,3-dihydro-1,1-dioxidebenzo[b]thiophene

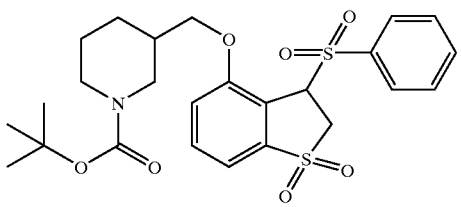

TLC: Rf 0.23 (hexane:ethyl acetate=1:1);

NMR (CD$_3$OD): δ7.95–7.45 (m, 6H), 7.40–7.05 (m, 2H), 5.53 (d, J=9 Hz, 1H), 4.15 (d, J=15 Hz, 1H), 3.92 (dd, J=9, 15 Hz, 1H), 4.05–3.55 (m, 4H), 3.20–2.40 (m. 2H), 2.00–1.20 (m, 5H), 1.47 and 1.44 (each s, 9H).

EXAMPLE 35 (40)

4-(2-(Pyrrolidin-1-yl)ethyl)oxy-3-phenylsulfonyl-2,3-dihydro-1,1-dioxidebenzo[b]thiophene

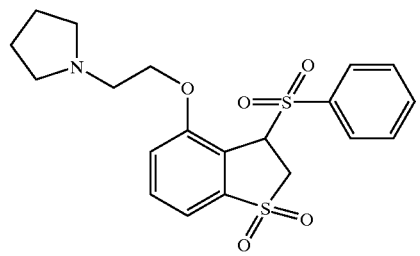

Free Compound

TLC: Rf 0.17 (chloroform:methanol=10:1);

NMR (CDCl$_3$): δ7.85–7.68 (m, 2H), 7.68–7.35 (m, 4H), 7.28 (d, J=8 Hz, 1H), 6.97 (d, J=8 Hz, 1H), 5.30 (d, J=9 Hz, 1H), 4.23 (d, J=15 Hz, 1H), 4.15–3.95 (m, 1H), 3.95–3.70 (m, 1H), 3.74 (dd, J=9, 15 Hz, 1H), 2.78 (t, J=6 Hz, 2H), 2.70–2.45 (m, 4H), 1.95–1.60 (m, 4H).

Hydrochloride

TLC: Rf 0.36 (ethyl acetate:acetic acid:water=3:1:1);

NMR (CDCl$_3$+CD$_3$OD): δ7.98–7.82 (m, 2H), 7.80–7.45 (m, 4H), 7.34 (d, J=8 Hz, 1H), 7.26 (d, J=8 Hz, 1H), 6.20–6.05 (m, 1H), 4.75–4.50 (m, 1H), 4.50–4.25 (m, 1H), 4.10–3.85 (m, 2H), 3.85–3.45 (m, 4H), 3.30–2.90 (m, 2H), 2.40–2.00 (m, 4H).

EXAMPLE 35 (41)

4-(2-(Piperidin-1-yl)ethyl)oxy-3-phenylsulfonyl-2,3-dihydro-1,1-dioxidebenzo[b]thiophene

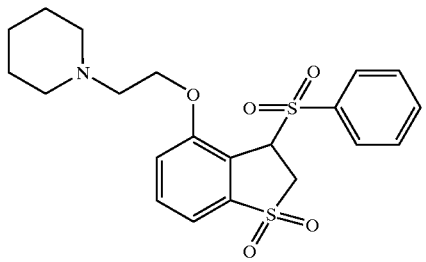

Free Compound

TLC: Rf 0.24 (chloroform:methanol=10:1);

NMR (CDCl$_3$): δ7.85–7.67 (m, 2H), 7.67–7.36 (m, 4H), 7.27 (d, J=8 Hz, 1H), 6.97 (d, J=8 Hz, 1H), 5.29 (d, J=9 Hz, 1H), 4.25 (d, J=15 Hz, 1H), 4.18–3.92 (m, 1H), 3.92–3.65 (m, 1H), 3.74 (dd, J=9, 15 Hz, 1H), 2.62 (t, J=6 Hz, 2H), 2.46 (t, J=6 Hz, 4H), 1.90–1.35 (m, 6H).

Hydrochloride

TLC: Rf 0.40 (ethyl acetate:acetic acid:water=3:1:1);

NMR (CDCl$_3$+CD$_3$OD): δ7.95–7.75 (m, 2H), 7.75–7.45 (m, 4H), 7.32 (d, J=8 Hz, 1H), 7.30 (d, J=8 Hz, 1H), 6.05–5.85 (m, 1H), 4.75–4.38 (m, 2H), 3.95–3.42 (m, 6H), 3.15–2.85 (m, 2H), 2.35–1.35 (m, 6H).

EXAMPLE 35 (42)

4-(2-(2-Acetyloxyethoxy)ethyl)oxy-3-phenylsulfonyl-2,3-dihydro-1,1-dioxidebenzo[b]thiophene

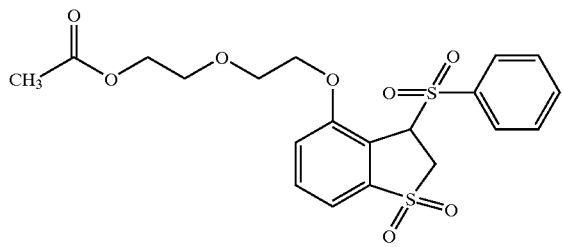

TLC: Rf 0.17 (ethyl acetate:hexane=2:1);

NMR (CDCl$_3$): δ7.82–7.70 (m, 2H), 7.65–7.35 (m, 4H), 7.27 (d, J=8 Hz, 1H), 7.00 (d, J=8 Hz, 1H), 5.30 (d, J=9 Hz, 1H), 4.32–4.05 (m, 4H), 4.05–3.88 (m, 1H), 3.84–3.75 (m, 5H), 2.05 (s, 3H).

EXAMPLE 35 (43)

4-(2-(4-Benzylpiperazin-1-yl)ethyl)oxy-3-phenylsulfonyl-2,3-dihydro-1,1-dioxidebenzo[b]thiophene

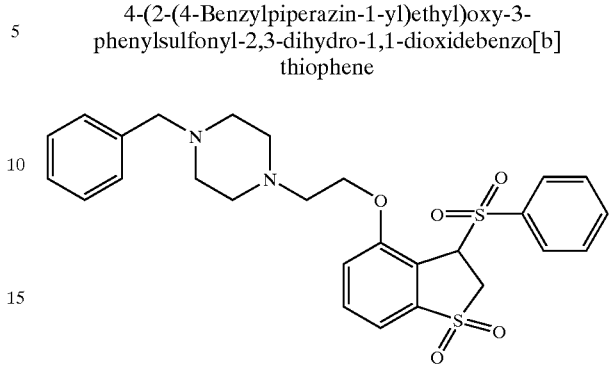

Free Compound

TLC: Rf 0.42 (chloroform:methanol=5:1);

NMR (CDCl$_3$): δ7.80–7.68 (m, 2H), 7.68–7.37 (m, 4H), 7.37–7.18 (m, 6H), 6.96 (d, J=8 Hz, 1H), 5.27 (d, J=9 Hz, 1H), 4.22 (d, J=15 Hz, 1H), 4.15–3.94 (m, 1H), 3.94–3.70 (m, 1H), 3.72 (dd, J=9, 15 Hz, 1H), 3.52 (s, 2H), 2.68 (t, J=6 Hz, 2H), 2.63–2.35 (m, 8H).

2hydrochloride

TLC: Rf 0.28 (ethyl acetate:acetic acid:water=3:1:1);

NMR (CD$_3$OD): δ7.90–7.22 (m, 13H), 6.13–6.00 (m, 1H), 4.68–4.35 (m, 2H), 4.46 (S, 2H), 4.10–3.40 (m, 12H).

EXAMPLE 35 (44)

4-Diethylcarbamoylmnethyloxy-3-phenylsulfonyl-2,3-dihydro-1,1-dioxidebenzo[b]thiophene

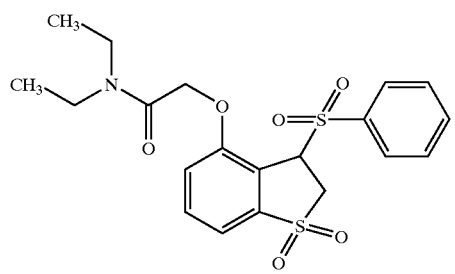

TLC: Rf 0.40 (ethyl acetate);

NMR (CDCl$_3$): δ7.83–7.77 (m, 2H), 7.68–7.59 (m, 1H), 7.56–7.45 (m, 3H), 7.32 (d, J=7.6 Hz, 1H), 7.01 (d, J=7.6 Hz, 1H), 5.44 (d, J=8.8 Hz, 1H), 4.59 (d, J=14.5 Hz, 1H), 4.51 (d, J=14.5 Hz, 1H), 4.15 (d, J=15.0 Hz, 1H), 3.74 (dd, J=15.0, 8.8 Hz, 1H), 3.39 (q, J=7.0 Hz, 2H), 3.30 (q, J=7.0 Hz, 2H), 1.22 (t, J=7.0 Hz, 3H), 1.14 (t, J=7.0 Hz, 3H).

EXAMPLE 35 (45)

4-Cyanomethyloxy-3-phenylsulfonyl-2,3-dihydro-1,1-dioxidebenzo[b]thiophene

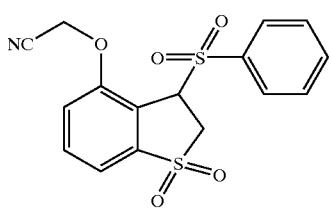

TLC: Rf 0.27 (hexane:ethyl acetate=1:2);

NMR (DMSO-$d_6$): δ7.82–7.72 (m, 4H), 7.68–7.60 (m, 2H), 7.50 (d, J=8.0 Hz, 1H), 7.41 (d, J=8.0 Hz, 1H), 5.60 (dd, J=9.0, 1.2 Hz, 1H), 5.04 (d, J=16.0 Hz, 1H), 4.90 (d, J=16.0 Hz, 1H), 4.20 (dd, J=15.2, 1.2 Hz, 1H), 4.00 (dd, J=15.2, 9.0 Hz, 1H).

EXAMPLE 35 (46)

5-(Pyridin-3-yloxy) methyl-4-methoxy-3-phenylsulfonyl-2,3-dihydro-1,1-dioxidebenzo[b]thiophene

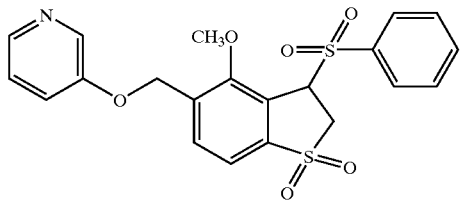

Free Compound

TLC: Rf 0.27 (ethyl acetate);

NMR (CDCl$_3$): δ8.37–8.36 (m, 1H), 8.31–8.29 (m, 1H), 7.76–7.71 (m, 3H), 7.66–7.61 (m, 1H), 7.49–7.43 (m, 3H), 7.27–7.25 (m, 2H), 5.25 (dd, J=9.5, 1.0 Hz, 1H), 5.16 (d, J=12.5 Hz, 1H), 5.12 (d, J=12.5 Hz, 1H), 4.15 (dd, J=15.0, 1.0 Hz, 1H), 3.90 (s, 3H), 3.81 (dd, J=15.0, 9.5 Hz, 1H).

Hydrochloride

TLC: Rf 0.27 (ethyl acetate);

NMR (DMSO-$d_6$): δ8.76 (d, J=2.5 Hz, 1H), 8.52 (d, J=5.0 Hz, 1H), 8.15 (dd, J=8.5, 2.5 Hz, 1H), 7.93–7.74 (m, 5H), 7.65–7.60 (m, 3H), 5.78 (d, J=8.5 Hz, 1H), 5.35 (s, 2H), 4.17 (d, J=15.0 Hz, 1H), 4.06 (d, J=15.0, 8.5 Hz, 1H), 3.69 (s, 3H).

EXAMPLE 35 (47)

5-(2-(t-Butoxycarbonylamino)ethyl)oxy-4-nitro-3-phenylsulfonyl-2,3-dihydro-1,1-dioxidebenzo[b]thiophene TLC: Rf 0.34 (hexane:ethyl acetate=1:2);

NMR (CDCl$_3$): δ7.86–7.70 (m, 4H), 7.63–7.54 (m, 2H), 7.41 (d, J=8.8 Hz, 1H), 5.69 (dd, J=9.0, 1.8 Hz, 1H), 5.07 (br, 1H), 4.38–4.22 (m, 2H), 3.90 (dd, J=15.0, 1.8 Hz, 1H), 3.75 (dd, J=15.0, 9.0 Hz, 1H), 3.68–3.52 (m, 2H), 1.46 (s, 9H).

EXAMPLE 35 (48)

5-((2E)-3-Ethoxycarbonyl-2-propenyl)oxy-3-phenylsulfonyl-2,3-dihydro-1,1-dioxidebenzo[b]thiophene TLC: Rf 0.41 (hexane:ethyl acetate=1:1);

NMR (CDCl$_3$): δ7.72–7.65 (m, 3H), 7.62–7.46 (m, 4H), 7.15 (dd, J=8.7, 2.1 Hz, 1H), 7.08 (dt, J=15.6, 4.2 Hz, 1H), 6.20 (dt, J=15.6, 2.1 Hz, 1H), 5.01 (dd, J=8.7, 4.8 Hz, 1H), 4.87–4.81 (m, 2H), 4.24 (q, J=7.2 Hz, 2H), 3.77 (dd, J=14.7, 4.8 Hz, 1H), 3.70 (dd, J=14.7, 8.7 Hz, 1H), 1.31 (t, J=7.2 Hz, 3H).

EXAMPLE 35 (49)

4-(2,4-Dimethoxyphenylmethyl)aminomethyl-3-phenylsulfonyl-2,3-dihydro-1,1-dioxidebenzo[b]thiophene Free Compound
TLC: Rf 0.35 (ethyl acetate);
NMR (CDCl$_3$): δ7.69 (dd, J=6.9, 1.5 Hz, 1H), 7.64–7.50 (m, 5H), 7.46–7.41 (m, 2H), 7.01 (d, J=8.0 Hz, 1H), 6.45 (d, J=2.5 Hz, 1H), 6.43 (dd, J=8.0, 2.5 Hz, 1H), 6.06 (dd, J=J=9.3, 1.2 Hz, 1H), 4.51 (d, J=14.1 Hz, 1H), 3.91 (d, J=14.1 Hz, 1H), 3.85 (dd, J=15.0, 1.2 Hz, 1H), 3.81 (s, 3H), 3.78 (s, 3H), 3.73 (d, J=13.0 Hz, 1H), 3.66 (d, J=13.0 Hz, 1H), 3.65 (dd, J=15.0, 9.3 Hz, 1H).

Hydrochloride

TLC: Rf 0.35 (ethyl acetate);

NMR (DMSO-$d_6$): δ9.40 (br, 2H), 8.20–8.11 (m, 1H), 7.86–7.59 (m, 7H), 7.42 (d, J=8.4 Hz, 1H), 6.61–6.56 (m, 2H), 6.09 (dd, J=6.8, 3.0 Hz, 1H), 4.65 (d, J=13.8 Hz, 1H), 4.38 (d, J=13.8 Hz, 1H), 4.22–4.06 (m, 2H), 3.88–3.85 (m, 2H), 3.80 (s, 3H), 3.79 (s, 3H).

EXAMPLE 35 (50)

4-(Pyridin-3-ylmethyl)aminomethyl-3-phenylsulfonyl-2,3-dihydro-1,1-dioxidebenzo[b]thiophene.2hydrochloride

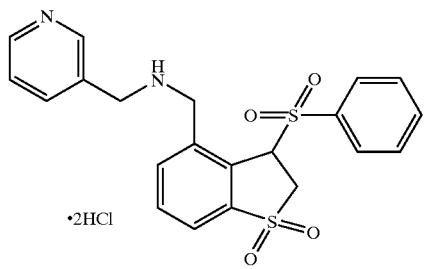

TLC: Rf 0.44 (chloroform:methanol=9:1);

NMR (CD$_3$OD): δ9.21 (s, 1H), 8.95 (d, J=5.6 Hz, 1H), 8.92–8.84 (m, 1H), 8.22 (dd, J=6.6, 2.2 Hz, 1H), 8.16 (dd, J=8.0, 5.6 Hz, 1H), 7.93–7.74 (m, 5H), 7.68–7.58 (m, 2H), 6.20 (dd, J=8.6, 1.6 Hz, 1H), 4.96 (d, J=13.2 Hz, 1H), 4.83–4.70 (m, 3H), 3.92 (dd, J=15.4, 8.6 Hz, 1H), 3.77 (dd, J=15.4, 1.6 Hz, 1H).

EXAMPLE 35 (51)

4-(2-Dimethylaminoethyl)aminomethyl-3-phenylsulfonyl-2,3-dihydro-1,1-dioxidebenzo[b]thiophene.2hydrochloride

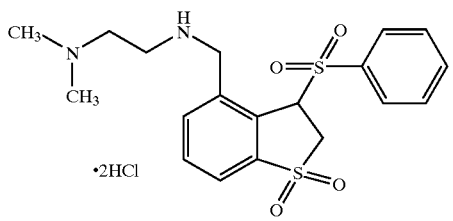

TLC: Rf 0.51 (chloroform:methanol:triethlamine=9:1:1);

NMR (DMSO-$d_6$): δ10.85–10.50 (br, 1H), 10.10–9.75 (br, 1H), 9.72–9.40 (br, 1H), 8.22 (dd, J=5.4, 3.0 Hz, 1H), 7.90–7.85 (m, 2H), 7.82–7.75 (m, 3H), 7.67–7.59 (m, 2H), 6.47 (t like, J=1.5 Hz, 1H), 4.72 (brd, J=12.0 Hz, 1H), 4.51 (brd, J=12.0 Hz, 1H), 3.91–3.84 (m, 2H), 3.70–3.30 (m, 4H), 2.85 (s, 6H).

EXAMPLE 35 (52)

4-(N,N-Bis(2-hydroxyethyl)amino)methyl-3-phenylsulfonyl-2,3-dihydro-1,1-dioxidebenzo[b]thiophene.hydrochloride

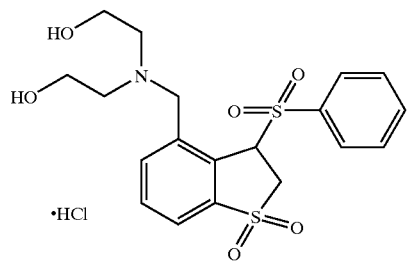

TLC: Rf 0.53 (chloroform:methanol=9:1);

NMR (DMSO-$d_6$): δ10.15–9.90 (br, 1H), 8.24 (d. J=6.6 Hz, 1H), 7.95–7.72 (m, 5H), 7.69–7.58 (m, 2H), 6.16 (d, J=8.7 Hz, 1H), 5.80–5.10 (br, 2H), 5.11 (brd, J=13.8 Hz, 1H), 4.70 (brd, J=13.8 Hz, 1H), 4.02 (dd, J=15.0, 8.7 Hz, 1H), 3.94–3.70 (m, 4H), 3.82 (d, J=15.0 Hz, 1H), 3.47–3.18 (m, 3H), 3.12–2.92 (m, 1H).

EXAMPLE 35 (53)

4-(2-(2-Hydroxyethoxy)ethyl)aminomethyl-3-phenylsulfonyl-2,3-dihydro-1,1-dioxidebenzo[b]thiophene.hydrochloride

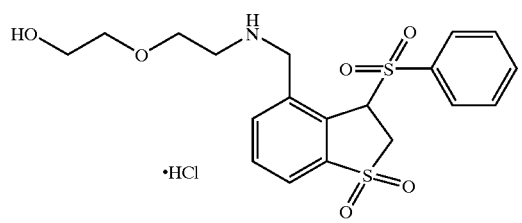

TLC: Rf 0.46 (methylene chloride:methanol=9:1);

NMR (DMSO-$d_6$): δ9.40–9.10 (br, 2H), 8.16 (dd, J=6.3, 2.4 Hz, 1H), 7.91–7.75 (m, 5H), 7.68–7.59 (m, 2H), 6.29 (dd, J=7.5, 2.4 Hz, 1H), 4.90–4.30 (br, 1H), 4.75–4.63 (m, 1H), 4.50–4.35 (m, 1H), 3.90 (dd, J=15.6, 7.5 Hz, 1H), 3.84 (dd, J=15.6, 2.4 Hz, 1H), 3.74 (t, J=5.1 Hz, 2H), 3.58–3.47 (m, 4H), 3.28–3.15 (m, 2H).

EXAMPLE 35 (54)

4-(4-Benzylpiperazine-1-yl)methyl-3-phenylsulfonyl-2,3-dihydro-1,1-dioxidebenzo[b]thiophene

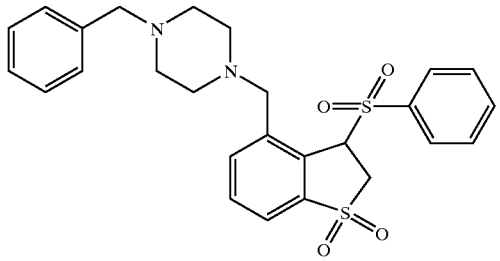

Free Compound
TLC: Rf 0.29 (chloroform:methanol=19:1);
NMR (CDCl$_3$): δ7.68–7.57 (m, 4H), 7.56–7.50 (m, 2H), 7.50–7.42 (m, 2H), 7.36–7.20 (m, 5H), 6.33 (d, J=9.0 Hz, 1H), 4.69 (d, J=14.1 Hz, 1H), 3.90 (d, J=15.0 Hz, 1H), 3.72 (dd, J=15.0, 9.0 Hz, 1H), 3.51 (s, 2H), 3.41 (d, J=14.1 Hz, 1H), 2.70–2.25 (m, 8H).
2hydrochloride
TLC: Rf 0.29 (chloroform:methanol=19:1);
NMR (DMSO-d$_6$): δ8.30–7.95 (br, 1H), 7.93–7.72 (m, 5H), 7.70–7.55 (m, 4H), 7.50–7.40 (m, 3H), 6.65–6.20 (br, 1H), 5.40–4.20 (br, 4H), 4.50–4.10 (br, 2H), 3.98 (dd, J=15.6, 9.0 Hz, 1H), 3.84 (d, J=15.6 Hz, 1H), 3.70–2.80 (m, 6H).

EXAMPLE 35 (55)

4-(4-(Pyridin-2-yl)piperazin-1-yl)methyl-3-phenylsulfonyl-2,3-dihydro-1,1-dioxidebenzo[b]thiophene

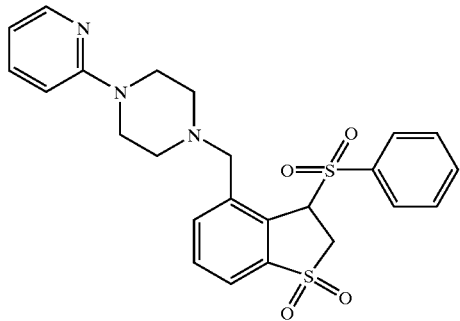

Free Compound
TLC: Rf 0.43 (chloroform:methanol=19:1);
NMR (CDCl$_3$): δ8.23–8.16 (m, 1H), 7.71–7.52 (m, 6H), 7.52–7.42 (m, 3H), 6.68–6.62 (m, 2H), 6.30 (d, J=9.0 Hz, 1H), 4.76 (d, J=14.1 Hz, 1H), 3.89 (d, J=15.0 Hz, 1H), 3.73 (dd, J=15.0, 9.0 Hz, 1H), 3.62–3.45 (m, 4H), 3.49 (d, J=14.1 Hz, 1H), 2.73–2.61 (m, 2H), 2.58–2.44 (m, 2H).
3hydrochloride
TLC: Rf 0.43 (chloroform:methanol=19:1);
NMR (DMSO-d$_6$): δ12.05–11.70 (br, 1H), 8.35 (d, J=6.3 Hz, 1H), 8.15–8.09 (m, 1H), 7.96–7.84 (m, 3H), 7.83–7.75 (m, 3H), 7.68–7.58 (m, 2H), 7.24 (d, J=8.7 Hz, 1H), 6.93 (t, J=6.3 Hz, 1H), 6.46 (d, J=8.7 Hz, 1H), 4.87 (d, J=13.8 Hz, 1H), 4.62 (d, J=13.8 Hz, 1H), 4.55–4.30 (m, 2H), 4.00 (dd, J=15.0, 8.7 Hz, 1H), 3.83 (d, J=15.0 Hz, 1H), 3.72–3.50 (m, 2H), 3.50–3.15 (m, 4H).

EXAMPLE 35 (56)

4-(4-Ethoxycarbonylpiperazin-1-yl)methyl-3-phenylsulfonyl-2,3-dihydro-1,1-dioxidebenzo[b]thiophene

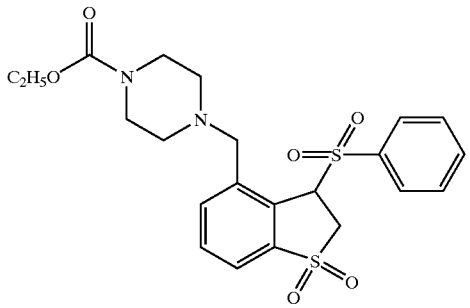

Free Compound
TLC: Rf 0.45 (chloroform:methanol=19:1);
NMR (CDCl$_3$): δ7.69–7.52 (m, 6H), 7.51–7.41 (m, 2H), 6.16 (d, J=9.0 Hz, 1H), 4.71 (d, J=14.4 Hz, 1H), 4.15 (q, J=7.2 Hz, 2H), 3.91 (d, J=15.0 Hz, 1H), 3.74 (dd, J=15.0, 9.0 Hz, 1H), 3.54–3.39 (m, 5H), 2.55–2.46 (m, 2H), 2.41–2.29 (m, 2H), 1.27 (t, J=7.2 Hz, 3H).
Hydrochloride
TLC: Rf 0.45 (chloroform:methanol=19:1);
NMR (DMSO-d$_6$): δ11.60–11.30 (br, 1H), 8.40–8.20 (br, 1H), 8.00–7.74 (m, 5H), 7.68–7.58 (m, 2H), 6.31 (brd, J=8.1 Hz, 1H), 4.98–4.70 (m, 1H), 4.70–4.52 (m, 1H), 4.20–3.89 (m, 2H), 4.07 (q, J=7.2 Hz, 2H), 3.82 (d, J=15.3 Hz, 1H), 3.77–3.60 (m, 1H), 3.52–2.90 (m, 6H), 1.18 (t, J=7.2 Hz, 3H).

EXAMPLE 35 (57)

4-(4-(2-Hydroxyethyl)piperazin-1-yl)methyl-3-phenylsulfonyl-2,3-dihydro-1,1-dioxidebenzo[b]thiophene

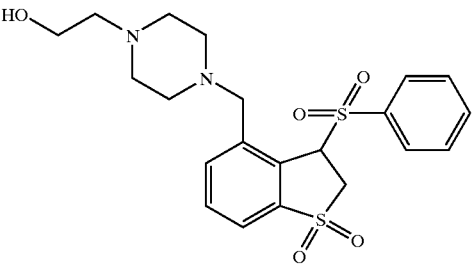

Free Compound
TLC: Rf 0.31 (chloroform:methanol 9:1);
NMR (CDCl$_3$): δ7.70–7.50 (m, 6H), 7.50–7.41 (m, 2H), 6.29 (d, J=9.0 Hz, 1H), 4.72 (d, J=14.1 Hz, 1H), 3.91 (d, J=15.0 Hz, 1H), 3.73 (dd, J=15.0, 9.0 Hz, 1H), 3.63 (t, J=5.1 Hz, 2H), 3.43 (d, J=14.1 Hz , 1H), 2.80–2.30 (m, 10H).
2hydrochloride
TLC: Rf 0.31 (chloroform:methanol=9:1);
NMR (DMSO-d$_6$): δ11.50–10.60 (br, 1H), 8.30–8.00 (br, 1H), 7.88–7.73 (m, 5H), 7.67–7.58 (m, 2H), 6.60–6.30 (br, 1H), 5.80–4.92 (br, 2H), 4.92–4.10 (br, 1H), 3.99 (dd, J=15.0, 8.7 Hz, 1H), 3.86 (d, J=15.0 Hz, 1 H), 3.81–3.74 (m, 2H), 3.73–2.80 (m, 10H).

EXAMPLE 35 (58)

4-(4-(Pyridin-4-yl)piperazin-1-yl)methyl-3-phenylsulfonyl-2,3-dihydro-1,1-dioxidebenzo[b]thiophene

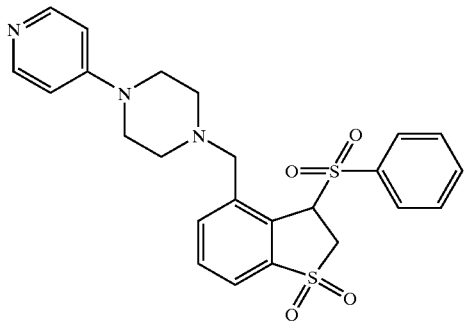

Free Compound
TLC: Rf 0.36 (chloroform:methanol=9:1);
NMR (DMSO-$d_6$): δ8.14 (d, J=6.6 Hz, 2H), 7.88–7.81 (m, 1H), 7.81–7.74 (m, 3H), 7.74–7.68 (m, 2H), 7.67–7.59 (m, 2H), 6.78 (d, J=6.6 Hz, 2H), 6.21 (d, J=9.0 Hz, 1H), 4.16 (d, J=14.4 Hz, 1H), 4.05 (dd, J=15.0, 9.0 Hz, 1H), 3.86 (d, J=15.0 Hz, 1H), 3.57 (d, J=14.4 Hz, 1H), 3.42–3.18 (m, 4H), 2.43 (t, J=4.8 Hz, 4H).
3hydrochloride
TLC: Rf 0.36 (chloroform:methanol=9:1);
NMR (DMSO-$d_6$): δ14.20–13.80 (br, 1H), 12.30–11.90 (br, 1H), 8.46–8.20 (br, 1H), 8.35 (d, J=6.9 Hz, 2H), 7.98–7.82 (m, 2H), 7.82–7.74 (m, 3H), 7.67–7.57 (m, 2H), 7.25 (d, J=6.9 Hz, 2H), 6.48 (brd, J=8.7 Hz, 1H), 5.05–4.75 (m, 1H), 4.75–4.52 (m, 1H), 4.52–4.15 (m, 2H), 3.98 (dd, J=15.3, 8.7 Hz, 1H), 3.95–3.55 (m, 6H), 3.84 (d, J=15.3 Hz, 1H).

EXAMPLE 35 (59)

4-Benzylaminomethyl-3-phenylsulfonyl-2,3-dihydro-1,1-dioxidebenzo[b]thiophene

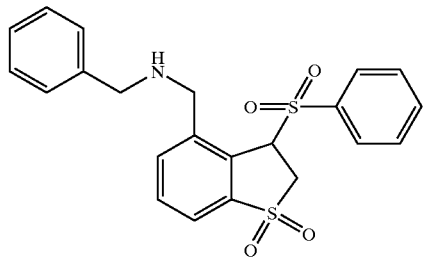

Free Compound
TLC: Rf 0.46 (ethyl acetate);
NMR (CDCl$_3$): δ7.74 (dd, J=7.2, 1.5 Hz, 1H), 7.65–7.51 (m, 5H), 7.45–7.40 (m, 2H), 7.36–7.25 (m, 5H), 5.84 (dd, J=9.3, 1.0 Hz, 1H), 4.49 (d, J=14.1 Hz, 1H), 3.98 (d, J=14.1 Hz, 1H), 3.85 (d, J=12.7 Hz, 1H), 3.84 (dd, J=15.0, 1.0 Hz, 1H), 3.77 (d, J=12.7 Hz, 1H), 3.65 (dd, J=15.0, 9.3 Hz, 1H).
Hydrochloride
TLC: Rf 0.49 (ethyl acetate:triethylamine=6:0.5);
NMR (DMSO-$d_6$): δ9.87 (brs, 1H), 9.57 (brs, 1H), 8.16 (d, J=6.6 Hz, 1H), 7.90–7.75 (m, 3H), 7.75–7.57 (m, 6H), 7.50–7.41 (m, 3H), 6.33–6.25 (m, 1H), 4.67 (d, J=13.5 Hz, 1H), 4.40 (d, J=13.5 Hz, 1H), 4.30 (s, 2H), 3.93–3.80 (m, 2H).

EXAMPLE 35 (60)

4-(1-benzylpiperidin-4-yl)aminomethyl-3-phenylsulfonyl-2,3-dihydro-1,1-dioxidebenzo[b]thiophene

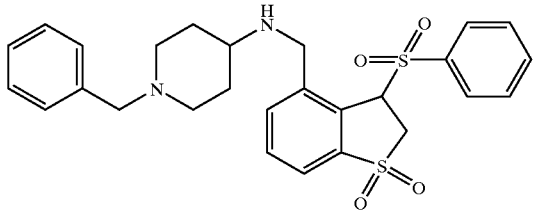

Free Compound
TLC: Rf 0.30 (ethyl acetate:methanol=2:1);
NMR (CDCl$_3$): δ7.70 (dd, J=7.3, 1.3 Hz, 1H), 7.65–7.41 (m, 7H), 7.32–7.24 (m, 5H), 6.09 (dd, J=9.3, 1.0 Hz, 1H), 4.61 (d, J=14.0 Hz, 1H), 3.98 (d, J=14.0 Hz, 1H), 3.87 (dd, J=15.0, 1.0 Hz, 1H), 3.72 (dd, J=15.0, 9.3 Hz, 1H), 3.50 (s, 2H), 2.90–2.81 (m, 2H), 2.58–2.51 (m, 1H), 2.09–1.96 (m, 3H), 1.83–1.79 (m, 1H), 1.52–1.38 (m, 2H).
2hydrochloride
TLC: Rf 0.30 (ethyl acetate:methanol=2:1);
NMR (CD$_3$OD): δ8.16–8.12 (m, 1H), 7.91–7.74 (m, 5H), 7.65–7.49 (m, 7H), 6.06 (dd, J=8.4, 1.8 Hz, 1H), 4.84–4.68 (m, 2H), 4.36 (br, 2H), 3.90 (dd, J=15.4, 8.4 Hz, 1H), 3.77 (dd, J=15.4, 1.8 Hz, 1H), 3.80–3.60 (m, 3H), 3.30–3.15 (m, 2H), 2.58–2.43 (m, 2H), 2.35–2.13 (m, 2H).

EXAMPLE 35 (61)

4-(Morpholin-4-yl)methyl-3-phenylsulfonyl-2,3-dihydro-1,1-dioxidebenzo[b]thiophene

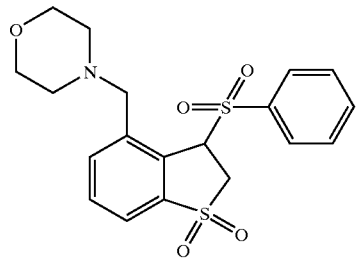

Free Compound
TLC: Rf 0.34 (hexane:ethyl acetate=1:2);
NMR (CDCl$_3$): δ7.68–7.51 (m, 6H), 7.48–7.42 (m, 2H), 6.21 (dd, J=9.3, 0.9Hz, 1H), 4.68 (d, J=14.3 Hz, 1H), 3.91 (dd, J=15.0, 0.9 Hz, 1H), 3.74 (dd, J=15.0, 9.3 Hz, 1H), 3.74–3.64 (m, 4H), 3.45 (d, J=14.3 Hz, 1H), 2.58–2.52 (m, 2H), 2.40–2.33 (m, 2H).
Hydrochloride
TLC: Rf 0.34 (hexane:ethyl acetate=1:2);
NMR (DMSO-$d_6$): δ11.48 (br, 1H), 8.31 (d, J=7.2 Hz, 1H), 7.94–7.79 (m, 5H), 7.68–7.62 (m, 2H), 6.44 (d, J=8.1 Hz, 1H), 4.85–4.79 (m, 1H), 4.62–4.57 (m, 1H), 4.05–3.81 (m, 6H), 3.50–3.13 (m, 4H).

EXAMPLE 35 (62)

4-Ethoxycarbonyl-3-phenylsulfonyl-2,3-dihydro-1,1-dioxidebenzo[b]thiophene

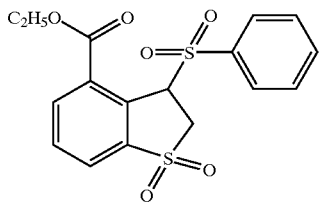

TLC: Rf 0.18 (methylene chloride);
NMR (CDCl$_3$): δ8.24 (dd, J=7.8 Hz, 1.5 Hz, 1H), 7.86 (dd, J=7.8 Hz, 1.5 Hz, 1H), 7.75 (t, J=7.8 Hz, 1H), 7.71–7.64 (m, 3H), 7.56–7.47 (m, 2H), 6.19 (dd, J=9.3 Hz, 1.5 Hz, 1H), 4.53–4.40 (m, 2H), 3.94 (dd, J=15.0 Hz, 1.5 Hz, 1H), 3.77 (dd, J=15.0 Hz, 9.3 Hz, 1H), 1.47 (t, J=7.2 Hz, 3H).

EXAMPLE 35 (63)

4-Benzyloxycarbonyl-3-phenylsulfonyl-2,3-dihydro-1,1-dioxidebenzo[b]thiophene

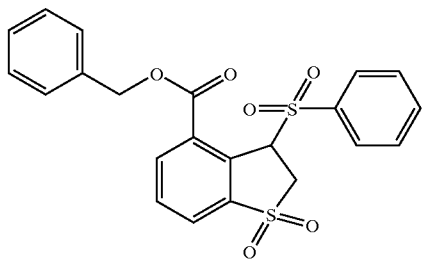

TLC: Rf 0.37 (chloroform:ethyl acetate=19:1);
NMR (CDCl$_3$): δ8.26 (dd, J=7.5, 1.2 Hz, 1H), 7.85 (dd, J=7.8, 1.2 Hz, 1H), 7.78–7.70 (m, 1H), 7.69–7.60 (m, 3H), 7.55–7.47 (m, 4H), 7.47–7.35 (m, 3H), 6.13 (dd, J=9.3, 1.2 Hz, 1H), 5.45 (d, J=12.3 Hz, 1H), 5.40 (d, J=12.3 Hz, 1H), 3.91 (dd, J=15.0, 1.2 Hz, 1H), 3.73 (dd, J=15.0, 9.3 Hz, 1H).

EXAMPLE 35 (64)

4-(Pyridin-3-yl)-3-phenylsulfonyl-2,3-dihydro-1,1-dioxdebenzo[b]thiophene.hydrochloride

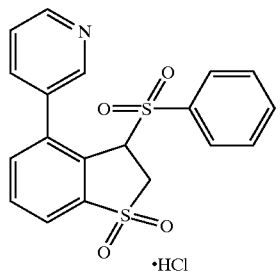

TLC: Rf 0.55 (chloroform:methanol=9:1);
NMR (DMSO-d$_6$): δ9.11 (s, 1H), 8.86 (d, J=5.4 Hz, 1H), 8.57 (d, J=5.4 Hz, 1H), 7.99–7.84 (m, 4H), 7.73–7.64 (m, 1H), 7.53–7.43 (m, 2H), 7.42–7.35 (m, 2H), 5.99 (dd, J=7.2, 3.0 Hz, 1H), 4.07 (dd, J=15.3, 7.2 Hz, 1H), 4.01 (dd, J=15.3, 3.0Hz, 1H).

EXAMPLE 35 (65)

6-(Pyridin-3-yl)-3-phenylsulfonyl-2,3-dihydro-1,1-dioxidebenzo[b]thiophene.hydrochloride

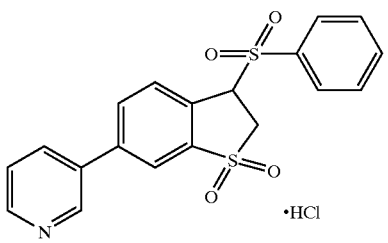

TLC: Rf 0.60 (chloroform:methanol=9:1);
NMR (DMSO-d$_6$): δ9.29 (d, J=2.1 Hz, 1H), 8.85 (d, J=5.1 Hz, 1H), 8.76 (d, J=7.8 Hz, 1H), 8.37 (s, 1H), 8.29 (dd, J=8.4, 2.1 Hz, 1H), 7.96 (dd, J=8.4, 5.1 Hz, 1H), 7.89–7.75 (m, 4H), 7.71–7.60 (m, 2H), 5.93 (dd, J=9.3, 3.0 Hz, 1H), 4.06 (dd, J=15.0, 9.3 Hz, 1H), 3.85 (dd, J=15.0, 3.0 Hz, 1H).

EXAMPLE 35 (66)

4-(4,4-Dimethyl-4,5-dihydroxazol-2-yl)-3-phenylsulfonyl-2,3-dihydro-1,1-dioxidebenzo[b]thiophene

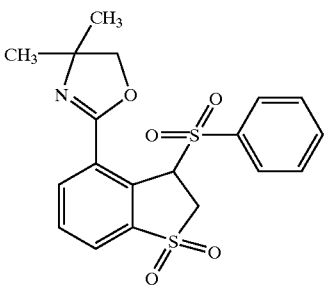

TLC: Rf 0.22 (ethyl acetate:hexane=1:1);
NMR (CDCl$_3$): δ8.23 (d, J=6.0 Hz, 1H), 7.73–7.67 (m, 2H), 7.67–7.54 (m, 3H), 7.48–7.40 (m, 2H), 6.36 (dd, J=9.0 Hz, 1.8 Hz, 1H), 4.26 (d, J=7.5 Hz, 1H), 4.22 (d, J=7.5 Hz, 1H), 3.89 (dd, J=15.0 Hz, 1.8 Hz, 1H), 3.78 (dd, J=15.0 Hz, 9.0 Hz, 1H), 1.50 (s, 3H), 1.45 (s, 3H).

EXAMPLE 35 (67)

6-Bromo-3-phenylsulfonyl-2,3-dihydro-1,1-dioxidebenzo[b]thiophene

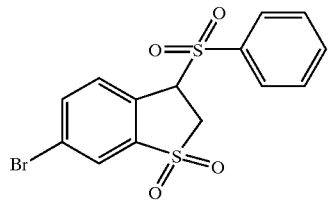

TLC: Rf 0.24 (methylene chloride);
NMR (DMSO-d$_6$): δ8.13 (d, J=2.0 Hz, 1H), 8.02 (dd, J=8.5, 2.0 Hz, 1H), 7.83–7.76 (m, 3H), 7.67–7.60 (m, 3H), 5.79 (dd, J=9.5, 3.0 Hz, 1H), 4.05 (dd, J=15.5, 9.5 Hz, 1H), 3.85 (dd, J=15.5, 3.0 Hz, 1H).

EXAMPLE 35 (68)

6-Amino-3-phenylsulfonyl-2,3-dihydro-1,1-dioxidebenzo[b]thiophene

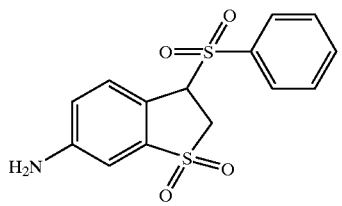

TLC: Rf 0.34 (hexane:ethyl acetate=1:2);

NMR (DMSO-$d_6$): δ7.79–7.71 (m, 3H), 7.64–7.56 (m, 2H), 7.28 (d, J=8.5 Hz, 1H), 6.89 (dd, J=8.5, 2.2 Hz, 1H), 6.68 (d, J=2.2 Hz, 1H), 6.00 (s, 2H), 5.47 (dd, J=9.2, 3.0 Hz, 1H), 3.89 (dd, J=15.2, 9.2 Hz, 1H), 3.64 (dd, J=15.2, 3.0 Hz, 1H).

EXAMPLES 36~36 (3)

By the same procedure as described in Example 28 using carboxylic acid corresponding to 4-carboxy-1,1-dioxidebenzo[b]thiophene and amine corresponding to (pyridin-3-ylmethyl)amine, the following compounds of the present invention were obtained.

EXAMPLE 36

5-Methylcarbamoyl-4-methoxy-1,1-dioxidebenzo[b]thiophene

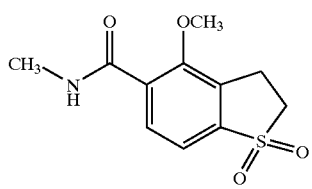

TLC: Rf 0.38 (methanol:ethyl acetate=5:95);

NMR(DMSO-$d_6$): δ8.40 (d, J=4.8 Hz, 1H), 7.75 (d, J=7.0 Hz, 1H), 7.65 (d, J=7.8 Hz, 1H), 7.59 (d, J=7.8 Hz, 1H), 7.44 (d, J=7.0 Hz, 1H), 3.89 (s, 3H), 2.78 (d, J=4.8 Hz, 3H).

EXAMPLE 36 (1)

4-Dimethylcarbamoyl-1,1-doxidebenzo[b]thiophene

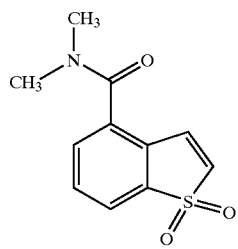

TLC: Rf 0.34 (methanol:ethyl acetate=5:95);

NMR(CDCl$_3$): δ7.76 (dd, J=7.0 Hz, 1.4 Hz, 1H), 7.58 (t, J=7.0 Hz, 1H), 7.51 (dd, J=7.0 Hz, 1.4 Hz, 1H), 7.33 (d, J=6.8 Hz, 1H), 6.78 (d, J=6.8 Hz, 1H), 3.17 (s, 3H), 3.00 (s, 3H).

EXAMPLE 36 (2)

4-Carbamoyl-1,1-dioxidebenzo[b]thiophene

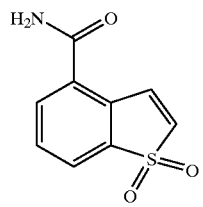

TLC Rf 0.50 (methanol:ethyl acetate=5:95);

NMR(DMSO-$d_6$): δ8.22 (brs, 1H), 7.96 (d, J=7.2 Hz, 1H), 7.88 (d, J=8.0 Hz, 1H), 7.78 (brs, 1H), 7.67 (t, J=8.0 Hz, 1H), 7.55 (d, J=8.0 Hz, 1H), 7.43 (d, J=7.2 Hz, 1H),

EXAMPLE 36 (3)

4-(Furan-2-ylmethyl)carbamoyl-1,1-dioxidebenzo[b]thiophene

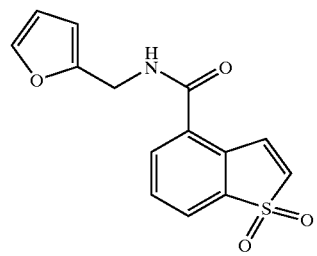

TLC: Rf 0.36 (ethyl acetate:hexane=1;1);

NMR (CDCl$_3$+DMSO-$d_6$): δ7.96 (dd, J=7.2, 0.9 Hz, 1H), 7.81–7.76 (m, 2H), 7.56 (t, J=7.8 Hz, 1H), 7.51 (t, J=5.7 Hz, 1H), 7.40–7.38 (m, 1H), 6.78 (d, J=7.2 Hz, 1H), 6.37–6.30 (m, 2H), 4.62 (d, J=5.7 Hz, 2H).

EXAMPLES 37~37 (6)

By the same procedure as described in Example 18 using an alcohol derivative corresponding to the compound prepared in Example 9 (12) and a halogenated compound corresponding to 4-nitrobenzylbromide, or by the same procedure as described in Example 29 using an alcohol derivative corresponding to 4-hydroxy-1,1-dioxidebenzo[b]thiophene and an alcohol derivative corresponding to 1-(3-hydroxypropyl)pyrrole, the following compounds of the present invention were obtained.

EXAMPLE 37

4-(2-(Pyridin-4-yl)ethyl)oxy-1,1-dioxidebenzo[b]thiophene

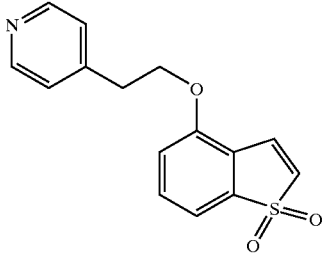

TLC: Rf 0.23 (hexane:ethyl acetate=1:3);

NMR (CDCl$_3$): δ8.56 (d, J=6.0 Hz, 2H), 7.46 (t, J=8.0 Hz, 1H), 7.31 (d, J=7.2 Hz, 1H), 7.29 (d, J=8.0 Hz, 1H), 7.21 (d, J=6.0 Hz, 2H), 7.04 (d, J=8.0 Hz, 1H), 6.60 (d, J=7.2 Hz, 1H), 4.33 (t, J=6.5 Hz, 2H), 3.14 (t, J=6.5 Hz, 2H).

EXAMPLE 37 (1)

4-(2-(Pyridin-3-yl)ethyl)oxy-1,1-dioxidebenzo[b]thiophene

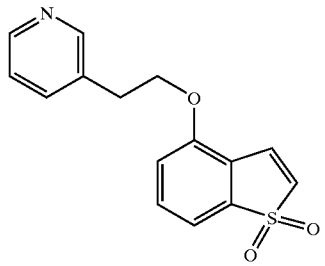

TLC: Rf 0.38 (ethyl acetate);

NMR(CDCl$_3$): δ8.56 (d, J=1.8 Hz, 1H), 8.52 (dd, J=4.8, 1.8 Hz, 1H), 7.60 (d, J=8.2 Hz, 1H), 7.45 (t, J=7.6 Hz, 1H), 7.35 (d, J=7.6 Hz, 1H), 7.28 (dd, J=7.0 Hz, 1H), 7.26 (d, J=7.6 Hz, 1H), 7.03 (d, J=8.2 Hz, 1H), 6.60 (d, J=7.0 Hz, 1H), 4.30 (t, J=6.4 Hz, 2H), 3.15 (t, J=6.4 Hz, 2H).

EXAMPLE 37(2)

4-Ethoxycarbonylmethyloxy-1,1-dioxidebenzo[b]thiophene

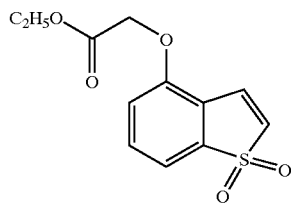

TLC: Rf 0.38 (hexane:ethyl acetate=1:1);

NMR (CDCl$_3$): δ7.53 (d, J=7.2 Hz, 1H), 7.47 (t, J=8.0 Hz, 1H), 7.34 (d, J=8.0 Hz, 1H), 6.94 (d, J=8.0 Hz, 1H), 6.65 (d, J=7.2 Hz, 1H), 4.72 (s, 2H), 4.27 (q, J=7.0 Hz, 2H), 1.30 (t, J=7.0 Hz, 3H).

EXAMPLE 37 (3)

6-Ethoxycarbonylmethyloxy-1,1-dioxidebenzo[b]thiophene

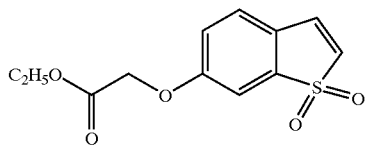

TLC: Rf 0.30 (hexane:ethyl acetate=1:1);

NMR (CDCl$_3$): δ7.28 (d, J=8.4 Hz, 1H), 7.24 (d, J=2.6 Hz, 1H), 7.17 (d, J=7.0 Hz, 1H), 7.05 (dd, J=8.4, 2.6 Hz, 1H), 6.63 (d, J=7.0 Hz, 1H), 4.68 (s, 2H), 4.29 (q, J=7.0 Hz, 2H), 1.31 (t, J=7.0 Hz, 3H).

EXAMPLE 37 (4)

6-Cyanomethyloxy-1,1-dioxidebenzo[b]thiophene

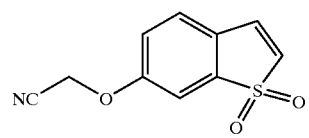

TLC: Rf 0.30 (hexane:ethyl acetate=1:1);

NMR (CDCl$_3$): δ7.36 (d, J=8.4Hz, 1H), 7.34 (dd, J=2.6, 0.83 Hz, 1H) 7.20 (dd, J=7.0, 0.8 Hz, 1H), 7.14 (dd, J=8.4, 2.6 Hz, 1H), 6.69 (d, J=7.0 Hz, 1H), 4.84 (s, 2H).

EXAMPLE 37 (5)

5-Ethoxycarbonylmethyloxy-1,1-dioxidebenzo[b]thiophene

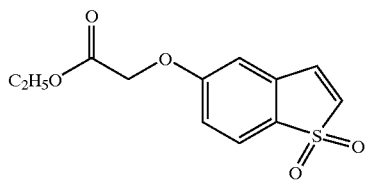

TLC: Rf 0.31 (ethyl acetate:hexane=1:1);

NMR (CDCl$_3$): δ7.64 (d, J=8.2 Hz, 1H), 7.15 (d, J=6.8 Hz, 1H), 6.98–6.86 (m, 2H), 6.74 (d, J=6.8 Hz, 1H), 4.69 (s, 2H), 4.29 (q, J=7.2 Hz, 2H), 1.31 (t, J=7.2 Hz, 3H).

EXAMPLE 37 (6)

7-Ethoxycarbonylmethyloxy-1,1-dioxidebenzo[b]thiophene

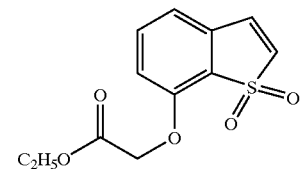

TLC: Rf 0.28 (ethyl acetate:hexane=1:1);

NMR (CDCl$_3$): δ7.46 (dd, J=8.6 Hz, 7.0 Hz, 1H), 7.14 (d, J=7.0 Hz, 1H), 6.96 (d, J=7.0 Hz, 1H), 6.89 (d, J=8.6 Hz,

1H), 6.68 (d, J=7.0 Hz, 1H), 4.84 (s, 2H), 4.28 (q, J=7.0 Hz, 2H), 1.29 (t, J=7.0 Hz, 3H).

EXAMPLES 38~38 (3)

By the same procedure as described in Example 32 using a carboxylic acid derivative corresponding to 4-carboxy-1,1-dioxidebenzo[b]thiophene and a halogenated compound corresponding to bromoethane, the following compounds of the present invention having the following physical data were obtained.

EXAMPLE 38

5-Benzyloxycarbonyl-4-methoxy-1,1-dioxidebenzo[b]thiophene

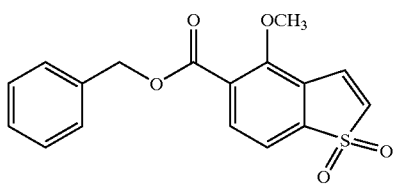

TLC: Rf 0.28 (hexane:ethyl acetate=2:1);

NMR (CDCl$_3$): δ7.98 (d, J=8.0 Hz, 1H), 7.51–7.36 (m, 7H), 6.73 (d, J=7.0 Hz, 1H), 5.38 (s, 2H), 3.87 (s, 3H).

EXAMPLE 38 (1)

5-Ethoxycarbonyl-1,1-dioxidebenzo[b]thiophene

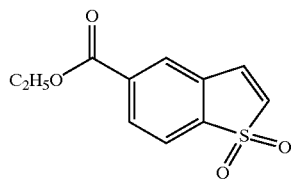

TLC: Rf 0.43 (hexane:ethyl acetate=1:1);

NMR (CDCl$_3$): δ8.22 (dd, J=8.0, 1.0 Hz, 1H), 8.03 (d, J=1.0 Hz, 1H),7.79 (d, J=8.0 Hz, 1H), 7.15 (d, J=7.0 Hz, 1H), 6.80 (d, J=7.0 Hz, 1H), 4.43 (q, J=7.0 Hz, 1H), 1.42 (t, J=7.0 Hz,, 3H).

EXAMPLE 38 (2)

7-Methoxycarbonyl-1,1-dioxidebenzo[b]thiophene

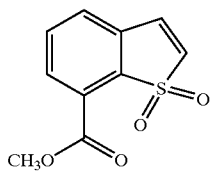

TLC: Rf 0.15 (hexane:ethyl acetate=2:1);

NMR (CDCl$_3$): δ8.11 (d, J=8 Hz, 1H), 7.66 (t, J=8 Hz, 1H), 7.55 (d, J=8 Hz, 1H), 7.20 (d, J=7 Hz, 1H), 6.77 (d, J=7 Hz, 1H), 4.05 (s, 3H).

EXAMPLE 38 (3)

7-Ethoxycarbonyl-1,1-dioxidebenzo[b]thiophene

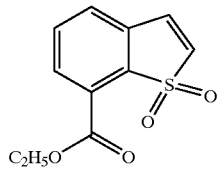

TLC: Rf 0.39 (ethyl acetate:hexane=1:1);

NMR (CDCl$_3$): δ8.13 (dd, J=7.6 Hz, 1.2 Hz, 1H), 7.65 (t, J=7.6 Hz, 1H), 7.52 (dd, J=7.6 Hz, 1.2 Hz, 1H), 7.18 (d, J=6.8 Hz, 1H), 6.76 (d, J=6.8 Hz, 1H), 4.53 (q, J=7.2 Hz, 2H), 1.48 (t, J=7.2 Hz, 1H).

EXAMPLE 39

5-t-Butoxycarbonyl-4-methoxy-1,1-dioxidebenzo[b]thiophene

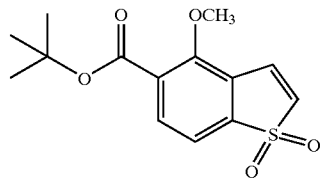

A suspension of 5-carboxy-4-methoxy-1,1-dioxidebenzo[b]thiophene (934 mg) in benzene (15 ml) was refluxed. Thereto was added dimethylformamidedi-t-butylacetal (4.02 g) dropwise. The mixture was refluxed for 1 hour. To the reaction mixture water was added. The mixture was extracted by benzene. The extract was washed by a saturated aqueous solution of sodium bicarbonate and a saturated aqueous solution of sodium chloride sucessively, dried over anhydrous sodium sulfate and concentrated. The residue was purified with column chromatography on silica gel (ethyl acetate:hexane=1:10) to give the compound of the present invention (942 mg) having the following physical data.

TLC: Rf 0.25 (ethyl acetate:hexane=1:4);

NMR (CDCl$_3$): δ7.87 (d, J=7.8 Hz, 1H), 7.47 (d, J=7.8 Hz, 1H), 7.45 (d, J=7.0 Hz, 1H), 6.73 (d, J=7.0 Hz, 1H), 3.95 (s, 3H), 1.62 (s, 9H).

EXAMPLE 40

5-((E)-2-(Ethoxycarbonyl)ethenyl)-4-methoxybenzo[b]thiophene

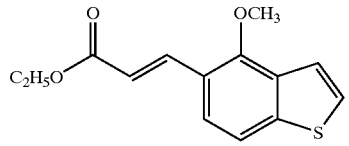

To a suspension of 62.5% sodium hydride (920 mg) in anhydrous tetrahydrofuran (40 ml), was added a solution of triethylphosphonoacetate (5.83 g) in anhydrous tetrahydrofuran (20 ml) dropwise. The mixture was stirred for 15 minutes. To the reaction mixture, was added a solution of 5-formyl-4-methoxybenzo[b]thiophene (3.84 g) in anhydrous tetrahydrofuran (20 ml) dropwise. The mixture was stirred at room temperature for 1 hour. To the reaction mixture, was added acetic acid (1.5 ml). The mixture was concentrated. The residue was purified with column chromatography on silica gel (hexane:ethyl acetate=9:1) to give the compound of the present invention (5.17 g) having the following physical data.

TLC: Rf 0.37 (hexane:ethyl acetate=5:1);

NMR (CDCl$_3$): δ8.13 (d, J=16.2 Hz, 1H), 7.62–7.41 (m, 4H), 6.53 (d, J=16.2 Hz, 1H), 4.29 (q, J=7.2 Hz, 2H), 4.00 (s, 3H), 1.36 (t, J=7.2 Hz, 3H).

EXAMPLE 41

5-(2-(Ethoxycarbonyl)ethyl)-4-methoxybenzo[b]thiophene

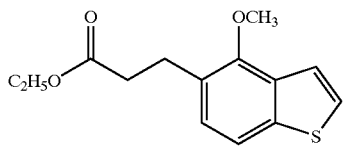

To a solution of the compound prepared in Example 40 (5.16 g) in ethanol (100 ml), 10% palladium carbon (200 mg) was added. Under an atmosphere of hydrogen the mixture was stirred at room temperature. The reaction mixture was filtrated through celite, and the filtrate was concentrated. The residue was purified with column chromatography on silica gel (hexane:ethyl acetate=9:1) to give the compound of the present invention (3.23 g) having the following physical data.

TLC: Rf 0.40 (hexane:ethyl acetate=5:1);

NMR (CDCl$_3$): δ7.56 (d, J=8.1 Hz, 1H), 7.41 (q, J=5.4 Hz, 2H), 7.20 (d, J=8.1 Hz, 1H), 4.14 (q, J=7.2 Hz, 2H), 3.97 (s, 3H), 3.07 (t, J=8.0 Hz, 2H), 2.66 (t, J=8.0 Hz, 2H), 1.24 (t, J=7.2 Hz, 3H).

EXAMPLE 42

5-(2-(Ethoxycarbonyl)ethyl)-4-methoxy-1,1-dioxidebenzo[b]thiophene

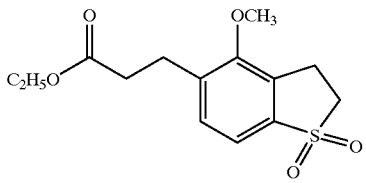

By the same procedure as described in 3 using the compound prepared in Example 41 instead of the compound prepared in Example 1, the compound of the present invention having the following physical data was obtained (with the proviso that 3-chloroperbenzoic acid was used instead of OXONE© as an oxidizer).

TLC: Rf 0.25 (hexane:ethyl acetate=2:1);

NMR (CDCl$_3$): δ7.45–7.36 (m, 3H), 6.70 (d, J=6.8 Hz, 1H), 4.15 (q, J=7.4 Hz, 2H), 3.92 (s, 3H), 3.01 (t, J=7.6 Hz, 2H), 2.62 (t, J=7.6 Hz, 2H), 1.24 (t, J=7.4 Hz, 3H).

EXAMPLE 43

5(4.4-Dimethyl-4,5-dihydroxazol-2-yl)-1,1-dioxidebenzo[b]thiophene

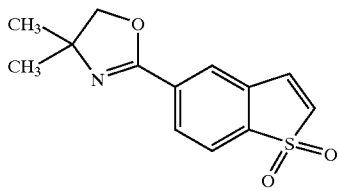

Using the compound which was obtained with using 5-carboxy-1,1-dioxidebenzo[b]thiophene and (2-hydroxy-1,1-dimethylethyl)amine instead of 4-carboxy-1,1-dioxidebenzo[b]thiophene and (pyridin-3-ylmethyl)amine respectively, by the same procedure as described in Example 28, by the same procedure as described in Example 34, the compound of the present invention having the following physical data was obtained.

TLC: Rf 0.39 (ethyl acetate:hexane=1:1);

NMR (CDCl$_3$): δ8.08 (dd, J=8.0 Hz, 1.2 Hz, 1H), 7.98 (d, J=1.2 Hz, 1H), 7.75 (d, J=8.0 Hz, 1H), 7.23 (d, J=7.0 Hz, 1H), 6.77 (d, J=7.0 Hz, 1H), 4.16 (s, 2H), 1.40 (s, 6H).

EXAMPLES 44~44 (24)

By the same procedure as described in Example 1 using the compounds prepared in Examples 36~36 (2), Examples 37~37 (6), Examples 38~38 (3), Example 39, Example 42, Example 36 (3), Example 43 instead of 1,1-dioxidebenzo[b]thiophene or a corresponding derivative and thiol derivatives corresponding to thiophenol, the following compounds of the present invention were obtained.

EXAMPLE 44

5-Methylcarbamoyl-4-methoxy-3-phenylthio-2,3-dihydro-1,1-dioxidebenzo[b]thiophene

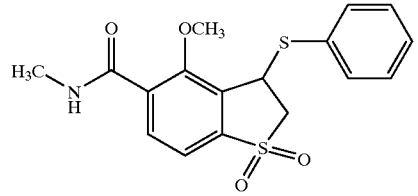

TLC: Rf 0.58 (methanol:ethyl acetate=5:95);

NMR (CDCl$_3$): δ8.10 (d, J=5.6 Hz, 1H), 7.56 (d, J=5.6 Hz, 1H), 7.54–7.48 (m, 2H), 7.43–7.35 (m, 3H), 7.17 (brs, 1H), 5.07 (dd, J=4.6 Hz, 1.4 Hz, 1H), 4.04 (s, 3H), 3.72 (dd, J=9.4 Hz, 4.6 Hz, 1H), 3.63 (dd, J=9.4 Hz, 1.4 Hz, 1H), 3.07 (d, J=4.8 Hz, 3H).

EXAMPLE 44 (1)

4-Dimethylcarbamoyl-3-phenylthio-2,3-dihydro-1,1-dioxidebenzo[b]thiophene

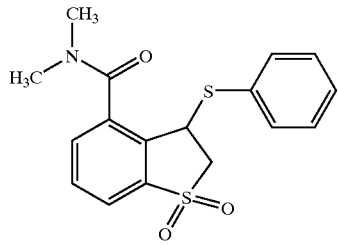

TLC: Rf 0.52 (methanol:ethyl acetate=5:95);

NMR (CDCl$_3$): δ7.78 (dd, J=7.5 Hz, 1.8 Hz, 1H), 7.63–7.51 (m, 4H), 7.43–7.34 (m, 3H), 5.41 (dd, J=7.8 Hz, 1.8 Hz, 1H), 3.74 (dd, J=14.1 Hz, 7.8 Hz, 1H), 3.61 (dd, J=14.1 Hz, 1.8 Hz, 1H), 3.17 (s, 3H), 3.00 (s, 3H).

EXAMPLE 44 (2)

4-Carbamoyl-3-phenylthio-2,3-dihydro-1,1-dioxidebenzo[b]thiophene

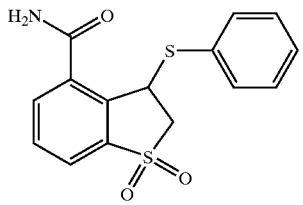

TLC: Rf 0.49 (methanol:ethyl acetate=5:95);

NMR (DMSO-d$_6$): δ8.19 (brs, 1H), 7.96–7.64 (m, 4H), 7.52–7.30 (m, 5H), 5.87 (d, J=7.4 Hz, 1H), 4.10 (dd, J=14.6 Hz, 7.4 Hz, 1H), 3.61 (d, J=14.6 Hz, 1H).

EXAMPLE 44 (3)

4-(2-(Pyridin-4-yl)ethyl)oxy--3-phenylthio-2,3-dihydro-1,1-dioxidebenzo[b]thiophene

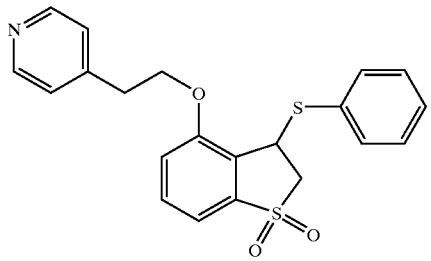

TLC: Rf 0.44 (ethyl acetate:methanol=10:1);

NMR (CDCl$_3$): δ8.50 (d, J=6 Hz, 2H), 7.60–7.13 (m, 9H), 7.07 (d, J=8 Hz, 1H), 4.93 (dd, J=2, 7 Hz, 1H), 4.50–4.15 (m, 2H), 3.80–3.50 (m, 2H), 3.15 (t, J=7 Hz, 2H).

EXAMPLE 44 (4)

4-(2-(Pyridin-3-yl)ethyl)oxy-3-phenylthio-2,3-dihydro-1,1-dioxdebenzo[b]thiophene

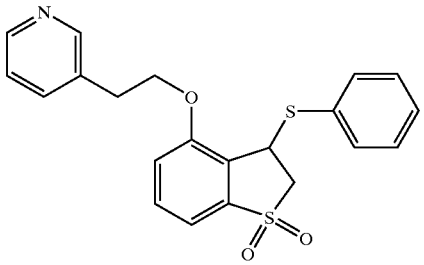

TLC: Rf 0.38 (ethyl acetate);

NMR (CDCl$_3$): δ8.57 (d, J=1.8 Hz, 1H) 8.48 (dd, J=5.0 Hz, 1.8 Hz, 1H), 7.63 (m, 1H), 7.54–7.32 (m, 7H), 7.19 (dd, J=7.8 Hz, 4.0 Hz, 1H), 7.05 (d, J=8.0 Hz, 1H), 4.97 (dd, J=6.2 Hz, 1.8 Hz, 1H), 4.32 (m, 2H), 3.67 (dd, J=14.2 Hz, 6.2 Hz, 1H), 3.58 (dd, J=14.2 Hz, 1.8 Hz, 1H), 3.16 (t, J=7.2 Hz, 2H).

EXAMPLE 44 (5)

4-Ethoxycarbonylmethyloxy-3-phenylthio-2,3-dihydro-1,1-dioxidebenzo[b]thiophene

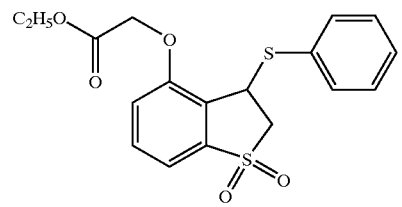

TLC: Rf 0.45 (hexane:ethyl acetate=1:1);

NMR (CDCl$_3$): δ7.57–7.53 (m, 2H), 7.49 (d, J=8.1 Hz, 1H), 7.38–7.33 (m, 4H), 6.96 (d, J=8.1 Hz, 1H), 5.16 (dd, J=7.0, 1.8 Hz, 1H), 4.71 (s, 2H), 4.28 (q, J=7.2 Hz, 2H), 3.72 (dd, J=14.0, 7.0 Hz, 1H), 3.62 (dd, J=14.0, 1.8 Hz, 1H), 1.30 (t, J=7.2 Hz, 3H).

EXAMPLE 44 (6)

6-Ethoxycarbonylmethyloxy-3-phenylthio-2,3-dihydro-1,1-dioxidebenzo[b]thiophene

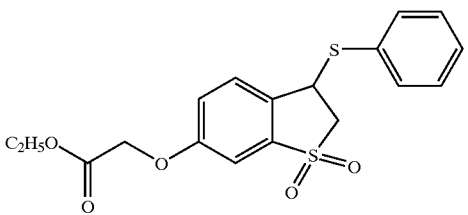

TLC: Rf 0.54 (hexane:ethyl acetate=1:1);

NMR (CDCl$_3$): δ7.62 (d, J=8.7 Hz, 1H), 7.43–7.40 (m, 2H), 7.35–7.33 (m, 3H), 7.25 (dd, J=8.7, 2.4 Hz, 1H), 7.10 (d, J=2.4 Hz, 1H), 4.91 (t, J=6.8 Hz, 1H), 4.66 (s, 2H), 4.28 (q, J=7.2 Hz, 2H), 3.81 (dd, J=13.7, 6.8 Hz, 1H), 3.52 (dd, J=13.7, 6.8 Hz, 1H), 1.31 (t, J=7.2 Hz, 3H).

EXAMPLE 44 (7)

6-Cyanomethyloxy-3-phenylthio-2,3-dihydro-1,1-dioxidebenzo[b]thiophene

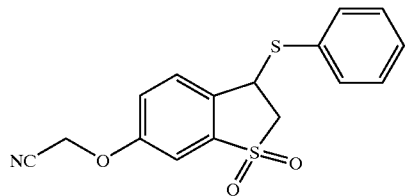

TLC: Rf 0.54 (hexane:ethyl acetate=2:1);

NMR (CDCl$_3$): δ7.69 (d, J=8.4 Hz, 1H), 7.44–7.41 (m, 2H), 7.38–7.34 (m, 3H), 7.28 (dd, J=8.4, 2.4 Hz, 1H), 7.24 (d, J=2.4 Hz, 1H), 4.93 (t, J=6.9 Hz, 1H), 4.83 (s, 2H), 3.83 (dd, J=13.7, 6.9 Hz, 1H), 3.54 (dd, J=13.7, 6.9 Hz, 1H).

EXAMPLE 44 (8)

5-Ethoxycarbonylmethyloxy-3-phenylthio-2,3-dihydro-1,1-dioxidebenzo[b]thiophene

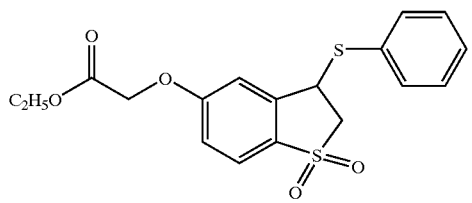

TLC: Rf 0.45 (ethyl acetate:hexane 1:1);

NMR (CDCl$_3$): δ7.64 (d, J=8.6 Hz, 1H), 7.48–7.30 (m, 5H), 7.15 (d, J=2.2 Hz, 1H), 7.06 (dd, J=8.6 Hz, 2.2 Hz, 1H), 4.90 (t, J=7.0 Hz, 1H), 4.69 (s, 2H), 4.29 (q, J=7.4 Hz, 2H), 3.79 (dd, J=13.6 Hz, 7.0 Hz, 1H), 3.50 (dd, J=13.6 Hz, 7.0 Hz, 1H), 1.32 (t, J=7.4 Hz, 3H).

EXAMPLE 44 (9)

7-Ethoxycarbonylmethyloxy-3-phenylthio-2,3-dihydro-1,1-dioxidebenzo[b]thiophene

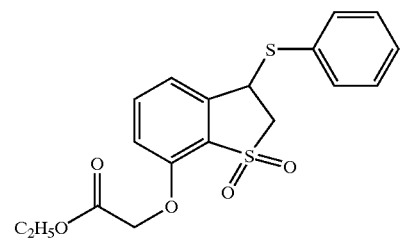

TLC: Rf 0.43 (ethyl acetate:hexane=1:1);

NMR (CDCl$_3$): δ7.55 (t, J=8.4 Hz, 1H), 7.46–7.27 (m, 6H), 6.82 (d, J=8.4 Hz, 1H), 4.91 (dd, J=7.6 Hz, 6.6 Hz, 1H), 4.80 (s, 2H), 4.26 (q, J=7.2 Hz, 2H), 3.80 (dd, J=13.6 Hz, 7.6 Hz, 1H), 3.54 (dd, J=13.6 Hz, 6.6 Hz, 1H), 1.28 (t, J=7.2 Hz, 3H).

EXAMPLE 44 (10)

5-Benzyloxycarbonyl-4-methoxy-3-phenylethio-2,3-dihydro-1,1-dioxidebenzo[b]thiophene

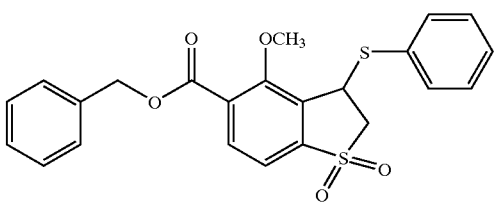

TLC: Rf 0.55 (hexane:ethyl acetate=1:1);

NMR (CDCl$_3$): δ7.99 (d, J=8.0 Hz, 1H), 7.54–7.34 (m, 1H), 5.40 (s, 2H), 5.08 (dd, J=6.0, 2.5 Hz, 1H), 3.97 (s, 3H), 3.69 (dd, J=14.0, 6.0 Hz, 1H), 3.60 (dd, J=14.0, 2.5 Hz, 1H).

EXAMPLE 44 (11)

5-Ethoxycarbonyl-3-phenylthio-2,3-dihydro-1,1-dioxidebenzo[b]thiophene

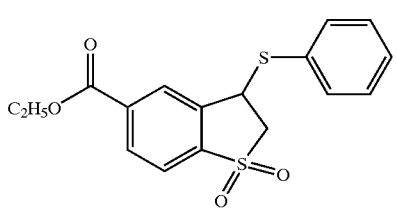

TLC: Rf 0.55 (hexane:ethyl acetate=1:1);

NMR (CDCl$_3$): δ8.36 (s, 1H), 8.20 (d, J=8.2 Hz, 1H), 7.78 (d, J=8.2 Hz, 1H), 7.47–7.33 (m, 5H), 4.97 (t, J=7.0 Hz, 1H), 4.44 (q, J=7.0 Hz, 2H), 3.84 (dd, J=13.7, 7.0 Hz, 1H), 3.54 (dd, J=13.7, 7.0 Hz, 1H), 1.43 (t, J=7.0 Hz, 3H).

EXAMPLE 44 (12)

7-Methoxycarbonyl-3-phenylthio-2,3-dihydro-1,1-dioxidebenzo[b]thiophene

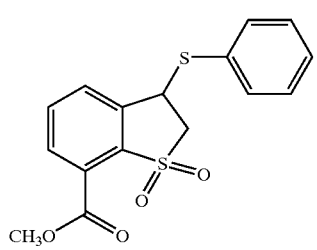

TLC: Rf 0.39 (ethyl acetate:hexane 1:1);

NMR (CDCl$_3$): δ8.12 (d, J=7.8 Hz, 1H), 7.93 (d, J=7.8 Hz, 1H), 7.72 (t, J=7.8 Hz, 1H), 7.48–7.33 (m, 5H), 4.92 (dd, J=7.6 Hz, 6.8 Hz, 1H), 4.01 (s, 3H), 3.86 (dd, J=13.6 Hz, 7.6 Hz, 1H), 3.56 (dd, J=13.6 Hz, 6.8 Hz, 1H).

EXAMPLE 44 (13)

7-Ethoxycarbonyl-3-phenylthio-2,3-dihydro-1,1-dioxidebenzo[b]thiophene

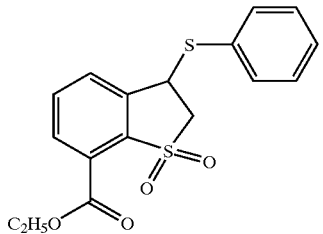

TLC: Rf 0.60 (ethyl acetate:hexane=1:1);

NMR (CDCl$_3$): δ8.13 (d, J=7.8 Hz, 1H), 7.91 (d, J=7.8 Hz, 1H), 7.72 (t, J=7.8 Hz, 1H), 7.46–7.38 (m, 2H), 7.38–7.30 (m, 3H), 4.92 (dd, J=7.8 Hz, 6.9 Hz, 1H), 4.48 (q, J=7.2 Hz, 2H), 3.84 (dd, J=13.5 Hz, 7.8 Hz, 1H), 3.55 (dd, J=13.5 Hz, 6.9 Hz, 1H), 1.44 (t, J=7.2 Hz, 3H).

EXAMPLE 44 (14)

5-t-Butoxycarbonyl-4-methoxy-3-phenylthio-2,3-dihydro-1,1-dioxidebenzo[b]thiophene

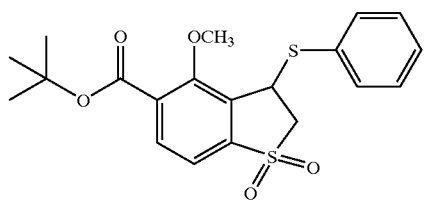

TLC: Rf 0.22 (ethyl acetate:hexane=1:4);

NMR (CDCl$_3$): δ7.88 (d, J=8.0 Hz, 1H), 7.58–7.49 (m, 2H), 7.46 (d, J=8.0 Hz, 1H), 7.43–7.34 (m, 3H), 5.10 (dd, J=6.0 Hz, 2.8 Hz, 1H), 4.08 (s, 3H), 3.70 (dd, J=13.8 Hz, 6.0 Hz, 1H), 3.61 (dd, J=13.8 Hz, 2.8 Hz, 1H), 1.63 (s, 9H).

EXAMPLE 44 (15)

5-(2-(Ethoxycarbonyl)ethyl)4-methoxy-3-phenylthio-2,3-dihydro-1,1-dioxidebenzo[b]thiophene

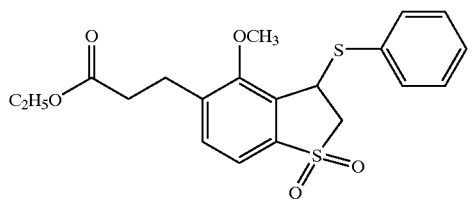

TLC: Rf 0.25 (hexane:ethyl acetate=2:1);

NMR (CDCl$_3$): δ7.55–7.50 (m, 2H), 7.44 (s, 2H), 7.43–7.30 (m, 3H), 5.08 (dd, J=6.9, 2.1 Hz, 1H), 4.15 (q, J=7.2 Hz, 2H), 4.05 (s, 3H), 3.68 (dd, J=15.2, 7.2 Hz, 1H), 3.60 (dd, J=15.2, 2.1 Hz, 1H), 3.18–3.00 (m, 2H), 2.66 (t, J=7.8 Hz, 2H), 1.25 (t, J=7.2 Hz, 3H).

EXAMPLE 44 (16)

4-(Furan-2-ylmethyl)carbamoyl-3-phenylthio-2,3-dihydro-1,1-dioxidebenzo[b]thiophene

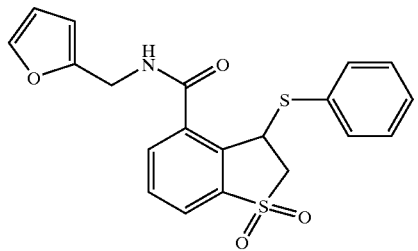

TLC: Rf 0.37 (ethyl acetate:benzene=1:2);

NMR (DMSO-d$_6$): δ9.24 (t, J=5.6 Hz, 1H), 7.93–7.82 (m, 2H), 7.77–7.66 (m, 1H), 7.55–7.51 (m, 1H), 7.47–7.31 (m, 5H), 6.37–6.29 (m, 2H), 5.75 (d, J=7.6 Hz, 1H), 4.46 (d, J=5.6 Hz, 2H), 4.12 (dd, J=14.2 Hz, 7.6 Hz, 1H), 3.62 (d, J=14.2 Hz, 1H).

EXAMPLE 44 (17)

5-(4,4-Dimethyl-4,5-dihydroxazol-2-yl)-3-phenylthio-2,3-dihydro-1,1-dioxidebenzo[b]thiophene

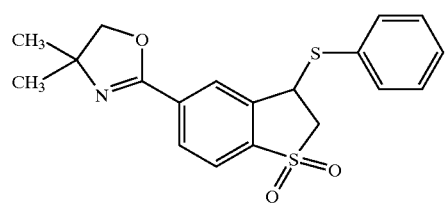

TLC: Rf 0.50 (ethyl acetate:hexane=1:1);

NMR (CDCl$_3$): δ8.32 (brs, 1H), 8.12 (d, J=8.2 Hz, 1H), 7.75 (d, J=8.2 Hz, 1H), 7.50–7.30 (m, 5H), 4.96 (dd, J=7.2 Hz, 6.6 Hz, 1H), 4.18 (s, 2H), 3.82 (dd, J=13.8 Hz, 7.2 Hz, 1H), 3.54 (dd, J=13.8 Hz, 6.6 Hz, 1H), 1.42 (s, 6H).

EXAMPLE 44 (18)

3-Benzylthio-2,3-dihydro-1,1-dioxidebenzo[b]thiophene

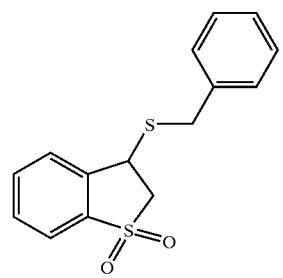

TLC: Rf 0.52 (hexane:ethyl acetate=1:1);

NMR (CDCl$_3$): δ3.42 (dd, J=13.8 Hz, 6.3 Hz, 1H), 3.69 (dd, J=13.8 Hz, 7.8 Hz, 1H), 3.78 (d, J=13.7 Hz, 1H), 3.86 (d, J=13.7 Hz, 1H), 4.53 (t-like, J=7.1 Hz, 1H), 7.27–7.33 (m, 5H), 7.46–7.56 (m,1H), 7.59–7.62 (m, 2H), 7.71 (d, J=7.6 Hz, 1H).

EXAMPLE 44 (19)

3-(3,4-Dichlorophenyl)thio-2,3-dihydro-1,1-dioxidebenzo[b]thiophene

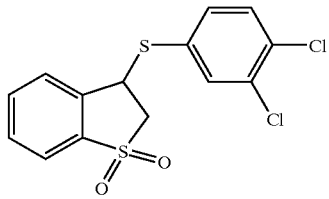

TLC: Rf 0.57 (hexane:ethyl acetate=1:1);

NMR (CDCl$_3$): δ3.48 (dd, J=13.6 Hz, 5.8 Hz, 1H), 3.83 (dd, J=13.6 Hz, 7.6 Hz, 1H), 4.97 (t-like, J=6.8 Hz, 1H), 7.23 (dd, J=8.3 Hz, 2.2 Hz, 1H), 7.41 (d, J=8.3 Hz, 1H), 7.51 (d, J=2.2 Hz, 1H), 7.54–7.62 (m, 1H), 7.66–7.69 (m, 2H), 7.74 (d, J=76 Hz, 1H).

EXAMPLE 44 (20)

3-(4-Nitrophenyl)thio-2,3-dihydro-1,1-dioxidebenzo[b]thiophene

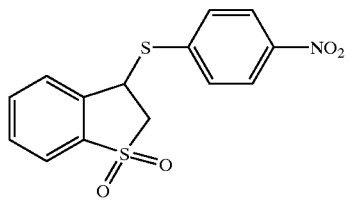

TLC: Rf 0.15 (methylene chloride);

NMR (CDCl$_3$): δ3.55 (dd, J=13.8 Hz, 6.0 Hz, 1H), 3.97 (dd, J=13.8 Hz, 7.5 Hz, 1H), 5.20 (t-like, J=6.8 Hz, 1H), 7.47 (d, J=8.7 Hz, 2H), 7.55–7.64 (m, 1H), 7.68–7.70 (m, 2H), 7.79 (d, J=7.6 Hz, 1H), 8.19 (d, J=8.7 Hz, 2H).

EXAMPLE 44 (21)

5-Hydroxymethyl-4-methoxy-3-phenylthio-2,3-dihydro-1,1-dioxidebenzo[b]thiophene

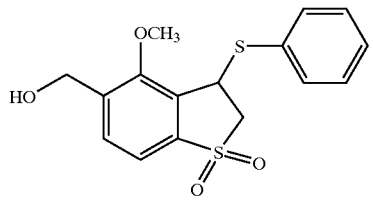

TLC: Rf 0.64 (ethyl acetate);

NMR (CDCl$_3$): δ7.68 (d, J=7.8 Hz, 1H), 7.55–7.47 (m, 3H), 7.39–7.35 (m, 3H), 5.08 (dd, J=6.6, 2.5 Hz, 1H), 4.84 (d, J=6.0 Hz, 2H), 4.06 (s, 3H), 3.69 (dd, J=13.9, 6.6 Hz, 1H), 3.58 (dd, J=13.9, 2.5 Hz, 1H), 2.15 (t, J=6.0 Hz, 1H).

EXAMPLE 44 (22)

4-Hydroxymethyl-3-phenylthio-2,3-dihydro-1,1-dioxidebenzo[b]thiophene

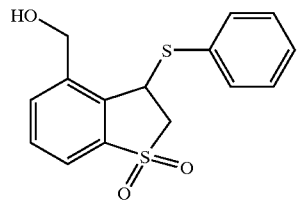

TLC: Rf 0.22 (chloroform:ethyl acetate=4:1);

NMR (CDCl$_3$): δ7.77–7.66 (m, 2H), 7.61 (d, J=7.4 Hz, 1H), 7.57–7.44 (m, 2H), 7.43–7.32 (m, 3H), 5.20 (dd, J=6.8, 2.0 Hz, 1H), 5.03 (s, 2H), 3.72 (dd, J=14.0, 6.8 Hz, 1H), 3.62 (dd, J=14.0, 2.0 Hz, 1H), 2.45–2.15 (br,1H).

EXAMPLE 44 (23)

6-Fluoro-3-phenylthio-2,3-dihydro-1,1-dioxidebenzo[b]thiophene

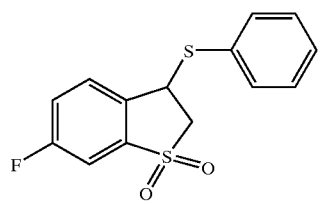

TLC: Rf 0.62 (ethyl acetate:hexane=1:4);

NMR (CDCl$_3$): δ7.70 (ddd, J=7.6 Hz, 4.4 Hz, 0.4 Hz, 1H), 7.47–7.29 (m, 7H), 4.93 (t, J=7.0 Hz, 1H), 3.84 (dd, J=13.8 Hz, 7.0 Hz, 1H), 3.55 (dd, J=13.8 Hz, 7.0 Hz, 1H).

EXAMPLE 44 (24)

4-Fluoro-3-phenylthio-2,3-dihydro-1,1-dioxidebenzo[b]thiophene

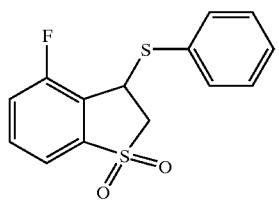

TLC: Rf 0.55 (ethyl acetate:hexane=1:4);

NMR (CDCl$_3$): δ7.64–7.45 (m, 4H), 7.42–7.27 (m, 4H), 5.06 (dd, J=7.4 Hz, 2.8 Hz, 1H), 3.77 (dd, J=14.2 Hz, 7.4 Hz, 1H), 3.63 (dd, J=14.2 Hz, 2.8 Hz, 1H).

EXAMPLES 45~45 (22)

Using the compounds prepared in Examples 44~44 (15) and Examples 44 (18)~44 (24) instead of the compound prepared in Example 1 by the same procedure as described in Example 3, or by the same reaction using 3-chloroperbenzoic acid instead of OXONE© as an oxidizer, and if necessary, by converting into a corresponding salt by known methods, the following compounds of the present invention were obtained.

EXAMPLE 45

5-Methylcarbamoyl-4-methoxy-3-phenylsulfonyl-2, 3-dihydro-1,1-dioxidebenzo[b]thiophene

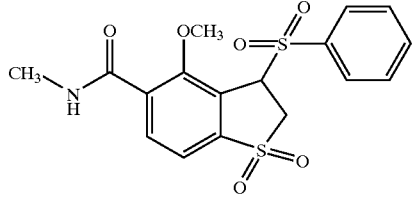

TLC: Rf 0.33 (methanol:ethyl acetate=5:95);

NMR (DMSO-$d_6$): δ8.47 (q-like, J=3.4 Hz, 1H), 7.87–7.73 (m, 3H), 7.69–7.60 (m, 3H), 7.50 (d, J=5.4 Hz, 1H), 5.65 (d, J=6.0 Hz, 1H), 4.13 (d, J=10.2 Hz, 1H), 3.98 (dd, J=10.2 Hz, 6.0 Hz, 1H), 3.59 (s, 3H), 2.77 (d, J=3.4 Hz, 3H).

EXAMPLE 45 (1)

4-Dimethylcarbamoyl-3-phenylsulfonyl-2,3-dihydro-1,1-dioxidebenzo[b]thiophene

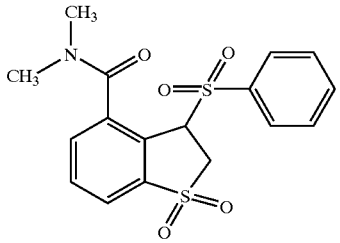

TLC: Rf 0.55 (methanol:ethyl acetate=5:95);

NMR (DMSO-$d_6$): δ7.93–7.73 (m, 6H), 7.70–7.62 (m, 2H), 5.86 (d, J=9.3 Hz, 1H), 4.12 (dd, J=15.3 Hz, 9.3 Hz, 1H), 3.91 (d, J=15.3 Hz, 1H), 3.07 (s, 3H), 3.03 (s, 3H).

EXAMPLE 45 (2)

4-Carbamoyl-3-phenylsulfonyl-2,3-dihydro-1,1-dioxidebenzo[b]thiophene

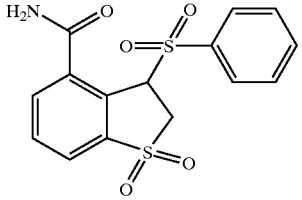

TLC: Rf 0.43 (methanol:ethyl acetate=5:95);

NMR (DMSO-$d_6$): δ8.30 (brs, 1H), 8.03 (d, J=7.8 Hz, 1H), 7.91 (d, J=7.8 Hz, 1H), 7.86–7.72 (m, 5H), 7.68 (brs, 1H), 7.63 (t, J=7.8 Hz, 1H), 6.37 (d, J=9.3 Hz, 1H), 4.08 (dd, J=15.3 Hz, 9.3 Hz, 1H), 3.95 (d, J=15.3 Hz, 1H).

EXAMPLE 45 (3)

4-(2-Pyridin-4-yl)ethyl)oxy-3-phenylsulfonyl-2,3-dihydro-1,1-dioxidebenzo[b]thiophene

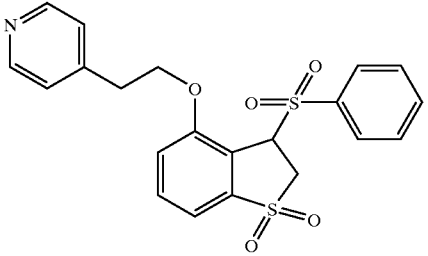

Free Compound

TLC: Rf 0.25 (ethyl acetate:methanol=10:1);

NMR (CDCl$_3$): δ8.58 (d, J=6 Hz, 2H), 7.80–7.35 (m, 6H), 7.35–7.14 (m, 3H), 6.98 (d, J=8 Hz, 1H) 5.12 (d, J=9 Hz, 1H), 4.30–4.05 (m, 3H), 3.70 (dd, J=9, 15 Hz, 1H), 3.25–2.90 (m, 2H).

Hydrochloride

TLC: Rf 0.25 (ethyl acetate:methanol=10:1);

NMR (DMSO-$d_6$): δ8.83 (d, J=6.6 Hz, 2H), 7.96 (d, J=6.6 Hz, 2H), 7.78–7.58 (m, 6H), 7.35–7.30 (m, 2H), 5.40 (d, J=8.5 Hz, 1H), 4.36–4.28 (m, 1H), 4.19–4.12 (m, 1H), 4.11 (d, J=15.0 Hz, 1H), 3.98 (dd, J=15.0, 8.5 Hz, 1H), 3.24–3.15 (m, 1H), 3.11–3.01 (m, 1H).

Methanesulfonic Acid Salt

TLC: Rf 0.25 (ethyl acetate:methanol=10:1);

NMR (DMSO-$d_6$): δ8.85 (d, J=6.6 Hz, 2H), 7.98 (d, J=6.6 Hz, 2H), 7.78–7.58 (m, 6H), 7.35–7.30 (m, 2H), 5.39 (d, J=8.5 Hz, 1H), 4.36–4.29 (m, 1H), 4.19–4.13 (m, 1H), 4.11 (d, J=15.0 Hz, 1H), 3.97 (dd, J=15.0, 8.5 Hz, 1H), 3.25–3.17 (m, 1H), 3.11–3.02 (m, 1H).

EXAMPLE 45 (4)

4-(2-(Pyridin-3-yl)ethyl)oxy-3-phenylsulfonyl-2,3-dihydro-1,1-dioxidebenzo[b]thiophene

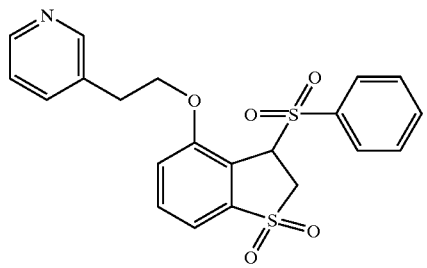

Free Compound

TLC: Rf 013 (ethyl acetate);

NMR (DMSO-$d_6$): δ8.46 (d, J=1.8 Hz, 1H), 8.43 (dd, J=4.8 Hz, 1.8 Hz, 1H), 7.86–7.54 (m, 6H), 7.42–7.30 (m, 4H), 5.43 (d, J=7.4 Hz, 1H), 4.26–3.82, (m, 4H), 2.75 (t, J=6.6 Hz, 2H).

Hydrochloride

TLC: Rf 0.13 (ethyl acetate);

NMR (DMSO-$d_6$): δ8.88 (s, 1H), 8.80 (d, J=5.7 Hz, 1H), 8.49 (d, J=7.8 Hz, 1H), 8.04–7.92 (m, 1H), 7.78–7.54 (m, 6H), 7.30 (d, J=7.8 Hz, 1H), 7.29 (d, J=8.4 Hz, 1H), 5.47 (d, J=7.8 Hz, 1H), 4.34–4.20 (m, 1H), 4.16–3.91 (m, 3H), 3.19–2.94 (m, 2H).

EXAMPLE 45 (5)

4-Ethoxycarbonylmethyloxy-3-phenylsulfonyl-2,3-dihydro-1,1-dioxidebenzo[b]thiophene

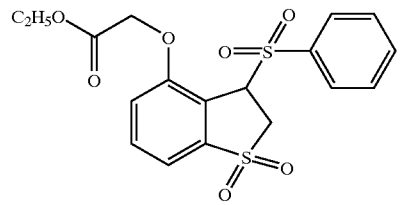

TLC: Rf 0.17 (hexane:ethyl acetate=1:1);

NMR (CDCl$_3$): δ7.82–7.78 (m, 2H), 7.68–7.60 (m, 1H), 7.58–7.44 (m, 3H), 7.36 (d, J=8.0 Hz, 1H), 6.86 (d, J=8.0 Hz, 1H), 5.38 (d, J=8.5 Hz, 1H), 4.45 (d, J=16.2 Hz, 1H), 4.30 (d, J=16.2 Hz, 1H), 4.25 (q, J=7.0 Hz, 2H), 4.24 (d, J=15.0 Hz, 1H), 3.76 (dd, J=15.0, 8.5 Hz, 1H), 1.30 (t, J=7.0 Hz, 3H).

EXAMPLE 45 (6)

6-Ethoxycarbonylmethyloxy-3-phenylsulfonyl-2,3-dihydro-1,1-dioxidebenzo[b]thiophene

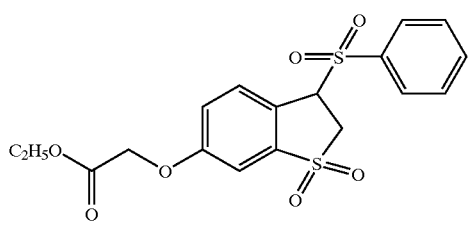

TLC: Rf 0.31 (hexane:ethyl acetate=1:1);

NMR (CDCl$_3$): δ7.90 (d, J=8.8 Hz, 1H), 7.71–7.62 (m, 3H), 7.55–7.46 (m, 2H), 7.30 (dd, J=8.8, 2.4 Hz, 1H), 7.02 (d, J=2.4 Hz, 1H), 5.00 (dd, J=7.8, 5.4 Hz, 1H), 4.67 (s, 2H), 4.28 (q, J=7.2 Hz, 2H), 3.80 (dd, J=15.0, 5.4 Hz, 1H), 3.72 (dd, J=15.0, 7.8 Hz, 1H), 1.30 (t, J=7.2 Hz, 3H).

EXAMPLE 45 (7)

6-Cyanomethyloxy-3-phenylsulfonyl-2,3-dihydro-1,1-dioxidebenzo[b]thiophene

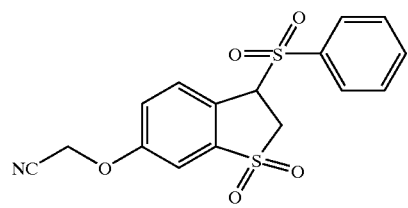

TLC: Rf 0.32 (hexane:ethyl acetate=2:1);

NMR (DMSO-d$_6$): δ7.81–7.75 (m, 3H), 7.68–7.60 (m, 3H), 7.53 (d, J=2.5 Hz, 1H), 7.48 (dd, J=8.5, 2.5 Hz, 1H), 5.73 (dd, J=9.5, 3.0 Hz, 1H), 5.33 (s, 2H), 4.03 (dd, J=15.0, 9.5 Hz, 1H), 3.81 (dd, J=15.0, 3.0 Hz, 1H).

EXAMPLE 45 (8)

5-Ethoxycarbonylmethyloxy-3-phenylsulfonyl-2,3-dihydro-1,1-dioxidebenzo[b]thiophene

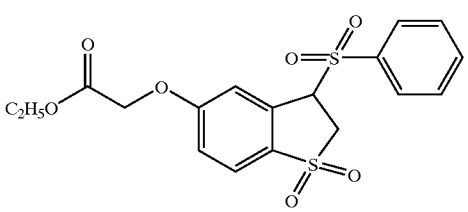

TLC: Rf 0.35 (ethyl acetate:hexane=1:1);

NMR (CDCl$_3$): δ7.73–7.61 (m, 3H), 7.58–7.45 (m,3H), 7.44 (d, J=2.2 Hz, 1H), 7.18 (dd, J=8.8 Hz, 2.2 Hz, 1H), 5.00 (t, J=7.0 Hz, 1H), 4.78 (s, 2H), 4.33 (q, J=7.2 Hz, 2H), 3.81–3.65 (m, 2H), 1.35 (t, J=7.2 Hz, 3H).

EXAMPLE 45 (9)

7-Ethoxycarbonylmethyloxy-3-phenylsulfonyl-2,3-dihydro-1,1-dioxidebenzo[b]thiophene

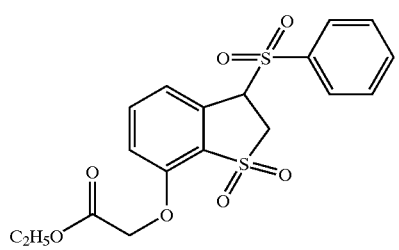

TLC: Rf 0.17 (ethyl acetate:hexane=1:1);

NMR (CDCl$_3$): δ7.72–7.47 (m, 7H), 6.91 (d, J=6.9 Hz, 1H), 5.03 (dd, J=8.7 Hz, 5.4 Hz, 1H), 4.76 (s, 2H), 4.24 (q, J=7.2 Hz, 2H), 3.79 (dd, J=14.7 Hz, 5.4 Hz, 1H), 3.73 (dd, J=14.7 Hz, 8.7 Hz, 1H), 1.27 (t, J=7.2 Hz, 3H).

EXAMPLE 45 (10)

5-Benzyloxycarbonyl-4-methoxy-3-phenylsulfonyl-2,3-dihydro-1,1-dioxidebenzo[b]thiophene

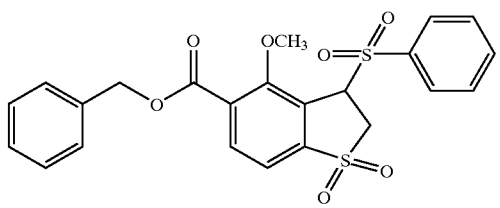

TLC: Rf 0.30 (hexane:ethyl acetate=1:1);

NMR (CDCl$_3$): δ7.90 (d, J=8.0 Hz, 1H), 7.76–7.71 (m, 2H), 7.63–7.55 (m, 1H), 7.47–7.36 (m, 8H), 5.37 (s, 2H), 5.24 (dd, J=9.0, 1.0 Hz, 1H), 4.16 (dd, J=15.0, 1.0 Hz, 1H), 3.74 (s, 3H), 3.73 (dd, J=15.0, 9.90 Hz, 1H).

EXAMPLE 45 (11)

5-Ethoxycarbonyl-3-phenylsulfonyl-2,3-dihydro-1,1-dioxidebenzo[b]thiophene

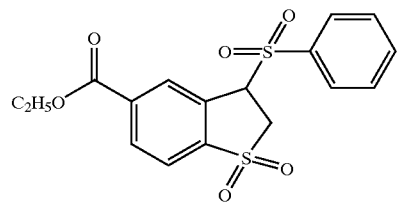

TLC: Rf 0.34 (hexane:ethyl acetate=1:1);

NMR (DMSO-$d_6$): δ8.23 (d-like, J=8.0 Hz, 1H), 8.12 (s, 1H), 7.97 (d, J=8.0 Hz, 1H), 7.85–7.78 (m, 3H), 7.69–7.61 (m, 2H), 5.91 (dd, J=9.3, 3.2 Hz, 1H), 4.38 (q, J=7.0 Hz, 2H), 4.10 (dd, J=15.3, 9.3 Hz, 1H), 3.91 (dd, J=5.3, 3.2 Hz, 1H), 1.35 (t, J=7.0 Hz, 3H).

EXAMPLE 45 (12)

7-Methoxycarbonyl-3-phenylsulfonyl-2,3-dihydro-1,1-dioxidebenzo[b]thiophene

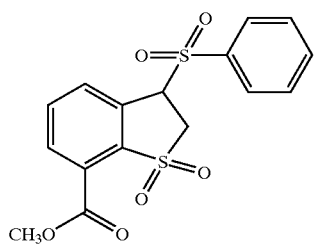

TLC: Rf 0.16 (ethyl acetate:hexane=1:1);

NMR (CDCl$_3$): δ8.23 (d, J=8.1 Hz, 2H), 7.81 (t, J=8.1 Hz, 1H), 7.72–7.64 (m, 3H), 7.55–7.47 (m, 2H), 5.07 (dd, J=9.3 Hz, 4.8 Hz, 1H), 3.97 (s, 3H), 3.84 (dd, J=14.7 Hz, 4.8 Hz, 1H), 3.75 (dd, J=14.7 Hz, 9.3 Hz, 1H).

EXAMPLE 45 (13)

7-Ethoxycarbonyl-3-phenylsulfonyl-2,3-dihydro-1,1-dioxidebenzo[b]thiophene

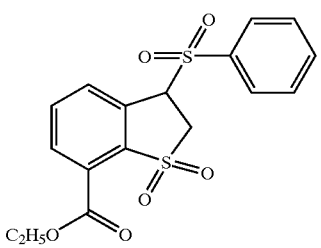

TLC: Rf 0.22 (ethyl acetate:hexane=1:1);

NMR (CDCl$_3$): δ8.25 (d, J=7.8 Hz, 1H), 8.23 (d, J=7.8 Hz, 1H), 7.80 (t, J=7.8 Hz, 1H), 7.73–7.65 (m, 3H), 7.56–7.48 (m, 2H), 5.06 (dd, J=9.3 Hz, 4.8 Hz, 1H), 4.44 (q, J=7.2 Hz, 2H), 3.83 (dd, J=14.7 Hz, 4.8 Hz, 1H), 3.73 (dd, J=14.7 Hz, 9.3 Hz, 1H), 1.40 (t, J=7.2 Hz, 3H).

EXAMPLE 45 (14)

5-t-Butoxycarbonyl-4-methoxy-3-phenylsulfonyl-2,3-dihydro-1,1-dioxidebenzo[b]thiophene

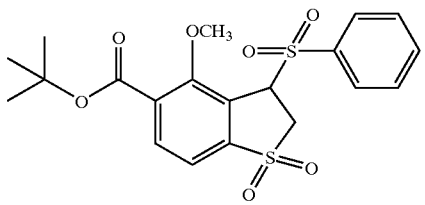

TLC: Rf 0.37 (ethyl acetate:hexane=1:1);

NMR (CDCl$_3$): δ7.80 (d, J=8.1 Hz, 1H), 7.78 (d, J=7.8 Hz, 2H), 7.66 (t, J=7.8 Hz, 1H), 7.51 (t, J=7.8 Hz, 2H), 7.37 (d, J=8.1 Hz, 1H), 5.27 (dd, J=9.3 Hz, 1.2 Hz, 1H), 4.14 (dd, J=15.0 Hz, 1.2 Hz, 1H), 3.86 (s, 3H), 3.74 (dd, J=15.0 Hz, 9.3 Hz, 1H), 1.61 (s, 9H).

EXAMPLE 45 (15)

5-(2-Ethoxycarbonylethyl)-4-methoxy-3-phenylsulfonyl-2,3-dihydro-1,1-dioxidebenzo[b]thiophene

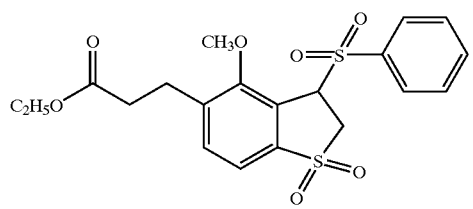

TLC: Rf 0.28 (ethyl acetate:hexane=1:1);

NMR (CDCl$_3$): δ7.77–7.70 (m, 2H), 7.61 (t, J=7.5 Hz, 1H), 7.50–7.35 (m, 4H), 5.19 (dd, J=9.3, 1.8 Hz, 1H), 4.23 (dd, J=15.0, 1.8 Hz, 1H), 4.16 (q, J=7.2 Hz, 2H), 3.81 (dd, J=15.0, 9.3 Hz, 1H), 3.80 (s, 3H), 3.00–2.87 (m, 2H), 2.65–2.40 (m, 2H), 1.27 (t, J=7.2 Hz, 3H).

EXAMPLE 45 (16)

3-Benzylsulfonyl-2,3-dihydro-1,1-dioxidebenzo[b]thiophene

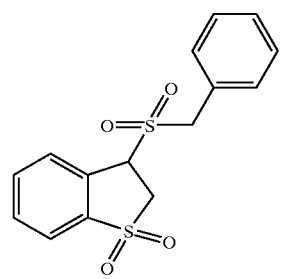

TLC: Rf 0.39 (hexane:ethyl acetate=1:1);

NMR (CDCl$_3$): δ3.89 (dd, J=15.0 Hz, 9.3 Hz, 1H), 3.98 (d, J=14.0 Hz, 1H), 4.03 (dd, J=15.0 Hz, 3.6 Hz, 1H), 4.31 (d, J=14.0 Hz, 1H), 4.91 (dd, J=9.3 Hz, 3.6 Hz, 1H), 7.21–7.35 (m, 5H), 7.62–7.71 (m, 2H), 7.80–7.90 (m, 2H).

EXAMPLE 45 (17)

3-(3,4-Dichlorophenyl)sulfonyl-2,3-dihydro-1,1-dioxidebenzo[b]thiophene

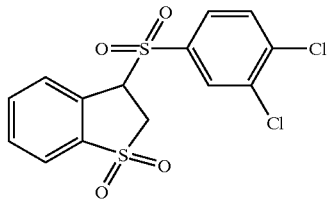

TLC: Rf 0.43 (hexane:ethyl acetate=1:1);

NMR (DMSO-$d_6$): δ7.98 (d, J=2.1 Hz, 1H), 7.75–7.89 (m, 5H), 7.63 (dd, J=8.4, 2.1 Hz, 1H), 5.91 (dd, J=8.0, 4.4 Hz, 1H), 4.04 (dd, J=15.4, 8.0 Hz, 1H), 3.95 (dd, J=15.4, 4.4 Hz, 1H).

EXAMPLE 45 (18)

3-(4-Nitrophenyl)sulfonyl-2,3-dihydro-1,1-dioxidebenzo[b]thiophene

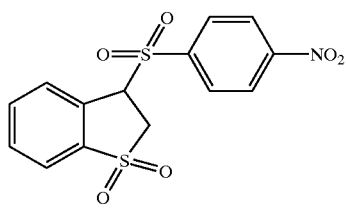

TLC: Rf 0.33 (hexane:ethyl acetate=1:1);

NMR (DMSO-$d_6$): δ8.41 (d, J=8.8 Hz, 2H), 8.04 (d, J=8.8 Hz, 2H), 7.76–7.85 (m, 4H), 5.97 (dd, J=9.0, 3.2 Hz, 1H), 4.04 (dd, J=15.4, 9.0 Hz, 1H), 3.90 (dd, J=15.4, 3.2 Hz, 1H).

EXAMPLE 45 (19)

5-Hydroxymethyl-4-methoxy-3-phenylsulfonyl-2,3-dihydro-1,1-dioxidebenzo[b]thiophene

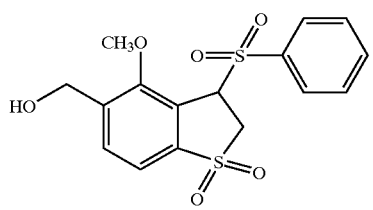

TLC: Rf 0.51 (ethyl acetate);

NMR (DMSO-$d_6$): δ7.80–7.72 (m, 4H), 7.64–7.51 (m, 3H), 5.66 (dd, J=8.5, 1.5 Hz, 1H), 5.43 (t, J=5.5 Hz, 1H), 4.52 (d, J=5.5 Hz, 1H), 4.13 (dd, J=15.0, 8.5 Hz, 1H), 4.00 (dd, J=15.0, 1.5 Hz, 1H), 3.58 (s, 3H).

EXAMPLE 45 (20)

4-Hydroxymethyl-3-phenylsulfonyl-2,3-dihydro-1,1-dioxidebenzo[b]thiophene

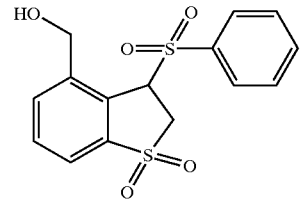

TLC: Rf 0.54 (chloroform:methanol=9:1);

NMR (CDCl$_3$): δ7.84 (d, J=7.5 Hz, 1H), 7.72–7.63 (m, 2H), 7.62–7.53 (m, 3H), 7.51–7.44 (m, 2H), 5.53 (d, J=9.3 Hz, 1H), 5.08 (d, J=13.5 Hz, 1H), 5.01 (d, J=13.5 Hz, 1H), 3.87 (d, J=15.0 Hz, 1H), 3.75 (dd, J=15.0, 9.3 Hz, 1H), 3.00–1.80 (br, 1H).

EXAMPLE 45 (21)

6-Fluoro-3-phenylsulfonyl-2,3-dihydro-1,1-dioxidebenzo[b]thiophene

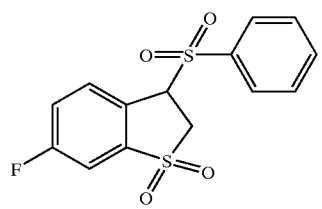

TLC: Rf 0.40 (ethyl acetate:hexane=1:1);

NMR (DMSO-$d_6$): δ7.85–7.58 (m, 8H), 5.77 (dd, J=9.6 Hz, 2.7 Hz, 1H), 4.07 (dd, J=15.6 Hz, 9.6 Hz, 1H), 3.87 (dd, J=15.6 Hz, 2.7 Hz, 1H).

EXAMPLE 45 (22)

4-Fluoro-3-phenylsulfonyl-2,3-dihydro-1,1-dioxidebenzo[b]thiophene

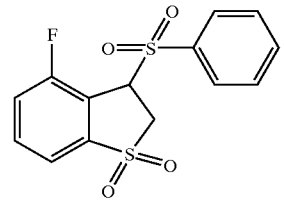

TLC: Rf 0.29 (ethyl acetate:hexane=1:1);

NMR (DMSO-$d_6$): δ7.83–7.57 (m, 8H), 5.81 (dd, J=9.0 Hz, 1.5 Hz, 1H), 4.09 (dd, J=15.6 Hz, 1.5 Hz, 1H), 3.99 (dd, J=15.6 Hz, 9.0 Hz, 1H).

EXAMPLE 46

5-Methoxycarbonyl-4-ethoxybenzo[b]thiophene

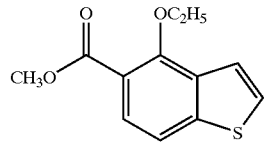

By the same procedure as described in Example 18 using 5-methoxycarbonyl-4-hydroxybenzo[b]thiophene instead of the compound prepared in Example 9 (12) and ethyl iodide instead of 4-nitrobenzylbromide, the compound of the present invention having the following physical data was obtained.

TLC: Rf 0.44 (hexane:ethyl acetate=4:1);

NMR (CDCl$_3$): δ7.82 (d, J=8 Hz, 1H), 7.63 (d, J=8 Hz, 1H), 7.54 (d, J=6 Hz, 1H), 7.43 (d, J=6 Hz, 1H), 4.21 (q, J=7 Hz, 2H), 3.95 (s, 3H), 1.49 (t, J=7 Hz, 3H).

EXAMPLE 47

5-Carboxy-4-ethoxybenzo[b]thiophene

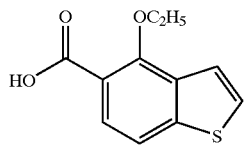

To the compound prepared in Example 46 (1.11 g), were added methanol (10 ml) and a 2N aqueous solution of sodium hydroxide (5.0 ml). The mixture was refluxed for 30 minutes. The reaction mixture was concentrated. The residue was acidified by addition of 1N hydrochloric acid. The mixture was extracted by ethyl acetate. The extract was washed by water and a saturated aqueous solution of sodium chloride successively, dried over anhydrous sodium sulfate and concentrated to give the compound of the present invention (1.02 g) having the following physical data.

TLC: Rf 0.06 (hexane:ethyl acetate=4:1);

NMR (CDCl$_3$): δ8.09 (d, J=8 Hz, 1H), 7.75 (d, J=8 Hz, 1H), 7.52 (d, J=6 Hz, 1H), 7.49 (d, J=6 Hz, 1H), 4.44 (q, J=7 Hz, 2H), 1.58 (t, J=7 Hz, 3H).

EXAMPLE 48

5-Benzyloxycarbonyl-4-ethoxybenzo[b]thiophene

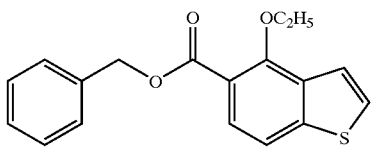

By the same procedure as described in Example 32 using the compound prepared in Example 47 instead of 4-carboxy-1,1-dioxidebenzo[b]thiophene, and benzyl bromide, the compound having the following physical data was obtained.

TLC: Rf 0.46 (hexane:ethyl acetate=4:1);

NMR (CDCl$_3$): δ7.85 (d, J=8 Hz, 1H), 7.62 (d, J=8 Hz, 1H), 7.56–7.26 (m, 7H), 5.40 (s, 2H), 4.15 (q, J=7 Hz, 2H), 1.37 (t, J=7 Hz, 3H).

EXAMPLE 49

5-Benzyloxycarbonyl-4-ethoxy-1,1-dioxidebenzo[b]thiophene

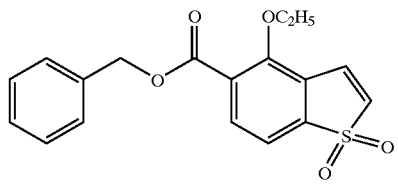

By the same procedure as described in 3 using the compound prepared in Example 48 instead of the compound prepared in Example 1, the compound having the following physical data was obtained (with the proviso that 3-chloroperbenzoic acid was used instead of OXONE© as an oxidizer).

TLC: Rf 0.10 (hexane:ethyl acetate 4:1);

NMR (CDCl$_3$): δ7.99 (d, J=8 Hz, 1H), 7.60–7.30 (m, 7H), 6.72 (d, J=7 Hz, 1H), 5.38 (s, 2H), 4.03 (q, J=7 Hz, 2H), 1.31 (t, J=7 Hz, 3H).

EXAMPLES 50~50 (2)

By the same procedure as described in Example 46→Example 47→Example 48→Example 49 using a corresponding halide compound instead of ethyl iodide, the following compounds of the present invention were obtained.

EXAMPLE 50

5-Benzyloxycarbonyl-4-hexyloxy-1,1-dioxidebenzo[b]thiophene

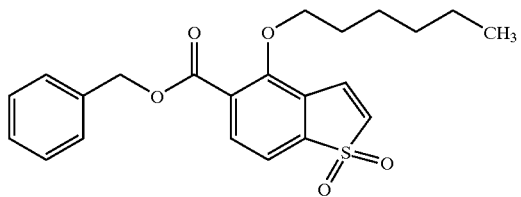

TLC: Rf 0.22 (hexane:ethyl acetate=4:1);

NMR (CDCl$_3$): δ7.97 (d, J=8 Hz, 1H), 7.55–7.30 (m, 7H), 6.72 (d, J=7 Hz, 1H), 5.38 (s, 2H), 3.93 (t, J=7 Hz, 2H), 1.80–1.45 (m, 2H), 1.45–1.10 (m, 6H), 0.90 (t, J=7 Hz, 3H).

EXAMPLE 50 (1)

5-Benzyloxycarbonyl-4-butoxy-1,1-dioxidebenzo[b]thiophene

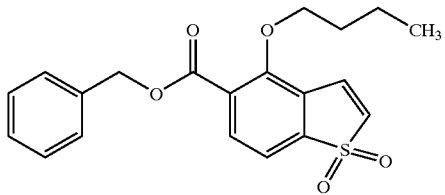

TLC: Rf 0.24 (hexane:ethyl acetate=4:1);

NMR (CDCl$_3$): δ7.98 (d, J=8 Hz, 1H), 7.58–7.38 (m, 7H), 6.72 (d, J=7 Hz, 1H), 5.38 (s, 2H), 3.94 (t, J=7 Hz, 2H), 1.78–1.50 (m, 2H), 1.50–1.20 (m, 2H), 0.92 (t, J=7 Hz, 3H).

EXAMPLE 50 (2)

5-Benzyloxycarbonyl-4-octyloxy-1,1-dioxidebenzo[b]thiophene

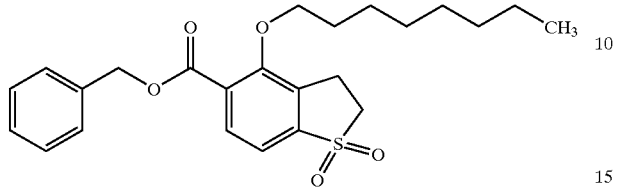

TLC: Rf 0.33 (hexane:ethyl acetate=4:1);

NMR (CDCl$_3$): δ7.97 (d, J=8 Hz, 1H), 7.60–7.25 (m, 7H), 6.72 (d, J=7 Hz, 1H), 5.38 (s, 2H), 3.92 (t, J=7 Hz, 2H), 1.82–1.45 (m, 2H), 1.45–1.05 (m, 10H), 0.89 (t, J=7 Hz, 3H).

EXAMPLES 51~51 (3)

By the same procedure as described in Example 27 using the compounds prepared in Example 49 and Examples 50~50 (2) instead of 5-methyl-1,1-dioxidebenzo[b]thiophene, the following compounds of the present invention were obtained.

EXAMPLE 51

5-Benzyloxycarbonyl-4-ethoxy-3-phenylsulfonyl-2,3-dihydro-1,1-dioxidebenzo[b]thiophene

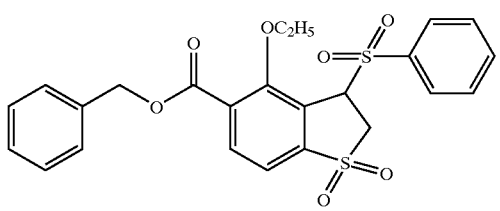

TLC: Rf 0.41 (chloroform:hexane:methanol=5:5:1);

NMR (CDCl$_3$): δ7.90 (d, J=8 Hz, 1H), 7.78–7.66 (m, 2H), 7.64–7.30 (m, 9H), 5.34 (s, 2H), 5.17 (d, J=9 Hz, 1H), 4.30 (dd, J=1, 15 Hz, 1H), 4.10–3.60 (m, 3H), 1.13 (t, J=7 Hz, 3H).

EXAMPLE 51 (1)

5-benzyloxycarbonyl-4-hexyloxy-3-phenylsulfonyl-2,3-dihydro-1,1-dioxidebenzo[b]thiophene

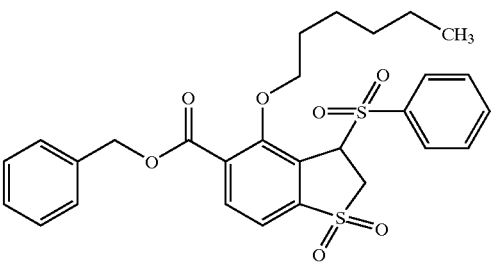

TLC: Rf 0.45 (chloroform:hexane:methanol=5:5:1);

NMR (CDCl$_3$): δ7.88 (d, J=8 Hz, 1H), 7.78–7.64 (m, 2H), 7.60–7.28 (m, 9H), 5.34 (s, 2H), 5.15 (d, J=9 Hz, 1H), 4.32 (dd, J=1, 15 Hz, 1H), 4.00–3.46 (m, 3H), 1.75–1.05 (m, 8H), 0.91 (t, J=7 Hz, 3H).

EXAMPLE 51 (2)

5-Benzyloxycarbonyl-4-butoxy-3-phenylsulfonyl-2,3-dihydro-1,1-dioxidebenzo[b]thiophene

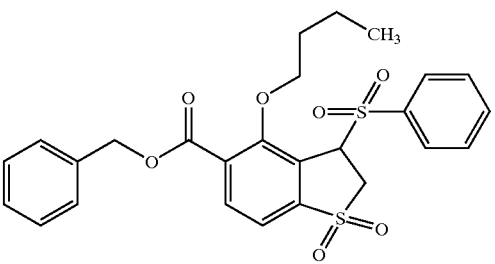

TLC: Rf 0.43 (chloroform:hexane:methanol 5:5:1);

NMR (CDCl$_3$): δ7.88 (d, J=8 Hz, 1H), 7.78–7.64 (m, 2H), 7.60–7.28 (m, 9H), 5.34 (s, 2H), 5.15 (d, J=9 Hz, 1H), 4.32 (dd, J=1, 15 Hz, 1H), 4.02–3.48 (m, 3H), 1.70–1.10 (m, 4H), 0.87 (t, J=7 Hz, 3H).

EXAMPLE 51 (3)

5-Benzyloxycarbony-4-octyloxy-3-phenylsulfonyl-2,3-dihydro-1,1-dioxidebenzo[b]thiophene

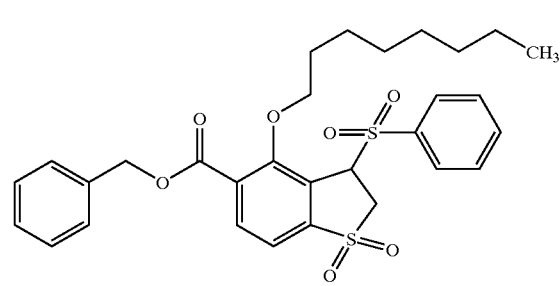

TLC: Rf 0.47 (chloroform:hexane:methanol=5:5:1);

NMR (CDCl$_3$): δ7.88 (d, J=8 Hz, 1H), 7.76–7.64 (m, 2H), 7.60–7.26 (m, 9H), 5.34 (s, 2H), 5.15 (d, J=9 Hz, 1H), 4.32 (dd, J=1, 15 Hz, 1H), 4.00–3.46 (m, 3H), 1.75–1.05 (m, 12H), 0.90 (t, J=7 Hz, 3H).

EXAMPLE 52

5-Carboxy-4-ethoxy-3-phenylsulfonyl-2,3-dihydro-1,1-dioxidebenzo[b]thiophene

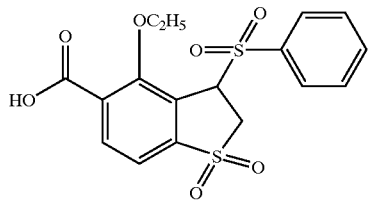

To a solution of the compound prepared in Example 51 (670 mg) in ethyl acetate (50 ml). Thereto was added 10% palladium carbon (220 mg). Under an atmosphere of hydrogen the mixture was stirred at room temperature for 2 hours. The reaction mixture was filtered through celite. The filtrate was washed by ethyl acetate and concentrated. The residue was dissolved in ethyl acetate under heating and was recrystallized by addition of hexane (5 ml). The crystal was separated by filtration and dried to give the compound of the present invention (471 mg) having the following physical data.

TLC: Rf 0.21 (chloroform:acetic acid=10:1);

NMR (CDCl$_3$+acetone-d$_6$): δ8.02 (d, J=8 Hz, 1H), 7.86–7.72 (m, 2H), 7.72–7.58 (m, 1H), 7.58–7.32 (m, 3H), 5.33 (d, J=9 Hz, 1H), 4.30 (d, J=15 Hz, 1H), 4.24–4.06 (m, 1H), 4.20 (bs, 1H), 4.02–3.74 (m, 2H), 1.25 (t, J=7 Hz, 3H).

EXAMPLES 52 (1)~52 (3)

By the same prdcedure as described in Example 52 using the compounds prepared in Examples 51 (1)~51 (3) instead of Example 51, the following compounds were obtained.

EXAMPLE 52 (1)

5-Carboxy-4-hexyloxy-3-phenylsulfonyl-2,3-dihydro-1,1I-dioxidebenzo[b]thiophene

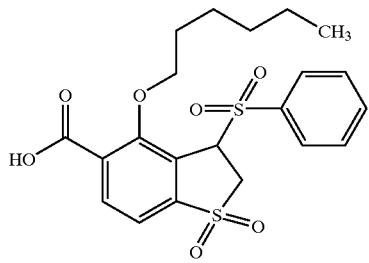

TLC: Rf 0.38 (chloroform:acetic acid=10:1);

NMR (CDCl$_3$+acetone-d$_6$): δ8.00 (d, J=8 Hz, 1H), 7.88–7.72 (m, 2H), 7.72–7.56 (m, 1H), 7.56–7.34 (m, 3H), 5.32 (d, J=9 Hz, 1H), 4.31 (dd, J=1, 15 Hz, 1H), 4.20 (brs, 1H), 4.14 (dt, J=7, 9 Hz, 1H), 4.02–3.66 (m, 2H), 1.80–1.45 (m, 2H), 1.45–1.12 (m, 6H), 0.91 (t, J=7 Hz, 3H).

EXAMPLE 52 (2)

5-Carboxy-4-butoxy-3-phenylsulfonyl-2,3-dihydro-1,1-dioxidebenzo[b]thiophene

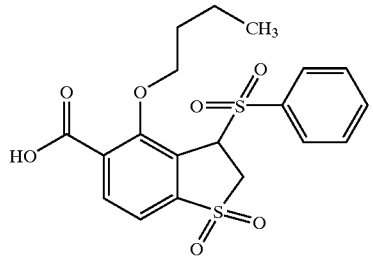

TLC: Rf 0.34 (chloroform:acetic acid=10:1);

NMR (CDCl$_3$+acetone-d$_6$): δ8.00 (d, J=8 Hz, 1H), 7.86–7.72 (m, 2H), 7.72–7.56 (m, 1H), 7.56–7.34 (m, 3H), 5.32 (d, J=9 Hz, 1H), 4.31 (dd, J=1, 15 Hz, 1H), 4.20 (brs, 1H), 4.15 (dt, J=7, 9 Hz, 1H ), 4.00–3.66 (m, 2H), 1.74–1.48 (m, 2H), 1.48–1.20 (m, 2H), 0.92 (t, J=7 Hz, 3H).

EXAMPLE 52 (3)

5-Carboxy-4-octyloxy-3-phenylsulfonyl-2,3-dihydro-1,1-dioxidebenzo[b]thiophene

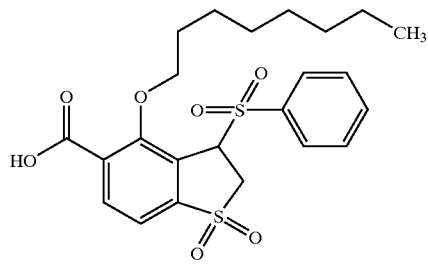

TLC: Rf 0.40 (chloroform:acetic acid=10:1);

NMR (CDCl$_3$+acetone-d$_6$): δ8.00 (d, J=8 Hz, 1H), 7.84–7.72 (m, 2H), 7.72–7.57 (m, 1H), 7.57–7.34 (m, 3H), 5.33 (d, J=9 Hz, 1H), 4.31 (dd, J=1, 15 Hz, 1H), 4.13 (dt, J=7, 9 Hz, 1H), 4.10 (brs, 1H ), 4.00–3.66 (m, 2H), 1.74–1.43 (m, 2H), 1.43–1.05 (m, 10H), 0.90 (t, J=7 Hz, 3H).

EXAMPLES 53~53 (3)

By the same procedure as described in Example 32 using the compounds prepared in Examples 52~52 (3) instead of 4-hydroxy 1,1-dioxidebenzo[b]thiophene and corresponding alcohol derivatives instead of 1-(3-hydroxypropyl) pyrrole, the following compounds of the present invention were obtained.

EXAMPLE 53

5-Methoxycarbonyl-4-ethoxy-3-phenylsulfonyl-2,3-dihydro-1,1-dioxidebenzo[b]thiophene

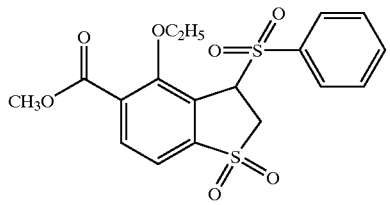

TLC: Rf 0.35 (chloroform:hexane:methanol=5:5:1);

NMR (CDCl₃): δ7.91 (d, J=8 Hz, 1H), 7.84–7.72 (m, 2H), 7.72–7.57 (m, 1H), 7.57–7.32 (m, 3H), 5.21 (d, J=9 Hz, 1H), 4.28 (dd, J=1, 15 Hz, 1H), 4.20–4.00 (m, 1H), 3.93 (s, 3H), 3.95–3.68 (m, 2H), 1.26 (t, J=7 Hz, 3H).

EXAMPLE 53 (1)

5-Methoxycarbonyl-4-hexyloxy-3-phenylsulfonyl-2,3-dihydro-1,1-dioxidebenzo[b]thiophene

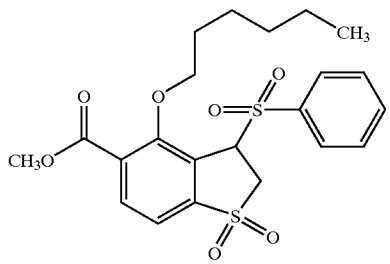

TLC: Rf 0.42 (chloroform:hexane:methanol=5:5:1);

NMR (CDCl₃): δ7.89 (d, J=8 Hz, 1H), 7.82–7.69 (m, 2H), 7.69–7.55 (m, 1H), 7.55–7.30 (m, 3H), 5.19 (d, J=9 Hz, 1H), 4.30 (d, J=15 Hz, 1H), 4.08 (dt, J=7, 9 Hz, 1H), 3.93 (s, 3H), 3.95–3.55 (m, 2H), 1.80–1.46 (m, 2H), 1.46–1.15 (m. 6H), 0.92 (t, J=7 Hz, 3H).

EXAMPLE 53 (2)

5-Methoxycarbonyl-4-butoxy-3-phenylsulfonyl-2,3-dihydro-1,1-dioxidebenzo[b]thiophene

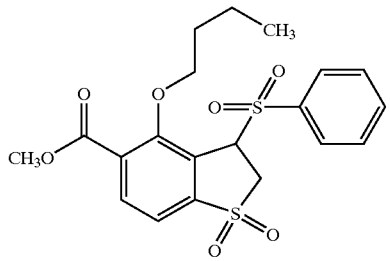

TLC: Rf 0.37 (chloroform:hexane:methanol=5:5:1);

NMR (CDCl₃): δ7.89 (d, J=8 Hz, 1H), 7.82–7.68 (m, 2H), 7.68–7.55 (m, 1H), 7.55–7.34 (m, 3H), 5.19 (d, J=9 Hz, 1H), 4.31 (dd, J=1, 15 Hz, 1H), 4.05 (dt, J=7, 9 Hz, 1H), 3.93 (s, 3H), 3.88–3.60 (m, 2H), 1.80–1.50 (m, 2H), 1.50–1.18 (m, 2H), 0.94 (t, J=7 Hz, 3H).

EXAMPLE 53 (3)

5-Methoxycarbonyl-4-octyloxy-3-phenylsulfonyl-2,3-dihydro-1,1-dioxidebenzo[b]thiophene

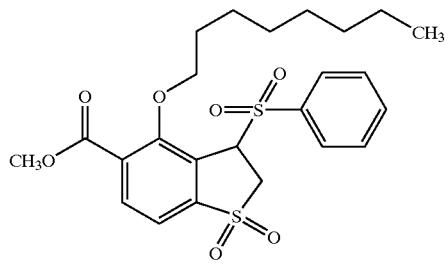

TLC: Rf 0.44 (chloroform:hexane:methanol=5:5:1);

NMR (CDCl₃): δ7.89 (d, J=8 Hz, 1H), 7.80–7.69 (m, 2H), 7.69–7.55 (m, 1H), 7.55–7.34 (m, 3H), 5.19 (d, J=9 Hz, 1H), 4.30 (dd, J=1, 15 Hz, 1H), 4.06 (dt, J=7, 9 Hz, 1H), 3.93 (s, 3H), 3.90–3.58 (m, 2H), 1.80–1.45 (m, 2H), 1.45–1.10 (m, 10H), 0.90 (t, J=7 Hz, 3H).

EXAMPLES 54~54 (19)

By the same procedure as described in Example 28 using the compounds prepared in Examples 52~52 (3) instead of 4-carboxy-1,1-dioxidebenzo[b]thiophene and amine derivatives corresponding to (pyridin-3-ylmethyl)amine, the following compounds of the present invention were obtained.

EXAMPLE 54

5-(4-(2-(2-Trifluoromethylphenyl)ethyl)piperazin-1-yl) carbonyl-4-ethoxy-3-phenylsulfonyl-2,3-dihydro-1,1-dioxidebenzo[b]thiophene

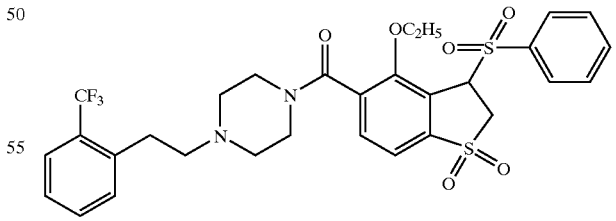

TLC: Rf 0.73 (chloroform:methanol 5:1);

NMR (CDCl₃): δ7.90 (d, J=8 Hz, 1H), 7.78–7.15 (m, 10H), 5.33 and 5.19 (each d, J=9 Hz, total 1H), 4.40–3.50 (m, 6H), 3.40–2.25 (m, 10H), 1.30–1.10 (m, 3H).

EXAMPLE 54 (1)

5-(4-(2-Chlorophenyl)piperazin-1-yl)carbonyl-4-ethoxy-3-phenylsulfonyl-2,3-dihydro-1,1-dioxidebenzo[b]thiophene

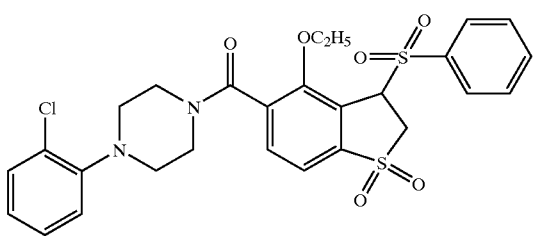

TLC: Rf 0.75 (chloroform:methanol=5:1);

NMR (CDCl$_3$): δ7.90 (d, J=8 Hz, 1H), 7.80–6.85 (m, 10H), 5.33 and 5.21 (each d, J=9 Hz, total 1H), 4.45–3.55 (m, 6H), 3.50–2.80 (m, 6H), 1.25 (t, J=7 Hz, 3H).

EXAMPLE 54 (2)

5-(2-Dimethylaminoethyl)carbamoyl-4-ethoxy-3-phenylsulfonyl-2,3-dihydro-1,1-dioxidebenzo[b]thiophene

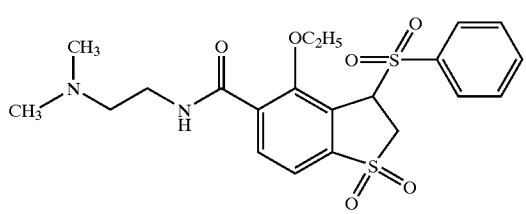

TLC: Rf 0.34 (chloroform:methanol=5:1);

NMR (CDCl$_3$): δ8.24 and 8.11 (each d, J=8 Hz, total 1H), 8.00–7.15 (m, 7H), 5.15 (d, J=9 Hz, 1H), 4.50–3.30 (m, 6H), 2.54 (t, J=7 Hz, 2H), 2.32 (s, 6H), 1.45–1.20 (m, 3H).

EXAMPLE 54 (3)

5-(2,3,4,5,6,7-Hexahydro-1H-azepin-1-yl)carbonyl-4-ethoxy-3-phenylsulfonyl-2,3-dihydro-1,1-dioxidebenzo[b]thiophene

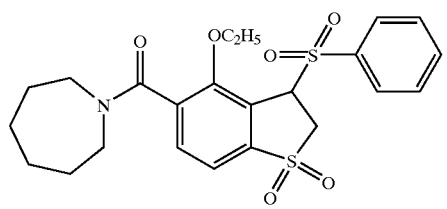

TLC: Rf 0.19 (ethyl acetate:hexane=2:1);

NMR (CDCl$_3$): δ7.87 (d, J=8 Hz, 1H), 7.80–7.20 (m, 6H), 5.32 and 5.20 (each d, J=9 Hz, total 1H), 4.40–2.90 (m, 8H), 2.10–1.00 (m, 1H).

EXAMPLE 54 (4)

5-(2,3-Dihydroindol-1-yl)carbonyl-4-ethoxy-3-phenylsulfonyl-2,3-dihydro-1,1-dioxidebenzo[b]thiophene

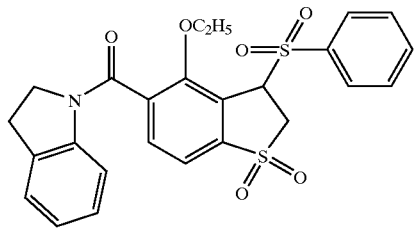

TLC: Rf 0.40 (ethyl acetate:hexane=2:1);

NMR (CDCl$_3$): δ8.29 (d, J=8 Hz, 1H), 8.05–6.90 (m, 10H), 5.38–5.10 (m, 1H), 4.50–3.40 (m, 6H), 3.16 (t, J=8 Hz, 2H), 1.40–1.00 (m, 3H).

EXAMPLE 54 (5)

5-(4-(2-(2-Trifluoromethylphenyl)ethyl)piperazin-1-yl)carbonyl-4-hexyloxy-3-phenylsulfonyl-2,3-dihydro-1,1-dioxidebenzo[b]thiophene

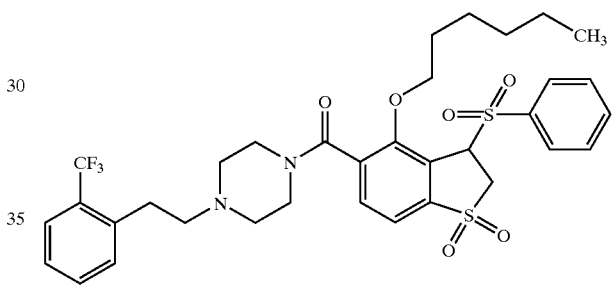

TLC: Rf 0.57 (chloroform:methanol=10:1);

NMR (CDCl$_3$): δ7.89 (d, J=8 Hz, 1H), 7.76–7.20 (m, 10H), 5.30 and 5.17 (each d, J=9 Hz, total 1H), 4.25 (d, J=15 Hz, 1H), 4.20–3.50 (m, 5H), 3.50–2.80 (m, 4H), 2.80–2.20 (m, 6H), 1.90–1.05 (m, 8H), 0.90 (t, J=7 Hz, 3H).

EXAMPLE 54 (6)

5-(4-(2-Chlorophenyl)piperazin-1-yl)carbonyl-4-hexyloxy-3-phenylsulfonyl-2,3-dihydro-1,1-dioxidebenzo[b]thiophene

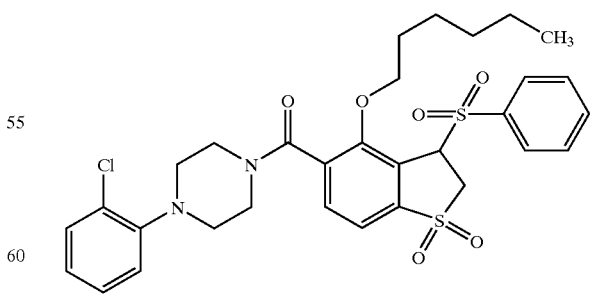

TLC: Rf 0.66 (chloroform:methanol=10:1);

NMR (DMSO-d$_6$): δ8.31 (s, 1H), 8.00–6.95 (m, 10H), 5.66 (d, J=9 Hz, 1H), 4.32 (d, J=15 Hz, 1H), 4.22–2.70 (m, 11H), 1.60–1.02 (m, 8H), 0.87 (t, J=7 Hz, 3H).

EXAMPLE 54 (7)

5-(2-Dimethylaminoethyl)carbamoyl-4-hexyloxy-3-phenylsulfonyl-2,3-dihydro-1,1-dioxidebenzo[b]thiophene

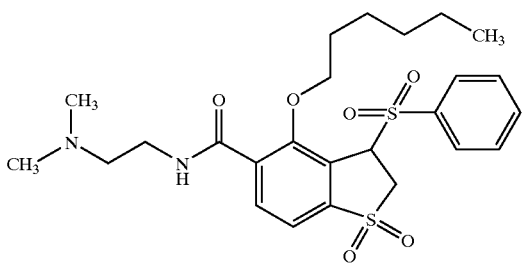

TLC: Rf 0.23 (chloroform:methanol=10:1);
NMR (CDCl$_3$): δ8.21 and 8.07 (each d, J=8 Hz, total 1H), 7.90–7.10 (m, 7H), 5.13 (d, J=9 Hz, 1H), 4.32 (d, J=15 Hz, 1H), 4.25–3.35 (m, 5H), 2.56 and 2.57 (each t, J=6 Hz, total 2H), 2.33 (s, 6H), 2.05–1.10 (m, 8H), 0.92 (t, J=7 Hz, 3H).

EXAMPLE 54 (8)

5-(2,3,4,5,6,7-Hexahydro-1H-azepin-1-yl)carbonyl-4-hexyloxy-3-phenylsulfonyl-2,3-dihydro-1,1-dioxidebenzo[b]thiophene

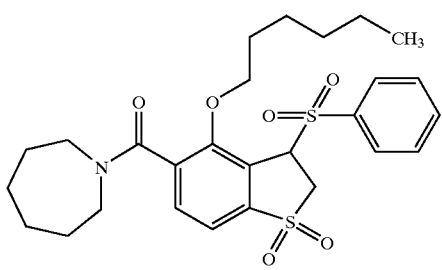

TLC: Rf 0.23 (hexane:ethyl acetate=1:1);
NMR (CDCl$_3$): δ7.86 (d, J=8 Hz, 1H), 7.78–7.20 (m, 6H), 5.30 and 5.18 (each d, J=9 Hz, total 1H), 4.25 (d, J=15 Hz, 1H), 4.35–3.00 (m, 7H), 2.10–1.10 (m, 16H), 0.91 (t, J=7 Hz, 3H).

EXAMPLE 54 (9)

5-(2,3-Dihydroindol-1-yl)carbonyl-4-hexyloxy-3-phenylsufonyl-2,3-dihydro-1,1-dioxidebenzo[b]thiophene

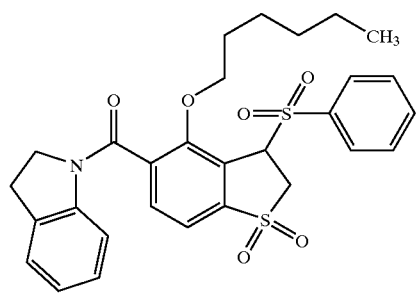

TLC: Rf 0.39 (hexane:ethyl acetate=1:1);
NMR (CDCl$_3$): δ8.29 (d, J=8 Hz, 1H), 8.10–6.80 (m, 10H), 5.40–5.05 (m, 1H), 4.50–3.35 (m, 6H), 3.16 (t, J=8 Hz, 2H), 1.90–0.95 (m, 8H), 0.95–0.75 (m, 3H).

EXAMPLE 54 (10)

5-(4-(2-(2-Trifluoromethylphenyl)ethyl)piperazin-1-yl) carbonyl-4-butoxy-3-phenylsulfonyl-2,3-dihydro-1,1-dioxidebenzo[b]thiophene

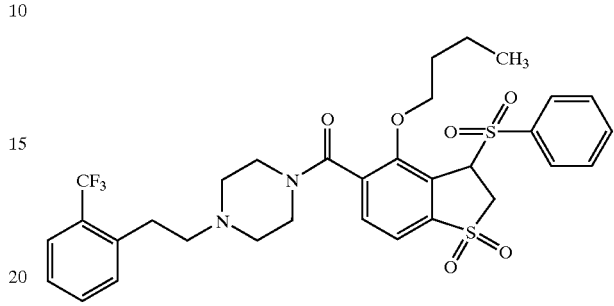

TLC: Rf 0.56 (chloroform:methanol=10:1);

NMR (CDCl$_3$): δ7.88 (d, J=8 Hz, 1H), 7.80–7.00 (m, 10H), 5.30 and 5.18 (each d, J=9 Hz, total 1H), 4.40–3.45 (m, 6H), 3.45–2.80 (m, 4H), 2.80–2.15 (m, 6H), 2.00–1.10 (m, 4H), 0.97 and 0.91 (each t, J=7 Hz, total 3H).

EXAMPLE 54 (11)

5-(4-(2-Chlorophenyl)piperazin-1-yl)carbonyl-4-butoxy-3-phenylsulfonyl-2,3-dihydro-1,1-dioxidebenzo[b]thiophene

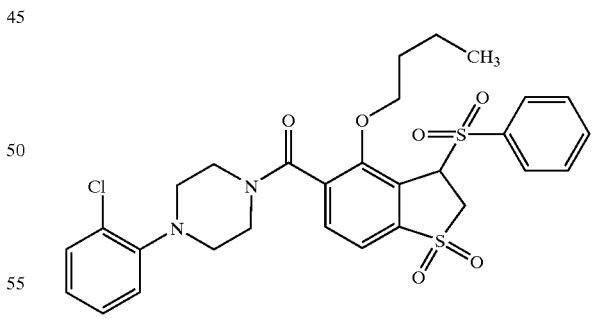

TLC: Rf 0.65 (chloroform:methanol 10:1);

NMR (CDCl$_3$): δ7.89 (d, J=8 Hz, 1H), 7.80–7.17 (m, 8H), 7.17–6.85 (m, 2H), 5.31 and 5.19 (each d, J=9 Hz, total 1H), 4.40–3.55 (m, 6H), 3.55–2.70 (m, 6H), 2.00–1.15 (m, 4H), 0.99 and 0.94 (each t, J=7 Hz, total 3H).

EXAMPLE 54 (12)

5-(2-Dimethylaminoethyl)carbamoyl-4-butoxy-3-phenylsulfonyl-2,3-dihydro-1,1-dioxidebenzo[b]thiophene

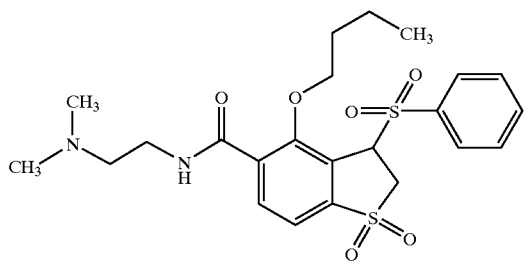

TLC: Rf 0.21 (chloroform:methanol=10:1);

NMR (CDCl$_3$): δ8.08 (d, J=8 Hz, 1H), 7.85–7.35 (m, 6H), 7.25 (broad peak, 1H), 5.13 (d, J=9 Hz, 1H), 4.32 (d, J=15 Hz, 1H), 4.05–3.66 (m, 3H), 3.66–3.35 (m, 2H), 2.52 (t, J=7 Hz, 2H), 2.31 (s, 6H), 1.90–1.15 (m, 4H), 0.96 (t, J=7 Hz, 3H).

EXAMPLE 54 (13)

5-(2,3,4,5,6,7-Hexahydro-1H-azepin-1-yl)carbonyl-4-butoxy-3-phenylsulfonyl-2,3-dihydro-1,1-dioxidebenzo[b]thiophene

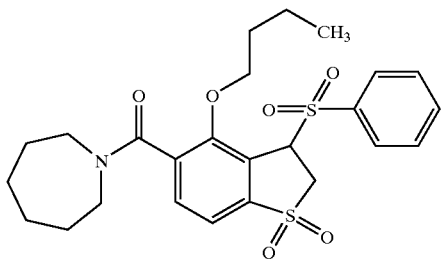

TLC: Rf 0.19 (ethyl acetate:hexane=1:1);

NMR (CDCl$_3$); δ7.85 (d, J=8 Hz, 1H), 7.76–7.20 (m, 6H), 5.29 and 5.18 (each d, J=9 Hz, total 1H), 4.25 (d, J=15 Hz, 1H), 4.25–3.60 (m, 4H), 3.60–3.00 (m, 3H), 2.10–1.10 (m, 12H), 0.96 and 0.92 (each t, J=7 Hz, total 3H).

EXAMPLE 54 (14)

5-(2,3-Dihydroindol-1-yl)carbonyl-4-butoxy-3-phenylsulfonyl-2,3-dihydro-1,1-dioxidebenzo[b]thiophene

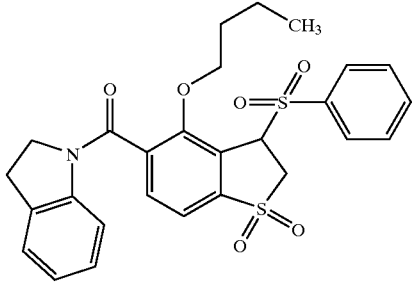

TLC: Rf 0.31 (ethyl acetate:hexane=1:1);

NMR (CDCl$_3$): δ8.29 (d, J=8 Hz, 1H), 8.05–7.42 (m, 6H), 7.42–6.95 (m, 4H), 5.36–5.06 (m, 1H), 4.50–3.40 (m, 6H), 3.16 (t, J=7 Hz), 1.90–1.05 (m, 4H), 0.81 (t, J=7 Hz, 3H).

EXAMPLE 54 (15)

5-(4-(2-(2-Trifluoromethylphenyl)ethyl)piperazin-1-yl)carbonyl-4octyloxy-3-phenylsulfonyl-2,3-dihydro-1,1-dioxidebenzo[b]thiophene

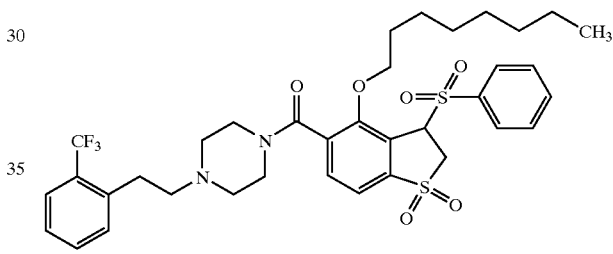

TLC: Rf 0.66 (chloroform:methanol=10:1);

NMR (CDCl$_3$): δ7.89 (d, J=8 Hz, 1H), 7.80–7.20 (m, 10H), 5.30 and 5.17 (each d, J=9 Hz, total 1H), 4.25 (d, J=15 Hz, 1H), 4.30–3.55 (m, 5H), 3.55–2.80 (m, 4H), 2.80–2.25 (m, 6H), 1.90–1.05 (m, 12H), 0.88 (t, J=7 Hz, 3H).

EXAMPLE 54 (16)

5-(4-(2-Chlorophenyl)piperazin-1-yl)carbonyl-4-octyloxy-3-phenylsulfonyl-2,3-dihydro-1,1-dioxidebenzo[b]thiophene

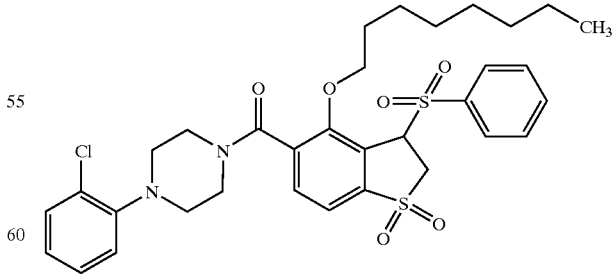

TLC: Rf 0.74 (chloroform:methanol=10:1);

NMR (CDCl$_3$): δ7.89 (d, J=8 Hz, 1H), 7.82–6.85 (m, 10H), 5.31 and 5.19 (each d, J=9 Hz, total 1H), 4.38–2.70 (m, 12H), 1.90–1.05 (m, 12H), 0.89 (t, J=7 Hz, 3H).

EXAMPLE 54 (17)

5-(2-Dimethylaminoethyl)carbamoyl-4-octyloxy-3-phenylsulfonyl-2,3-dihydro-1,1-dioxidebenzo[b]thiophene

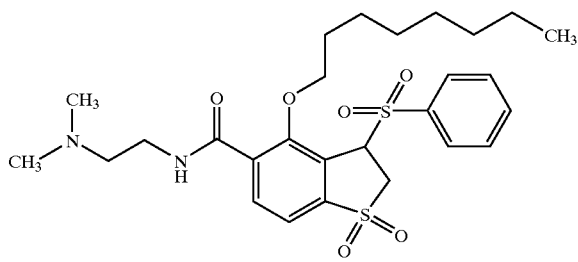

TLC: Rf 0.34 (chloroform:methanol=10:1);

NMR (CDCl$_3$): δ7.99 (d, J=8 Hz, 1H), 7.92–7.10 (m, 7H), 5.30–5.00 (m, 1H), 4.40–3.45 (m, 6H), 2.70 (t, J=6 Hz, 2H), 2.46 (s, 6H), 1.95–1.05 (m, 12H), 0.90 (t, J=7 Hz, 3H).

EXAMPLE 54 (18)

5-(2,3,4,5,6,7-Hexahydro-1H-azepin-1-yl)carbonyl-4-octyloxy-3-phenylsulfonyl-2,3-dihydro-1,1-dioxidebenzo[b]thiophene

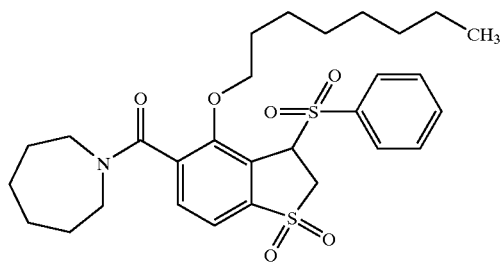

TLC: Rf 0.26 (hexane:ethyl acetate=1:1);

NMR (CDCl$_3$): δ7.85 (d, J=8 Hz, 1H), 7.88–7.15 (m, 6H), 5.29 and 5.18 (each d, J=9 Hz, total 1H), 4.40–3.00 (m, 8H), 2.10–1.05 (m, 20H), 0.90 (t, J=7 Hz, 3H).

EXAMPLE 54 (19)

5-(2,3-Dihydroindol-1-yl)carbonyl-4-octyloxy-3-phenylsulfonyl-2,3-dihydro-1,1-dioxidebenzo[b]thiophene

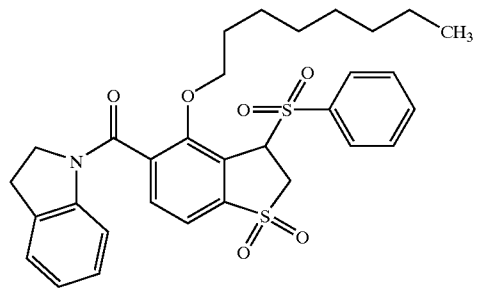

TLC: Rf 0.43 (hexane:ethyl acetate=1:1);

NMR (CDCl$_3$): δ8.29 (d, J=8 Hz, 1H), 8.10–6.80 (m, 10H), 5.40–5.05 (m, 1H), 4.60–3.40 (m, 6H), 3.16 (t, J=8 Hz, 2H), 1.90–1.00 (m, 12H), 0.85 (t, J=7 Hz, 3H).

EXAMPLE 55

5-Hydroxy-4-formylbenzo[b]thiophene

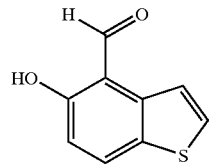

To a solution of 5-hydroxybenzo[b]thiophene (3.0 g) in methylene chloride (60 ml), were added at 0° C. dichloromethyl methyl ether (4.52 ml) and titanium tetrachloride (5.48 ml) dropwise. The mixture was stirred at room temperature for 30 minutes. The reaction mixture was poured onto ice-water. The mixture was extracted by ethyl acetate. The extract was washed by a saturated aqueous solution of sodium chloride, dried over anhydrous magnesium sulfate and concentrated. The residue was purified with column chromatography on silica gel (methylene chloride) to give the compound of the present invention (1.50 g) having the following physical data.

TLC: Rf 0.69 (hexane:ethyl acetate=2:1);

NMR (CDCl$_3$): δ11.97 (s, 1H), 10.55 (s, 1H), 7.96 (d, J=8.8 Hz, 1H), 7.77 (d, J=5.6 Hz, 1H), 7.72 (d, J=5.6 Hz, 1H), 7.02 (d, J=8.8 Hz, 1H).

EXAMPLE 56

5-Benzyloxy-4-formylbenzo[b]thiophene

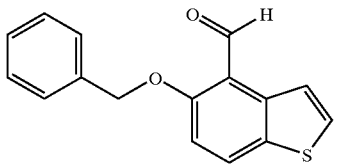

By the same procedure as described in Example 18 using the compound prepared in Example 55 instead of the compound prepared in Example 9 (12) and benzylbromide instead of 4-nitrobenzylbromide, the compound of the present invention having the following physical data was obtained.

TLC: Rf 0.65 (hexane:ethyl acetate=2:1);

NMR (CDCl$_3$): δ10.81 (s, 1H), 8.43 (d, J=5.6 Hz, 1H), 8.00 (d, J=8.8 Hz, 1H), 7.68 (d, J=5.6 Hz, 1H), 7.55–7.30 (m, 5H), 7.15 (d, J=8.8 Hz, 1H), 5.28 (s, 2H).

EXAMPLE 57

5-Benzyloxy-4-hydroxymethylbenzo[b]thiophene

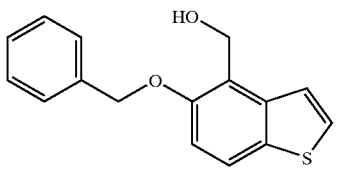

To a solution of the compound prepared in Example 56 (1.24 g) in methylene chloride (9.0 ml), were added sodium borohydride (246 mg) and methanol, (3.0 ml). The mixture was stirred at room temperature for 30 minutes. The reaction mixture was poured onto 1N hydrochloric acid and was extracted by ethyl acetate. The extract was washed by a saturated aqueous solution of sodium chloride, dried over anhydrous magnesium sulfate and concentrated. The residue was purified with chromatography on silica gel (hexane:ethyl acetate=4:1) to give the compound of the present invention (1.25 g) having the following physical data.

TLC: Rf 0.40 (hexane:ethyl acetate=2:1);

NMR (CDCl$_3$): δ7.76 (d, J=8.8 Hz, 1H), 7.54–7.28 (m, 7H), 7.12 (d, J=8.8 Hz, 1H), 5.20 (s, 2H), 5.04 (br-s, 2H), 2.30–2.12 (br, 1H).

EXAMPLE 58

5-Benzyloxy-4-hydroxymethyl-1,1-dioxidebenzo[b]thiophene

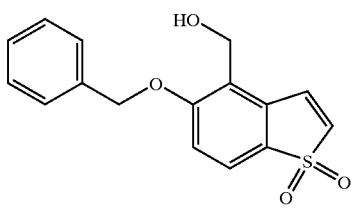

By the same procedure as described in Example 3 using the compound prepared in Example 57 instead of the compound prepared in Example 1, the compound having the following physical data was obtained (with the proviso that 3-chloroperbenzoic acid was used instead of OXONE© as an oxidizer.).

TLC: Rf 0.43 (hexane:ethyl acetate=1:1);

NMR (CDCl$_3$): δ7.61 (d, J=7.0 Hz, 1H), 7.56 (d, J=7.0 Hz, 1H), 7.48–7.34 (m, 5H), 7.02 (d, J=8.4 Hz, 1H), 6.75 (d, J=7.0 Hz, 1H), 5.18 (s, 2H), 4.84 (brs, 2H), 2.26–2.10 (br, 1H).

EXAMPLE 59

5-Benzyloxy-4-hydroxymethyl-3-phenylthio-2,3-dihydro-1,1-dioxidebenzo[b]thiophene

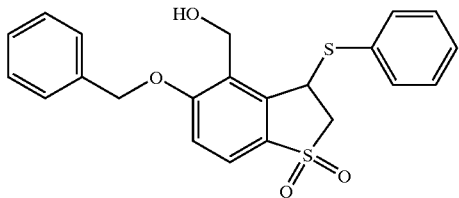

By the same procedure as described in Example 1 using the compound prepared in Example 58 instead of 1,1-dioxidebenzo[b]thiophene, and thiophenol, the compound of the present invention having the following physical data was obtained.

TLC: Rf 0.60 (chloroform:ethyl acetate=19:1);

NMR (CDCl$_3$): δ7.67 (d, J=8.4 Hz, 1H), 7.57–7.48 (m, 2H), 7.46–7.32 (m, 8H), 7.16 (d, J=8.4 Hz, 1H), 5.24 (s, 2H), 5.19 (dd, J=6.6, 1.8 Hz, 1H), 4.99 (d, J=6.0 Hz, 2H), 3.71 (dd, J=14.0, 6.6 Hz, 1H), 3.59 (dd, J=14.0, 1.8 Hz, 1H), 2.59 (t, J=6.0 Hz, 1H).

EXAMPLE 60

5-Benzyloxy-4-bromomethyl-3-phenylthio-2,3-dihydro-1,1-dioxidebenzo[b]thiophene

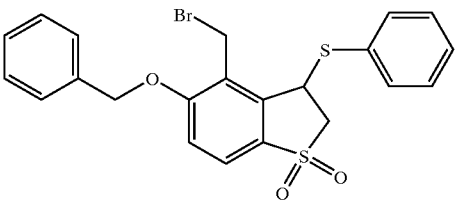

To a solution of the compound prepared in Example 59 (1.45 g) in methylene chloride (15 ml), was added triphenylphosphine (1.38 g) and carbon tetrabromide (1.74 g). The mixture was stirred at room temperature for 30 minutes. The reaction mixture was concentrated. The residue was purified with column chromatography on silica gel (hexane:ethyl acetate=2:1) to give the compound of the present invention having the following physical data.

TLC: Rf 0.76 (hexane:ethyl acetate=1:1);

NMR (CDCl$_3$): δ7.66 (d, J=8.8 Hz, 1H), 7.60–7.51 (m, 2H), 7.50–7.30 (m, 8H), 7.12 (d, J=8.8 Hz, 1H), 5.27 (s, 2H), 5.15 (dd, J=6.8, 1.6 Hz, 1H), 5.02 (d, J=10 Hz, 1H), 4.94 (d, J=10 Hz, 1H), 3.74 (dd, J=13.8, 6.8 Hz, 1H), 3.60 (dd, J=13.8, 1.6 Hz, 1H).

EXAMPLE 61

5-Benzyloxy-4-aminomethyl-3-phenylthio-2,3-dihydro-1,1-dioxidebenzo[b]thiophene

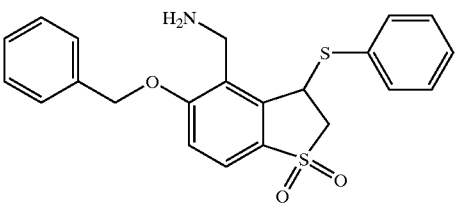

To a solution of 28% aqueous ammonia solution (6.75 ml) in tetrahydrofuran (30 ml), were added a solution of the compound prepared in Example 60 (1.60 g) in tetrahydrofuran (30 ml) and potassium carbonate (700 mg) successively. The mixture was stirred at room temperature for 1.5 hours. The reaction mixture was concentrated. The residue was purified with column chromatography on silica gel (chloroform:methanol=20:1) to give the compound of the present invention (747 mg) having the following physical data.

TLC: Rf 0.05 (hexane:ethyl acetate 1:1);

NMR (CDCl$_3$): δ7.63 (d, J=8.5 Hz, 1H), 7.58–7.48 (m, 2H), 7.46–7.28 (m, 8H), 7.14 (d, J=8.5 Hz, 1H), 5.23 (s, 2H), 5.13 (dd, J=6.4, 1.6 Hz, 1H), 4.12 (d, J=13.6 Hz, 1H), 4.02 (d, J=13.6 Hz, 1H), 3.70 (dd, J=14.0, 6.0 Hz, 1H), 3.59 (dd, J=14.0, 1.6 Hz, 1H).

EXAMPLE 62

5-Benzyloxy-4-t-butoxycarbonylaminomethyl-3-phenylthio-2,3-dihydro-1,1-dioxidebenzo[b]thiophene

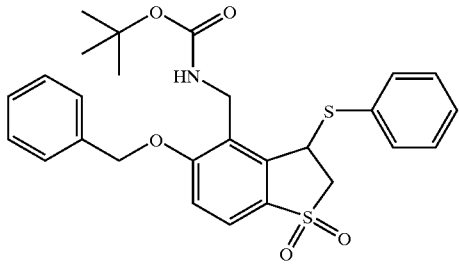

To the solution of the compound prepared in Example 61 (735 mg) in tetrahydrofuran (12 ml) and water (3.0 ml), were added sodium bicarbonate (165 mg) and di-t-butyldicarbonate (430 mg) at 0° C. The mixture was stirred at room temperature for 1 hour. The reaction mixture was poured onto water and was extracted by ethyl acetate. The extract was washed by a saturated aqueous solution of sodium chloride, dried over anhydrous magnesium sulfate and concentrated. The residue was purified with column chromatography on silica gel (hexane:ethyl acetate=2:1) to give the compound of the present invention (867 mg) having the following physical data.

TLC: Rf 0.73 (hexane:ethyl acetate=1:1);

NMR (CDCl$_3$): δ7.70–7.56 (m, 3H), 7.48–7.30 (m, 8H), 7.12 (d, J=8.8 Hz, 1H), 5.66 (br-d, J=5.8 Hz, 1H), 5.22 (s, 2H), 5.20–4.88 (m, 2H), 4.25–4.10 (m, 1H), 3.71 (dd, J=14.0, 6.8 Hz, 1H), 3.56 (d, J=14.0 Hz, 1H), 1.41 (s, 9H).

EXAMPLE 63

5-Benzyloxy-4-t-butoxycarbonylaminomethyl-3-phenylsulfonyl-2,3-dihydro-1,1-dioxidebenzo[b]thiophene

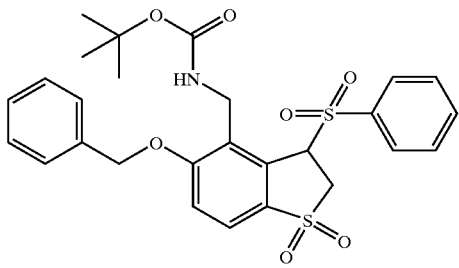

By the same procedure as described in Example 3 using the compound prepared in Example 62 instead of the compound prepared in Example 1, the compound of the present invention having the following physical data (with the proviso that 3-chloroperbenzoic acid was used instead of OXONE© as an oxidizer.).

TLC: Rf 0.31 (hexane:ethyl acetate=2:1);

NMR (CDCl$_3$): δ7.83–7.76 (m, 2H), 7.71–7.64 (m, 1H), 7.60 (d, J=8.7 Hz, 1H), 756–7.38 (m, 7H), 7.19 (d, J=8.7 Hz, 1H), 6.05 (brd, J=6.9 Hz, 1H), 5.27–515 (m, 1H), 5.25 (s, 2H), 5.10–4.95 (m, 1H), 4.27–4.16 (m, 1H), 3.81 (dd, J=15.3, 2.1 Hz, 1H), 3.74 (dd, J=15.3, 8.1, 1H), 1.37 (s, 9H).

EXAMPLE 64

5-Benzyloxy-4-aminomethyl-3-phenylsulfonyl-2,3-dihydro-1,1-dioxidebenzo[b]thiophene.hydrochloride

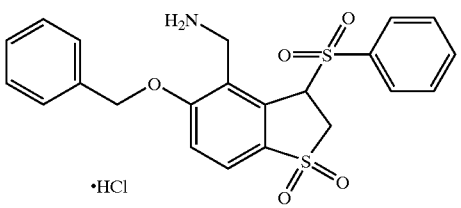

By the same procedure as described in Example 7 using the compound prepared in Example 63 instead of the compound prepared in Example 6 (8), the compound of the present invention having the following physical data was obtained.

TLC: Rf 0.43 (chloroform:methanol=9:1);

NMR (DMSO-d$_6$): δ8.18 (brs, 3H), 7.86 (d, J=9.0 Hz, 1H), 7.83–7.75 (m, 3H), 7.67–7.48 (m, 5H), 7.47–7.33 (m, 3H), 6.37 (dd, J=6.0, 3.9 Hz, 1H), 5.41 (d, J=12.3 Hz, 1H), 5.33 (d, J=12.3 Hz, 1H), 4.44 (d, J=13.8 Hz, 1H), 4.24 (d, J=13.8 Hz, 1H), 3.90–3.76 (m, 2H).

EXAMPLE 65

5-Hydroxy-4-t-butoxycarbonylaminomethyl-3-phenylsulfonyl-2,3-dihydro-1,1-dioxidebenzo[b]thiophene

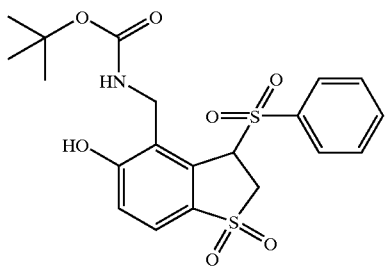

By the same procedure as described in Example 52 using the compound prepared in Example 63 instead of the compound prepared in Example 51, the compound of the present invention having the following physical data was obtained.

TLC: Rf 0.22 (hexane:ethyl acetate=1:1);

NMR (CDCl$_3$): δ10.75 (s, 1H), 7.75–7.58 (m, 3H), 7.56–7.41 (m, 3H), 7.18 (d, J=8.6 Hz, 1H), 6.35–6.50 (m, 1H), 5.24–5.15 (m, 1H), 4.76–4.60 (m, 1H), 4.34 (dd, J=16.0, 5.4 Hz, 1H), 3.86–3.66 (m, 2H), 1.37 (s, 9H).

EXAMPLES 66~66 (1)

By the same procedure as described in Example 29 using the compound prepared in Example 65 instead of 4-hydroxy-1,1-dioxidebenzo[b]thiophene and alcohol derivatives corresponding to 1-(3-hydroxypropyl)pyrrole, the following compounds of the present invention were obtained.

EXAMPLE 66

5-Methoxy-4-t-butoxycarbonylaminomethyl-3-phenylsulfonyl-2,3-dihydro-1,1-dioxidebenzo[b]thiophene

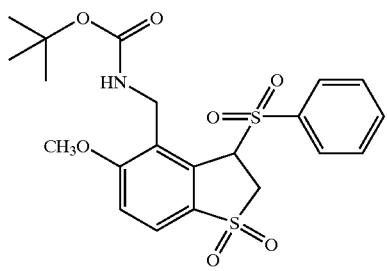

TLC: Rf 0.28 (hexane:ethyl acetate=1:1);

NMR (CDCl$_3$): δ7.86–7.75 (m, 2H), 7.74–7.47 (m, 4H), 7.14 (d, J=8.8 Hz, 1H), 6.10–6.00 (m, 1H), 5.32–5.18 (m, 1H), 5.10–4.92 (m, 1H), 4.25–4.10(m, 1H), 4.00 (s, 3H), 3.85–3.65 (m, 2H), 1.38 (s, 9H).

EXAMPLE 66 (1)

5-(3-Phenylpropyl)oxy-4-t-butoxycarbonylaminomethyl-3-phenylsulfonyl-2,3-dihydro-1,1-dioxidebenzo[b]thiophene

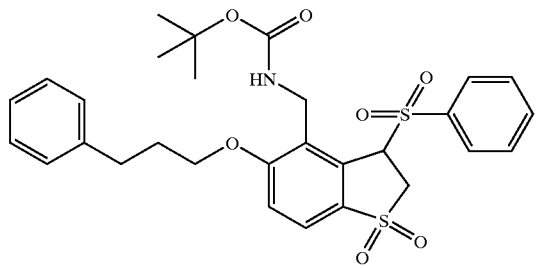

TLC: Rf 0.51 (hexane:ethyl acetate=1:1);

NMR (CDCl$_3$): δ7.87–7.73 (m, 2H), 7.73–7.40 (m, 6H), 7.40–7.16 (m, 3H), 7.07 (d, J=8.8 Hz, 1H), 6.55–6.30 (br, 1H), 6.07–5.95 (m, 1H), 5.26–5.12 (m, 1 H), 5.10–4.90 (m, 1H), 4.20–4.05 (m, 2H), 3.86–3.64 (m, 2H), 2.86 (t, J=7.0 Hz, 2H), 2.33–2.15 (m, 2H), 1.38 (s, 9H).

EXAMPLES 67~67(1)

By the same procedure as described in Example 7 using the compounds prepared in Examples 66~66 (1) instead of the compound prepared in Example 6 (8), the following compounds of the present invention were obtained.

EXAMPLE 67

5-Methoxy-4-aminomethyl-3-phenylsulfonyl-2,3-dihydro-1,1-dioxidebenzo[b]thiophene.hydrochloride

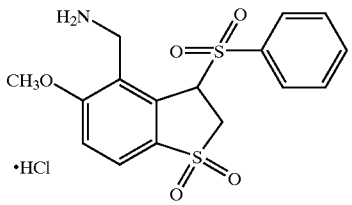

TLC: Rf 0.19 (chloroform:methanol=4:1);

NMR (DMSO-d$_6$): δ8.19 (brs, 3H), 7.89–7.76 (m, 4H), 7.68–7.60 (m, 2H), 7.47 (d, J=8.7 Hz, 1H), 6.39 (t, J=5.4 Hz, 1H), 4.47–4.28 (br, 1H), 4.25–4.08 (br, 1H), 3.98 (s, 3H), 3.82 (d, J=5.4 Hz, 2H).

EXAMPLE 67 (1)

5-(3-Phenylpropyl)oxy-4-aminomethyl-3-phenylsulfonyl-2,3-dihydro-1,1-dioxidebenzo[b]thiophene.hydrochloride

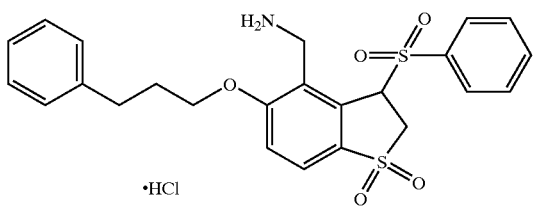

TLC: Rf 0.43 (chloroform:methanol=9:1); NMR (DMSO-d$_6$): δ8.14 (brs, 3H), 7.86–7.76 (m, 4H), 7.68–7.61 (m, 2H), 7.45 (d, J=8.7 Hz, 1H), 7.34–7.27 (m, 4H), 7.25–7.15 (m, 1H), 6.45–6.34 (m, 1H), 4.47–4.13 (m, 4H), 3.89–3.75 (m, 2H), 2.86–2.73 (m, 2H), 2.22–2.08 (m, 2H).

EXAMPLE 68

5-Benzyloxy-4-hydroxymethyl-3-phenylsulfonyl-2,3-dihydro-1,1-dioxidebenzo[b]thiophene

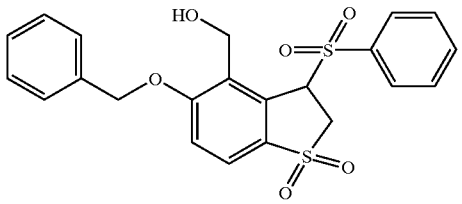

By the same procedure as described in Example 3 using the compound prepared in Example 59 instead of the compound prepared in Example 1 the compound of the present invention having the following physical data was obtained (with the proviso that 3-chloroperbenzoic acid was used instead of OXONE© as an oxidizer).

TLC: Rf 0.25 (hexane:ethyl acetate=1:1);

NMR (CDCl$_3$): δ7.72–7.58 (m, 3H), 7.56–7.30 (m, 8H), 7.20 (d, J=8.8 Hz, 1H), 5.53 (dd, J=8.4, 1.8 Hz, 1H), 5.33 (d,

J=11.8 Hz, 1H), 5.25 (d, J=11.8 Hz, 1H), 5.10–5.01 (m, 2H), 3.87 (dd, J=15.4, 1.8 Hz, 1H), 3.75 (dd, J=15.4, 1.8 Hz, 1H), 3.40–3.28 (m, 1H),

EXAMPLE 69

5-Benzyoxy-4-carboxy-3-phenylsulfonyl-2,3-dihydro-1,1-dioxidebenzo[b]thiophene

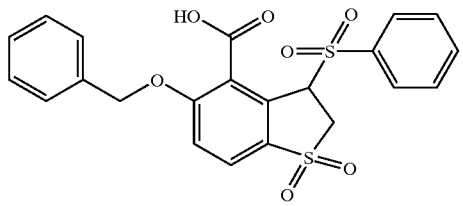

To a solution of the compound prepared in Example 68 (444 mg) in methylene chloride (10 ml) were added pyridinium dichromate (564 mg) and magnesium sulfate (500 mg). The mixture was stirred at room temperature for 6 hours. The undissolved ingredients were filtered off. The filtrate was poured onto 1N hydrochloric acid and was extracted by methylene chloride. The extract was washed by a saturated aqueous solution of sodium chloride, dried over anhydrous magnesium sulfate and concentrated. The residue was washed by methanol and was dried. The obtained solid was dissolved in dimethylformamide (16 ml) and water (4.0 ml). Thereto, were added 2-methyl-2-butene (0.48 ml), sodium phosphate bishydrate (120 mg) and sodium hypochloric acid (358 mg). The mixture was stirred at room temperature for 1 hour. The reaction mixture was poured onto 0.5N hydrochloric acid and was extracted by ethyl acetate. The extract was concentrated. The residue was washed by ether to give the compound of the present invention (305 mg) having the following physical data.

TLC: Rf 0.17 (chloroform:methanol=9:1);

NMR (DMSO-$d_6$): δ13.52 (s, 1H), 7.92–7.68 (m, 4H), 7.67–7.30 (m, 8H), 5.88 (d, J=9.0 Hz, 1H), 5.37 (s, 2H), 4.09 (dd, J=15.0, 9.0 Hz, 1H), 3.88 (d, J=15.0 Hz, 1H).

EXAMPLE 70

5-Benzyloxy-4-(pyridin-3-ylmethyl)carbamoyl-3-phenylsulfonyl-2,3-dihydro-1,1-dioxidebenzo[b]thiophene

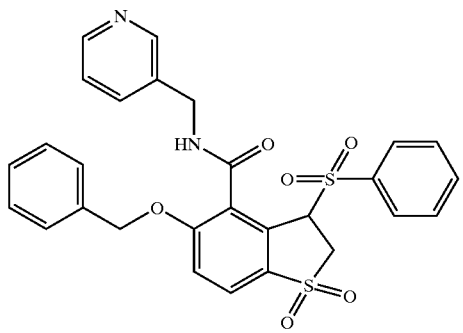

By the same procedure as described in Example 28 using the compound prepared in Example 69 instead of 4-carboxy-1,1-dioxidebenzo[b]thiophene, and (pyridin-3-ylmethyl)amine, the compound of the present invention having the following physical data was obtained.

TLC: Rf 0.53 (chloroform:methanol=9:1);

NMR (DMSO-$d_6$): δ9.05 (t, J=6.0 Hz, 1H), 8.59 (d, J=1.5 Hz, 1H), 8.41 (dd, J=4.8, 1.5 Hz, 1H), 7.85 (d, J=8.7 Hz, 1H), 7.80–7.72 (m, 3H), 7.65–7.55 (m, 4H), 7.48–7.41 (m, 2H), 7.38–7.30 (m, 3H), 7.15 (dd, J=8.1, 4.8 Hz, 1H), 5.96 (d, J=9.0 Hz, 1H), 5.29 (s, 2H), 4.63 (dd, J=15.0, 6.0 Hz, 1H), 4.35 (dd, J=15.0, 6.0 Hz, 1H), 4.06 (dd, J=15.0, 9.0 Hz, 1H), 3.87 (d, J=15.0 Hz, 1H).

EXAMPLE 71

5-Hydroxy-4-(pyridin-3-ylmethyl)carbamoyl-3-phenylsulfonyl-2,3-dihydro-1,1-dioxidebenzo[b]thiophene

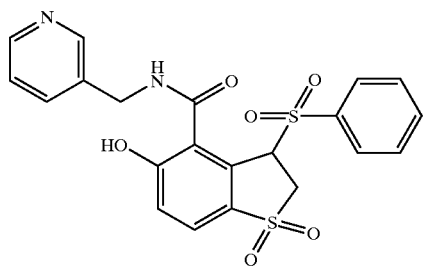

By the same procedure as described in Example 52 using the compound prepared in Example 70 instead of the compound prepared in Example 51, the compound of the present invention having the following physical data was obtained.

TLC: Rf 0.29 (chloroform:methanol=9:1);

NMR (DMSO-$d_6$): δ11.70 (br, 1H), 9.10–8.90 (br, 1H), 8.66 (d, 1H), 8.44 (dd, 1H), 7.88–7.81 (m, 1H), 7.78–7.68 (m, 3H), 7.67–7.54 (m, 3H), 7.34 (dd, J=7.5, 4.8 Hz, 1H), 7.23 (d, J=8.7 Hz, 1H), 6.14 (d, J=9.0 Hz, 1H), 4.67 (dd, J=15.3, 6.3 Hz, 1 H), 4.39 (dd, J=15.3, 5.4 Hz, 1H), 4.02 (dd, J=15.0, 9.0 Hz, 1H), 3.84 (d, J=15.0 Hz, 1H).

EXAMPLES 72~72 (31)

By the same procedure as described in Example 28 using carboxylic acids corresponding to 4-carboxy-1,1-dioxidebenzo[b]thiophene and amine derivatives corresponding to (pyridin-3-ylmethyl)amine, and if necessary, by converting into the corresponding salts by known methods, the following compounds of the present invention were obtained.

EXAMPLE 72

4-(1,1-Dimethyl-2-hydroxyethyl)carbamoyl-1,1-dioxidebenzo[b]thiophene

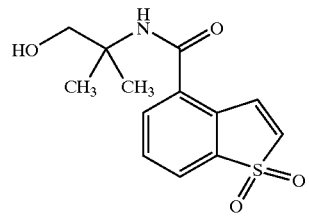

TLC: Rf 0.64 (ethyl acetate);

NMR (DMSO-$d_6$): δ8.05 (brs, 1H), 7.91 (d, J=7.4 Hz, 1H), 7.76 (d, J=7.0 Hz, 1H), 7.75 (d, J=7.4 Hz, 1H), 7.63 (t, J=7.4 Hz, 1H), 7.43 (d, J=7.0 Hz, 1H), 4.87 (t, J=5.8 Hz, 1H), 3.54 (d, J=5.8 Hz, 2H), 1.29 (s, 6H).

EXAMPLE 72 (1)

4-(2-Hydroxyethyl)carbamoyl-1,1-dioxidebenzo[b]thiophene

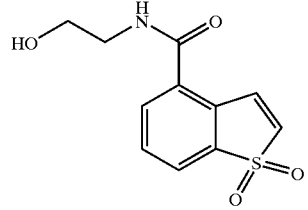

TLC: Rf 0.30 (ethyl acetate);

NMR (DMSO-d$_6$): δ8.72 (t, J=5.6 Hz, 1H), 7.95 (d, J=7.4 Hz, 1H), 7.88–7.80 (m, 2H), 7.66 (t, J=7.4 Hz, 1H), 7.45 (d, J=7.0 Hz, 1H), 4.77 (t, J=5.6 Hz, 1H), 3.53 (q, J=5.6 Hz, 2H), 3.33 (q, J=5.6 Hz, 2H).

EXAMPLE 72 (2)

4-(4-(2-Hydroxyethyl)piperazin-1-yl)carbonyl-1,1-dioxidebenzo[b]thiophene

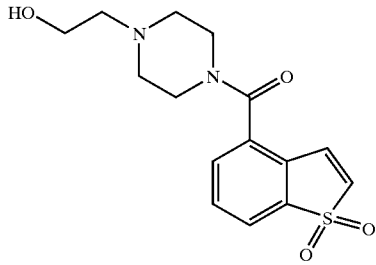

TLC: Rf 0.45 (ethyl acetate:methanol=9:1)

NMR (CDCl$_3$): δ7.76 (d, J=7.5 Hz, 1H), 7.57 (t, J=7.5 Hz, 1H), 7.47 (dd, J=7.5, 1.2 Hz, 1H), 7.32 (dd, J=7.2, 1.2 Hz, 1H), 6.79 (d, J=7.2 Hz, 1H), 4.26–4.19 (m, 1H), 4.03–3.96 (m, 1H), 3.88–3.78 (m, 2H), 3.35 (br, 2H), 2.72–2.67 (m, 2H), 2.67–2.60 (m, 2H), 2.50–2.42 (m, 2H).

EXAMPLE 72 (3)

4-(N-Methyl-N-methoxycarbamoyl)-1,1-dioxidebenzo[b]thiophene

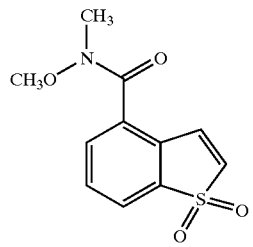

TLC: Rf 0.22 (hexane:ethyl acetate=1:1);

NMR (CDCl$_3$): δ7.78 (dt, J=7.8, 1.0 Hz, 1H), 7.72 (dd, J=7.8, 1.0 Hz, 1H), 7.57 (t, J=7.8 Hz, 1H), 7.41 (dd, J=7.0, 1.0 Hz, 1H), 6.76 (d, J=7.0 Hz, 1H), 3.49 (s, 3H), 3.40 (s, 3H).

EXAMPLE 72 (4)

4-(4-(Thiazol-2-ylsulfamoyl)phenyl)carbamoyl-1,1-dioxidebenzo[b]thiophene

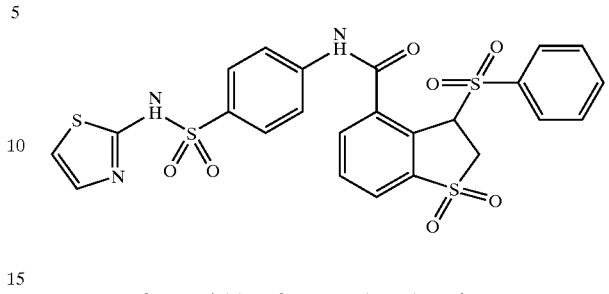

TLC: Rf 0.20 (chloroform:methanol=9:1);

NMR (CDCl$_3$+DMSO-d$_6$): δ10.71 (s, 1H), 7.98 (d, J=7.5 Hz, 1H), 7.90–7.67 (m, 6H), 7.67 (t, J=7.8 Hz, 1H), 6.97 (d, J=7.5 Hz, 1H), 6.94 (d, J=5 Hz, 1H), 6.52 (d, J=5 Hz, 1H), 5.30 (broad peak, 1H).

EXAMPLE 72 (5)

4-((1R)-1-t-Butoxycarbonyl-2-methylpropyl)carbamoyl-1,1-dioxidebenzo[b]thiophene

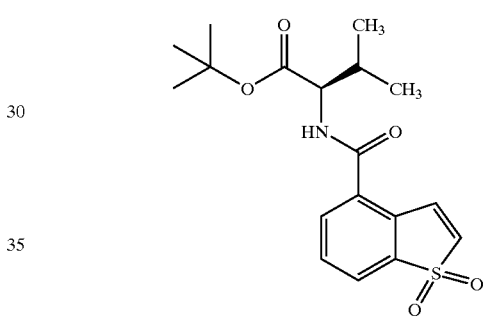

TLC: Rf 0.48 (hexane:ethyl acetate=1:1);

NMR (CDCl$_3$): δ7.95 (dd, J=7.2, 1.0 Hz, 1H), 7.81 (d, J=7.8 Hz, 1H), 7.76 (dd, J=7.8, 1.0 Hz, 1H), 7.59 (t, J=7.8 Hz, 1H), 6.78 (d, J=7.2 Hz, 6.55 (d, J=8.4 Hz, 1H), 4.64 (dd, J=8.4, 4.5 Hz, 1H), 2.36–2.25 (m, 1H), 1.51 (s, 9H), 1.02 (d, J=6.9 Hz, 3H), 0.98 (d, J=6.9 Hz, 3H).

EXAMPLE 72 (6)

6-(1-Benzylpiperidin-4-yl)carbamoyl-4-methoxy-1,1-dioxidebenzo[b]thiophene

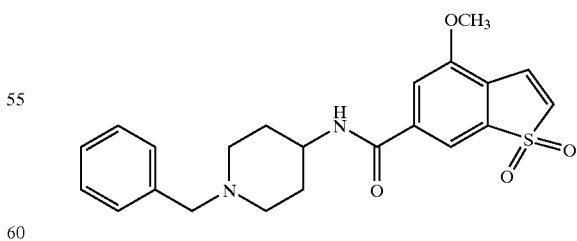

TLC: Rf 0.44 (ethyl acetate methanol=4:1);

NMR (CDCl$_3$): δ7.66 (s, 1H), 7.54 (s, 1H), 7.45 (d, J=7.0 Hz, 1H), 7.40–7.20 (m, 5H), 6.73 (d, J=7.0 Hz, 1H), 6.40–6.20 (m, 1H), 4.10–3.90 (m, 1H), 3.97 (s, 3H), 3.53 (s, 2H), 3.00–2.80 (m, 2H), 2.30–2.1.0 (m, 2H), 2.10–1.90 (m, 2H), 1.70–1.50 (m, 2H).

EXAMPLE 72 (7)

6-(2-Diethylaminoethyl)carbamoyl-4-methoxy-1,1-dioxidebenzo[b]thiophene

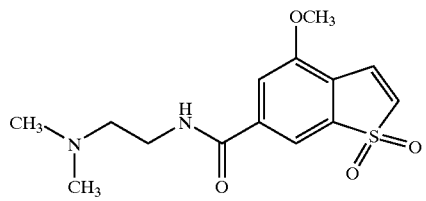

TLC: Rf 0.33 (ethyl acetate:methanol:triethylamine=14:4:1);

NMR (CDCl$_3$): δ7.71 (s, 1H), 7.57 (s, 1H), 7.46 (d, J=6.9 Hz, 1H), 7.10–7.00 (m, 1H), 6.71 (d, J=6.9 Hz, 1H), 3.98 (s, 3H), 3.52 (q, J=5.5 Hz, 2H), 2.53 (t, J=5.5 Hz, 2H), 2.208 (s, 6H).

EXAMPLE 72 (8)

6-(Pyridin-3-ylmethyl)carbamoyl-4-methoxy-1,1-dioxidebenzo[b]thiophene

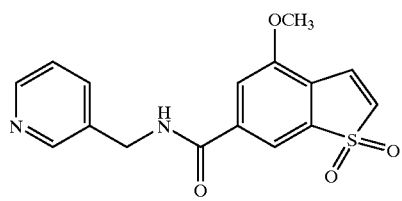

TLC: Rf 0.49 (ethyl acetate:methanol=4:1);

NMR (DMSO-d$_6$): δ9.36 (t, J=6.0 Hz, 1H), 8.58 (s, 1H), 8.48 (d, J=4.5 Hz, 1H), 7.88 (s, 1H), 7.81 (s, 1H), 7.75(d, J=7.8Hz, 1H), 7.64(d, J=7.0Hz, 1H), 7.42 (d, J=7.0 Hz, 1H), 7.36 (dd, J=7.8, 4.5 Hz, 1H), 4.53 (d, J=6.0 Hz, 2H), 3.99 (s, 3H).

EXAMPLE 72 (9)

5-(6-Dimethylaminohexyl)oxycarbonyl-1,1-dioxidebenzo[b]thiophene.hydrochloride

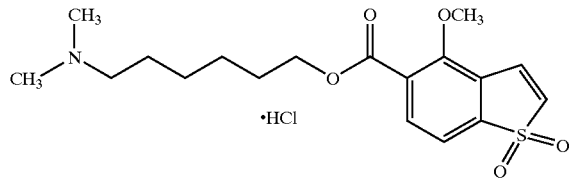

TLC: Rf 0.16 (chloroform:methanol=9:1);

NMR (CDCl$_3$): δ12.60–12.30 (br, 1H), 7.96 (d, J=7.4 Hz, 1H), 7.54–7.43 (m, 2H), 6.76 (d, J=7.2 Hz, 1H), 4.35 (t, J=6.6 Hz, 2H), 3.97 (s, 3H), 3.06–2.90 (m, 2H), 2.81 (s, 3H), 2.79 (s, 3H), 2.03–1.73 (m, 4H), 1.57–1.35 (m, 4H).

EXAMPLE 72 (10)

4-(4-t-Butoxycarbonylpiperazin-1-yl)carbonyl-1,1-dioxidebenzo[b]thiophene

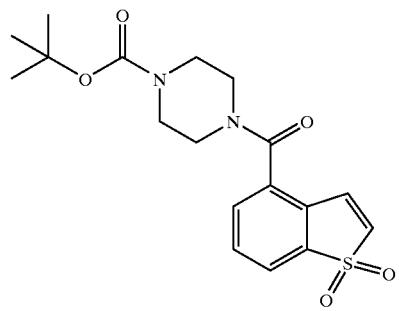

TLC: Rf 0.65 (methylene chloride:methanol=10:1);

NMR (CDCl$_3$): δ7.78 (dd, J=7.2, 1.2 Hz, 1H), 7.59 (t, J=7.2 Hz, 1H), 7.48 (dd, J=7.2, 1.2 Hz, 1H), 7.32 (d, J=6.9 Hz, 1H), 6.80 (d, J=6.9 Hz, 1H), 3.85–3.70 (m, 2H), 3.65–3.45 (m, 2H), 3.45–3.24 (m, 4H), 1.47 (s, 9H).

EXAMPLE 72 (11)

4-(Piperazin-1-yl)carbonyl-1,1-dioxidebenzo[b]thiophene.hydrochloride

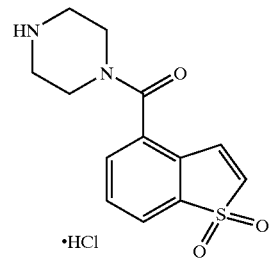

TLC: Rf 0.13 (methylene chloride:methanol=10:1);

NMR (DMSO-d$_6$): δ9.35 (bs, 2H), 7.96 (d, J=6.9 Hz, 1H), 7.80–7.73 (m, 2H), 7.60 (d, J=7.2 Hz, 1H), 7.51 (d, J=7.2 Hz, 1H), 4.00–3.80 (m, 2H), 3.60–3.40 (m, 2H), 3.30–3.15 (m, 2H), 3.15–3.00 (m, 2H).

EXAMPLE 72 (12)

4-(4-(4-Methoxyphenylmethyl)piperazin-1-yl)carbonyl-1,1-dioxidebenzo[b]thiophene.hydrochloride

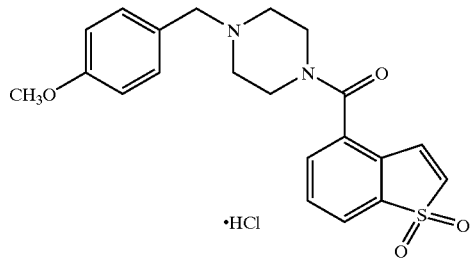

TLC: Rf 0.50 (methylene chloride:methanol=10:1);

NMR (DMSO-d$_6$): δ7.97 (t, J=4.2 Hz, 1H), 7.71 (d, J=4.2 Hz, 2H), 7.58–7.43 (m, 2H), 7.54 (d, J=4.2 Hz, 2H), 7.01 (d,

J=8.4 Hz, 2H), 4.65–4.50 (m, 1H), 4.30–4.20 (m, 2H), 3.78 (s, 3H), 3.70–3.00 (m, 8H).

EXAMPLE 72 (13)

4-(4-(4-Phenylphenylmethyl)piperazin-1-yl)carbonyl-1,1-dioxidebenzo[b]thiophene.hydrochloride

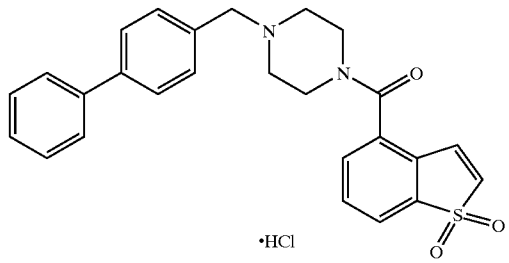

TLC: Rf 0.33 (ethyl acetate);

NMR (DMSO-$d_6$): δ8.00–7.92 (m, 1H), 7.80–7.64 (m, 8H), 7.60–7.35 (m, 5H), 4.65–4.50 (m, 1H), 4.48–4.30 (m, 2H), 3.70–3.00 (m, 8H).

EXAMPLE 72 (14)

4-(4-(Naphthalen-1-ylmethyl)piperazin-1-yl)carbonyl-1,1-dioxidebenzo[b]thiophene.hydrochloride

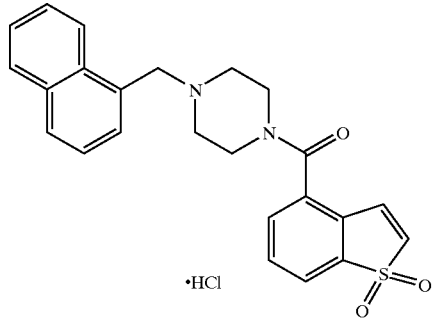

TLC: Rf 0.70 (ethyl acetate);

NMR (DMSO-$d_6$): δ8.42–7.30 (m, 1H), 8.13–7.77 (m, 4H), 7.76–7.40 (m, 7H), 4.93–4.76 (m, 2H), 4.66–4.53 (m, 1H), 3.64–3.00 (m, 8H).

EXAMPLE 72 (15)

4-(4-(4-Ethylphenylmethyl)piperazin-1-yl)carbonyl-1,1-dioxidebenzo[b]thiophene.hydrochloride

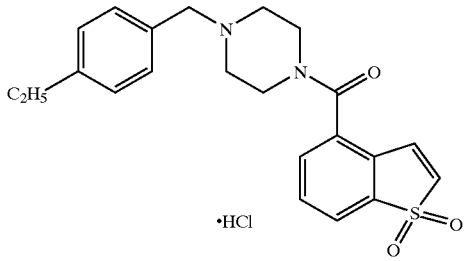

TLC: Rf 0.40 (ethyl acetate);

NMR (DMSO-$d_6$): δ7.98 (t, J=4.2 Hz, 1H), 7.71 (d, J=4.2 Hz, 2H), 7.56 (d, J=7.2 Hz, 1H), 7.52 (d, J=7.2 Hz, 1H), 7.47 (d, J=7.8 Hz, 2H), 7.31 (d, J=7.8 Hz, 2H, 4.66–4.45 (m, 1H), 4.33–4.20 (m, 2H), 3.66–3.00 (m, 8H), 2.63 (q, J=7.5 Hz, 2H), 1.19 (t, J=7.5 Hz, 3H).

EXAMPLE 72 (16)

4-(4-(Naphthalen-2-ylcarbonylmethyl)piperazin-1-yl)carbonyl-1,1-dioxidebenzo[b]thiophene.hydrochloride

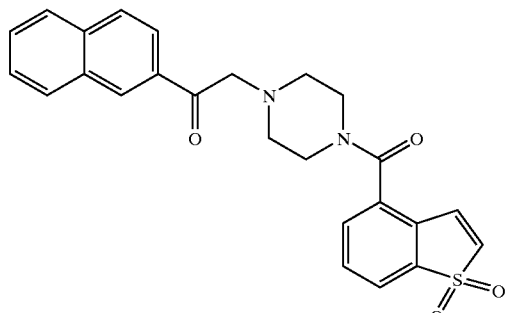

TLC: Rf 0.40 (ethyl acetate);

NMR (DMSO-$d_6$): δ8.72 (s, 1H), 8.20–7.93 (m, 5H), 7.80–7.64 (m, 4H), 7.60 (d, J=7.2 Hz, 1H), 7.55 (d, J=7.2 Hz, 1H), 5.30–5.10 (m, 2H), 4.60–4.40 (m, 1H), 3.80–3.10 (m, 8H).

EXAMPLE 72 (17)

4-(4-(Pyridin-2-ylmethyl)piperazin-1-yl)carbonyl-1,1-dioxidebenzo[b]thiophene.2hydrochloride

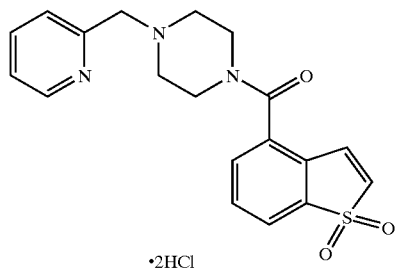

TLC: Rf 0.46 (methylene chloride:methanol=10:1);
NMR (DMSO-$d_6$): δ8.69 (d, J=5.1 Hz, 1H), 8.00–7.90 (m, 2H), 7.75–7.64 (m, 3H), 7.60–7.46 (m, 3H), 4.50 (s, 2H), 4.09–3.90 (m, 2H), 3.67–3.59 (m, 2H), 3.48–3.35 (m, 2H), 3.33–3.20 (m, 2H).

EXAMPLE 72 (18)

4-(4-(Pyridin-3-ylmethyl)piperazin-1-yl)carbonyl-1,1-dioxidebenzo[b]thiophene.2hydrochloride

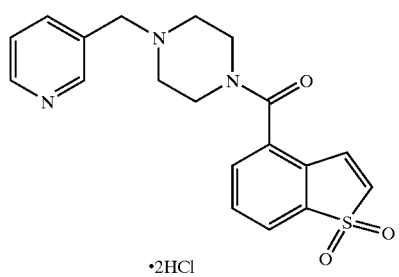

TLC: Rf 0.46 (methylene chloride:methanol=10:1);
NMR (DMSO-$d_6$): δ8.90 (s, 1H), 8.80–8.73 (m, 1H), 8.36–8.30 (m, 1H), 7.98–7.92 (m, 1H), 7.80–7.66 (m, 3H), 7.57 (d, J=7.2 Hz, 1H), 7.52 (d, J=7.2 Hz, 1H), 4.50–3.00 (m, 10H).

EXAMPLE 72 (19)

4-(4-benzoylpiperazin-1-yl)carbonyl-1,1-dioxidebenzo[b]thiophene

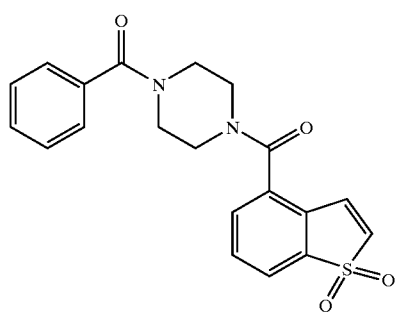

TLC: Rf 0.52 (methylene chloride:methanol=10:1)
NMR (CDCl$_3$): δ7.79 (d, J=7.5 Hz, 1H), 7.59 (t, J=7.5 Hz, 1H), 7.53–7.36 (m, 6H), 7.34 (d, J=6.0 Hz, 1H), 6.81 (d, J=7.5 Hz, 1H), 4.00–3.25 (m, 8H).

EXAMPLE 72 (20)

4-(4-(Furan-2-ylcarbonyl)piperazin-1-yl)carbonyl-1,1-dioxidebenzo[b]thiophene

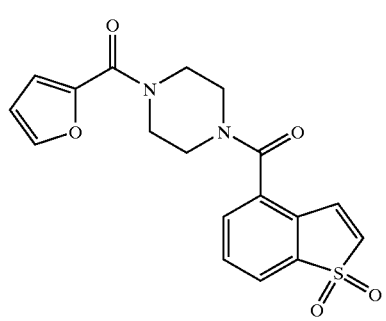

TLC: Rf 0.46 (methylene chloride:methanol=10:1);
NMR (CDCl$_3$): δ7.80 (d, J=6.9 Hz, 1H), 7.61 (t, J=7.8 Hz, 1H), 7.51 (d, J=7.8 Hz, 2H), 7.35 (d, J=6.9 Hz, 1H), 7.11 (d, J=3.6 Hz, 1H), 6.81 (d, J=6.9 Hz, 1H), 6.52 (d, J=3.6 Hz, 1H), 4.06–3.36 (m, 8H).

EXAMPLE 72 (21)

4-(4-Benzylcarbonylpiperazin-1-yl)carbonyl-1,1-dioxidebenzo[b]thiophene

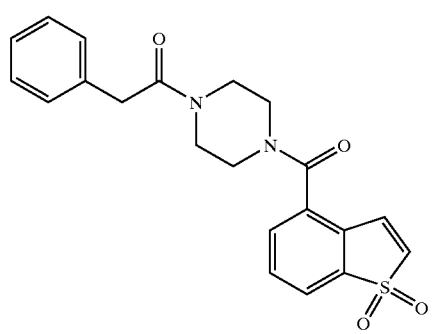

TLC: Rf 0.47 (methylene chloride:methanol=10:1);
NMR (CDCl$_3$): δ7.77 (d, J=7.5 Hz, 1H), 7.57 (t, J=7.5 Hz, 1H), 7.48–7.14 (m, 6H), 7.28 (d, J=7.2 Hz, 1H), 6.78 (d, J=7.2 Hz, 1H), 3.86–3.00 (m, 10 H).

EXAMPLE 72 (22)

4-(2-(pyrrolidin-1-yl) ethyl)carbamoyl-1,1-dioxidebenzo[b]thiophene

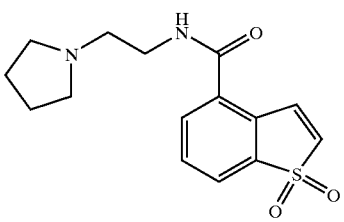

TLC: Rf 0.26 (ethyl acetate:acetic acid:water=3:1:1);
NMR (CDCl$_3$): δ8.00 (dd, J=7.5 Hz and 1 Hz, 1H), 7.79 (dt, J=7.5 Hz and 1 Hz, 1H), 7.72 (dd, J=7.5 Hz and 1 Hz, 1H), 7.57 (t, J=7.5 Hz, 1H), 6.90 (broad s, 1H), 6.76 (d, J=7.5 Hz, 1H), 3.55 (m, 2H), 2.73 (t, J=6 Hz, 2H), 2.57 (m, 4H), 1.80 (m, 4H).

EXAMPLE 72 (23)

4-(3-(Pyrrolidin-1-yl)propyl)carbamoyl-1,1-dioxidebenzo[b]thiophene

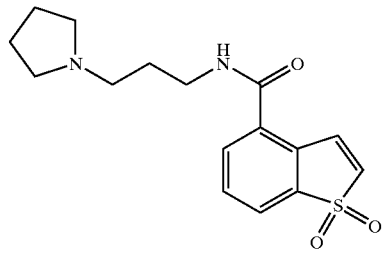

TLC: Rf 0.19 (ethyl acetate:acetic acid:water=3:1:1);

NMR (CDCl$_3$): δ9.30 (broad s, 1H), 8.17 (d, J=7.5 Hz, 1H), 7.7 8 (d, J=7.5 Hz, 1H), 7.64 (d, J=7.5 Hz, 1H), 7.52 (t, J=7.5 Hz, 1H), 6.76 (d, J=7.5 Hz, 1H), 3.58 (m, 2H), 2.76 (t, J=6 Hz, 2H), 2.59 (m, 4H), 2.00–1.70 (m, 6H).

EXAMPLE 72 (24)

4-(4-(2-Methylphenyl)piperazin-1-yl)carbonyl-1,1-dioxidebenzo[b]thiophene.hydrochloride

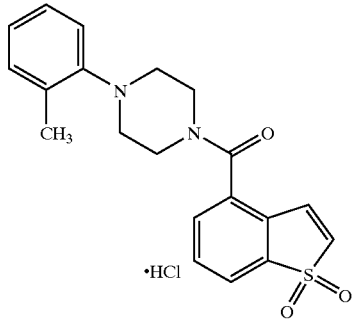

TLC: Rf 0.64 (ethyl acetate:hexane=2:1);

NMR (DMSO-d$_6$): δ7.97–7.90 (m, 1H), 7.74–7.65 (m, 2H), 7.57 (d, J=7.2 Hz, 1H), 7.51 (d, J=7.2 Hz, 1H), 7.20–7.10 (m, 2H), 7.06–6.93 (m, 2H), 3.90–3.78 (m, 2H), 3.45–3.34 (m, 2H), 3.00–2.90 (m, 2H), 2.85–2.74 (m, 2H), 2.27 (s, 3H).

EXAMPLE 72 (25)

4-(4-(3-Methylphenyl)piperazin-1-yl)carbonyl-1,1-dioxidebenzo[b]thiophene.hydrochloride

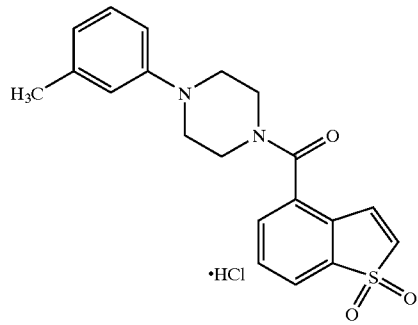

TLC: Rf 0.48 (ethyl acetate:hexane=2:1);

NMR (DMSO-d$_6$): δ8.00–7.92 (m, 1H), 7.74–7.66 (m, 2H), 7.56 (d, J=7.2 Hz, 1H), 7.49 (d, J=7.2 Hz, 1H), 7.14 (t, J=7.8 Hz, 1H), 6.90–6.80 (m, 2H), 6.71 (d, J=7.8 Hz, 1H), 3.90–3.80(m, 2H), 3.46–3.36 (m, 2H), 3.36–3.24 (m, 2H), 3.18–3.08 (m, 2H), 2.56 (s, 3H).

EXAMPLE 72 (26)

4-(4-(2-Fluorophenyl)piperazin-1-yl)carbonyl-1,1-dioxidebenzo[b]thiophene.hydrochloride

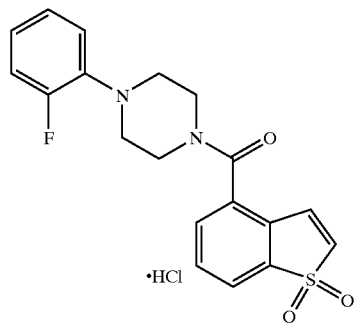

TLC: Rf 0.59 (ethyl acetate:hexane=2:1);

NMR (DMSO-d$_6$): δ8.00–7.90 (m, 1H), 7.74–7.66 (m, 2H), 7.56 (d, J=7.2 Hz, 1H), 7.50 (d, J=7.2 Hz, 1H), 7.20–6.96 (m, 4H), 3.90–3.80 (m, 2H), 3.46–3.36 (m, 2H), 3.18–3.06 (m, 2H), 3.02–2.90 (m, 2H).

EXAMPLE 72 (27)

4-(4-(4-Fluorophenyl)piperazin-1-yl)carbonyl-1,1-dioxidebenzo[b]thiophene.hydrochloride

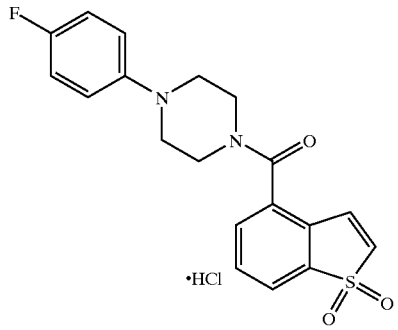

TLC: Rf 0.40 (ethyl acetate:hexane=2:1);

NMR (DMSO-$d_6$): δ8.00–7.90 (m, 1H), 7.74–7.65 (m, 2H), 7.54 (d, J=6.9 Hz, 1H), 7.49 (d, J=6.9 Hz, 1H), 7.14–6.97 (m, 4H), 3.89–3.78 (m, 2H), 3.45–3.34 (m, 2H), 3.30–3.19 (m, 2H), 3.13–3.00 (m, 2H).

EXAMPLE 72 (28)

4-(4-(4-Methoxyphenyl)piperazin-1-yl)carbonyl-1,1-dioxidebenzo[b]thiophene.hydrochloride

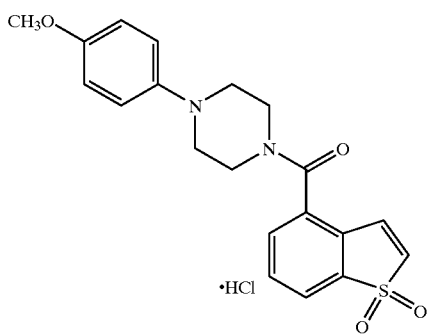

TLC: Hf 0.22 (ethyl acetate:hexane=2:1);

NMR (DMSO-$d_6$): δ8.00–7.92 (m, 1H), 7.77–7.66 (m, 2H), 7.58 (d, J=6.9 Hz, 1H), 7.50 (d, J=6.9 Hz, 1H), 7.13–7.08 (m, 2H), 6.96–6.86 (m, 2H), 4.10–3.70 (m, 2H), 3.72 (s, 3H), 3.54–3.40 (m, 2H), 3.38–3.22 (m, 2H), 3.20–3.06 (m, 2H).

EXAMPLE 72 (29)

4-(4-(3-Trifluoromethylphenyl)piperazin-1-yl)carbonyl-1,1-dioxidebenzo[b]thiophene.hydrochloride

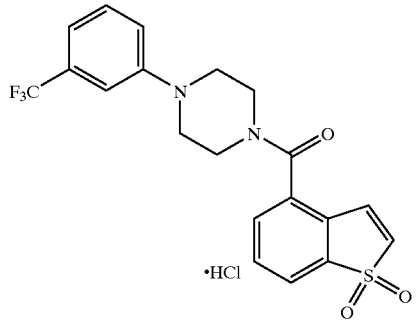

TLC: Rf 0.47 (ethyl acetate:hexane=2:1);

NMR (DMSO-$d_6$): δ7.98–7.93 (m, 1H), 7.74–7.67 (m, 2H), 7.56 (d, J=6.9 Hz, 1H), 7.49 (d, J=6.9 Hz, 1H), 7.48–7.40 (m, 1H), 7.27–7.16 (m, 2H), 7.14–7.07 (m, 1H), 3.88–3.67 (m, 2H), 3.46–3.34 (m, 4H), 3.27–3.18 (m, 2H).

EXAMPLE 72 (30)

4-((3R)-1-Benzylpyrrolidin-3-yl)carbamoyl-1,1-dioxidebenzo[b]thiophene

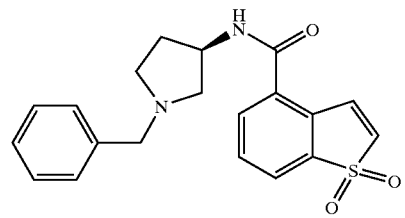

TLC: Rf 0.45 (chloroform:methanol=9:1);

NMR (CDCl$_3$): δ7.92 (dd, J=1.0 Hz and 7.0 Hz, 1H), 7.77 (d, J=7.5 Hz, 1H), 7.68 (dd, J=1.0 Hz and 7.5 Hz, 1H), 7.54 (t, J=7.5 Hz, 1H), 7.40–7.20 (m, 5H), 6.75 (d, J=7.0 Hz, 1H), 6.70 (m, 1H), 4.65 (m, 1H), 3.66 (s, 2H), 3.05–2.95 (m, 1H), 2.78 (dd, J=1.0 Hz and 10 Hz, 1H), 2.60 (dd, J=6.0 Hz and 10 Hz, 1H), 2.50–2.20 (m, 2H), 1.85–1.70 (m, 1H).

EXAMPLE 72 (31)

4-((3S)-1-Benzylpyrrolidin-3-yl)carbamoyl-1,1-dioxidebenzo[b]thiophene

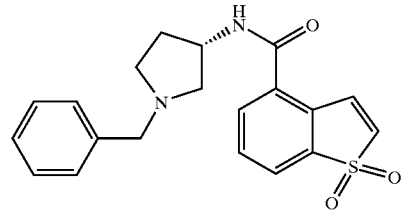

TLC: Rf 0.45 (chloroform:methanol=9:1);

NMR (CDCl$_3$): δ7.92 (dd, J=1.0 Hz and 7.0 Hz, 1H), 7.77 (d, J=7.5 Hz, 1H), 7.68 (dd, J=1.0 Hz and 7.5 Hz, 1H), 7.54

(t, J=7.5 Hz, 1H), 7.40–7.20 (m, 5H), 6.75 (d, J=7.0 Hz, 1H), 6.70 (m, 1H), 4.65 (m, 1H), 3.66 (s, 2H), 3.05–2.95 (m, 1H), 2.78 (dd, J=1.0 Hz and 10 Hz, 1H), 2.60 (dd, J=6.0 Hz and 10 Hz, 1H), 2.50–2.20 (m, 2H), 1.85–1.70 (m, 1H).

EXAMPLES 73~73 (29)

By the same procedure as described in Example 18 using an alcohol derivative corresponding to the compound prepared in Example 9 (12) and a halogenated compound corresponding to 4-nitrobenzylbromide, or by the same procedure as described in Example 29 using an alcohol derivative corresponding to 4-hydroxy-1,1-dioxidebenzo[b] thiophene and an alcohol derivative corresponding to 1-(3-hydroxypropyl)pyrrole, the following compounds of the present invention were obtained, with the proviso that when the compounds of the following Examples 73 (26)–73 (29) were prepared by the same procedure as described in Example 18, an aqueous solution of sodium hydroxide was used instead of potassium carbonate.

EXAMPLE 73

5-Acetylmethyloxy-1,1-dioxidebenzo[b]thiophene

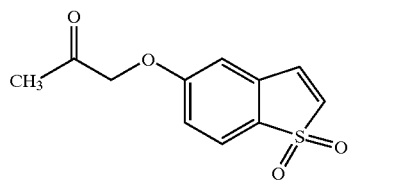

TLC: Rf 0.25 (ethyl acetate:hexane:methylene chloride= 1:1:1);

NMR (CDCl$_3$): δ7.65 (d, J=8.2 Hz, 1H), 7.15 (d, J=6.8Hz, 1H), 6.92 (dd, J=8.2 Hz, 2.2 Hz, 1H), 6.87 (d, J=2.2 Hz, 1H), 6.75 (d, J=6.8 Hz, 1H), 4.64 (s, 2H), 2.30 (s, 3H).

EXAMPLE 73 (1)

5-Cyanomethyloxy-1,1-dioxidebenzo[b]thiophene

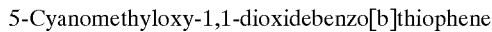

TLC: Rf 0.36 (hexane:ethyl acetate=1:1);

NMR (CDCl$_3$): δ7.72 (d, J=8.4 Hz, 1H), 7.18 (d, J=7.2 Hz, 1H), 7.07 (dd, J=8.4, 2.4 Hz, 1H), 6.98 (d, J=2.4 Hz, 1H), 6.79 (d, J=7.2 Hz, 1H), 4.86 (s, 2H).

EXAMPLE 73 (2)

5-t-Butoxycarbonylmethyloxy-1,1-dioxidebenzo[b]thiophene

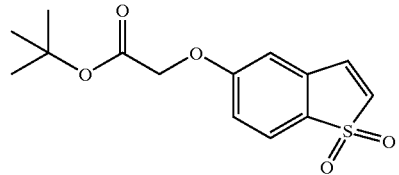

TLC: Rf 0.54 (hexane:ethyl acetate=1:1);

NMR (CDCl$_3$): δ7.63 (d, J=8.4 Hz, 1H), 7.13 (d, J=6.9 Hz, 1H), 6.91 (dd, J=8.4, 2.4 Hz, 1H), 6.88 (d, J=2.4 Hz, 1H), 6.73 (d, J=6.9 Hz, 1H), 4.58 (s, 2H), 1.49 (s, 9H).

EXAMPLE 73 (3)

5-(3-(Ethoxycarbonyl)propyloxy-1,1-dioxidebenzo[b]thiophene

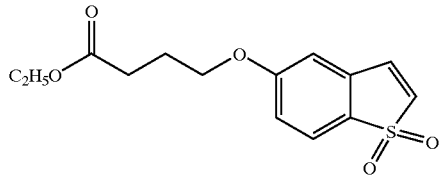

TLC: Rf 0.50 (hexane:ethyl acetate=1:1);

NMR (CDCl$_3$): δ7.61 (d, J=8.7 Hz, 1H), 7.12 (d, J=6.9 Hz, 1H), 6.94 (dd, J=8.7, 2.0 Hz, 1H), 6.84 (d, J=2.0 Hz, 1H), 6.71 (d, J=6.9 Hz, 1H), 4.15 (q, J=7.2 Hz, 2H), 4.08 (t, J=6.6 Hz, 1H), 2.51 (t, J=6.6 Hz, 1H), 2.13 (quint, J=6.6 Hz, 1H), 1.26 (t, J=7.2 Hz, 3H).

EXAMPLE 73 (4)

5-(4-(Ethoxycarbonyl)butyl)oxy-1,1-dioxidebenzo[b]thiophene

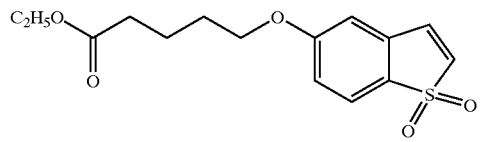

TLC: Rf 0.48 (hexane:ethyl acetate=1:1);

NMR (CDCl$_3$): δ7.61 (dd, J=8.4, 0.9 Hz, 1H), 7.12 (dd, J=6.9, 0.9 Hz, 1H), 6.93 (dd, J=8.4, 2.4 Hz, 1H), 6.84 (d, J=2.4 Hz, 1H), 6.71 (d, J=6.9 Hz, 1H), 4.13 (q, J=7.0 Hz, 2H), 4.03 (t, J=6.0 Hz, 2H), 2.39 (t, J=7.0 Hz, 2H), 1.88–1.80 (m, 4H), 1.26 (t, J=7.0 Hz, 3H).

EXAMPLE 73 (5)

4-(Pyridin-3-ylmethyl)oxy-1,1-dioxidebenzo[b]thiophene

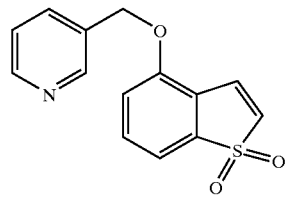

TLC: Rf 0.42 (ethyl acetate:methanol=9:1);

NMR (CDCl$_3$): δ5.19 (s, 2H), 6.63 (d, J=7.0 Hz, 1H), 7.13 (d, J=8.0 Hz, 1H), 7.33 (d, J=8.0 Hz, 1H), 7.37 (dd, J=8.0 Hz, 5.0 Hz, 1H), 7.45 (dd, J=7.0 Hz, 1.0 Hz, 1H), 7.49 (t, J=8.0 Hz, 1H), 7.75 (dt, J=8.0 Hz, 2.0 Hz, 1H), 8.64 (dd, J=5.0 Hz, 2.0 Hz, 1H), 8.70 (d, J=2.0 Hz, 1H),

EXAMPLE 73 (6)

4-(Pyridin-4-ylmethyl)oxy-1,1-dioxidebenzo[b]thiophene

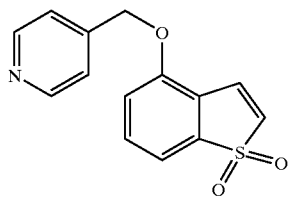

TLC: Rf 0.16 (methylene chloride:ethyl acetate=1:21);

NMR (CDCl$_3$): δ8.66 (d, J=6.0 Hz, 2H), 7.51 (dd, J=7.0, 1.0 Hz, 1H), 7.47 (t, J=8.0 Hz, 1H), 7.36–7.31 (m, 3H), 7.03 (d, J=8.0 Hz, 1H), 6.67 (d, J=70 Hz, 1H), 5.21 (s, 2H).

EXAMPLE 73 (7)

4-(4-Trifluoromethylphenylmethyl)oxy-3-phenylthio-2,3-dihydro-1,1-dioxidebenzo[b]thiophene

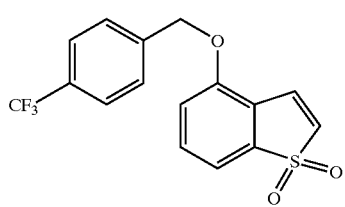

TLC: Rf 0.67 (hexane:ethyl acetate=1:2);

NMR (CDCl$_3$): δ7.70 (d, J=7.5 Hz, 2H), 7.60–7.30 (m, 5H), 7.10 (d, J=10 Hz, 1H), 6.65 (d, J=7.5 Hz, 1H), 5.25 (s, 2H).

EXAMPLE 73 (8)

4-(3,5-Dimethylisoxazol-4-ylmethyl)oxy-1,1-dioxidebenzo[b]thiophene

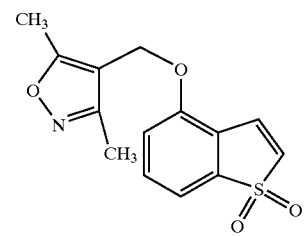

TLC: Rf 0.53 (hexane:ethyl acetate=1:2);

(CDCl$_3$): δ7.60–7.40 (m, 1H), 7.40–7.30 (m, 2H), 7.10 (d, J=7.5 Hz, 1H), 6.60 (d, J=7.5 Hz, 1H), 4.90 (s, 2H), 2.40 (s, 3H), 2.30 (s, 3H).

EXAMPLE 73 (9)

4-(4-Methoxycarbonylphenylmethyl)oxy-1,1-dioxidebenzo[b]thiophene

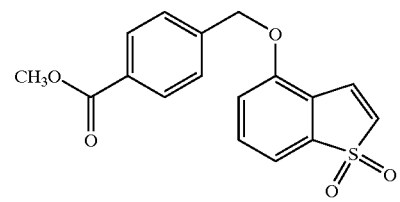

TLC: Rf 0.58 (hexane:ethyl acetate=1:2);

NMR (CDCl$_3$): δ8.10 (d, J=7.5 Hz, 2H), 7.55–7.30 (m, 5H), 7.10 (d, J=10 Hz, 1H), 6.65 (d, J=7.5 Hz, 1H), 5.25 (s, 2H), 3.95 (s, 3H).

EXAMPLE 73 (10)

4-(Benzotriazol-1-ylmethyl)oxy-1,1-dioxidebenzo[b]thiophene

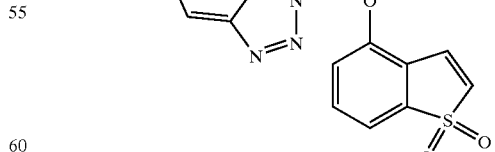

TLC: Rf 0.62 (hexane:ethyl acetate=1:2);

NMR (CDCl$_3$): δ8.20–8.10 (m, 1H), 7.70–7.30 (m, 7H), 6.65 (s, 2H), 6.60 (d, J=7.5 Hz, 1H).

EXAMPLE 73 (11)

4-(2,6-Dimethylphenyl)carbamoylmethyloxy-1,1-dioxidebenzo[b]thiophene

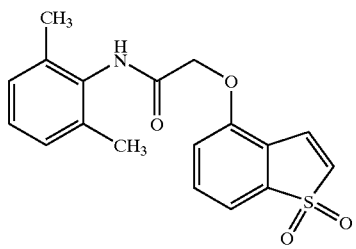

TLC: Rf 0.50 (hexane:ethyl acetate=1:2);

NMR (CDCl$_3$): δ7.65–7.40 (m, 4H), 7.20–7.00 (m, 4H), 6.75 (d, J=7.5 Hz, 1H), 4.80 (s, 2H), 2.20 (s, 6H).

EXAMPLE 73 (12)

4-Trimethylsilylmethyloxy-1,1,-dioxidebenzo[b]thiophene

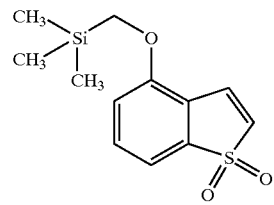

TLC: Rf 0.60 (hexane:ethyl acetate=1:1);

NMR (CDCl$_3$): δ7.50–7.35 (m, 2H), 7.30–7.10 (m, 2H), 6.60 (d, J=7.5 Hz, 1H), 3.70 (s, 2H), 0.20 (s, 9H).

EXAMPLE 73 (13)

4-(Pyridin-2-ylmethyl)oxy-1,1-dioxidebenzo[b]thiophene

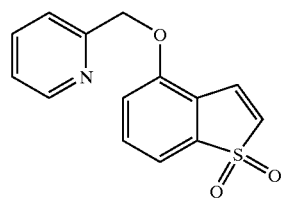

TLC: Rf 0.31 (hexane:ethyl acetate=1:2);

NMR (CDCl$_3$): δ8.70–8.55 (m, 1H), 7.85–7.70 (m, 1H), 7.60–7.20 (m, 5H), 7.10 (d, J=7.5 Hz, 1H), 6.65 (d, J=7.5 Hz, 1H), 5.35 (s, 2H).

EXAMPLE 73 (14)

4-(2-(Pyridin-3-ylcarbonyl)aminoethyl)oxy-1,1-dioxidebenzo[b]thiophene

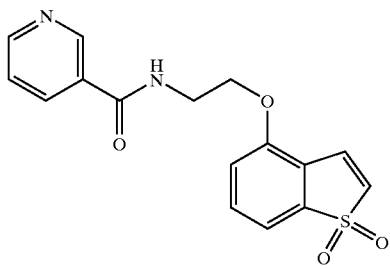

TLC: Rf 0.33 (ethyl acetate:methanol=9:1);

NMR (CDCl$_3$): δ8.98 (dd, J=1.8, 0.9 Hz, 1H), 8.72 (dd, J=4.5, 1.8 Hz, 1H), 8.12 (dt, J=8.0, 1.8 Hz, 1H), 7.49–7.42 (m, 2H), 7.28 (d, J=7.0 Hz, 1H), 7.08 (d, J=8.0 Hz, 1H), 6.83 (br, 1H), 6.58 (d, J=7.0 Hz, 1H), 4.30 (t, J=5.4 Hz, 2H), 3.93 (q, J=5.4 Hz, 2H).

EXAMPLE 73 (15)

4-(3-(Pyridin-3-yl)propyl)oxy-1,1-dioxidebenzo[b]thiophene

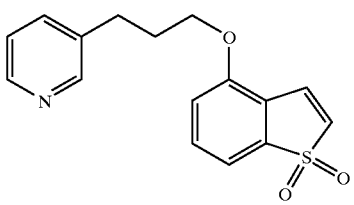

TLC: Rf 0.32 (ethyl acetate:methanol=10:1);

NMR (CDCl$_3$+CD$_3$OD): δ8.52–8.25 (m, 2H), 7.80–7.18 (m, 5H), 7.07 (d, J=8 Hz), 1H), 6.68 (d, J=7 Hz, 1H), 4.14 (t, J=7 Hz, 2H), 2.87 (t, J=7 Hz, 2H), 2.35–2.10 (m, 2H).

EXAMPLE 73 (16)

4-(2-(Pyridin-2-yl)ethyl)oxy-1,1-dioxidebenzo[b]thiophene

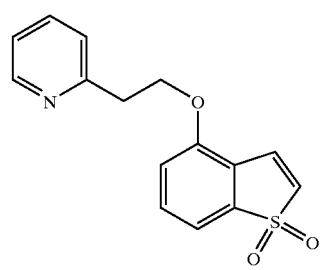

TLC: Rf 0.39 (ethyl acetate:methanol=10:1);

NMR (CDCl$_3$): δ8.57 (d, J=5 Hz, 1H), 7.64 (dt, J=2, 7 Hz, 1H), 7.45 (t, J=8 Hz, 1H), 7.35–6.98 (m, 5H), 6.56 (d, J=7 Hz, 1H), 4.50 (t, J=7 Hz, 2H), 3.29 (t, J=7 Hz, 2H).

EXAMPLE 73 (17)

4-(1-t-Butoxycarbonylpiperidin-4-yl)oxy-1,1-dioxidebenzo[b]thiophene

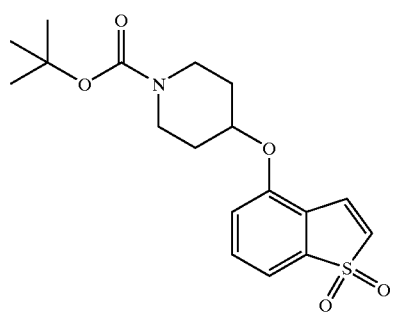

TLC: Rf 0.63 (ethyl acetate:hexane=1:1);

NMR (CDCl$_3$): δ7.55–7.38 (m, 2H), 7.30 (d, J=8 Hz, 1H), 7.07 (d, J=8 Hz, 1H), 6.23 (d, J=7 Hz, 1H), 4.70–4.50 (m, 1H), 3.85–3.58 (m, 2H), 3.50–3.28 (m, 2H), 2.15–1.88 (m, 2H), 1.88–1.66 (m, 2H), 1.47 (s, 9H).

EXAMPLE 73 (18)

4-(5-Methyl-1-tritylimidazol-4-ylmethyl)oxy-1,1-dioxidebenzo[b]thiophene

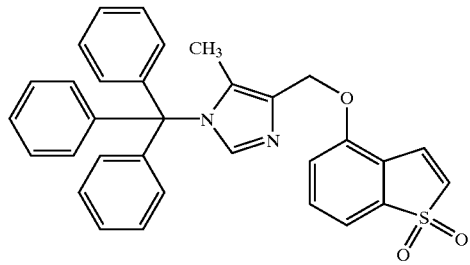

TLC: Rf 0.11 (hexane:ethyl acetate=1:1);

NMR (CDCl$_3$): δ7.55–7.23 (m, 14H), 7.23–7.00 (m, 6H), 6.56 (d, J=7 Hz, 1H), 5.13 (s, 2H), 1.45 (s, 3H).

EXAMPLE 73(19)

4-(1,2,4-oxadiazol-3-ylmethyl)oxy-1,1-dioxidebenzo[b]thiophene

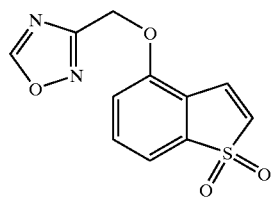

TLC: Rf 0.45 (hexane:ethyl acetate=1:2);

NMR (DMSO-d$_6$): δ9.70 (s, 1H), 7.62 (t, J=8.0 Hz, 1H), 7.57 (d, J=6.9 Hz, 1H), 7.50 (d, J=8.0 Hz, 1H), 7.46 (d, J=8.0 Hz, 1H), 7.31 (d, J=6.9 Hz, 1H), 5.58 (s, 2H).

EXAMPLE 73 (20)

6-(Pyridin-3-ylmethyl)oxy-1,1-dioxidebenzo[b]thiophene

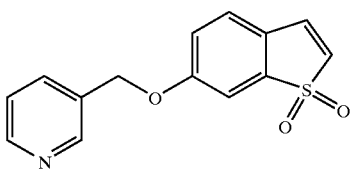

TLC: Rf 0.40 (ethyl acetate);

NMR (CDCl$_3$): δ8.69 (d, J=1.7 Hz, 1H), 8.62 (dd, J=5.0, 1.7 Hz, 1H), 7.77 (d, J=7.8 Hz, 1H), 7.39–7.27 (m, 3H), 7.18 (d, J=7.0 Hz, 1H), 7.09 (dd, J=8.2, 2.2 Hz, 1H), 6.58 (d, J=7.0 Hz, 1H), 5.14 (s, 2H).

EXAMPLE 73 (21)

6-(3-Nitrophenylmethyl)oxy-1,1-dioxidebenzo[b]thiophene

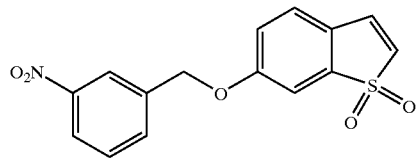

MS (APCl, Pos.): m/z 318 (M+H)$^+$.

EXAMPLE 73 (22)

6-(3-(t-Butoxycarbonylamino)propyl)oxy-1,1-dioxidebenzo[b]thiophene

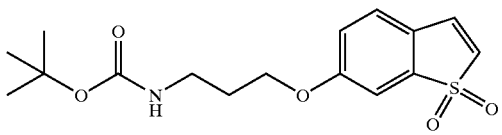

TLC: Rf 0.14 (hexane:ethyl acetate=2:1);

NMR (CDCl$_3$): δ7.27–7.23 (m, 2H), 7.16 (d, J=6.9 Hz, 1H), 7.01 (dd, J=8.3, 2.3 Hz, 1H), 6.60 (d, J=6.9 Hz, 1H), 4.69 (br, 1H), 4.08 (t, J=6.6 Hz, 2H), 3.32 (q, J=6.6 Hz, 2H), 2.01 (quint, J=6.6 Hz, 2H), 1.44 (s, 9H).

EXAMPLE 73 (23)

7-t-Butoxycarbonylmethylmethyloxy-1,1-dioxidebenzo[b]thiophene

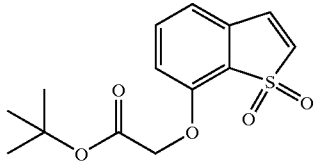

TLC: Rf 0.41 (hexane:ethyl acetate=1:1);

NMR (CDCl$_3$): δ7.45 (dd, J=8.5, 7.5 Hz, 1H), 7.12 (d, J=6.9 Hz, 1H), 6.94 (d, J=7.5 Hz, 1H), 6.86 (d, J=8.5 Hz, 1H), 6.66 (d, J=6.9 Hz, 1H), 4.72 (s, 2H), 1.46 (s, 9H).

EXAMPLE 73 (24)

6-(Pyridin-3-yloxy)methyl-4-methoxy-1,1-dioxidebenzo[b]thiophene

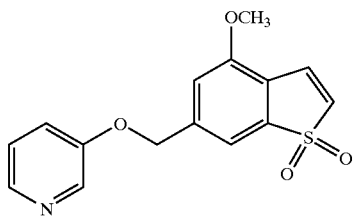

TLC: Rf 0.36 (ethyl acetate);

NMR (CD$_3$OD): δ8.35 (d, J=3.0 Hz, 1H), 8.17 (d, J=4.0 Hz, 1H), 7.60–7.50 (m, 1H), 7.53 (d, J=7.2 Hz, 1H), 7.45–7.35 (m, 3H), 6.87 (d, J=7.2 Hz, 1H), 5.27 (s, 2h), 3.98 (s, 3H).

EXAMPLE 73 (25)

4,7-Bis(3-hydroxypropyl)-1,1-dioxidebenzo[b]thiophene

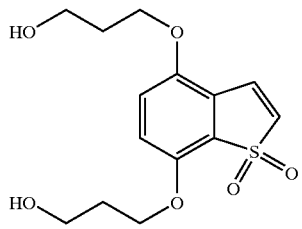

TLC: Rf 0.44 (ethyl acetate:methanol=9:1);

NMR (CDCl$_3$): δ7.34 (d, J=7.0 Hz, 1H), 7.04 (d, J=9.2 Hz, 1H), 6.97 (d, J=9.2 Hz, 1H), 6.54 (d, J=7.0 Hz, 1H), 4.24 (t, J=5.8 Hz, 2H), 4.14 (t, J=5.8 Hz, 2H), 3.89 (t, J=5.8 Hz, 2H), 3.83 (t, J=5.8 Hz, 2H), 2.00–2.08 (m, 4H).

EXAMPLE 73 (26)

5-Carboxy-4-ethoxy-1,1-dioxidebenzo[b]thiophene

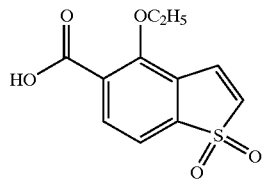

TLC: Rf 0.38 (chloroform:methanol=10:1);

NMR (CD$_3$OD): δ8.00 (d, J=7 Hz, 1H), 7.61 (dd, J=1, 7 Hz, 1H), 7.52 (dd, J=1, 7 Hz, 1H), 7.03 (d, J=7 Hz, 1H), 4.16 (q, J=7 Hz, 2H), 1.42 (t, J=7 Hz, 3H).

EXAMPLE 73 (27)

5-Carboxy-4-butoxy-1,1-dioxidebenzo[b]thiophene

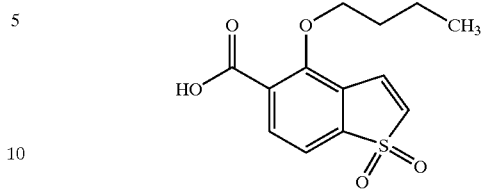

TLC: Rf 0.48 (chloroform:methanol=10:1);

NMR (CD$_3$OD): δ7.98 (d, J=7 Hz, 1H), 7.58 (dd, J=1, 7 Hz, 1H), 7.51 (dd, J=1, 7 Hz, 1H), 7.03 (d, J=7 Hz, 1H), 4.01 (t, J=7 Hz, 2H), 1.95–1.66 (m, 2H), 1.66–1.36 (m, 2H), 0.99 (t, J=7 Hz, 3H).

EXAMPLE 73 (28)

5-Carboxy-4-hexyloxy-1,1-dioxidebenzo[b]thiophene

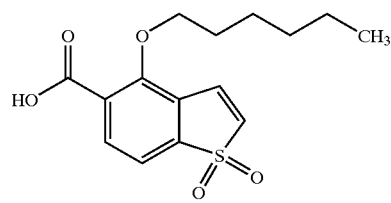

TLC: Rf 0.50 (chloroform:methanol=10:1);

NMR (CD$_3$OD): δ7.98 (d, J=7 Hz, 1H), 7.58 (dd, J=1, 7 Hz, 1H), 7.51 (dd, J=1, 7 Hz, 1H), 7.03 (d, J=7 Hz, 1H), 4.10 (t, J=7 Hz, 2H), 1.95–1.65 (m, 2H), 1.65–1.05 (m, 6H), 0.92 (t, J=7 Hz, 3H).

EXAMPLE 73 (29)

5-Carboxy-4-octyloxy-1,1-dioxidebenzo[b]thiophene

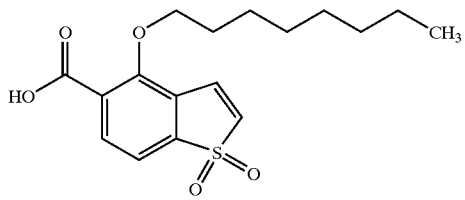

TLC: Rf 0.50 (chloroform:methanol=10:1);

NMR (CD$_3$OD): δ7.98 (d, J=7 Hz, 1H), 7.57 (dd, J=1, 7 Hz, 1H), 7.51 (dd, J=1, 7 Hz, 1H), 7.03 (d, J=7 Hz, 1H), 4.10 (t, J=7 Hz, 2H), 1.95–1.65 (m, 2H), 1.65–1.05 (m, 10H), 0.90 (t, J=7 Hz, 3H).

EXAMPLES 74~74 (5)

By the same procedure as described in Example 32 using carboxylic acid derivative corresponding to 4-carboxy-1,1-dioxidebenzo[b]thiophene and a halogenated compound corresponding to bromoethane, the compounds of the present invention having the following physical data were obtained, with the proviso that in the preparation of the compound of Example 74, 1 mol equivalent of bromoethane was used.

EXAMPLE 74

5-Ethoxycarbonyl-4-hydroxy-1,1-dioxidebenzo[b]thiophene

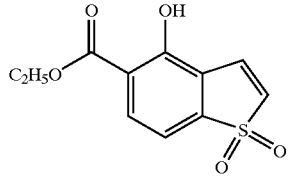

TLC: Rf 0.32 (hexane:ethyl acetate=2:1);

NMR (CDCl$_3$): δ11.37 (s, 1H), 8.07 (d, J=8.0 Hz, 1H), 7.52 (dd, J=7.0, 0.8 Hz, 1H), 7.24 (dd, J=8.0, 0.8 Hz, 1H), 6.66 (d, J=7.0 Hz, 1H), 4.47 (q, J=7.0 Hz, 2H), 1.45 (t, J=7.0 Hz, 3H).

EXAMPLE 74 (1)

5-Ethoxycarbonyl-4-methoxy-1,1-dioxidebenzo[b]thiophene

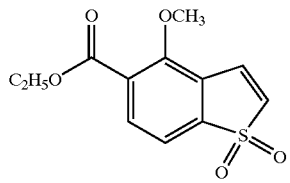

TLC: Rf 0.31 (hexane:ethyl acetate=2:1);

NMR (CDCl$_3$): δ7.98 (d, J=7.4 Hz, 1H), 7.49 (t, J=7.4 Hz, 2H), 6.75 (d, J=7.4 Hz), 1H), 4.43 (q, J=7.0 Hz, 2H), 3.97 (s, 3H), 1.43 (t, J=7.0 Hz, 3H).

EXAMPLE 74 (2)

5-Isopropyloxycarbonyl-4-methoxy-1,1-dioxidebenzo[b]thiophene

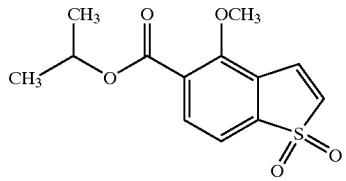

TLC: Rf 0.36 (hexane:ethyl acetate=2:1);

NMR (CDCl$_3$): δ7.94 (d, J=7.8 Hz, 1H), 7.52–7.42 (m, 2H), 6.74 (d, J=7.2 Hz, 1H), 5.38–5.19 (m, 1H), 3.96 (s, 3H), 1.40 (d, J=6.2 Hz, 6H).

EXAMPLE 74 (3)

5-(2-Methylpropyl)oxycarbonyl-4-methoxy-1,1-dioxidebenzo[b]thiophene

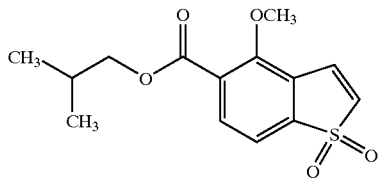

TLC: Rf 0.42 (hexane:ethyl acetate=2:1);

NMR (CDCl$_3$): δ7.97 (d, J=7.8 Hz, 1H), 7.53–7.43 (m, 2H), 6.75 (d, J=7.2 Hz, 1H), 4.15 (d, J=6.8 Hz, 2H), 3.97 (s, 3H), 2.20–1.98 (m, 1H), 1.03 (d, J=6.6 Hz, 6H).

EXAMPLE 74(4)

6-Methoxycarbonyl-4-methoxy-1,1-dioxidebenzo[b]thiophene

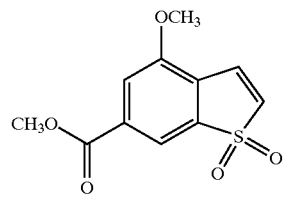

TLC: Rf 0.41 (hexane:ethyl acetate=1:1);

NMR (CDCl$_3$): δ7.95 (t, J=1.0 Hz, 1H), 7.75 (d, J=1.0 Hz, 1H), 7.46 (dd, J=7.0, 1.0 Hz, 1H), 6.74 (d, J=7.0 Hz, 1H), 3.98 (s, 3H), 3.96 (s, 3H).

EXAMPLE 74 (5)

6-Methoxymethoxycarbonyl-4-methoxy-1,1-dioxidebenzo[b]thiophene

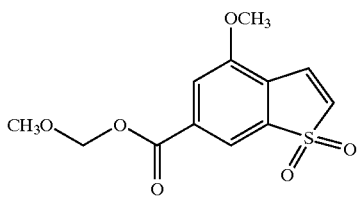

TLC: Rf 0.38 (hexane:ethyl acetate=1:1);

NMR (CDCl$_3$): δ7.99 (s, 1H), 7.79 (s, 1H), 7.47 (d, J=7.0 Hz, 1H), 6.76 (d, J=7.0 Hz, 1H), 5.52 (s, 2H), 4.00 (s, 3H), 3.58 (s, 3H).

EXAMPLES 75~75(2)

By the same procedure as described in Example 31 using 4-bromomethyl-1,1-dioxidebenzo[b]thiophene and amine derivative corresponding to 2,4-dimethoxybenzylamine hydrochloride, the following compounds of the present invention were obtained.

With the proviso that in the preparation of the compounds of Example 75 and Example 75 (2), more than 2 mol equivalent of 4-bromomethyl-1,1-dioxidebenzo[b]thiophene versus amine derivative.

EXAMPLE 75

4-(N-(Pyridin-2-ylmethyl)-N-(1,1-dioxidebenzo[b]thiophen-4-ylmethyl)amino)methyl-1,1-dioxidebenzo[b]thiophene

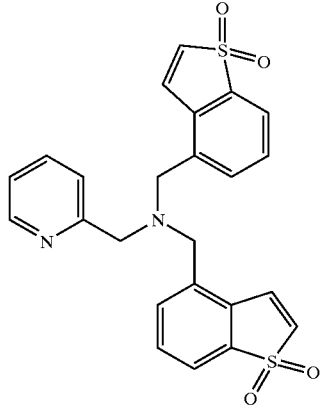

TLC: Rf 0.48 (methanol:methylene chloride=1:10);

NMR (CDCl$_3$): δ8.59 (d, J=4.6 Hz, 1H), 7.72–7.55 (m, 3H), 7.55–7.38 (m, 4H), 7.35–7.16 (m, 3H), 7.10 (d, J=7.8 Hz, 1H), 6.68 (d, J=7.0 Hz, 2H), 3.76 (s, 4H), 3.73 (s, 2H).

EXAMPLE 75 (1)

4-(Pyridin-2-ylmethyl)aminomethyl-1,1-dioxidebenzo[b]thiophene

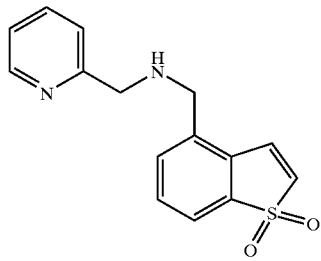

TLC: Rf 0.31 (methylene chloride:methanol=10:1);

NMR (CD$_3$OD+CDCl$_3$): δ8.75–8.52 (m, 1H), 7.96–7.72 (m, 4H), 7.64 (t, J=8 Hz, 1H), 7.55–7.25 (m, 2H), 6.93 (d, J=7 Hz, 1H), 4.43 (s, 2H), 4.38 (s, 2H).

EXAMPLE 75 (2)

4-(N-(2,4-Dimethoxyphenylmethyl)-N-(1,1-dioxidebenzo[b]thiophene-4-ylmethyl)amino)methyl-1,1-dioxidebenzo[b]thiophene

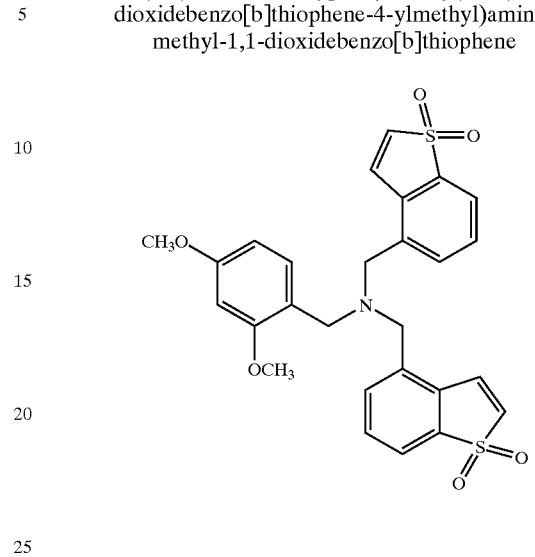

TLC: Rf 0.57 (ethyl acetate:benzene=1:1);

NMR (CDCl$_3$): δ7.65–7.55 (m, 2H), 7.50–7.38 (m, 4H), 7.07–6.99 (m, 1H), 6.87 (d, J=7.0 Hz, 2H), 6.57 (d, J=7.0 Hz, 2H), 6.48–6.40 (m, 2H), 3.81 (s, 3H), 3.63 (s, 3H), 3.60 (s, 4H), 3.45 (s, 2H).

EXAMPLES 76~76 (1)

By the same procedure as described in Example 1 using a derivative corresponding to 1,1-dioxidebenzo[b]thiophene and thiophenol, the following compounds of the present invention were obtained.

EXAMPLE 76

4,7-Dimethoxy-3-phenylthio-2,3-dihydro-1,1-dioxidebenzo[b]thiophene

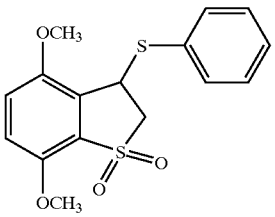

TLC: Rf 0.27 (hexane:methylene chloride=1:10);

NMR (CDCl$_3$): δ7.52–7.47 (m, 2H), 7.35–7.32 (m, 3H), 7.02 (d, J=8.9 Hz, 1H), 6.91 (d, J=8.9 Hz, 1H), 5.00 (dd, J=7.0, 1.6 Hz, 1H), 3.92 (s, 3H), 3.85 (s, 3H), 3.73 (dd, J=13.9, 7.0 Hz, 1H), 3.59 (dd, J=13.9, 1.6 Hz, 1H).

EXAMPLE 76 (1)

6-Bromo-3-phenylthio-2,3-dihydro-1,1-dioxidebenzo[b]thiophene

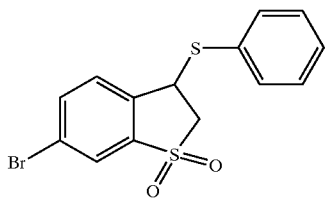

TLC: Rf 0.45 (hexane:ethyl acetate=2:1);

NMR (CDCl$_3$): δ7.83 (d, J=1.8 Hz, 1H), 7.75 (dd, J=8.3, 1.8 Hz, 1H), 7.58 (d, J=8.3 Hz, 1H), 7.43–7.40 (m, 2H), 7.37–7.34 (m, 3H), 4.88 (t, J=6.9 Hz, 1H), 3.80 (dd, J=13.8, 6.9 Hz, 1H), 3.50 (dd, J=13.8, 6.9 Hz, 1H).

EXAMPLE 77

5-Acetyloxy-4-nitro-1,1-dioxidebenzo[b]thiophene

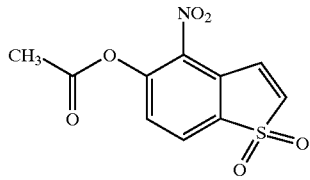

By the same procedure as described in Example 12 using 5-hydroxy-4-nitro-1,1-dioxidebenzo[b]thiophene instead of the compound prepared in Example 11, the compound of the present invention having the following physical data was obtained.

TLC: Rf 0.49 (hexane:ethyl acetate=1:1);

NMR (DMSO-d$_6$): δ8.32 (dd, J=8.0, 1.0 Hz, 1H), 7.78 (d, J=7.0 Hz, 1H), 7.76 (d, J=8.0 Hz, 1H), 7.69 (dd, J=7.0, 1.0 Hz, 1H), 2.35 (s, 3H).

EXAMPLES 78~78 (1)

By the same procedure as described in Example 7 using the compounds prepared in Example 35 (39) and Example 35 (47) instead of the compound prepared in Example 6 (8), the following compounds of the present invention were obtained.

EXAMPLE 78

4-(Piperidin-3-ylmethyl)oxy-3-phenylsulfonyl-2,3-dihydro-1,1-dioxidebenzo[b]thiophene.hydrochloride

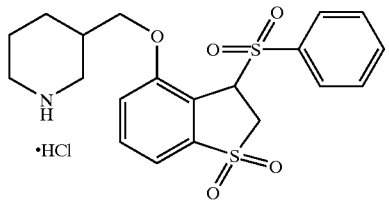

TLC: Rf 0.41 and 0.50 (ethyl acetate:acetic acid:water=3:1:1);

NMR (CD$_3$OD): δ7.85–7.42 (m, 6H), 7.35–7.18 (m, 2H), 5.68–5.50 (m, 1H), 4.15–3.90 (m, 3H), 3.90–3.50 (m, 2H), 3.50–3.30 (m, 1H), 3.20–2.90 (m, 2H), 2.45–2.15 (m, 1H), 2.15–1.40 (m, 4H).

EXAMPLE 78 (1)

5-(2-Aminoethyl)oxy-4-nitro-3-phenylsulfonyl-2,3-dihydro-1,1-dioxidebenzo[b]thiophene.hydrochloride

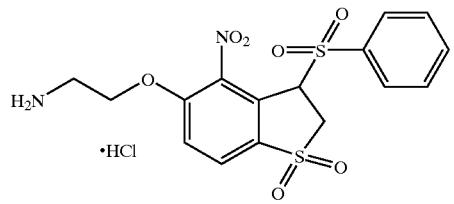

TLC: Rf 0.17 (ethyl acetate:methanol=2:21);

NMR (DMSO-d$_6$): δ8.25 (br, 3H), 8.16 (d, J=8.7 Hz, 1H), 7.86–7.65 (m, 6H), 5.99 (d, J=7.2 Hz, 1H), 4.63–4.50 (m, 2H), 4.15–4.00 (m, 2H), 3.30–3.26 (m, 2H).

EXAMPLE 79

4-(2-(2-Hydroxyethoxy)ethyl)oxy-3-phenylsulfonyl-2,3-dihydro-1,1-dioxidebenzo[b]thiophene

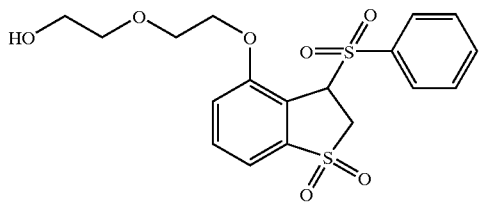

To a solution of the compound prepared in Example 35 (42) (258 mg) in ethanol, was added 47% aqueous solution of hydrobromic acid (1.0 ml). The mixture was refluxed for 1 hour. The reaction mixture was concentrated. The residue was dissolved in ethyl acetate. The mixture was washed by a saturated aqueous solution of sodium bicarbonate and a saturated aqueous solution of sodium chloride successively, dried over anhydrous sodium sulfate and concentrated. The residue was recrystallized from ethyl acetate to give the compound of the present invention (174 mg) having the following physical data.

TLC: Rf 0.22 (ethyl acetate);

NMR (CDCl$_3$): δ7.85–7.72 (m, 2H), 7.66–7.34 (m, 4H), 7.25 (d, J=8 Hz, 1H), 6.99 (d, J=8 Hz, 1H), 5.34 (d, J=9 Hz, 1H), 4.19 (d, J=15 Hz, 1H), 4.25–3.95 (m, 3H), 3.95–3.55 (m, 7H), 2.50 (brs, 1H).

EXAMPLE 80

4-(4,5-Dihydroxazol-2-yl)-1,1-dioxidebenzo[b]thiophene

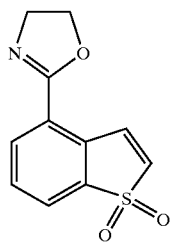

The compound prepared in Example 72 (1) (369 mg) was dissolved in diisopropylethylamine (0.55 ml) and methylene chloride (40 ml). The mixture was cooled to −78° C. Thereto was added trifluoromethanesulfonate anhydride (0.30 ml). The mixture was stirred at 0° C. for 2.5 hours and thereto was added trifluoromethanesulfonate anhydride (0.15 ml). The mixture was stirred at room temperature for 1 hour. To the reaction mixture, were added ethyl acetate and 1N hydrochloric acid. The mixture was extracted by ethyl acetate. The extract was washed by 1N sodium hydroxide and a saturated aqueous solution of sodium chloride successively, dried over anhydrous sodium sulfate and concentrated. The residue was purified with column chromatography on silica gel (ethyl acetate:hexane=1:1) to give the compound of the present invention (97 mg) having the following physical data.

TLC: Rf 0.53 (ethyl acetate);

NMR (CDCl$_3$): δ8.42 (d, J=7.0 Hz, 1H), 8.10 (d, J=7.8 Hz, 1H), 7.80 (d, J=7.8 Hz, 1H), 7.57 (t, J=7.8 Hz, 1H), 6.77 (d, J=7.0 Hz, 1H), 4.46 (t, J=9.4 Hz, 2H), 4.13 (t, J=9.4 Hz, 2H).

EXAMPLE 80 (1)

5-(4,5-Dihydroxazol-2-yl)-1,1-dioxidebenzo[b]thiophene

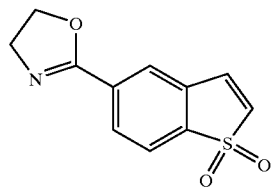

By the same procedure as described in Example 80 using the compound prepared in Example 28 (25) instead of the compound prepared in Example 72 (1), the compound of the present invention having the following physical data was obtained.

TLC: Rf 0.39 (ethyl acetate);

NMR (CDCl$_3$): δ8.10 (dd, J=7.8 Hz, 1.2 Hz, 1H), 7.97 (d, J=1.2 Hz, 1H), 7.76 (d, J=7.8 Hz, 1H), 7.25 (d, J=6.8 Hz, 1H), 6.78 (d, J=6.8 Hz, 1H), 4.50 (t, J=9.6 Hz, 2H), 4.11 (t, J=9.6 Hz, 2H).

EXAMPLES 81~81 (1)

By the same procedure as described in Example 52 using the compounds prepared in Example 45 (10) and Example 35 (63) instead of the compound prepared in Example 51, the following compounds of the present invention were obtained.

EXAMPLE 81

5-Carboxy-4-methoxy-3-phenylsulfonyl-2,3-dihydro-1,1-dioxidebenzo[b]thiophene

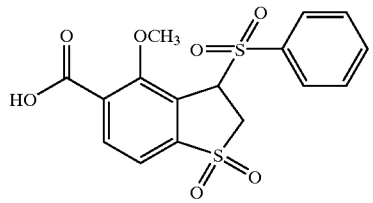

TLC: Rf 0.22 (ethyl acetate:methanol=2:1);

NMR (DMSO-d$_6$): δ7.91 (d, J=8.0 Hz, 1H), 7.86–7.74 (m, 3H), 7.68–7.61 (m, 2H), 7.56 (d, J=8.0 Hz, 1H), 5.68 (d, J=8.5 Hz, 1H), 4.19 (d, J=15.5 Hz, 1H), 4.01 (dd, J=15.5, 8.5 Hz, 1H), 3.66 (s, 3H), 3.35 (br, 1H).

EXAMPLE 81 (1)

4-Carboxy-3-phenylsulfonyl-2,3-dihydro-1,1-dioxidebenzo[b]thiophene

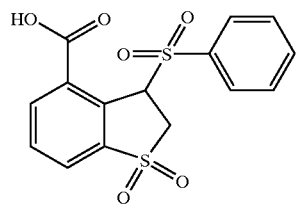

Free Compound

TLC: Rf 0.11 (chloroform:methanol=9:1);

NMR (DMSO-d$_6$): δ13.78 (s, 1H), 8.24 (d, J=7.5 Hz, 1H), 8.05 (d, J=7.8 Hz, 1H), 7.91–7.84 (m, 1H), 7.82–7.74 (m, 3H), 7.69–7.61 (m, 2H), 6.27 (dd, J=7.8, 2.1 Hz, 1), 4.20–3.95 (m, 2H).

Sodium Salt

TLC: Rf 0.11 (chloroform:methanol=9:1);

NMR (DMSO-d$_6$): δ8.22 (dd, J=7.4 Hz and 1.4 Hz, 1H), 7.95–7.85 (m, 3H), 7.85–7.70 (m, 2H), 7.70–7.55 (m, 2H), 6.62 (dd, J=8.0 Hz and 2.0 Hz, 1H), 4.10 (dd, J=15 Hz and 8.0 Hz, 1H), 3.95 (dd, J=15 Hz and 2.0 Hz, 1H).

EXAMPLE 82

4-Formyl-3-phenylsulfonyl-2,3-dihydro-1,1-dioxidebenzo[b]thiophene

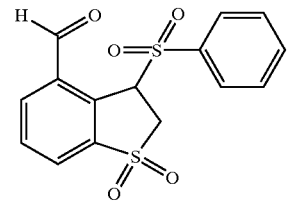

To a solution of the compound prepared in Example 45 (20) (1.46 g) in methylene chloride (40 ml), were added pyridinium dichromate (2.44 g) and magnesium sulfate (1.0 g). The mixture was stirred at room temperature for 6 hours. The undissolved ingredients were filtered off. The filtrate was poured onto 1N hydrochloric acid. The mixture was extracted by ethyl acetate. The extract was washed by a saturated aqueous solution of sodium chloride, dried over magnesium sulfate and concentrated. The residue was washed by methanol to give the compound of the present invention (1.03 g) having the following physical data.

TLC: Rf 0.65 (chloroform:methanol=9:1);

NMR (DMSO-$d_6$): δ10.29 (s, 1H), 8.29 (dd, J=7.4, 1.2 Hz, 1H), 8.16 (dd, J=7.6, 1.2 Hz, 1H), 8.03–7.92 (m, 1H), 7.86–7.72 (m, 3H), 7.71–7.57 (m, 2H), 6.41 (dd, J=8.0, 2.2 Hz, 1H), 4.08 (dd, J=15.2, 8.0 Hz, 1H), 3.97 (dd, J=15.2, 2.2 Hz, 1H).

EXAMPLES 83~83 (3)

By the same procedure as described in Example 21 using the compounds prepared in Example 73 (2), Example 73 (23), Example 28 (12) and Example 72 (5) instead of the compound prepared in Example 20 (27), the following compounds of the present invention were obtained.

EXAMPLE 83

5-Carboxymethyloxy-1,1-dioxidebenzo[b]thiophene

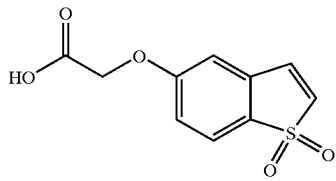

TLC: Rf 0.18 (ethyl acetate:methanol=5:1);

NMR (DMSO-$d_6$): δ7.75 (dd, J=8.3, 0.9 Hz, 1H), 7.53 (dd, J=6.9, 0.9 Hz, 1H), 7.34 (d, J=6.9 Hz, 1H), 7.16 (d, J=2.7 Hz, 1H), 7.07 (dd, J=8.3, 2.7 Hz, 1H), 4.83 (s, 2H).

EXAMPLE 83 (1)

7-Carboxymethyloxy-1,1-dioxidebenzo[b]thiophene

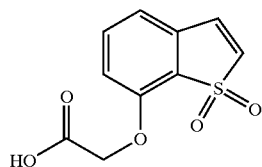

TLC: Rf 0.21 (ethyl acetate:methanol=4.1);

NMR (DMSO-$d_6$): δ7.57 (t, J=7.8 Hz, 1H), 7.51 (d, J=6.9 Hz, 1H), 7.25 (d, J=6.9 Hz, 1H), 7.11 (d, J=7.8 Hz, 2H), 4.92 (s, 2H).

EXAMPLE 83 (2)

4-((1S)-1-Carboxy-2-methylpropyl)carbamoyl-1,1-dioxidebenzo[b]thiophene

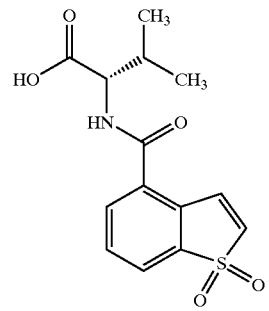

TLC: Rf 0.16 (ethyl acetate:methanol=4:1);

NMR (DMSO-$d_6$): δ8.89 (d, J=7.8 Hz, 1H), 7.97 (d, J=7.3 Hz, 1H), 7.81 (d, J=7.3 Hz, 1H), 7.77 (d, J=7.3 Hz, 1H), 7.69 (t, J=7.3 Hz, 1H), 7.48 (d, J=7.3 Hz, 1H), 4.33 (dd, J=7.8, 6.0 Hz, 1H), 2.23–2.12 (m, 1H), 0.97 (d, J=6.6 Hz, 3H), 0.96 (d, J=6.6 Hz, 3H).

EXAMPLE 83 (3)

4-((1R)-1-Carboxy-2-methylpropyl)carbamoyl-1,1-dioxidebenzo[b]thiophene

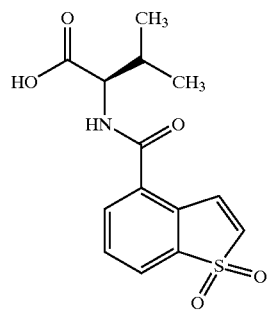

TLC: Rf 0.16 (ethyl acetate:methanol=4:1);

NMR (DMSO-$d_6$): δ8.89 (d, J=7.8 Hz, 1H), 7.97 (d, J=7.3 Hz, 1H), 7.81 (d, J=7.3 Hz, 1H), 7.77 (d, J=7.3 Hz, 1H), 7.69 (t, J=7.3 Hz, 1H), 7.47 (d, J=7.3 Hz, 1H) 4.33 (dd, J=7.8, 6.0 Hz, 1H), 2.25–2.13 (m, 1H), 0.97 (d, J=6.6 Hz, 3H), 0.96 (d, J=6.6 Hz, 3H).

EXAMPLE 84

5-(3-Carboxypropyl)oxy-1,1-dioxidebenzo[b]thiophene

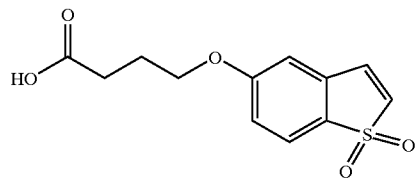

To a solution of the compound prepared in Example 73 (3) (98 mg) in dimethylsulfoxide (5.0 ml), were added phosphate buffer (pH 7.4, 25 ml) and porcine liver esterase (100 μl). The mixture was stirred at room temperature for 18 hours. The reaction mixture was poured onto 1N hydrochloric acid. The mixture was extracted by ethyl acetate. The extract was washed by a saturated aqueous solution of sodium chloride, dried over anhydrous magnesium sulfate and concentrated to give the compound of the present invention (90 mg) having the following physical data.

TLC: Rf 0.26 (chloroform:methanol=9:1);

NMR (CDCl$_3$): δ7.62 (d, J=8.4 Hz, 1H), 7.13 (d, J=6.8 Hz, 1H), 6.95 (dd, J=8.4, 2.2 Hz, 1H), 6.85 (d, J=2.2 Hz, 1H), 6.73 (d, J=6.8 Hz, 1H), 4.10 (t, J=6.2 Hz, 2H), 2.58 (t, J=7.0 Hz, 2H), 2.24–2.07 (m, 2H).

EXAMPLE 84 (1)

5-((2E)-3-Carboxy-2-propenyl)oxy-1,1-dioxidebenzo[b]thiophene

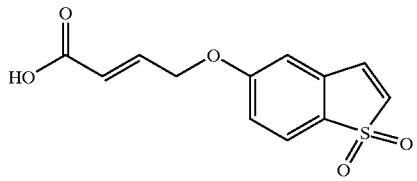

By the same procedure as described in Example 84 using the compound prepared in Example 30 (13) in stead of the compound prepared in Example 73 (3), the compound of the present invention having the following physical data was obtained.

TLC: Rf 0.14 (chloroform:methanol=9:1);

NMR (CD$_3$OD): δ7.64 (d, J=8.8 Hz, 1H), 7.38 (d, J=7.0 Hz, 1H), 7.16–7.00 (m, 3H), 6.95 (d, J=7.0 Hz, 1H), 6.13 (dt, J=15.8, 2.0 Hz, 1H), 4.89–4.80 (m, 2H).

EXAMPLE 85

5-(4-Phenylbutyl)aminomethy-4-methoxy-3-phenylsulfonyl-2,3-dihydro-1,1-dioxidebenzo[b]thiophene

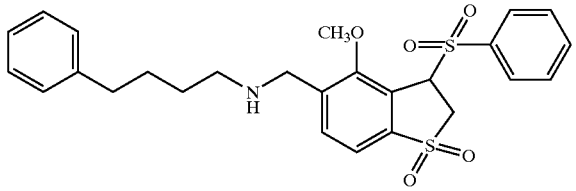

To a solution of 4-Phenylbutylamine (164 mg) and the compound prepared in Example 15 (366 mg) in methylene chloride (3.0 ml), was added sodium sulfate (1.0 g) at room temperature. The mixture was stirred for 1 hour. To the reaction mixture were added sodium borocyanohydride (63 mg), methanol (3.0 ml) and 4N solution of hydrogen chloride in dioxane (0.3 ml). The mixture was stirred at room temperature for 1 hour. The reaction mixture was concentrated. To the residue was added chloroform. The undissolved ingredients were filtered off. The filtrate was concentrated. The residue was purified with column chromatography on silica gel (chloroform:methanol=100:5) to give the compound of the present invention (340 mg) having the following physical data, and then converted into hydrochloride by a known method to give the compound of the present invention having the following physical data.

Free Compound

TLC: Rf 0.42 (chloroform:methanol=10:1);

NMR (CDCl$_3$): δ7.80–7.50 (m, 6H), 7.33–7.12 (m, 6H), 5.34 (d, J=4.8 Hz, 1H), 4.15–3.90 (m, 4H), 3.75 (s, 3H), 2.98 (t, J=7.8 Hz, 2H), 2.63 (t, J=7.8 Hz, 2H), 1.88–1.60 (m, 4H).

Hydrochloride

TLC: Rf 0.42 (chloroform:methanol=10:1);

NMR (CDCl$_3$): δ9.49 (bs, 2H), 7.93 (d, J=8.1 Hz, 1H), 7.77–7.70 (m, 2H), 7.65 (t, J=8.1 Hz, 1H), 7.50 (t, J=8.1 Hz, 2H), 7.35–7.12 (m, 6H), 5.27 (d, J=8.1 Hz, 1H), 4.18–4.02 (m, 2H), 3.98 (d, J=15.0 Hz, 1H), 3.88 (s, 3H), 3.85 (dd, J=15.0, 8.1 Hz, 1H), 3.00–2.85 (m, 2H), 2.63 (t, J=7.5 Hz, 2H), 2.00–1.60 (m, 4H).

EXAMPLE 85 (1)

5-(Pyridin-3-ylmethyl)aminomethyl-4-methoxy-3-phenylsulfonyl-2,3-dihydro-1,1-dioxidebenzo[b]thiophene

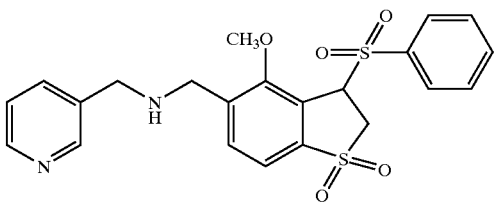

By the same procedure as described in Example 85 using the compound prepared in Example 15, and (pyridin-3-ylmethyl)amine instead of 4-phenylbutylamine, the compound of the present invention having the following physical data was obtained. And then, by converting into hydrochloride using the obtained compound by a known method, the compound of the present invention having the following physical data was obtained.

Free Compound

TLC: Rf 0.35 (chloroform:methanol=10:1);

NMR (CDCl$_3$): δ8.59 (d, J=2.0 Hz, 1H), 8.55 (dd, J=4.8, 2.0 Hz, 1H), 7.80–7.65 (m, 4H), 7.58 (d, J=6.0 Hz, 1H), 7.43 (dd, J=7.6, 2.0 Hz, 3H), 7.30 (dd, J=7.6, 4.8 Hz, 1H), 5.20 (d, J=8.2 Hz, 1H), 4.17 (d, J=13.4 Hz, 1H), 3.95–3.70 (m, 5H), 3.80 (s, 3H).

2hydrochloride

TLC: Rf 0.35 (chloroform:methanol=10:1);

NMR (DMSO-d$_6$): δ10.35 (brs, 1H), 10.15 (bs, 1H), 9.03 (s, 1H), 8.85 (d, J=5.2 Hz, 1H), 8.55 (d, J=8.4 Hz, 1H), 8.06 (d, J=8.4 Hz, 1H), 7.95–7.72 (m, 4H), 7.70–7.55 (m, 3H), 5.85–5.77 (m, 1H), 4.40–4.00 (m, 6H), 3.69 (s, 3H).

EXAMPLE 86

6-Dimethylamino-3-phenylsulfonyl-2,3-dihydro-1,1-dioxidebenzo[b]thiophene

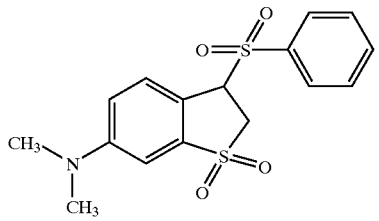

By the same procedure as described in Example 8 using the compound prepared in Example 35 (68) instead of the compound prepared in Example 7, the compound of the present invention having the following physical data was obtained.

TLC: Rf 0.48 (hexane:ethyl acetate=1:2);

NMR (DMSO-$d_6$): δ7.81–7.74 (m, 3H), 7.66–7.58 (m, 2H), 7.40 (d, J=9.0 Hz, 1H), 7.09 (dd, J=9.0, 2.5 Hz, 1H), 6.80 (d, J=2.5 Hz, 1H), 5.56 (dd, J=9.5, 3.0 Hz, 1H), 3.91 (dd, J=15.0, 9.5 Hz, 1H), 3.67 (dd, J=15.0, 3.0 Hz, 1H), 2.99 (s, 6H).

EXAMPLE 87

4-(2-Dimethylaminoethyl)carbamoyl-3-phenylsulfonyl-2,3-dihydro-1,1-dioxidebenzo[b]thiophene.hydrochloride

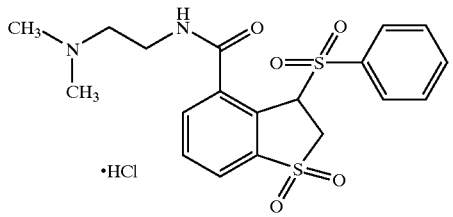

By the same procedure as described in Example 28 using the compound prepared in Example 81 (1) instead of 4-carboxy-1,1-dioxidebenzo[b]thiophene, and (2-dimethylaminoethyl)amine instead of (pyridin-3-ylmethyl)amine, and then by converting into hydrochloride by known methods, the following compound of the present invention was obtained.

TLC: Rf 0.62 (chloroform:methanol:triethylamine= 8:2:1);

NMR (DMSO-$d_6$): δ10.40–10.20 (br, 1H), 9.19 (t, J=5.4 Hz, 1H), 8.13 (d, J=6.9 Hz, 1H), 7.94 (d, J=7.5 Hz, 1H), 7.87 (d, J=7.8 Hz, 1H), 7.84–7.72 (m, 3H), 7.67–7.58 (m, 2H), 6.27 (d, J=9.0 Hz, 1H), 4.13 (dd, J=9.0, 15.0 Hz, 1H), 3.96 (d, J=15.0 Hz, 1H), 3.77–3.55 (m, 2H), 3.40–3.22 (m, 2H), 2.87–2.74 (m, 6H).

EXAMPLES 88~88 (2)

Using the compounds prepared in Example 18 (40), Example 20 (4) and Example 45 (3) instead of the compound prepared in Example 1 by the same procedure as described in Example 3 or by the same reaction using 3-chloroperbenzoic acid instead of OXONE© as an oxidizer, the following compounds of the present invention were prepared.

EXAMPLE 88

4,7-Bis(pyridin-3-ylmethyloxy)-3-phenylsulfonyl-2,3-dihydro-1,1-dioxidebenzo[b]thiophene

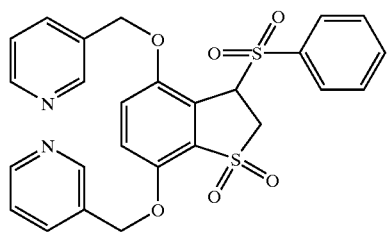

TLC: Rf 0.36 (ethyl acetate:methanol=2:1);

NMR (CDCl$_3$): δ8.65–8.60 (m, 3H), 8.57 (dd, J=5.0,1.5 Hz, 1H), 7.90–7.80 (m, 2H), 7.68–7.65 (m, 2H), 7.60–7.55 (m, 1H), 7.41–7.31 (m, 4H), 7.01 (d, J=9.0 Hz, 1H), 6.98 (d, J=9.0 Hz, 1H), 5.25 (d, J=13.0 Hz, 1H), 5.21 (dd, J=9.5, 1.0 Hz, 1H), 5.20 (d, J=13.0 Hz, 1H), 4.96 (d, J=12.0 Hz, 1H), 4.87 (d, J=12.0 Hz, 1H), 4.12 (dd, J=15.0, 1.0 Hz, 1H), 3.75 (dd, J=15.0, 9.5 Hz, 1H).

EXAMPLE 88 (1)

4-(N-Oxidepyridin-3-ylmethyl)oxy-3-phenylsulfonyl-2,3-dihydro-1,1-dioxidebenzo[b]thiophene

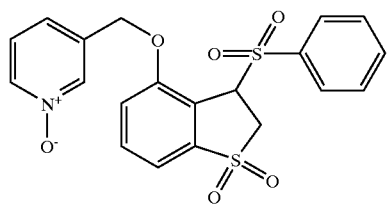

TLC: Rf 0.30 (ethyl acetate:methanol=2:1);

NMR (DMSO-$d_6$): δ8.29 (s, 1H), 8.20 (d, J=6.2 Hz, 1H), 7.73–7.57 (m, 4H), 7.51–7.31 (m, 6H), 5.77 (d, J=8.8 Hz, 1H), 5.10 (d, J=12.8 Hz, 1H), 4.90 (d, J=12.8 Hz, 1H), 4.18 (d, J=15.0 Hz, 1H), 3.95 (dd, J=15.0, 8.8 Hz, 1H).

EXAMPLE 88 (2)

4-(2-(N-Oxidepyridin-4-yl)ethyl)oxy-3-phenylsulfonyl-2,3-dihydro-1,1-dioxidebenzo[b]thiophene

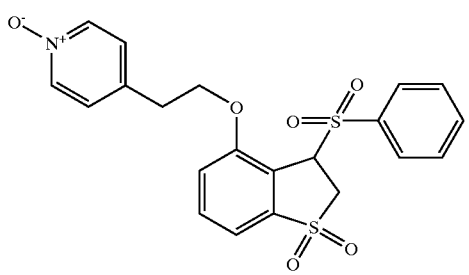

TLC: Rf 0.23 (ethyl acetate:methanol=9:1);

NMR (DMSO-$d_6$): δ8.11 (d, J=6.9 Hz, 2H), 7.79–7.72 (m, 3H), 7.65–7.60 (m, 3H), 7.34 (d, J=7.5 Hz, 1H), 7.28–7.25

(m, 3H), 5.41 (d, J=8.5 Hz, 1H), 4.16 (d, J=15.0 Hz, 1H), 4.15–3.90 (m, 2H), 4.02 (dd, J=15.0, 8.5 Hz, 1H), 2.88–2.66 (m, 2H).

EXAMPLE 89

4-methoxy-3-(4-hydroxyphenyl)thio-2,3-dihydro-1,1-dioxidebenzo[b]thiophene

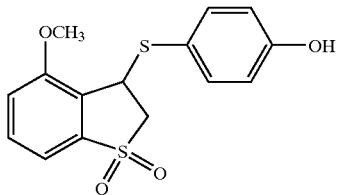

By the same procedure as describe in 1 using the compound prepared in Example 28 (27) instead of 1,1-dioxidebenzo[b]thiophene and 4-mercaptphenol instead of thiophenol, the compound of the present invention having the following physical data was obtained.

TLC: Rf 0.27 (hexane:ethyl acetate=1:1);

NMR (CDCl$_3$): δ7.60–7.00 (m, 3H), 7.35 (d, J=7.5 Hz, 2H), 6.80 (d, J=7.5 Hz, 2H), 6.00 (s, 1H), 4.90 (dd, J=5.0, 1.2 Hz, 1H), 3.90 (s, 3H), 3.75–3.50 (m, 2H).

EXAMPLE 90

4-Methoxy-3-(4-(pyridin-3-ylmethyloxy)phenyl)thio-2,3-dihydro-1,1-dioxidebenzo[b]thiophene

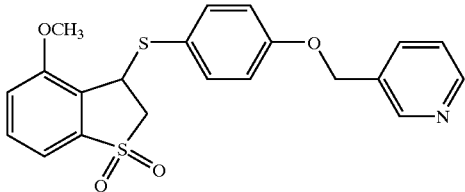

By the same procedure as described in Example 18 using the compound prepared in Example 89 instead of the compound prepared in Example 9 (12) and a halogenated compound corresponding to 4-nitrobenzylbromide, the compound of the present invention having the following physical data was obtained.

TLC: Rf 0.22 (ethyl acetate).

EXAMPLE 91

4-Methoxy-3-(4-(pyridin-3-ylmethyloxy)phenyl)sulfonyl-2,3-dihydro-1,1-dioxidebenzo[b]thiophene.hydrochloride

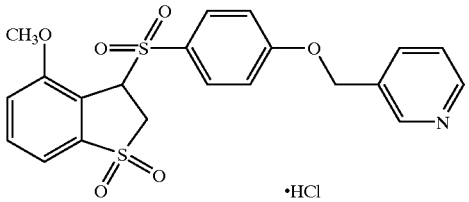

By the same procedure as described in Example 3 using the compound prepared in Example 90 instead of the compound prepared in Example 1, the compound of the present invention having the following physical data was obtained.

TLC: Rf 0.39 (ethyl acetate:triethylamine=95:5);

NMR (DMSO-d$_6$): δ9.05 (br.s, 1H), 8.90 (d, J=5.0 Hz, 1H), 8.55 (d, J=7.5 Hz, 1H), 8.00 (dd, J=7.5, 5.0 Hz, 1H), 7.80–8.60 (m, 3H), 7.50–7.15 (m, 4H), 5.60–5.40 (m, 3H), 4.20 (d, J=15 Hz, 1H), 4.00 (dd, J=15, 7.5 Hz, 1H), 3.45 (s, 3H).

EXAMPLES 92~92 (1)

By the same procedure as described in Example 1 using the compounds prepared in Example 28 (27) and Example 28 (26) instead of 1,1-dioxidebenzo[b]thiophene, and thiophenol, the following compounds of the present invention were obtained.

EXAMPLE 92

5-(2-Dimethylaminoethyl)carbamoyl-4-methoxy-3-phenylthio-2,3-dihydro-1,1-dioxidebenzo[b]thiophene

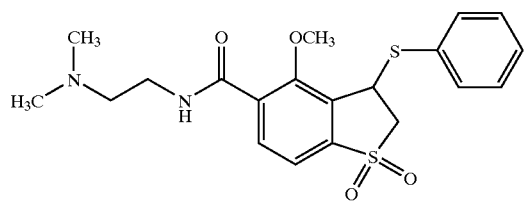

TLC: Rf 0.40 (ethyl acetate:methanol:triethylamine=8:1:1);

NMR (CDCl$_3$): δ8.10 (d, J=8.0 Hz, 1H), 7.67 (br, 1H), 7.55–7.48 (m, 3H), 7.39–7.36 (m, 3H), 5.10 (dd, J=6.5, 2.0 Hz, 1H), 4.06 (s, 3H), 3.71 (dd, J=14.0, 6.5 Hz, 1H), 3.61 (dd, J=14.0, 2.0 Hz, 1H), 3.57 (q, J=6.0 Hz, 2H), 2.53 (t, J=6.0 Hz, 2H), 2.29 (s, 6H).

EXAMPLE 92 (1)

5-(Pyridin-3-ylmethyl)carbamoyl-4-methoxy-3-phenylthio-2,3-dihydro-1,1-dioxidebenzo[b]thiophene

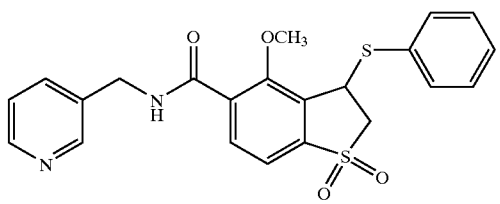

TLC: Rf 0.46 (ethyl acetate:methanol=9:1);

NMR (CDCl$_3$): δ8.60–8.52 (m, 2H), 8.06 (d, J=8.0 Hz, 1H), 7.77–7.74 (m, 2H), 7.53–7.45 (m, 3H), 7.37–7.30 (m, 4H), 5.03 (dd, J=6.5, 2.0 Hz, 1H), 4.67 (d, J=6.0 Hz, 2H), 3.92 (s, 3H), 3.70 (dd, J=14.0, 6.5 Hz, 1H), 3.58 (dd, J=14.0, 2.0 Hz, 1H).

EXAMPLE 93

4-(2-(Piperidin-1-yl)ethyl)aminomethyl-1,1-dioxidebenzo[b]thiophene

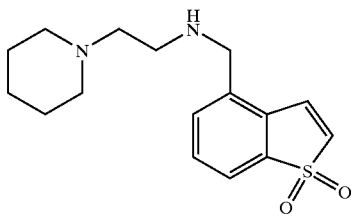

By the same procedure as described in Example 31 using 4-bromomethyl-1,1-dioxidebenzo[b]thiophene, and 1-(2-aminoethyl)piperidine instead of 2,4-dimethoxybenzylamine.hydrochloride, the compound of the present invention having the following physical data was obtained. And then, the obtained compound was converted into hydrochloride by a known method to give the compound of the present invention having the following physical data.

Free Compound
TLC: Rf 0.16 (ethyl acetate:methanol:triethylamine=90:5:5);
NMR (CDCl$_3$): δ7.75–7.60 (m, 2H), 7.60–7.40 (m, 2H), 6.70 (d, J=7.5 Hz, 1H), 3.90 (s, 2H), 2.70 (t, J=7.5 Hz, 2H), 2.50–2.20 (m, 4H), 2.40 (t, J=7.5 Hz, 2H), 1.65–1.35 (m, 6H).

2hydrochloride
TLC: Rf 0.28 (ethyl acetate:methanol:triethylamine=8:1:0.5);
NMR (DMSO-d$_6$+pyridine-d$_5$): δ8.15 (d, J=7.5 Hz, 1H), 8.00 (d, J=7.5 Hz, 1H), 7.90 (d, J=7.5 Hz, 1H), 7.70 (t, J=7.5 Hz, 1H), 7.50 (d, J=7.5 Hz, 1H), 4.40 (s, 2H), 3.55–3.30 (m, 4H), 3.30–3.10 (m, 4H), 1.90–1.70 (m, 4H), 1.65–1.50 (m, 2H).

EXAMPLE 94

4-(2-(Piperidin-1-yl)ethyl)aminomethyl-3-phenylsulfonyl-2,3-dihydro-1,1-dioxidebenzo[b]thiophene

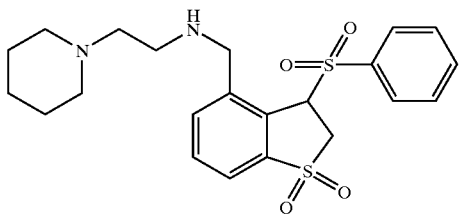

By the same procedure as described in Example 27 using the compound prepared in Example 93 instead of 5-methyl-1,1-dioxidebenzo[b]thiophene, the compound of the present invention having the following physical data was obtained. And then, the obtained compound was converted into hydrochloride by a known method to give the compound of the present invention having the following physical data.

Free Compound
TLC: Rf 0.18 (ethyl acetate:methanol:triethylamine=90:5:5);
NMR (CDCl$_3$): δ7.80–7.40 (m, 8H), 6.10 (d, J=10 Hz, 1H), 4.60 (d, J=15 Hz, 1H), 3.95 (d, J=15 Hz, 1H), 3.90 (d, J=15 Hz, 1H), 3.75 (dd, J=15, 10 Hz, 1H), 2.80–2.60 (m, 2H), 2.60–2.20 (m, 6H), 1.60–1.30 (m, 6H).

2hydrochloride
TLC: Rf 0.30 (ethyl acetate:methanol:triethylamine=8:1:0.5);
NMR (DMSO-d$_6$+pyridine-d$_5$): δ8.35 (d, J=7.5 Hz, 1H), 8.00–7.75 (m, 5H), 7.65 (t, J=7.5 Hz, 2H), 6.70 (d, J=7.5 Hz, 1H), 4.80 (d, J=15 Hz, 1H), 4.50 (d, J=15 Hz, 1H), 4.20–3.95 (m, 2H), 3.65–3.35 (m, 4H), 3.30–3.00 (m, 4H), 2.00–1.70 (m, 4H), 1.70–1.40 (m, 2H).

EXAMPLE 95

4-t-Butoxycarbonylaminobenzo[b]thiophene

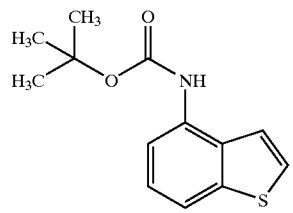

To a suspension of 4-carboxybenzo[b]thiophene (3.2 g) in t-butanol (170 ml), were added triethylamine (7.5 ml) and diphenylphosphorylamide (4.2 ml). The mixture was stirred at 95° C. for 2 hours. The precipitate was filtered off and the filtrate was concentrated. The residue was extracted with ethyl acetate. The extract was washed by water, dried over anhydrous magnesium sulfate and concentrated. The residue was purified with column chromatopgaphy on silica gel (hexane:ethyl acetate=5:1) to give the compound of the present invention (3.0 g) having the following physical data.

TLC: Rf 0.41 (hexane:ethyl acetate=3:1);
NMR (CDCl$_3$): δ7.81–7.78 (m, 1H), 7.60 (d, J=8.0 Hz, 1H), 7.44–7.24 (m, 3H), 6.74 (br, 1H), 1.55 (s, 9H).

EXAMPLE 96

4-t-Butoxycarbonylamino-1,1-dioxidebenzo[b]thiophene

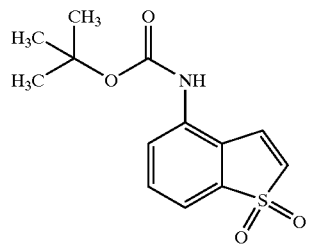

To a solution of the compound prepared in Example 95 (3.0 g) in chloroform (100 ml) was added m-chloroperbenzoic acid (8.2 g) at 0° C. The mixture was stirred at room temperature for 3 hours. The reaction mixture was concentrated. The residue was extracted with ethyl acetate. The extract was washed by an aqueous solution of sodium hydroxide, water and a saturated solution of sodium chloride successively, dried over anhydrous magnesium sulfate and concentrated. The residue was dissolved in methylene chloride and was allowed to stand overnight. The crystals that appeared were filtered. The filtrate was concentrated. The residue was purified with column chromatography on silica gel (methylene chloride), combined with the said crystals, to give the compound of the present invention (3.0 g) having the following physical data.

TLC: Rf 0.41 (hexane:ethyl acetate=1:1);

NMR (CDCl$_3$): δ7.83–7.80 (m, 1H), 7.49 (t, J=7.5 Hz, 1H), 7.46–7.43 (m, 1H), 7.31 (dd, J=7.2, 1.0 Hz, 1H), 6.70 (d, J=7.2 Hz, 1H), 6.54 (br, 1H), 1.53 (s, 9H).

EXAMPLE 97

4-Amino-1,1-dioxidebenzo[b]thiophene.hydrochloride

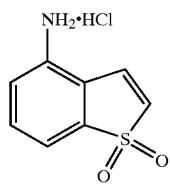

To a solution of the compound prepared in Example 96 (2.5 g) in ethyl acetate (30 ml) was added 4N solution of hydrogen chloride in ethyl acetate (10 ml). The mixture was stirred at room temperature for 3 hours. After removing the solvent, the residue was washed by ethyl acetate to give the compound of the present invention (1.8 g) having the following physical data.

TLC: Rf 0.29 (hexane:ethyl acetate=1:2);

NMR (CD$_3$OD): δ7.63 (dd, J=7.0, 1.0 Hz, 1H), 7.61 (t, J=7.5 Hz, 1H), 7.54 (dt, J=7.5, 1.0 Hz, 1H), 7.42 (dd, J=7.5, 1.0 Hz, 1H), 7.08 (d, J=7.0 Hz, 1H).

EXAMPLE 98

4-(4-Fluorobenzylcarbonylamino)-1,1-dioxidebenzo[b]thiophene

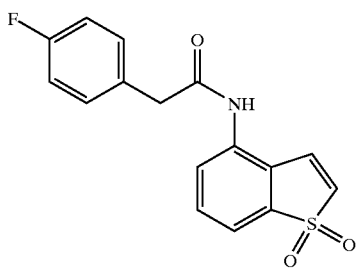

To a solution of the compound prepared in Example 97 (100 mg), 4-fluorophenylacetic acid (192 mg) and triethylamine (1 ml) in dimethylformamide (3 ml) was added propanephosphonic acid cyclic anhydride (50% solution in dimethylformamide; 3 ml). The mixture was stirred at room temperature for 1.5 hours. To the reaction mixture was added ethyl acetate. The mixture was washed by water, a saturated aqueous solution of sodium bicarbonate and a saturated aqueous solution of sodium chloride, and concentrated. The residue was purified with column chromatography on silica gel (hexane:ethyl acetate=1:1), followed by recrystallization from ethyl acetate-hexane to give the compound of the present invention having the following physical data.

TLC: Rf 0.63 (ethyl acetate);

NMR (DMSO-d$_6$): δ10.27 (s, 1H), 7.88–7.82 (m, 1H), 7.64 (d, J=7.0 Hz, 1H), 7.61–7.55 (m, 2H), 7.41–7.34 (m, 3H), 7.16 (t, J=9.0 Hz, 2H), 3.75 (s, 2H).

EXAMPLES 98 (1)–98 (5)

By the same procedure as described in Example 98 using the compound prepared in Example 97 and a carboxylic acid derivative corresponding to 4-fluorophenylacetic acid, the compounds of the present invention having the following physical data.

EXAMPLE 98 (1)

4-(Pyridin-3-ylcarbonyl)amino-1,1-dioxidebenz[b]thiophene

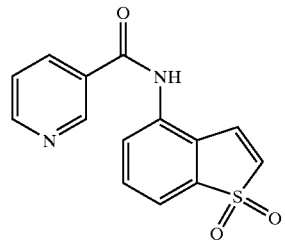

TLC: Rf 0.18 (ethyl acetate);

NMR (DMSO-d$_6$): δ10.69 (s, 1H), 9.17 (d, J=2.0 Hz, 1H), 8.80 (dd, J=5.0, 2.0 Hz, 1H), 8.34 (dt, J=7.8, 2.0 Hz, 1H), 7.82 (dd, J=7.5, 1.5 Hz, 1H), 7.72–7.63 (m, 3H), 7.60 (dd, J=7.8, 5.0 Hz, 1H), 7.36 (d, J=7.2 Hz, 1H).

EXAMPLE 98 (2)

4-(3-Chlorobenzoyl)amino-1,1-dioxidebenzo[b]thiophene

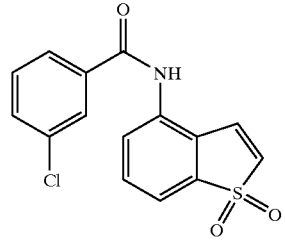

TLC: Rf 0.25 (hexane:ethyl acetate=1:1);

NMR (DMSO-d$_6$): δ10.62 (s, 1H), 8.07 (t, J=1.5 Hz, 1H), 7.96 (dt, J=7.7, 1.5 Hz, 1H), 7.78 (dd, J=7.7, 1.5 Hz, 1H), 7.73–7.64 (m, 4H), 7.60 (t, J=7.7 Hz, 1H), 7.35 (d, J=6.6 Hz, 1H).

EXAMPLE 98 (3)

4-Benzylcarbonylamino-1,1-dioxidebenzo[b]thiophene

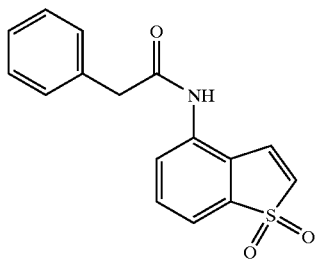

TLC: Rf 0.45 (hexane:ethyl acetate=1:2);

NMR (CDCl$_3$): δ7.75–7.72 (m, 1H), 7.48–7.35 (m, 7H), 7.29 (br, 1H), 6.79 (d, J=7.2 Hz, 1H), 6.58 (d, J=7.2 Hz, 1H), 3.79 (s, 2H).

EXAMPLE 98 (4)

4-(Dimethylaminoacetyl)amino-1,1-dioxidebenzo[b]thiophene

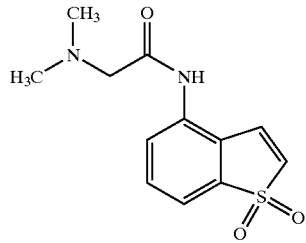

TLC: Rf 0.31 (ethyl acetate:methanol=4:1);

NMR (CDCl$_3$): δ9.52 (br, 1H), 8.06 (m, 1H), 7.56–7.48 (m, 2H), 7.28–7.25 (m, 1H), 6.73 (d, J=7.0 Hz, 1H), 3.15 (s, 2H), 2.44 (s, 6H).

EXAMPLE 98 (5)

4-Acetylamino-1,1-dioxidebenzo[b]thiophene

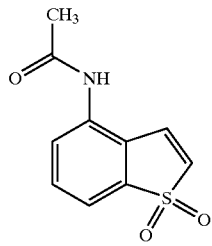

TLC: Hf 0.25 (ethyl acetate);

NMR (DMSO-d$_6$): δ10.05 (s, 1H), 7.89–7.83 (m, 1H), 7.70 (d, J=7.0 Hz, 1H), 7.61–7.55 (m, 2H), 7.33 (d, J=7.0 Hz, 1H), 2.12 (s, 3H).

EXAMPLES 99~99 (10)

By the same procedure as described in Example 28 using 4-carboxy-1,1-dioxidebenzo[b]thiophene (prepared in Example 107 hereinafter described) and a corresponding amine derivative instead of (pyridin-3-ylmethylamine, and if necessary, by converting into the corresponding salt by known methods by a known method, the compounds of the present invention having the following physical data were obtained.

EXAMPLE 99

4-(3-(2-Oxopyrrolidin-1-yl)propyl)carbamoyl-1,1-dioxidebenzo[b]thiophene

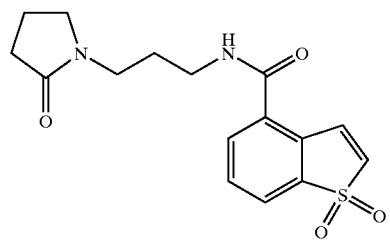

TLC: Rf 0.36 (chloroform:methanol=9:1);

NMR (CDCl$_3$): δ8.19 (dd, J=7.0 Hz and 1.0 Hz, 1H), 8.05 (broad s, 1H), 7.95 (dd, J=8.0 Hz and 1.0 Hz, 1H), 7.79 (d, J=8.0 Hz, 1H), 7.60 (t, J=8.0 Hz, 1H), 6.75 (d, J=7.0 Hz, 1H), 3.50–3.35 (m, 6H), 2.46 (t, J=8.0 Hz, 2H), 2.20–2.00 (m, 2H), 1.90–1.70 (m, 2H).

EXAMPLE 99 (1)

4-(2-Dimethylaminoethyl)carbamoyl-1,1-dioxidebenzo[b]thiophene

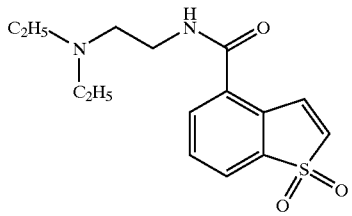

TLC: Rf 0.20 (ethyl acetate:acetic acid:water=3:1:1);

NMR (CDCl$_3$): δ8.03 (dd, J=7.2 Hz and 1.0 Hz, 1H), 7.79 (dt, J=7.8 Hz and 1.0 Hz, 1H), 7.69 (dd, J=7.8 Hz and 1.0 Hz, 1H), 7.57 (t, J=7.8 Hz, 1H), 6.77 (d, J=7.2 Hz, 1H), 3.49 (m, 2H), 2.67 (t, J=6.0 Hz, 2H), 2.58 (q, J=7.2 Hz, 4H), 1.04 (t, J=7.2 Hz, 6H).

EXAMPLE 99 (2)

4-(2-(N-Ethyl-N-(3-methylphenyl)aamino)ethyl)carbamoyl-1,1-dioxidebenzo[b]thiophene

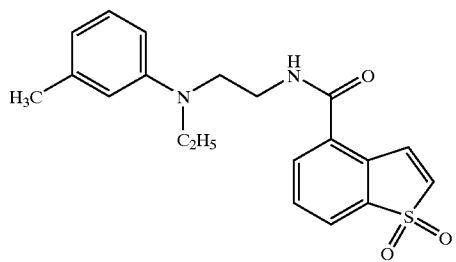

TLC: Rf 0.61 (chloroform:methanol=9:1);
NMR (CDCl$_3$): δ7.91 (d, J=7.0 Hz, 1H), 7.74 (m, 1H), 7.55–7.40 (m, 2H), 7.13 (dd, J=9.0 Hz and 7.4 Hz, 1H), 6.73 (d, J=7.0 Hz, 1H), 6.70–6.55 (m, 3H), 6.35 (broad s, 1H), 3.75–3.50 (m, 4H), 3.19 (q, J=7.0 Hz, 2H), 2.29 (s, 3H), 1.16 (t, J=7.0 Hz, 3H).

EXAMPLE 99 (3)

4-(2,4,6-Trimethoxybenzyl)carbamoyl-1,1-dioxidebenzo[b]thiophene

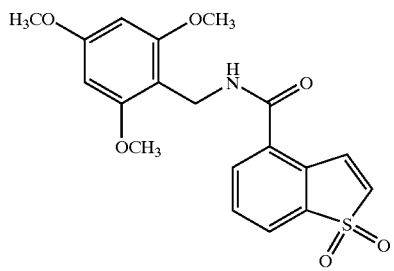

TLC: Rf 0.63 (chloroform:methanol=9:1);
NMR (CDCl$_3$+DMSO-d$_6$): δ7.89 (d, J=7.0 Hz, 1H), 7.80–7.65 (m, 3H), 7.55 (t, J=7.4 Hz, 1H), 6.88 (d, J=7.0 Hz, 1H), 6.17 (s, 2H), 4.56 (d, J=4.8 Hz, 2H), 3.84 (s, 6H), 3.82 (s, 3H).

EXAMPLE 99 (4)

4-(4-(2-Hydroxyethyl)piperazin-1-yl)carbonyl-1,1-dioxidebenzo[b]thioiphene.hydrochloride

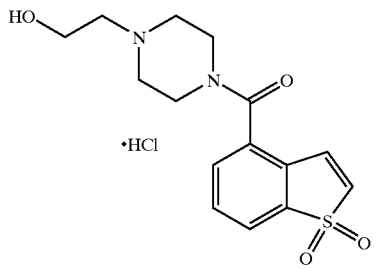

TLC: Rf 0.33 (methylene chloride:methanol=10:1);
NMR (DMSO-d$_6$): δ8.00–7.93 (m, 1H), 7.76–7.66 (m, 2H), 7.58 (d, J=6.9 Hz, 1H), 7.52 (d, J=6.9 Hz, 1H), 5.40 (bs, 1H), 4.64–4.46 (m, 1H), 6.85 3.73 (m, 2H), 3.70–3.00 (m, 10H).

EXAMPLE 99 (5)

4-(4-Benzyloxycarbonylpiperazin-1-yl)carbonyl-1,1-dioxidebenzo[b]thiophene

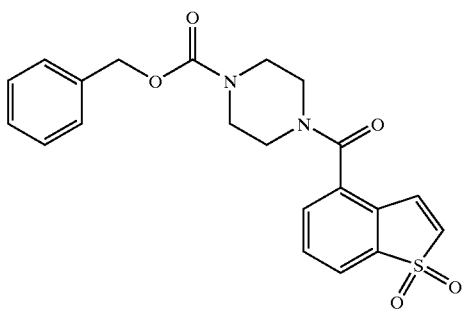

TLC: Rf 0.64 (methylene chloride:methanol=10:1);
NMR (CDCl$_3$): δ7.78 (d, J=7.5 Hz, 1H), 7.59 (t, J=7.5 Hz, 1H), 7.47 (d, J=7.5 Hz, 1H), 7.36 (s, 5H), 7.32 (d, J=6.9 Hz, 1H), 6.79 (d, J=6.9 Hz, 1H), 5.16 (s, 2H), 3.88–3.72 (m, 2H), 3.70–3.56 (m, 2 H), 3.54–3.40 (m, 2H), 3.40–3.25 (m, 2H).

EXAMPLE 99 (6)

4-(N-Ethyl-N-2-(piperidin-1-yl)ethyl)carbamoyl-1,1-dioxidebenzo[b]thiophene

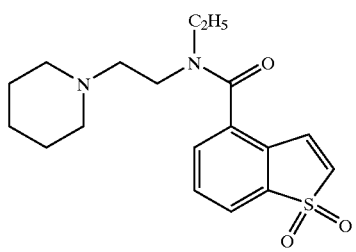

TLC: Rf 0.25 (chloroform:methanol=9:1);
NMR (CDCl$_3$): δ7.80–7.20 (m, 4H), 6.75 (d, J=6.8 Hz, 1H), 3.80–3.50 (m, 2H), 3.35–3.10 (m, 2H), 2.70–2.10 (m, 6H), 1.70–1.20 (m, 6H), 1.26 and 1.06 (each t, J=7.0 Hz, total 3H).

EXAMPLE 99 (7)

4-(3-(Imidazol-1-yl)propyl)carbamoyl-1,1-dioxidebenzo[b]thiophene

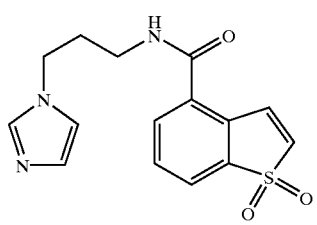

TLC: Rf 0.43 (chloroform:methanol=4:1);
NMR (CDCl$_3$): δ7.95 (d, J=7.0 Hz, 1H), 7.72 (d, J=7.6 Hz, 1H), 7.69 (d, J=7.6 Hz, 1H), 7.52 (t, J=7.6 Hz, 1H), 7.55 (broad s, 1H), 7.41 (s, 1H), 6.98 (s, 1H), 6.96 (s, 1H), 6.76 (d, J=7.0 Hz, 1H), 4.07 (t, J=6.6 Hz, 2H), 3.44 (q, J=6.6 Hz, 2H), 2.14 (m, 2H).

EXAMPLE 99 (8)

4-(N-2-(Piperidin-1-yl)ethyl-N-methyl)carbamoyl-1,1-dioxidebenzo[b]thiophene

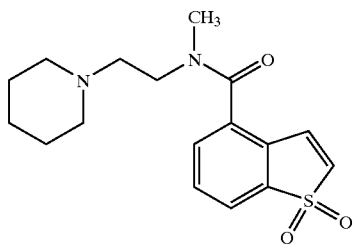

TLC: Rf 0.30 (methylene chloride:methanol=9:1);

NMR (CDCl$_3$): δ7.85–7.30 (m, 4H), 6.76 (d, J=7.2 Hz, 1H), 3.74 and 3.30 (each t, J=6.0 Hz, total 2H), 3.14 and 2.88 (each s, total 3H), 2.70–2.10 (m, 6H), 1.70–1.30 (m, 6H).

EXAMPLE 99 (9)

4-(4-(1,3-Dioxaindan-5-ylmethyl)piperazin-1-yl)carbonyl-1,1-dioxidebenzo[b]thiophene

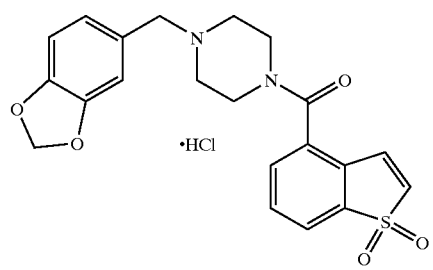

TLC: Rf 0.26 (ethyl acetate);

NMR (DMSO-d$_6$): δ8.00–7.92 (m, 1H), 7.74–7.65 (m, 2H), 7.56 (d, J=6.9 Hz, 1H), 7.52 (d, J=6.9 Hz, 1H), 7.21 (s, 1H), 7.03–6.95 (m, 2H), 6.07 (s, 2H), 4.64–4.50 (m, 1H), 4.28–4.15 (m, 2H), 3.70–2.96 (m, 8H).

EXAMPLE 99 (10)

4-(4-((2E)-3-Phenyl-2-propenyl)piperazin-1-yl)carbonyl-1,1-dioxidebenzo[b]thiophene.hydrochloride

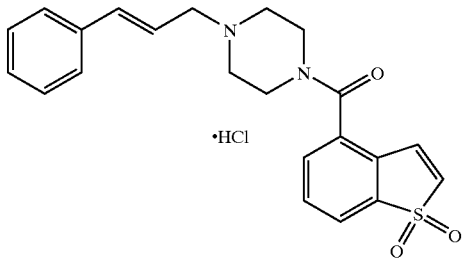

TLC: Rf 0.10 (ethyl acetate);

NMR (DMSO-d$_6$): δ8.00–7.92 (m, 1H), 7.76–7.65 (m, 2H),7.58 (d, J=6.9 Hz, 1H), 7.53–7.46 (m, 2H),7.51 (d, J=6.9 Hz, 1H), 7.45–7.28 (m, 3H), 6.84 (d, J=15.3 Hz, 1H), 6.47–6.33 (m, 1H), 4.60 (m,1H), 3.98–3.84 (m, 2H), 3.70–2.97 (m, 8H).

EXAMPLES 100~100 (24)

By the same procedure as described in Example 28 using the compound prepared in Example 81 (1) instead of 4-carboxy-1,1-dioxidebenzo[b]thiophene, and an amine derivative instead of (pyridin-3-yl)ethylamine, and if necessary, by converting into the corresponding salt by a known method, the following compounds of the present invention having the following physical data were obtained.

EXAMPLE 100

4-(Furan-2-ylmethyl)carbamoyl-3-phenylsulfonyl-2,3-dihydro-1,1-dioxidebenzo[b]thiophene

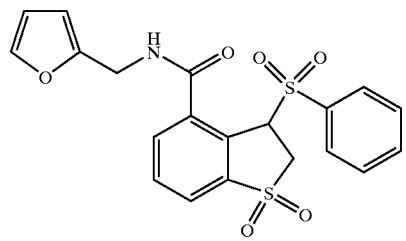

TLC: Rf 0.43 (hexane:ethyl acetate=1:2);

NMR (DMSO-d$_6$): δ9.29 (t, J=5.5 Hz, 1H), 7.99 (d, J=7.6 Hz, 1H), 7.95 (d, J=7.6 Hz, 1H), 7.83 (t, J=7.6 Hz, 1H), 7.79–7.76 (m, 3H), 7.67–7.60 (m, 3H), 6.48–6.35 (m, 2H), 6.25 (d, J=9.0 Hz, 1H), 4.55 (dd, J=15.5, 5.5 Hz, 1H), 4.40 (dd, J=15.5, 5.5 Hz, 1H), 4.10 (dd, J=15.3, 9.0 Hz, 1H), 4.00 (d, J=15.3 Hz, 1H).

EXAMPLE 100 (1)

4-(2,4,6-Trimethoxybenzyl)carbamoyl-3-phenylsulfonyl-2,3-dihydro-1,1-dioxidebenzo[b]thiophene

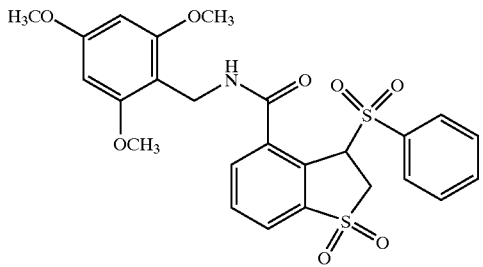

TLC: Rf 0.55 (ethyl acetate);

NMR (DMSO-d$_6$): δ8.40 (t, J=4.8 Hz, 1H), 7.89–7.86 (m, 2H), 7.86–7.69 (m, 4H), 7.67–7.58 (m, 2H), 6.25 (s, 2H), 6.18 (dd, J=8.1, 2.1 Hz, 1H), 4.46–4.30 (m, 2H), 4.11–3.94 (m, 2H), 3.77 (s, 9H).

EXAMPLE 100 (2)

4-(3-(2-Oxopyrrolidin-1-yl)propyl)carbamoyl-3-phenylsulfonyl-2,3-dihydro-1,1-dioxidebenzo[b]thiophene

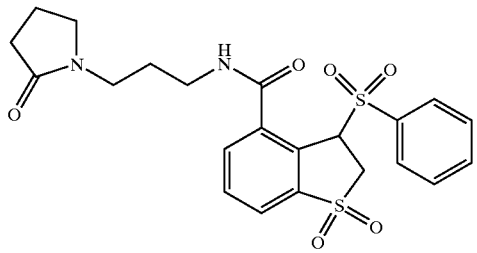

TLC: Rf 0.44 (ethyl acetate:methanol=2:1);

NMR (CDCl$_3$): δ8.20–8.08 (m, 1H), 8.02 (d, J=7.5 Hz, 1H), 7.83–7.62 (m, 5H), 7.59–7.49 (m, 2H), 6.40 (dd, J=9.3, 1.2 Hz, 1H), 3.89–3.61 (m, 4H), 3.51–3.33 (m, 2H), 3.32–3.20 (m, 1H), 3.20–3.06 (m, 1H), 2.53–2.33 (m, 2H), 2.15–1.88 (m, 3H), 1.85–1.74 (m, 1H).

EXAMPLE 100 (3)

4-((3S)-1-Benzylpyrrolidin-3-yl)carbamoyl-3-phenylsulfonyl-2,3-dihydro-1,1-dioxidebenzo[b]thiophene

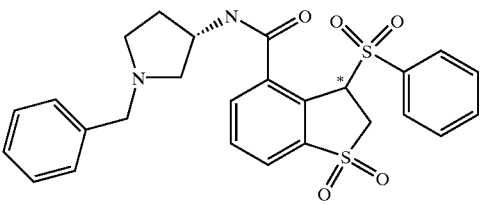

More Polar Compound

TLC: Rf 0.27 (methanol:ethyl acetate:triethylamine= 1:8:0.05);

NMR (CDCl$_3$): δ7.90–7.80 (m, 4H), 7.75–7.66 (m, 2H), 7.62–7.53 (m, 2H), 7.37–7.13 (m, 5H), 6.70 (d, J=8.7 Hz, 1H), 6.24–6.17 (m, 1H), 4.74–4.62 (m, 1H), 3.80 (dd, J=15.0, 1.5 Hz, 1H), 3.68 (d, J=12.9 Hz, 1 H), 3.63 (dd, J=15.0, 9.3 Hz, 1H), 3.57 (d, J=12.9 Hz, 1H), 3.00–2.86 (m, 2H), 2.72 (dd, J=9.9, 6.3 Hz, 1H), 2.51–2.31 (m, 2H), 1.89–1.77 (m, 1H).

Less Polar Compound

TLC: Rf 0.35 (methanol:ethyl acetate:triethylamine= 1:8:0.05);

NMR (CDCl$_3$): δ7.94–7.87 (m, 2H), 7.87–7.78 (m, 2H), 7.75–7.66 (m, 2H), 7.64–7.56 (m, 2H), 7.41–7.23 (m, 5H), 6.73 (d, J=8.1 Hz, 1H), 6.28–6.21 (m, 1H), 4.71–4.59 (m, 1H), 3.80 (dd, J=14.7, 1.2 Hz, 1H), 3.64 (s, 2H), 3.62 (dd, J=14.7, 9.3 Hz, 1H), 2.95–2.84 (m, 2H), 2.80–2.67 (m, 2H), 2.46–2.30 (m, 2H), 2.12–1.95 (m, 1H).

The determination of the absolute configuration of * is not performed, but the said more polar and less polar isomers are each single optically active compounds.

EXAMPLE 100 (4)

4-(2-(Pyrrolidin-1-yl)ethyl)carbamoyl-3-phenylsulfonyl-2,3-dihydro-1,1-dioxidebenzo[b]thiophene

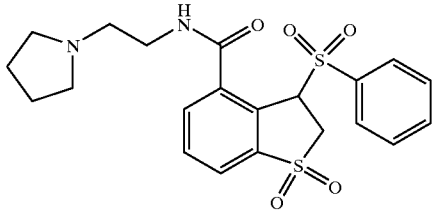

Free Compound

TLC: Rf 0.33 (ethyl acetate:methanol:triethylamine= 4:2:0.5);

NMR (CDCl$_3$): δ7.93–7.78 (m, 4H), 7.75–7.66 (m, 2H), 7.63–7.53 (m, 2H), 7.10 (brs, 1H), 6.31–6.24 (m, 1H), 3.83 (dd, J=15.0, 1.5 Hz , 1H), 3.73–3.49 (m ,3H), 2.80 (t, J=5.7 Hz, 2H), 2.69–2.53 (m, 4H), 1.86–1.73 (m, 4H).

Hydrochloride

TLC: Rf 0.37 (ethyl acetate methanol:triethylamine= 4:2:0.5);

NMR (DMSO-d$_6$): δ9.18 (t, J=5.4 Hz, 1H), 8.14 (d, J=7.5 Hz, 1H), 7.96–7.90 (m, 1H), 7.85 (t, J=7.5 Hz, 1H), 7.81–7.72 (m, 3H), 7.67–7.58 (m, 2H), 6.27 (d, J=9.3 Hz, 1H), 4.13 (dd, J=15.6, 9.3 Hz, 1H), 3.96 (d, J=15.6 Hz, 1H), 3.78–3.50 (m, 4H), 3.48–3.28 (m, 2H), 3.06–2.94 (m, 2H), 2.09–1.78 (m, 4H).

EXAMPLE 100 (5)

4-(2-Diethylaminoethyl)carbamoyl-3-phenylsulfonyl-2,3-dihydro-1,1-dioxidebenzo[b]thiophene

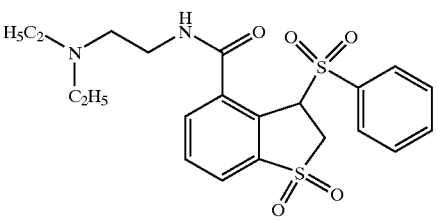

Free Compound

TLC: Rf 0.47 (ethyl acetate:methanol:triethylamine= 4:2:0.5);

NMR (CDCl$_3$): δ7.92–7.80 (m, 4H), 7.76–7.66 (m, 2H), 7.62–7.56 (m, 2H), 7.03 (brs, 1H), 6.29 (dd, J=9.0, 1.5 Hz, 1H), 3.84 (dd, J=14.4, 1.5 Hz, 1H), 3.72–3.44 (m, 3H), 2.73 (t, J=6.0 Hz, 2H), 2.60 (q, J=7.2 Hz, 4H), 1.04 (t, J=7.2 Hz, 6).

Hydrochloride

TLC: Rf 0.49 (ethyl acetate:methanol:triethylamine= 4:2:0.5);

NMR (DMSO-d$_6$): δ10.32 (brs, 1H), 9.30–9.20 (m, 1H), 8.08 (d, J=7.5 Hz, 1H), 7.94 (d, J=7.5 Hz, 1H), 7.86 (t, J=7.5 Hz, 1H), 7.82–7.72 (m, 3H), 7.68–7.58 (m, 2H), 6.29 (d, J=9.3 Hz, 1H), 4.12 (dd, J=15.6, 9.3 Hz, 1H), 3.96 (d, J=15.6 Hz, 1H), 3.80–3.57 (m, 2H), 3.40–3.08 (m, 6H), 1.24 (t, J=7.2 Hz, 6H).

EXAMPLE 100 (6)

4-(2-(N-Ethyl-N-(3-methylphenyl)amino)ethyl)carbamoyl-3-phenylsulfonyl-2,3-dihydro-1,1-dioxidebenzo[b]thiophene

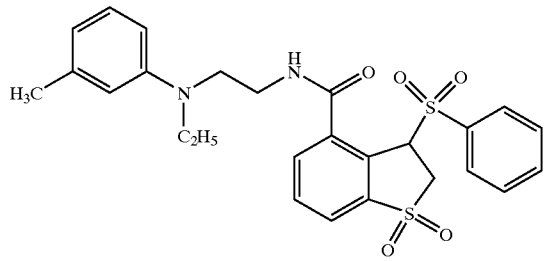

Free Compound

TLC: Rf 0.49 (ethyl acetate:triethylamine=6:0.5);

NMR (CDCl₃): δ7.94–7.87 (m, 2H), 7.82 (d, J=6.9 Hz, 1H), 7.75–7.67 (m, 1H), 7.67–7.54 (m, 4H), 7.17–7.11 (m, 1H), 6.72–6.64 (m, 2H), 6.56 (d, J=7.8 Hz, 1H), 6.49 (brs, 1H), 6.26 (dd, J=9.0, 1.2 Hz, 1H), 3.81 (dd, J=14.7, 1.2 Hz, 1H), 3.77–3.47 (m, 5H), 3.43 (q, J=7.2 Hz, 2H), 2.30 (s, 3H), 1.15 (t, J=7.2 Hz, 3H).

Hydrochloride

TLC: Rf 0.47 (ethyl acetate:triethylamine=6:0.5);

NMR (CD₃OD): δ7.98–7.60 (m, 6H), 7.59–7.26 (m, 6H), 6.36–6.15 (m, 1H), 4.09–3.89 (m, 4H), 3.88–3.40 (m, 4H), 2.44 (s, 3H), 1.17 (t, J=7.2 Hz, 3H).

EXAMPLE 100 (7)

4-(N-Ethyl-N-2-(piperdin-1-yl)ethyl)carbamoyl-3-phenylsulfonyl-2,3-dihydro-1,1-dioxidebenzo[b]thiophene

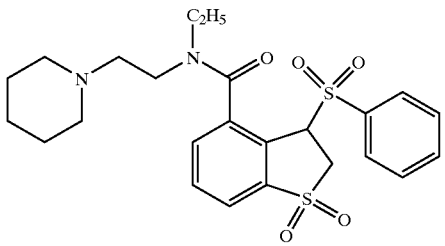

Free Compound

TLC: Rf 0.29 (methylene chloride:methanol=6:1);

NMR (CDCl₃): δ8.00–7.55 (m, 8H), 5.85 (d, J=8 Hz, 1H), 3.85–3.30 (m, 6H), 2.85–2.50 (m, 2H), 2.55 (m, 2H), 2.40 (m, 2H), 1.80–1.40 (m, 6H), 1.34 and 1.36 (each t, J=7 Hz, total 3H).

Hydrochloride

TLC: Rf 0.29 (methylene chloride:methanol=6:1);

NMR (CDCl₃+DMSO-d₆): δ11.30 (broad s, 1H), 7.95–7.60 (m, 8H), 5.89 (d, J=8 Hz, 1H), 4.20–3.80 (m, 3H), 3.80–3.20 (m, 7H), 3.00 (m, 2H), 2.11 (m, 2.00 (m, 3H), 1.50 (m, 1H), 1.41 (t, J=7 Hz, 3H).

EXAMPLE 100 (8)

4-(3-(Imidazol-1-yl)propyl)carbamoyl-3-phenylsulfonyl-2,3-dihydro-1,1-dioxidebenzo[b]thiophene

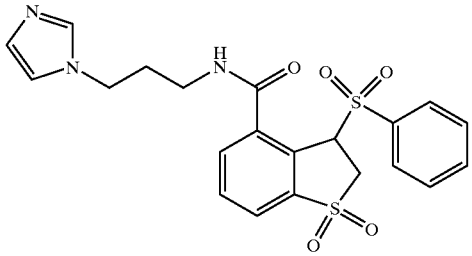

Free Compound

TLC: Rf 0.50 (methylene chloride:methanol=4:1);

NMR (CDCl₃): δ7.90–7.50 (m, 9H), 7.56 (s, 1H), 6.98 (s, 1H), 6.93 (s, 1H), 6.27 (dd, J=2 Hz and 7 Hz, 1H), 4.20–3.95 (m, 2H), 3.80–3.55 (m, 3H), 3.30 (m, 1H), 2.13 (m, 2H).

Hydrochloride

TLC: Rf 0.50 (methylene chloride:methanol=4:1);

NMR (CDCl₃+DMSO-d₆): δ9.59 (s, 1H), 9.49 (t-like, 1H), 8.23 (t, J=4.4 Hz, 1H), 7.85–7.60 (m, 5H), 7.60–7.40 (m, 4H), 7.29 (s, 1H), 6.23 (dd, J=4.0 Hz and 6.8 Hz,1H), 4.65–4.35 (m, 2H), 3.82 (m, 2H), 3.65 (m, 1H), 3.25 (m, 1H), 2.40 (m, 1H), 2.20 (m, 1H).

EXAMPLE 100 (9)

4-((3R)-1-Benzylpyrrolidin-3-yl)carbamoyl-3-phenylsuilfonyl-2,3-dihydro-1,1-dioxidebenzo[b]thiophene

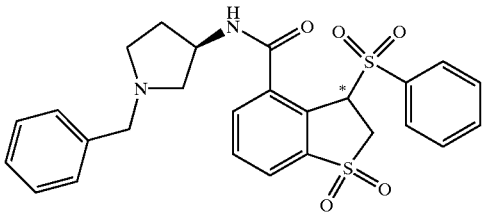

Less Polar Compound

TLC: Rf 0.35 (methanol:ethyl acetate:triethylamine= 1:8:0.05);

NMR (CDCl₃): δ7.94–7.87 (m, 2H), 7.87–7.78 (m, 2H), 7.75–7.67 (m, 2H), 7.64–7.56 (m, 2H), 7.38–7.26 (m, 5H), 6.68 (d, J=8.1 Hz, 1H), 6.28–6.20 (m, 1H), 4.73–4.59 (m, 1H), 3.80 (dd, J=14.7, 1.5 Hz, 1H), 3.66 (s, 2H), 3.63 (dd, J=14.7, 9.3 Hz, 1H), 2.96–2.87 (m, 1H), 2.82–2.66 (m, 2H), 2.47–2.30 (m, 2H), 2.12–1.86 (m, 1H).

More Polar Compound

TLC: Rf 0.27 (methanol:ethyl acetate:triethylamine= 1:8:0.05);

NMR (CDCl₃): δ7.90–7.78 (m, 4H), 7.74–7.65 (m, 2H), 7.62–7.52 (m, 2H), 7.36–7.13 (m, 5H), 6.79 (d, J=8.4 Hz, 1H), 6.25–6.18 (m, 1H), 4.72–4.60 (m, 1H), 3.80 (dd, J=15.0, 1.5 Hz, 1H), 3.65 (d, J=12.9 Hz, 1 H), 3.62 (dd, J=15.0, 9.0 Hz, 1H), 3.54 (d, J=12.9 Hz, 1H), 2.96–2.83 (m, 2H), 2.72 (dd, J=9.9, 6.3 Hz, 1H), 2.49–2.32 (m, 2H), 1.90–1.73 (m, 1H).

The determination of the absolute configuration of * is not performed, but the said more polar and less polar isomers are each single optically active compounds.

EXAMPLE 100 (10)

4-(3-(Pyrrolidin-1-yl)propy)carbamoyl-3-phenylsulfonyl-2,3-dihydro-1,1-dioxidebenzo[b]thiophene

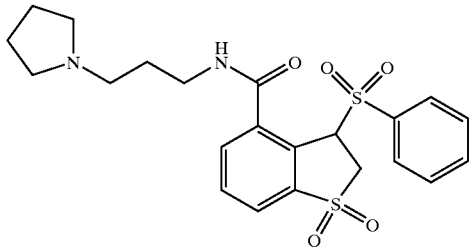

Free Compound

TLC: Rf 0.25 (methanol:ethyl acetate:triethylamine= 2:4:0.5);

NMR (CDCl$_3$): δ9.16–9.06 (m, 1H), 7.91–7.84 (m, 2H), 7.84–7.77 (m, 2H), 7.75–7.62 (m, 2H), 7.61–7.53 (m, 2H), 6.44–6.37 (m, 1H), 3.85 (dd, J=14.7, 1.2 Hz, 1H), 3.80–3.61 (m, 2H), 3.59–3.44 (m, 1H), 2.91–2.72 (m, 2H), 2.71–2.59 (m, 4H), 2.00–1.63 (m, 6H).

Hydrochloride

TLC: Rf 0.26 (methanol:ethyl acetate:triethylamine= 2:4:0.5);

NMR (DMSO-d$_6$): δ10.43 (brs, 1H), 9.00 (t, J=5.7 Hz, 1H), 8.02 (d, J=7.5 Hz, 1H), 7.94 (d, J=7.5 Hz, 1H), 7.90–7.74 (m, 4H), 7.71–7.61 (m, 2H), 6.30 (d, J=9.0 Hz, 1H), 4.11 (dd, J=15.0, 9.0 Hz, 1H), 3.94 (d, J=15.0 Hz, 1H), 3.60–3.10 (m, 6H), 3.10–2.78 (m, 2H), 2.11–1.73 (m, 6H).

EXAMPLE 100 (11)

4-(N-2-(Piperidin-1-yl)ethyl-N-methyl)carbamoyl-3-phenylsulfonyl-2,3-dihydro-1,1-dioxidebenzo[b]thiophene

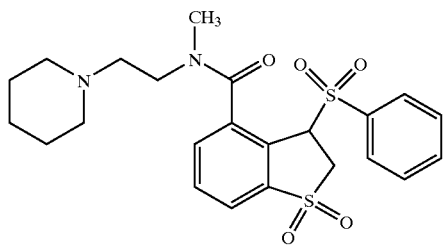

Free Compound

TLC: Rf 0.29 (methylene chloride:methanol=6:1);

NMR (CDCl$_3$): δ8.05–7.55 (m, 8H), 5.88 (dd, J=8.8 Hz and 2.0 Hz, 1H), 4.00–3.55 and 3.30 (each m, total 4H), 3.20 and 3.17 (each s, total 3H), 2.80–2.35 (m, 6H), 1.70–1.40 (m, 6H).

Hydrochloride

TLC: Rf 0.29 (methylene chloride:methanol=6:1);

NMR (DMSO-d$_6$): δ10.49 (broad s, 1H), 8.15 (d, J=6.2 Hz, 1H), 8.00–7.60 (m, 7H), 5.87 (d, J=8.8 Hz, 1H), 4.25–3.70 (m, 4H), 3.70–2.80 (m, 6H), 3.33 and 3.16 (each s, total 3H), 2.00–1.60 (m, 5H), 1.44 (m, 1H).

EXAMPLE 100 (12)

4-(3,5-Dimethoxybenzyl)carbamoyl-3-phenylsulfonyl-2,3-dihydro-1,1-dioxidebenzo[b]thiophene

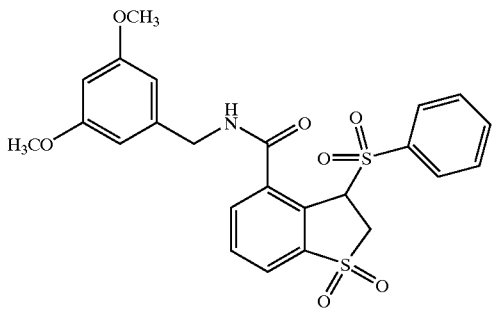

TLC: Rf 0.45 (methylene chloride:ethyl acetate=4:1);

NMR (DMSO-d$_6$): δ9.26 (t, J=5.8 Hz, 1H), 7.78 (d, J=7.6 Hz, 1H), 7.91 (dd, J=7.6, 1.0 Hz, 1H), 7.84 (dd, J=7.0, 1.0 Hz, 1H), 7.13 (t, J=7.6 Hz, 1H), 7.45 (d, J=7.0Hz, 1H), 6.51 (d, J=2.2 Hz, 2H), 6.39 (t, J=2.2Hz, 1H), 4.42 (d, J=5.8 Hz, 2H), 3.73 (s, 6H).

EXAMPLE 100 (13)

4-(3-(Piperidin-1-yl)propyl)carbamoyl-3-phenylsulfonyl-2,3-dihydro-1,1-dioxidebenzo[b]thiophene hydrochloride

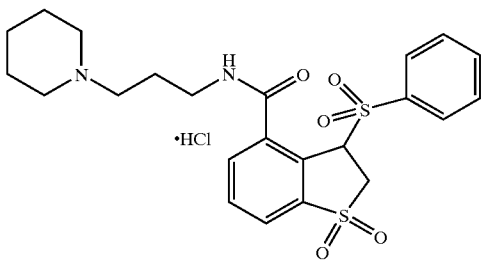

TLC: Rf 0.30 (ethyl:acetate methanol:triethylamine= 8:1.5:0.5);

NMR (DMSO-d$_6$): δ10.40 (broad s, 1H), 9.08 (t, J=5.3 Hz, 1H), 8.10–7.60 (m, 8H), 6.33 (d, J=9.2 Hz, 1H), 4.13 (dd, J=15.0 Hz and 9.2 Hz, 1H), 3.94 (d, J=15.0 Hz, 1H), 3.60–3.00 (m, 6H), 2.80 (m, 2H), 2.05 (t, J=6.5 Hz, 2H), 1.73 (m, 5H), 1.36 (m, 1H).

EXAMPLE 100 (14)

4-(2-Diisopropylaminoethyl)carbamoyl-3-phenylsulfonyl-2,3-dihydro-1,1-dioxidebenzo[b]thiophene.hydrochloride

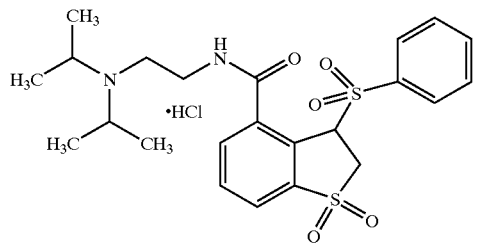

TLC: Rf 0.46 (ethyl acetate:methanol:triethylamine= 8:1.5:0.5);

NMR (DMSO-$d_6$): δ10.01 (s, 1H), 9.27 (t, J=5.7 Hz, 1H), 8.09 (d, J=7.0 Hz, 1H), 7.97 (d, J=7.0 Hz, 1H), 7.88 (t, J=7.0 Hz, 1H), 7.80–7.76 (m, 3H), 7.68–7.60 (m, 2H), 6.36 (d, J=9.0Hz, 1H), 4.11 (dd, J=15.3Hz and 9.0 Hz, 1H), 3.96 (d, J=15.3 Hz, 1H), 3.90–3.60 (m, 4H), 3.33 (m, 1H), 3.18 (m, 1H), 1.42 (d, J=6.6 Hz, 3H), 1.38 (d, J=6.6 Hz, 3H), 1.34 (d, J=6.6 Hz, 3H), 1.32 (d, J=6.6 Hz, 3H).

EXAMPLE 100 (15)

4-(2-(Morpholin-4-yl)ethyl)carbamoyl-3-phenylsulfonyl-2,3-dihydro-1,1-dioxidebenzo[b]thiophene.hydrochloride

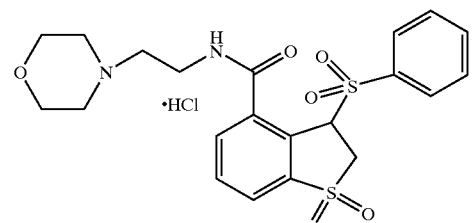

TLC: Rf 0.33 (ethyl acetate:methanol:triethylamine= 8:1.5:0.5);

NMR (DMSO-$d_6$): δ11.14 (broad s, 1H), 9.27 (broad t-like, 1H), 8.13 (d, J=7.5 Hz, 1H), 7.93 (d, J=7.5 Hz, 1H), 7.86 (t, J=7.5 Hz, 1H), 7.82–7.70 (m, 3H), 7.70–7.60 (m, 2H), 6.30 (d, J=8.4 Hz, 1H), 4.14 (dd, J=15.6 Hz and 8.4 Hz, 1H), 4.00–3.65 (m, 7H), 3.65–3.00 (m, 6H).

EXAMPLE 100 (16)

4-(N-2-(Piperidin-1-yl)ethyl-N-propyl)carbamoyl-3-phenylsulfonyl-2,3-dihydro-1,1-dioxidebenzo[b]thiophene.hydrochloride

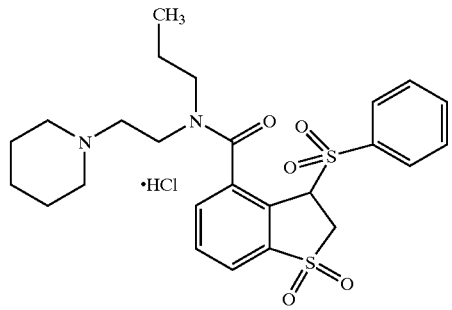

TLC: Rf 0.47 (ethyl acetate:methanol:triethylamine= 8:1.5:0.5);

NMR (DMSO-$d_6$): δ10.70 and 10.66 (each broad s, total 1H), 8.00–7.65 (m, 8H), 5.83 (d, J=8.7 Hz, 1H), 4.14 (dd, J=15.3 Hz and 8.7 Hz, 1H), 4.00–3.70 (m, 3H), 3.65–3.10 (m, 6H), 3.10–2.80 (m, 2H), 2.00–1.60 (m, 6H), 1.40 (m, 1H), 0.98 and 0.86 (each t, J=7.2 Hz, total 3H).

EXAMPLE 100 (17)

4-(N-2-(Piperidin-1-yl)ethyl-N-isopropyl)carbamoyl-3-phenylsulfonyl-2,3-dihydro-1,1-dioxidebenzo[b]thiophene.hydrochloride

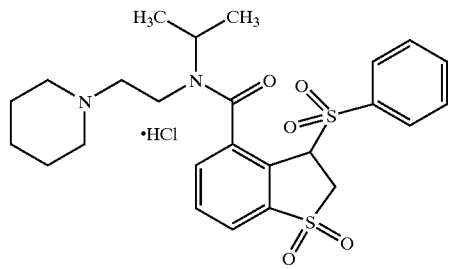

TLC;Rf 0.55 (ethyl acetate:methanol:triethylamine= 8:1.5:0.5);

NMR (DMSO-$d_6$): δ10.78 (broad s, 1H), 8.00–7.60 (m, 8H), 5.90 (d, J=9.2 Hz, 1H), 4.40–4.03 (m, 3H), 4.00–2.80 (m, 8H), 2.00–1.60 (m, 5H), 1.40 (m, 1H), 1.44 and 1.28 and 1.04 (each d, J=6.4 Hz, total 6H).

EXAMPLE 100 (18)

4-(4-Benzoylpiperazin-1-yl)carbonyl-3-phenylsulfonyl-2,3-dihydro-1,1-dioxidebenzo[b]thiophene

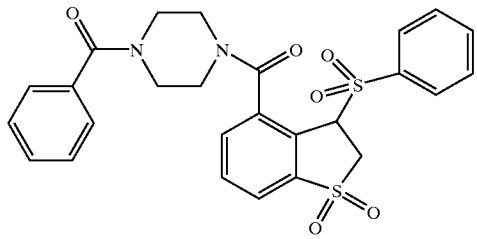

TLC: Rf 0.48 (methylene chloride:methanol=10 1);

NMR (DMSO-$d_6$): δ7.95–7.80 (m, 3H), 7.80–7.56 (m, 5H), 7.42 (s, 5H), 5.92 (dd, J=9.0, 1.5 Hz, 1H), 4.40–4.00 (m, 2H), 3.90–3.40 (m, 6H), 3.72 (dd, J=15.0, 1,5 Hz, 1H), 3.65 (dd, J=15.0, 9.0 H z, 1 H).

EXAMPLE 100 (19)

4-(4-(4-Ethylbenzyl)piperazin-1-yl)carbonyl-3-phenylsulfonyl-2,3-dihydro-1,1-dioxidebenzo[b]thiophene.hydrochloride

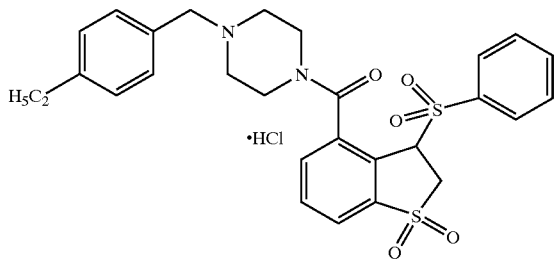

TLC: Rf 0.55 (methylene chloride:methanol=10:1);

NMR (DMSO-$d_6$): δ7.88–7.73 (m, 6H), 7.67–7.63 (m, 2H), 7.47 (d, J=7.0 Hz, 2H), 7.21 (d, J=7.0 Hz, 2H), 5.87 (dd, J=10.0, 1.5 Hz, 1H), 4.16 (bs, 2H), 4.05 (dd, J=15.0, 10.0 HZ, 1H), 3.79 (dd, J=15.0, 1.5 Hz, 1H), 3.30–2.90 (m, 8H), 2.58 (q, J=8.0 Hz, 2H), 1.17 (t, J=8.0 Hz, 3H).

EXAMPLE 100 (20)

4-(4-((4-Phenylbenzyl)piperazin-1-yl)carbonyl-3-phenylsulfonyl-2,3-dihydro-1,1-dioxidebenzo[b]thiophene.hydrochloride

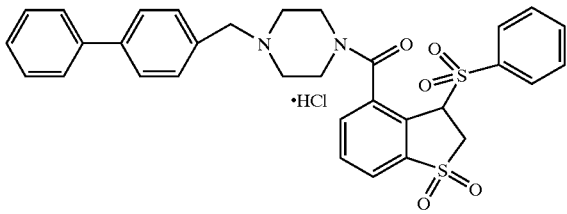

TLC: Rf 0.55 (methylene chloride:methanol=10:1);

NMR (DMSO-$d_6$): δ7.88–7.78 (m, 3H), 7.78–7.72 (m, 3H), 7.67–7.58 (m, 7H), 7.48–7.41 (m, 3H), 7.38–7.34 (m, 1H), 5.88 (d, J=9.5 Hz, 1H), 4.21 (bs, 2H), 4.10–3.70 (m, 8H), 4.06 (dd, J=15.5, 9.5 Hz, 1H), 3.79 (d 15.5 Hz, 1H), 3.19 (s, 2H).

EXAMPLE 100 (21)

4-(4-(1,3-Dioxaindan-5-ylmethyl)piperazin-1-yl)carbonyl-3-phenylsulfonyl-2,3-dihydro-1,1-dioxidebenzo[b]thiophene.hydrochloride

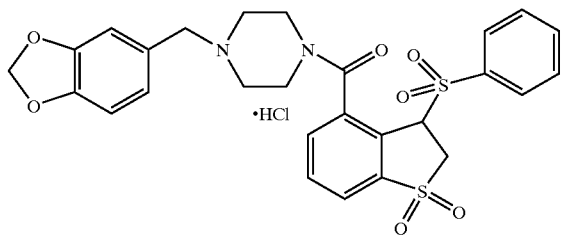

TLC: Rf0.54 (methylene chloride:methanol=10:1);

NMR (DMSO-$d_6$): δ7.86–7.76 (m, 4H), 7.74 (d, J=8.0 Hz, 2H), 7.64 (t, J=8.0 Hz, 2H), 7.08 (bs, 1H), 6.98–6.92 (m, 1H), 6.83 (d, J=8.0 Hz, 1H), 5.96–5.92 (m, 2H), 5.86 (d, J=8.5 Hz, 1H), 4.15–3.70 (m, 2H), 4.04 (dd, J=15.0, 8.5 Hz, 1H), 3.78 (d, J=15.0 Hz, 1H), 3.15–2.80 (m, 8H).

EXAMPLE 100 (22)

4-(4-Benzyloxycarbonylpiperazin-1-yl)carbonyl-3-phenylsulfonyl-2,3-dihydro-1,1-dioxidebenzo[b]thiophene

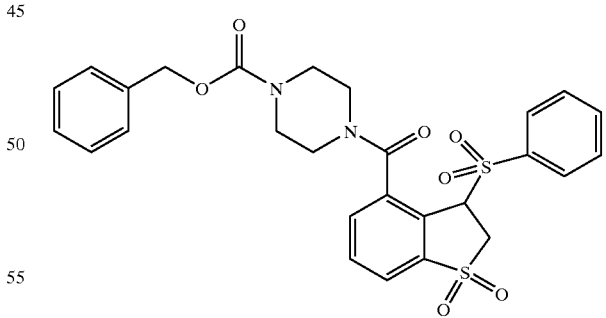

TLC: Rf 0.80 (methylene chloride:methanol=10:1);

NMR (DMSO-$d_6$): δ7.96–7.80 (m, 4H), 7.76 (d, J=7.5 Hz, 2H), 7.66 (t, J=7.5 Hz, 2H), 7.45–7.36 (m, 5H), 5.89 (d, J=8.7 Hz, 1H), 5.11 (s, 2H), 4.13 (dd, J=14.7, 8.7 Hz, 1H), 3.93 (d, J=14.7 Hz, 1H), 3.80–3.40 (m, 8H).

EXAMPLE 100 (23)

4-(4-(2-Methylphenyl)piperazin-1-yl)carbonyl-3-phenylsulfonyl-2,3-dihydro-1,1-diozidebenzo[b]thiophene.hydrochloride

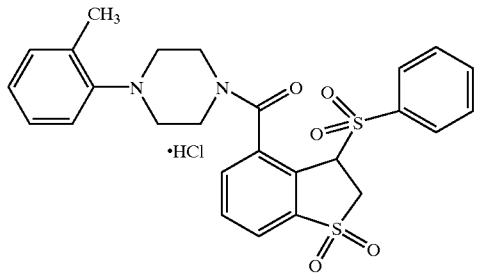

TLC: Rf 0.80 (methylene chloride:methanol=10:1);

NMR (DMSO-d$_6$): δ7.97–7.90 (m, 2H), 7.90–7.74 (m, 4H), 7.74–7.63 (m, 2H), 7.23–7.10 (m, 2H), 7.10–6.83 (m, 2H), 5.92 (d, J=9.6 Hz, 1H), 4.15 (dd, J=15.3, 9.6 Hz, 1H), 3.93 (d, J=15.3 Hz, 1H), 3.92–3.80 (m, 2H), 3.08–2.90 (m, 6H), 2.30 (s, 3H).

EXAMPLE 100 (24)

4-(4-(4-Methoxyphenyl)piperazin-1-yl)carbonyl-3-phenylsulfonyl-2,3-dihydro-1,1-dioxidebenzo[b]thiophene.hydrochloride

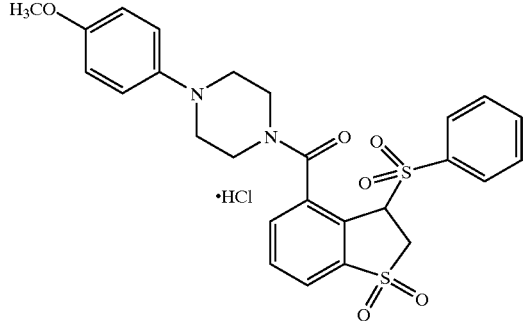

TLC: Rf 0.75 (methylene chloride:methanol=10:1);

NMR (DMSO-d$_6$): δ8.02–7.92 (m, 2H), 7.92–7.73 (m, 4H), 7.72–7.64 (m, 2H), 7.36–7.14 (m, 2H), 7.00–6.90 (m, 2H), 5.91 (d, J=9.6 Hz, 1H), 4.20–3.76 (m, 4H), 4.14 (dd, J=15.3, 9.6 Hz, 1H), 3.93 (d, J=15.3 Hz, 1H), 3.72 (s, 3H), 3.45–3.26 (m, 4H).

EXAMPLES 101~101 (1)

By the same procedure as described in Example 1 using the compounds prepared in Examples 28 (11) and 73 (16) instead of 1,1-dioxidebenzo[b]thiophene, the following compounds of the present invention were obtained.

EXAMPLE 101

4-(2-(Piperidin-1-yl)ethyl)carbamoyl-3-phenylthio-2,3-dihydro-1,1-dioxidebenzo[b]thiophene

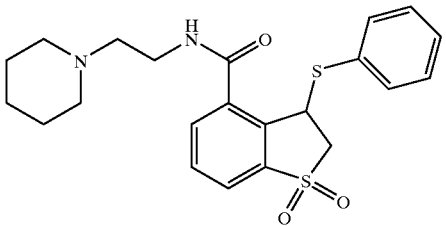

TLC: Rf 0.40 (methanol:water:acetic acid=1:1:0.1);

NMR (CDCl$_3$): δ7.81 (dd, J=7.6, 1.1 Hz, 1H), 7.75 (dd, J=7.6, 1.1 Hz, 1H), 7.61 (t, J=7.6 Hz, 1H), 7.56–7.53 (m, 2H), 7.38–7.35 (m, 3H), 6.91 (br, 1H), 5.74 (dd, J=7.3, 1.3 Hz, 1H), 3.72 (dd, J=13.9, 7.3 Hz, 1H), 3.68–3.58 (m, 1H), 3.60 (dd, J=13.9, 1.3 Hz, 1H), 3.55–3.45 (m, 1H), 2.55 (t, J=5.8 Hz, 2H), 2.38 (br, 4), 1.56–1.48 (m, 4H), 1.44–1.39 (m, 2H).

EXAMPLE 101 (1)

4-(2-(Pyridin-2-yl)ethyl)oxy-3-phenylthio-1,1-dioxidebenzo[b]thiophene

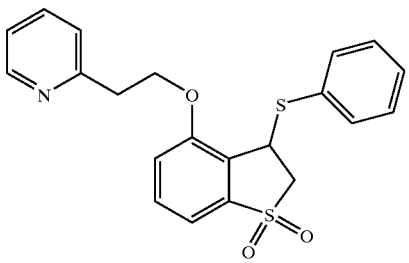

TLC: Rf 0.30 (hexane:ethyl acetate=1:1);

NMR (CDCl$_3$): δ8.54 (ddd, J=4.8, 1.7, 1.0 Hz, 1H), 7.54 (dt, J=7.7, 1.7 Hz, 1H), 7.49 (t, J=8.0 Hz, 1H), 7.43–7.40 (m, 2H), 7.34–7.22 (m, 5H), 7.15–7.10 (m, 2H), 4.91 (dd, J=6.9, 1.8 Hz, 1H), 4.52 (t, J=6.6 Hz, 2H), 3.66 (dd, J=13.8, 6.9 Hz, 1H), 3.57 (dd, J=13.8, 1.8 Hz, 1H), 3.31 (t, J=6.6 Hz, 2H).

EXAMPLE 102

4-(2-(Piperidin-1-yl)ethyl)carbamoyl-3-(4-nitrophenyl)sulfonyl-2,3-dihydro-1,1-dioxidebenzo[b]thiophene

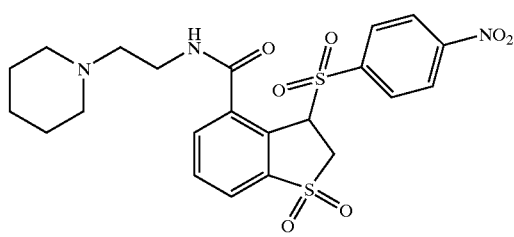

By the same procedure as described in Example 27 using the compound prepared in Example 28 (11) instead of 5-methyl-1,1-dioxidebenzo[b]thiophene, and 4-nitrobenzenesulfonic acid sodium salt instead of benzenesulfonic acid sodium salt, and if necessary, by converting into hydrochloride by a known method, the compounds of the present invention having the following physical data were obtained.

Free Compound

TLC: Rf 0.40(methanol:water:acetic acid=5:5:0.5);

NMR (CDCl$_3$): δ8.35 (d, J=8.7 Hz, 2H), 8.01 (d, J=8.7 Hz, 2H), 7.91 (dd, J=7.5, 1.7 Hz,1H), 7.81 (dd, J=7.5, 1.7 Hz, 1H), 7.76 (t, J=7.5 Hz,1H), 7.59 (br, 1H), 6.42 (dd, J=9.2,1.5 Hz,1H), 3.88 (dd, J=15.0, 1.5 Hz, 1H), 3.75 (dd, J=15.0, 9.2 Hz, 1H), 3.75–3.64 (m, 1H), 3.57–3.48 (m, 1H), 2.77–2.65 (m, 2H), 2.53 (br, 4H), 1.66–1.57 (m, 4H), 1.52–1.45 (m, 2H).

Hydrochloride

TLC: Rf 0.40 (methanol:water:acetic acid=5:5:0.5);

NMR (DMSO-d$_6$): δ9.98 (br, 1H), 9.28 (br, 1H), 8.42 (d, J=8.7 Hz, 2H), 8.11 (d, J=7.5 Hz, 1H), 8.03 (d, J=8.7 Hz, 2H), 7.97 (d, J=7.5 Hz, 1H), 7.89 (t, J=7.5 Hz, 1H), 6.41 (dd, J=7.3, 3.2 Hz, 1H), 4.16 (dd, J=15.5, 7.3 Hz, 1H), 4.10 (dd, J=15.5, 3.2 Hz, 1H), 3.72–3.70 (m, 2H), 3.57–3.48 (m, 2H), 3.32–3.25 (m, 2H), 2.96 (br, 2H), 1.82–1.68 (m, 5H), 1.45–1.35 (m, 1H).

EXAMPLES 103~103 (41)

By the same procedure as described in Example 31 using 4-methylsulfonyloxymethyl-3-phenylsulfonyl-2,3-dihydro-1,1-dioxidebenzo[b]thiophene instead of 4-bromomethyl-1,1-dioxidebenzo[b]thiophene and an amine derivative corresponding to 2,4-dimethoxybenzylamine hydrochloride, and if necessary, by converting into the corresponding salt by a known method, the following compounds of the present invention were obtained.

EXAMPLE 103

4-(N-2-(Piperidin-1-yl)ethyl-N-methyl)aminomethyl-3-phenylsulfonyl-2,3-dihydro-1,1-dioxidebenzo[b]thiophene.2hydrochloride

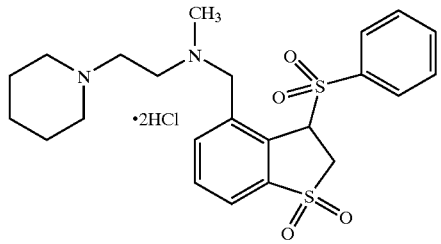

TLC: Rf 0.48 (methanol:ethyl acetate:triethylamine=2:8:0.5);

NMR (CD$_3$OD+D$_2$O (4 drops)): δ8.16 (d, J=7.5 Hz, 1H), 7.90 (t, J=7.5 Hz, 1H), 7.85–7.73 (m, 4H), 7.64–7.55 (m, 2H), 6.18–6.10 (m, 1H), 4.93 (d, J=14.4 Hz, 1H), 4.60 (d, J=14.4 Hz, 1H), 4.03 (dd, J=15.6, 9.0 Hz, 1H), 3.84 (dd, J=15.6, 0.9 Hz, 1H), 3.72–3.00 (m, 8H) 2.74 (s, 3H), 2.00–1.55 (m, 6H).

EXAMPLE 103 (1)

4-(2-(N-Ethyl-N-3-methylphenyl)aminoethyl)aminomethyl-3-phenylsulfonyl-2,3-dihydro-1,1-dioxidebenzo[b]thiophene.2hydrochloride

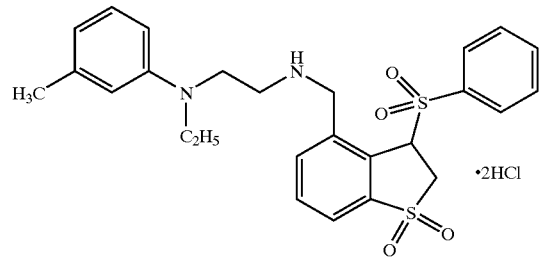

TLC: Rf 0.45 (ethyl acetate:triethylamine=6:0.5);

NMR (DMSO-d$_6$): δ9.64 (brs, 2H), 8.21 (d, J=6.3 Hz, 1H), 7.89–7.74 (m, 5H), 7.67–7.58 (m, 2H), 7.18–7.04 (m, 1H), 6.96–6.50 (m, 3H), 6.46 (dd, J=6.9, 3.0 Hz, 1H), 4.73–4.59 (m, 1H), 4.49–4.35 (m, 1H), 3.97–3.80 (m, 2H), 3.80–3.58 (m, 2H), 3.50–3.33 (m, 2H), 3.29–3.10 (m, 2H), 2.25 (s, 3H), 1.06 (t, J=6.9 Hz, 3H).

EXAMPLE 103 (2)

4-(N-Benzyl-N-ethyl)aminomethyl-3-phenylsulfonyl-2,3-dihydro-1,1-dioxidebenzo[b]thiophene.hydrochloride

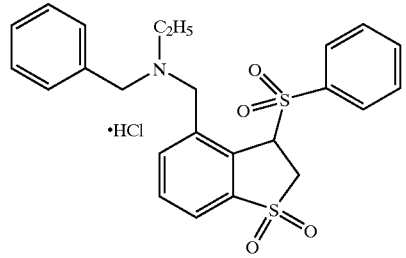

TLC: Rf 0.67 (ethyl acetate:triethylamine=6:0.5);

NMR (CD$_3$OD+pyridine-d$_5$): δ7.92 (d, J=7.2 Hz, 1H), 7.71–7.58 (m, 4H), 7.57–7.45 (m, 3H), 7.32–7.15 (m, 5H), 5.84 (dd, J=8.4, 1.8 Hz, 1H), 4.33 (d, J=14.7 Hz, 1H), 3.90–3.62 (m, 4H), 3.60 (d, J=13.2 Hz, 1H), 2.65 .(q, J=7.2 Hz, 2H), 1.14 (t, J=7.2 Hz, 3H).

EXAMPLE 103 (3)

4-(2-Diethylaminoethyl)aminomethyl-3-phenylsulfonyl-2,3-dihydro-1,1-dioxidebenzo[b]thiophene.2hydrochloride

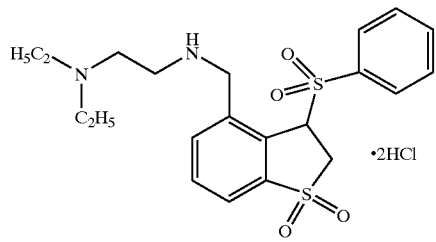

TLC: Rf 0.35 (methanol:ethyl acetate:triethylamine= 2:8:0.5);

NMR (DMSO-d$_6$): δ10.66 (brs, 1H), 9.96 (brs, 1H), 9.76 (brs, 1H), 8.26–8.26 (m, 1H), 7.91–7.74 (m, 5H), 7.67–7.57 (m, 2H), 6.54–6.45 (m, 1H), 4.83–4.65 (m, 1H), 4.60–4.42 (m, 1H), 3.96–3.82 (m, 2H), 3.70–3.37 (m, 4H), 3.28–3.10 (m, 4H), 1.26 (t, J=7.2 Hz, 6H).

EXAMPLE 103 (4)

4-(4-Methylbenzyl)aminomethyl-3-phenylsulfonyl-2,3-dihydro-1,1-dioxidebenzo[b]thiophene.hydrochloride

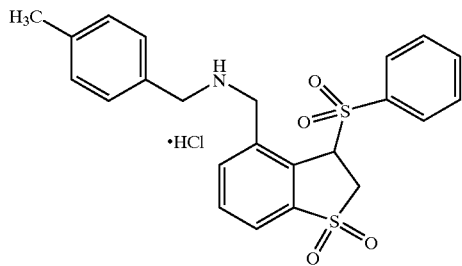

TLC: Rf 0.47 (ethyl acetate:triethylamine 6:0.5);

NMR (DMSO-d$_6$): δ9.83 (brs, 1H), 9.54 (brs, 1H), 8.16 (d, J=6.9 Hz, 1H), 7.89–7.75 (m, 3H), 7.75–7.68 (m, 2H), 7.68–7.59 (m, 2H), 7.50 (d, J=8.1 Hz, 2H), 7.25 (d, J=8.1 Hz, 2H), 6.29 (dd, J=4.8, 3.9 Hz, 1H ), 4.72–4.58 (m, 1H), 4.44–4.32 (m,1H), 4.25 (brs, 2H), 3.93–3.80 (m, 2H), 2.32 (s, 3H).

EXAMPLE 103 (5)

4-(N-Ethyl-N-2-(piperidin-1-yl)ethyl)aminomethyl-3-phenylsulfonyl-2,3-dihydro-1,1-dioxidebenzo[b]thiophene.2hydrochloride

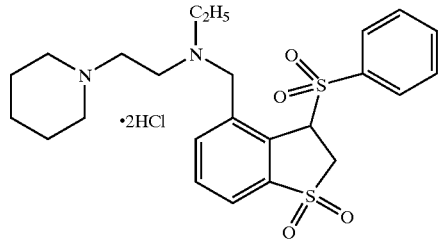

TLC: Rf 0.47 (methanol:ethyl acetate:triethylamine= 2:8:0.5);

NMR (CD$_3$OD–D$_2$O (1 drop)): δ8.24 (d, J=7.5 Hz, 1H), 7.92–7.69 (m, 5H), 7.61–7.52 (m, 2H), 6.21–6.10 (m, 1H), 5.15 (d, J=14.4 Hz, 1H), 4.70 (d, J=14.4 Hz, 1H), 4.05 (dd, J=15.3, 9.0 Hz, 1H), 3.84 (dd, J=15.3, 0.9 Hz, 1H), 3.76–2.80 (m, 10H), 1.98–1.50 (m, 6H), 1.45 (t, J=7.2 Hz, 3H).

EXAMPLE 103 (6)

4-(2-Methoxybenzyl)aminomethyl-3-phenylsulfonyl-2,3-dihydro-1,1-dioxidebenzo[b]thiophene.hydrochloride

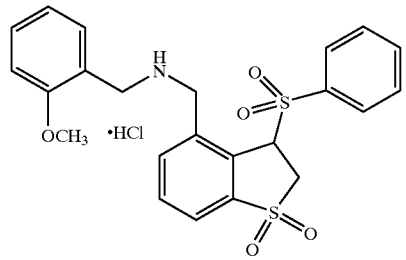

TLC: Rf 0.49 (ethyl acetate:triethylamine=6:0.5);

NMR (DMSO-d$_6$): δ9.51 (brs, 2H), 8.21–8.11 (m, 1H), 7.89–7.75 (m, 3H), 7.74–7.58 (m, 4H), 7.51 (d, J=7.5 Hz, 1H), 7.47–7.38 (m, 1H), 7.08 (d, J=8.1 Hz, 1H), 7.01 (t, J=7.5 Hz, 1H), 6.16–6.06 (m, 1H), 4.77–4.62 (m, 1H), 4.52–4.37 (m, 1H), 4.31–4.12 (m, 2H), 3.95–3.82 (m, 2H), 3.81 (s, 3H).

EXAMPLE 103 (7)

4-(3-Phenylpropyl)aminomethyl-3-phenylsulfonyl-2,3-dihydro-1,1-dioxidebenzo[b]thiophene.hydrochloride

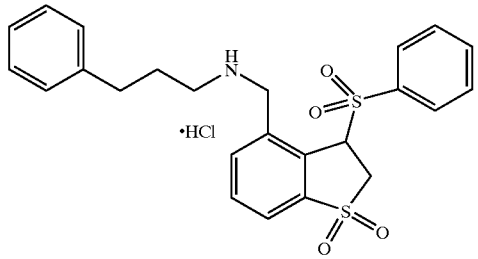

TLC: Rf 0.37(ethyl acetate:triethylamine=6:0.5);

NMR (DMSO-d$_6$): δ9.50 (brs, 1H), 9.17 (brs, 1H), 8.16 (d, J=6.3 Hz, 1H), 7.90–7.73 (m, 5H), 7.68–7.58 (m, 2H), 7.35–7.16 (m, 5H), 6.44 (dd, J=6.9, 3.0 Hz, 1H), 4.69–4.54 (m, 1H), 4.45–4.31 (m, 1H), 3.95–3.79 (m, 2H), 3.14–2.95 (m 2H), 2.68 (t, J=7.2 Hz, 2H), 2.09–1.91 (m, 2H).

EXAMPLE 103 (8)

4-(3,5-Dimethoxybenzyl)aminomethyl-3-phenylsulfonyl-2,3-dihydro-1,1-dioxidebenzo[b]thiophene.hydrochloride

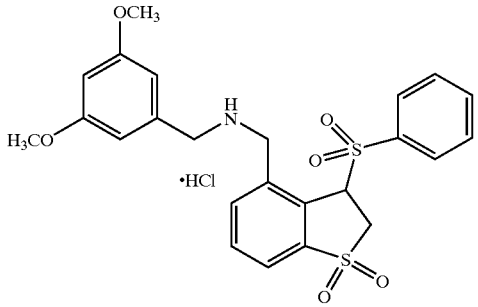

TLC: Rf 0.43(ethyl acetate:triethylamine=6:0.5);

NMR (DMSO-d$_6$): δ9.94 (brs, 1H), 9.65 (brs, 1H), 8.17 (d, J=6.9 Hz, 1H), 7.90–7.75 (m, 3H), 7.75–7.67 (m, 2H), 7.67–7.58 (m, 2H), 6.87 (d, J=2.1 Hz, 2H), 6.55 (t, J=2.1 Hz, 1H), 6.30 (t, J=4.5 Hz, 1H), 4.72–4.57 (m, 1H), 4.43–4.28 (m, 1H), 4.23 (brs, 2H), 4.00–3.67 (m, 2H), 3.75 (s, 6H).

EXAMPLE 103 (9)

4-((3R)-1-Benzylpyrrolidin-3-yl)aminomethyl-3-phenylsulfonyl-2,3-dihydro-1,1-dioxidebenzo[b]thiophene.2hydrochloride

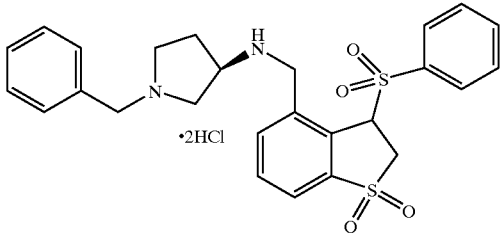

TLC: Rf 0.45(methanol:ethyl acetate:triethylamine=2:8:0.5);

NMR (CD$_3$OD): δ8.20 (d, J=6.9 Hz, 1H), 7.91–7.70 (m, 5H), 7.66–7.54 (m, 4H), 7.53–7.43 (m, 3H), 6.18–6.05 (m, 1H), 4.77 (d, J=14.1 Hz, 1H), 4.67–4.32 (m, 4H), 4.02–3.66 (m, 5H), 3.62–3.38 (m, 1H), 2.88–2.40 (m, 2H).

EXAMPLE 103 (10)

4-((3S)-1-Benzylpyrrolidin-3-yl)aminomethyl-3-phenylsulfonyl-2,3-dihydro-1,1-dioxidebenzo[b]thiophene.2hydrochloride

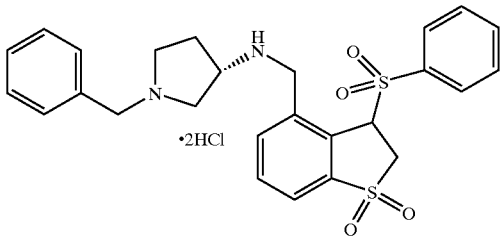

TLC: Rf 0.45(methanol:ethyl acetate:triethylamine=2:8:0.5);

NMR (CD$_3$OD): δ8.20 (d, J=6.9 Hz, 1H), 7.91–7.70 (m, 5H), 7.66–7.54 (m, 4H), 7.53–7.43 (m, 3H), 6.18–6.04 (m, 1H), 4.78 (d, J=12.9 Hz, 1H), 4.68–4.32 (m, 4H), 4.02–3.66 (m, 5H), 3.62–3.38 (m, 1H), 2.88–2.40 (m, 2H).

EXAMPLE 103 (11)

4-(2-Phenylethyl)aminomethyl-3-phenylsulfonyl-2,3-dihydro-1,1-dioxidebenzo[b]thiophene

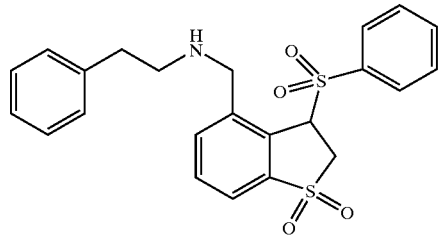

Free Compound
TLC: Rf 0.28 (ethyl acetate);
NMR (CDCl$_3$): δ7.65–7.40 (m, 8H), 7.30–7.15 (m, 5H), 5.90 (dd, J=9.3, 0.9 Hz, 1H), 4.66 (d, J=14.2 Hz, 1H), 3.92

(d, J=14.2 Hz, 1H), 3.73 (dd, J=15.0, 0.9 Hz, 1H), 3.42 (dd, J=15.0, 9.3 Hz, 1H), 3.01–2.74 (m, 4H).
Hydrochloride
TLC: Rf 0.28 (ethyl acetate);
NMR (DMSO-$d_6$): δ9.55 (br, 1H), 9.35 (br, 1H), 8.18 (dd, J=6.2, 2.5 Hz, 1H), 7.94–7.87 (m, 2H), 7.82–7.78 (m, 3H), 7.67–7.62 (m, 2H), 7.38–7.33 (m, 2H), 7.29–7.25 (m, 3H), 6.41 (dd, J=7.5, 2.1 Hz, 1H), 4.69–4.65 (m, 1H), 4.45–4.41 (m, 1H), 3.92 (dd, J=15.3, 7.5 Hz, 1H), 3.84 (dd, J=15.3, 2.1 Hz, 1H), 3.32–3.25 (m, 2H), 3,08–2.98 (m, 2H).

EXAMPLE 103 (12)

4-(N-Benzyl-N-methyl)aminomethyl-3-phenylsulfonyl-2,3-dihydro-1,1-dioxidebenzo[b]thiophene

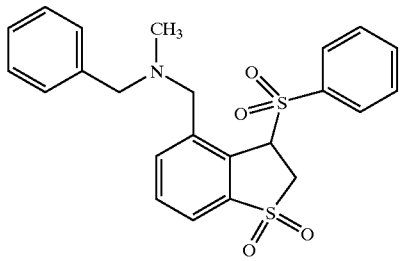

Free Compound
TLC: Rf 0.42 (hexane:ethyl acetate=1:2);
NMR (CDCl$_3$): δ7.71 (dd, J=7.2, 1.2 Hz, 1H), 7.64–7.49 (m, 5H), 7.44–7.39 (m, 2H), 7.34–7.20 (m, 5H), 6.08 (dd, J=9.3, 1.0 Hz, 1H), 4.66 (d, J=14.1 Hz, 1H), 3.88 (dd, J=15.0, 1.0 Hz, 1H), 3.69 (dd, J=15.0, 9.3 Hz, 1H), 3.61 (d, J=12.9 Hz, 1H), 3.53 (d, J=14.1 Hz, 1H), 3.47 (d, J=12.9 Hz, 1H), 2.16 (s, 3H).
Hydrochloride
TLC: Rf 0.42 (hexane:ethyl acetate=1:2);
NMR (CD$_3$OD+pyridine-$d_5$) δ7.92 (d, J=7.5 Hz 1H), 7.73–7.63 (m, 5H), 7.56–7.50 (m, 2H), 7.37–7.31 (m, 5H), 5.99 (dd, J=7.0, 3.0 Hz, 1H), 4.52 (d, J=14.4 Hz, 1H), 3.94–3.85 (m, 3H), 3.83 (d, J=13.0 Hz, 1H), 3.76 (d, J=13.0 Hz, 1H), 2.32 (s, 3H).

EXAMPLE 103 (13)

4-(3-(2-Oxopyrrolidin-1-yl)propyl)aminomethyl-3-phenylsulfonyl-2,3-dihydro-1,1-dioxidebenzo[b]thiophene

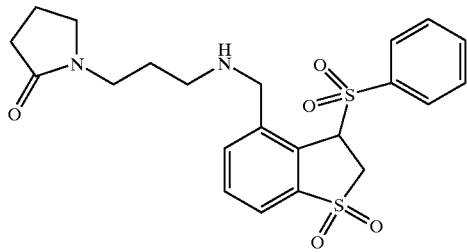

Free Compound
TLC: Rf 0.27 (ethyl acetate:methanol:triethylamine= 8:1:1);
NMR (CDCl$_3$): δ7.72 (dd7 J=7.5, 1.5 Hz, 1H), 7.65–7.54 (m, 4H), 7.51 (dd, J=7.5, 1.5 Hz, 1H), 7.47–7.42 (m, 2H), 5.98 (t-like, J=5.1 Hz, 1H), 4.56 (d, J=13.8 Hz, 1H), 3.91–3.87 (m, 3H), 3.40–3.30 (m, 4H), 2.67–2.53 (m, 2H), 2.41–2.38 (m, 2H), 2.05–1.95 (m, 2H), 1.78–1.69 (m, 2H).

Hydrochloride
TLC: Rf 0.27 (ethyl acetate:methanol:triethylamine= 8:1:1);
NMR (DMSO-$d_6$): δ9.32 (m, 1H), 9.08 (m, 1H) 8.14 (dd, J=6.3, 2.1 Hz, 1H), 7.90–7.78 (m, 5H), 7.67–7.62 (m, 2H), 6.40 (dd, J=7.5, 2.0 Hz, 1H), 4.66–4.60 (m, 1H), 4.43–4.37 (m, 1H), 3.94–3.81 (m, 2H), 3.38–3.25 (m, 4H), 3.03–2.97 (m, 2H), 2.26 (t, J=8.0 Hz, 2H), 1.99–1.83 (m, 4H).

EXAMPLE 103 (14)

4-(4-Aminobenzyl)aminomethyl-3-phenylsulfonyl-2,3-dihydro-1,1-dioxidebenzo[b]thiophene

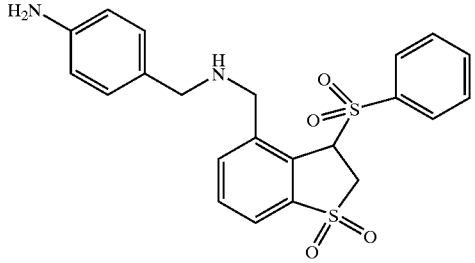

Free Compound
TLC: Rf 0.47 (ethyl acetate:methanol:triethylamine= 8:1:1);
NMR (DMSO-$d_6$): δ7.90 (dd, J=7.0, 2.0 Hz, 1H), 7.80–7.61 (m, 7H), 6.97 (d, J=8.5 Hz, 2H), 6.52 (d, J=8.5 Hz, 2H), 5.81 (dd, J=8.0, 1.8 Hz, 1H), 4.93 (s, 2H), 4.01 (d, J=14.7 Hz, 1H), 3.91 (dd, J=15.0, 8.0 Hz, 1H), 3.84 (dd, J=15.0, 1.8 Hz, 1H), 3.77 (d, J=14.7 Hz, 1H), 3.48 (s, 2H).
Hydrochloride
TLC: Rf 0.47 (ethyl acetate:methanol:triethylamine= 8:1:1);
NMR (DMSO-$d_6$): δ9.90 (br, 1H), 9.59 (br, 1H), 8.18 (dd, J=7.0, 1.5 Hz, 1H), 7.88–7.60 (m, 9H), 7.21 (d, J=7.8 Hz, 2H), 6.37–6.34 (m, 1H), 4.70–4.64 (m, 1H), 4.42–4.32 (m, 1H), 4.28 (s, 2H), 3.93–3.82 (m, 2H).

EXAMPLE 103 (15)

4-(4-((2E)-3-Phenyl-2-propenyl)piperazin-1-yl)methyl-3-phenylsulfonyl-2,3-dihydro-1,1-dioxidebenzo[b]thiophene

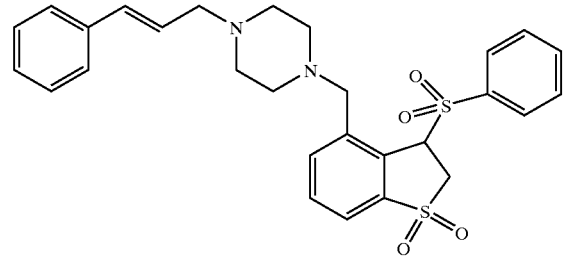

Free Compound
TLC: Rf 0.48 (ethyl acetate:methanol=9:1);
NMR (CDCl$_3$): δ7.65–7.20 (m, 13H), 6.52 (d, J=15.9 Hz, 1H), 6.30 (dd, J=9.3, 1.2 Hz, 1H), 6.26 (dt, J=15.9, 6.8 Hz, 1H), 4.70 (d, J=14.3 Hz, 1H), 3.91 (dd, J=15.0, 1.2 Hz, 1H), 3.73 (dd, J=15.0, 9.3 Hz, 1H), 3.42 (d, J=14.3 Hz, 1H), 3.16 (d, J=6.8 Hz, 2H), 2.60–2.40 (m, 8H).

Hydrochloride

TLC: Rf 0.48 (ethyl acetate:methanol=9:1);

NMR (CD$_3$OD+D$_2$O): δ7.93 (d, J=7.0 Hz, 1H), 7.78–7.72 (m, 4H), 7.66 (d, J=7.0 Hz, 1H), 7.61–7.50 (m, 2H), 7.41–7.33 (m, 3H), 6.95 (d, J=15.6 Hz, 1H), 6.33 (dt, J=15.6, 7.7 Hz, 1H), 6.16 (d, J=9.0 Hz, 1H), 4.54 (d, J=14.5 Hz, 1H), 4.02 (dd, J=15.0, 9.0 Hz, 1H), 3.96 (d, J=7.7 Hz 2H), 3.89 (d, J=15.0 Hz 1H), 3.85 (d, J=14.5 Hz, 1H), 3.42 (br, 4H), 3.29 (br, 4H).

EXAMPLE 103 (16)

4-(2-Aminobenzyl)aminomethyl-3-phenylsulfonyl-2,3-dihydro-1,1-dioxidebenzo[b]thiophene

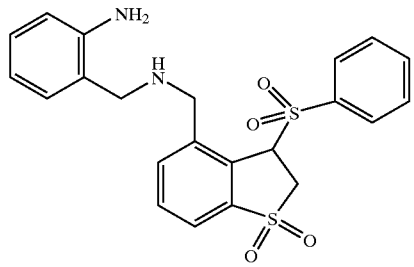

Free Compound

TLC: Rf 0.30 (ethyl acetate);

NMR (CDCl$_3$): δ7.74 (d, J=7.5 Hz, 1H), 7.65–7.55 (m, 2H), 7.51–7.39 (m, 5H), 7.09 (dt, J=7.5, 1.5 Hz, 1H), 6.97 (dd, J=7.5, 1.5 Hz, 1H), 6.67 (dt, J=7.5, 1.5 Hz, 1H), 6.63 (dd, J=7.5, 1.5 Hz, 1H), 5.43 (dd, J=9.5, 1.2 Hz, 1H), 4.29 (d, J=14.3 Hz, 1H), 4.02 (d, J=14.3 Hz, 1H), 3.88 (d, J=12.6 Hz, 1H), 3.82 (dd, J=15.0, 1.2 Hz, 1H), 3.81 (d, J=12.6 Hz, 1H), 3.66 (dd, J=15.0, 9.5 Hz, 1H).

Hydrochloride

TLC: Rf 0.30 (ethyl acetate);

NMR (DMSO-d$_6$): δ8.17 (dd, J=6.3, 2.4 Hz, 1H), 7.87–7.71 (m, 5H), 7.66–7.61 (m, 2H), 7.50 (br, 2H), 7.29 (dd, J=7.5, 1.2 Hz, 1H), 7.13 (dt, J=7.5, 1.2 Hz, 1H), 6.75 (d, J=7.5 Hz, 1H), 6.63 (t, J=7.5 Hz, 1H), 6.21 (t-like, J=5.0 Hz, 1H), 4.72 (d, J=13.8 Hz, 1H), 4.46 (d, J=13.8 Hz, 1H), 4.26–4.17 (m, 2H), 3.93–3.82 (m, 2H).

EXAMPLE 103 (17)

4-(4-Benzylpiperidin-1-yl)methyl-3-phenylsulfonyl-2,3-dihydro-1,1-dioxidebenzo[b]thiophene

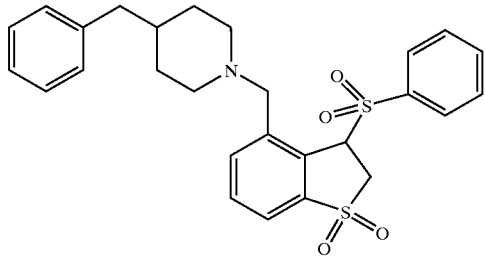

Free Compound

TLC: Rf 0.50 (hexane:ethyl acetate=1:1);

NMR (CDCl$_3$): δ7.66–7.56 (m, 4H), 7.53–7.51 (m, 2H), 7.48–7.43 (m, 2H), 7.30–7.25 (m, 2H), 7.21–7.11 (m, 3H), 6.36 (d, J=9.3 Hz, 1H), 4.62 (d, J=14.4 Hz, 1H), 3.89 (d, J=15.0 Hz, 1H), 3.71 (dd, J=15.0, 9.3 Hz, 1H), 3.35 (d, J=14.4 Hz, 1H), 3.04–3.00 (m, 1H), 2.53 (d, J=6.9 Hz, 2H), 2.55–2.50 (m, 1H), 2.05 (dt, J=11.5, 2.5 Hz, 1H), 1.85 (dt, J=11.5, 2.5 Hz, 1H), 1.74–1.68 (m, 1H), 1.62–1.15 (m, 2H), 1.35 (dt, J=12.0, 3.5 Hz, 1H), 1.16–1.02 (m, 1H).

Hydrochloride

TLC: Rf 0.50 (hexane:ethyl acetate=1:1);

NMR (DMSO-d$_6$): δ10.42 (br, 1H), 8.22 (d, J=7.0 Hz, 1H), 7.92–7.72 (m, 5H), 7.65–7.60 (m, 2H), 7.31–7.15 (m, 5H), 6.30 (d, J=9.0 Hz, 1H), 4.72 (dd, J=13.8, 5.3 Hz, 1H), 4.53 (dd, J=13.8, 5.3 Hz, 1H), 4.02 (dd, J=15.3, 9.0 Hz, 1H), 3.83 (d, J=15.3 Hz, 1H), 3.42–3.39 (m, 1H), 3.12–3.00 (m, 3H), 2.60–2.42 (m, 2H), 1.79–1.49 (m, 5H).

EXAMPLE 103 (18)

4-(4-Chlorobenzyl)aminomethyl-3-phenylsulfonyl-2,3-dihydro-1,1-dioxidebenzo[b]thiophene

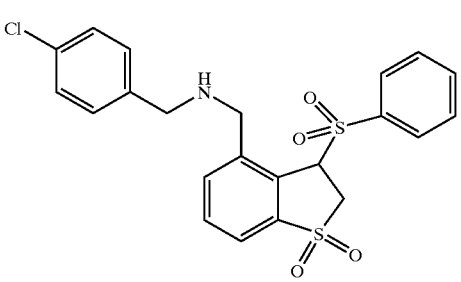

Free Compound

TLC: Rf 0.43(ethyl acetate);

NMR (CDCl$_3$): δ7.75 (dd, J=7.0, 1.2 Hz, 1H), 7.66–7.51 (m, 5H), 7.47–7.42 (m, 2H), 7.32 (d, J=8.4 Hz, 2H), 7.24 (d, J=8.4 Hz, 2H), 5.81 (dd, J=9.3, 1.3 Hz, 1H), 4.48 (d, J=14.0 Hz, 1H), 3.99 (d, J=14.0 Hz, 1H), 3.86 (dd, J=15.0, 1.3 Hz, 1H), 3.84 (d, J=13.3 Hz, 1H), 3.78 (d, J=13.3 Hz, 1H), 3.68 (dd, J=15.0, 9.3 Hz, 1H).

Hydrochloride

TLC: Rf 0.43 (ethyl acetate);

NMR (DMSO-d$_6$): δ9.86 (br, 1H), 9.55 (br, 1H), 8.16 (dd, J=6.6, 1.8 Hz, 1H), 7.88–7.72 (m, 5H), 7.67–7.62 (m, 4H), 7.53 (d, J=8.4 Hz, 2H), 6.31 (dd, J=6.2, 3.5 Hz, 1H), 4.70–4.66 (m, 1H), 4.43–4.39 (m, 1H), 4.32 (s, 2H), 3.90 (dd, J=15.5, 6.2 Hz, 1H), 3.84 (dd, J=15.5, 3.5 Hz, 1H).

EXAMPLE 103 (19)

4-(3-Chlorobenzyl)aminomethyl-3-phenylsulfonyl-2,3-dihydro-1,1-dioxidebenzo[b]thiophene

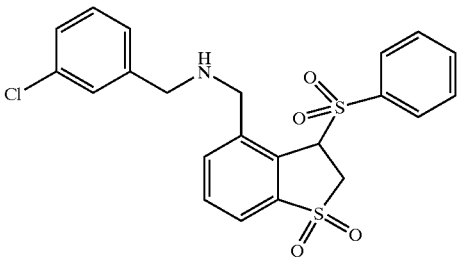

Free Compound

TLC: Rf 0.51(ethyl acetate);

NMR (CDCl$_3$): δ7.76 (dd, J=7.0, 1.2 Hz, 1H), 7.67–7.40 (m, 7H), 7.30–7.14 (m, 4H), 5.80 (dd, J=9.2, 1.4 Hz, 1H), 4.48 (d, J=14.0 Hz, 1H), 3.99 (d, J=14.0 Hz, 1H), 3.87 (dd, J=15.4, 1.4 Hz, 1H), 3.86 (d, J=13.6 Hz, 1H), 3.77 (d, J=13.6 Hz, 1H), 3.69 (dd, J=15.4, 9.2 Hz, 1H).

Hydrochloride

TLC: Rf 0.51 (ethyl acetate);

NMR (DMSO-d$_6$): δ9.92 (br, 1H), 9.62 (br, 1H), 8.18 (dd, J=6.6, 1.8 Hz, 1H), 7.88–7.74 (m, 6H), 7.67–7.59 (m, 3H), 7.52–7.45 (m, 2H), 6.39 (dd, J=5.7, 4.2 Hz, 1H), 4.74–4.69 (m, 1H), 4.44–4.40 (m, 1H), 4.35 (s, 2H), 3.90 (dd, J=15.6, 5.7 Hz, 1H), 3.84 (dd, J=15.6, 4.2 Hz, 1H).

EXAMPLE 103 (20)

4-(3-Methoxybenzyl)aminomethyl-3-phenylsulfonyl-2,3-dihydro-1,1-dioxidebenzo[b]thiophene

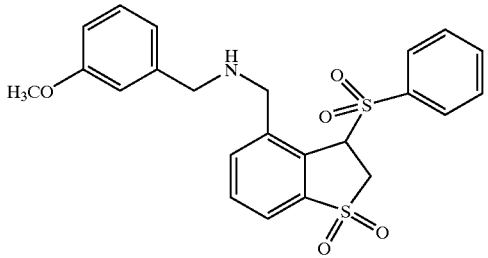

Free Compound

TLC: Rf 0.41(ethyl acetate);

NMR (CDCl$_3$): δ7.75 (dd, J=7.2, 1.2 Hz, 1H), 7.65–7.50 (m, 5H), 7.46–7.40 (m, 2H), 7.26–7.21 (m, 1H), 6.86–6.79 (m, 3H), 5.81 (dd, J=9.3, 1.2 Hz, 1H), 4.48 (d, J=14.1 Hz, 1H), 3.98 (d, J=14.1 Hz, 1H), 3.84 (d, J=13.5 Hz 1H), 3.84 (dd, J=15.0, 1.2 Hz, 1H), 3.80 (s, 3H), 3.74 (d, J=13.5 Hz, 1H), 3.66 (dd, J=15.0, 9.3 Hz, 1H).

Hydrochloride

TLC: Rf 0.41 (ethyl acetate);

NMR (DMSO-d$_6$): δ9.83 (br, 1H), 9.55 (br, 1H), 8.16 (dd, J=6.6, 1.8 Hz, 1H), 7.89–7.78 (m, 3H), 7.73–7.61 (m, 4H), 7.36 (t, J=7.9 Hz, 1H), 7.30 (d, J=2.5 Hz, 1H), 7.15 (d, J=7.9Hz, 1H), 7.00 (dd, J=7.9, 2.5Hz, 1H), 6.27 (dd, J=6.0, 3.9 Hz, 1H), 4.70–4.65 (m, 1H), 4.42–4.37 (m, 1H), 4.29 (br, 2H), 3.89 (dd, J=15.5, 6.0 Hz, 1H), 3.84 (dd, J=15.5, 3.9 Hz, 1H), 3.78 (s, 3H).

EXAMPLE 103 (21)

4-(3,4-Dichlorobenzyl)aminomethyl-3-phenylsulfonyl-2,3-dihydro-1,1-dioxidebenzo[b]thiophene

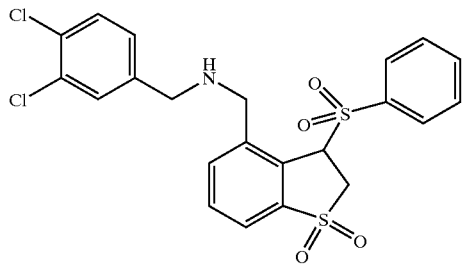

Free Compound

TLC: Rf 0.42(ethyl acetate);

NMR (CDCl$_3$): δ7.77 (dd, J=7.2, 1.2 Hz, 1H), 7.67–7.52 (m, 5H), 7.47–7.39 (m, 4H), 7.15 (dd, J=8.3, 2.0 Hz, 1H), 5.76 (dd, J=9.5, 1.2 Hz, 1H), 4.45 (d, J=13.8 Hz, 1H), 4.00 (d, J=13.8 Hz, 1H), 3.86 (d, J=15.0, 1.2 Hz, 1H), 3.84 (d, J=13.8 Hz, 1H), 3.78 (d, J=13.8 Hz, 1H), 3.70 (dd, J=15.0, 9.5 Hz, 1 H).

Hydrochloride

TLC: Rf 0.42 (ethyl acetate);

NMR (DMSO-d$_6$): δ9.94 (br, 1H), 9.62 (br, 1H), 8.17 (dd, J=6.6, 2.1 Hz, 1H), 7.96 (d, J=1.8 Hz, 1H), 7.89–7.73 (m, 6H), 7.67–7.60 (m, 3H), 6.40 (dd, J=5.5, 4.2 Hz, 1H), 4.75–4.68 (m, 1H), 4.45–4.40 (m, 1H), 4.35 (s, 2H), 3.95 (dd, J=15.5, 5.5 Hz, 1H), 3.85 (dd, J=15.5, 4.2 Hz, 1H).

EXAMPLE 103 (22)

4-(1,3-Dioxaindan-5-ylmethyl)aminomethyl-3-phenylsulfonyl-2,3-dihydro-1,1-dioxidebenzo[b]thiophene

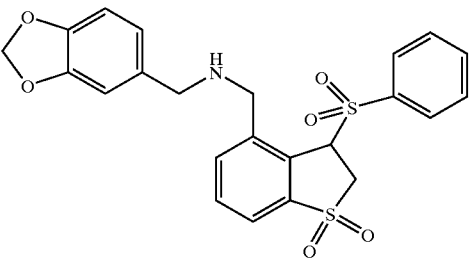

Free Compound

TLC: Rf 0.43(ethyl acetate);

NMR (CDCl$_3$): δ7.73 (dd, J=7.5, 1.2 Hz, 1H), 7.65–7.49 (m, 5H), 7.46–7.41 (m, 2H), 6.77 (d, J=1.5 Hz, 1H), 6.74 (d, J=8.0 Hz, 1H), 6.69 (dd, J=8.0, 1.5 Hz, 1H), 5.95–5.94 (m, 2H), 5.88 (dd, J=9.5, 1.0 Hz, 1H), 4.50 (d, J=14.0 Hz, 1H), 3.96 (d, J=14.0 Hz, 1H), 3.86 (dd, J=15.0, 1.0 Hz, 1H), 3.77 (d, J=13.0 Hz, 1H), 3.68 (d, J=13.0 Hz, 1H), 3.68 (dd, J=15.0, 9.5 Hz, 1H).

Hydrochloride

TLC: Rf 0.43 (ethyl acetate);

NMR (DMSO-d$_6$): δ9.78 (br, 1H), 9.47 (br, 1H), 8.15 (dd, J=6.6, 1.8 Hz, 1H), 7.88–7.72 (m, 5H), 7.66–7.61 (m, 2H), 7.25 (d, J=1.5 Hz, 1H), 7.08 (dd, J=7.8, 1.5 Hz, 1H), 6.99 (d, J=7.8 Hz, 1H), 6.30 (t-like, J=4.5 Hz, 1H), 6.05 (s, 2H), 4.67–4.61 (m, 1H), 4.38–4.33 (m, 1H), 4.23 (s, 2H), 3.93–3.83 (m, 2H).

EXAMPLE 103 (23)

4-(2,3-Dimethoxybenzyl)aminomethyl-3-phenylsulfonyl-2,3-dihydro-1,1-dioxidebenzo[b]thiophene

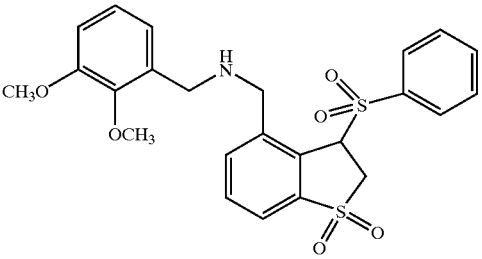

Free Compound

TLC: Rf 0.36(ethyl acetate);

NMR (CDCl$_3$): δ7.71 (dd, J=7.0, 1.3 Hz, 1H), 7.63–7.48 (m, 5H), 7.45–7.39 (m, 2H), 7.00 (t, J=7.8 Hz, 1H), 6.84 (dd, J=7.8, 1.5 Hz, 1H), 6.78 (dd, J=7.8, 1.5 Hz, 1H), 6.06 (dd, J=9.3, 1.3 Hz, 1H), 4.52 (d, J=14.1 Hz, 1H), 3.92 (d, J=14.1 Hz, 1H), 3.86 (s, 3H), 3.85 (dd, J=15.0, 1.3 Hz, 1H), 3.80 (d,

J=13.3 Hz, 1H), 3.76 (s, 3H), 3.73 (dd, J=15.0, 9.3 Hz, 1H), 3.69 (d, J=13.3 Hz, 1H).

Hydrochloride

TLC: Rf 0.36 (ethyl acetate);

NMR (DMSO-d$_6$): δ9.70–9.60 (br, 2H), 8.17 (dd, J=6.6, 2.1 Hz, 1H), 7.89–7.73 (m, 5H), 7.67–7.62 (m, 2H), 7.25–7.21 (m, 1H), 7.15–7.13 (m, 2H), 6.12 (dd, J=6.8, 2.5 Hz, 1H), 4.71–4.67 (m, 1H), 4.45–4.41 (m, 1H), 4.32–4.20 (m, 2H), 3.93–3.83 (m, 2H), 3.83 (s, 3H), 3.80 (s, 3H).

EXAMPLE 103 (24)

4-(3,4,5-Trimethoxybenzyl)aminomethyl-3-phenylsulfonyl-2,3-dihydro-1,1-dioxidebenzo[b]thiophene

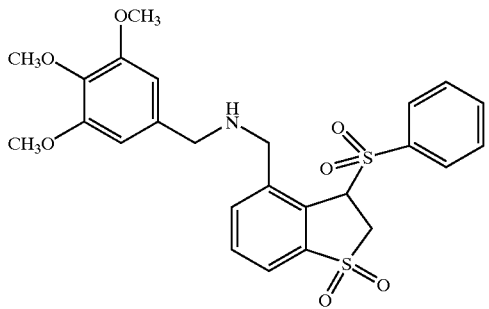

Free Compound

TLC: Rf 0.20(ethyl acetate);

NMR (CDCl$_3$): δ7.79 (dd, J=7.2, 1.2 Hz, 1H), 7.66–7.52 (m, 5H), 7.47–7.42 (m, 2H), 6.54 (s, 2H), 5.72 (dd, J=9.3, 1.2 Hz, 1H), 4.45 (d, J=14.0 Hz, 1H), 4.03 (d, J=14.0 Hz, 1H), 3.86 (s, 6H), 3.84 (s, 3H), 3.84 (dd, J=15.0, 1.2 Hz, 1H), 3.82 (d, J=13.5 Hz, 1H), 3.74 (d, J=13.5 Hz, 1H), 3.66 (dd, J=15.0, 9.3 Hz, 1H).

Hydrochloride

TLC: Rf 0.20 (ethyl acetate);

NMR (D MSO-d$_6$): δ9.98 (br, 1H), 9.63 (br, 1H), 8.18 (dd, J=6.6, 1.5 Hz, 1H), 7.89–7.78 (m, 3H), 7.72–7.60 (m, 4H), 7.06 (s, 2H), 6.30 (dd, J=6.0, 3.5 Hz, 1H), 4.69–4.66 (m, 1H), 4.39–4.37 (m, 1H), 4.24 (s, 2H), 3.92–3.84 (m, 2H), 3.80 (s, 6H), 3.67 (s, 3H).

EXAMPLE 103 (25)

4-(4-(t-Butyloxycarbonyl)piperazin-1-yl)methyl-3-phenylsulfonyl-2,3-dihydro-1,1-dioxidebenzo[b]thiophene

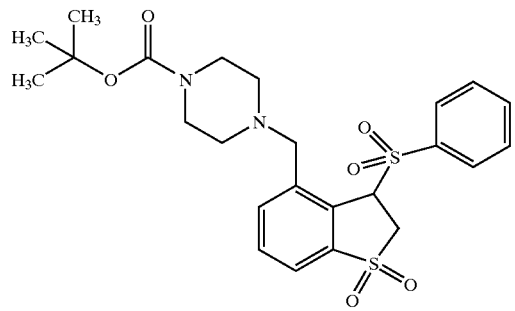

Free Compound

TLC: Rf 0.49 (hexane:ethyl acetate=1:2);

NMR (CDCl$_3$): δ7.66–7.52 (m, 6H), 7.48–7.43 (m, 2H), 6.18 (dd, J=9.0, 1.0 Hz, 1H), 4.69 (d, J=14.3 Hz, 1H), 3.89 (dd, J=15.0, 1.0 Hz, 1H), 3.72 (dd, J=15.0, 9.0 Hz, 1H), 3.49–3.35 (m, 4H), 3.45 (d, J=14.3 Hz, 1H), 2.52–2.45 (m, 2H), 2.36–2.29 (m, 2H), 1.46 (s, 9H).

Hydrochloride

TLC: Rf 0.49 (hexane:ethyl acetate 1:2);

NMR (CD$_3$OD): δ8.11 (d, J=7.2 Hz, 1H), 7.92–7.83 (m, 2H), 7.77–7.73 (m, 3H), 7.60–7.55 (m, 2H), 6.03 (dd, J=8.7, 1.0 Hz, 1H), 5.01 (d, J=14.3 Hz, 1H), 4.71 (d, J=14.3 Hz, 1H), 4.22 (br, 2H), 3.99 (dd, J=15.3, 8.7 Hz, 1H), 3.84 (dd, J=15.3, 1.0 Hz, 1H), 3.65–3.25 (br, 6H), 1.47 (s, 9H).

EXAMPLE 103 (26)

4-(2-Diisopropylaminoethyl)aminomethyl-3-phenylsulfonyl-2,3-dihydro-1,1-dioxidebenzo[b]thiophene.2hydrochloride

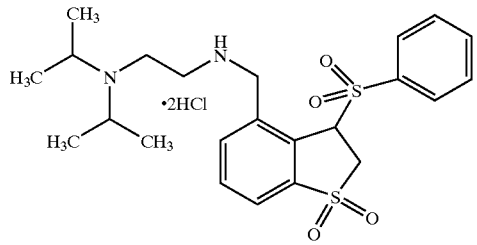

TLC: Rf 0.43(methanol:ethyl acetate:triethylamine= 2:8:0.5);

NMR (CD$_3$OD+D$_2$O): δ8.18 (d, J=7.5 Hz, 1H), 7.97–7.76 (m, 5H), 7.70–7.60 (m, 2H), 6.20–6.12 (m, 1H), 4.85 (d, J=13.8 Hz, 1H); 4.67 (d, J=13.8 Hz, 1H), 4.01–3.50 (m, 8H), 1.44(d, J=6.3 Hz, 12H).

EXAMPLE 103 (27)

4-(2-(Morpholin-4-yl)ethyl)aminomethyl-3-phenylsulfonyl-2,3-dihydro-1,1-dioxidebenzo[b]thiophene.2hydrochloride

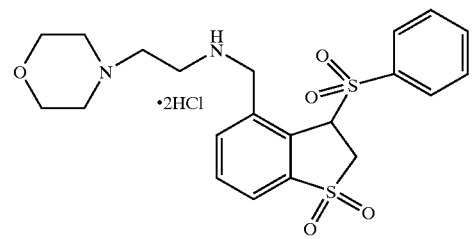

TLC: Rf 0.37(methanol:ethyl acetate:triethylamine= 2:8:0.5);

NMR (CD$_3$OD+D$_2$O): δ8.18 (d, J=7.5 Hz, 1H), 7.97–7.76 (m, 5H), 7.69–7.60 (m, 2H), 6.17–6.10 (m, 1H), 4.86 (d, J=13.8 Hz, 1H), 4.69 (d, J=13.8 Hz, 1H), 4.05–3.90 (m, 5H), 3.89–3.71 (m, 3H), 3.67–3.53 (m, 2H), 3.51–3.33 (m, 4H).

EXAMPLE 103 (28)

4-(N-2-(Piperidin-1-yl)ethyl-N-propyl)aminomethyl-3-phenylsulfonyl-2,3-dihydro-1,1-dioxidebenzo[b]thiophene

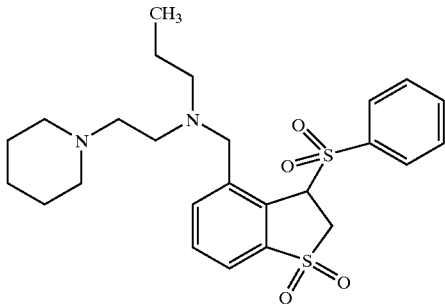

Free Compound
TLC: Rf 0.51 (ethyl acetate:triethylamine=9:1);
NMR (CDCl$_3$): δ7.68 (d, J=7.2 Hz, 1H), 7.64–7.46 (m, 5H), 7.44–7.39 (m, 2H), 6.29 (dd, J=9.3,1.2 Hz, 1H), 4.69 (d, J=14.4 Hz, 1H), 3.90 (dd, J=15.0, 1.2 Hz, 1H), 3.72 (dd, J=15.0, 9.3 Hz, 1H), 3.58 (d, J=14.4 Hz, 1H), 2.70–2.30 (m, 10H), 1.57–1.38 (m, 8H), 0.79 (t, J=7.2 Hz, 3H).
Hydrochloride
TLC: Rf 0.51 (ethyl acetate:triethylamine=9:1);
NMR (CD$_3$OD+pyridine-d$_5$): δ7.93 (d, J=7.2 Hz, 1H), 7.74–7.68 (m, 4H), 7.61–7.52 (m, 3H), 6.01 (dd, J=8.7, 1.2 Hz, 1H), 4.38 (d, J=14.7 Hz, 1H), 3.99 (dd, J=15.3, 8.7 Hz, 1H), 3.89 (dd, J=15.3, 1.2 Hz, 1H), 3.85 (d, J=14.7 Hz, 1H), 3.27–3.22 (m, 2H), 3.14 (br, 4H), 2.97–2.81 (m, 2H), 2.61–2.45 (m, 2H), 1.85–1.77 (m, 4H), 1.65–1.53 (m, 4H), 0.89 (t, J=7.3 Hz, 3H).

EXAMPLE 103 (29)

4-(N-2-(Piperidin-1-yl)ethyl-N-isopropyl)aminomethyl-3-phenylsulfonyl-2,3-dihydro-1,1-dioxidebenzo[b]thiophene

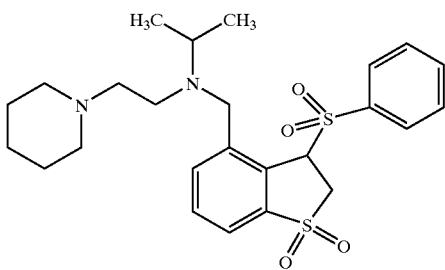

Free Compound
TLC: Rf 0.48 (ethyl acetate:triethylamine=9:1);
NMR (CDCl$_3$): δ7.77 (d, J=7.2 Hz, 1H), 7.65–7.47 (m, 5H), 7.45–7.40 (m, 2H), 6.09 (d, J=9.0, 1.0 Hz, 1H), 4.54 (d, J=15.0 Hz, 1H), 3.88 (dd, J=15.0, 1.0 Hz, 1H), 3.74 (d, J=15.0 Hz, 1H), 3.73 (dd, J=15.0, 9.0 Hz, 1H), 2.84 (sept, J=6.6 Hz, 1H), 2.57–2.51 (m, 2H), 2.38–2.17 (m, 6H), 1.55–1.48 (m, 4H), 1.42–1.35 (m, 2H), 1.06 (d, J=6.6 Hz, 3H), 1.03 (d, J=6.6 Hz, 3H).
Hydrochloride
TLC: Rf 0.48 (ethyl acetate:triethylamine=9:1);
NMR (CD$_3$OD+pyridine-d$_5$) δ7.99 (d, J=7.5 Hz, 1H), 7.75–7.70 (m, 4H), 7.61–7.54 (m, 3H), 5.93 (dd, J=8.7, 1.5 Hz, 1H), 4.27 (d, J=15.6 Hz, 1H), 3.99 (dd, J=15.3, 8.7 Hz, 1 H), 3.96 (d, J=15.6 Hz, 1H), 3.88 (dd, J=15.3, 1.5 Hz, 1H), 3.20–2.80 (m, 9H), 1.82–1.75 (m, 4H), 1.63–1.58 (m, 2H), 1.17–1.14 (m, 6H).

EXAMPLE 103 (30)

4-(3,4-Dimethoxybenzyl)aminomethyl-3-phenylsulfonyl-2,3-dihydro-1,1-dioxidebenzo[b]thiophene

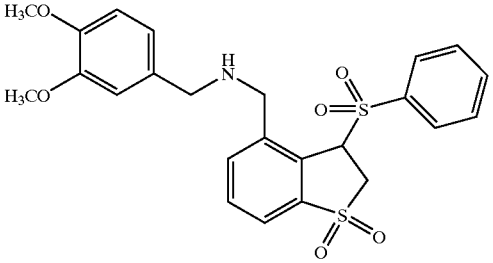

Free Compound
TLC: Rf 0.19 (ethyl acetate);
NMR (CDCl$_3$) δ7.76 (dd, J=7.2, 1.0 Hz, 1H), 7.65–7.51 (m, 5H), 7.46–7.41 (m, 2H), 6.84–6.82 (m, 3H), 5.79 (d, J=9.3 Hz, 1H), 4.47 (d, J=14.0 Hz, 1H), 4.00 (d, J=14.0 Hz, 1H), 3.87 (s, 6H), 3.85 (d, J=15.0 Hz, 1H), 3.82 (d, J=13.2 Hz, 1H), 3.73 (d, J=13.2 Hz, 1H), 3.66 (dd, J=15.0, 9.3 Hz, 1 H).
Hydrochloride
TLC: Rf 0.19 (ethyl acetate);
NMR (DMSO-d$_6$): δ10.00–9.70 (br, 2H), 8.38–8.28 (m, 1H), 8.06–7.94 (m, 3H), 7.88–7.76 (m, 4H), 7.56 (d, J=1.4 Hz, 1H), 7.27 (dd, J=8.4, 1.4 Hz, 1H), 7.18 (d, J=8.4 Hz, 1H), 6.43–6.38 (m, 1H), 4.80 (d, J=12.8 Hz, 1H), 4.53 (d, J=12.8 Hz, 1H), 4.40 (s, 2H), 4.13–4.00 (m, 2H), 3.94 (s, 6H).

EXAMPLE 103 (31)

4-(3-(2-Methylpiperidin-1-yl)propyl)aminomethyl-3-phenylsulfonyl-2,3-dihydro-1,1-dioxidebenzo[b]thiophene.2hydrochloride

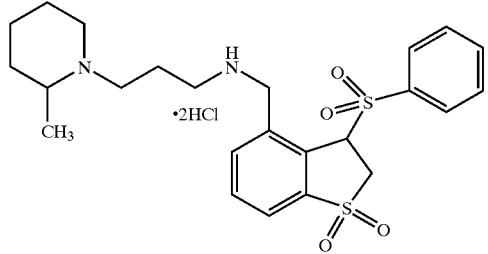

TLC: Rf 0.33 (ethyl acetate:methanol:triethylamine=8:2:0.5);
NMR (CD$_3$OD): δ8.18 (d, J=7.2 Hz, 1H), 7.92–7.73 (m, 5H), 7.67–7.57 (m, 2H), 6.22–6.23 (m, 1H), 4.80 (d, J=13.5 Hz, 1H), 4.62 (d, J=13.5 Hz, 1h), 3.98–3.91 (m, 1H), 3.83–3.74 (m, 1H), 3.64–2.98 (m, 7H), 2.37–2.17 (m, 2H), 2.07–1.52 (m, 6H), 1.41 (d, J=6.3 Hz, 3H).

EXAMPLE 103 (32)

4-(4-(Piperidin-1-yl)piperidin-1-yl)methyl-3-phenylsulfonyl-2,3-dihydro-1,1-dioxidebenzo[b]thiophene.2hydrochloride

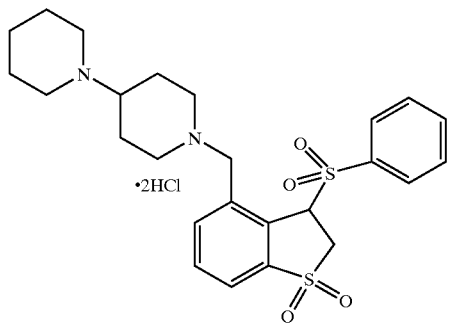

TLC: Rf 0.41 (ethyl acetate:methanol:triethylamine= 8:2:0.5);

NMR (D$_2$O): δ8.17–8.08 (m, 1H), 8.03–7.94 (m, 2H), 7.91–7.82 (m, 1H), 7.79–7.73 (m, 2H), 7.72–7.62 (m, 2H), 4.71 (d, J=14.4 Hz,1H), 4.65 (d, J=14.4 Hz, 1H), 4.21–4.05 (m, 2H), 3.87–3.75 (m, 1H), 3.69–3.48 (m, 4H), 3.38–2.98 (m, 4H), 2.52–2.32 (m, 2H), 2.19–1.93 (m, 4H), 1.91–1.65 (m, 3H), 1.59–1.40 (m, 1H).

EXAMPLE 103 (33)

4-(3-(Piperidin-1-yl)propyl)aminomethyl-3-phenylsulfonyl-2,3-dihydro-1,1-dioxidebenzo[b]thiophene.2hydrochloride

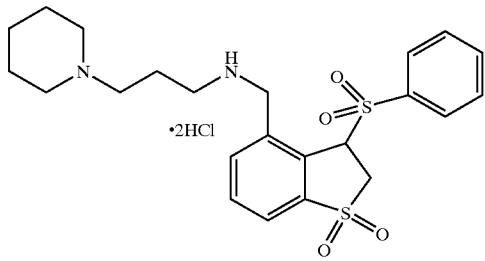

TLC: Rf 0.25 (methanol:ethyl acetate:triethylamine= 2:8:0.5);

NMR (CD$_3$OD+D$_2$O): δ8.16 (d, J=7.2 Hz, 1H), 7.95–7.74 (m, 5H), 7.69–7.59 (m, 2H), 6.17–6.08 (m, 1H), 4.78 (d, J=14.1 Hz, 1H), 4.62 (d, J=14.1 Hz, 1H), 4.02–3.88 (m, 1H), 3.85–3.73 (m, 1H), 3.73–2.76 (m, 8H), 2.38–2.21 (m, 2H), 2.14–1.44 (m, 6H).

EXAMPLE 103 (34)

4-(3-Bromobenzyl)aminomethyl-3-phenylsulfonyl-2,3-dihydro-1,1-dioxidebenzo[b]thiophene.hydrochloride

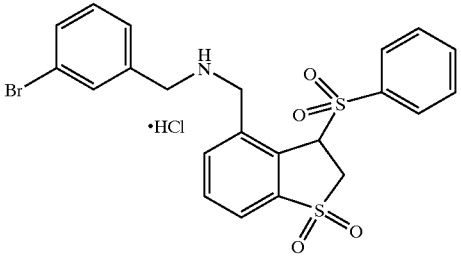

TLC: Rf 0.50 (ethyl acetate:triethylamine=6:0.5);

NMR (DMSO-d$_6$): δ9.83 (brs, 1H), 9.56 (brs, 1H), 8.16 (d, J=6.6 Hz, 1H), 7.90–7.70 (m, 6H), 7.68–7.58 (m, 4H), 7.41 (t, J=7.5 Hz, 1H), 6.41–6.28 (m, 1H), 4.80–4.60 (m, 1H), 4.52–4.22 (m, 3H), 3.96–3.80 (m, 2H).

EXAMPLE 103 (35)

4-(4-Nitrobenzyl)aminomethyl-3-phenylsulfonyl-2,3-dihydro-1,1-dioxidebenzo[b]thiophene.hydrochloride

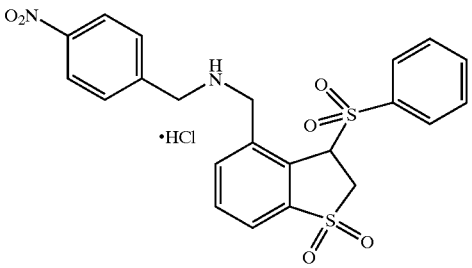

TLC: Rf 0.34 (ethyl acetate:triethylamine=6:0.5);

NMR (DMSO-d$_6$): δ10.05 (brs, 1H), 9.79 (brs, 1H), 8.29 (d, J=8.1 Hz, 2H), 8.18 (d, J=6.6 Hz, 1H), 7.94–7.70 (m, 7H), 7.67–7.57 (m, 2H), 6.48–6.33 (m, 1H), 4.83–4.64 (m, 1H), 4.59–4.35 (m, 3H), 3.95–3.81 (m, 2H).

EXAMPLE 103 (36)

4-(4-Aminosulfonylbenzyl)aminomethyl-3-phenylsulfonyl-2,3-dihydro-1,1-dioxidebenzo[b]thiophene

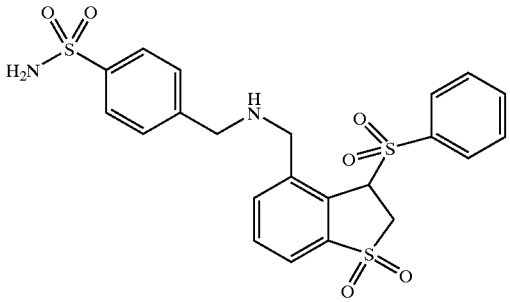

Free Compound
TLC: Rf 0.40 (ethyl acetate:methanol=9:1);
NMR (DMSO-d$_6$): δ7.93 (dd, J=7.0, 1.5 Hz, 1H), 7.79–7.66 (m, 7H), 7.63–7.58 (m, 2H), 7.53 (d, J=8.0 Hz, 2H), 7.31 (s, 2H), 5.93 (dd, J=8.3, 1.5 Hz, 1H), 4.07 (d, J=14.1 Hz, 1H), 3.95 (dd, J=15.0, 8.3 Hz, 1H), 3.87 (dd, J=15.0, 1.5 Hz, 1H), 3.82 (d, J=14.1 Hz, 1H), 3.75 (s, 2H), 2.86 (br, 1H).

Hydrochloride

TLC: Rf 0.40 (ethyl acetate:methanol=9:1);

NMR (DMSO-$d_6$): δ9.80 (br, 1H), 9.52 (br, 1H), 8.15 (d, J=7.0 Hz, 1H), 7.89–7.74 (m, 9H), 7.67–7.62 (m, 2H), 7.44 (s, 2H), 6.37–6.32 (m, 1H), 4.78–4.70 (m, 1H), 4.47–4.41 (m, 1H), 4.41 (s, 2H), 3.96–3.84 (m, 2H).

EXAMPLE 103 (37)

4-(Piperazin-1-yl)methyl-3-phenylsulfonyl-2,3-dihydro-1,1-dioxidebenzo[b]thiophene·2hydrochloride

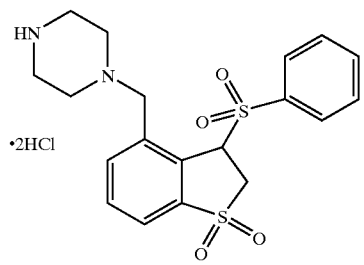

TLC: Rf 0.10 (ethyl acetate:methanol:triethylamine 8:2:1);

NMR (CD$_3$OD+D$_2$O): δ7.96 (d, J=7.8 Hz, 1H), 7.80–7.67 (m, 5H), 7.61–7.56 (m, 2H), 6.16 (dd, J=9.0, 1.3 Hz, 1H), 4.60 (d, J=14.5 Hz, 1H), 4.01 (dd, J=15.4, 9.0 Hz, 1H), 3.95 (d, J=14.5 Hz, 1H), 3.89 (dd, J=15.4, 1.3 Hz, 1H), 3.37–3.33 (m, 4H), 2.98–2.90 (m, 4H).

EXAMPLE 103 (38)

4-(2,4,6-Trimethoxybenzyl)methyl-3-phenylsulfonyl-2,3-dihydro-1,1-dioxidebenzo[b]thiophene

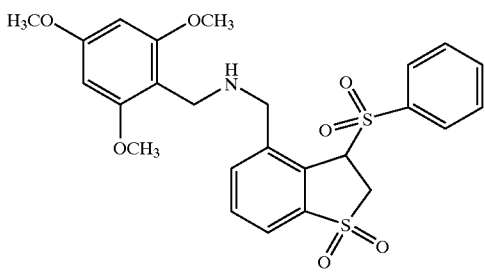

Free Compound

TLC: Rf 0.38 (ethyl acetate:methanol=9:1);

NMR (CDCl$_3$): δ7.69 (dd, J=7.0, 1.5 Hz, 1H), 7.64–7.49 (m, 5H), 7.45–7.40 (m, 2H), 6.19 (dd, J=9.0, 1.0 Hz, 1H), 6.12 (s, 2H), 4.50 (d, J=14.3 Hz, 1H), 3.88 (d, J=14.3 Hz, 1H), 3.85 (dd, J=15.0, 1.0 Hz, 1H), 3.81 (s, 3H), 3.75 (s, 6H), 3.73 (d, J=12.6 Hz, 1H), 3.65 (d, J=12.6 Hz, 1H), 3.64 (dd, J=15.0, 9.0 Hz, 1H).

Hydrochloride

TLC: Rf 0.38 (ethyl acetate:methanol=9:1);

NMR (DMSO-$d_6$): δ9.11 (br, 1H), 8.94 (br, 1H), 8.16–8.13 (m, 1H), 7.88–7.87 (m, 2H), 7.84–7.79 (m, 1H), 7.71–7.61 (m, 4H), 6.31 (s, 2H), 5.92 (dd, J=8.0, 1.8 Hz, 1H), 4.66–4.62 (m, 1H), 4.39–4.34 (m, 1H), 4.18–4.13 (m, 1H), 3.97–3.91 (m, 1H), 3.92 (dd, J=15.3, 8.0 Hz, 1H), 3.83 (dd, J=15.3, 1.8 Hz, 1H), 3.82 (s, 3H), 3.79 (s, 6H).

EXAMPLE 103 (39)

4-(Piperidin-1-yl)carbonylmethylaminomethyl-3-phenylsulfonyl-2,3-dihydro-1,1-dioxidebenzo[b]thiophene

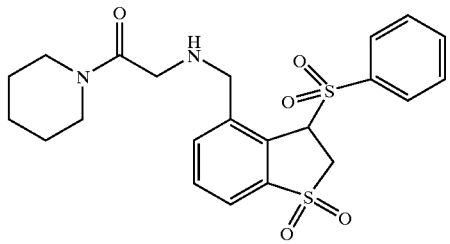

Free Compound

TLC: Rf 0.42 (ethyl acetate:methanol:triethylamine= 8:1:1);

NMR (CDCl$_3$): δ7.75.(dd, J=6.9, 2.1 Hz, 1H), 7.66–7.60 (m, 3H), 7.58–7.53 (m, 2H), 7.48–7.43 (m, 2H), 6.13 (dd, J=9.0, 1.2 Hz, 1H), 4.61 (d, J=13.8 Hz, 1H), 3.97 (d, J=13.8 Hz, 1H), 3.87 (dd, J=15.0, 1.2 Hz, 1H), 3.75 (dd, J=15.0, 9.0 Hz, 1H), 3.58 (t, J=5.2 Hz, 2H), 3.50 (d, J=16.0 Hz, 1H), 3.41 (d, J=16.0 Hz, 1H), 3.30 (t, J=5.2 Hz, 2H), 1.69–1.55 (m, 6H).

Hydrochloride

TLC: Rf 0.42 (ethyl acetate:methanol:triethylamine= 8:1:1);

NMR (DMSO-$d_6$): δ9.63 (br, 1H), 9.18 (br, 1H), 8.11 (d, J=7.2 Hz, 1H), 7.93–7.80 (m, 5H), 7.70–7.64 (m, 2H), 6.28 (dd, J=6.0, 4.0 Hz, 1H), 4.83 (d, J=13.2 Hz, 1H), 4.32 (d, J=13.2 Hz, 1H), 4.28–4.16 (m, 2H), 3.85 (dd, J=15.3, 6.0 Hz, 1H), 3.80 (dd, J=15.3, 4.0 Hz, 1H), 3.54–3.50 (m, 2H), 3.37–3.32 (m, 2H), 1.64–1.49 (m, 6H).

EXAMPLE 103 (40)

4-(Pyrrolidin-1-yl)ethylaminomethyl-3-phenylsulfonyl-2,3-dihydro-1,1-dioxidebenzo[b]thiophene·2hydrochloride

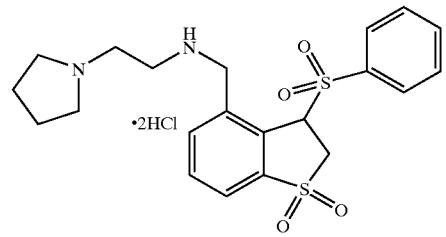

TLC: Rf 0.22(methanol:ethyl acetate:triethylamine= 2:8:0.5);

NMR (CD$_3$OD+D$_2$O): δ8.16 (d, J=7.5 Hz, 1H), 7.94–7.75 (m, 5H), 7.68–7.58 (m, 2H), 6.15–6.08 (m, 1H), 4.81 (d, J=13.8 Hz, 1H), 4.63 (d, J=13.8 Hz, 1H), 4.01–3.88 (m, 1H), 3.86–3.76 (m, 1H), 3.75–3.62 (m, 4H), 3.62–3.38 (m, 4H), 2.20–2.06 (m, 4H).

EXAMPLE 103 (41)

4-(4-(1,3-Dioxaindan-5-ylmethyl)piperazin-1-yl)methyl-1,1-dioxidebenzo[b]thiophene.2hydrochloride

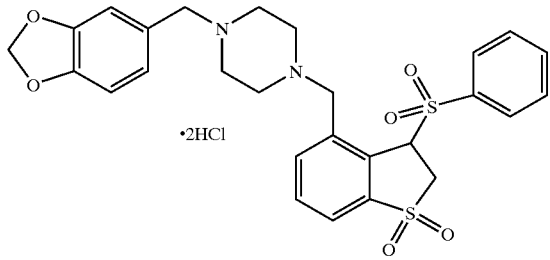

TLC: Rf 0.51 (ethyl acetate:triethylamine=6:0.5);

NMR (CD$_3$OD+D$_2$O): δ7.90 (d, J=7.5 Hz, 1H), 7.79–7.52 (m, 7H), 7.04–6.96 (m, 2H), 6.95–6.87 (m, 1H), 6.15–6.07 (m, 1H), 6.01 (s, 2H), 4.45 (d, J=14.4 Hz, 1H), 4.25 (s, 2H), 4.01 (dd, J=15.6, 8.7 Hz, 1H), 3.90 (dd, J=15.6, 1.2 Hz, 1H), 3.77 (d, J=14.4 Hz, 1H), 3.50–3.10 (br, 4H), 2.98–2.63 (br, 4H).

EXAMPLE 104

4-Cyano-6,7-dihydrobenzo[b]thiophene

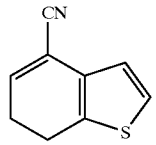

To a suspension of zinc iodide (6.2 g) in acetonitrile (200 ml) were added 4-keto-4,5,6,7-tetrahydrothianaphthene (20 g) and trimethylsilylcyanide (18 ml) successively. The mixture was stirred at room temperature for 5 hours. The reaction mixture was concentrated. The residue was dissolved in pyridine (65 ml), followed by adding phosphryl chloride (15 ml) dropwise at room temperature. The mixture was refluxed for 30 minutes. The reaction mixture was cooled with ice and thereto was added dropwise isopropanol. The reaction mixture was poured onto ice water and extracted with ethyl acetate. The extract was washed by hydrochloric acid, water and a saturated aqueous solution of sodium chloride successively, dried over anhydrous magnesium sulfate and concentrated to give the title compound (17 g) having the following physical data.

TLC: Rf 0.45 (hexane:ethyl acetate=3:1);

NMR (CDCl$_3$): δ7.12 (d, J=5.4 Hz, 1H), 7.07 (d, J=5.4 Hz, 1H), 6.62 (t, J=4.8 Hz, 1H), 2.93 (t, J=9.0 Hz, 2H), 2.60 (td, J=9.0, 4.8 Hz, 2H).

EXAMPLE 105

4-Cyanobenzo[b]thiophene

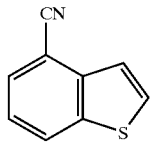

To a solution of the compound prepared in Example 104 (17 g) in benzene (200 ml), was added 2,3-dichloro-5,6-dicyano-1,4-benzoquinone (30 g). The mixture was refluxed for 1.5 hours. The mixture was filtered. The filtrate was concentrated. The residue was extracted with a mixed solvent (hexane:ethyl acetate=1:1). The extract was washed by an aqueous solution of sodium hydroxide, water and a saturated aqueous solution of sodium chloride successively, dried over anhydrous magnesium sulfate and concentrated. The residue was purified with column chromatopgaphy on silica gel (hexane:ethyl acetate=100:1) to give the title compound (14.5 g) having the following physical data.

TLC: Rf 0.40 (hexane:ethyl acetate=4:1);

NMR (CDCl$_3$): δ7.45 (t, J=7.5 Hz, 1H), 7.60 (d, J=5.0 Hz, 1H), 7.70 (d, J=5.0 Hz, 1H), 7.75 (d, J=7.5Hz, 1H), 8.10 (d, J=7.5 Hz, 1H).

EXAMPLE 106

4-Carboxybenzo[b]thiophene

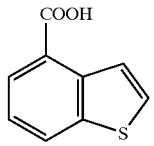

1) To a suspension of the compound prepared in Example 105 (14.5 g) in ethyleneglycol (50 ml) was added 85% potassium hydroxide (19 g). The mixture was stirred at 180° C. for 2 hours. The reaction mixture was poured into hydrochloric acid, and the acidic mixture was extracted with ethyl acetate. The extract was washed by water and a saturated aqueous solution of sodium chloride sucessively, dried over anhydrous magnesium sulfate and concentrated under reduced pressure. The residue was recrystallized from a mixed solvent of ethyl acetate and hexane to give the title compound (12.2 g) having the following physical data.

The above title compound may be prepared by the following method.

2) A mixture of the compound prepared in Example 104 (1.61 g), nitrobenzene (2.46 g), ethyleneglycol (10 ml) and 10% palladium carbon (161 mg) was stirred at 200° C. for 3 hours and at 180° C. for 17 hours. To the reaction mixture, sodium hydroxide was added at 150° C. The mixture was stirred at 180° C. for 1 hour. The reaction mixture was cooled to room temperature. Thereto were added water (10 ml) and activated charcoal. The mixture was filtrated. The filtrate was washed by ethyl acetate (20 ml). To aqueous layer was added concentrated hydrochloric acid (2.5 ml). The mixture was extracted with ethyl acetate, washed by water and a saturated aqueous solution of sodium chloride, dried over anhydrous magnesium sulfate and concentrated. The residue was recrystallized from acetonitrile (25 ml) to give the title compound (1.46 g).

TLC: Rf 0.10 (hexane:ethyl acetate=4:1);

NMR (CDCl$_3$): δ8.32 (dd, J=5.6, 1.0 Hz, 1H), 8.27 (dd, J=7.6, 1.0 Hz, 1H), 8.18–8.11 (m, 1H), 7.68 (d, J=5.6 Hz, 1H), 7.51–7.41 (m, 1H).

EXAMPLE 107

4-Carboxy-1,1-dioxidebenzo[b]thiophene

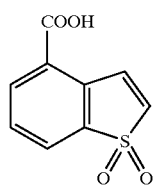

To a suspension of the compound prepared in Example 106 (35 g) in methanol (720 ml), was added a suspension of OXONE@ (362 g) in pure water (720 ml) at room temperature. The mixture was stirred at 40° C. for 2 hours. The reaction mixture was filtered. The filtrate was concentrated. The residue was extracted with ethyl acetate. The organic layer was washed by a saturated aqueous solution of sodium chloride, dried over anhydrous magnesium sulfate and concentrated under reduced pressure. The residue was crystallized from hexane, followed by drying to give the compound of the present invention (30 g) having the following physical data.

TLC: Rf 0.18 (ethyl acetate);

NMR (CDCl$_3$): δ8.28 (d, J=7.5 Hz, 1H), 8.26 (d, J=7.5 Hz, 1H), 7.94 (d, J=7.5 Hz, 1H), 7.66 (t, J=7.5 Hz, 1H), 6.87 (d, J=7.5 Hz, 1H).

Examples Relates to Different Method for Preparation of the Compounds of the Present Invention The compounds prepared in Examples 35 (49)~(61), Example 70, Example 94, Examples 103~103 (29) may be prepared by the same procedure as described hereinafter in Example 108 or Example 109.

1) For example, the compound described in Example 35 (50) may be prepared by the following procedure.

EXAMPLE 108

4-(Pyridin-3-ylmethyl)aminomethyl-3-phenylsulfonyl-2,3-dihydro-1,1-dioxidebenzo[b]thiophene.2hydrochloride

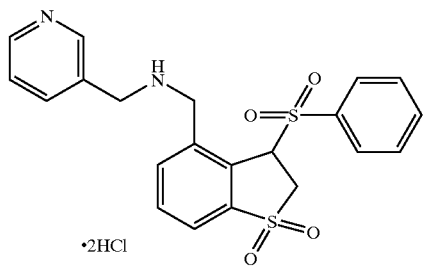

Under an atmosphere of argon, to a solution of the compound prepared in Example 82 in dimethylformamide (5 ml) was added a solution of 3-(aminomethyl)pyridine (73 ∥l) in dimethylformamide (1 ml), followed by adding 5% palladium-carbon (50 mg). Then, an atmosphere was replaced by hydrogen. The mixture was stirred at room temperature for 1.5 hours. The reaction mixture was filtered. The filtrate was concentrated. The obtained residue was purified with column chromatography on silica gel (chloroform:methanol=25:1) followed by converting into hydrochloride by addition of 4N hydrochloride/ethyl acetate and recrystallization using ethanol to give the compound of the present invention (231 mg).

A free compound of the compound described in Example 35 (52) may be prepared by the following procedure.

EXAMPLE 109

4-(N,N-Bis(2-hydroxyethyl)amino)methyl-3-phenylsulfonyl-2,3-dihydro-1,1-dioxidebenzo[b]thiophene

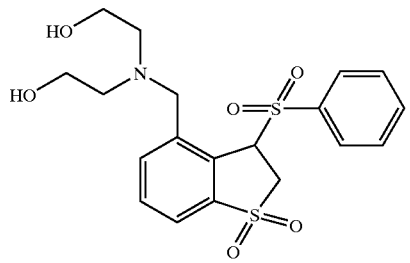

To a suspension of the compound prepared in Example 82 (168 mg) in methylene chloride (2 ml) were added diethanolamine (53 μl), sodium borocyanohydride (63 mg), concentrated hydrochloric acid (2 drops) and methanol (0.5 ml). The mixture was stirred at room temperature for 6 hours. The reaction mixture was poured into water, and extracted with a mixed solvent (methylene chloride and methanol). The organic layer was washed by a saturated aqueous solution of sodium chloride, dried over anhydrous magnesium sulfate and concentrated. The residue was purified with column chromatography on silica gel to give the compound of the present invention (50 mg).

2) The compound prepared in Example 81 (1) may be prepared by the same procedure as described in Example 27 using the compound prepared in Example 107 instead of 5-methyl-1,1-dioxidebenzo[b]thiophene, and if necesary, by converting into a corresponding free compound by a known method.

3) The compounds prepared in Examples 35~35 (32), Examples 45 (1)~45 (2), Example 70, Example 71 and Example 87 may be prepared by the same procedure as described in Example 100.

For example, the compound prepared in Example 35 (11) may be prepared by the same procedure as described in Example 100 using the compound (free compound or sodium salt) prepared in Example 81 (1), and 2-(piperidin-1-yl)ethylamine instead of furan-2-ylmethylamine.

[Formulation Example]

Formulation Example 1

The following components were admixed in a conventional method and punched out to obtain 100 tablets each containing 50 mg of active ingredient.

| | |
|---|---|
| 4-(Pyridin-3-ylmethyl)oxy-3-phenylsulfonyl-2,3-dihydro-1,1-dioxidebenzo[b]thiophene | 5.0 g |
| Carboxymethylcellulose calcium (disintegrating agent) | 0.2 g |
| Magnesium stearate (lubricating agent) | 0.1 g |
| Microcrystalline cellulose | 4.7 g |

Formulation Example 2

The following components were admixed in a conventional method, and the solution was sterilized in a conventional method, placed 5 ml portions into ampoules and freeze-dried in a conventional method to obtain 100 ampoules each containing 20 mg of active ingredient.

| | |
|---|---|
| 4-(Pyridin-3-ylmethyl)oxy-3-phenylsulfonyl-2,3-dihydro-1,1-dioxidebenzo[b]thiophene | 2.0 g |
| Mannitol | 20 g |
| Distilled water | 550 ml |

What is claimed is:

1. An inhibitor of interleukin-6 and/or interleukin-12 production comprising, as an active ingredient, a fused thiophene derivative of the formula (I)

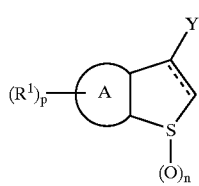

(I)

wherein === is a single or double bond,
Y is
(i)

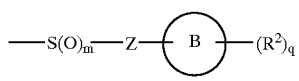

or
(ii) hydrogen
(with the proviso that when === is a double bond, Y is hydrogen, and when === is a single bond, Y is

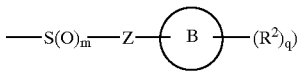

m and n are each independently 0 or an integer of 1–2,
p is 0 or an integer of 1–4,
q is 0 or an integer of 1–5,
Z is single bond, C1–8 alkylene, C2–8 alkenylene or C2–8 alkynylene,

is
(i) benzene ring or
(ii) 6-membered monocyclic hetero aryl containing 1–2 nitrogen atom(s),

is
(i) C3–15 mono-, bi- or tricyclic carbo ring or
(ii) 4–18 membered mono-, bi- or tricyclic hetero ring containing 1–4 nitrogen atoms, 1–2 oxygen atoms and/or one sulfur atom, each $R^1$ of $(R^1)p$ is independently,
(i) C1–8 alkyl,
(ii) C2–8 alkenyl,
(iii) C2–8 alkynyl,
(iv) nitro,
(v) cyano,
(vi) halogen,
(vii) $Cyc^1$,
(viii) C1–8 alkyl, C2–8 alkenyl or C2–8 alkynyl substituted with halogen or $Cyc^1$ or
(ix) —$A^1$—$A^2$—$A^3$,
$A^1$ is
(i) single bond,
(ii) C1–8 alkylene,
(iii) C2–8 alkenylene or
(iv) C2–8 alkynylene,
$A^2$ is
(i) —O—,
(ii) —$NR^3$—,
(iii) —C(O)—,
(iv) —CH(OH)—,
(v) —C(O)$NR^4$—,
(vi) —$NR^5$C(O)—,
(vii) —C(O)O—,
(viii) —OC(O)—,
(ix) —$SO_2NR^6$—,
(x) —$NR^7SO_2$—,
(xi) —C(O)$NR^9$O—,
(xii) —OC(O)$NR^{10}$—,
(xiii) —$NR^{11}$C(O)$NR^{12}$—,
(xiv) —$NR^{13}$C(O)O— or
(xv) —OC(O)O—
wherein $R^3$, $R^4$, $R^5$, $R^6$, $R^7$, $R^9$, $R^{10}$, $R^{11}$, $R^{12}$ and $R^{13}$ are each independently, hydrogen, C1–8 alkyl, phenyl or C1–8 alkyl substituted with $Cyc^1$, cyano, —$OR^{14}$, wherein $R^{14}$ is hydrogen or C1–8 alkyl, with the proviso that the linkage of the right side of each group represented by $A^2$ binds to $A^3$,
$A^3$ is
(i) hydrogen,
(ii) C1–8 alkyl,
(iii) C2–8 alkenyl,
(iv) C2–8 alkynyl,
(v) $Cyc^1$ or
(vi) C1–8 alkyl, C2–8 alkenyl or C2–8 alkynyl substituted with 1–3 groups selected from the following (a)–(i):
(a) halogen,
(b) cyano,
(c) —P(O)$(R^{15})_2$,
(d) —Si$(R^{16})_3$,
(e) $Cyc^1$,
(f) —C(O)$R^{17}$,
(g) —$OR^{18}$,
(h) —$NR^{19}R^{20}$,
(i) —$SR^{21}$;
each $R^{15}$ is independently, hydroxy or C1–8 alkoxy,
each $R^{16}$ is independently C1–8 alkyl, $R^{17}$ is
- (i) hydrogen,
- (ii) C1–8 alkyl,
- (iii) hydroxy,
- (iv) C1–8 alkoxy,
- (v) $Cyc^1$ or
- (vi) —$NR^{22}R^{23}$, (wherein $R^{22}$ is hydrogen, C1–8 alkyl, phenyl or C1–8 alkyl substituted with phenyl, and wherein $R^{23}$ is hydrogen, C1–8 alkyl, $Cyc^1$ or C1–8 alkyl substituted with $Cyc^1$ or $NR^{24}R^{25}$, wherein $R^{24}$ and $R^{25}$ are each independently hydrogen, C1–8 alky, phenyl, C1–8 alkyl substituted with phenyl, $R^{18}$ is
- (i) hydrogen,
- (ii) C1–8 alkyl,
- (iii) C2–8 alkenyl,
- (iv) $Cyc^1$ or
- (v) C1–8 alkyl substituted with (a) $Cyc^1$, (b) $Si(R^{26})_3$ wherein each $R^{26}$ is independently C1–8 alkyl, or (c) —$OR^{27}$, wherein $R^{27}$ is hydrogen, C1–8 alkyl or C2–5 acyl, $R^{19}$ is
- (i) hydrogen,
- (ii) C1–8 alkyl,
- (iii) phenyl or
- (iv) C1–8 alkyl substituted with phenyl, $R^{20}$ is
- (i) hydrogen,
- (ii) C1–8 alkyl or
- (iii) —$C(O)R^{28}$, wherein $R^{28}$ is C1–8 alkyl, C1–8 alkoxy, $Cyc^1$ or $NR^{29}R^{30}$, wherein $R^{29}$ and $R^{30}$ are each independently, hydrogen or C1–8 alkyl,
- (iv) $Cyc^1$ or
- (v) C1–8 alkyl substituted with $Cyc^1$ or cyano, $R^{21}$ is
- (i) hydrogen,
- (ii) C1–8 alkyl or
- (iii) $Cyc^1$, $Cyc^1$ is
- (i) C3–15 mono-, bi- or tricyclic carbo ring or
- (ii) 4–18 membered mono-, bi- or tricyclic hetero ring containing 1–4 nitrogen atom(s), 1–2 oxygen atom(s) and/or one sulfur atom, wherein the said carbocyclic ring or heterocyclic ring may be substituted with one or more of (i) C1–8 alkyl, (ii) C2–8 alkenyl, (iii) C2–8 alkynyl, (iv) oxo, (v) cyano, (vi) nitro, (vii) trihalomethyl, (viii) trihalomethoxy, (ix) halogen, (x) diphenylmethyl, (xi) triphenylmethyl, (xii) $Cyc^2$, (xiii) —$OR^{31}$, (xiv) —$SR^{32}$, (xv) —$NR^{33}R^{34}$, (xvi) —$SO_2NR^{35}R^{36}$, (xvii) —$C(O)R^{37}$ or (xviii) C1–8 alkyl, C2–8 alkenyl or C2–8 alkynyl substituted with $Cyc^2$, hydroxy, halogen or —$C(O)$—$Cyc^2$, $R^{31}$ and $R^{32}$ are each independently, hydrogen, C1–8 alkyl or $Cyc^2$, $R^{33}$ is hydrogen or C1–8 alkyl, $R^{34}$ is hydrogen, C1–8 alkyl or —$C(O)$—$Cyc^2$, $R^{35}$ is hydrogen or C1–8 alkyl, $R^{36}$ is hydrogen, C1–8 alkyl or $Cyc^2$, $R^{37}$ is hydrogen, C1–8 alkyl, —$OR^{38}$, —$NR^{39}R^{40}$, $Cyc^2$, or C1–8 alkyl substituted with $Cyc^2$ or —$C(O)$—$Cyc^2$, $R_{38}$, $R^{39}$ and $R^{40}$ are each independently, hydrogen, C1–8 alkyl, or C1–8 alkyl substituted with $Cyc^2$, $CyC^2$ is
- (i) C3–15 mono-, bi- or tricyclic carbo ring or
- (ii) 4–18 membered mono-, bi- or tricyclic hetero ring containing 1–4 nitrogen atom(s), 1–2 oxygen atom(s) and/or one sulfur atom, wherein the said carbocyclic ring or heterocyclic ring may be substituted with one or more of (i) C1–8 alkyl, (ii) C2–8 alkenyl, (iii) C2–8 alkynyl, (iv) oxo, (v) cyano, (vi) nitro, (vii) trihalomethyl, (viii) trihalomethoxy, (ix) halogen, (x) —$OR^{41}$, (xi) —$SR^{42}$, (xii) —$NR^{43}R^{44}$, (xiii) —$SO_2NR^{45}R^{46}$, (xiv) —$C(O)R^{47}$, (xv) C1–8 alkyl, C2–8 alkenyl or C2–8 alkynyl substituted with hydroxy or halogen or (xvi) phenyl, $R^{41}$, $R^{42}$, $R^{43}$, $R^{44}$, $R^{45}$ and $R^{46}$ are each independently, hydrogen or C1–8 alkyl, $R^{47}$ is hydrogen, C1–8 alkyl or C1–8 alkoxy each $R^2$ of $(R^2)q$ is independently,
- (i) C1–8 alkyl,
- (ii) C2–8 alkenyl,
- (iii) C2–8 alkynyl,
- (iv) —$OR^{48}$,
- (v) —$NR^{49}R^{50}$,
- (vi) —$C(O)R^{51}$,
- (vii) nitro,
- (viii) cyano,
- (ix) halogen or
- (x) C1–8 alkyl, C2–8 alkenyl or C2–8 alkynyl substituted with —$OR^{48}$, —$NR^{49}R^{50}$, —$C(O)R^{51}$, halogen or $Cyc^3$, $R^{48}$ is
- (i) hydrogen,
- (ii) C1–8 alkyl,
- (iii) C2–8 alkenyl,
- (iv) C2–8 alkynyl,
- (v) $Cyc^3$ or
- (vi) C1–8 alkyl, C2–8 alkenyl or C2–8 alkynyl substituted with halogen, —$OR^{52}$, —$NR^{53}R^{54}$, —$C(O)R^{55}$ or $Cyc^3$, $R^{49}$ and $R^{50}$ are each independently, hydrogen, C1–8 alkyl or —$COR^{59}$, $R^{51}$ is hydrogen, C1–8 alkyl, hydroxy, C1–8 alkoxy or —$NR^{60}R^{61}$, $R^{52}$ is hydrogen, C1–8 alkyl, $Cyc^3$, or C1–8 alkyl substituted with $Cyc^3$, $R^{53}$ and $R^{54}$ are each independently, hydrogen, C1–8 alkyl, C2–8 alkenyl, C2–8 alkynyl or —$C(O)R^{56}$, wherein $R^{56}$ is C1–8 alkyl, C1–8 alkoxy, $Cyc^3$, or C1–8 alkyl substituted with $Cyc^3$, $R^{55}$ is hydroxy, C1–8 alkoxy, or —$NR^{57}R^{58}$, wherein $R^{57}$ and $R^{58}$ are each independently, hydrogen, C1–8 alkyl, or C1–8 alkyl substituted with $Cyc^3$, $R^{59}$ is C1–8 alkyl or C1–8 alkoxy, $R^{60}$ and $R^{61}$ are each independently, hydrogen or C1–8 alkyl, $Cyc^3$ is
- (i) C3–15 mono-, bi- or tricyclic carbo ring or
- (ii) 4–18 membered mono-, bi- or tricyclic hetero ring containing 1–4 nitrogen atom(s), 1–2 oxygen atom(s) and/or one sulfur atom, wherein the said carbocyclic ring or heterocyclic ring may be substituted with one or more of (i) C1–8 alkyl, (ii) C1–8 alkoxy, (iii) nitro, (iv) halogen, (v) cyano, (vi) hydroxy, (vii) benzyloxy, (viii) —$NR^{62}R^{63}$, (ix) —$COOR^{64}$, (x) trihalomethyl, (xi) trihalomethoxy, (xii) phenyl, (xiii) phenoxy, (xiv) phenylthio, (xv)

C1–8 alkyl or C1–8 alkoxy substituted with phenyl, phenoxy, phenylthio, hydroxy, —NR$^{62}$R$^{63}$ or —COOR$^{64}$, R$^{62}$ and R$^{63}$ are each independently, hydrogen or C1–8 alkyl, R$^{64}$ is hydrogen or C1–8 alkyl, with the proviso that when A$^2$ is (vi) —NR$^5$C(O)—, (x) —NR$^7$SO$_2$—, (xiv) —NR$^{13}$C(O)O— or (xv) —OC(O)O—, then A$^3$ is not hydrogen, an N-oxide derivative thereof or a non-toxic salt thereof.

2. An agent for the prevention and/or treatment of various inflammatory diseases, sepsis, multiple myeloma, plasma cell leukemia, osteoporosis, cachexia, psoriasis, nephritis, renal cell carcinoma, Kaposi's sarcoma, rheumatoid arthritis, gammopathy, Castleman's disease, atrial myxoma, diabetes mellitus, autoimmune diseases, hepatitis, multiple sclerosis, colitis, graft versus host immune diseases, infectious diseases, wherein said agent contains a fused thiophene derivative of the formula (I), as set forth in claim 1, an N-oxide derivative thereof or a non-toxic salt thereof as an active ingredient.

3. An inhibitor of interleukin-6 and/or interleukin-12 production according to claim 1, comprising a compound which is (1) 3-(thiophen-2-yl)thio-2,3-dihydro-1,1-dioxidebenzo[b]thiophene,
(2) 6-nitro-3-(thiophen-2-yl)thio-2,3-dihydro-1,1-dioxidebenzo[b]thiophene,
(3) 3-(thiophen-2-yl)sulfonyl-2,3-dihydro-1,1-dioxidebenzo[b]thiophene,
(4) 4,5-dimethyl-1,1-dioxidebenzo[b]thiophene,
(5) 4,6-dimethyl-1,1-dioxidebenzo[b]thiophene,
(6) 4,7-dimethyl-1,1-dioxidebenzo[b]thiophene,
(7) 5,6-dimethyl-1,1-dioxidebenzo[b]thiophene,
(8) 5,7-dimethyl-1 1-dioxidebenzo[b]thiophene,
(9) 6,7-dimethyl-1,1-dioxidebenzo[b]thiophene,
(10) 4-carboxymethyl-1,1-dioxidebenzo[b]thiophene,
(11) 6-(2,2-bis(ethoxycarbonyl)ethenyl)amino-1,1-dioxidebenzo[b]thiophene,
(12) 4-methylaminocarbonyloxy-1,1-dioxidebenzo[b]thiophene,
(13) 5-(2-(N-(5-methoxy-1,2,3,4-tetrahydronaphthalen-1-ylmethyl)-N-methylamino)ethyl)-1,1-dioxidebenzo[b]thiophene,
(14) 5-(2-hydroxyethyl)-1,1-dioxidebenzo[b]thiopherie,
(15) 5-bromo-7-methyl-1,1-dioxidebenzo[b]thiophene,
(16) 7-bromo-5-methyl-1,1-dioxidebenzo[b]thiophene,
(17) 5-bromo-6-methyl-1,1-dioxidebennzo[b]thiophene,
(18) 5-bromo-4-methyl-1,1-dioxidebenzo[b]thiophene,
(19) 6-bromo-5-methyl-1,1-dioxidebenzo[b]thiophene,
(20) 4-bromo-5-methyl-1,1-dioxidebenzo[b]thiophene,
(21) 6-amino-1,1-dioxidebenzo[b]thiophene,
(22) 6-acetylamino-1,1-dioxidebenzo[b]thiophene,
(23) 6-(4-diethylaminophenyl)-1,1-dioxidebenzo[b]thiophene,
(24) 1,1-dioxidethieno[2,3-b]pyridine,
(25) 1,1-dioxidethieno[3,2-b]pyridine,
(26) 1,1-dioxidethieno[2,3-c]pyridine,
(27) 5-amino-1,1-dioxidebenzo[b]thiophene,
(28) 5-(3-methyl-5-oxo-4,5-dihydropyrazol-1-yl)-1,1-dioxidebenzo[b]thiophene,
(29) 4-(2-(1,1-dioxidebenzo[b]thiophen-3-yl)ethyl)-1,1-dioxidebenzo[b]thiophene,
(30) 7-methyl-1,1-dioxidethieno[2,3-c]pyridine,
(31) 1,1-dioxidebenzo[b]thiophene,
(32) 4-(4-methoxyphenyl)-1,1-dioxidethieno[3,2-c]pyridine,
(33) 5-((E)-2-(ethoxycarbonyl)ethenyl)-4-methoxybenzo[b]thiophene,
(34) 5-(2-(ethoxycarbonyl)ethyl-4-methoxybenzo[b]thiophene,
(35) 5-methoxycarbonyl-4-ethoxybenzo[b]thiophene,
(36) 5-carboxy-4-ethoxybenzo[b]thiophene,
(37) 5-benzyloxycarbonyl-4-ethoxybenzo[b]thiophene,
(38) 5-hydroxy-4-formylbenzo[b]thiophene,
(39) 5-benzyloxy4-formylbenzo[b]thiophene,
(40) 5-benzyloxy-4-hydroxymethylbenzo[b]thiophene or
(41) 4-t-butoxycarbonylaminobenzo[b]thiophene, or an N-oxide derivative thereof, or a non-toxic salt thereof as active ingredient.

4. A method for preparation of a compound of the formula (XI)

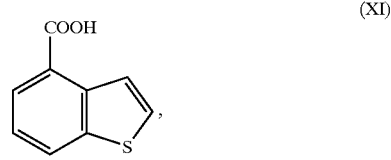

(XI)

said method comprising cyanization of a compound of formula (XII)

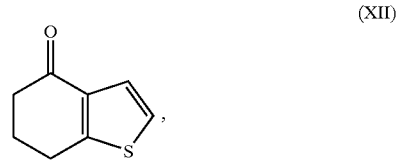

(XII)

to obtain a compound of the formula (XIII)

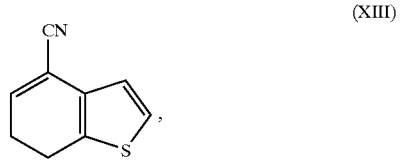

(XIII)

dehydration of the compound of the formula (XIII) to obtain a compound of formula (XIV)

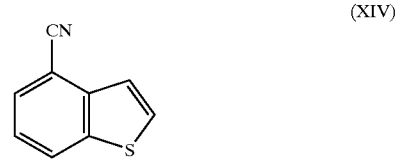

(XIV)

and hydrolysis of the compound of the formula (XIV).

* * * * *